(12) United States Patent
Chin et al.

(10) Patent No.: US 12,264,173 B2
(45) Date of Patent: Apr. 1, 2025

(54) ANTIVIRAL COMPOUNDS

(71) Applicant: GILEAD SCIENCES, INC., Foster City, CA (US)

(72) Inventors: Gregory F. Chin, San Francisco, CA (US); Byoung-Kwon Chun, Pleasanton, CA (US); Michael O. Clarke, Redwood City, CA (US); Bindu Goyal, Fremont, CA (US); Hon C. Hui, San Mateo, CA (US); Petr Jansa, Foster City, CA (US); Richard L. Mackman, Millbrae, CA (US); Dustin S. Siegel, Half Moon Bay, CA (US); Hai Yang, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 76 days.

(21) Appl. No.: 18/354,362

(22) Filed: Jul. 18, 2023

(65) Prior Publication Data
US 2024/0174704 A1   May 30, 2024

Related U.S. Application Data

(62) Division of application No. 17/178,463, filed on Feb. 18, 2021, now Pat. No. 11,767,337.

(60) Provisional application No. 62/977,881, filed on Feb. 18, 2020.

(51) Int. Cl.
| | | |
|---|---|---|
| A61P 31/14 | (2006.01) |
| A61K 31/661 | (2006.01) |
| A61K 31/675 | (2006.01) |
| A61P 31/12 | (2006.01) |
| C07F 9/6561 | (2006.01) |

(52) U.S. Cl.
CPC .......... *C07F 9/6561* (2013.01); *A61K 31/661* (2013.01); *A61K 31/675* (2013.01); *A61P 31/12* (2018.01); *A61P 31/14* (2018.01)

(58) Field of Classification Search
CPC ........ A61P 31/12; A61P 31/14; A61K 31/661; A61K 31/675
See application file for complete search history.

(56) References Cited

U.S. PATENT DOCUMENTS

| 4,707,540 A | 11/1987 | Manser et al. |
|---|---|---|
| 5,446,137 A | 8/1995 | Maag et al. |
| 6,699,994 B1 | 3/2004 | Babu et al. |
| 7,393,856 B2 | 7/2008 | Bellinger-kawahara et al. |
| 8,101,745 B2 | 1/2012 | Hostetler et al. |
| 8,119,607 B2 | 2/2012 | Francom et al. |
| 8,242,085 B2 | 8/2012 | Babu et al. |
| 8,318,700 B2 | 11/2012 | Hostetler et al. |
| 8,440,813 B2 | 5/2013 | Babu et al. |
| 9,370,528 B2 | 6/2016 | Schentag et al. |
| 9,388,208 B2 | 7/2016 | Clarke et al. |
| 9,701,682 B2 | 7/2017 | Clarke et al. |
| 9,724,360 B2 | 8/2017 | Chun et al. |
| 9,777,035 B2 | 10/2017 | Girijavallabhan et al. |
| 9,815,864 B2 | 11/2017 | Beigelman et al. |
| 10,004,719 B1 | 6/2018 | Hsu et al. |
| 10,059,716 B2 | 8/2018 | Clarke et al. |
| 10,251,904 B2 | 4/2019 | Clarke et al. |
| 10,377,761 B2 | 8/2019 | Clarke et al. |
| 10,682,368 B2 | 6/2020 | Perron et al. |
| 2002/0035082 A1 | 3/2002 | Grinstaff et al. |
| 2002/0188137 A1 | 12/2002 | Dershem et al. |
| 2003/0170891 A1 | 9/2003 | Mcswiggen |
| 2003/0175950 A1 | 9/2003 | Mcswiggen |
| 2003/0199516 A1 | 10/2003 | Moser et al. |
| 2004/0009959 A1 | 1/2004 | Potter et al. |
| 2004/0157838 A1 | 8/2004 | Griffith |
| 2004/0157839 A1 | 8/2004 | Griffith |
| 2004/0214837 A1 | 10/2004 | Griffith et al. |
| 2004/0229839 A1 | 11/2004 | Babu et al. |
| 2004/0229840 A1 | 11/2004 | Bhat et al. |
| 2006/0121312 A1 | 6/2006 | Yamada et al. |
| 2006/0194144 A1 | 8/2006 | Sooriyakumaran et al. |
| 2006/0281922 A1 | 12/2006 | Gao et al. |
| 2007/0232635 A1 | 10/2007 | Chelliah et al. |
| 2009/0318380 A1 | 12/2009 | Sofia et al. |
| 2009/0323011 A1 | 12/2009 | He et al. |
| 2009/0323012 A1 | 12/2009 | He et al. |
| 2010/0035836 A1 | 2/2010 | Francom et al. |
| 2010/0040804 A1 | 2/2010 | Zhang |
| 2010/0096603 A1 | 4/2010 | Wang et al. |
| 2010/0184942 A1 | 7/2010 | Chen et al. |
| 2010/0186626 A1 | 7/2010 | Shin et al. |
| 2011/0212994 A1 | 9/2011 | Clem et al. |
| 2011/0216273 A1 | 9/2011 | He et al. |
| 2011/0287927 A1 | 11/2011 | Grasset et al. |

(Continued)

FOREIGN PATENT DOCUMENTS

| CN | 102000103 A | 4/2011 |
|---|---|---|
| CN | 102286047 A | 12/2011 |

(Continued)

OTHER PUBLICATIONS

1st Examination Report in India appl. No. 202217043229, mailed on Sep. 21, 2023.

(Continued)

*Primary Examiner* — Laura L Stockton
(74) *Attorney, Agent, or Firm* — Mintz, Levin, Cohn, Ferris, Glovsky and Popeo, P.C.

(57) ABSTRACT

The present disclosure provides compounds for treating a variety of diseases, such as respiratory syncytial virus (RSV), HRV, hMPV, Ebola, Zika, West Nile, Dengue, and HCV.

20 Claims, No Drawings
Specification includes a Sequence Listing.

(56) References Cited

U.S. PATENT DOCUMENTS

| | | |
|---|---|---|
| 2011/0319459 A1 | 12/2011 | Gupta et al. |
| 2012/0009147 A1 | 1/2012 | Cho et al. |
| 2012/0020921 A1 | 1/2012 | Cho et al. |
| 2012/0035115 A1 | 2/2012 | Manoharan et al. |
| 2012/0070411 A1 | 3/2012 | Beigelman et al. |
| 2012/0070415 A1 | 3/2012 | Beigelman et al. |
| 2012/0071434 A1 | 3/2012 | Smith et al. |
| 2012/0214735 A1 | 8/2012 | Bhuniya et al. |
| 2012/0214762 A1 | 8/2012 | Staben et al. |
| 2012/0219568 A1 | 8/2012 | Liu et al. |
| 2012/0264649 A1 | 10/2012 | Bazan et al. |
| 2013/0303669 A1 | 11/2013 | Morimoto et al. |
| 2014/0038991 A1 | 2/2014 | Yu et al. |
| 2014/0200215 A1 | 7/2014 | Buckman et al. |
| 2014/0309413 A1 | 10/2014 | Rose et al. |
| 2015/0011497 A1 | 1/2015 | Beigelman et al. |
| 2015/0051167 A1 | 2/2015 | Wang et al. |
| 2015/0105341 A1 | 4/2015 | Beigelman et al. |
| 2015/0252265 A1 | 9/2015 | Archetti et al. |
| 2015/0274767 A1 | 10/2015 | Girijavallabhan et al. |
| 2015/0366887 A1 | 12/2015 | Blatt et al. |
| 2015/0366888 A1 | 12/2015 | Blatt et al. |
| 2016/0024107 A1 | 1/2016 | Clarke et al. |
| 2016/0053175 A1 | 2/2016 | Song et al. |
| 2016/0122374 A1 | 5/2016 | Chun et al. |
| 2016/0244668 A1 | 8/2016 | Saito et al. |
| 2016/0257657 A1 | 9/2016 | Wipf et al. |
| 2017/0071964 A1 | 3/2017 | Clarke et al. |
| 2017/0186964 A1 | 6/2017 | Cho et al. |
| 2018/0002366 A1 | 1/2018 | Girijavallabhan et al. |
| 2018/0044369 A1 | 2/2018 | Beigelman et al. |
| 2018/0079774 A1 | 3/2018 | Beigelman et al. |
| 2018/0226580 A1 | 8/2018 | Fitzgerald et al. |
| 2019/0185748 A1 | 6/2019 | Liao |
| 2019/0185754 A1 | 6/2019 | Archetti et al. |
| 2019/0241807 A1 | 8/2019 | Mizusaki et al. |
| 2021/0060051 A1 | 3/2021 | Schinazi et al. |
| 2021/0284669 A1 | 9/2021 | Chun et al. |
| 2021/0284670 A1 | 9/2021 | Chin et al. |
| 2021/0292348 A1 | 9/2021 | Byun et al. |
| 2022/0356196 A1 | 11/2022 | Byun et al. |
| 2023/0295201 A1 | 9/2023 | Byun et al. |

FOREIGN PATENT DOCUMENTS

| | | |
|---|---|---|
| CN | 102603836 A | 7/2012 |
| CN | 103709220 A | 4/2014 |
| CN | 104086612 A | 10/2014 |
| CN | 105646629 A | 6/2016 |
| CN | 105777580 A | 7/2016 |
| CN | 106518766 A | 3/2017 |
| CN | 106518767 A | 3/2017 |
| CN | 106892920 A | 6/2017 |
| CN | 107286190 A | 10/2017 |
| CN | 108276352 A | 7/2018 |
| CN | 109748921 A | 5/2019 |
| CN | 109748943 A | 5/2019 |
| CN | 109748944 A | 5/2019 |
| CN | 110215456 A | 9/2019 |
| CN | 110330540 A | 10/2019 |
| CN | 110724174 A | 1/2020 |
| CN | 110776512 A | 2/2020 |
| CN | 111620909 A | 9/2020 |
| DE | 2626792 A1 | 12/1977 |
| DE | 3528753 A1 | 2/1987 |
| DE | 4232852 A1 | 3/1994 |
| DE | 19934799 A1 | 2/2001 |
| DE | 10064823 A1 | 6/2002 |
| EP | 0284952 A2 | 10/1988 |
| EP | 0419944 A2 | 4/1991 |
| EP | 0458214 A1 | 11/1991 |
| EP | 0682098 A2 | 11/1995 |
| EP | 0924265 A2 | 6/1999 |
| EP | 1046631 A1 | 10/2000 |
| EP | 1170353 A2 | 1/2002 |
| EP | 1593713 A1 | 11/2005 |
| EP | 1975718 A2 | 10/2008 |
| EP | 1978077 A1 | 10/2008 |
| EP | 2098226 A1 | 9/2009 |
| EP | 2388069 A1 | 11/2011 |
| EP | 2778169 A1 | 9/2014 |
| EP | 2896678 A1 | 7/2015 |
| EP | 2980182 A1 | 2/2016 |
| FR | 2354774 A1 | 1/1978 |
| FR | 2669639 A1 | 5/1992 |
| IN | 167775 B | 12/1990 |
| JP | S6286363 A | 4/1987 |
| JP | H0931092 A | 2/1997 |
| JP | H09328497 A | 12/1997 |
| JP | 2002326995 A | 11/2002 |
| JP | 2002326996 A | 11/2002 |
| JP | 2003246770 A | 9/2003 |
| JP | 2004315613 A | 11/2004 |
| JP | 2005120172 A | 5/2005 |
| JP | 2006232875 A | 9/2006 |
| JP | 2008007634 A | 1/2008 |
| JP | 2012216832 A | 11/2012 |
| JP | 5295692 B2 | 9/2013 |
| JP | 2014145852 A | 8/2014 |
| JP | 2016132779 A | 7/2016 |
| JP | 2018044028 A | 3/2018 |
| JP | 2018203945 A | 12/2018 |
| KR | 1020120135501 A | 12/2012 |
| KR | 1020160098975 A | 8/2016 |
| KR | 1020160110899 A | 9/2016 |
| KR | 1020160110900 A | 9/2016 |
| KR | 1020190041918 A | 4/2019 |
| KR | 1020190076339 A | 7/2019 |
| NL | 7606413 A | 12/1977 |
| WO | 198807043 A1 | 9/1988 |
| WO | 199110671 A1 | 7/1991 |
| WO | 199201695 A1 | 2/1992 |
| WO | 199201696 A1 | 2/1992 |
| WO | 199214805 A1 | 9/1992 |
| WO | 199316075 A1 | 8/1993 |
| WO | 199614329 A1 | 5/1996 |
| WO | 199640705 A1 | 12/1996 |
| WO | 199816184 A2 | 4/1998 |
| WO | 199900399 A1 | 1/1999 |
| WO | 199914226 A2 | 3/1999 |
| WO | 199926933 A1 | 6/1999 |
| WO | 199926941 A1 | 6/1999 |
| WO | 199951565 A1 | 10/1999 |
| WO | 199961583 A2 | 12/1999 |
| WO | 200001381 A1 | 1/2000 |
| WO | 200032152 A2 | 6/2000 |
| WO | 200034276 A1 | 6/2000 |
| WO | 200063154 A1 | 10/2000 |
| WO | 200066604 A2 | 11/2000 |
| WO | 200100197 A2 | 1/2001 |
| WO | 200110842 A2 | 2/2001 |
| WO | 200114320 A2 | 3/2001 |
| WO | 200119841 A1 | 3/2001 |
| WO | 200121577 A2 | 3/2001 |
| WO | 200123357 A2 | 4/2001 |
| WO | 200147862 A1 | 7/2001 |
| WO | 200164642 A2 | 9/2001 |
| WO | 200177091 A2 | 10/2001 |
| WO | 200207516 A2 | 1/2002 |
| WO | 200228813 A1 | 4/2002 |
| WO | 200234711 A1 | 5/2002 |
| WO | 200234736 A1 | 5/2002 |
| WO | 200239987 A2 | 5/2002 |
| WO | 2002062766 A2 | 8/2002 |
| WO | 2002094185 A2 | 11/2002 |
| WO | 2002100415 A2 | 12/2002 |
| WO | 2003039523 A2 | 5/2003 |
| WO | 2003041649 A2 | 5/2003 |
| WO | 2003049772 A2 | 6/2003 |
| WO | 2003088908 A2 | 10/2003 |
| WO | 2003090748 A1 | 11/2003 |
| WO | 2003091262 A1 | 11/2003 |
| WO | 2004002999 A2 | 1/2004 |
| WO | 2004007472 A1 | 1/2004 |

(56) References Cited

FOREIGN PATENT DOCUMENTS

| | | |
|---|---|---|
| WO | 2004014312 A2 | 2/2004 |
| WO | 2004037159 A2 | 5/2004 |
| WO | 2004041752 A2 | 5/2004 |
| WO | 2004080966 A1 | 9/2004 |
| WO | 2004083177 A2 | 9/2004 |
| WO | 2004083263 A1 | 9/2004 |
| WO | 2004087153 A2 | 10/2004 |
| WO | 2004091499 A2 | 10/2004 |
| WO | 2004106356 A1 | 12/2004 |
| WO | 2004110350 A2 | 12/2004 |
| WO | 2005020885 A2 | 3/2005 |
| WO | 2005021568 A2 | 3/2005 |
| WO | 2005023771 A1 | 3/2005 |
| WO | 2005025515 A2 | 3/2005 |
| WO | 2005040135 A1 | 5/2005 |
| WO | 2005058832 A1 | 6/2005 |
| WO | 2005093476 A1 | 10/2005 |
| WO | 2005095544 A1 | 10/2005 |
| WO | 2005097052 A1 | 10/2005 |
| WO | 2005111099 A1 | 11/2005 |
| WO | 2006001463 A1 | 1/2006 |
| WO | 2006006490 A1 | 1/2006 |
| WO | 2006008438 A1 | 1/2006 |
| WO | 2006016101 A1 | 2/2006 |
| WO | 2006030193 A1 | 3/2006 |
| WO | 2006038594 A1 | 4/2006 |
| WO | 2006048634 A1 | 5/2006 |
| WO | 2006061094 A1 | 6/2006 |
| WO | 2006063717 A2 | 6/2006 |
| WO | 2006066074 A2 | 6/2006 |
| WO | 2006094347 A1 | 9/2006 |
| WO | 2006098380 A1 | 9/2006 |
| WO | 2006105440 A2 | 10/2006 |
| WO | 2006110656 A2 | 10/2006 |
| WO | 2006119800 A1 | 11/2006 |
| WO | 2006130217 A2 | 12/2006 |
| WO | 2007007588 A1 | 1/2007 |
| WO | 2007011759 A2 | 1/2007 |
| WO | 2007024021 A1 | 3/2007 |
| WO | 2007031185 A1 | 3/2007 |
| WO | 2007056143 A2 | 5/2007 |
| WO | 2007056170 A2 | 5/2007 |
| WO | 2007076034 A2 | 7/2007 |
| WO | 2007084667 A2 | 7/2007 |
| WO | 2007095188 A2 | 8/2007 |
| WO | 2007125320 A1 | 11/2007 |
| WO | 2007130783 A2 | 11/2007 |
| WO | 2008001195 A2 | 1/2008 |
| WO | 2008011557 A2 | 1/2008 |
| WO | 2008012555 A2 | 1/2008 |
| WO | 2008021388 A1 | 2/2008 |
| WO | 2008024364 A2 | 2/2008 |
| WO | 2008082601 A2 | 7/2008 |
| WO | 2008089105 A2 | 7/2008 |
| WO | 2008092006 A2 | 7/2008 |
| WO | 2008095040 A2 | 8/2008 |
| WO | 2008109177 A2 | 9/2008 |
| WO | 2008109180 A2 | 9/2008 |
| WO | 2008109181 A2 | 9/2008 |
| WO | 2008117047 A1 | 10/2008 |
| WO | 2008121360 A1 | 10/2008 |
| WO | 2008133966 A1 | 11/2008 |
| WO | 2008141079 A1 | 11/2008 |
| WO | 2008151437 A1 | 12/2008 |
| WO | 2009001097 A2 | 12/2008 |
| WO | 2009009951 A1 | 1/2009 |
| WO | 2009011228 A1 | 1/2009 |
| WO | 2009011229 A1 | 1/2009 |
| WO | 2009067409 A1 | 5/2009 |
| WO | 2009069095 A2 | 6/2009 |
| WO | 2009076593 A1 | 6/2009 |
| WO | 2009076618 A2 | 6/2009 |
| WO | 2009086192 A1 | 7/2009 |
| WO | 2009086201 A1 | 7/2009 |
| WO | 2009111653 A2 | 9/2009 |
| WO | 2009132123 A1 | 10/2009 |
| WO | 2009132135 A1 | 10/2009 |
| WO | 2009151921 A1 | 12/2009 |
| WO | 2009152095 A2 | 12/2009 |
| WO | 2010001174 A1 | 1/2010 |
| WO | 2010007116 A2 | 1/2010 |
| WO | 2010026153 A1 | 3/2010 |
| WO | 2010036407 A2 | 4/2010 |
| WO | 2010060952 A1 | 6/2010 |
| WO | 2010073126 A2 | 7/2010 |
| WO | 2010084115 A2 | 7/2010 |
| WO | 2010091386 A2 | 8/2010 |
| WO | 2010108135 A1 | 9/2010 |
| WO | 2010108140 A1 | 9/2010 |
| WO | 2010145778 A1 | 12/2010 |
| WO | 2011005860 A2 | 1/2011 |
| WO | 2011015037 A1 | 2/2011 |
| WO | 2011016430 A1 | 2/2011 |
| WO | 2011031896 A2 | 3/2011 |
| WO | 2011032169 A2 | 3/2011 |
| WO | 2011035231 A1 | 3/2011 |
| WO | 2011035250 A1 | 3/2011 |
| WO | 2011035842 A1 | 3/2011 |
| WO | 2011036557 A1 | 3/2011 |
| WO | 2011038207 A1 | 3/2011 |
| WO | 2011057214 A2 | 5/2011 |
| WO | 2011086075 A1 | 7/2011 |
| WO | 2011097300 A1 | 8/2011 |
| WO | 2011100131 A2 | 8/2011 |
| WO | 2011109799 A1 | 9/2011 |
| WO | 2011119869 A1 | 9/2011 |
| WO | 2011146401 A1 | 11/2011 |
| WO | 2011150288 A1 | 12/2011 |
| WO | 2011156632 A2 | 12/2011 |
| WO | 2012012465 A1 | 1/2012 |
| WO | 2012012776 A1 | 1/2012 |
| WO | 2012031539 A1 | 3/2012 |
| WO | 2012034626 A1 | 3/2012 |
| WO | 2012037038 A1 | 3/2012 |
| WO | 2012040124 A1 | 3/2012 |
| WO | 2012040126 A1 | 3/2012 |
| WO | 2012040127 A1 | 3/2012 |
| WO | 2012068340 A2 | 5/2012 |
| WO | 2012083048 A2 | 6/2012 |
| WO | 2012087596 A1 | 6/2012 |
| WO | 2012088155 A1 | 6/2012 |
| WO | 2012088438 A1 | 6/2012 |
| WO | 2012092471 A2 | 7/2012 |
| WO | 2012121973 A1 | 9/2012 |
| WO | 2012128944 A1 | 9/2012 |
| WO | 2012139028 A2 | 10/2012 |
| WO | 2012142075 A1 | 10/2012 |
| WO | 2012142085 A1 | 10/2012 |
| WO | 2012142523 A2 | 10/2012 |
| WO | 2012160392 A1 | 11/2012 |
| WO | 2012168348 A1 | 12/2012 |
| WO | 2013000855 A1 | 1/2013 |
| WO | 2013007586 A1 | 1/2013 |
| WO | 2013030288 A1 | 3/2013 |
| WO | 2013033270 A2 | 3/2013 |
| WO | 2013040492 A2 | 3/2013 |
| WO | 2013040568 A1 | 3/2013 |
| WO | 2013044030 A1 | 3/2013 |
| WO | 2013056132 A2 | 4/2013 |
| WO | 2013072466 A1 | 5/2013 |
| WO | 2013087765 A1 | 6/2013 |
| WO | 2013090420 A2 | 6/2013 |
| WO | 2013096679 A1 | 6/2013 |
| WO | 2013096680 A1 | 6/2013 |
| WO | 2013101552 A1 | 7/2013 |
| WO | 2013135339 A2 | 9/2013 |
| WO | 2013138236 A1 | 9/2013 |
| WO | 2013142124 A1 | 9/2013 |
| WO | 2013142157 A1 | 9/2013 |
| WO | 2013142159 A1 | 9/2013 |
| WO | 2013142525 A1 | 9/2013 |
| WO | 2013147795 A1 | 10/2013 |
| WO | 2013151975 A1 | 10/2013 |
| WO | 2013182262 A1 | 12/2013 |

(56) References Cited

FOREIGN PATENT DOCUMENTS

| | | |
|---|---|---|
| WO | 2014005125 A2 | 1/2014 |
| WO | 2014008236 A1 | 1/2014 |
| WO | 2014015936 A1 | 1/2014 |
| WO | 2014026198 A1 | 2/2014 |
| WO | 2014031872 A2 | 2/2014 |
| WO | 2014035140 A2 | 3/2014 |
| WO | 2014048998 A1 | 4/2014 |
| WO | 2014057095 A1 | 4/2014 |
| WO | 2014058801 A1 | 4/2014 |
| WO | 2014059901 A1 | 4/2014 |
| WO | 2014059902 A1 | 4/2014 |
| WO | 2014090369 A1 | 6/2014 |
| WO | 2014100498 A1 | 6/2014 |
| WO | 2014100505 A1 | 6/2014 |
| WO | 2014102077 A1 | 7/2014 |
| WO | 2014124458 A1 | 8/2014 |
| WO | 2014134127 A1 | 9/2014 |
| WO | 2014134251 A1 | 9/2014 |
| WO | 2014149164 A1 | 9/2014 |
| WO | 2014160012 A2 | 10/2014 |
| WO | 2014209979 A1 | 12/2014 |
| WO | 2015003146 A1 | 1/2015 |
| WO | 2015006280 A1 | 1/2015 |
| WO | 2015016187 A1 | 2/2015 |
| WO | 2015024120 A1 | 2/2015 |
| WO | 2015031710 A1 | 3/2015 |
| WO | 2015038596 A1 | 3/2015 |
| WO | 2015046827 A1 | 4/2015 |
| WO | 2015051169 A2 | 4/2015 |
| WO | 2015061742 A2 | 4/2015 |
| WO | 2015069939 A1 | 5/2015 |
| WO | 2015089511 A2 | 6/2015 |
| WO | 2015118898 A1 | 8/2015 |
| WO | 2015120237 A2 | 8/2015 |
| WO | 2015129672 A1 | 9/2015 |
| WO | 2015143712 A1 | 10/2015 |
| WO | 2015148746 A1 | 10/2015 |
| WO | 2015148869 A1 | 10/2015 |
| WO | 2015160251 A1 | 10/2015 |
| WO | 2015196118 A1 | 12/2015 |
| WO | 2015196128 A2 | 12/2015 |
| WO | 2015196130 A2 | 12/2015 |
| WO | 2015198915 A1 | 12/2015 |
| WO | 2015200205 A1 | 12/2015 |
| WO | 2015200219 A1 | 12/2015 |
| WO | 2016010026 A1 | 1/2016 |
| WO | 2016018697 A1 | 2/2016 |
| WO | 2016029186 A1 | 2/2016 |
| WO | 2016031406 A1 | 3/2016 |
| WO | 2016041877 A1 | 3/2016 |
| WO | 2016066582 A1 | 5/2016 |
| WO | 2016069825 A1 | 5/2016 |
| WO | 2016069826 A1 | 5/2016 |
| WO | 2016069827 A1 | 5/2016 |
| WO | 2016069975 A1 | 5/2016 |
| WO | 2016070952 A1 | 5/2016 |
| WO | 2016074762 A1 | 5/2016 |
| WO | 2016096076 A1 | 6/2016 |
| WO | 2016100441 A1 | 6/2016 |
| WO | 2016100569 A1 | 6/2016 |
| WO | 2016107664 A1 | 7/2016 |
| WO | 2016115222 A1 | 7/2016 |
| WO | 2016116124 A1 | 7/2016 |
| WO | 2016116254 A1 | 7/2016 |
| WO | 2016116508 A1 | 7/2016 |
| WO | 2016117271 A1 | 7/2016 |
| WO | 2016145142 A1 | 9/2016 |
| WO | 2016148170 A1 | 9/2016 |
| WO | 2016152340 A1 | 9/2016 |
| WO | 2016161176 A1 | 10/2016 |
| WO | 2016162644 A1 | 10/2016 |
| WO | 2016170948 A1 | 10/2016 |
| WO | 2016172631 A2 | 10/2016 |
| WO | 2016178876 A2 | 11/2016 |
| WO | 2016184361 A1 | 11/2016 |
| WO | 2016192902 A1 | 12/2016 |
| WO | 2017005673 A1 | 1/2017 |
| WO | 2017019817 A1 | 2/2017 |
| WO | 2017019822 A1 | 2/2017 |
| WO | 2017019830 A1 | 2/2017 |
| WO | 2017023894 A1 | 2/2017 |
| WO | 2017024310 A1 | 2/2017 |
| WO | 2017027646 A1 | 2/2017 |
| WO | 2017032840 A1 | 3/2017 |
| WO | 2017041893 A1 | 3/2017 |
| WO | 2017045612 A1 | 3/2017 |
| WO | 2017045615 A1 | 3/2017 |
| WO | 2017045616 A1 | 3/2017 |
| WO | 2017045740 A1 | 3/2017 |
| WO | 2017049060 A1 | 3/2017 |
| WO | 2017058807 A1 | 4/2017 |
| WO | 2017059357 A1 | 4/2017 |
| WO | 2017066781 A1 | 4/2017 |
| WO | 2017066782 A1 | 4/2017 |
| WO | 2017066791 A1 | 4/2017 |
| WO | 2017066793 A1 | 4/2017 |
| WO | 2017066797 A1 | 4/2017 |
| WO | 2017068875 A1 | 4/2017 |
| WO | 2017073931 A1 | 5/2017 |
| WO | 2017073932 A1 | 5/2017 |
| WO | 2017073933 A1 | 5/2017 |
| WO | 2017091767 A2 | 6/2017 |
| WO | 2017093214 A1 | 6/2017 |
| WO | 2017097401 A1 | 6/2017 |
| WO | 2017153186 A1 | 9/2017 |
| WO | 2017156262 A1 | 9/2017 |
| WO | 2017161028 A1 | 9/2017 |
| WO | 2017165489 A1 | 9/2017 |
| WO | 2017184668 A1 | 10/2017 |
| WO | 2017205980 A1 | 12/2017 |
| WO | 2017207993 A1 | 12/2017 |
| WO | 2018015323 A2 | 1/2018 |
| WO | 2018031818 A2 | 2/2018 |
| WO | 2018065356 A1 | 4/2018 |
| WO | 2018067615 A1 | 4/2018 |
| WO | 2018098206 A1 | 5/2018 |
| WO | 2018106818 A1 | 6/2018 |
| WO | 2018106820 A1 | 6/2018 |
| WO | 2018110529 A1 | 6/2018 |
| WO | 2018116901 A1 | 6/2018 |
| WO | 2018119263 A1 | 6/2018 |
| WO | 2018138685 A2 | 8/2018 |
| WO | 2018169946 A1 | 9/2018 |
| WO | 2018175746 A1 | 9/2018 |
| WO | 2018183635 A1 | 10/2018 |
| WO | 2018184590 A1 | 10/2018 |
| WO | 2018189134 A1 | 10/2018 |
| WO | 2018204198 A1 | 11/2018 |
| WO | 2018208667 A1 | 11/2018 |
| WO | 2018213185 A1 | 11/2018 |
| WO | 2018218171 A1 | 11/2018 |
| WO | 2018218281 A1 | 12/2018 |
| WO | 2018222172 A1 | 12/2018 |
| WO | 2018226976 A1 | 12/2018 |
| WO | 2018237194 A1 | 12/2018 |
| WO | 2019014247 A1 | 1/2019 |
| WO | 2019018185 A1 | 1/2019 |
| WO | 2019051269 A1 | 3/2019 |
| WO | 2019052935 A1 | 3/2019 |
| WO | 2019053696 A1 | 3/2019 |
| WO | 2019084271 A1 | 5/2019 |
| WO | 2019086400 A1 | 5/2019 |
| WO | 2019092171 A1 | 5/2019 |
| WO | 2019098109 A1 | 5/2019 |
| WO | 2019125974 A1 | 6/2019 |
| WO | 2019129059 A1 | 7/2019 |
| WO | 2019133712 A1 | 7/2019 |
| WO | 2019154953 A1 | 8/2019 |
| WO | 2019154956 A1 | 8/2019 |
| WO | 2019173682 A1 | 9/2019 |
| WO | 2019195056 A1 | 10/2019 |
| WO | 2019215076 A1 | 11/2019 |
| WO | 2019218797 A1 | 11/2019 |
| WO | 2020032152 A1 | 2/2020 |

(56) References Cited

FOREIGN PATENT DOCUMENTS

| WO | 2020033413 A2 | 2/2020 |
| WO | 2021167882 A1 | 8/2021 |
| WO | 2021168004 A1 | 8/2021 |
| WO | 2021168008 A1 | 8/2021 |
| WO | 2021168038 A1 | 8/2021 |

OTHER PUBLICATIONS

CAPLUS—Chemical Abstracts Accession No. 2015:832846 Document No. 162: 643613 for WO 2015069939A1, CAPCLUS., 2015.
English translation of the 1st office action and search report in Taiwan (ROC) application 110105126, mailed on Jan. 6, 2022, 3 pages.
European Patent Office Communication for EP Application No. 21710378.7, mailed on Sep. 27, 2022, 3 pages.
International Preliminary Report on Patentability issued in International Application No. PCT/US2021/018458, mailed on Sep. 1, 2022, 12 pages.
International Search Report and Written Opinion received for PCT Application No. PCT/US2021/018169, mailed on Apr. 26, 2021, 19 pages.
International Search Report and Written Opinion received for PCT Application No. PCT/US2021/018410, mailed on May 10, 2021, 11 pages.
International Search Report and Written Opinion received for PCT Application No. PCT/US2021/018415, mailed on May 11, 2021, 14 pages.
International Search Report and Written Opinion received for PCT Application No. PCT/US2021/018458, mailed on May 18, 2021, 17 pages.
Notice of Allowance in Taiwan (ROC) Application No. 110105126, dated Nov. 22, 2022, 3 pages.
Office Action in Japan application No. 2022-549499, mailed on Aug. 23, 2023, 6 pages.
Cockerill et al. (2019) "State of the Art in Respiratory Syncytial Virus Drug Discovery and Development", Journal of Medicinal Chemistry, 62(7):3206-3227.
Colombo et al. (1985) "Asymetric Dihydroxylations via Chiral Oxazolidines", Tetrahedron Letters, 26(44):5459-5462.
Griffon et al. (2001) "Synthesis and Antiproliferative Activity of Some 4'-C-Hydroxymethyl-A- and -B-D-Arabino-Pentofuranosyl Pyrimidine Nucleosides", Nucleosides, Nucleotides & Nucleic Acids, 20(4-7):649-652.
Griffon et al. (2006) "Synthesis and Biological Evaluation of Some 4'-C-(Hydroxymethyl)-α- and -β-D-Arabinofuranosyl Pyrimidine and Adenine Nucleosides", Collection of Czechoslovak Chemical Communications, 71(7):1063-1087.
Koshkin et al. (Apr. 2, 1998) "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", Tetrahedron, 54(14):3607-3630.
Leisvuori, Anna (Sep. 2015) "Prodrug Strategies of Antiviral Nucleotides: Studies on Enzymatically and Thermally Removable Phosphate Protecting Groups", Turun Yliopisto, University of Turku, 86 pages.
Musich et al. (1978) "Synthesis of Anthopleurine, The Alarm Pheromone from Anthopleura Elegantissima", Journal of the American Chemical Society, 100(15):4865-4872.
Overend et al. (1970) "Branched Chain Sugars Part 12 Branched Sugars Derived from Methyl 2 3 o iso Propylidene Beta I erythro Pento Pyranosid 4 ulose and a Synthesis of I apiose", Carbohydrate Research, 15(2):185-195.
Patil et al. (Jul. 25, 1994) "4-Aza-7,9-Dideazaadenosine, a New Cytotoxic Synthetic C-Nucleoside Analogue of Adenosine", Tetrahedron Letters, 35(30):5339-5342.
Patil et al. (Jul./Aug. 1994) "Synthesis of Pyrrolo[2,1-f][1,2,4]triazine Congeners of Nucleic Acid Purines via the N-Amination of 2-Substituted Pyrroles", Journal of Heterocyclic Chemistry, 31(4):781-786.
Rui et al. (Apr. 30, 2001) "Chronic Obstructive Pulmonary Disease", Clinical Pharmacotherapeutics, 337.
Shrestha et al. (Nov. 7, 2011) "Synthesis and Properties of a Bridged Nucleic Acid with a Perhydro-1,2-oxazin-3-one Ring", Journal of Organic Chemistry, 76(24):9891-9899.
Timpe et al. (Jan. 1975) "3-desoxyhex-2-enono-1,4-lactone aus D-hexofuran(osid)-urono-6,3-lactonen", Carbohydrate Research, 39(1):53-60.
Waga et al. (Jan. 26, 1993) "Synthesis of 4'-C-Methylnucleosides", Bioscience, Biotechnology, Biochemistry, 57(9):1433-1438.
Wenska et al. (Nov. 8, 2006) "Synthesis of Conformationally Constrained 2'-N,4'-C-Ethylene-Bridged Adenosine (aza-ENA-A)", Heterocycles, 73(1):303-324.
Xie et al., (2021) "Weinreb Amide Approach to the Practical Synthesis of a Key Remdesivir Intermediate", The Journal of Organic Chemistry, 86(7):5065-5072.
Youssefyeh et al. (1977) "Synthetic Routes to 4'-hydroxymethylnucleosides", Tetrahedron Letters, 18(5):435-438.
CDC "Dengue" (https://www.cdc.gov/dengue/healthcare-providers/treatment.html) (Year: 2023).
CDC "Human metapneumovirus" (https://www.cdc.gov/ncird/human-metapneumovirus.html) (Year: 2023).
Krilov ("Respiratory Syncytial virus infection Medication" Medscape https://emedicine.medscape.com/article971488-medication?form=fpf, 2003). (Year: 2023).
Rueckert, (Chapter 21, Picornaviridae; The viruses and their replication. pp. 609-610. Fields Virology, vol. 1, Third Edition, Bernard Field, 1995.
Wikipedia, "Flaviviridae." (Year: 2023).
Wikipedia, "Pneumoviridae" (Year: 2023).
Office Action in Canada appl. No. 3171497 mailed Oct. 3, 2023.

SEQUENCE LISTING

```
Sequence total quantity: 1
SEQ ID NO: 1           moltype = RNA  length = 244
FEATURE                Location/Qualifiers
source                 1..244
                       mol_type = other RNA
                       organism = synthetic construct
misc_feature           1..244
                       note = Synthetic polynucleotide
SEQUENCE: 1
tcagtcagtc agtcagtcag tcagtcagtc agtcagtcag tcagtcagtc agtcagtcag   60
tcagtcagtc agtcagtcag tccaagtcca agtccaagtc caagtccaag tccaagtcca  120
agtccaagtc caagtccaag tccaagtcca agtccaagtc caagtcagtc agtcagtcag  180
tcagtcagtc agtcagtcag tcagtcagtc agtcagtcag tcagtcagtc agtcagtcag  240
tcag                                                                244
```

ANTIVIRAL COMPOUNDS

CROSS-REFERENCES TO RELATED APPLICATIONS

This application is a Divisional of U.S. Non-Provisional application Ser. No. 17/178,463, filed 18 Feb. 2021, which claims the benefit of priority to U.S. Provisional Patent Application No. 62/977,881 filed 18 Feb. 2020, titled ANTIVIRAL COMPOUNDS, the entirety of which is incorporated herein by reference.

SEQUENCE LISTING

The instant application contains a Sequence Listing which has been submitted electronically in ASCII format and is hereby incorporated by reference in its entirety. Said ASCII copy, created on Jul. 17, 2023, is named 2023-07-17 Sequence_Listing_ST26 052838-514D01US 1223-US-DI-V.xml and is 2,530 bytes in size.

BACKGROUND OF THE INVENTION

Pneumoviridae viruses are negative-sense, single-stranded, RNA viruses that are responsible for many prevalent human and animal diseases. The Pneumoviridae family of viruses includes human respiratory syncytial virus (HRSV) and human metapneumovirus. Almost all children will have had an HRSV infection by their second birthday. HRSV is the major cause of lower respiratory tract infections in infancy and childhood with 0.5% to 2% of those infected requiring hospitalization.

No vaccine to prevent HRSV infection is currently available. The monoclonal antibody palivizumab is available for immunoprophylaxis, but its use is restricted to infants at high risk, e.g., premature infants or those with either congenital heart or lung disease, and the cost for general use is often prohibitive. In addition, nucleoside analog ribavirin has been approved as the only antiviral agent to treat HRSV infections but has limited efficacy. Therefore, there is a need for anti-Pneumoviridae therapeutics.

Examples of pyrrolo[2,3-d]pyrimidine compounds useful for treating viral infections are described in U.S. 2012/0009147 A1 (Cho et al.), U.S. 2012/0020921 A1 (Cho et al.), WO 2008/089105 A2 (Babu et al.), WO 2008/141079 A1 (Babu et al.), WO 2009/132135 A1 (Butler et al.), WO 2010/002877 A2 (Francom), WO 2011/035231 A1 (Cho et al.), WO 2011/035250 A1 (Butler et al.), WO 2011/150288 A1 (Cho et al.), WO 2012/012465 (Cho et al.), WO 2012/012776 A1 (Mackman et al.), WO 2012/037038 (Clarke et al.), WO 2012/087596 A1 (Delaney et al.), and WO 2012/142075 A1 (Girijavallabhan et al.).

Thus, there is a need for compositions and methods for treating Pneumoviridae viral infections, such as HRSV infections, that are effective and have acceptable toxicity profiles, Flaviviridae infections, including dengue, and EBOV infections. The present disclosure addresses these and other needs.

BRIEF SUMMARY OF THE INVENTION

In some embodiments, the present disclosure provides a compound of Formula (II):

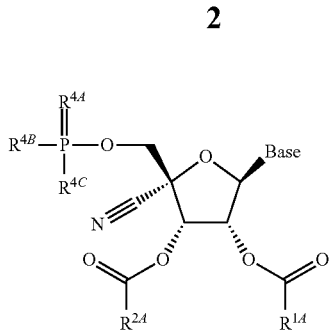

Formula (II)

or a pharmaceutically acceptable salt thereof, wherein:
Base is

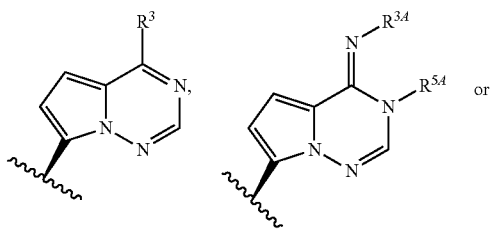

or

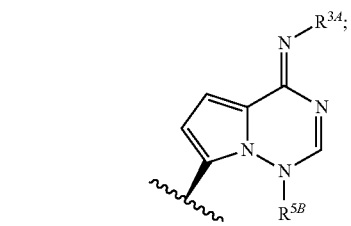

$R^{1A}$ and $R^{2A}$ are each independently:
  (A) $C_{1-12}$ alkyl optionally substituted with 1 to 3 $R^{1B}$,
  (B) 3 to 6 membered heterocyclyl having 1 to 3 heteroatoms independently selected from N, O and S, wherein the 3 to 6 membered heterocyclyl is optionally substituted with 1 to 3 $R^{1C}$, or
  (C) phenyl, wherein each $R^{1B}$ is independently halogen, —OH, —NH$_2$, $C_{1-6}$ alkoxy, methoxyethoxy, $C_3$-8 cycloalkyl, or 3 to 6 membered heterocyclyl having 1 to 3 heteroatoms independently selected from N, O and S, and each $R^{1C}$ is independently $C_{1-3}$ alkyl;
$R^3$ is —N(H)$R^{3A}$ or —N=C($R^{3B}$)($R^{3C}$); $R^{3A}$ is H, —CH$_2$OP(O)(OH)$_2$, or —C(O)$R^{3D}$, wherein $R^{3D}$ is $C_{1-6}$ alkyl optionally substituted with 1 methoxy, or 3 to 6 membered heterocyclyl having 1 to 3 heteroatoms independently selected from N, O and S, optionally substituted with $C_{1-3}$ alkyl; $R^{3B}$ is H or $C_{1-3}$ alkyl; $R^{3C}$ is —N($R^{3C1}$)($R^{3C2}$); $R^{3C1}$ and $R^{3C2}$ are each independently H or $C_{1-6}$ alkyl; or $R^{3C1}$ and $R^{3C2}$ together with the atom to which they are attached form a 3 to 6 membered heterocyclyl having 1 to 3 heteroatoms independently selected from N, O and S, optionally substituted with $C_{1-6}$ alkyl;
$R^{4A}$ is O or S;
$R^{4B}$ and $R^{4C}$ are each independently
  (A) —OH;
  (B) —O$R^{4B1}$, wherein $R^{4B1}$ is $C_{1-6}$ alkyl optionally substituted with 1 to 3 $R^{4B2}$ groups, or $C_{6-12}$ aryl, wherein each $R^{4B2}$ group is independently $C_{1-6}$ alkoxy, —S—$R^{4B3}$ or —S(O)$_2$—$R^{4B3}$, and each $R^{4B3}$ group is independently $C_{1-6}$ alkyl;

(C)

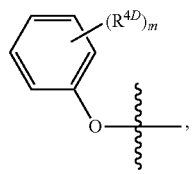

wherein m is 0, 1, 2, 3, 4, or 5; and each $R^{4D}$ is independently $C_{1-3}$ alkyl optionally substituted with 1 to 3 $R^{4D1}$ groups, $C_{1-3}$ alkoxy optionally substituted with 1 to 3 $R^{4D2}$ groups, or —C(O)N($R^{4D3}$)$_2$, wherein each $R^{4D1}$ group is independently —NH$_2$ or —C(O)O$R^{4D3}$, each $R^{4D2}$ is independently $C_{1-3}$ alkoxy, and each $R^{4D3}$ is independently $C_{1-3}$ alkyl;

(D)

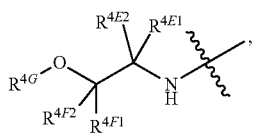

wherein $R^{4E1}$ and $R^{4E2}$ are each independently H or $C_{1-6}$ alkyl, $R^{4F1}$ and $R^{4F2}$ are each independently H or $C_{1-6}$ alkyl, or $R^{4F1}$ and $R^{4F2}$ together are oxo, $R^{4G}$ is $C_{1-12}$ alkyl optionally substituted with 1 to 3 $R^{4G1}$, $C_{3-7}$ cycloalkyl optionally substituted with 1 to 3 $R^{4G2}$, 3 to 8 membered heterocyclyl having 1 to 3 heteroatoms selected from N, O and S, optionally substituted with 1 to 3 $R^{4G3}$, or —C(O)$R^{4G4}$, each $R^{4G1}$ is independently —OH, $C_{1-6}$ alkyl, $C_{1-3}$ alkoxy, —(CH$_2$OCH$_2$)$_{1-5}$—CH$_3$, —N($R^{4G8}$)$_2$, —OP(O)(OH)$_2$, $C_{3-7}$ cycloalkyl optionally substituted with 1 to 3 $R^{4G9}$, 3 to 6 membered heterocyclyl having 1 to 3 heteroatoms independently selected from N, O and S, optionally substituted with 1 to 3 $R^{4G10}$, or phenyl, each $R^{4G2}$ is independently $C_{1-6}$ alkyl, $C_{1-3}$ haloalkyl, —OH or —NH$_2$, each $R^{4G3}$ is independently halogen or $C_{1-3}$ alkyl, each $R^{4G4}$ is independently $C_{1-12}$ alkyl, each $R^{4G8}$ is independently $C_{1-6}$ alkyl, each $R^{4G9}$ is independently $C_{1-3}$ haloalkyl, —OH or —NH$_2$, and each $R^{4G10}$ is independently $C_{1-3}$ haloalkyl; or (E) —(OP(O)(OH))$_{1-2}$—OH; and $R^{5A}$ and $R^{5B}$ are each $C_{1-6}$ alkyl substituted with —OP(O)(OH)$_2$.

In another embodiment, the present disclosure provides a pharmaceutical formulation comprising a pharmaceutically effective amount of a compound of the present disclosure, or a pharmaceutically acceptable salt thereof, and a pharmaceutically acceptable carrier or excipient.

In another embodiment, the present disclosure provides a method of treating a Pneumoviridae virus infection in a human in need thereof, the method comprising administering to the human a therapeutically effective amount of a compound of the present disclosure, or a pharmaceutically acceptable salt thereof.

In another embodiment, the present disclosure provides a method of treating a Picornaviridae virus infection in a human in need thereof, the method comprising administering to the human a therapeutically effective amount of a compound of the present disclosure, or a pharmaceutically acceptable salt thereof.

In another embodiment, the present disclosure provides a method of treating a Flaviviridae virus infection in a human in need thereof, the method comprising administering to the human a therapeutically effective amount of a compound of the present disclosure, or a pharmaceutically acceptable salt thereof.

In another embodiment, the present disclosure provides a method of treating a Filoviridae virus infection in a human in need thereof, the method comprising administering to the human a therapeutically effective amount of a compound of the present disclosure, or a pharmaceutically acceptable salt thereof.

In another embodiment, the present disclosure provides a method for manufacturing a medicament for treating a Pneumoviridae virus infection in a human in need thereof, characterized in that a compound of the present disclosure, or a pharmaceutically acceptable salt thereof, is used.

In another embodiment, the present disclosure provides a method for manufacturing a medicament for treating a Picornaviridae virus infection in a human in need thereof, characterized in that a compound of the present disclosure, or a pharmaceutically acceptable salt thereof, is used.

In another embodiment, the present disclosure provides a method for manufacturing a medicament for treating a Flaviviridae virus infection in a human in need thereof, characterized in that a compound of the present disclosure, or a pharmaceutically acceptable salt thereof, is used reof.

In another embodiment, the present disclosure provides a method for manufacturing a medicament for treating a Filoviridae virus infection in a human in need thereof, characterized in that a compound of the present disclosure, or a pharmaceutically acceptable salt thereof, is used.

In another embodiment, the present disclosure provides use of a compound of the present disclosure, or a pharmaceutically acceptable salt thereof, for the manufacture of a medicament for the treatment in a human of a Pneumoviridae virus infection.

In another embodiment, the present disclosure provides use of a compound of the present disclosure, or a pharmaceutically acceptable salt thereof, for the manufacture of a medicament for the treatment in a human of a Picornaviridae virus infection.

In another embodiment, the present disclosure provides use of a compound of the present disclosure, or a pharmaceutically acceptable salt thereof, for the manufacture of a medicament for the treatment in a human of a Flaviviridae virus infection.

In another embodiment, the present disclosure provides use of a compound of the present disclosure, or a pharmaceutically acceptable salt thereof, for the manufacture of a medicament for the treatment in a human of a Filoviridae virus infection.

In another embodiment, the present disclosure provides the compound of the present disclosure, or a pharmaceutically acceptable salt thereof, for use in the treatment of a Pneumoviridae virus infection in a human in need thereof.

In another embodiment, the present disclosure provides the compound of the present disclosure, or a pharmaceutically acceptable salt thereof, for use in the treatment of a Picornaviridae virus infection in a human in need thereof.

In another embodiment, the present disclosure provides the compound of the present disclosure, or a pharmaceutically acceptable salt thereof, for use in the treatment of a Flaviviridae virus infection in a human in need thereof.

In another embodiment, the present disclosure provides the compound of the present disclosure, or a pharmaceutically acceptable salt thereof, for use in the treatment of a Filoviridae virus infection in a human in need thereof.

In another embodiment, the present disclosure provides a method for the treatment or prophylaxis of an exacerbation of a respiratory condition by a viral infection in a human in need thereof, the method comprising administering to the human a therapeutically effective amount of a compound of the present disclosure, or a pharmaceutically acceptable salt thereof, wherein the respiratory condition is chronic obstructive pulmonary disease.

In another embodiment, the present disclosure provides a method for manufacturing a medicament for the treatment or prophylaxis of an exacerbation of a respiratory condition by a viral infection in a human in need thereof, characterized in that a compound of the present disclosure, or a pharmaceutically acceptable salt thereof, is used, wherein the respiratory condition is chronic obstructive pulmonary disease.

In another embodiment, the present disclosure provides use of a compound of the present disclosure, or a pharmaceutically acceptable salt thereof, for the manufacture of a medicament for the treatment or prophylaxis in a human of an exacerbation of a respiratory condition by a viral infection, wherein the respiratory condition is chronic obstructive pulmonary disease.

In another embodiment, the present disclosure provides the compound of the present disclosure, or a pharmaceutically acceptable salt thereof, for use in the treatment or prophylaxis of an exacerbation of a respiratory condition by a viral infection in a human in need thereof, wherein the respiratory condition is chronic obstructive pulmonary disease.

DETAILED DESCRIPTION OF THE INVENTION

I. General

The present disclosure provides 2',3'-diester-4'-cyano nucleoside compounds for the treatment of viral infections, such as Ebola, Zika, West Nile, Yellow Fever, Dengue, HCV, RSV, and others.

II. Definitions

"Alkyl" is a linear or branched saturated monovalent hydrocarbon. For example, an alkyl group can have 1 to 18 carbon atoms (i.e., $C_{1-18}$ alkyl) or 1 to 8 carbon atoms (i.e., $C_{1-8}$ alkyl) or 1 to 6 carbon atoms (i.e., $C_{1-6}$ alkyl) or 1 to 4 carbon atoms (i.e., $C_{1-4}$ alkyl). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), and 3,3-dimethyl-2-butyl (—CH(CH$_3$)C(CH$_3$)$_3$). Other alkyl groups include heptyl, octyl, nonyl, decyl, undecyl, dodecyl, pentadcyl, hexadecyl, heptadecyl and octadecyl.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Alkoxy-alkoxy" refers an alkoxy group linked to a second alkoxy group which is linked to the remainder of the compound. Alkoxy is as defined above, and can include, but is not limited to, methoxy-methoxy (CH$_3$OCH$_2$O—), methoxy-ethoxy (CH$_3$OCH$_2$CH$_2$O—) and others.

"Hydroxy" refers to —OH.

"Halo" or "halogen" as used herein refers to fluoro (—F), chloro (—Cl), bromo (—Br) and iodo (—I).

"Haloalkyl" as used herein refers to an alkyl as defined herein, wherein one or more hydrogen atoms of the alkyl are independently replaced by a halo substituent, which may be the same or different. For example, $C_{1-4}$ haloalkyl is a $C_{1-4}$ alkyl wherein one or more of the hydrogen atoms of the $C_{1-4}$ alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

"Cycloalkyl" refers to a single saturated or partially unsaturated all carbon ring having 3 to 20 annular carbon atoms (i.e., $C_{3-20}$ cycloalkyl), for example from 3 to 12 annular atoms, for example from 3 to 10 annular atoms, or 3 to 8 annular atoms, or 3 to 6 annular atoms, or 3 to 5 annular atoms, or 3 to 4 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocycles such as a bicyclic carbocycles (e.g., bicyclic carbocycles having about 6 to 12 annular carbon atoms such as bicyclo[3.1.0]hexane and bicyclo[2.1.1]hexane), and polycyclic carbocycles (e.g., tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Heterocyclyl" or "heterocycle" or "heterocycloalkyl" as used herein refers to a single saturated or partially unsaturated non-aromatic ring or a non-aromatic multiple ring system that has at least one heteroatom in the ring (i.e., at least one annular heteroatom selected from oxygen, nitrogen, and sulfur). Unless otherwise specified, a heterocyclyl group has from 3 to about 20 annular atoms, for example from 3 to 12 annular atoms, for example from 3 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring (e.g., bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3.3]heptan-6-yl, 6-oxa-1-azaspiro[3.3]heptan-1-yl, 2-thia-6-azaspiro[3.3]heptan-6-yl, 2,6-diazaspiro[3.3]heptan-2-yl, 2-azabicyclo[3.1.0]hexan-2-yl, 3-azabicyclo[3.1.0]hexanyl, 2-azabicyclo[2.1.1]hexanyl, 2-azabicyclo[2.2.1]heptan-2-yl, 4-azaspiro[2.4]heptanyl, 5-azaspiro[2.4]heptanyl, and the like.

"Aryl" as used herein refers to a single all carbon aromatic ring or a multiple condensed all carbon ring system wherein at least one of the rings is aromatic. For example, in some embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like.

"Heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4 (3H)-one, and triazolyl.

A "compound of the present disclosure" includes compounds disclosed herein, for example a compound of the present disclosure includes compounds of Formula (II), (IIa), (IIb), (IIc), (IId), (IIe), (IIf), (IIg), (IIh), (IIi), (IIj), (IIk), (IIm) and (IIn), including the compounds of the Examples.

"Pharmaceutically effective amount" refers to an amount of a compound of the present disclosure in a formulation or combination thereof, that provides the desired therapeutic or pharmaceutical result.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: (a) inhibiting the disease or condition (e.g., decreasing one or more symptoms resulting from the disease or condition, and/or diminishing the extent of the disease or condition); (b) slowing or arresting the development of one or more symptoms associated with the disease or condition (e.g., stabilizing the disease or condition, delaying the worsening or progression of the disease or condition); and (c) relieving the disease or condition, e.g., causing the regression of clinical symptoms, ameliorating the disease state, delaying the progression of the disease, increasing the quality of life, and/or prolonging survival.

"Prophylaxis" refers to preventing or retarding the progression of clinical illness in patients suffering from a viral infection.

"Respiratory condition" refers to a disease or condition such as a respiratory infection caused by a viral infection, allergic rhinitis, nasal congestion, rhinorrhea, perennial rhinitis, nasal inflammation, asthma of all types, chronic obstructive pulmonary disease (COPD), chronic or acute bronchoconstriction, chronic bronchitis, small airways obstruction, emphysema, chronic b eosinophilic pneumonia, adult respiratory distress syndrome, exacerbation of airways hyperreactivity consequent to other drug therapy, pulmonary vascular disease (including pulmonary arterial hypertension), acute lung injury, bronchiectasis, sinusitis, allergic conjunctivitis, idiopathic pulmonary fibrosis or atopic dermatitis, particularly asthma or allergic rhinitis or atopic dermatitis or allergic conjunctivitis.

"Exacerbation of a respiratory condition" refers to exacerbations induced by viral infections. Representative viral infections include, but are not limited to, respiratory syncytial virus (RSV), rhinovirus and metapneumovirus.

"Therapeutically effective amount" or "effective amount" as used herein refers to an amount that is effective to elicit the desired biological or medical response, including the amount of a compound that, when administered to a subject for treating a disease, is sufficient to effect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds described herein may be prepared and/or formulated as pharmaceutically acceptable salts or when appropriate as a free base. Pharmaceutically acceptable salts are non-toxic salts of a free base form of a compound that possess the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, $21^{st}$ Edition, Lippincott Williams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism," Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Substitution with positron emitting isotopes, such as $^{11}C$, $^{18}F$, $^{15}$ and $^{13}N$, can be useful in Positron Emission Topography (PET) studies for examining substrate receptor occupancy. Isotopically-labeled compounds of Formula (I), can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

"Racemates" refers to a mixture of enantiomers. The mixture can comprise equal or unequal amounts of each enantiomer.

"Stereoisomer" and "stereoisomers" refer to compounds that differ in the chirality of one or more stereocenters. Stereoisomers include enantiomers and diastereomers. The compounds may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

"Tautomer" refers to alternate forms of a compound that differ in the position of a proton, such as enol-keto and imine-enamine tautomers, or the tautomeric forms of heteroaryl groups containing a ring atom attached to both a ring —NH— and a ring =N— such as pyrazoles, imidazoles, benzimidazoles, triazoles, and tetrazoles.

Unless defined otherwise, all technical and scientific terms used herein have the same meaning as commonly understood by one of ordinary skill in the art. A dash at the front or end of a chemical group is a matter of convenience; chemical groups may be depicted with or without one or more dashes without losing their ordinary meaning. A wavy line drawn through a line in a structure indicates a point of attachment of a group. A dashed line indicates an optional bond. Unless chemically or structurally required, no directionality is indicated or implied by the order in which a chemical group is written or the point at which it is attached to the remainder of the molecule. For instance, the group "—SO$_2$CH$_2$—" is equivalent to "—CH$_2$SO$_2$—" and both may be connected in either direction. Similarly, an "arylalkyl" group, for example, may be attached to the remainder of the molecule at either an aryl or an alkyl portion of the group. A prefix such as "C$_{u-v}$" or (C$_u$-C$_v$) indicates that the following group has from u to v carbon atoms. For example, "C$_{1-6}$alkyl" and "C$_1$-C$_6$ alkyl" both indicate that the alkyl group has from 1 to 6 carbon atoms.

"Solvate" as used herein refers to the result of the interaction of a solvent and a compound. Solvates of salts of the compounds described herein are also provided. Hydrates of the compounds described herein are also provided.

"Prodrug" as used herein refers to a derivative of a drug that upon administration to the human body is converted to the parent drug according to some chemical or enzymatic pathway.

III. Compounds

The present disclosure provides compounds of Formula (II), (IIa), (IIb), (IIc), (IId), (IIe), (IIf), (IIg), (IIh), (IIi), (IIj), (IIk), (IIm) and (IIn).

In some embodiments, the present disclosure provides a compound of Formula (II):

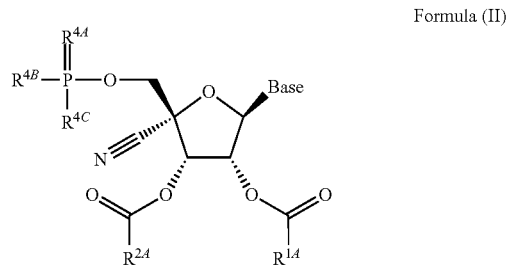

Formula (II)

or a pharmaceutically acceptable salt thereof, wherein:
Base is

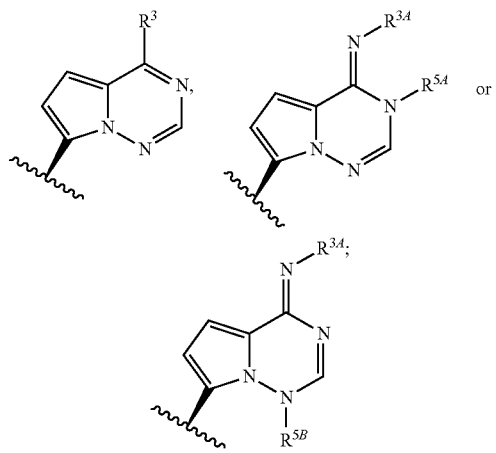

$R^{1A}$ and $R^{2A}$ are each independently:
(A) C$_{1-12}$ alkyl optionally substituted with 1 to 3 $R^{1B}$,
(B) 3 to 6 membered heterocyclyl having 1 to 3 heteroatoms independently selected from N, O and S, wherein the 3 to 6 membered heterocyclyl is optionally substituted with 1 to 3 $R^{1C}$, or (C) phenyl, wherein each $R^{1B}$ is independently halogen, —OH, —NH$_2$, C$_{1-6}$ alkoxy, methoxyethoxy, C$_{3-8}$ cycloalkyl, or 3 to 6 membered heterocyclyl having 1 to 3 heteroatoms independently selected from N, O and S, and each $R^{1C}$ is independently C$_{1-3}$ alkyl;

$R^3$ is —N(H)$R^{3A}$ or —N═C($R^{3B}$)($R^{3C}$); $R^{3A}$ is H, —CH$_2$OP(O)(OH)$_2$, or —C(O)$R^{3D}$, wherein $R^{3D}$ is C$_{1-6}$ alkyl optionally substituted with 1 methoxy, or 3 to 6 membered heterocyclyl having 1 to 3 heteroatoms independently selected from N, O and S, optionally substituted with C$_{1-3}$ alkyl; $R^{3B}$ is H or C$_{1-3}$ alkyl; $R^{3C}$ is —N($R^{3C1}$)($R^{3C2}$); $R^{3C1}$ and $R^{3C2}$ are each independently H or C$_{1-6}$ alkyl; or $R^{3C1}$ and $R^{3C2}$ together with the atom to which they are attached form a 3 to 6 membered heterocyclyl having 1 to 3 heteroatoms independently selected from N, O and S, optionally substituted with C$_{1-6}$ alkyl;

$R^{4A}$ is O or S;

$R^{4B}$ and $R^{4C}$ are each independently (A) —OH;

(B) —O$R^{4B1}$, wherein $R^{4B1}$ is C$_{1-6}$ alkyl optionally substituted with 1 to 3 $R^{4B2}$ groups, or C$_{6-12}$ aryl, wherein each $R^{4B2}$ group is independently C$_{1-6}$ alkoxy, —S—$R^{4B3}$ or —S(O)$_2$—$R^{4B3}$, and each $R^{4B3}$ group is independently C$_{1-6}$ alkyl;

(C)

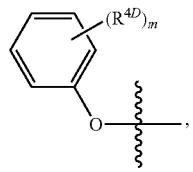

wherein m is 0, 1, 2, 3, 4, or 5; and each $R^{4D}$ is independently C$_{1-3}$ alkyl optionally substituted with 1 to 3 $R^{4D1}$ groups, C$_{1-3}$ alkoxy optionally substituted with 1 to 3 $R^{4D2}$ groups, or —C(O)N($R^{4D3}$)$_2$, wherein each $R^{4D1}$ group is independently —NH$_2$ or —C(O)O$R^{4D3}$, each $R^{4D2}$ is independently C$_{1-3}$ alkoxy, and each $R^{4D3}$ is independently C$_{1-3}$ alkyl;

(D)

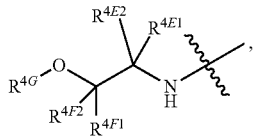

wherein $R^{4E1}$ and $R^{4E2}$ are each independently H or C$_{1-6}$ alkyl, $R^{4F1}$ and $R^{4F2}$ are each independently H or C$_{1-6}$ alkyl, or $R^{4F1}$ and $R^{4F2}$ together are oxo, $R^{4G}$ is C$_{1-12}$ alkyl optionally substituted with 1 to 3 $R^{4G1}$, C$_{3-7}$ cycloalkyl optionally substituted with 1 to 3 $R^{4G2}$, 3 to 8 membered heterocyclyl having 1 to 3 heteroatoms selected from N, O and S, optionally substituted with 1 to 3 $R^{4G3}$, or —C(O)$R^{4G4}$, each $R^{4G1}$ is independently —OH, C$_{1-6}$ alkyl, C$_{1-3}$ alkoxy, —(CH$_2$OCH$_2$)$_{1-5}$—CH$_3$, —N($R^{4G8}$)$_2$, —OP(O)(OH)$_2$, C$_{3-7}$ cycloalkyl optionally substituted with 1 to 3 $R^{4G9}$, 3 to 6 membered heterocyclyl having 1 to 3 heteroatoms independently selected from N, O and S, optionally substituted with 1 to 3 $R^{4G10}$, or phenyl, each $R^{4G2}$ is independently C$_{1-6}$ alkyl, C$_{1-3}$ haloalkyl, —OH or —NH$_2$, each $R^{4G3}$ is independently halogen or C$_{1-3}$ alkyl, each $R^{4G4}$ is independently C$_{1-12}$ alkyl, each $R^{4G8}$ is independently C$_{1}$-6 alkyl, each $R^{4G9}$ is independently C$_{1-3}$ haloalkyl, —OH or —NH$_2$, and each $R^{4G10}$ is independently C$_{1-3}$ haloalkyl; or (E) —(OP(O)(OH))$_{1-2}$—OH; and $R^{5A}$ and $R^{5B}$ are each C$_{1-6}$ alkyl substituted with —OP(O)(OH)$_2$.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein Base is

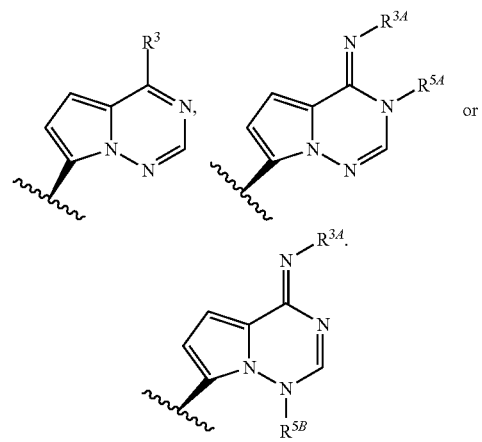

In some embodiments, the compound can be represented by Formula (II), (IIa), (IIb), (IIc), (IId), (IIe), (IIf), (IIg), (Ih), (IIi), (IIj), (IIk), (IIm) or (IIn), or a pharmaceutically acceptable salt thereof, wherein Base is

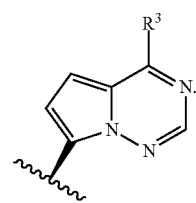

In some embodiments, the compound can be represented by Formula (II), (IIa), (IIb), (IIc), (IId), (IIe), (IIf), (IIg), (Ih), (IIi), (IIj), (IIk), (IIm) or (IIn), or a pharmaceutically acceptable salt thereof, wherein Base is

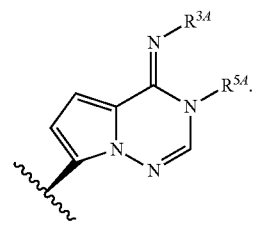

In some embodiments, the compound can be represented by Formula (II), (IIa), (IIb), (IIc), (IId), (IIe), (IIf), (IIg), (Ih), (IIi), (IIj), (IIk), (IIm) or (IIn), or a pharmaceutically acceptable salt thereof, wherein Base is

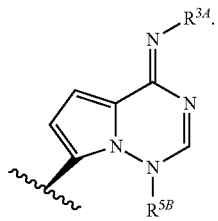

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently: (A) $C_{1-12}$ alkyl optionally substituted with 1 to 3 $R^{1B}$, (B) 3 to 6 membered heterocyclyl having 1 to 3 heteroatoms independently selected from N, O and S, wherein the 3 to 6 membered heterocyclyl is optionally substituted with 1 to 3 $R^{1C}$, or (C) phenyl, wherein each $R^{1B}$ is independently —OH, —NH$_2$, $C_{1-6}$ alkoxy, methoxyethoxy, $C_{3-8}$ cycloalkyl, or 3 to 6 membered heterocyclyl having 1 to 3 heteroatoms independently selected from N, O and S, and each $R^{1C}$ is independently $C_{1-3}$ alkyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are $C_{1-12}$ alkyl optionally substituted with 1 to 3 $R^{1B}$. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each selected from the group consisting of methyl, ethyl, n-propyl, isopropyl, n-butyl, isobutyl, tert-butyl, and isopentyl, each optionally substituted with 1 to 3 $R^{1B}$. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein each $R^{1B}$ can independently be methoxy, methoxyethoxy, morpholinyl, —OH, or —NH$_2$. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl optionally substituted with methoxy, methoxyethoxy, or morpholinyl, ethyl optionally substituted with methoxy, n-propyl, isopropyl, n-butyl, isobutyl optionally substituted with —OH or —NH$_2$, tert-butyl, or isopentyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl, ethyl, n-propyl, isopropyl, n-butyl, isobutyl, tert-butyl, or isopentyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl, ethyl, or isopropyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each methyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each ethyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each isopropyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each 3 to 6 membered heterocyclyl having 1 to 3 heteroatoms independently selected from N, O and S, wherein the 3 to 6 membered heterocyclyl is optionally substituted with 1 to 3 $R^{1C}$, wherein each $R^{1C}$ is independently $C_{1-3}$ alkyl, hydroxy, or halogen. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each 4 to 6 membered heterocyclyl having 1 heteroatom selected from N and O, wherein the 4 to 6 membered heterocyclyl is optionally substituted with 1 $R^{1C}$, wherein each $R^{1C}$ is independently $C_{1-3}$ alkyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each oxetanyl, tetrahydropyranyl or piperidinyl, each optionally substituted with 1 $R^{1C}$, wherein each $R^{1C}$ is independently $C_{1-3}$ alkyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein each $R^{1C}$ is methyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently oxetanyl, tetrahydropyranyl, or piperidinyl optionally substituted with methyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each phenyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^3$ is —N(H)$R^{3A}$ or —N=C($R^{3B}$)($R^{3C}$), $R^{3A}$ is H, —CH$_2$OP(O)(OH)$_2$, or —C(O)$R^{3D}$, wherein $R^{3D}$ is $C_{1-6}$ alkyl optionally substituted with 1 methoxy, or 3 to 6 membered heterocyclyl having 1 to 3 heteroatoms independently selected from N, O and S, optionally substituted with $C_{1-3}$ alkyl, $R^{3B}$ is H or $C_{1-3}$ alkyl, $R^{3C}$ is —N($R^{3C1}$)($R^{3C2}$), $R^{3C1}$ and $R^{3C2}$ are each independently H or $C_{1-6}$ alkyl, or $R^{3C1}$ and $R^{3C2}$ together with the atom to which they are attached form a 3 to 6 membered heterocyclyl having 1 to 3 heteroatoms independently selected from N, O and S, optionally substituted with $C_{1-6}$ alkyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^3$ is —N(H)$R^{3A}$, and $R^{3A}$ is H, —CH$_2$OP(O)(OH)$_2$, or —C(O)$R^{3D}$, wherein $R^{3D}$ is $C_{1-6}$ alkyl optionally substituted with 1 methoxy, or 3 to 6 membered heterocyclyl having 1 to 3 heteroatoms independently selected from N, O and S, optionally substituted with $C_{1-3}$ alkyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^3$ is —N(H)$R^{3A}$ and $R^{3A}$ is H, —CH$_2$OP(O)(OH)$_2$, or —C(O)$R^{3D}$, wherein $R^{3D}$ is C$_{1-3}$ alkyl optionally substituted with 1 methoxy, or piperidine optionally substituted with methyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{3A}$ is H. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^3$ is —NH$_2$. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^3$ is —N=C($R^{3B}$)($R^{3C}$), wherein $R^{3B}$ is H or methyl, $R^{3C}$ is —N($R^{3C1}$)($R^{3C2}$), $R^{3C1}$ and $R^{3C2}$ are each independently H or methyl, or $R^{3C1}$ and $R^{3C2}$ together with the atom to which they are attached form piperazine, optionally substituted with methyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4A}$ is O or S. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4A}$ is O. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4A}$ is S.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein one of $R^{4B}$ and $R^{4C}$ is —OH.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein one of $R^{4B}$ and $R^{4C}$ is —O$R^{4B1}$, wherein $R^{4B1}$ is C$_{1-6}$ alkyl optionally substituted with 1 to 3 $R^{4B2}$ groups, or C$_{6-12}$ aryl, wherein each $R^{4B2}$ group is independently C$_{1-6}$ alkoxy, —S—$R^{4B3}$, or —S(O)$_2$—$R^{4B3}$, and each $R^{4B3}$ group is independently C$_{1-6}$ alkyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4B1}$ is C$_{1-6}$ alkyl optionally substituted with 1 to 3 $R^{4B2}$ groups. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein each $R^{4B2}$ group is independently C$_{1-6}$ alkoxy, —S—$R^{4B3}$, or —S(O)$_2$—$R^{4B3}$, and each $R^{4B3}$ group is independently C$_{1-6}$ alkyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4B1}$ is C$_{1-6}$ alkyl optionally substituted with 1 to 3 $R^{4B2}$ groups, wherein each $R^{4B2}$ group is independently C$_{1-6}$ alkoxy, —S—$R^{4B3}$, or —S(O)$_2$—$R^{4B3}$, and each $R^{4B3}$ group is methyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein one of $R^{4B}$ and $R^{4C}$ is —O—C$_{1-6}$ alkyl optionally substituted with methoxy, methylthio or methylsulfonyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein one of $R^{4B}$ and $R^{4C}$ is

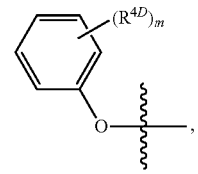

wherein m is 0, 1, 2, 3, 4, or 5; and each $R^{4D}$ is independently C$_1$-3 alkyl optionally substituted with 1 to 3 $R^{4D1}$ groups, C$_{1-3}$ alkoxy optionally substituted with 1 to 3 $R^{4D2}$ groups, or —C(O)N($R^{4D3}$)$_2$, wherein each $R^{4D1}$ group is independently —NH$_2$ or —C(O)OR$^{4D3}$, each $R^{4D2}$ is independently C$_{1-3}$ alkoxy, and each $R^{4D3}$ is independently C$_1$-3 alkyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein m is 0, 1 or 2; and each $R^{4D}$ is independently C$_{1-3}$ alkyl optionally substituted with 1 $R^{4D1}$ group, C$_{1-3}$ alkoxy optionally substituted with methoxy, or —C(O)N($R^{4D3}$)$_2$, wherein each $R^{4D1}$ group is independently —NH$_2$ or —C(O)OR$^{4D3}$, and each $R^{4D3}$ is independently C$_{1-3}$ alkyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein m is 0 or 1. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein m is 0.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein one of $R^{4B}$ and $R^{4C}$ is:

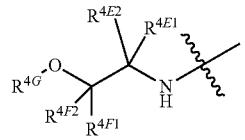

wherein $R^{4E1}$ and $R^{4E2}$ are each independently H or C$_{1-6}$ alkyl, $R^{4F1}$ and $R^{4F2}$ are each independently H or C$_{1-6}$ alkyl, or $R^{4F1}$ and $R^{4F2}$ together are oxo, $R^{4G}$ is C$_{1-12}$ alkyl optionally substituted with 1 to 3 $R^{4G1}$, C$_{3-7}$ cycloalkyl optionally substituted with 1 to 3 $R^{4G2}$, 3 to 8 membered heterocyclyl having 1 to 3 heteroatoms selected from N, O and S, optionally substituted with 1 to 3 $R^{4G3}$, or —C(O)$R^{4G4}$, each $R^{4G1}$ is independently —OH, C$_{1-6}$ alkyl, C$_{1-3}$ alkoxy, —(CH$_2$OCH$_2$)$_{1-5}$—CH$_3$, —N($R^{4G8}$)$_2$, —OP(O)(OH)$_2$, C$_{3-7}$ cycloalkyl optionally substituted with 1 to 3 $R^{4G9}$, 3 to 6 membered heterocyclyl having 1 to 3 heteroatoms independently selected from N, O and S, optionally substituted with 1 to 3 $R^{4G10}$, or phenyl, each $R^{4G2}$ is independently $C_{1-6}$ alkyl, $C_{1-3}$ haloalkyl, —OH or —NH$_2$, each $R^{4G3}$ is independently halogen or $C_{1-3}$ alkyl, each $R^{4G4}$ is independently $C_{1-12}$ alkyl, each $R^{4G8}$ is independently $C_{1-6}$ alkyl, each $R^{4G9}$ is independently $C_{1-3}$ haloalkyl, or —NH$_2$; and each $R^{4G10}$ is independently $C_{1-3}$ haloalkyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein one of $R^{4B}$ and $R^{4C}$ is:

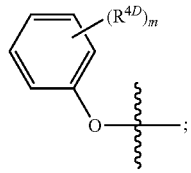

and
the other of $R^{4B}$ and $R^{4C}$ is:

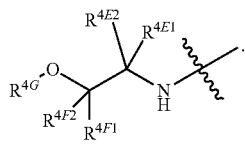

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4E1}$ and $R^{4E2}$ are each independently H or $C_{1-6}$ alkyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4E1}$ and $R^{4E2}$ are each independently H or methyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4F1}$ and $R^{4F2}$ are each independently H or $C_{1-6}$ alkyl, or $R^{4F1}$ and $R^{4F2}$ together are oxo. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4F1}$ and $R^{4F2}$ are each independently H or methyl, or $R^{4F1}$ and $R^{4F2}$ together are oxo. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4F1}$ and $R^{4F2}$ together are oxo.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein one of $R^{4B}$ and $R^{4C}$ is:

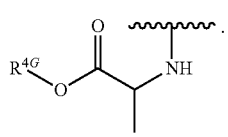

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein one of $R^{4B}$ and $R^{4C}$ is:

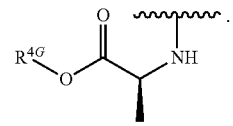

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is $C_{1-12}$ alkyl optionally substituted with 1 to 3 $R^{4G1}$. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is methyl, ethyl, n-propyl, isopropyl, n-butyl, isobutyl, t-butyl or 2-ethyl-butyl, each optionally substituted with 1 to 3 $R^{4G1}$.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein each $R^{4G1}$ is independently —OH, $C_{1-6}$ alkyl, $C_{1-3}$ alkoxy, —(CH$_2$OCH$_2$)$_{1-5}$—CH$_3$, —N(R$^{4G8}$)$_2$, —OP(O)(OH)$_2$, $C_{3-7}$ cycloalkyl optionally substituted with 1 to 3 $R^{4G9}$, 3 to 6 membered heterocyclyl having 1 to 3 heteroatoms independently selected from N, O and S, optionally substituted with 1 to 3 $R^{4G10}$, or phenyl, wherein each $R^{4G8}$ is independently $C_{1-6}$ alkyl, each $R^{4G9}$ is independently $C_{1-3}$ haloalkyl, or —NH$_2$, and each $R^{4G10}$ is independently $C_{1-3}$ alkyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein each $R^{4G1}$ is independently —OH, $C_{1-6}$ alkyl, $C_{1-3}$ alkoxy, —(CH$_2$OCH$_2$)$_{1-5}$—CH$_3$, —N(R$^{4G8}$)$_2$, —OP(O)(OH)$_2$, $C_{4-6}$ cycloalkyl optionally substituted with 1 to 3 $R^{4G9}$ 4 to 6 membered heterocyclyl having 1 to 2 heteroatoms independently selected from N and O, optionally substituted with 1 to 3 $R^{4G10}$, or phenyl, wherein each $R^{4G8}$ is independently $C_{1-6}$ alkyl, each $R^{4G9}$ is independently $C_{1-3}$ haloalkyl or —NH$_2$, and each $R^{4G10}$ is independently $C_{1-3}$ haloalkyl. In some embodiments, the compound can be represented by Formula (II), (IIa), (IIb), (IIc), (IId), (IIe), (IIf), (IIg), (Ih), (IIi), (IIj), (IIk), (IIm) or (IIn), or a pharmaceutically acceptable salt thereof, wherein each $R^{4G1}$ is independently —OH, methyl, OMe, —(CH$_2$OCH$_2$)$_2$—CH$_3$, —N(iPr)$_2$, —OP(O)(OH)$_2$, cyclopropyl, cyclobutyl, cyclohexyl optionally substituted with —NH$_2$ or CF$_3$, oxetanyl, piperidinyl optionally substituted with CF$_3$ or CH$_2$CF$_3$, tetrahydropyranyl, morpholinyl, or phenyl.

In some embodiments, the compound can be represented by Formula (II), (IIa), (IIb), (IIc), (IId), (IIe), (IIf), (IIg), (Ih), (IIi), (IIj), (IIk), (IIm) or (IIn), or a pharmaceutically acceptable salt thereof, wherein $R^{4G}$ is methyl optionally substituted with $R^{4G1}$, ethyl optionally substituted with morpholinyl or —N(R$^{4G8}$)$_2$, n-propyl optionally substituted with methoxy or morpholinyl, isopropyl, n-butyl optionally substituted with $C_{1-3}$ alkyl, isobutyl optionally substituted with —OH or —OP(O)(OH)$_2$, wherein $R^{4G1}$ is cyclopropyl, cyclobutyl, cyclohexyl optionally substituted with $R^{4G9}$, oxetanyl, piperidinyl optionally substituted with $R^{4G10}$ tetrahydropyranyl, or phenyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G8}$ is $C_{1-3}$ alkyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G8}$ is isopropyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G9}$ is $C_{1-3}$ haloalkyl or —NH$_2$. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G9}$ is —CF$_3$ or —NH$_2$. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G10}$ is $C_{1-3}$ haloalkyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G10}$ is —CF$_3$ or 2,2,2-trifluoroethyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is methyl optionally substituted with $R^{4G1}$, ethyl optionally substituted with morpholinyl or —N(C$_{1-3}$ alkyl)$_2$, n-propyl optionally substituted with methoxy or morpholinyl, isopropyl, n-butyl optionally substituted with $C_{1-3}$ alkyl, isobutyl optionally substituted with —OH or —OP(O)(OH)$_2$, wherein $R^{4G1}$ is cyclopropyl, cyclobutyl, cyclohexyl optionally substituted with —NH$_2$ or $C_{1-3}$ haloalkyl, oxetanyl, piperidinyl optionally substituted with $C_{1-3}$ alkyl or $C_{1-3}$ haloalkyl, tetrahydropyranyl, or phenyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is $C_{3-7}$ cycloalkyl optionally substituted with 1 to 3 $R^{4G2}$. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is cyclopropyl, cyclobutyl, cyclopentyl, or cyclohexyl, each optionally substituted with 1 to 3 $R^{4G2}$. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein each $R^{4G2}$ is independently $C_{1-6}$ alkyl, $C_{1-3}$ haloalkyl or —NH$_2$. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein each $R^{4G2}$ is tert-butyl, —CF$_3$ or —NH$_2$.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is 3 to 8 membered heterocyclyl having 1 to 3 heteroatoms selected from N, O and S, optionally substituted with 1 to 3 $R^{4G3}$. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is 3 to 6 membered heterocyclyl having 1 to 3 heteroatoms selected from N, O and S, optionally substituted with 1 to 3 $R^{4G3}$. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is a 4-6 membered heterocyclyl having 1 to 2 heteroatoms selected from N and O, optionally substituted with 1 to 3 $R^{4G3}$. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is oxetanyl, pyrrolidinyl, piperidinyl, tetrahydrofuranyl, or tetrahydropyranyl, each optionally substituted with 1 to 3 $R^{4G3}$. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein each $R^{4G3}$ is independently halogen or $C_{1-3}$ alkyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein each $R^{4G3}$ is independently F, methyl or ethyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is —C(O)$R^{4G4}$. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein each $R^{4G4}$ is independently $C_{1-12}$ alkyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is —C(O)$C_{1-6}$ alkyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is —C(O)-tert-butyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein one of $R^{4B}$ and $R^{4C}$ is —(OP(O)(OH))$_{1-2}$—OH. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein one of $R^{4B}$ and $R^{4C}$ is —(OP(O)(OH))$_{1-2}$—OH and one of $R^{4B}$ and $R^{4C}$ is —OH.

In some embodiments, the compound can be represented by Formula (II), (IIa) or (IIb), or a pharmaceutically acceptable salt thereof, wherein $R^{5A}$ and $R^{5B}$ are each —CH$_2$OP(O)(OH)$_2$. In some embodiments, the compound can be represented by Formula (II) or (IIa), wherein $R^{5A}$ is —CH$_2$OP(O)(OH)$_2$. In some embodiments, the compound can be represented by Formula (II) or (IIb), or a pharmaceutically acceptable salt thereof, wherein $R^{5B}$ is —CH$_2$OP(O)(OH)$_2$.

In some embodiments, the compound of the present disclosure, or a pharmaceutically acceptable salt thereof, is represented by Formula (IIa):

Formula (IIa)

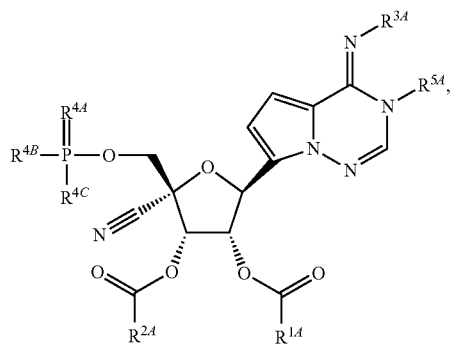

wherein $R^{5A}$ is —CH$_2$OP(O)(OH)$_2$.

In some embodiments, the compound of the present disclosure, or a pharmaceutically acceptable salt thereof, is represented by Formula (IIb):

Formula (IIb)

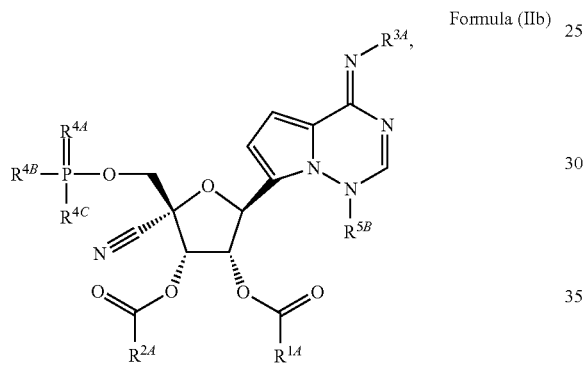

wherein $R^{5B}$ is —CH$_2$OP(O)(OH)$_2$.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl optionally substituted with methoxy, methoxyethoxy, or morpholinyl, ethyl optionally substituted with methoxy, n-propyl, isopropyl, n-butyl, isobutyl optionally substituted with —OH or —NH$_2$, tert-butyl, isopentyl, oxetanyl, tetrahydropyranyl, piperidinyl optionally substituted with methyl, or phenyl;

$R^3$ is —N(H)$R^{3A}$ or —N=C($R^{3B}$) ($R^{3C}$); $R^{3A}$ is H, —C(H)$_2$OP(O)(OH)$_2$, or —C(O)$R^{3D}$; $R^{3D}$ is methyl, ethyl optionally substituted with methoxy, isopropyl, or piperidinyl optionally substituted with methyl; $R^{3B}$ is H or methyl; $R^{3C}$ is —N($R^{3C1}$)($R^{3C2}$); $R^{3C1}$ and $R^{3C2}$ are independently H or methyl; or $R^{3C1}$ and $R^{3C2}$ together with the atom to which they are attached form a piperazinyl optionally substituted with methyl;

$R^{4A}$ is O or S; and $R^{4B}$ and $R^{4C}$ are each independently (A) —OH;

(B) —O—C$_{1-6}$ alkyl optionally substituted with methoxy, methylthio or methylsulfonyl;

(C)

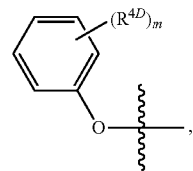

wherein m is 0, 1 or 2; and each $R^{4D}$ is independently C$_{1-3}$ alkyl optionally substituted with 1 $R^{4D1}$ group, C$_{1-3}$ alkoxy optionally substituted with methoxy, or —C(O)N($R^{4D3}$)$_2$, wherein each $R^{4D1}$ group is independently —NH$_2$ or —C(O)O$R^{4D3}$ and each $R^{4D3}$ is independently C$_{1-3}$ alkyl; or (D)

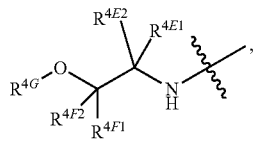

wherein $R^{4E1}$ and $R^{4E2}$ are each independently H or methyl, $R^{4F1}$ and $R^{4F2}$ are each independently H or methyl, or $R^{4F1}$ and $R^{4F2}$ together are oxo, $R^{4G}$ is methyl optionally substituted with $R^{4G1}$, ethyl optionally substituted with morpholinyl or —N(C$_{1-3}$ alkyl)$_2$, n-propyl optionally substituted with methoxy or morpholinyl, isopropyl, n-butyl optionally substituted with C$_{1-3}$ alkyl, isobutyl optionally substituted with —OH or —OP(O)(OH)$_2$, cyclopropyl, cyclobutyl, cyclopentyl, cyclohexyl optionally substituted with 1 to 3 groups each independently —NH$_2$, C$_{1-6}$ alkyl, or C$_{1-3}$ haloalkyl, oxetanyl, pyrrolidinyl optionally substituted with 1 to 3 methyl, piperidinyl optionally substituted with halogen or C$_{1-3}$ alkyl, tetrahydrofuranyl, tetrahydropyranyl, or —C(O)C$_{1-6}$ alkyl, and $R^{4G1}$ is cyclopropyl, cyclobutyl, cyclohexyl optionally substituted with —NH$_2$ or C$_{1-3}$ haloalkyl, oxetanyl, piperidinyl optionally substituted with C$_{1-3}$ haloalkyl, tetrahydropyranyl, or phenyl.

In some embodiments, the compound of the present disclosure, or a pharmaceutically acceptable salt thereof, can be represented by Formula (IIc):

Formula (IIc)

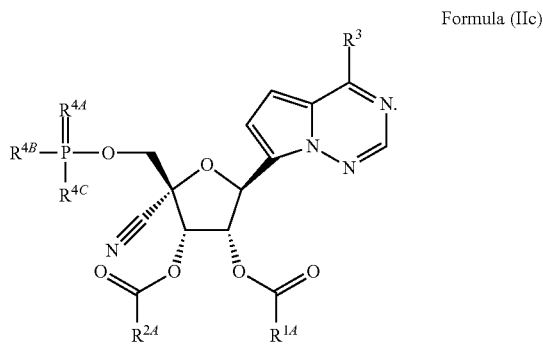

In some embodiments, the compound of the present disclosure, or a pharmaceutically acceptable salt thereof, can be represented by Formula (IId):

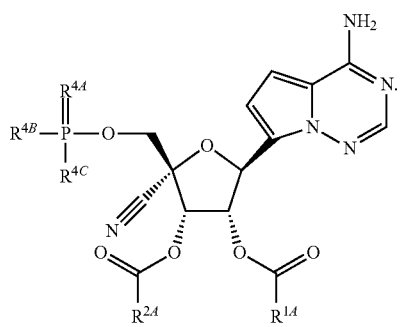

Formula (IId)

In some embodiments, the compound of the present disclosure, or a pharmaceutically acceptable salt thereof, can be represented by Formula (IId):

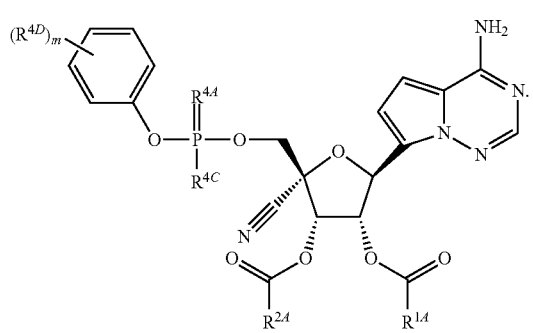

Formula (IIe)

In some embodiments, the compound of the present disclosure, or a pharmaceutically acceptable salt thereof, can be represented by Formula (IIf):

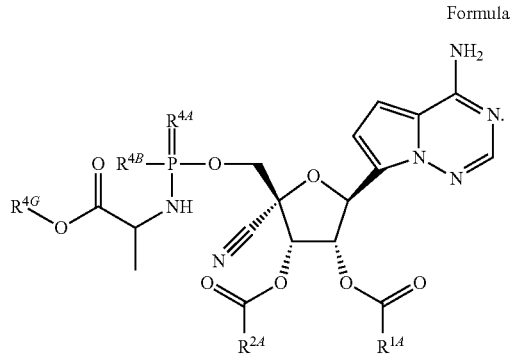

Formula (IIf)

In some embodiments, the compound of the present disclosure, or a pharmaceutically acceptable salt thereof, can be represented by Formula (IIg):

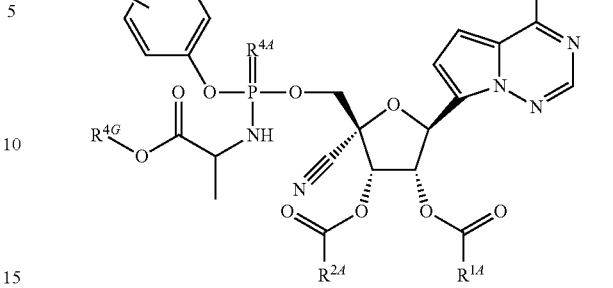

Formula (IIg)

wherein m is 0 or 1.

In some embodiments, the compound of the present disclosure, or a pharmaceutically acceptable salt thereof, can be represented by Formula (IIh):

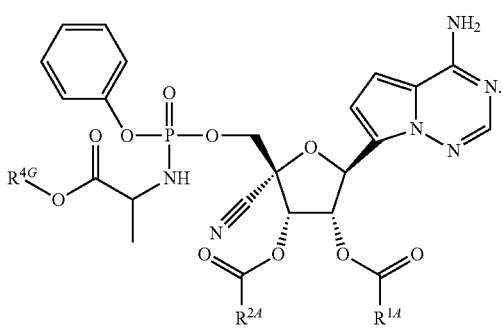

Formula (IIh)

In some embodiments, the compound of the present disclosure, or a pharmaceutically acceptable salt thereof, can be represented by Formula (IIi):

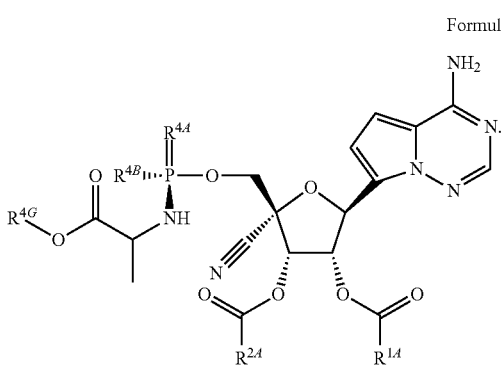

Formula (IIi)

In some embodiments, the compound of the present disclosure, or a pharmaceutically acceptable salt thereof, can be represented by Formula (IIj):

Formula (IIj)

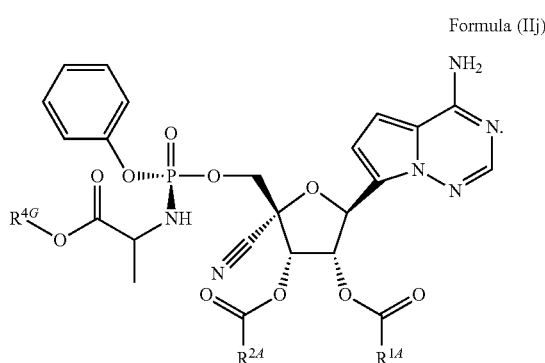

In some embodiments, the compound of the present disclosure, or a pharmaceutically acceptable salt thereof, can be represented by Formula (IIk):

Formula (IIk)

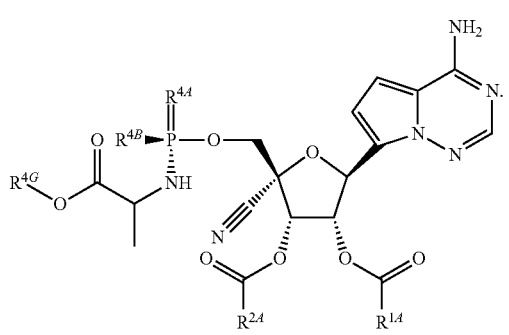

In some embodiments, the compound of the present disclosure, or a pharmaceutically acceptable salt thereof, can be represented by Formula (IIm):

Formula (IIm)

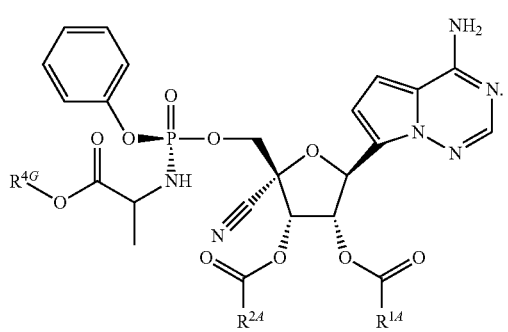

In some embodiments, the compound of the present disclosure, or a pharmaceutically acceptable salt thereof, can be represented by Formula (IIn):

Formula (IIn)

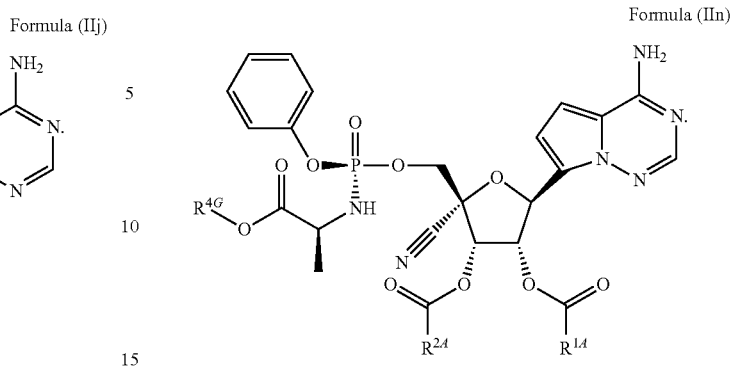

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl, ethyl, n-propyl, isopropyl, n-butyl, isobutyl, tert-butyl, or isopentyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl, ethyl, or isopropyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently ethyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently isopropyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is methyl, ethyl, n-propyl, isopropyl, n-butyl, t-butyl or 2-ethyl-butyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is methyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is ethyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is n-propyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is isopropyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is n-butyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is t-butyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{4G}$ is 2-ethyl-butyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl, ethyl, n-propyl, isopropyl, n-butyl, isobutyl, tert-butyl, or isopentyl, $R^{4G}$ is methyl optionally substituted with $R^{4G1}$, ethyl optionally substituted with morpholinyl or —N(C$_{1-3}$ alkyl)$_2$, n-propyl optionally substituted with methoxy or morpholinyl, isopropyl, n-butyl optionally substituted with C$_{1-3}$ alkyl, isobutyl optionally substituted with —OH or —OP(O)(OH)$_2$, cyclopropyl, cyclobutyl, cyclopentyl, cyclohexyl optionally substituted with 1 to 3 groups each independently —NH$_2$, C$_{1-6}$ alkyl, or C$_{1-3}$ haloalkyl, oxetanyl, pyrrolidinyl optionally substituted with 1 to 3 methyl, piperidinyl optionally substituted with halogen or C$_{1-3}$ alkyl, tetrahydrofuranyl, tetrahydropyranyl, or —C(O)C$_{1-6}$ alkyl, and $R^{4G1}$ is cyclopropyl, cyclobutyl, cyclohexyl optionally substituted with —NH$_2$ or C$_{1-3}$ haloalkyl, oxetanyl, piperidinyl optionally substituted with C$_{1-3}$ alkyl or C$_{1-3}$ haloalkyl, tetrahydropyranyl, or phenyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl, ethyl, or isopropyl, $R^{4G}$ is methyl optionally substituted with $R^{4G1}$, ethyl optionally substituted with morpholinyl or —N(C$_{1-3}$ alkyl)$_2$, n-propyl optionally substituted with methoxy or morpholinyl, isopropyl, n-butyl optionally substituted with C$_{1-3}$ alkyl, isobutyl optionally substituted with —OH or —OP(O)(OH)$_2$, cyclopropyl, cyclobutyl, cyclopentyl, cyclohexyl optionally substituted with 1 to 3 groups each independently —NH$_2$, C$_{1-6}$ alkyl, or C$_{1-3}$ haloalkyl, oxetanyl, pyrrolidinyl optionally substituted with 1 to 3 methyl, piperidinyl optionally substituted with halogen or C$_{1-3}$ alkyl, tetrahydrofuranyl, tetrahydropyranyl, or —C(O)C$_{1-6}$ alkyl, and $R^{4G1}$ is cyclopropyl, cyclobutyl, cyclohexyl optionally substituted with —NH$_2$ or C$_{1-3}$ haloalkyl, oxetanyl, piperidinyl optionally substituted with C$_{1-3}$ alkyl or C$_{1-3}$ haloalkyl, tetrahydropyranyl, or phenyl.

In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl, ethyl, n-propyl, isopropyl, n-butyl, isobutyl, tert-butyl, or isopentyl, and $R^{4G}$ is methyl, ethyl, n-propyl, isopropyl, n-butyl, t-butyl or 2-ethyl-butyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl, ethyl, or isopropyl, and $R^{4G}$ is methyl, ethyl, n-propyl, isopropyl, n-butyl, t-butyl or 2-ethyl-butyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each methyl, and $R^{4G}$ is methyl, ethyl, n-propyl, isopropyl, n-butyl, t-butyl or 2-ethyl-butyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each ethyl, and $R^{4G}$ is methyl, ethyl, n-propyl, isopropyl, n-butyl, t-butyl or 2-ethyl-butyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each isopropyl, and $R^{4G}$ is methyl, ethyl, n-propyl, isopropyl, n-butyl, t-butyl or 2-ethyl-butyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl, ethyl, or isopropyl, and $R^{4G}$ is methyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl, ethyl, or isopropyl, $R^{4G}$ is ethyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl, ethyl, or isopropyl, $R^{4G}$ is n-propyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl, ethyl, or isopropyl, $R^{4G}$ is isopropyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl, ethyl, or isopropyl, $R^{4G}$ is n-butyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl, ethyl, or isopropyl, $R^{4G}$ is t-butyl. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein $R^{1A}$ and $R^{2A}$ are each independently methyl, ethyl, or isopropyl, $R^{4G}$ is 2-ethyl-butyl.

The compounds of the present disclosure include the compounds of Table 1A, Table 1B, Table 1C, Table 1D, Table 1E, Table 1F, Table 1G, Table 1H, and Table 1I. In some embodiments, the compound can be represented by Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, wherein the compound is selected from the group consisting of the compounds in Table 1A, Table 1B, Table 1C, Table 1D, Table 1E, Table 1F, Table 1G, Table 1H, and Table 1I:

TABLE 1A
Compounds
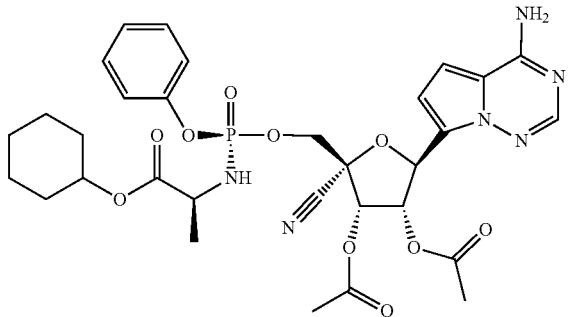 [SMILES: CC(=O)O[C@H]1[C@H](c2ccc3c(N)ncnn23)O[C@](C#N)(CO[P@@](=O)(N[C@@H](C)C(=O)OC2CCCCC2)Oc2ccccc2)[C@H]1OC(C)=O]
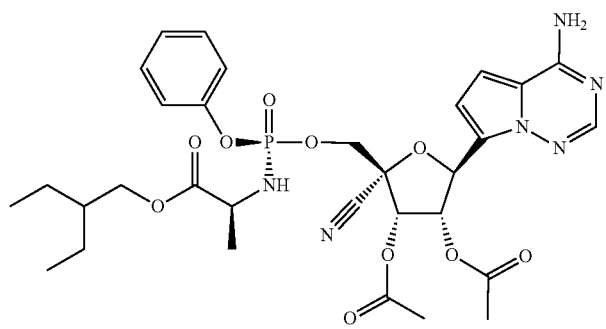 [SMILES: CCC(CC)COC(=O)[C@H](C)N[P@](=O)(OC[C@@]1(C#N)O[C@@H](c2ccc3c(N)ncnn23)[C@H](OC(C)=O)[C@@H]1OC(C)=O)Oc1ccccc1]
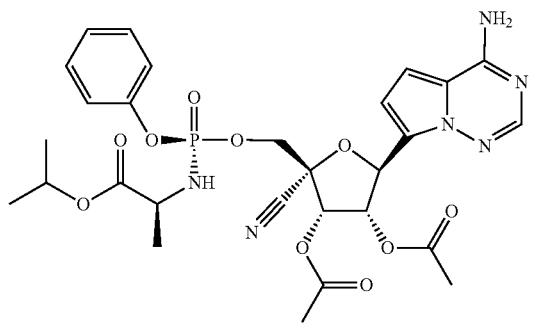 [SMILES: CC(=O)O[C@H]1[C@H](c2ccc3c(N)ncnn23)O[C@](C#N)(CO[P@@](=O)(N[C@@H](C)C(=O)OC(C)C)Oc2ccccc2)[C@H]1OC(C)=O]
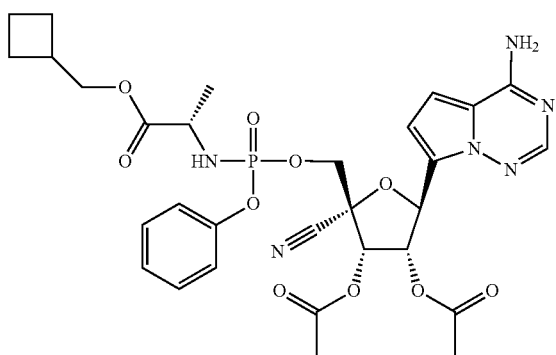 [SMILES: CC(=O)O[C@H]1[C@H](c2ccc3c(N)ncnn23)O[C@](C#N)(COP(=O)(N[C@@H](C)C(=O)OCC2CCC2)Oc2ccccc2)[C@H]1OC(C)=O]

TABLE 1A-continued
Compounds
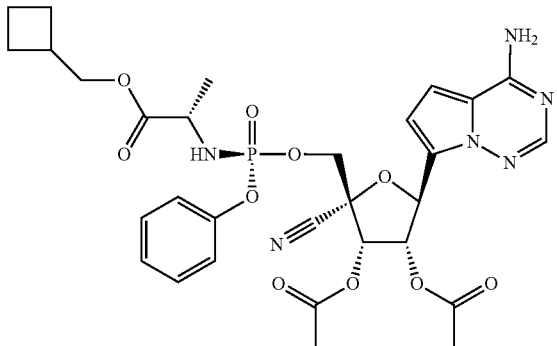 [SMILES: CC(=O)O[C@H]1[C@H](c2ccc3c(N)ncnn23)O[C@](C#N)(CO[P@](=O)(N[C@@H](C)C(=O)OCC2CCC2)Oc2ccccc2)[C@H]1OC(C)=O]
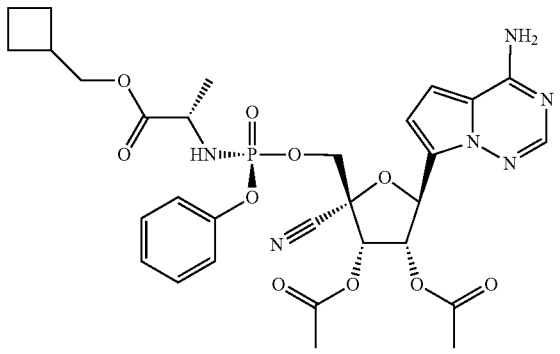 [SMILES: CC(=O)O[C@H]1[C@H](c2ccc3c(N)ncnn23)O[C@](C#N)(CO[P@@](=O)(N[C@@H](C)C(=O)OCC2CCC2)Oc2ccccc2)[C@H]1OC(C)=O]
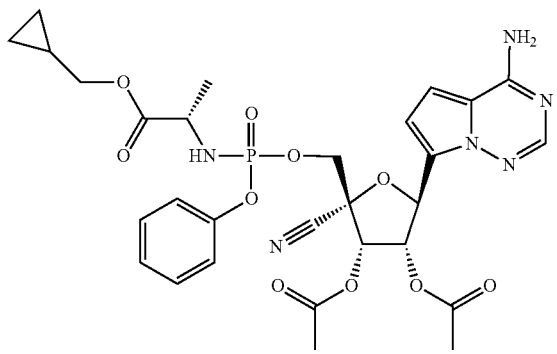 [SMILES: CC(=O)O[C@H]1[C@H](c2ccc3c(N)ncnn23)O[C@](C#N)(COP(=O)(N[C@@H](C)C(=O)OCC2CC2)Oc2ccccc2)[C@H]1OC(C)=O]
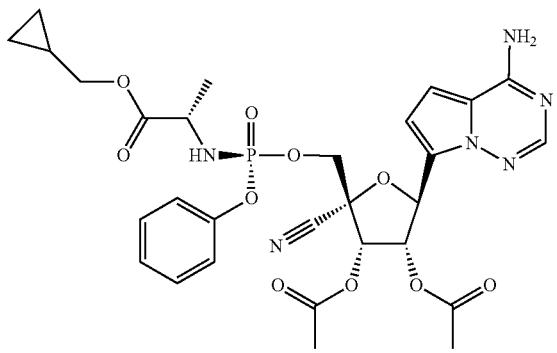 [SMILES: CC(=O)O[C@H]1[C@H](c2ccc3c(N)ncnn23)O[C@](C#N)(CO[P@](=O)(N[C@@H](C)C(=O)OCC2CC2)Oc2ccccc2)[C@H]1OC(C)=O]

TABLE 1A-continued
Compounds
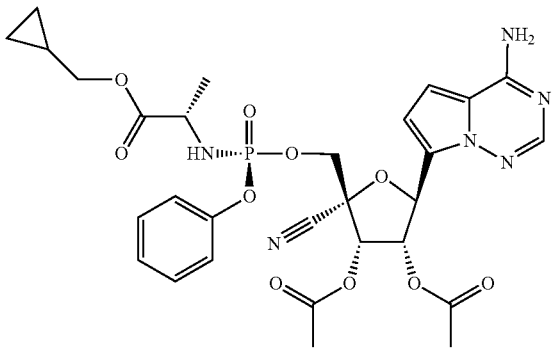 [SMILES: CC(=O)O[C@H]1[C@H](c2ccc3c(N)ncnn23)O[C@](C#N)(CO[P@@](=O)(N[C@@H](C)C(=O)OCC2CC2)Oc2ccccc2)[C@H]1OC(C)=O]
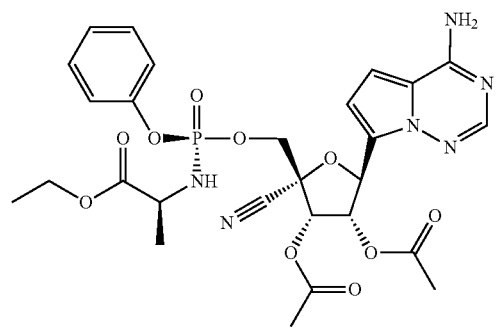 [SMILES: CCOC(=O)[C@H](C)N[P@](=O)(OC[C@@]1(C#N)O[C@@H](c2ccc3c(N)ncnn23)[C@H](OC(C)=O)[C@@H]1OC(C)=O)Oc1ccccc1]
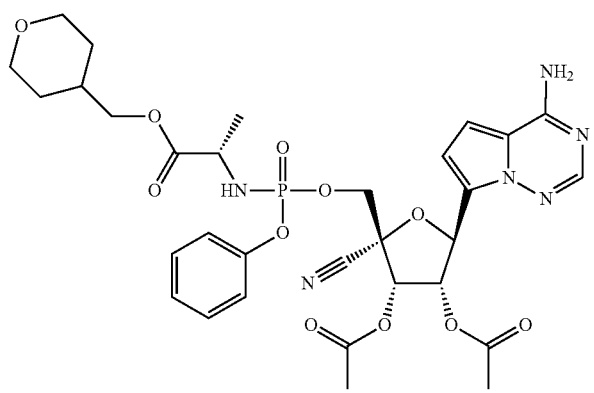 [SMILES: CC(=O)O[C@H]1[C@H](c2ccc3c(N)ncnn23)O[C@](C#N)(COP(=O)(N[C@@H](C)C(=O)OCC2CCOCC2)Oc2ccccc2)[C@H]1OC(C)=O]
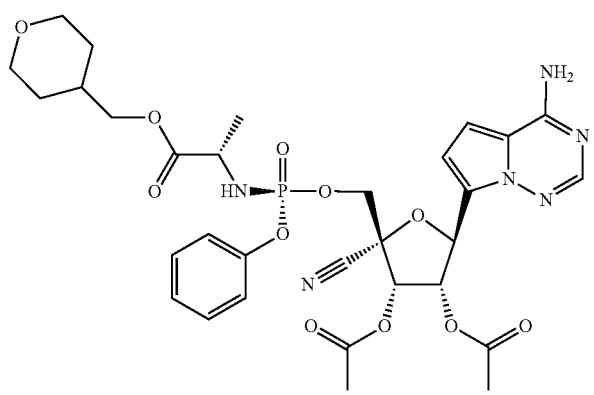 [SMILES: CC(=O)O[C@H]1[C@H](c2ccc3c(N)ncnn23)O[C@](C#N)(CO[P@](=O)(N[C@@H](C)C(=O)OCC2CCOCC2)Oc2ccccc2)[C@H]1OC(C)=O]

TABLE 1A-continued
Compounds
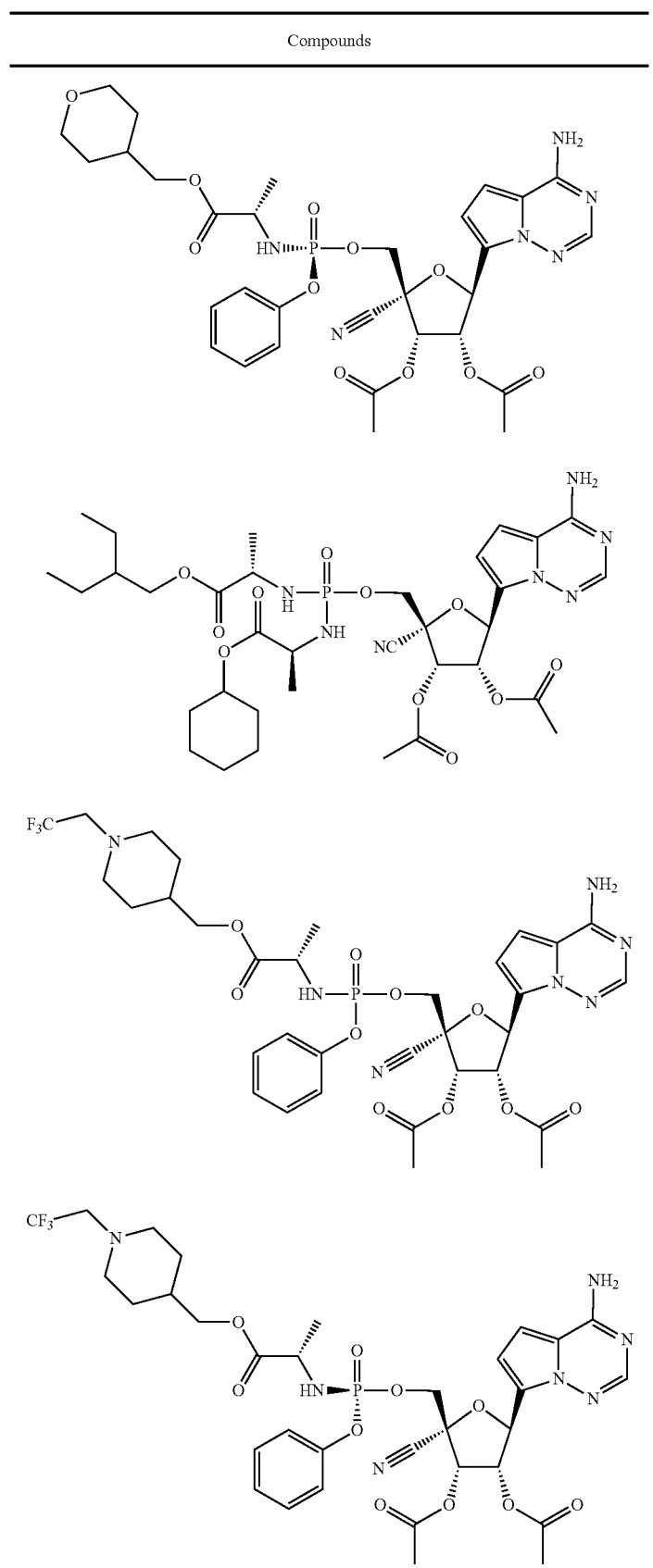

TABLE 1A-continued
Compounds
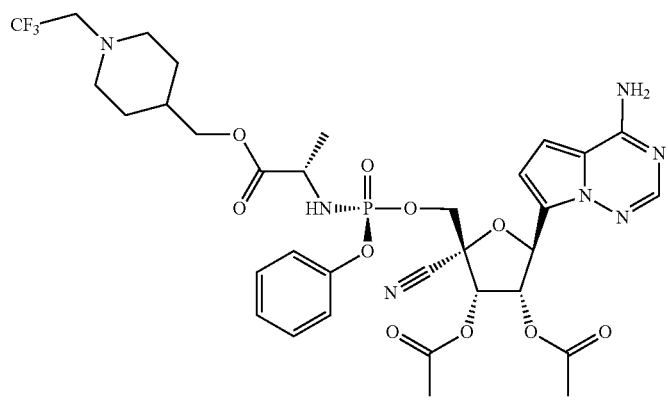 [SMILES: CC(=O)O[C@H]1[C@H](c2ccc3c(N)ncnn23)O[C@](C#N)(CO[P@@](=O)(N[C@@H](C)C(=O)OCC2CCN(CC(F)(F)F)CC2)Oc2ccccc2)[C@H]1OC(C)=O]
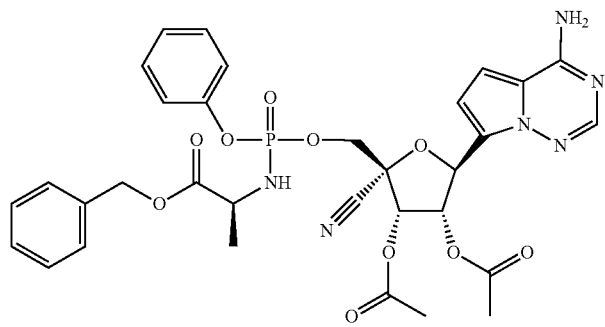 [SMILES: CC(=O)O[C@H]1[C@H](c2ccc3c(N)ncnn23)O[C@](C#N)(COP(=O)(N[C@@H](C)C(=O)OCc2ccccc2)Oc2ccccc2)[C@H]1OC(C)=O]
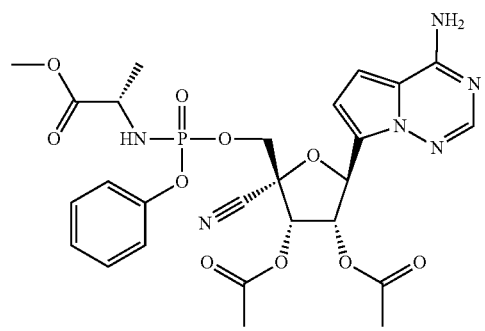 [SMILES: COC(=O)[C@H](C)NP(=O)(OC[C@@]1(C#N)O[C@@H](c2ccc3c(N)ncnn23)[C@H](OC(C)=O)[C@@H]1OC(C)=O)Oc1ccccc1]
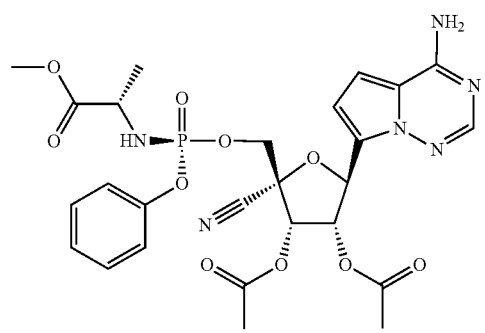 [SMILES: COC(=O)[C@H](C)N[P@@](=O)(OC[C@@]1(C#N)O[C@@H](c2ccc3c(N)ncnn23)[C@H](OC(C)=O)[C@@H]1OC(C)=O)Oc1ccccc1]

TABLE 1A-continued

Compounds

TABLE 1A-continued

Compounds

TABLE 1A-continued

Compounds

TABLE 1B

Compounds

TABLE 1B-continued

Compounds

TABLE 1B-continued
Compounds
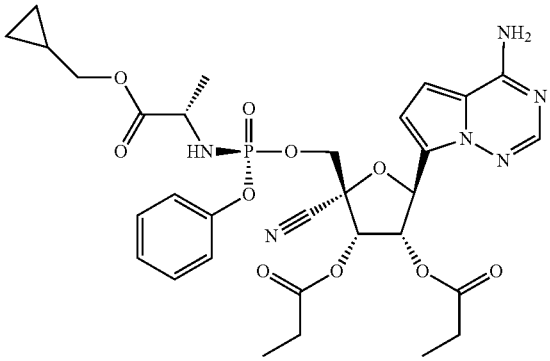 [SMILES: CCC(=O)O[C@H]1[C@H](c2ccc3c(N)ncnn23)O[C@](C#N)(CO[P@](=O)(N[C@@H](C)C(=O)OCC2CC2)Oc2ccccc2)[C@H]1OC(=O)CC]
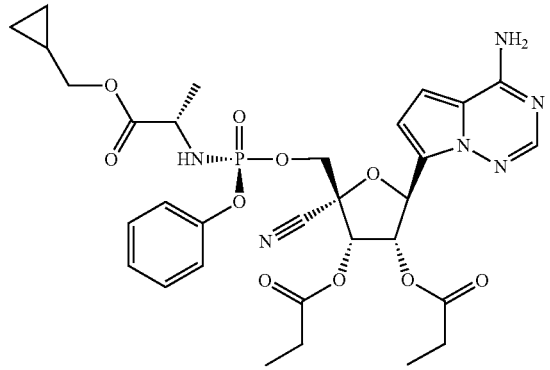 [SMILES: CCC(=O)O[C@H]1[C@H](c2ccc3c(N)ncnn23)O[C@](C#N)(CO[P@@](=O)(N[C@@H](C)C(=O)OCC2CC2)Oc2ccccc2)[C@H]1OC(=O)CC]
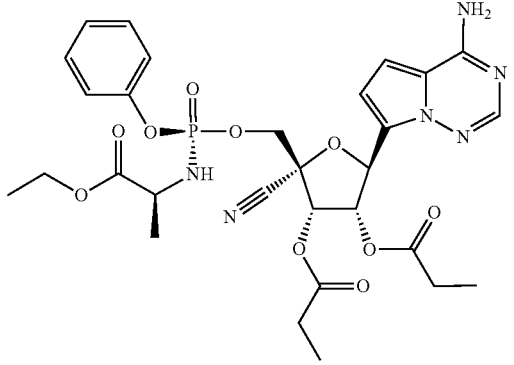 [SMILES: CCOC(=O)[C@H](C)N[P@](=O)(OC[C@@]1(C#N)O[C@@H](c2ccc3c(N)ncnn23)[C@H](OC(=O)CC)[C@@H]1OC(=O)CC)Oc1ccccc1]
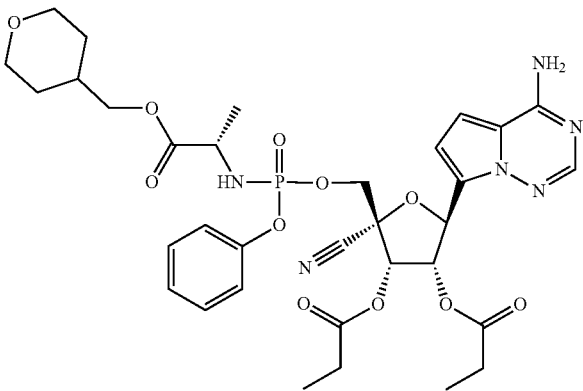 [SMILES: CCC(=O)O[C@H]1[C@H](c2ccc3c(N)ncnn23)O[C@](C#N)(COP(=O)(N[C@@H](C)C(=O)OCC2CCOCC2)Oc2ccccc2)[C@H]1OC(=O)CC]

TABLE 1B-continued

Compounds

TABLE 1B-continued
Compounds
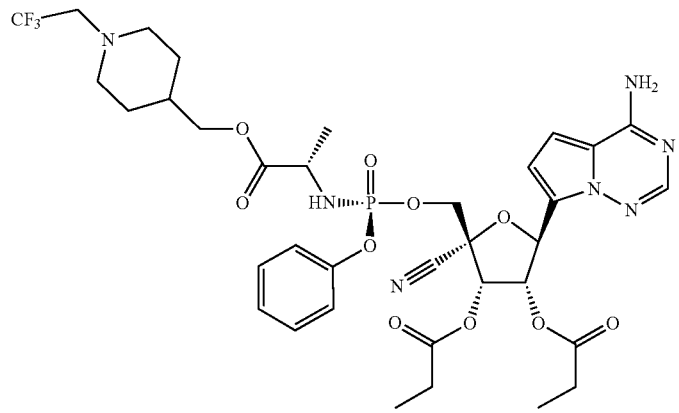 [SMILES: CCC(=O)O[C@H]1[C@H](c2ccc3c(N)ncnn23)O[C@](C#N)(CO[P@@](=O)(N[C@@H](C)C(=O)OCC2CCN(CC(F)(F)F)CC2)Oc2ccccc2)[C@H]1OC(=O)CC]
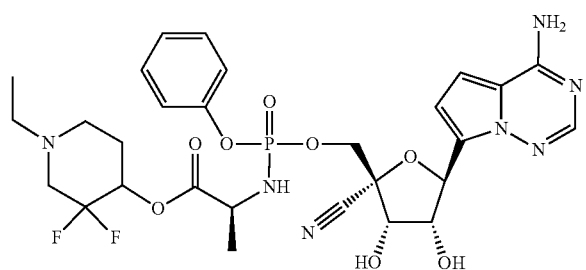 [SMILES: CCN1CCC(OC(=O)[C@H](C)NP(=O)(OC[C@@]2(C#N)O[C@@H](c3ccc4c(N)ncnn34)[C@H](O)[C@@H]2O)Oc2ccccc2)C(F)(F)C1]
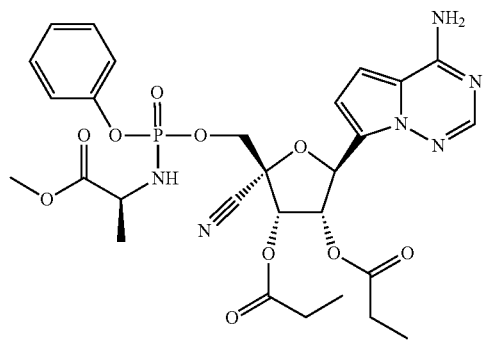 [SMILES: CCC(=O)O[C@H]1[C@H](c2ccc3c(N)ncnn23)O[C@](C#N)(COP(=O)(N[C@@H](C)C(=O)OC)Oc2ccccc2)[C@H]1OC(=O)CC]
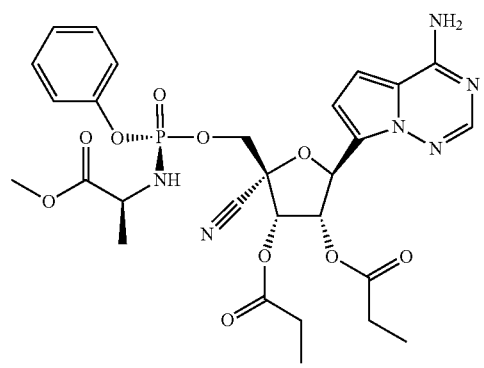

TABLE 1B-continued
Compounds
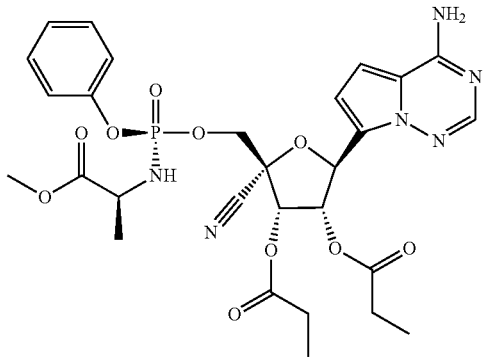 [SMILES: CCC(=O)O[C@H]1[C@H](c2ccc3c(N)ncnn23)O[C@](C#N)(CO[P@@](=O)(N[C@@H](C)C(=O)OC)Oc2ccccc2)[C@H]1OC(=O)CC]
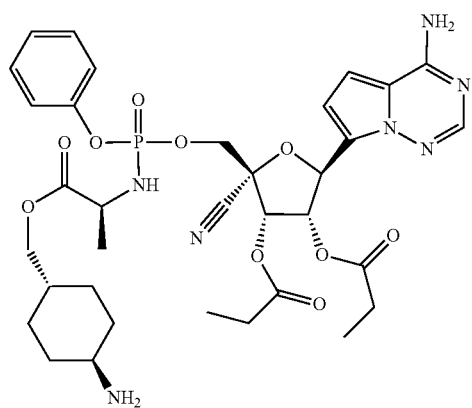 [SMILES: CCC(=O)O[C@H]1[C@H](c2ccc3c(N)ncnn23)O[C@](C#N)(COP(=O)(N[C@@H](C)C(=O)OC[C@H]2CC[C@H](N)CC2)Oc2ccccc2)[C@H]1OC(=O)CC]
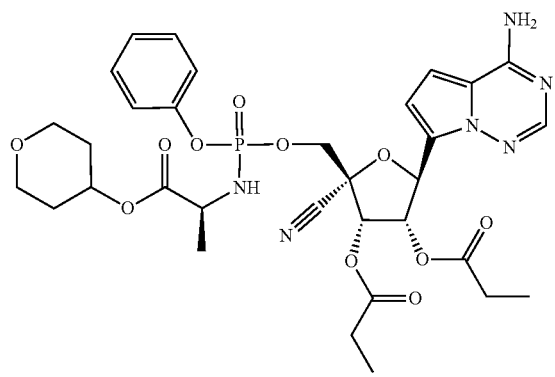 [SMILES: CCC(=O)O[C@H]1[C@H](c2ccc3c(N)ncnn23)O[C@](C#N)(COP(=O)(N[C@@H](C)C(=O)OC2CCOCC2)Oc2ccccc2)[C@H]1OC(=O)CC]
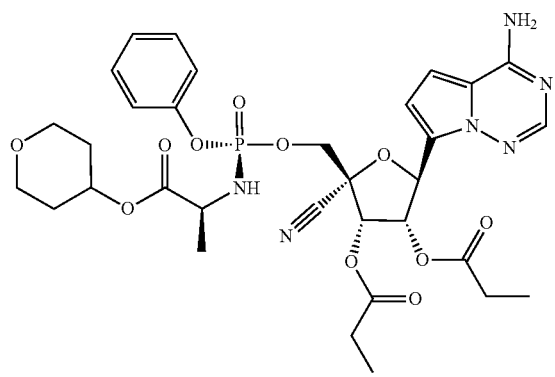 [SMILES: CCC(=O)O[C@H]1[C@H](c2ccc3c(N)ncnn23)O[C@](C#N)(CO[P@](=O)(N[C@@H](C)C(=O)OC2CCOCC2)Oc2ccccc2)[C@H]1OC(=O)CC]

TABLE 1B-continued
Compounds
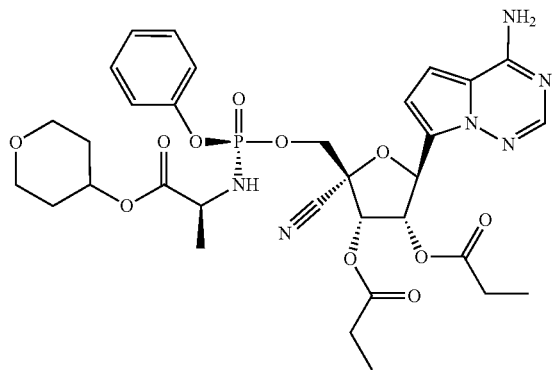 [SMILES: CCC(=O)O[C@H]1[C@H](c2ccc3c(N)ncnn23)O[C@](C#N)(CO[P@@](=O)(N[C@@H](C)C(=O)OC2CCOCC2)Oc2ccccc2)[C@H]1OC(=O)CC]
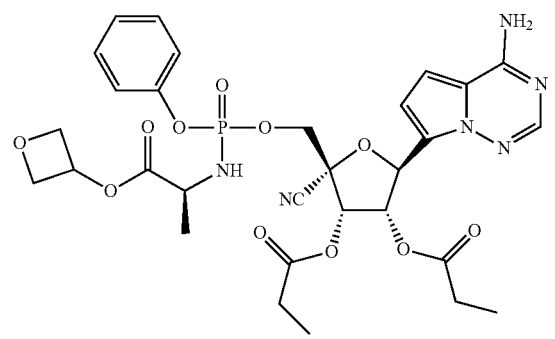
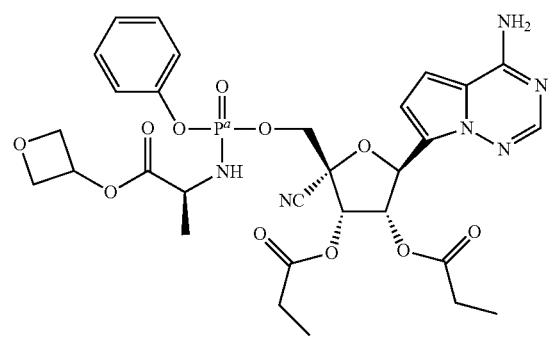
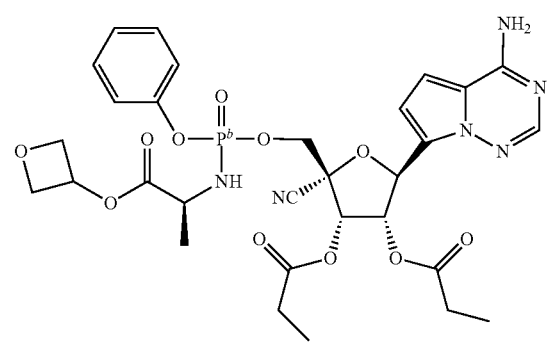

TABLE 1B-continued

Compounds

TABLE 1B-continued

Compounds

TABLE 1B-continued
Compounds
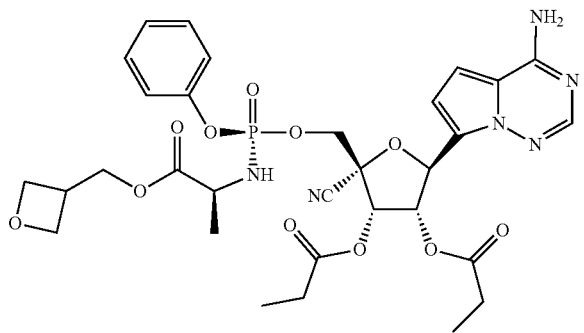 [SMILES: CCC(=O)O[C@H]1[C@H](c2ccc3c(N)ncnn23)O[C@](C#N)(CO[P@@](=O)(N[C@@H](C)C(=O)OCC2COC2)Oc2ccccc2)[C@H]1OC(=O)CC]
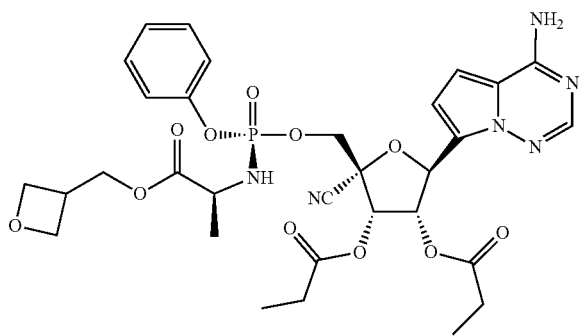 [SMILES: CCC(=O)O[C@H]1[C@H](c2ccc3c(N)ncnn23)O[C@](C#N)(CO[P@](=O)(N[C@@H](C)C(=O)OCC2COC2)Oc2ccccc2)[C@H]1OC(=O)CC]
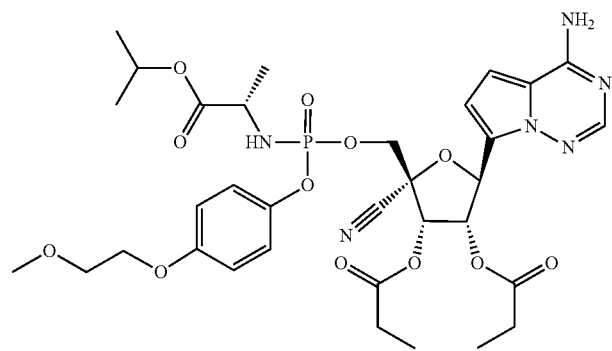 [SMILES: CCC(=O)O[C@H]1[C@H](c2ccc3c(N)ncnn23)O[C@](C#N)(COP(=O)(N[C@@H](C)C(=O)OC(C)C)Oc2ccc(OCCOC)cc2)[C@H]1OC(=O)CC]
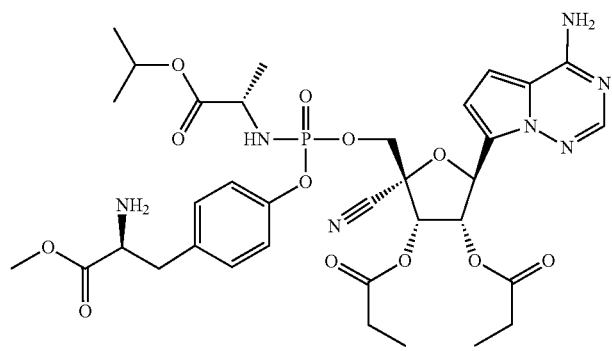 [SMILES: CCC(=O)O[C@H]1[C@H](c2ccc3c(N)ncnn23)O[C@](C#N)(COP(=O)(N[C@@H](C)C(=O)OC(C)C)Oc2ccc(C[C@H](N)C(=O)OC)cc2)[C@H]1OC(=O)CC]

TABLE 1B-continued
Compounds
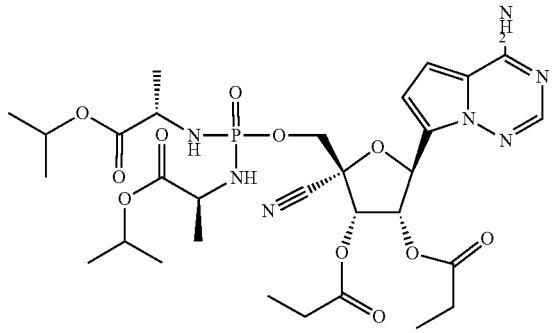 [SMILES: CCC(=O)O[C@H]1[C@H](c2ccc3c(N)ncnn23)O[C@](C#N)(COP(=O)(N[C@@H](C)C(=O)OC(C)C)N[C@@H](C)C(=O)OC(C)C)[C@H]1OC(=O)CC]
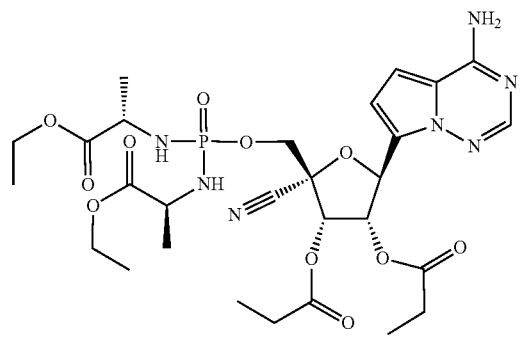 [SMILES: CCOC(=O)[C@H](C)NP(=O)(N[C@@H](C)C(=O)OCC)OC[C@@]1(C#N)O[C@@H](c2ccc3c(N)ncnn23)[C@H](OC(=O)CC)[C@@H]1OC(=O)CC]
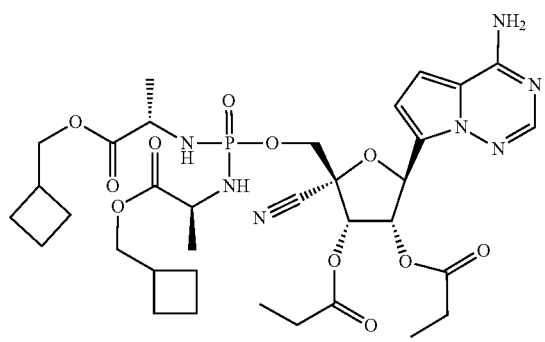 [SMILES: CCC(=O)O[C@H]1[C@H](c2ccc3c(N)ncnn23)O[C@](C#N)(COP(=O)(N[C@@H](C)C(=O)OCC2CCC2)N[C@@H](C)C(=O)OCC2CCC2)[C@H]1OC(=O)CC]
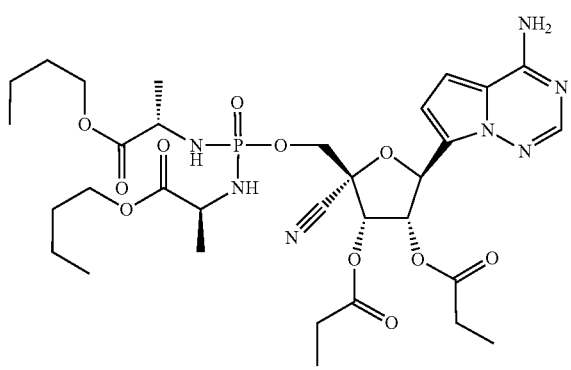 [SMILES: CCCCOC(=O)[C@H](C)NP(=O)(N[C@@H](C)C(=O)OCCCC)OC[C@@]1(C#N)O[C@@H](c2ccc3c(N)ncnn23)[C@H](OC(=O)CC)[C@@H]1OC(=O)CC]

TABLE 1C
Compounds
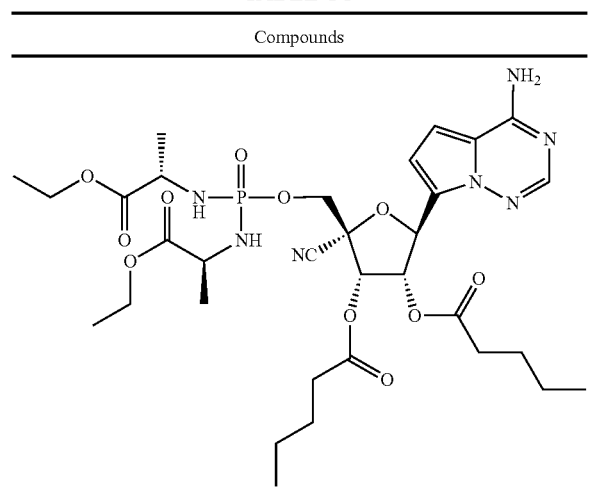
TABLE 1C-continued
Compounds
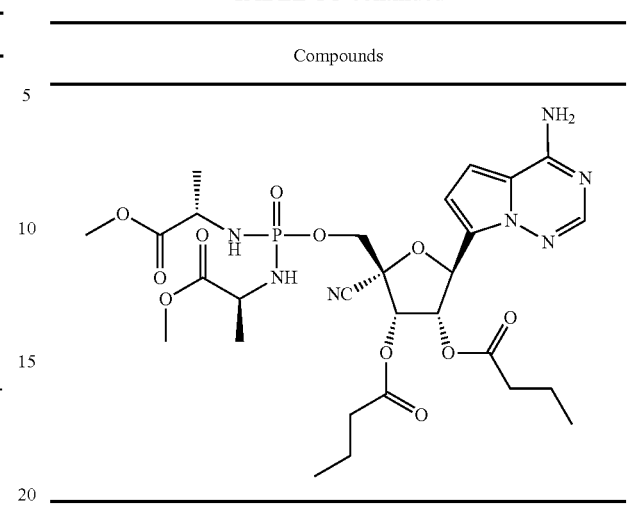
TABLE 1D
Compounds
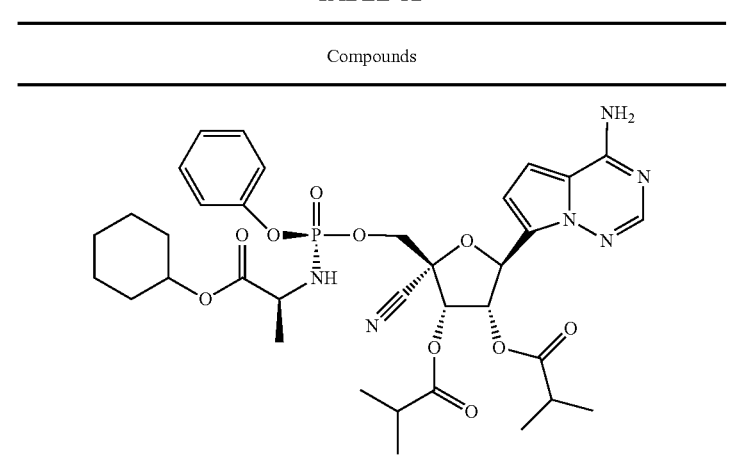
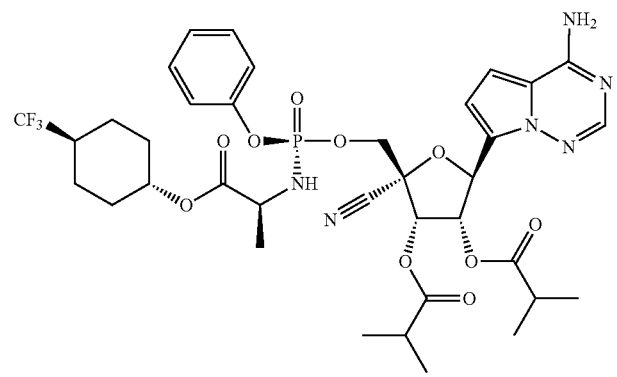 [SMILES: CC(C)C(=O)O[C@H]1[C@H](c2ccc3c(N)ncnn23)O[C@](C#N)(CO[P@@](=O)(N[C@@H](C)C(=O)O[C@H]2CC[C@H](C(F)(F)F)CC2)Oc2ccccc2)[C@H]1OC(=O)C(C)C]

TABLE 1D-continued
Compounds
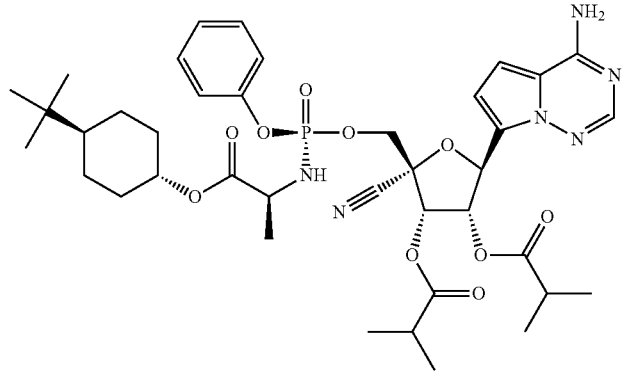 [SMILES: CC(C)C(=O)O[C@H]1[C@H](c2ccc3c(N)ncnn23)O[C@](C#N)(CO[P@@](=O)(N[C@@H](C)C(=O)O[C@H]2CC[C@H](C(C)(C)C)CC2)Oc2ccccc2)[C@H]1OC(=O)C(C)C]
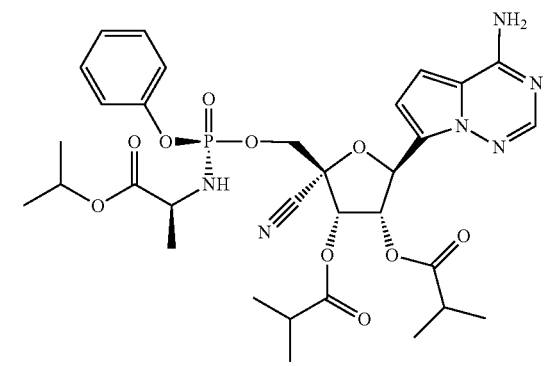 [SMILES: CC(C)OC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccccc1]
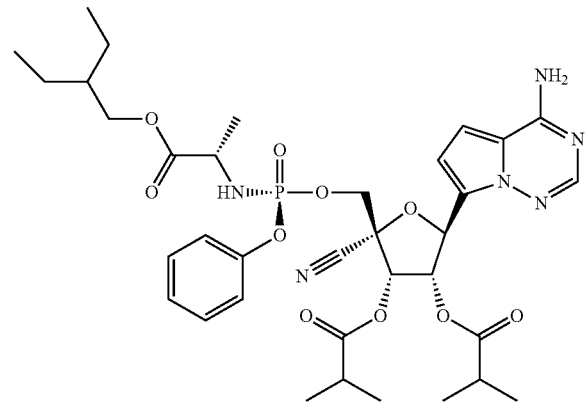 [SMILES: CCC(CC)COC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccccc1]
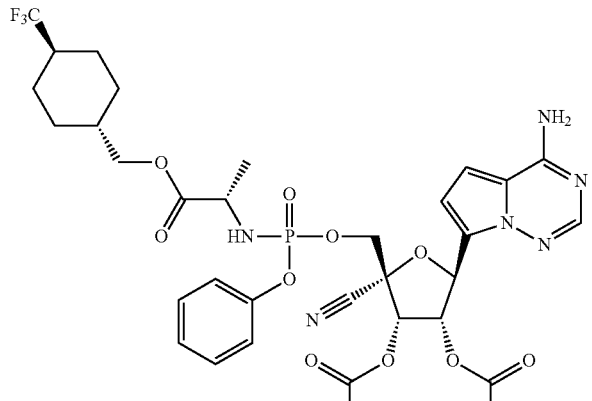

TABLE 1D-continued
Compounds
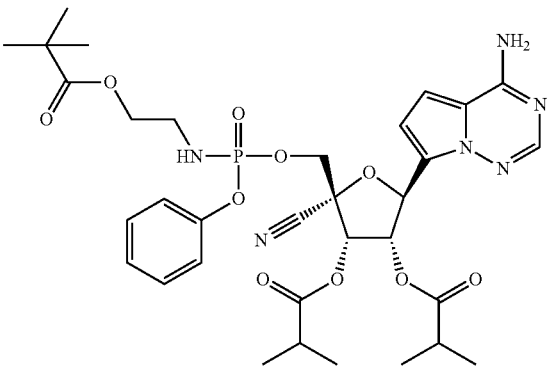 [SMILES: CC(C)C(=O)O[C@H]1[C@H](c2ccc3c(N)ncnn23)O[C@](C#N)(COP(=O)(NCCOC(=O)C(C)(C)C)Oc2ccccc2)[C@H]1OC(=O)C(C)C]
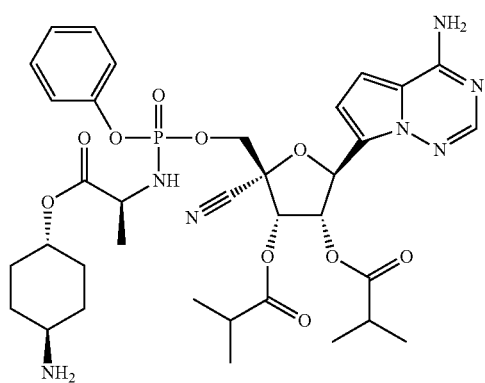 [SMILES: CC(C)C(=O)O[C@H]1[C@H](c2ccc3c(N)ncnn23)O[C@](C#N)(COP(=O)(N[C@@H](C)C(=O)O[C@H]2CC[C@H](N)CC2)Oc2ccccc2)[C@H]1OC(=O)C(C)C]
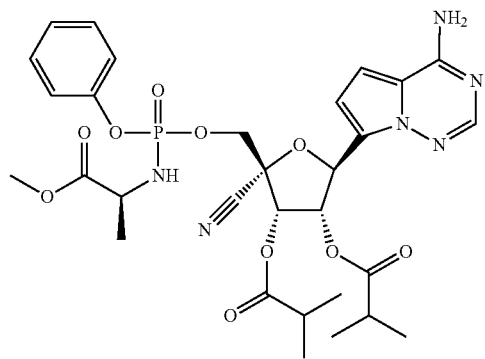 [SMILES: COC(=O)[C@H](C)NP(=O)(OC[C@@]1(C#N)O[C@@H](c2ccc3c(N)ncnn23)[C@H](OC(=O)C(C)C)[C@@H]1OC(=O)C(C)C)Oc1ccccc1]
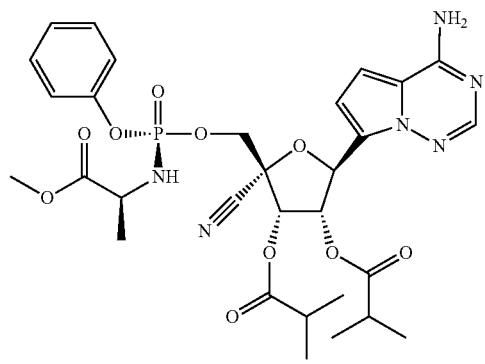 [SMILES: COC(=O)[C@H](C)N[P@@](=O)(OC[C@@]1(C#N)O[C@@H](c2ccc3c(N)ncnn23)[C@H](OC(=O)C(C)C)[C@@H]1OC(=O)C(C)C)Oc1ccccc1]

TABLE 1D-continued
Compounds
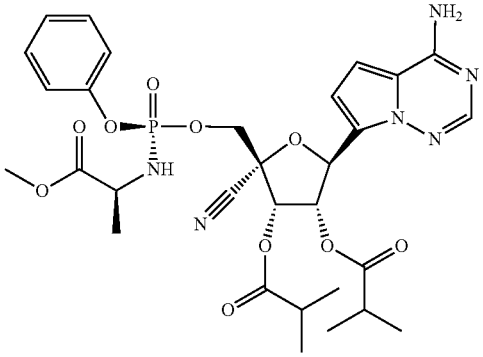 [SMILES: COC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccccc1]
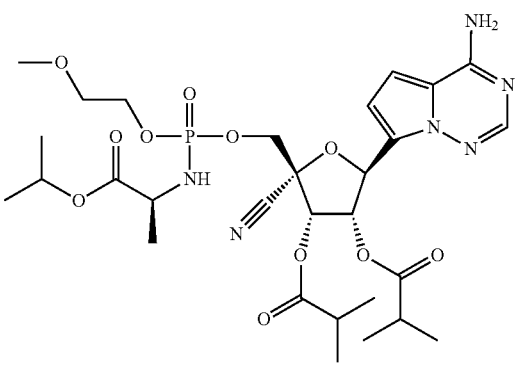 [SMILES: COCCOP(=O)(N[C@@H](C)C(=O)OC(C)C)OC[C@@]1(C#N)O[C@@H](c2ccc3c(N)ncnn23)[C@H](OC(=O)C(C)C)[C@@H]1OC(=O)C(C)C]
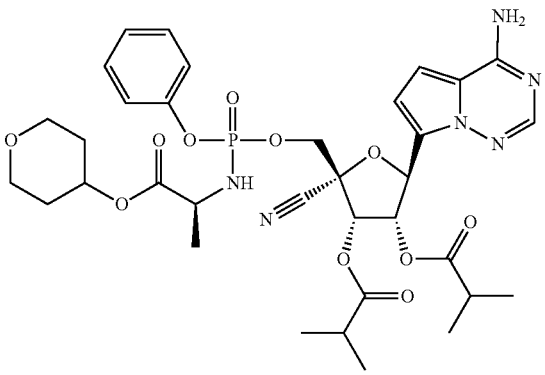 [SMILES: CC(C)C(=O)O[C@H]1[C@H](c2ccc3c(N)ncnn23)O[C@](C#N)(COP(=O)(N[C@@H](C)C(=O)OC2CCOCC2)Oc2ccccc2)[C@H]1OC(=O)C(C)C]
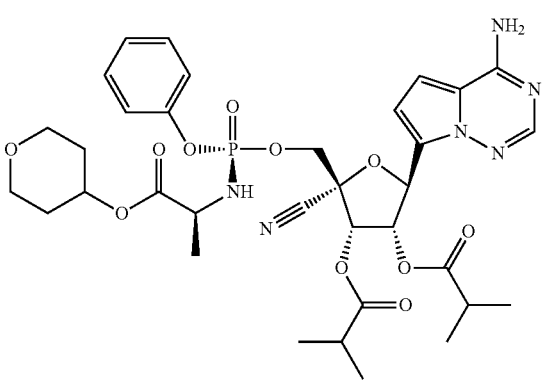 [SMILES: CC(C)C(=O)O[C@H]1[C@H](c2ccc3c(N)ncnn23)O[C@](C#N)(CO[P@](=O)(N[C@@H](C)C(=O)OC2CCOCC2)Oc2ccccc2)[C@H]1OC(=O)C(C)C]

TABLE 1D-continued
Compounds
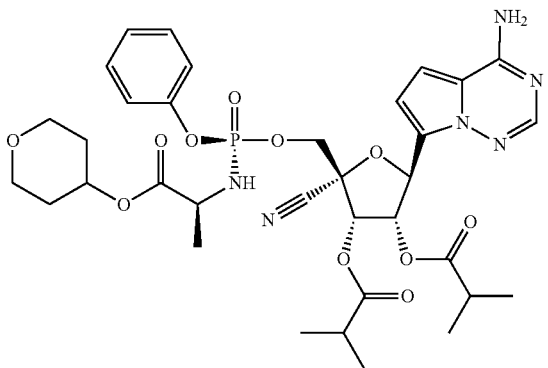 [SMILES: CC(C)C(=O)O[C@H]1[C@H](c2ccc3c(N)ncnn23)O[C@](C#N)(CO[P@@](=O)(N[C@@H](C)C(=O)OC2CCOCC2)Oc2ccccc2)[C@H]1OC(=O)C(C)C]
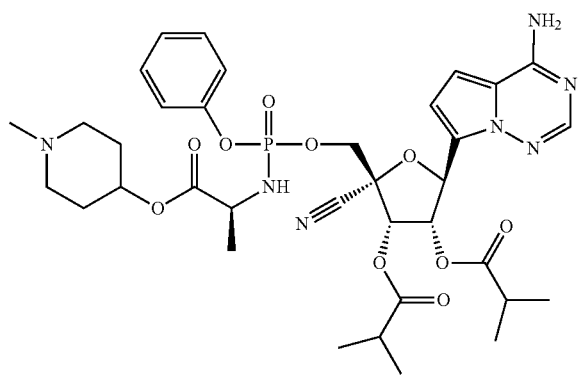 [SMILES: CC(C)C(=O)O[C@H]1[C@H](c2ccc3c(N)ncnn23)O[C@](C#N)(COP(=O)(N[C@@H](C)C(=O)OC2CCN(C)CC2)Oc2ccccc2)[C@H]1OC(=O)C(C)C]
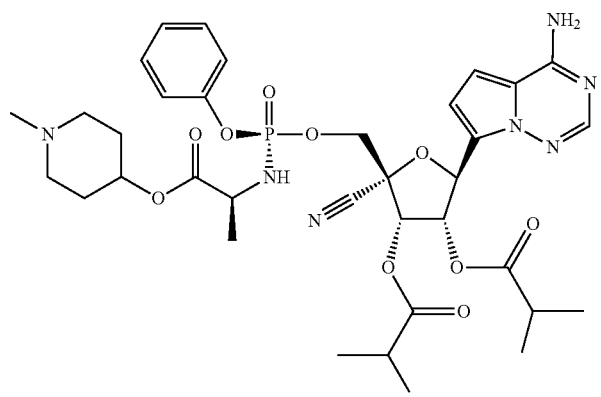 [SMILES: CC(C)C(=O)O[C@H]1[C@H](c2ccc3c(N)ncnn23)O[C@](C#N)(CO[P@@](=O)(N[C@@H](C)C(=O)OC2CCN(C)CC2)Oc2ccccc2)[C@H]1OC(=O)C(C)C]
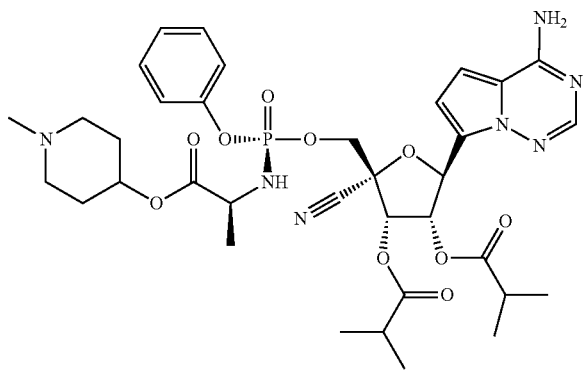 [SMILES: CC(C)C(=O)O[C@H]1[C@H](c2ccc3c(N)ncnn23)O[C@](C#N)(CO[P@](=O)(N[C@@H](C)C(=O)OC2CCN(C)CC2)Oc2ccccc2)[C@H]1OC(=O)C(C)C]

TABLE 1D-continued
Compounds
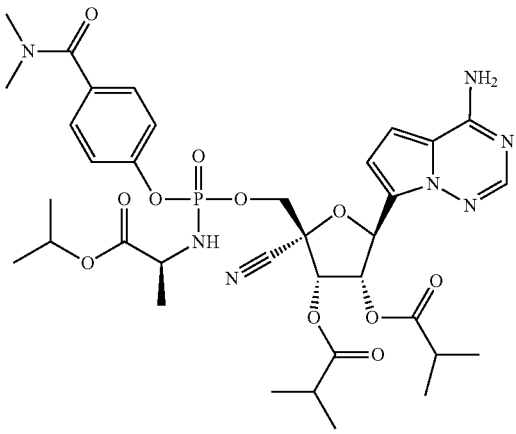 [SMILES: CC(C)OC(=O)[C@H](C)NP(=O)(OC[C@@]1(C#N)O[C@@H](c2ccc3c(N)ncnn23)[C@H](OC(=O)C(C)C)[C@@H]1OC(=O)C(C)C)Oc1ccc(C(=O)N(C)C)cc1]
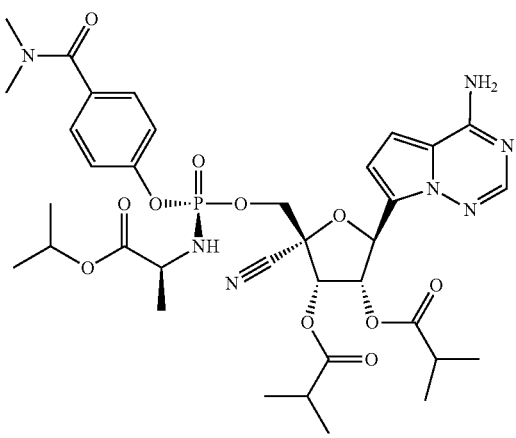 [SMILES: CC(C)OC(=O)[C@H](C)N[P@@](=O)(OC[C@@]1(C#N)O[C@@H](c2ccc3c(N)ncnn23)[C@H](OC(=O)C(C)C)[C@@H]1OC(=O)C(C)C)Oc1ccc(C(=O)N(C)C)cc1]
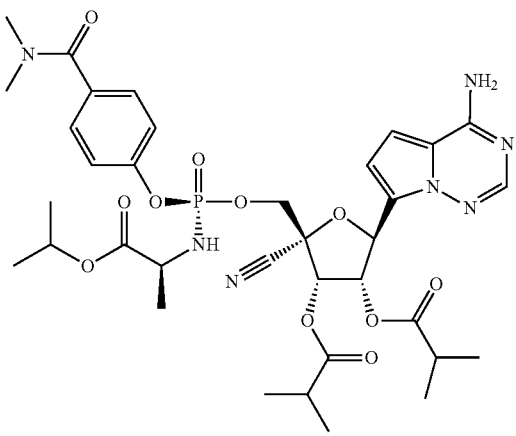 [SMILES: CC(C)OC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccc(C(=O)N(C)C)cc1]

TABLE 1D-continued
Compounds
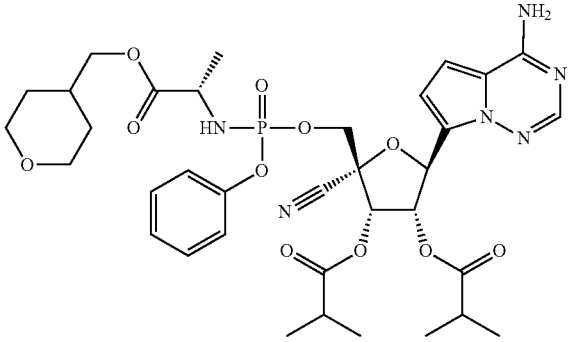 [SMILES: CC(C)C(=O)O[C@H]1[C@H](c2ccc3c(N)ncnn23)O[C@](C#N)(COP(=O)(N[C@@H](C)C(=O)OCC2CCOCC2)Oc2ccccc2)[C@H]1OC(=O)C(C)C]
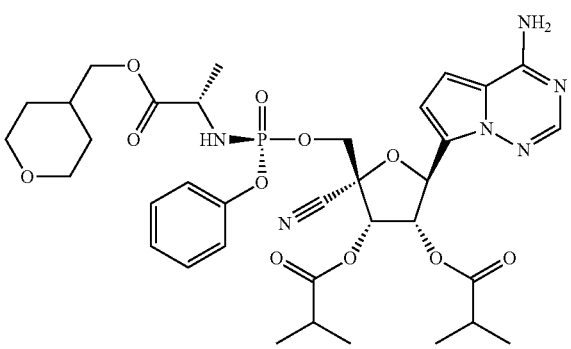 [SMILES: CC(C)C(=O)O[C@H]1[C@H](c2ccc3c(N)ncnn23)O[C@](C#N)(CO[P@](=O)(N[C@@H](C)C(=O)OCC2CCOCC2)Oc2ccccc2)[C@H]1OC(=O)C(C)C]
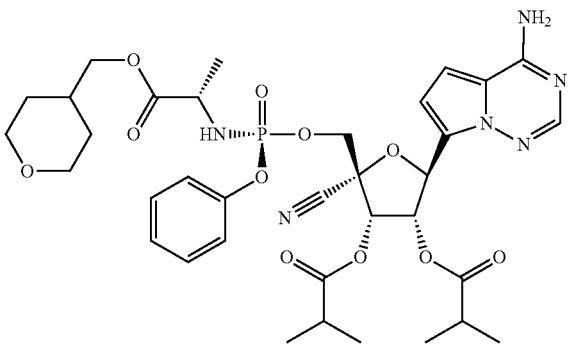 [SMILES: CC(C)C(=O)O[C@H]1[C@H](c2ccc3c(N)ncnn23)O[C@](C#N)(CO[P@@](=O)(N[C@@H](C)C(=O)OCC2CCOCC2)Oc2ccccc2)[C@H]1OC(=O)C(C)C]
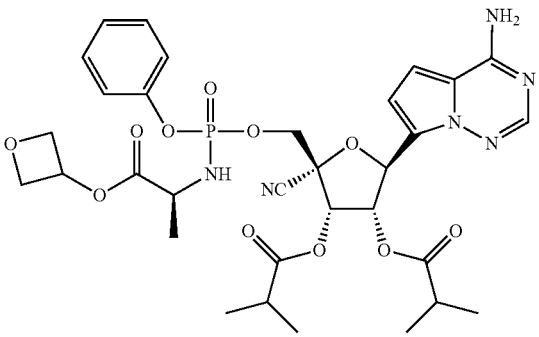 [SMILES: CC(C)C(=O)O[C@H]1[C@H](c2ccc3c(N)ncnn23)O[C@](C#N)(COP(=O)(N[C@@H](C)C(=O)OC2COC2)Oc2ccccc2)[C@H]1OC(=O)C(C)C]

TABLE 1D-continued

Compounds

TABLE 1D-continued

Compounds

TABLE 1D-continued

Compounds

TABLE 1D-continued
Compounds
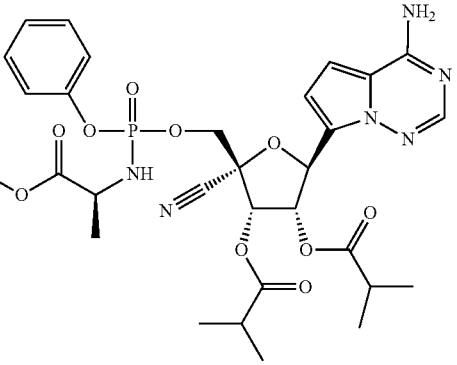
TABLE 1E
Compounds
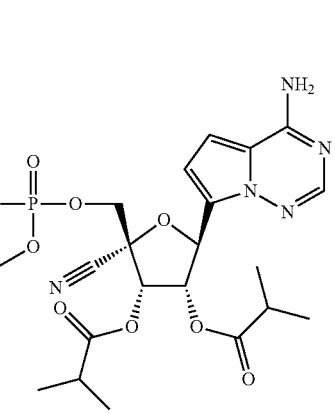
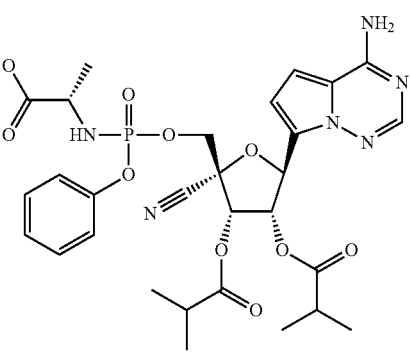
TABLE 1E-continued
Compounds
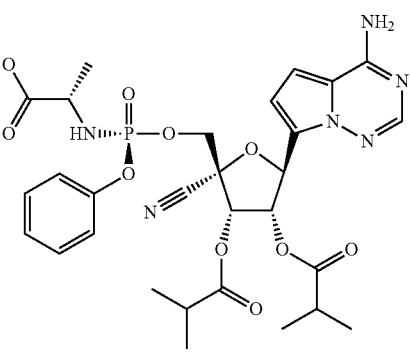
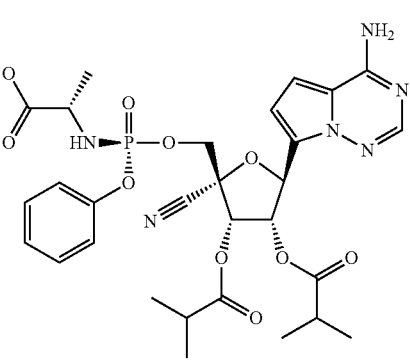
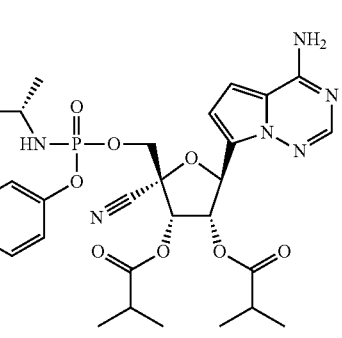

TABLE 1E-continued
Compounds
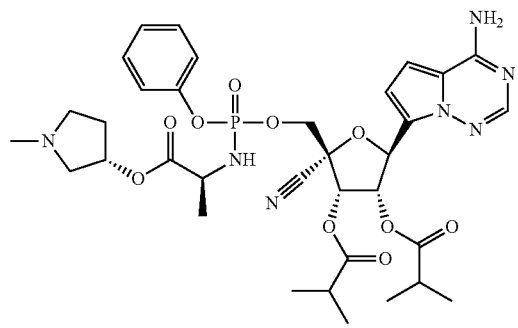 [SMILES: CC(C)C(=O)O[C@H]1[C@H](c2ccc3c(N)ncnn23)O[C@](C#N)(COP(=O)(N[C@@H](C)C(=O)O[C@H]2CCN(C)C2)Oc2ccccc2)[C@H]1OC(=O)C(C)C]
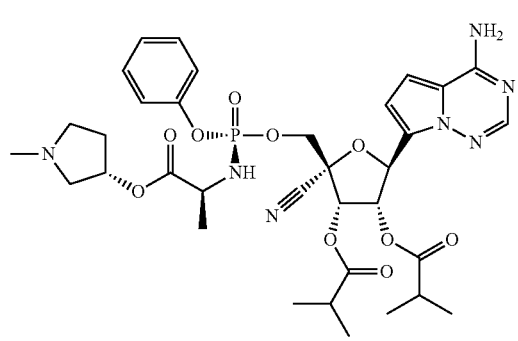 [SMILES: CC(C)C(=O)O[C@H]1[C@H](c2ccc3c(N)ncnn23)O[C@](C#N)(CO[P@](=O)(N[C@@H](C)C(=O)O[C@H]2CCN(C)C2)Oc2ccccc2)[C@H]1OC(=O)C(C)C]
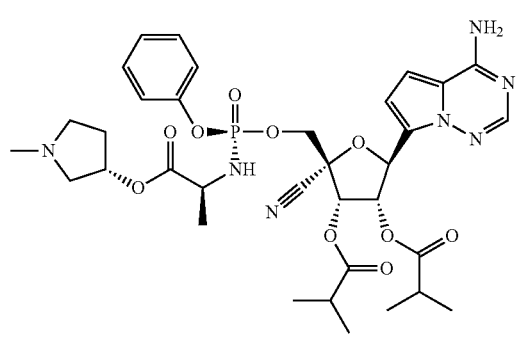 [SMILES: CC(C)C(=O)O[C@H]1[C@H](c2ccc3c(N)ncnn23)O[C@](C#N)(CO[P@@](=O)(N[C@@H](C)C(=O)O[C@H]2CCN(C)C2)Oc2ccccc2)[C@H]1OC(=O)C(C)C]
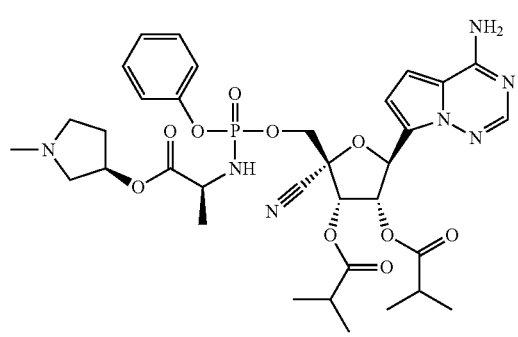 [SMILES: CC(C)C(=O)O[C@H]1[C@H](c2ccc3c(N)ncnn23)O[C@](C#N)(COP(=O)(N[C@@H](C)C(=O)O[C@@H]2CCN(C)C2)Oc2ccccc2)[C@H]1OC(=O)C(C)C]
TABLE 1E-continued
Compounds
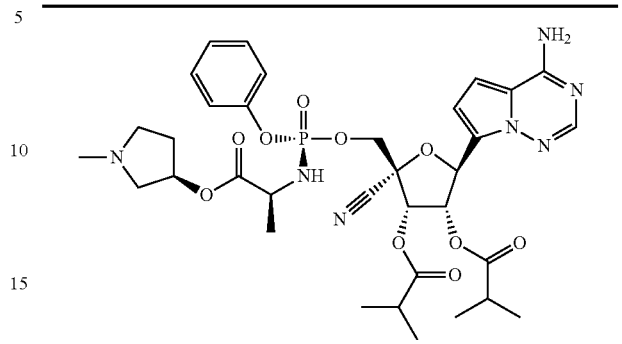
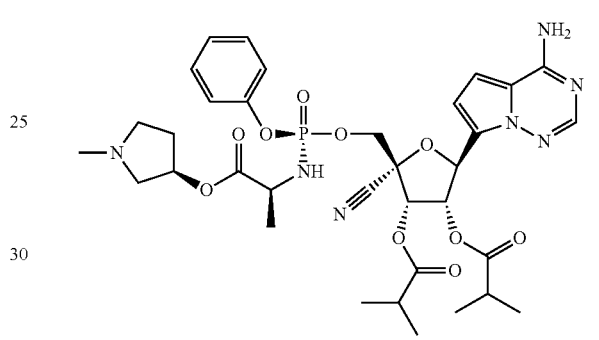
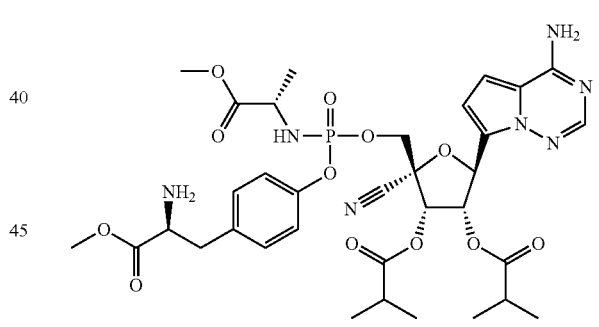
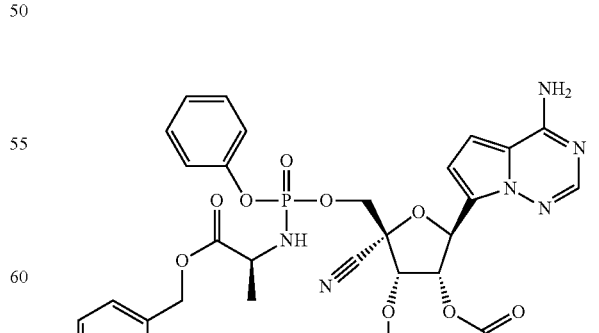

TABLE 1E-continued
Compounds
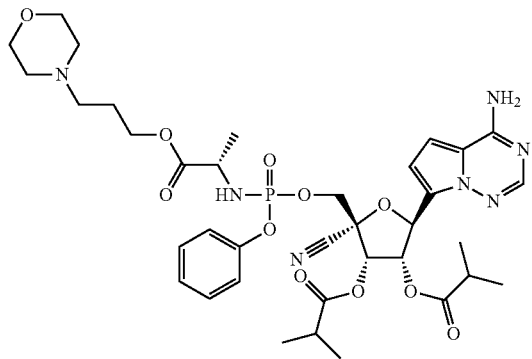 [SMILES: CC(C)C(=O)O[C@H]1[C@H](c2ccc3c(N)ncnn23)O[C@](C#N)(COP(=O)(N[C@@H](C)C(=O)OCCCN2CCOCC2)Oc2ccccc2)[C@H]1OC(=O)C(C)C]
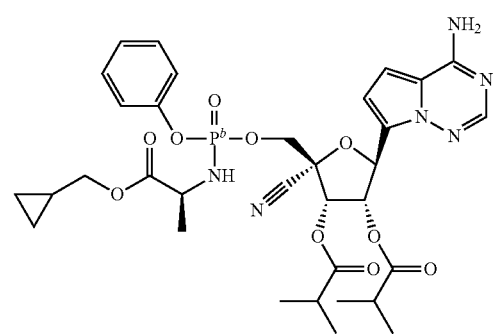
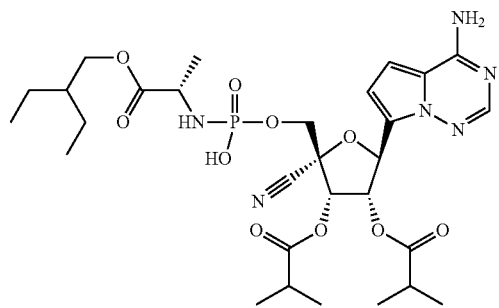 [SMILES: CCC(CC)COC(=O)[C@H](C)NP(=O)(O)OC[C@@]1(C#N)O[C@@H](c2ccc3c(N)ncnn23)[C@H](OC(=O)C(C)C)[C@@H]1OC(=O)C(C)C]
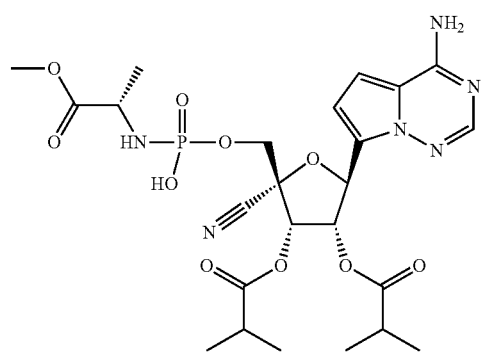 [SMILES: COC(=O)[C@H](C)NP(=O)(O)OC[C@@]1(C#N)O[C@@H](c2ccc3c(N)ncnn23)[C@H](OC(=O)C(C)C)[C@@H]1OC(=O)C(C)C]
TABLE 1E-continued
Compounds
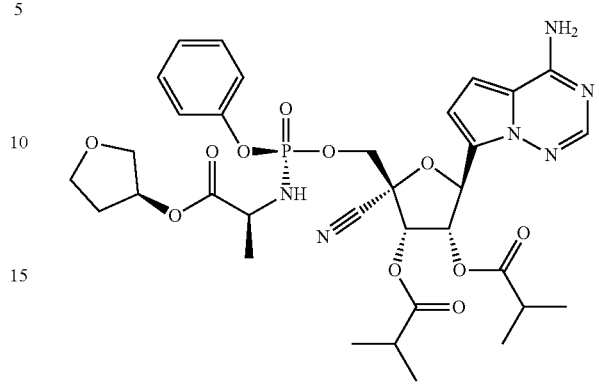
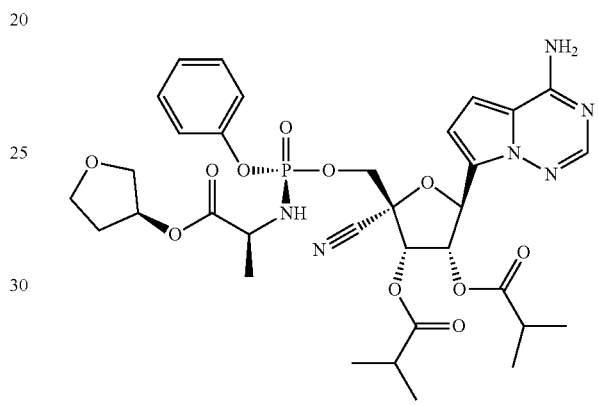
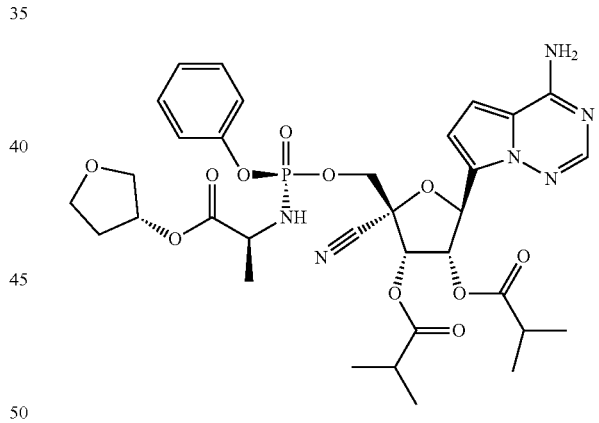
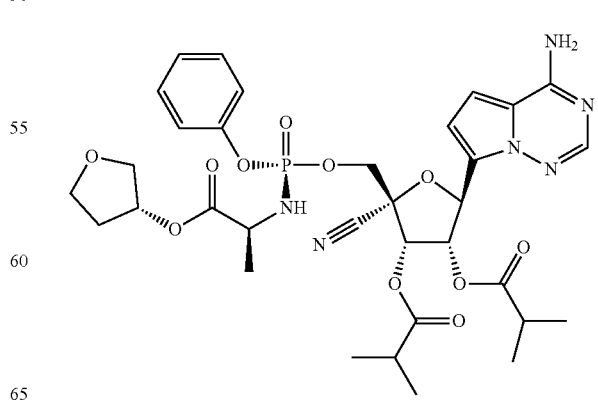

TABLE 1E-continued
Compounds
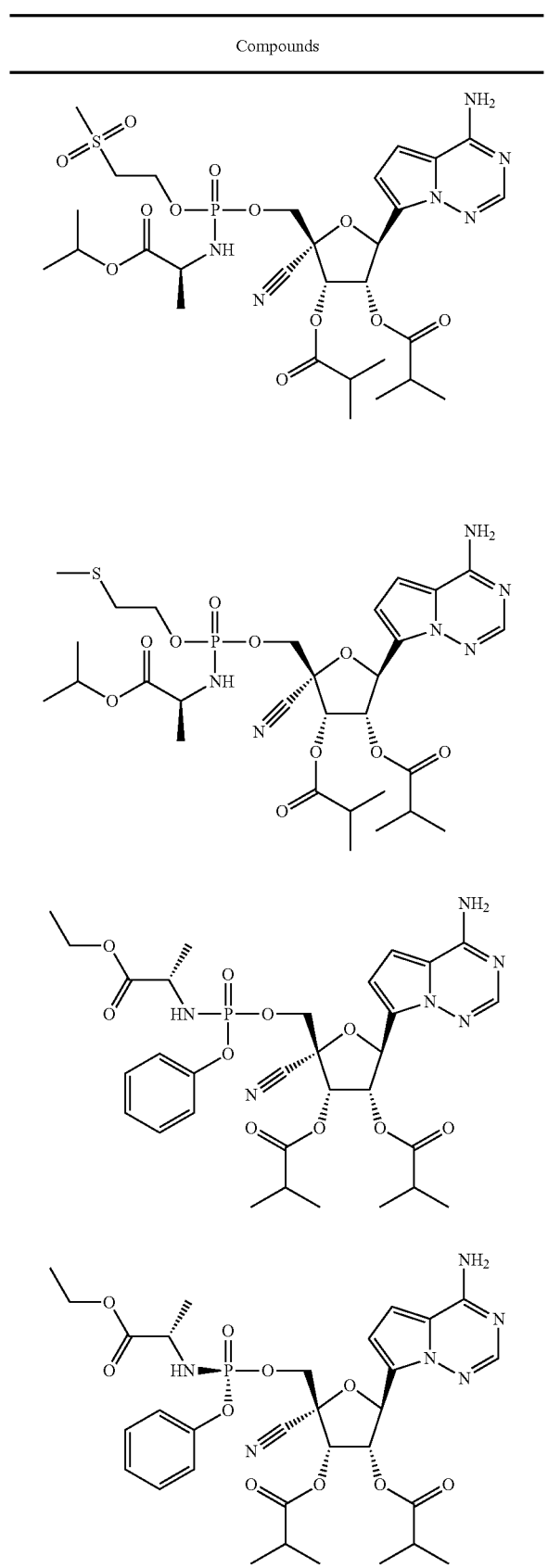
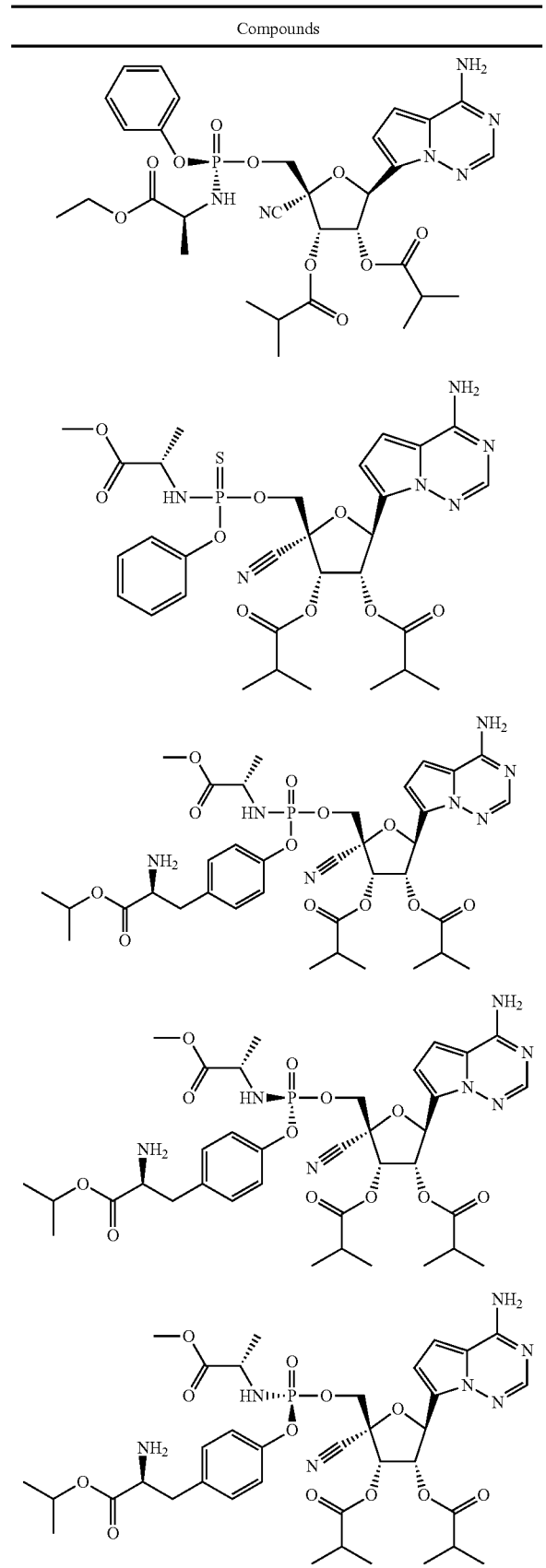

TABLE 1E-continued
Compounds
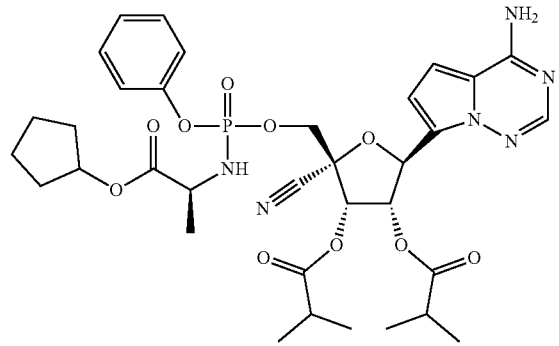 [SMILES: CC(C)C(=O)O[C@H]1[C@H](c2ccc3c(N)ncnn23)O[C@](C#N)(COP(=O)(N[C@@H](C)C(=O)OC2CCCC2)Oc2ccccc2)[C@H]1OC(=O)C(C)C]
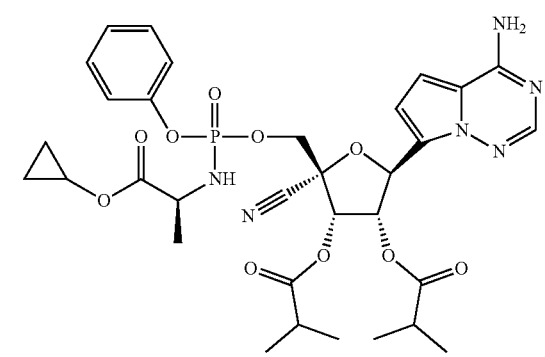 [SMILES: CC(C)C(=O)O[C@H]1[C@H](c2ccc3c(N)ncnn23)O[C@](C#N)(COP(=O)(N[C@@H](C)C(=O)OC2CC2)Oc2ccccc2)[C@H]1OC(=O)C(C)C]
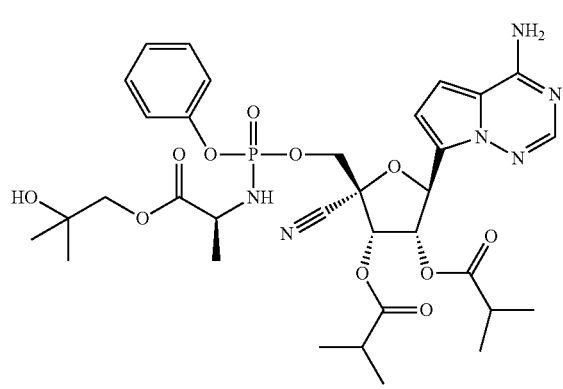 [SMILES: CC(C)C(=O)O[C@H]1[C@H](c2ccc3c(N)ncnn23)O[C@](C#N)(COP(=O)(N[C@@H](C)C(=O)OCC(C)(C)O)Oc2ccccc2)[C@H]1OC(=O)C(C)C]
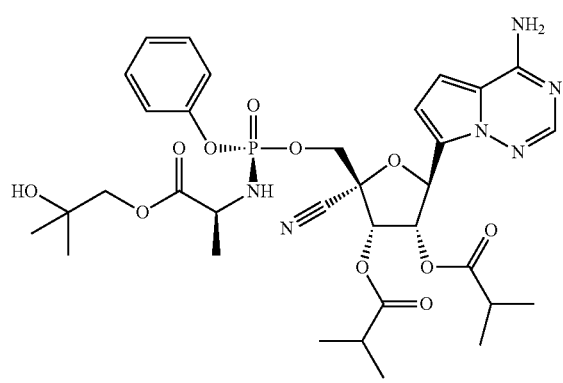 [SMILES: CC(C)C(=O)O[C@H]1[C@H](c2ccc3c(N)ncnn23)O[C@](C#N)(CO[P@](=O)(N[C@@H](C)C(=O)OCC(C)(C)O)Oc2ccccc2)[C@H]1OC(=O)C(C)C]
TABLE 1E-continued
Compounds
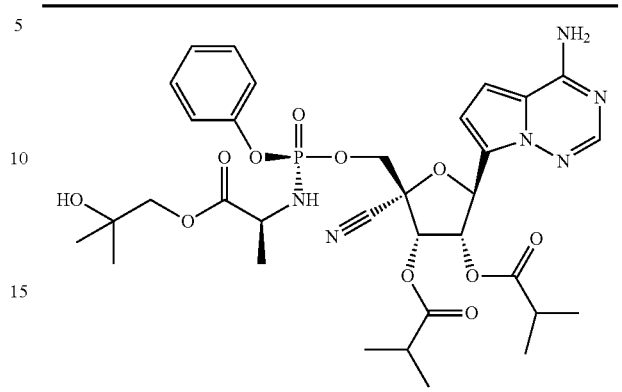
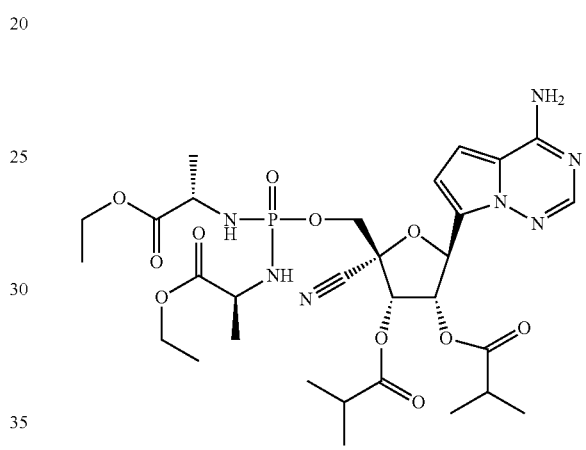
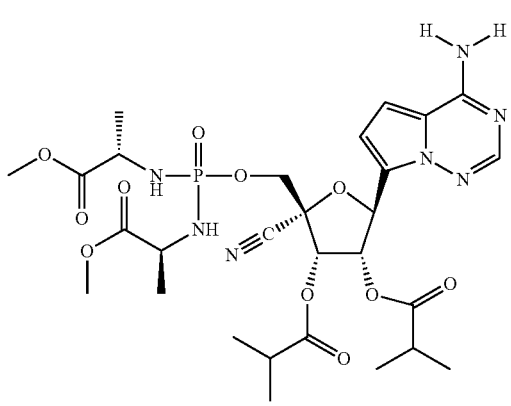 [SMILES: COC(=O)[C@H](C)NP(=O)(N[C@@H](C)C(=O)OC)OC[C@@]1(C#N)O[C@@H](c2ccc3c(N)ncnn23)[C@H](OC(=O)C(C)C)[C@@H]1OC(=O)C(C)C]
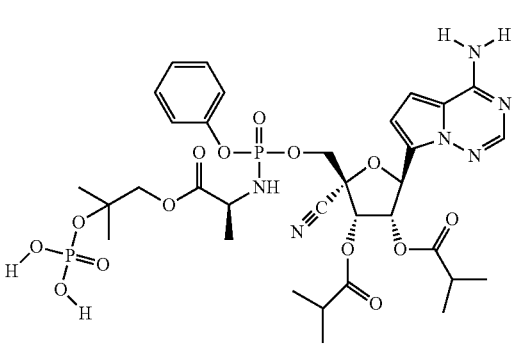 [SMILES: CC(C)C(=O)O[C@H]1[C@H](c2ccc3c(N)ncnn23)O[C@](C#N)(COP(=O)(N[C@@H](C)C(=O)OCC(C)(C)OP(=O)(O)O)Oc2ccccc2)[C@H]1OC(=O)C(C)C]

TABLE 1E-continued
Compounds
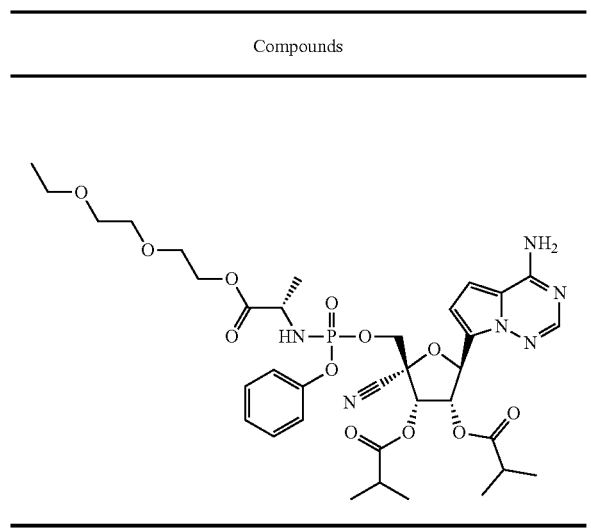
TABLE 1F
Compounds
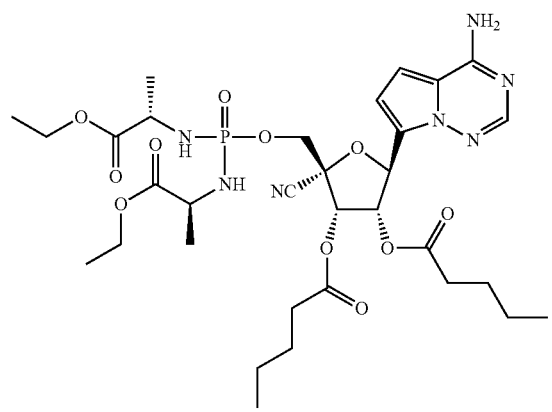 [SMILES: CCCCC(=O)O[C@H]1[C@H](c2ccc3c(N)ncnn23)O[C@](C#N)(COP(=O)(N[C@@H](C)C(=O)OCC)N[C@@H](C)C(=O)OCC)[C@H]1OC(=O)CCCC]
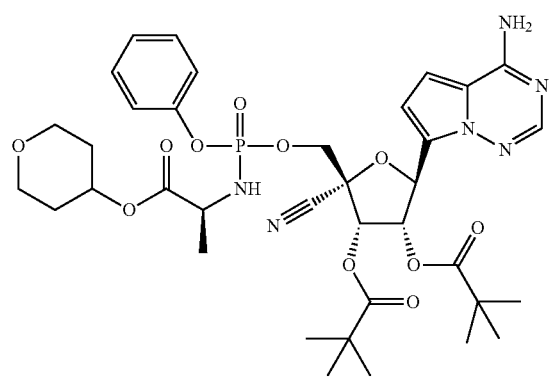 [SMILES: C[C@H](NP(=O)(OC[C@@]1(C#N)O[C@@H](c2ccc3c(N)ncnn23)[C@H](OC(=O)C(C)(C)C)[C@@H]1OC(=O)C(C)(C)C)Oc1ccccc1)C(=O)OC1CCOCC1]
TABLE 1F-continued
Compounds
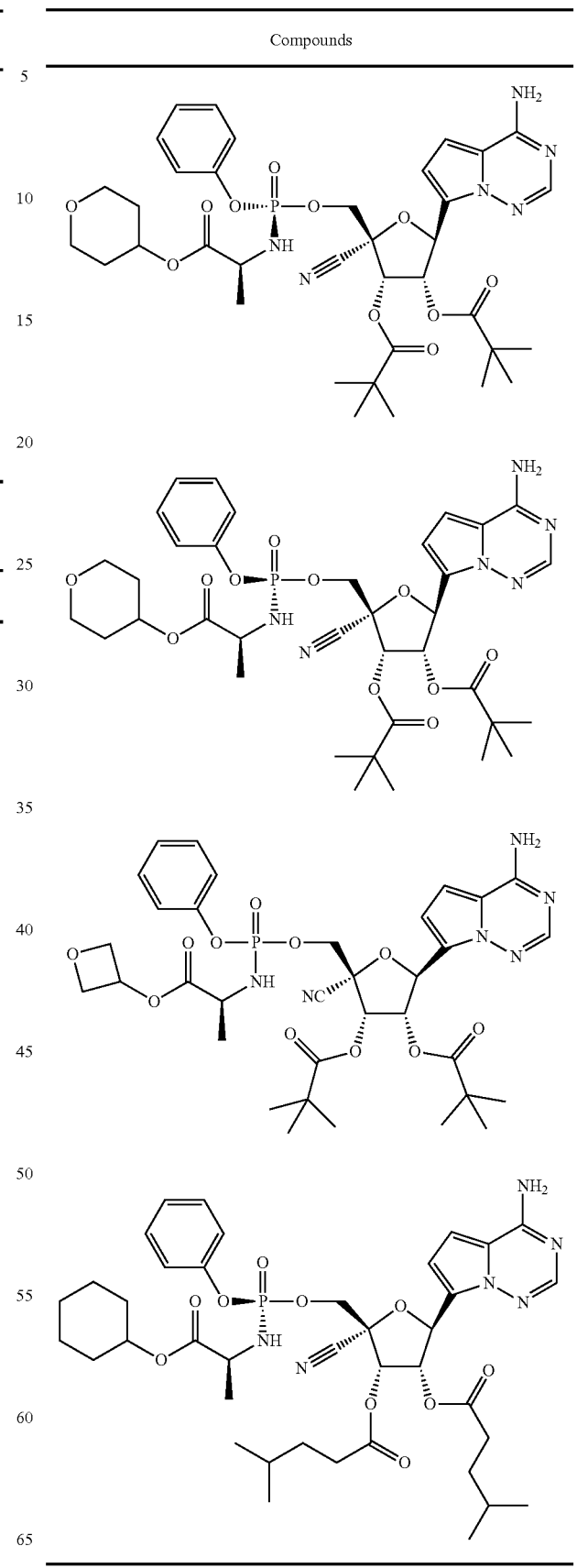

TABLE 1G

Compounds

TABLE 1G-continued

Compounds

TABLE 1G-continued

Compounds

TABLE 1H

Compounds

TABLE 1I
| Compounds |
|---|
| 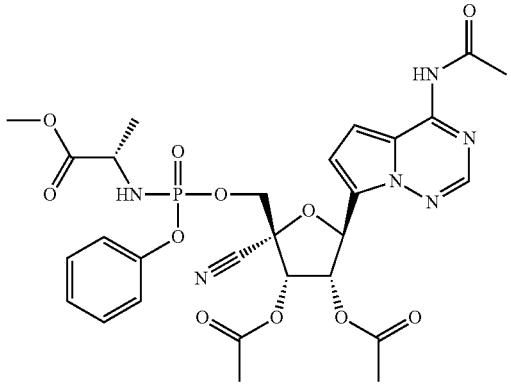 [SMILES: COC(=O)[C@H](C)NP(=O)(OC[C@@]1(C#N)O[C@@H](c2ccc3c(NC(C)=O)ncnn23)[C@H](OC(C)=O)[C@@H]1OC(C)=O)Oc1ccccc1] |
| 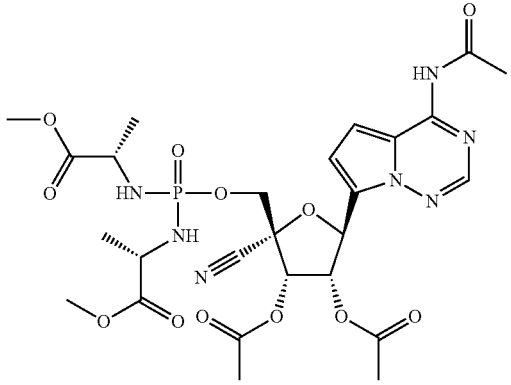 [SMILES: COC(=O)[C@H](C)NP(=O)(N[C@@H](C)C(=O)OC)OC[C@@]1(C#N)O[C@@H](c2ccc3c(NC(C)=O)ncnn23)[C@H](OC(C)=O)[C@@H]1OC(C)=O] |
| 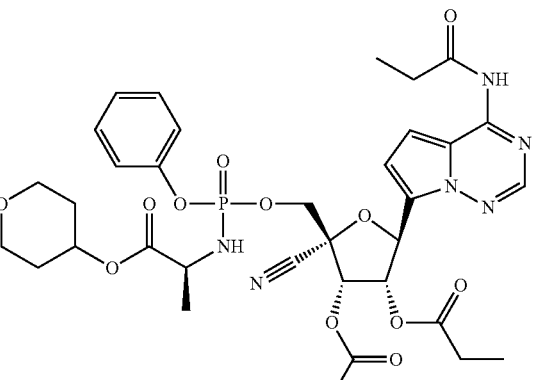 |
|  |
TABLE 1I-continued
| Compounds |
|---|
| 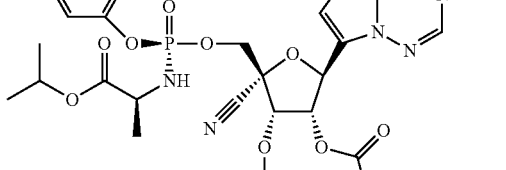 |
| 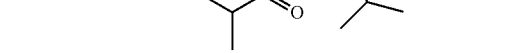 |
| 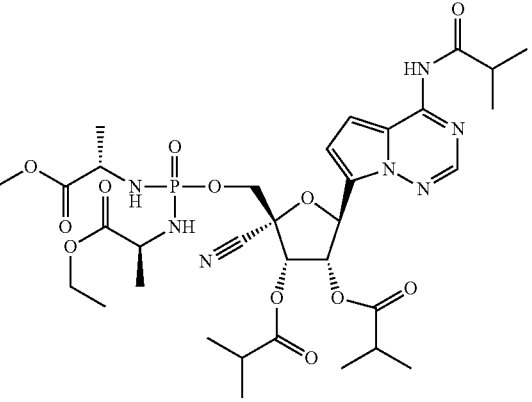 |

TABLE 1I-continued
Compounds
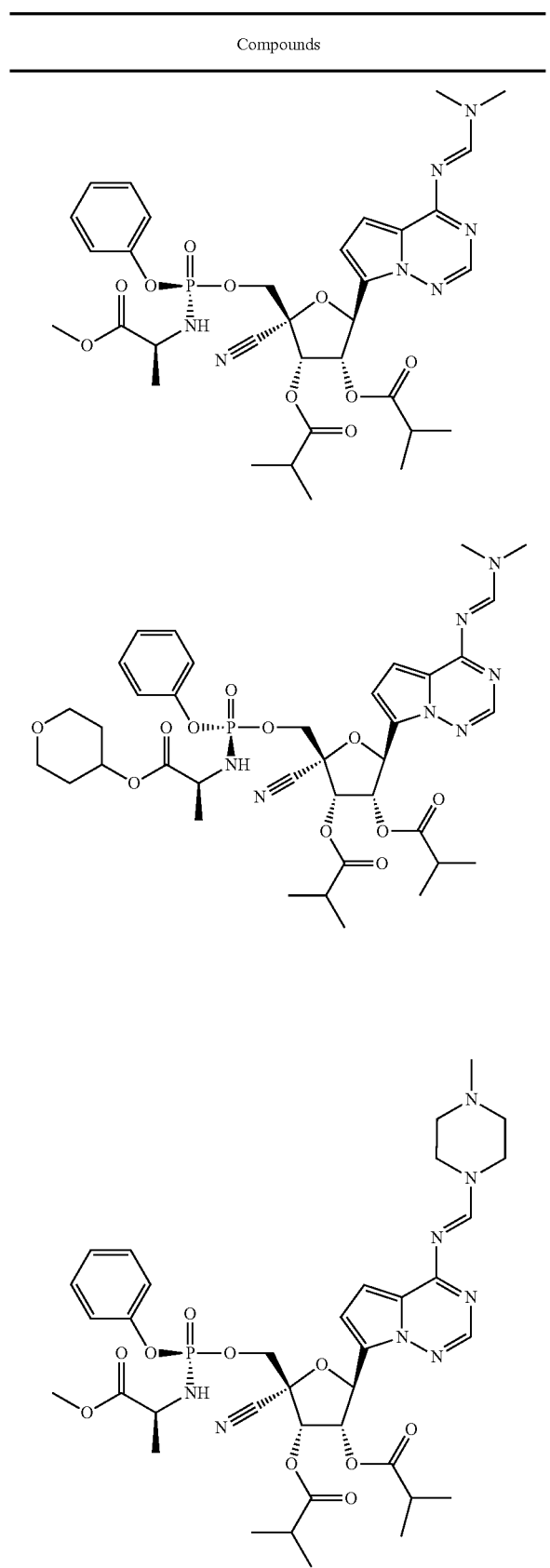
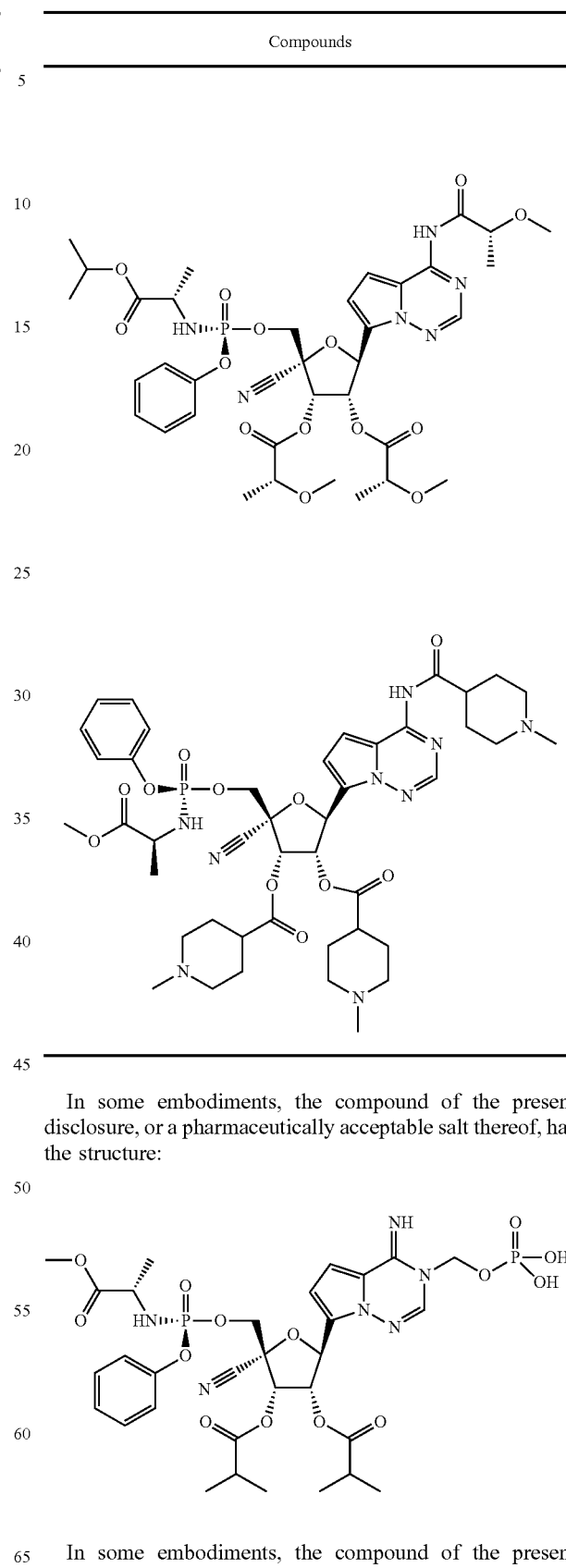
In some embodiments, the compound of the present disclosure, or a pharmaceutically acceptable salt thereof, has the structure:
In some embodiments, the compound of the present disclosure, or a pharmaceutically acceptable salt thereof, has the structure:

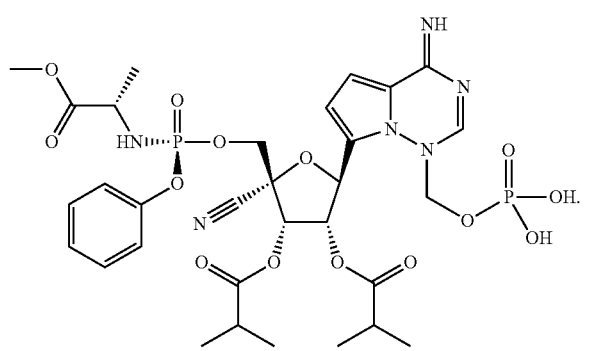 [SMILES: COC(=O)[C@H](C)N[P@](=O)(OC[C@@]1(C#N)O[C@@H](c2ccc3c(=N)ncn(COP(=O)(O)O)n23)[C@H](OC(=O)C(C)C)[C@@H]1OC(=O)C(C)C)Oc1ccccc1]
In some embodiments, the compound of the present disclosure, or a pharmaceutically acceptable salt thereof, wherein the compound is:
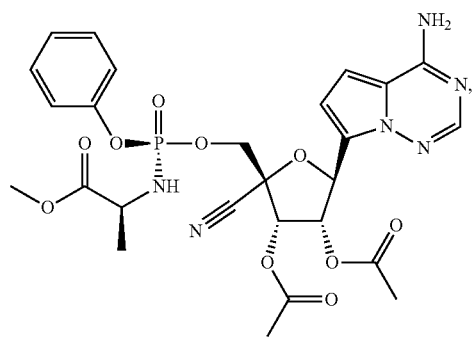
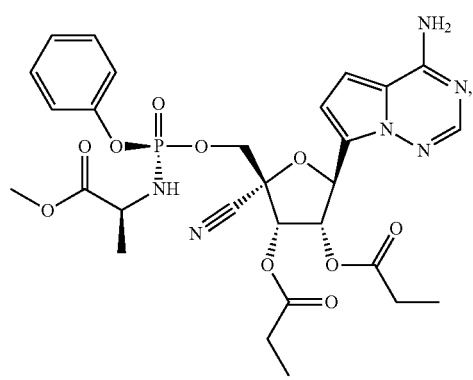
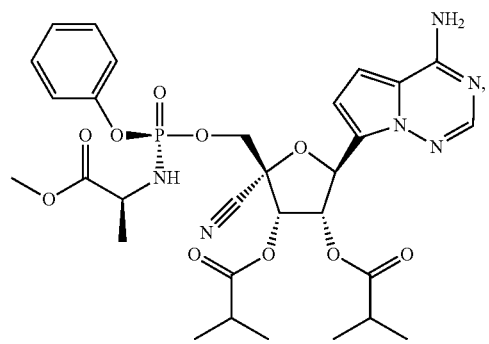
-continued
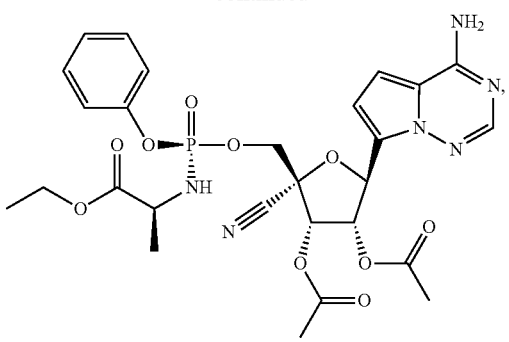
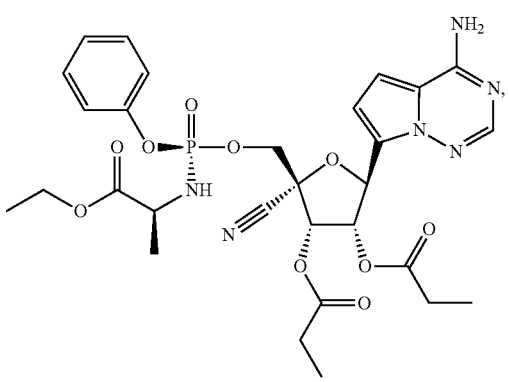
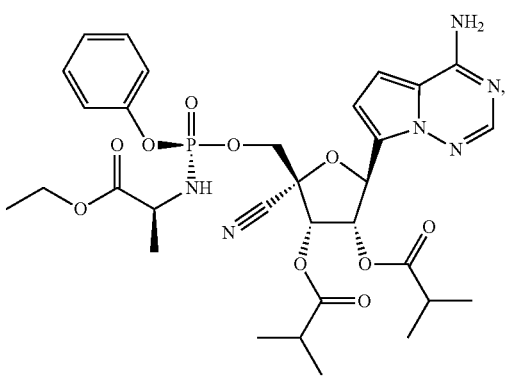
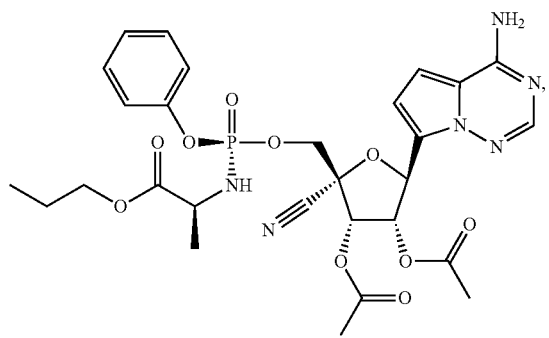

109
-continued
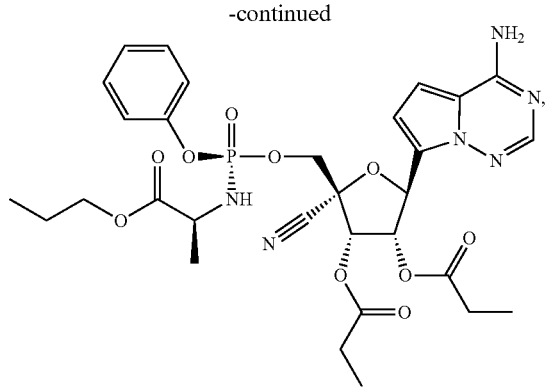
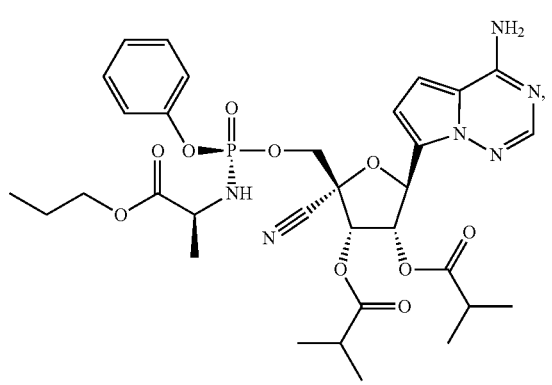
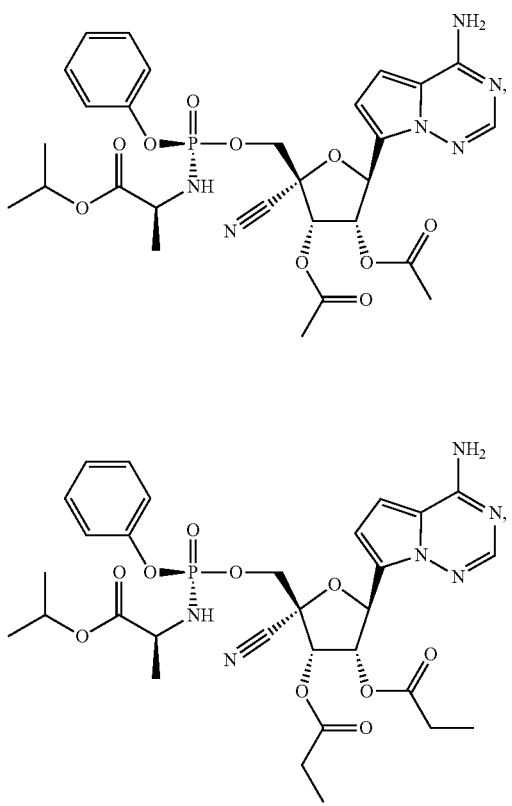
110
-continued
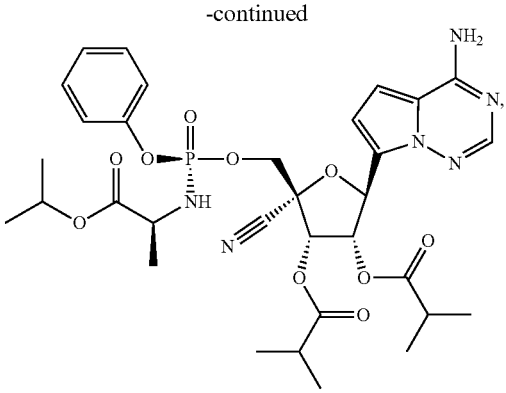
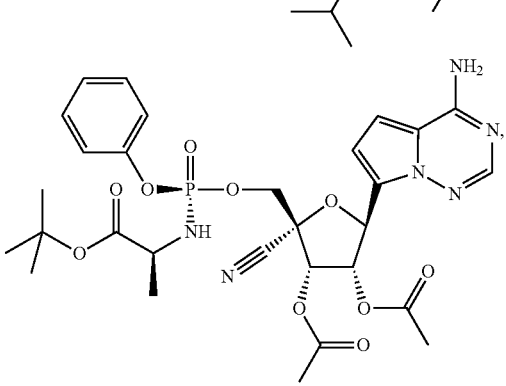

111
-continued

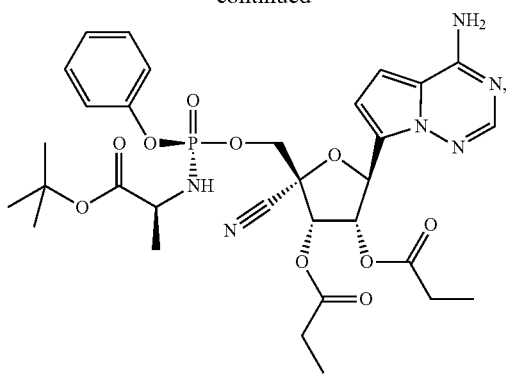

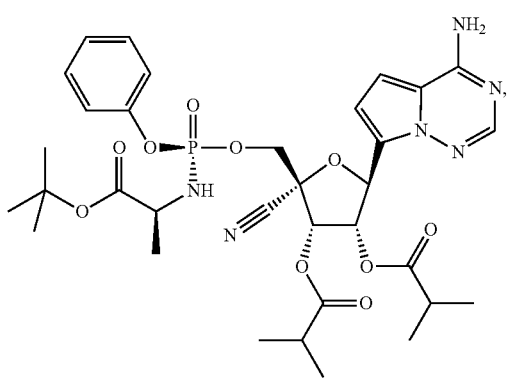

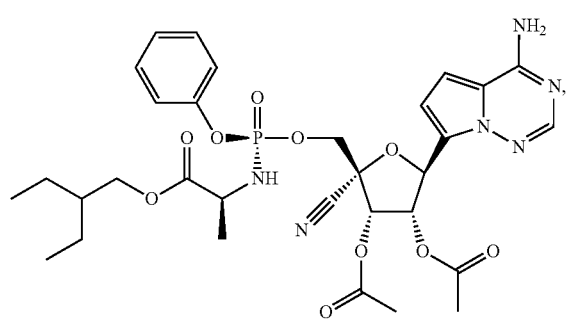

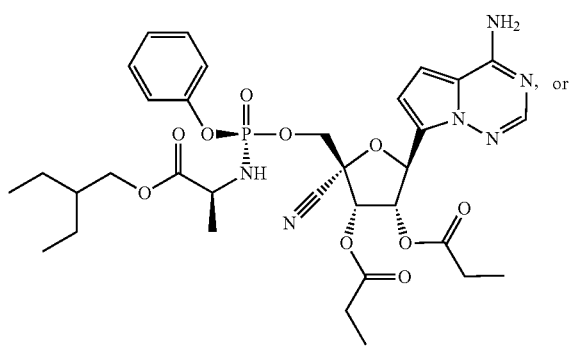

112
-continued

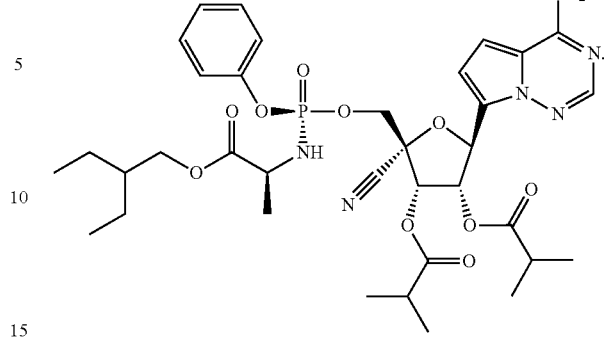

In some embodiments, the compound of the present disclosure, or a pharmaceutically acceptable salt thereof, wherein the compound is:

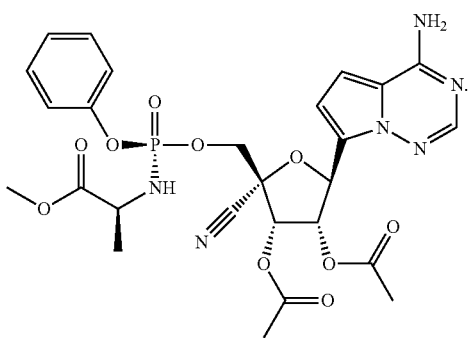 [SMILES: COC(=O)[C@H](C)N[P@](=O)(OC[C@@]1(C#N)O[C@@H](c2ccc3c(N)ncnn23)[C@H](OC(C)=O)[C@@H]1OC(C)=O)Oc1ccccc1]

In some embodiments, the compound of the present disclosure, or a pharmaceutically acceptable salt thereof, wherein the compound is:

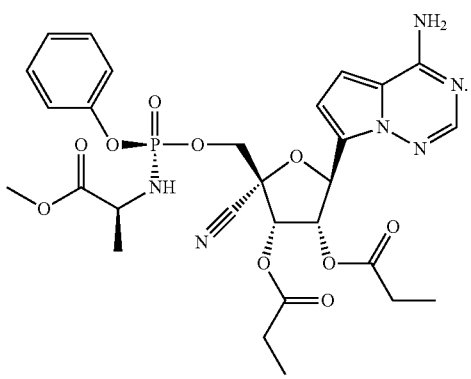 [SMILES: CCC(=O)O[C@H]1[C@H](c2ccc3c(N)ncnn23)O[C@](C#N)(CO[P@@](=O)(N[C@@H](C)C(=O)OC)Oc2ccccc2)[C@H]1OC(=O)CC]

In some embodiments, the compound of the present disclosure, or a pharmaceutically acceptable salt thereof, wherein the compound is:

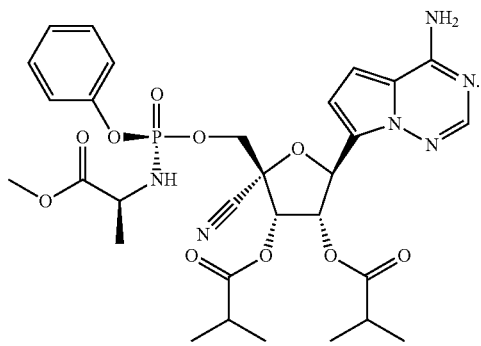 [SMILES: COC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccccc1]

In some embodiments, the compound of the present disclosure, or a pharmaceutically acceptable salt thereof, wherein the compound is:

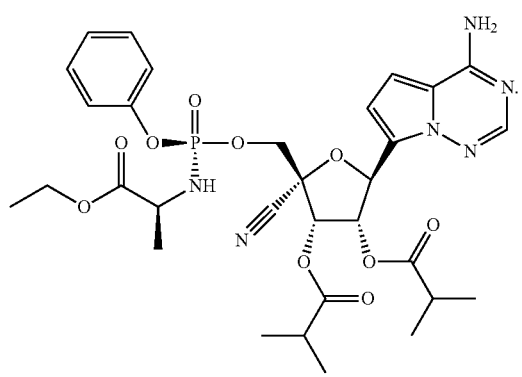 [SMILES: CCOC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccccc1]

In some embodiments, the compound of the present disclosure, or a pharmaceutically acceptable salt thereof, wherein the compound is:

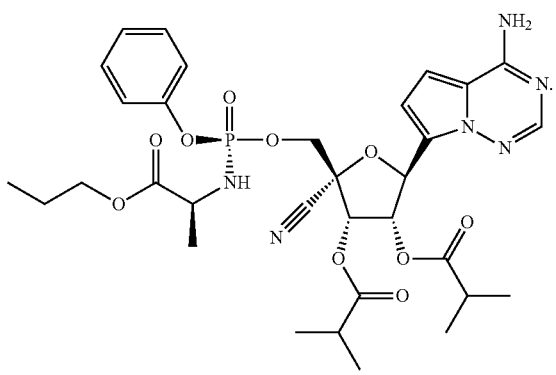 [SMILES: CCCOC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccccc1]

In some embodiments, the compound of the present disclosure, or a pharmaceutically acceptable salt thereof, wherein the compound is:

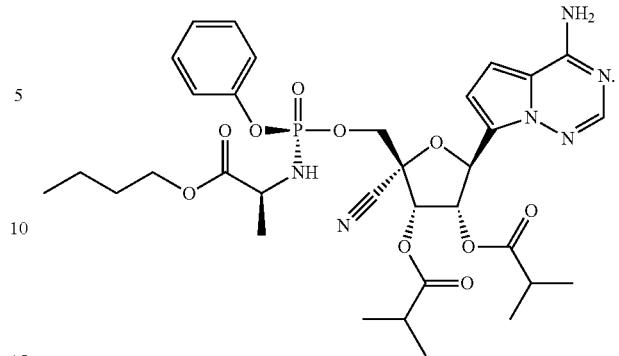

In some embodiments, the compound of the present disclosure, or a pharmaceutically acceptable salt thereof, wherein the compound is:

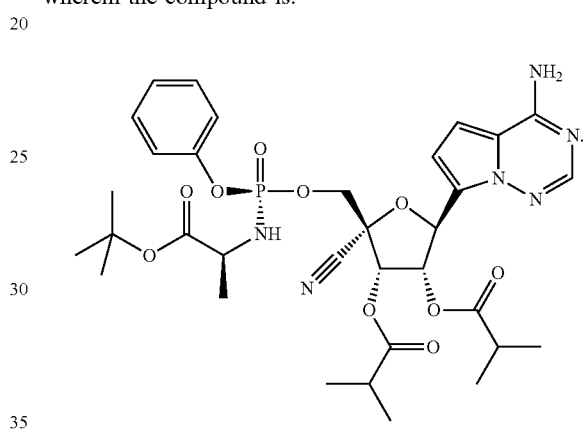

In some embodiments, the compound of the present disclosure, or a pharmaceutically acceptable salt thereof, wherein the compound is:

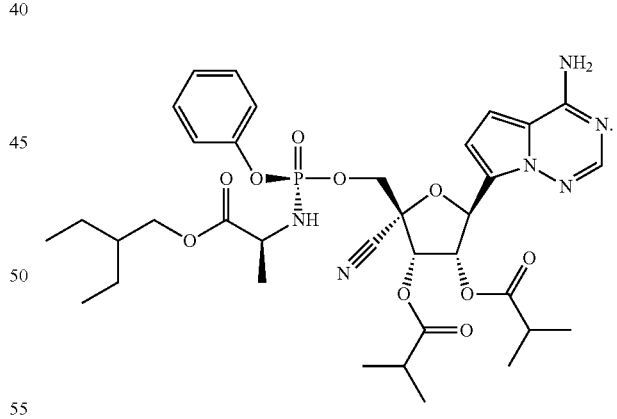

Also falling within the scope herein are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabelled (e.g., $^{14}$C or $^3$H) compound, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds even if they possess no HSV antiviral activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs typically will be stable in the digestive system but may be substantially hydrolyzed to the parental drug in the digestive lumen, liver, lung or other metabolic organ, or within cells in general. As used herein, a prodrug is understood to be a compound that is chemically designed to efficiently liberate the parent drug after overcoming biological barriers to oral delivery.

IV. Pharmaceutical Formulations

In some embodiments, the present disclosure provides a pharmaceutical formulation comprising a pharmaceutically effective amount of a compound of the present disclosure, or a pharmaceutically acceptable salt thereof, and a pharmaceutically acceptable carrier or excipient. Also provided herein is a pharmaceutical formulation comprising a pharmaceutically effective amount of a compound of Formula (II), (IIa), (IIb), (IIc), (IId), (IIe), (IIf), (IIg), (IIh), (IIi), (IIj), (IIk), (IIm) and (IIn), or a pharmaceutically acceptable salt, solvate, and/or ester thereof, and a pharmaceutically acceptable carrier or excipient.

The compounds herein are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, comprise at least one active ingredient, as above defined, together with one or more acceptable carriers and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, PA). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues, e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation include Tween® 60, Span® 80, cetostearyl alcohol, benzyl alcohol, myristyl alcohol, glyceryl monostearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations herein comprise a combination together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, solutions, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions may be in the form of a sterile injectable or intravenous preparations, such as a sterile injectable aqueous or oleaginous suspension. This suspension may be formulated according to the known art using those suitable dispersing or wetting agents and suspending agents which have been mentioned above. The sterile injectable or intravenous preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of Pneumoviridae infections as described below.

Another embodiments provides a novel, efficacious, safe, nonirritating and physiologically compatible inhalable composition comprising a compound of Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, suitable for treating Pneumoviridae infections and potentially associated bronchiolitis. Preferred pharmaceutically acceptable salts are inorganic acid salts including hydrochloride, hydrobromide, sulfate or phosphate salts as they may cause less pulmonary irritation. Preferably, the inhalable formulation is delivered to the endobronchial space in an aerosol comprising particles with a mass median aerodynamic diameter (MMAD) between about 1 and about 5 µm. Preferably, the compound of Formula (II), (IIa), (IIb), (IIc), (IId), (IIe), (IIf), (IIg), (IIh), (IIi), (IIj), (IIk), (IIm) or (IIn) is formulated for aerosol delivery using a nebulizer, pressurized metered dose inhaler (pMDI), or dry powder inhaler (DPI).

Non-limiting examples of nebulizers include atomizing, jet, ultrasonic, pressurized, vibrating porous plate, or equivalent nebulizers including those nebulizers utilizing adaptive aerosol delivery technology (Denyer, *J. Aerosol medicine Pulmonary Drug Delivery* 2010, 23 Supp 1, S1-S10). A jet nebulizer utilizes air pressure to break a liquid solution into aerosol droplets. An ultrasonic nebulizer works by a piezoelectric crystal that shears a liquid into small aerosol droplets. A pressurized nebulization system forces solution under pressure through small pores to generate aerosol droplets. A vibrating porous plate device utilizes rapid vibration to shear a stream of liquid into appropriate droplet sizes.

In a preferred embodiment, the formulation for nebulization is delivered to the endobronchial space in an aerosol comprising particles with a MMAD predominantly between about 1 µm and about 5 µm using a nebulizer able to aerosolize the formulation of the compound of Formula (II), (IIa), (IIb), (IIc), (IId), (IIe), (IIf), (IIg), (IIh), (IIi), (IIj), (IIk), (IIm) or (IIn) into particles of the required MMAD. To be optimally therapeutically effective and to avoid upper respiratory and systemic side effects, the majority of aerosolized particles should not have a MMAD greater than about 5 µm. If an aerosol contains a large number of particles with a MMAD larger than 5 µm, the particles are deposited in the upper airways decreasing the amount of drug delivered to the site of inflammation and bronchoconstriction in the lower respiratory tract. If the MMAD of the aerosol is smaller than about 1 µm, then the particles have a tendency to remain suspended in the inhaled air and are subsequently exhaled during expiration.

When formulated and delivered according to the method herein, the aerosol formulation for nebulization delivers a therapeutically efficacious dose of the compound of Formula (II), (IIa), (IIb), (IIc), (IId), (IIe), (IIf), (IIg), (IIh), (IIi), (IIj), (IIk), (IIm) or (IIn) to the site of Pneumoviridae infection sufficient to treat the Pneumoviridae infection. The amount of drug administered must be adjusted to reflect the efficiency of the delivery of a therapeutically efficacious dose of the compound of Formula (II), (IIa), (IIb), (IIc), (IId), (IIe), (IIf), (IIg), (IIh), (IIi), (IIj), (IIk), (IIm) or (IIn). In a preferred embodiment, a combination of the aqueous aerosol formulation with the atomizing, jet, pressurized, vibrating porous plate, or ultrasonic nebulizer permits, depending on the nebulizer, about, at least, 20, to about 90%, typically about 70% delivery of the administered dose of the compound of Formula (II), (IIa), (IIb), (IIc), (IId), (IIe), (IIf), (IIg), (IIh), (IIi), (IIj), (IIk), (IIm) or (IIn) into the airways. In a preferred embodiment, at least about 30 to about 50% of the active compound is delivered. More preferably, about 70 to about 90% of the active compound is delivered.

In another embodiment, a compound of Formula (II), (IIa), (IIb), (IIc), (IId), (IIe), (IIf), (IIg), (IIh), (IIi), (IIj), (IIk), (IIm) or (IIn) or a pharmaceutically acceptable salt thereof, is delivered as a dry inhalable powder. The compounds are administered endobronchially as a dry powder formulation to efficacious deliver fine particles of compound into the endobronchial space using dry powder or metered dose inhalers. For delivery by DPI, the compound of Formula (II), (IIa), (IIb), (IIc), (IId), (IIe), (IIf), (IIg), (IIh), (IIi), (IIj), (IIk), (IIm) or (IIn) is processed into particles with, predominantly, MMAD between about 1 µm and about 5 µm by milling spray drying, critical fluid processing, or precipitation from solution. Media milling, jet milling and spray-drying devices and procedures capable of producing the particle sizes with a MMAD between about 1 µm and about 5 µm are well known in the art. In one embodiment, excipients are added to the compound of Formula (II), (IIa), (IIb), (IIc), (IId), (IIe), (IIf), (IIg), (IIh), (IIi), (IIj), (IIk), (IIm) or (IIn) before processing into particles of the required sizes. In another embodiment, excipients are blended with the particles of the required size to aid in dispersion of the drug particles, for example by using lactose as an excipient.

Particle size determinations are made using devices well known in the art. For example a multi-stage Anderson cascade impactor or other suitable method such as those specifically cited within the US Pharmacopoeia Chapter 601 as characterizing devices for aerosols within metered-dose and dry powder inhalers.

In another preferred embodiment, a compound of Formula (II), (IIa), (IIb), (IIc), (IId), (IIe), (IIf), (IIg), (IIh), (IIi), (IIj), (IIk), (IIm) or (IIn) is delivered as a dry powder using a device such as a dry powder inhaler or other dry powder dispersion devices. Non-limiting examples of dry powder inhalers and devices include those disclosed in U.S. Pat. Nos. 5,458,135; 5,740,794; 5,775,320; 5,785,049; 3,906,950; 4,013,075; 4,069,819; 4,995,385; 5,522,385; 4,668,218; 4,667,668; 4,805,811 and 5,388,572. There are two major designs of dry powder inhalers. One design is a metering device in which a reservoir for the drug is place within the device and the patient adds a dose of the drug into the inhalation chamber. The second design is a factory-metered device in which each individual dose has been manufactured in a separate container. Both systems depend on the formulation of the drug into small particles of MMAD from 1 µm and about 5 µm and often involve co-formulation with larger excipient particles such as, but not limited to, lactose. Drug powder is placed in the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs. In preferred embodiments, a compound of Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, is delivered as a dry powder using either type of dry powder inhaler as described herein, wherein the MMAD of the dry powder, exclusive of any excipients, is predominantly in the range of 1 µm to about 5 µm.

In another embodiment, a compound of Formula (II), (IIa), (IIb), (IIc), (IId), (IIe), (IIf), (IIg), (IIh), (IIi), (IIj), (IIk), (IIm) or (IIn) is delivered as a dry powder using a metered dose inhaler. Non-limiting examples of metered dose inhalers and devices include those disclosed in U.S. Pat. Nos. 5,261,538; 5,544,647; 5,622,163; 4,955,371; 3,565,070; 3,361,306 and 6,116,234. In preferred embodiments, a compound of Formula (II), (IIa), (IIb), (IIc), (IId), (IIe), (IIf), (IIg), (IIh), (IIi), (IIj), (IIk), (IIm) or (IIn), or a pharmaceutically acceptable salt thereof, is delivered as a dry powder using a metered dose inhaler wherein the MMAD of the dry powder, exclusive of any excipients, is predominantly in the range of about 1-5 µm.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations may include other agents conventional in the art having regard to the type of formulation in question, for example those suitable for oral administration may include flavoring agents.

Further provided are veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds herein are used to provide controlled release pharmaceutical formulations containing as active ingredient one or more of the compounds ("controlled release formulations") in which the release of the active ingredient is controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

V. Routes of Administration

One or more of the compounds of Formula (II), (IIa), (IIb), (IIc), (IId), (IIe), (IIf), (IIg), (IIh), (IIi), (IIj), (IIk), (IIm) or (IIn) (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds herein is that they are orally bioavailable and can be dosed orally.

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with for example the condition of the recipient. An advantage of certain compounds disclosed herein is that they are orally bioavailable and can be dosed orally.

A compound of the present disclosure, may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In some embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from 1 mg to 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, 125, 150, 175, 200, 225, 250, 275, 300, 325, 350, 375, 400, 425, 450, 475, or about 500 mg per dose. Other therapeutically effective amounts of the compound of the present disclosure are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In some embodiments, a single dose can be administered once every week. A single dose can also be administered once every month.

Other therapeutically effective amounts of the compound of the present disclosure are about 20, 25, 30, 35, 40, 45, 50, 55, 60, 65, 70, 75, 80, 85, 90, 95, or about 100 mg per dose.

The frequency of dosage of the compound of the present disclosure are will be determined by the needs of the individual patient and can be, for example, once per day or twice, or more times, per day. Administration of the compound continues for as long as necessary to treat the viral infection. For example, a compound can be administered to a human being infected with a virus for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

In one embodiment, pharmaceutical compositions comprising a compound of the present disclosure, or a pharmaceutically acceptable salt thereof, in combination with one or more (e.g., one, two, three, four, one or two, one to three, or one to four) additional therapeutic agents, and a pharmaceutically acceptable excipient are provided.

In one embodiment, kits comprising a compound of the present disclosure, or a pharmaceutically acceptable salt thereof, in combination with one or more (e.g., one, two, three, four, one or two, one to three, or one to four) additional therapeutic agents are provided.

In some embodiments, a compound of the present disclosure, or a pharmaceutically acceptable salt thereof, is combined with one, two, three, four or more additional therapeutic agents. In some embodiments, a compound of the present disclosure, or a pharmaceutically acceptable salt thereof, is combined with two additional therapeutic agents. In other embodiments, a compound of the present disclosure, or a pharmaceutically acceptable salt thereof, is combined with three additional therapeutic agents. In further embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In some embodiments, when a compound of the present disclosure is combined with one or more additional therapeutic agents as described herein, the components of the composition are administered as a simultaneous or sequential regimen. When administered sequentially, the combination may be administered in two or more administrations.

In some embodiments, a compound of the present disclosure is combined with one or more additional therapeutic agents in a unitary dosage form for simultaneous administration to a patient, for example as a solid dosage form for oral administration.

In some embodiments, a compound of the present disclosure is co-administered with one or more additional therapeutic agents.

In order to prolong the effect of a compound of the present disclosure, it is often desirable to slow the absorption of a compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending a compound in an oil vehicle. Injectable depot forms are made by forming microencapsule matrices of a compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping a compound in liposomes or microemulsions that are compatible with body tissues.

VI. Combination Therapy

The compounds of Formula (II), (IIa), (IIb), (IIc), (IId), (IIe), (IIf), (IIg), (IIh), (IIi), (IIj), (IIk), (IIm) or (IIn) and compositions provided herein are also used in combination with other active therapeutic agents for the treatment of virus infections, such as Pneumoviridae, Picornaviridae, Flaviviridae, or Filoviridae virus infections.

Combination Therapy for the Treatment of Pneumoviridae

The compounds and compositions provided herein are also used in combination with other active therapeutic agents. For the treatment of Pneumoviridae virus infections, preferably, the other active therapeutic agent is active against Pneumoviridae virus infections, particularly respiratory syncytial virus infections and/or metapneumovirus infections. Non-limiting examples of these other active therapeutic agents active against RSV are ribavirin, palivizumab, motavizumab, RSV-IGIV (RespiGam®), MEDI-557, A-60444 (also known as RSV604), MDT-637, BMS-433771, ALN-RSVO, ALX-0171 and mixtures thereof. Other non-limiting examples of other active therapeutic agents active against respiratory syncytial virus infections include respiratory syncytial virus protein F inhibitors, such as AK-0529; RV-521, ALX-0171, JNJ-53718678, BTA-585, and presatovir; RNA polymerase inhibitors, such as lumicitabine and ALS-8112; anti-RSV G protein antibodies, such as anti-G-protein mAb; viral replication inhibitors, such as nitazoxanide.

In some embodiments, the other active therapeutic agent may be a vaccine for the treatment or prevention of RSV, including but not limited to MVA-BN RSV, RSV-F, MEDI-8897, JNJ-64400141, DPX-RSV, SynGEM, GSK-3389245A, GSK-300389-1A, RSV-MEDI deltaM2-2 vaccine, VRC-RSVRGP084-OOVP, Ad35-RSV-FA2, Ad26-RSV-FA2, and RSV fusion glycoprotein subunit vaccine.

Non-limiting examples of other active therapeutic agents active against metapneumovirus infections include sialidase modulators such as DAS-181; RNA polymerase inhibitors, such as ALS-8112; and antibodies for the treatment of Metapneumovirus infections, such as EV-046113.

In some embodiments, the other active therapeutic agent may be a vaccine for the treatment or prevention of metapneumovirus infections, including but not limited to mRNA-1653 and rHMPV-Pa vaccine.

Combination Therapy for the Treatment of Picornaviridae

The compounds and compositions provided herein are also used in combination with other active therapeutic agents. For the treatment of Picornaviridae virus infections, preferably, the other active therapeutic agent is active against Picornaviridae virus infections, particularly Enterovirus infections. Non-limiting examples of these other active therapeutic agents are capsid binding inhibitors such as pleconaril, BTA-798 (vapendavir) and other compounds disclosed by Wu, et al. (U.S. Pat. No. 7,078,403) and Watson (U.S. Pat. No. 7,166,604); fusion sialidase protein such as DAS-181; a capsid protein VP1 inhibitor such as VVX-003 and AZN-001; a viral protease inhibitor such as CW-33; a phosphatidylinositol 4 kinase beta inhibitor such as GSK-480 and GSK-533; anti-EV71 antibody.

In some embodiments, the other active therapeutic agent may be a vaccine for the treatment or prevention of Picornaviridae virus infections, including but not limited to EV71 vaccines, TAK-021, and EV-D68 adenovector-based vaccine.

Combination Therapy for Respiratory Infections

Many of the infections of the Pneumoviridae and Picornaviridae viruses are respiratory infections. Therefore, additional active therapeutics used to treat respiratory symptoms and sequelae of infection may be used in combination with the compounds provided herein. The additional agents are preferably administered orally or by direct inhalation. For example, other preferred additional therapeutic agents in combination with the compounds provided herein for the treatment of viral respiratory infections include, but are not limited to, bronchodilators and corticosteroids.

Glucocorticoids

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds provided herein are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone, AZD-7594, ciclesonide; or a pharmaceutically acceptable salts thereof.

Anti-Inflammatory Agents

Other anti-inflammatory agents working through anti-inflammatory cascade mechanisms are also useful as additional therapeutic agents in combination with the compounds provided herein for the treatment of viral respiratory infections. Applying "anti-inflammatory signal transduction modulators" (referred to in this text as AISTM), like phosphodiesterase inhibitors (e.g., PDE-4, PDE-5, or PDE-7 specific), transcription factor inhibitors (e.g., blocking NFκB through IKK inhibition), or kinase inhibitors (e.g., blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluorophenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

β2-Adrenoreceptor Agonist Bronchodilators

Combinations comprising inhaled β2-adrenoreceptor agonist bronchodilators such as formoterol, albuterol or salmeterol with the compounds provided herein are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds provided herein are also suitable, but non-limiting, combinations useful for the treatment of respiratory viral infections.

Other examples of Beta 2 adrenoceptor agonists are bedoradrine, vilanterol, indacaterol, olodaterol, tulobuterol, formoterol, abediterol, salbutanol, arformoterol, levalbuterol, fenoterol, and TD-5471.

Anticholinergics

For the treatment or prophylaxis of pulmonary bronchoconstriction, anticholinergics are of potential use and, therefore, useful as an additional therapeutic agent in combination with the compounds provided herein for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo[3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester; revefenacin, glycopyrronium bromide, umeclidinium bromide, tiotropium bromide, aclidinium bromide, bencycloquidium bromide.

Mucolytic Agents

The compounds provided herein and the compositions provided herein may also be combined with mucolytic agents to treat both the infection and symptoms of respiratory infections. A non-limiting example of a mucolytic agent is ambroxol. Similarly, the compounds of Formula (I), (Ia), (Ib), (Ic), (Id), (Ie), (If), (Ig), (Ih), (Ij), (Ik), (Im) or (In) may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, *J. Pediatrics* 2007, 266). Thus, the compounds provided herein may also be combined with nebulized hypertonic saline particularly when the Pneumoviridae virus infection is complicated with bronchiolitis. The combination of the compounds of Formula (I) or Formula (II) with hypertonic saline may also comprise any of the additional agents discussed above. In one embodiment, nebulized about 3% hypertonic saline is used.

Combination Therapy for the Treatment of COPD

The compounds and compositions provided herein are also used in combination with other active therapeutic agents. For the treatment of respiratory exacerbations of COPD, the other active therapeutic agents include other active against COPD. Non-limiting examples of these other active therapeutic agents include anti-IL5 antibodies, such as benralizumab, mepolizumab; dipeptidyl peptidase I (DPP1) inhibitors, such as AZD-7986 (INS-1007); DNA gyrase inhibitor/topoisomerase IV inhibitors, such as ciprofloxacin hydrochloride; MDR associated protein 4/phosphodiesterase (PDE) 3 and 4 inhibitors, such as RPL-554; CFTR stimulators, such as ivacaftor, QBW-251; MMP-9/MMP-12 inhibitors, such as RBx-10017609; Adenosine A1 receptor antagonists, such as PBF-680; GATA 3 transcription factor inhibitors, such as SB-010; muscarinic receptor modulator/nicotinic acetylcholine receptor agonists, such as ASM-024; MARCKS protein inhibitors, such as BIG-11006; kit tyrosine kinase/PDGF inhibitors such as masitinib; phosphodiesterase (PDE) 4 inhibitors, such as roflumilast, CHF-6001; phosphoinositide-3 kinase delta inhibitors, such as nemiralisib; 5-Lipoxygenase inhibitors, such as TA-270; muscarinic receptor antagonist/beta 2 adrenoceptor agonist, such as batefenterol succinate, AZD-887, ipratropium bromide; TRN-157; elastase inhibitors, such as erdosteine; metalloprotease-12 inhibitors such as FP-025; interleukin 18 ligand inhibitors, such as tadekinig alfa; skeletal muscle troponin activators, such as CK-2127107; p38 MAP kinase inhibitors, such as acumapimod; IL-17 receptor modulators, such as CNTO-6785; CXCR2 chemokine antagonists, such as danirixin; leukocyte elastase inhibitors, such as POL-6014; epoxide hydrolase inhibitors, such as GSK-2256294; HNE inhibitors, such as CHF-6333;

VIP agonists, such as aviptadil; phosphoinositide-3 kinase delta/gamma inhibitors, such as RV-1729; complement $C_3$ inhibitors, such as APL-1; and G-protein coupled receptor-44 antagonists, such as AM-211.

Other non-limiting examples of active therapeutic agents also include budesonide, adipocell, nitric oxide, PUR-1800, YLP-001, LT-4001, azithromycin, gamunex, QBKPN, sodium pyruvate, MUL-1867, mannitol, MV-130, MEDI-3506, BI-443651, VR-096, OPK-0018, TEV-48107, doxofylline, TEV-46017, OligoG-COPD-5/20, Stempeucel®, ZP-051, lysine acetylsalicylate.

In some embodiments, the other active therapeutic agent may be a vaccine that is active against COPD, including but not limited to MV-130 and GSK-2838497A.

Combination Therapy for the Treatment of Dengue

The compounds and compositions provided herein are also used in combination with other active therapeutic agents. For the treatment of Flaviviridae virus infections, preferably, the other active therapeutic agent is active against Flaviviridae virus infections, particularly dengue infections. Non-limiting examples of these other active therapeutic agents are host cell factor modulators, such as GBV-006; fenretinide ABX-220, BRM-211; alpha-glucosidase 1 inhibitors, such as celgosivir; platelet activating factor receptor (PAFR) antagonists, such as modipafant; cadherin-5/Factor Ia modulators, such as FX-06; NS4B inhibitors, such as JNJ-8359; viral RNA splicing modulators, such as ABX-202; a NS5 polymerase inhibitor; a NS3 protease inhibitor; and a TLR modulator.

In some embodiments, the other active therapeutic agent may be a vaccine for the treatment or prevention of dengue, including but not limited to TetraVax-DV, Dengvaxia®, DPIV-001, TAK-003, live attenuated dengue vaccine, tetravalent dengue fever vaccine, tetravalent DNA vaccine, rDEN2delta30-7169; and DENV-1 PIV.

Combination Therapy for the Treatment of Ebola

The compounds and compositions provided herein are also used in combination with other active therapeutic agents. For the treatment of Filoviridae virus infections, preferably, the other active therapeutic agent is active against Filoviridae virus infections, particularly Marburg virus, Ebola virus and Cueva virus infections. Non-limiting examples of these other active therapeutic agents are: ribavirin, palivizumab, motavizumab, RSV-IGIV (RespiGam©), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), TKM-Ebola, T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), rNAPc2, OS-2966, brincidofovir, remdesivir; RNA polymerase inhibitors, such as galidesivir, favipiravir (also known as T-705 or Avigan), JK-05; host cell factor modulators, such as GMV-006; cadherin-5/factor Ia modulators, such as FX-06; and antibodies for the treatment of Ebola, such as REGN-3470-3471-3479 and ZMapp.

Other non-limiting active therapeutic agents active against Ebola include an alpha-glucosidase 1 inhibitor, a cathepsin B inhibitor, a CD29 antagonist, a dendritic ICAM-3 grabbing nonintegrin 1 inhibitor, an estrogen receptor antagonist, a factor VII antagonist HLA class II antigen modulator, a host cell factor modulator, a Interferon alpha ligand, a neutral alpha glucosidase AB inhibitor, a niemann-Pick $C_1$ protein inhibitor, a nucleoprotein inhibitor, a polymerase cofactor VP35 inhibitor, a Serine protease inhibitor, a tissue factor inhibitor, a TLR-3 agonist, a viral envelope glycoprotein inhibitor, and an Ebola virus entry inhibitors (NPC1 inhibitors).

In some embodiments, the other active therapeutic agent may be a vaccine for the treatment or prevention of Ebola, including but not limited to VRC-EBOADC076-00-VP, adenovirus-based Ebola vaccine, rVSV-EBOV, rVSVN4CT1-EBOVGP, MVA-BN Filo+Ad26-ZEBOV regimen, INO-4212, VRC-EBODNA023-00-VP, VRC-EBOADC069-00-VP, GamEvac-combi vaccine, SRC VB Vector, HPIV3/EboGP vaccine, MVA-EBOZ, Ebola recombinant glycoprotein vaccine, Vaxart adenovirus vector 5-based Ebola vaccine, FiloVax vaccine, GOVX-E301, and GOVX-E302.

The compounds and compositions provided herein may also be used in combination with phosphoramidate morpholino oligomers (PMOs), which are synthetic antisense oligonucleotide analogs designed to interfere with translational processes by forming base-pair duplexes with specific RNA sequences. Examples of PMOs include but are not limited to AVI-7287, AVI-7288, AVI-7537, AVI-7539, AVI-6002, and AVI-6003.

The compounds and compositions provided herein are also intended for use with general care provided to patients with Filoviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

VII. Methods of Treating Viral Infections

The present disclosure provides methods for treating a variety of diseases, such as respiratory syncytial virus (RSV), ebola, Zika, West Nile, Dengue, and HCV using compounds of Formula (I), (Ia), (Ib), (Ic), (Id), (Ie), (If), (Ig), (Ih), (Ij), (Ik), (Im) or (In).

Paramyxoviridae

In some embodiments, the present disclosure provides methods for treating a Paramyxoviridae infection, comprising administering to an individual (e.g., a human) infected with Paramyxoviridae virus a therapeutically effective amount a compound of the present disclosure or a pharmaceutically acceptable salt thereof. Paramyxoviridae viruses include, but are not limited to Nipah virus and parainfluenze virus.

Pneumoviridae

In some embodiments, the present disclosure provides a method of treating a Pneumoviridae virus infection in a human in need thereof, the method comprising administering to the human a therapeutically effective amount of a compound of the present disclosure, or a pharmaceutically acceptable salt thereof. Pneumoviridae viruses include, but are not limited to, respiratory snycytial virus, and human metapneumovirus. In some embodiments, the Pneumoviridae virus infection is a respiratory syncytial virus infection.

In some embodiments, the Pneumoviridae virus infection is human metapneumovirus infection.

In some embodiments, the present disclosure provides a method for manufacturing a medicament for treating a Pneumoviridae virus infection in a human in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a human of a Pneumoviridae virus infection. In some embodiments, the Pneumoviridae virus infection is a respiratory syncytial virus infection. In some embodiments, the Pneumoviridae virus infection is human metapneumovirus infection.

In some embodiments, the present disclosure provides a compound of the present disclosure, or a pharmaceutically acceptable salt thereof, for use in the treatment of a Pneumoviridae virus infection in a human in need thereof. In some embodiments, the Pneumoviridae virus infection is a respiratory syncytial virus infection. In some embodiments, the Pneumoviridae virus infection is human metapneumovirus infection.

In some embodiments, the present disclosure provides methods for treating a RSV infection, comprising administering to an individual (e.g., a human) infected with respiratory syncytial virus a therapeutically effective amount a compound of the present disclosure or a pharmaceutically acceptable salt thereof. Typically, the individual is suffering from a chronic respiratory syncytial viral infection, although it is within the scope of the present disclosure to treat people who are acutely infected with RSV.

In some embodiments, a method of inhibiting RSV replication is provided, comprising administering a compound of the present disclosure, or a pharmaceutically acceptable salt thereof, to an individual (e.g., a human).

In some embodiments, the present disclosure provides a method for reducing the viral load associated with RSV infection, wherein the method comprises administering to an individual (e.g., a human) infected with RSV a therapeutically effective amount of a compound of the present disclosure, or a pharmaceutically acceptable salt thereof, wherein the therapeutically effective amount is sufficient to reduce the RSV viral load in the individual.

As described more fully herein, compounds of the present disclosure can be administered with one or more additional therapeutic agent(s) to an individual (e.g., a human) infected with RSV. The additional therapeutic agent(s) can be administered to the infected individual (e.g., a human) at the same time as a compound of the present disclosure or before or after administration of a compound of the present disclosure.

In some embodiments, a compound of the present disclosure, or a pharmaceutically acceptable salt thereof, for use in treating or preventing a RSV infection is provided. In some embodiments, a compound of the present disclosure (e.g., a compound of Formula (I), (Ia), (Ib), (Ic), (Id), (Ie), (If), (Ig), (Ih), (Ij), (Ik), (Im) or (In)), or a pharmaceutically acceptable salt thereof, for the manufacture of a medicament for treating or preventing a RSV infection is provided.

As described more fully herein, compounds of the present disclosure can be administered with one or more additional therapeutic agent(s) to an individual (e.g., a human) infected with RSV. Further, in some embodiments, when used to treat or prevent RSV, a compound of the present disclosure may be administered with one or more (e.g., one, two, three, four or more) additional therapeutic agent(s) selected from the group consisting of RSV combination drugs, RSV vaccines, RSV DNA polymerase inhibitors, immunomodulators toll-like receptor (TLR) modulators, interferon alpha receptor ligands, hyaluronidase inhibitors, respiratory syncytial surface antigen inhibitors, cytotoxic T-lymphocyte-associated protein 4 (ipi4) inhibitors, cyclophilin inhibitors, RSV viral entry inhibitors, antisense oligonucleotide targeting viral mRNA, short interfering RNAs (siRNA) and ddRNAi endonuclease modulators, ribonucelotide reductase inhibitors, RSV E antigen inhibitors, covalently closed circular DNA (cccDNA) inhibitors, farnesoid X receptor agonists, RSV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, RSV replication inhibitors, arginase inhibitors, and other RSV drugs.

Picornaviridae

In some embodiments, the present disclosure provides a method of treating a Picornaviridae virus infection in a human in need thereof, the method comprising administering to the human a therapeutically effective amount of a compound of the present disclosure, or a pharmaceutically acceptable salt thereof. Picornaviridae viruses are eneteroviruses causing a heterogeneous group of infections including herpangina, aseptic meningitis, a common-cold-like syndrome (human rhinovirus infection), a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis. In some embodiments, the Picornaviridae virus infection is human rhinovirus infection.

In some embodiments, the present disclosure provides a method for manufacturing a medicament for treating a Picornaviridae virus infection in a human in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a human of a Picornaviridae virus infection. In some embodiments, the Picornaviridae virus infection is human rhinovirus infection.

In some embodiments, the present disclosure provides a compound of the present disclosure, or a pharmaceutically acceptable salt thereof, for use in the treatment of a Picornaviridae virus infection in a human in need thereof. In some embodiments, the Picornaviridae virus infection is human rhinovirus infection.

Flaviviridae

In some embodiments, the present disclosure provides a method of treating a Flaviviridae virus infection in a human in need thereof, the method comprising administering to the human a therapeutically effective amount of a compound of the present disclosure, or a pharmaceutically acceptable salt thereof. Representative Flaviviridae viruses include, but are not limited to, dengue, Yellow fever, West Nile, Zika, Japanese encephalitis virus, and Hepatitis C (HCV). In some embodiments, the Flaviviridae virus infection is a dengue virus infection. In some embodiments, the Flaviviridae virus infection is a Yellow fever virus infection. In some embodiments, the Flaviviridae virus infection is a West Nile virus infection. In some embodiments, the Flaviviridae virus infection is a Zika virus infection. In some embodiments, the Flaviviridae virus infection is a Japanese ensephalitis virus infection. In some embodiments, the Flaviviridae virus infection is a Hepatitis C virus infection.

In some embodiments, the present disclosure provides a method for manufacturing a medicament for treating a Flaviviridae virus infection in a human in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a human of a Flaviviridae virus infection. In some embodiments, the Flaviviridae virus infection is a dengue virus infection. In some embodiments, the Flaviviridae virus infection is a Yellow fever virus infection. In some embodiments, the Flaviviridae virus infection is a West Nile virus infection. In some embodiments, the Flaviviridae virus infection is a Zika virus infection. In some embodiments, the Flaviviridae virus infection is a Hepatitis C virus infection.

In some embodiments, the present disclosure provides a compound of the present disclosure, or a pharmaceutically acceptable salt thereof, for use in the treatment of a Flaviviridae virus infection in a human in need thereof. In some embodiments, the Flaviviridae virus infection is a dengue virus infection. In some embodiments, the Flaviviridae virus infection is a Yellow fever virus infection. In some embodiments, the Flaviviridae virus infection is a West Nile virus infection. In some embodiments, the Flaviviridae virus infection is a Zika virus infection. In some embodiments, the Flaviviridae virus infection is a Hepatitis C virus infection.

Filoviridae

In some embodiments, the present disclosure provides a method of treating a Filoviridae virus infection in a human in need thereof, the method comprising administering to the human a therapeutically effective amount of a compound of the present disclosure, or a pharmaceutically acceptable salt thereof. Representative Filoviridae viruses include, but are not limited to, Ebola and Marburg. In some embodiments, the Filoviridae virus infection is an Ebola virus infection.

In some embodiments, the present disclosure provides a method for manufacturing a medicament for treating a Filoviridae virus infection in a human in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a human of a Filoviridae virus infection. In some embodiments, the Filoviridae virus infection is an Ebola virus infection.

In some embodiments, the present disclosure provides a compound of the present disclosure, or a pharmaceutically acceptable salt thereof, for use in the treatment of a Filoviridae virus infection in a human in need thereof. In some embodiments, the Filoviridae virus infection is an Ebola virus infection.

VIII. Methods of Treatment or Prophylaxis of an Exacerbation of a Respiratory Condition by a Virus Infection The compounds of Formula (II), (IIa), (IIb), (IIc), (IId), (IIe), (IIf), (IIg), (IIh), (IIi), (IIj), (IIk), (IIm) or (IIn) can also be used for the treatment or prophylaxis of an exacerbation of a respiratory condition by a viral infection in a human in need thereof.

In some embodiments, the present disclosure provides a method for the treatment or prophylaxis of an exacerbation of a respiratory condition by a viral infection in a human in need thereof, the method comprising administering to the human a therapeutically effective amount of a compound of the present disclosure, or a pharmaceutically acceptable salt thereof, wherein the respiratory condition is chronic obstructive pulmonary disease. In some embodiments, the viral infection is caused by respiratory syncytial virus, rhinovirus or metapneumovirus.

In some embodiments, the present disclosure provides a method for the treatment or prophylaxis of an exacerbation of a respiratory condition by a viral infection in a human in need thereof, the method comprising administering to the human a therapeutically effective amount of the compound of the present disclosure, or a pharmaceutically acceptable salt thereof, wherein the respiratory condition is asthma. In some embodiments, the viral infection is caused by respiratory syncytial virus, rhinovirus, enteroviruses or metapneumovirus.

In some embodiments, the present disclosure provides a method for manufacturing a medicament for the treatment or prophylaxis of an exacerbation of a respiratory condition by a viral infection in a human in need thereof, characterized in that a compound of the present disclosure, or a pharmaceutically acceptable salt thereof, is used, wherein the respiratory condition is chronic obstructive pulmonary disease. In some embodiments, the viral infection is caused by respiratory syncytial virus, rhinovirus or metapneumovirus.

In some embodiments, the present disclosure provides a method for manufacturing a medicament for the treatment or prophylaxis of an exacerbation of a respiratory condition by a viral infection in a human in need thereof, characterized in that the compound of the present disclosure, or a pharmaceutically acceptable salt thereof, is used, wherein the respiratory condition is asthma. In some embodiments, the viral infection is caused by respiratory syncytial virus, rhinovirus, enteroviruses or metapneumovirus.

In some embodiments, the present disclosure provides use of a compound of the present disclosure, or a pharmaceutically acceptable salt thereof, for the manufacture of a medicament for the treatment or prophylaxis in a human of an exacerbation of a respiratory condition by a viral infection, wherein the respiratory condition is chronic obstructive pulmonary disease. In some embodiments, the viral infection is caused by respiratory syncytial virus, rhinovirus or metapneumovirus.

In some embodiments, the present disclosure provides use of the compound of the present disclosure, or a pharmaceutically acceptable salt thereof, for the manufacture of a medicament for the treatment or prophylaxis in a human of an exacerbation of a respiratory condition by a viral infection, wherein the respiratory condition is asthma. In some embodiments, the viral infection is caused by respiratory syncytial virus, rhinovirus, enteroviruses or metapneumovirus.

In some embodiments, the present disclosure provides the compound of the present disclosure, or a pharmaceutically acceptable salt thereof, for use in the treatment or prophylaxis of an exacerbation of a respiratory condition by a viral infection in a human in need thereof, wherein the respiratory condition is chronic obstructive pulmonary disease. In some embodiments, the viral infection is caused by respiratory syncytial virus, rhinovirus or metapneumovirus.

In some embodiments, the present disclosure provides the compound of the present disclosure, or a pharmaceutically acceptable salt thereof, for use in the treatment or prophylaxis of an exacerbation of a respiratory condition by a viral infection in a human in need thereof, wherein the respiratory condition is asthma. In some embodiments, the viral infection is caused by respiratory syncytial virus, rhinovirus, enteroviruses or metapneumovirus.

IX. Examples

Abbreviations. Certain abbreviations and acronyms are used in describing the experimental details. Although most of these would be understood by one skilled in the art, Table 2 contains a list of many of these abbreviations and acronyms.

TABLE 2

List of abbreviations and acronyms.

| Abbreviation | Meaning |
| --- | --- |
| Ac | acetate |
| ACN | acetonitrile |
| AIBN | azobisisobutyronitrile |
| Bn | benzyl |
| Bu | butyl |
| Bz | benzoyl |
| BzCl | benzoyl chloride |
| CDI | 1,1'-carbonyldiimidazole |
| DAST | diethylaminosulfur trifluoride |
| DBU | 1,8-diazabicyclo[5.4.0]undec-7-ene |
| DCE | 1,2-dichloroethane |
| DCM | dichloromethane |
| DIC | N,N'-diisopropylcarbodiimide |
| DIPEA | N,N-diisopropylethylamine |
| DMAP | 4-dimethylamiopyridine |
| DMDO | dimethydioxirane |
| DMSO | dimethylsulfoxide |
| DMF | dimethylformamide |
| DMTrCl | 4,4'-dimethoxytritylchloride |
| DMTr | 4,4'-dimethoxytrityl |
| EDCI | N-(3-dimethylaminopropyl)-N'-ethylcarbodiimide hydrochloride |
| Et | ethyl |
| EtOAc | ethylacetate |
| Imid | imidazole |
| KOtBu | potassium tert-butoxide |
| LC | liquid chromatography |
| MCPBA | meta-chloroperbenzoic acid |
| Me | methyl |
| m/z | mass to charge ratio |
| MS or ms | mass spectrum |
| NIS | N-iodosuccinimide |
| NMP | N-methyl-2-pyrrolidone |
| Ph | phenyl |
| Ph$_3$P | triphenylphosphine |
| PMB | para-methoxybenzyl |
| PMBCl | para-methoxybenzyl chloride |
| PhOC(S)Cl | phenylchlorothionoformate |
| (PhO)$_3$PMeI | methyltriphenoxyphosphonium iodide |
| Pyr | pyridine |
| RT | room temperature |
| SFC | supercritical fluid chromatography |
| TBAF | tetrabutylammonium flouride |
| TBME | tert-butyl methyl ether |
| TBS | tert-butyldimethylsilyl |
| TBSCl | tert-Butyldimethylsilyl chloride |
| TMSN$_3$ | trimethylsilyl azide |
| TEA | triethylamine |
| TES | triethylsilane |
| TFA | trifluoroacetic acid |
| THF | tetrahydrofuran |
| TMS | trimethylsilyl |
| TMSCl | trimethylsilyl chloride |
| t$_R$ | retention time |
| Ts | 4-toluenesulfonyl |
| TsOH | tosylic acid |
| δ | parts per million referenced to residual non-deuterated solvent peak |

Compounds can be subjected to preparatory HPLC (Phenomenex Gemini 10 u C18 110 Å AXIA 250×21.2 mm column, 30-70% acetonitrile/water gradient with 0.1% TFA). Some compounds are afforded as the TFA salt following this preparatory HPLC process.

Compound structures using a "P$^a$" or "P$^b$" designation refers to the (R)- or (S)-isomer where the specific stereochemistry at that position is unassigned.

A. Intermediates

Intermediate 1. (2R,3S,4R,5S)-5-(4-aminopyrrolo[2,1-f][1,2,4]triazin-7-yl)-3,4-dihydroxy-2-(hydroxymethyl)tetrahydrofuran-2-carbonitrile

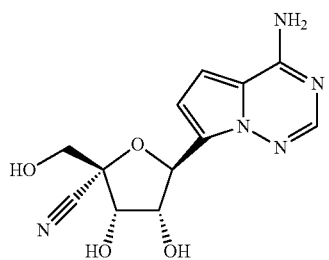 [SMILES: N#C[C@]1(CO)O[C@@H](c2ccc3c(N)ncnn23)[C@H](O)[C@@H]1O]

The product can be prepared according WO2015/069939. For example, pages 43-54 of WO2015/069939 provide a process for preparing the compound, identified as compound 1 in WO2015/069939.

Intermediate 2. tert-butyl (7-((3aS,4S,6R,6aS)-6-cyano-6-(hydroxymethyl)-2,2-dimethyltetrahydrofuro[3,4-d][1,3]dioxol-4-yl)pyrrolo[2,1-f][1,2,4]triazin-4-yl)carbamate

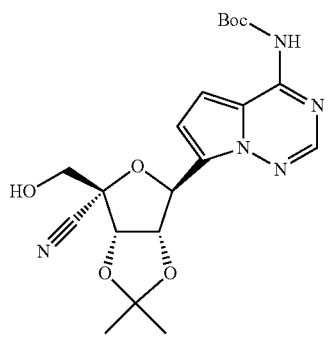 [SMILES: CC(C)(C)OC(=O)Nc1ncnn2c([C@@H]3O[C@](C#N)(CO)[C@H]4OC(C)(C)O[C@@H]34)ccc12]

Compound 14j from WO2015/069939 (21.79 g, 39.93 mmol) in THF (400 mL) was cooled in an ice bath. TBAF 1.0 M in THF (50.0 mL, 50.0 mmol) was added in one portion. The mixture was allowed to come to ambient temperature and stirred for about 30 min. The reaction was determined to be complete by LCMS. The reaction mixture was quenched with water and the organics were removed under reduced pressure. The crude was partitioned between EtOAc and Water. The layers were separated and the aqueous was washed with EtOAc. The organics were combined and dried over sodium sulfate. The solids were filtered off and the solvent removed under reduced pressure. The crude was purified by silica gel chromatography 330 g column 30-100% EtOAc in Hexanes to afford the product. MS m/z=431.74 [M+1]. ¹H NMR (400 MHz, DMSO-d6) δ 10.53 (s, 1H), 8.25 (s, 1H), 7.21 (s, 1H), 7.03 (d, J=4.6 Hz, 1H), 5.77 (t, J=6.1 Hz, 1H), 5.59 (d, J=4.0 Hz, 1H), 5.27 (dd, J=6.7, 4.1 Hz, 1H), 4.94 (d, J=6.7 Hz, 1H), 3.66 (dd, J=6.1, 2.4 Hz, 2H), 1.62 (s, 3H), 1.50 (s, 9H), 1.33 (s, 3H).

Intermediate 3. (3aS,4R,6S,6aS)-6-(4-aminopyrrolo[2,1-f][1,2,4]triazin-7-yl)-4-(((tert-butyldimethylsilyl)oxy)methyl)-2,2-dimethyltetrahydrofuro[3,4-d][1,3]dioxole-4-carbonitrile

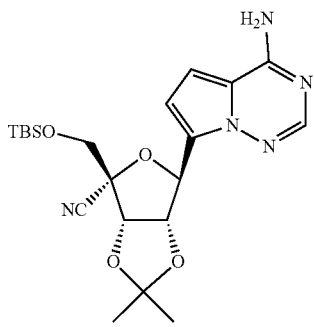 [SMILES: CC1(C)O[C@H]2[C@H](c3ccc4c(N)ncnn34)O[C@](C#N)(CO[Si](C)(C)C(C)(C)C)[C@H]2O1]

The product can be prepared according to WO2015/069939. For example, pages 127-138 of WO2015/069939 provide a process for preparing the compound, identified as compound 14k in WO2015/069939.

Intermediate 4. (3aS,4R,6S,6aS)-6-(4-aminopyrrolo[2,1-f][1,2,4]triazin-7-yl)-4-(hydroxymethyl)-2,2-dimethyltetrahydrofuro[3,4-d][1,3]dioxole-4-carbonitrile

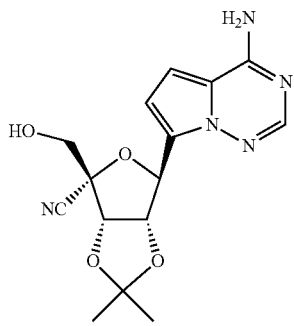 [SMILES: CC1(C)O[C@H]2[C@H](c3ccc4c(N)ncnn34)O[C@](C#N)(CO)[C@H]2O1]

Took up Intermediate 3 (8.41 g, 18.87 mmol) in THF (100 mL). Added TBAF 1.0 M in THF (28.31 mL, 28.31 mmol) in one portion at ambient temperature. Allowed to stir at ambient temperature for 10 min. The reaction was determined to be complete by LCMS. The reaction mixture was quenched with water and the organics were removed under reduced pressure. The crude was partitioned between EtOAc and Water. The layers were separated and the aqueous was washed with EtOAc. The organics were combined and dried over sodium sulfate. The solids were filtered off and the solvent removed under reduced pressure. The crude was purified by silica gel chromatography 120 g column 0-10% CH₃OH in CH₂Cl₂ to afford the product. LC/MS: $t_R$=0.76 min, MS m/z=332.14 [M+1]; LC system: Thermo Accela 1250 UHPLC. MS system: Thermo LCQ Fleet; Column: Kinetex 2.6p XB-C18 100 A, 50×3.00 mm. Solvents: Acetonitrile with 0.1% formic acid, Water with 0.1% formic acid. Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min. ¹H NMR (400 MHz, DMSO-d₆) δ 7.87-7.80 (m, 3H), 6.85 (d, J=4.5 Hz, 1H), 6.82 (d, J=4.5 Hz, 1H), 5.74 (t, J=5.8 Hz, 1H), 5.52 (d, J=4.2 Hz, 1H), 5.24 (dd, J=6.8, 4.2 Hz, 1H), 4.92 (d, J=6.8 Hz, 1H), 3.65 (dd, J=6.1, 1.7 Hz, 2H), 1.61 (s, 3H), 1.33 (s, 3H).

Intermediate 5. (2R,3S,4R,5S)-5-(4-aminopyrrolo[2,1-f][1,2,4]triazin-7-yl)-2-(((tert-butyldimethylsilyl)oxy)methyl)-3,4-dihydroxytetrahydrofuran-2-carbonitrile

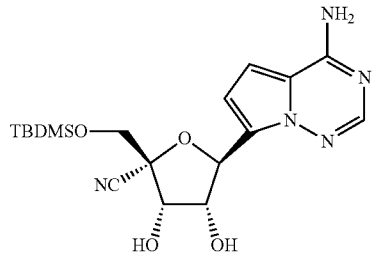 [SMILES: CC(C)(C)[Si](C)(C)OC[C@@]1(C#N)O[C@@H](c2ccc3c(N)ncnn23)[C@H](O)[C@@H]1O]

Dissolved Intermediate 1 (2 g, 6.18 mmol) in 50 mL DMF, to the solution were added tert-butylchlorodimethylsilane (1 g, 7 mmol) and imidazole (1.26 g, 19 mmol). The resulting mixture was stirred at RT for 2 h and the reaction was diluted with EtOAc, washed with NH₄Cl solution, the organic solvent was evaporated and the residue was purified by silica gel column chromatography eluting with 0-100% EtOAc in hexane to afford the product. LCMS: MS m/z=406.36 [M+1], $t_R$=1.45 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.25 min; HPLC system: Agilent 1290 II; Column: Phenomenex Kinetex C18, 2.6 u 110 A, 100×4.6 mm; Solvents: A: Water with 0.1% TFA, B: Acetonitrile with 0.1% TFA; Gradient: 2-98% B with 8.5 min gradient at 1.5 m/min.

Intermediate 6. (2R,3S,4S,5S)-5-(4-aminopyrrolo[2,1-f][1,2,4]triazin-7-yl)-2-(((tert-butyldimethylsilyl)oxy)methyl)-2-cyanotetrahydrofuran-3,4-diyl bis(2-methylpropanoate)

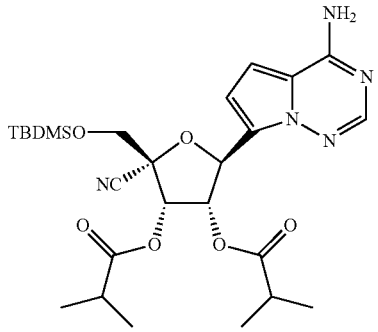 [SMILES: CC(C)C(=O)O[C@H]1[C@H](c2ccc3c(N)ncnn23)O[C@](C#N)(CO[Si](C)(C)C(C)(C)C)[C@H]1OC(=O)C(C)C]

Dissolved Intermediate 5 (1.8 g, 4.44 mmol) in 15 mL THF, to the solution were added isobutyric anhydride (1.54 g, 9.8 mmol) and DMAP (179 mg, 1.45 mmol). The resulting mixture was stirred at RT for 5 min and the reaction was quenched with MeOH and then diluted with EtOAc, washed with brine, the organic solvent was dried over $Na_2SO_4$ and evaporated under vacuum. The residue was purified by silica gel column chromatography eluting with 0-100% EtOAc in hexane to afford the product. LCMS: MS m/z=546.16 [M+1], $t_R$=1.92 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.88 min; HPLC system: Agilent 1290 II; Column: Phenomenex Kinetex C18, 2.6 u 110 A, 100×4.6 mm; Solvents: A: Water with 0.1% TFA, B: Acetonitrile with 0.1% TFA; Gradient: 2-98% B with 8.5 min gradient at 1.5 mL/min.

Intermediate 7. (2R,3S,4S,5S)-5-(4-aminopyrrolo[2,1-f][1,2,4]triazin-7-yl)-2-cyano-2-(hydroxymethyl)tetrahydrofuran-3,4-diyl bis(2-methylpropanoate)

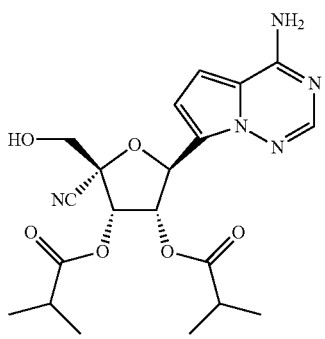 [SMILES: CC(C)C(=O)O[C@H]1[C@H](c2ccc3c(N)ncnn23)O[C@](C#N)(CO)[C@H]1OC(=O)C(C)C]

Dissolved Intermediate 6 (3.2 g, 5.86 mmol) in 25 mL THF in a 100 mL plastic bottle, to the solution was added HF-pyridine (10 g, 0.35 mmol). The resulting mixture was stirred at RT for 3 h and the reaction was quenched with $NaHCO_3$ and then diluted with EtOAc, washed with brine, the organic solvent was dried over $Na_2SO_4$ and evaporated under vacuum. The residue was purified by silica gel column chromatography eluting with 0-100% EtOAc in hexane to afford the product. $^1$H NMR (400 MHz, Acetonitrile-d3) δ 7.90 (s, 1H), 6.83-6.74 (m, 2H), 6.33 (s, 2H), 5.84-5.74 (m, 2H), 5.62 (d, J=5.4 Hz, 1H), 4.31 (dd, J=8.4, 5.2 Hz, 1H), 3.94 (dd, J=12.2, 5.0 Hz, 1H), 3.87 (dd, J=12.2, 8.4 Hz, 1H), 2.70 (hept, J=7.0 Hz, 1H), 2.56 (hept, J=7.0 Hz, 1H), 1.28-1.17 (m, 6H), 1.12 (dd, J=15.1, 7.0 Hz, 6H). LCMS: MS m/z=432.24 [M+1], $t_R$=1.47 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=2.74 min; HPLC system: Agilent 1290 II; Column: Phenomenex Kinetex C18, 2.6 u 110 A, 100×4.6 mm; Solvents: A: Water with 0.1% TFA, B: Acetonitrile with 0.1% TFA; Gradient: 2-98% B with 8.5 min gradient at 1.5 m/min.

Intermediate 8. Cyclopentyl L-Alaninate HC Salt

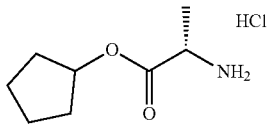

To a mixture of (tert-butoxycarbonyl)-L-alanine (3.95 g, 20.9 mmol), cyclopentanol (1.5 g, 17.4 mmol) and 1-Ethyl-3-(3-dimethylaminopropyl)carbodiimide HCl salt (EDCI) (3.5 g, 22.6 mmol) in acetonitrile (100 mL) was added 4-(Dimethylamino)pyridine (DMAP, 3.2 g, 26.1 mmol). Then the mixture was stirred at room temperature for 2 h, and then the reaction mixture was diluted with EtOAc, washed with brine, dried organic solvent over sodium sulfate, and then concentrated in vacuum. The obtained residue was purified by silica gel chromatography eluting with 0-100% ethyl acetate in hexanes to afford intermediate which was dissolved in 10 mL DCM, to the solution was added 4 N HCl in dioxane (3 mL). The reaction mixture was stirred at RT for 30 min, the solvent was then evaporated and the residue was dried over high vacuum to afford crude product. $^1$H NMR (400 MHz, Chloroform-d) δ 8.75-8.42 (m, 2H), 5.20 (tt, J=5.6, 2.5 Hz, 1H), 4.22-4.07 (m, 1H), 1.87-1.58 (m, 8H), 1.54 (dd, J=12.6, 7.2 Hz, 3H).

Intermediate 9. Cyclopropyl L-Alaninate HCl Salt

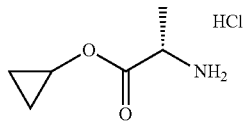

To a mixture of (tert-butoxycarbonyl)-L-alanine (5.86 g, 31 mmol), cyclopropanol (1.5 g, 25.8 mmol) and 1-Ethyl-3-(3-dimethylaminopropyl)carbodiimide HCl salt (EDCI) (5.2 g, 33.6 mmol) in acetonitrile (100 mL) was added 4-(Dimethylamino)pyridine (DMAP, 4.7 g, 38.7 mmol). Then the mixture was stirred at room temperature for 2 h, and then the reaction mixture was diluted with EtOAc, washed with brine, dried organic solvent over sodium sulfate, and then concentrated in vacuum. The obtained residue was purified by silica gel chromatography eluting with 0-100% ethyl acetate in hexanes to afford intermediate which was dissolved in 10 mL DCM, to the solution was added 4 N HCl in dioxane (3 mL). The reaction mixture was stirred at RT for 30 min, the solvent was then evaporated and the residue was dried over high vacuum to afford crude product. $^1$H NMR (400 MHz, Chloroform-d) δ 8.68 (s, 2H), 4.22 (tt, J=6.3, 3.2 Hz, 1H), 1.68 (d, J=7.3 Hz, 3H), 1.42 (s, 1H), 0.86-0.69 (m, 2H), 0.70 (dd, J=7.1, 3.6 Hz, 2H).

Intermediate 10. Formacetal 1 and 2: 1,1-Dimethoxy-N,N-dimethylmethanamine and 1-(dimethoxymethyl)-4-methylpiperazine

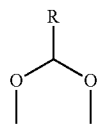

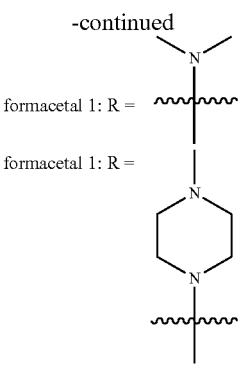

formacetal 1: R = formacetal 1: R =

A mixture of N-methylpiperazine (1.5 mL, 15.93 mmol) and DMF-dimethylacetal (1 mL, 7.50 mmol) was heated in a sealed tube at 100° C. for 3 days, concentrated under high vacuum at 60° C. to remove excess N-methyl piperazine, and then used in next reaction. Based on the next reaction's product compositions, the product was a mixture of formacetal 1 and formacetal 2 with ca 1:2 ratio.

Intermediate 11. (S)-cyclohexyl 2-aminopropanoate hydrochloride

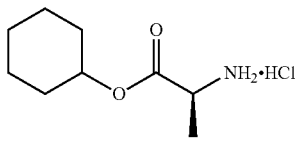

To a mixture of L-alanine (5 g, 56.12 mmol) and cyclohexanol (56 g, 561 mmol) was added TMSCI (20 mL). The resulting mixture was stirred at about 70° C. for about 15 h and concentrated in vacuo at about 80° C., co-evaporated with toluene, dissolved in hexanes, and stirred at about room temperature, during which solid was precipitated. The solid was collected by filtration and the filter cake was washed with 5% EtOAc in hexanes several times, and dried under high vacuum for about 15 h to give the product. $^1$H NMR (400 MHz, Chloroform-d) δ 8.76 (s, 3H), 4.85 (tt, J=8.7, 3.8 Hz, 1H), 4.17 (p, J=6.5 Hz, 1H), 1.84 (dd, J=9.9, 5.5 Hz, 2H), 1.70 (d, J=7.3 Hz, 5H), 1.57-1.42 (m, 3H), 1.32 (ddddd, J=20.3, 12.8, 9.9, 6.4, 3.1 Hz, 3H).

Intermediate 12. (S)-2-ethylbutyl 2-((tert-butoxycarbonyl)amino)-4-methylpentanoate

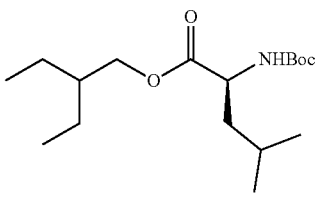 [SMILES: CCC(CC)COC(=O)[C@H](CC(C)C)NC(=O)OC(C)(C)C]

Took up (S)-2-((tert-butoxycarbonyl)amino)-4-methylpentanoic acid (1.09 g, 4.71 mmol) in acetonitrile (10 mL) and added 2-ethyl-1-butanol (2.88 mL, 23.56 mmol) followed by EDCI (878 mg, 5.66 mmol) and DMAP (863 mg, 7.07 mmol) in one portion. Allowed to stir at room temperature overnight. Concentrated and diluted with CH$_2$Cl$_2$. Purified by silica gel chromatography 0-40% EtOAc/Hex to afford the product. $^1$H NMR (400 MHz, DMSO-d6) δ 7.19 (d, J=8.7 Hz, 1H), 4.00-3.84 (m, 3H), 1.67-1.22 (m, 17H), 0.91-0.80 (m, 12H).

Intermediate 13. (S)-2-ethylbutyl 2-amino-4-methylpentanoate hydrochloride

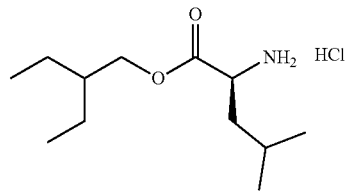

Took up (S)-2-ethylbutyl 2-((tert-butoxycarbonyl)amino)-4-methylpentanoate in CH$_2$Cl$_2$ (10 mL) and 4 N HCl in dioxane (10 mL, 40 mmol). Stirred at ambient temperature for 1 h. Concentrated under reduced pressure and co-evaporated with hexanes. Placed under high vacuum for 1 h and the product was used as is without purification for the next step. $^1$H NMR (400 MHz, DMSO-d$_6$) δ 8.43 (s, 3H), 4.08 (d, J=5.6 Hz, 2H), 3.92 (m, 1H), 1.69 (m, 1H), 1.61 (m, 2H), 1.47 (m, 1H), 1.34 (m, 4H), 0.83 (m, 12H).

Intermediate 14. 2-(Benzyloxy)-2-methylpropyl ((4-nitrophenoxy)(phenoxy)phosphoryl)-L-alaninate

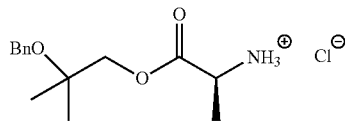 [SMILES: C[C@H]([NH3+])C(=O)OCC(C)(C)OCc1ccccc1 ; [Cl-]]

To a mixture of Boc-L-alanine (1.26 g, 6.66 mmol), 2-benzyloxy-2-methylpropanol (1.0 g, 5.55 mmol), and EDCI (1.12 g, 7.21 mmol) in acetonitrile (20 mL) was added DMAP (2.04 g, 8.32 mmol). Then the mixture was stirred at room temperature for 2 h, then diluted with EtOAc, washed with brine, dried over sodium sulfate, and concentrated in vacuo. The obtained residue was purified by silica gel chromatography (EtOAc 0 to 60% in hexanes) to give a Boc-L-alanine propyl ester, which was dissolved in DCM (10 mL) and 4 N HCl in dioxane (5.5 mL, 22.19 mmol) was added at room temperature. The resulting mixture was stirred at room temperature for 2 h, concentrated in vacuo, re-dissolved in ACN (10 mL), lyophilized overnight to afford the product. $^1$H NMR (400 MHz, Chloroform-d) δ 8.82 (s, 3H), 7.42-7.07 (m, 5H), 4.44 (s, 2H), 4.24 (m, 2H), 4.08 (d, J=11.2 Hz, 1H), 1.70 (d, J=7.0 Hz, 3H), 1.28 (d, J=2.4 Hz, 6H). LCMS m/z=251.97 (freebase M+H), t$_R$=0.85 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

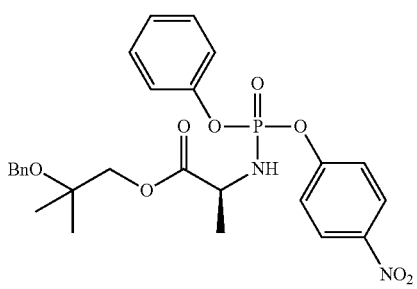 [SMILES: C[C@H](NP(=O)(Oc1ccccc1)Oc1ccc([N+](=O)[O-])cc1)C(=O)OCC(C)(C)OCc1ccccc1]

2-(Benzyloxy)-2-methylpropyl ((4-nitrophenoxy)(phenoxy)phosphoryl)-L-alaninate. To a solution of 2-(Benzyloxy)-2-methylpropyl L-alaninate HCl salt (832 mg, 2.89 mmol) in DCM (20 mL) was added phenyl phosphorodichloridate (0.43 mL, 2.89 mmol) in one portion at −78° C. and triethylamine (0.80 mL, 5.76 mmol) was added dropwise over 5 min at −78° C. The resulting mixture was stirred for 30 min after removal of dry ice bath and cooled to −78° C. and p-nitrophenol (402 mg, 2.89 mmol) was added in one portion and triethylamine (0.40 mL, 2.89 mmol) added over 5 min at −78° C. The resulting mixture was stirred for 50 min after removal of dry ice bath, then diluted with DCM, washed with brine, concentrated in vacuo, and the resulting residue purified by silica gel column chromatography (EtOAc 0 to 60% in hexanes) to give the product. $^1$H NMR (400 MHz, Chloroform-d) δ 8.23-8.13 (m, 2H), 7.41-7.27 (m, 3H), 7.28-7.14 (m, 4H), 4.45 (m, 2H), 4.27-4.15 (m, 2H), 4.07 (m, 1H), 3.89 (m, 1H), 1.41 (m, 3H), 1.27 (m, 6H). $^{31}$P NMR (162 MHz, Chloroform-d) δ −3.10, −3.18. LCMS m/z=528.78 (M+H), $t_R$=1.70 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

Intermediate 15. cyclobutylmethyl ((4-nitrophenoxy)(phenoxy)phosphoryl)-L-alaninate

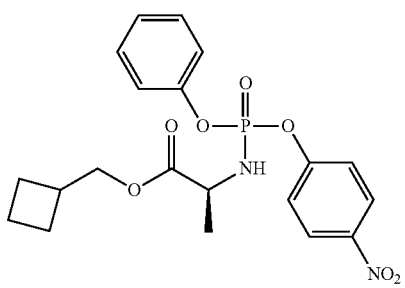 [SMILES: C[C@H](NP(=O)(Oc1ccccc1)Oc1ccc([N+](=O)[O-])cc1)C(=O)OCC1CCC1]

L-Alanine cyclobutylmethyl ester-HCl (1.2 g, 7.16 mmol) was suspended in methylene chloride (10 mL), cooled to −78° C., and phenyl dichlorophosphate (1.07 mL, 7.16 mmol) added quickly. Triethylamine (2.0 mL, 14.32 mmol) was added over 60 min at −78° C. and the resulting mixture was stirred at room temperature for 3 h. The reaction mixture was cooled to 0° C. and 4-nitrophenol (996 mg, 7.16 mmol) was added in one portion. Then triethylamine (1.0 mL, 7.16 mmol) was added over 60 min. Then the mixture was stirred for 3 h at room temperature, filtered, the filtrate concentrated to one third volume, and filtered again. The filtrate was concentrated and the residue purified by silica gel column chromatography (EtOAc 0 to 35% in hexanes) to give the product. $^1$H NMR (400 MHz, chloroform-d) δ 8.28-8.16 (m, 2H), 7.45-7.32 (m, 4H), 7.29-7.16 (m, 3H), 4.23-4.01 (m, 3H), 3.95-3.83 (m, 1H), 2.59 (m, 1H), 2.03 (m, 2H), 1.98-1.80 (m, 2H), 1.73 (m, 2H), 1.42 (d, J=3.2 Hz, 1.5H), 1.40 (d, J=3.3 Hz, 1.5H). $^{31}$P NMR (162 MHz, chloroform-d) δ −3.06, −3.11.

Intermediate 16. 2-ethylbutyl ((benzyloxy)(4-nitrophenoxy)phosphoryl)-L-alaninate

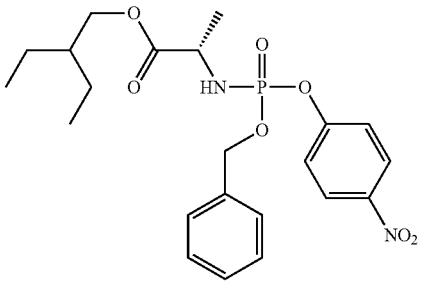 [SMILES: CCC(CC)COC(=O)[C@H](C)NP(=O)(OCc1ccccc1)Oc1ccc([N+](=O)[O-])cc1]

4-Nitrophenyl phosphorodichloridate (2.00 g, 7.81 mmol) and triethylamine (2.18 mL, 15.6 mmol) were sequentially added to a suspension of 2-ethylbutyl L-alaninate hydrochloride (1.091 g, 18.9 mmol) in dichloromethane (23 mL) at 0° C. under an argon atmosphere. After 1 h, benzyl alcohol (0.810 mL, 7.81 mmol) and triethylamine (1.09 mL, 7.81 mmol) were then sequentially added at 0° C., and the resulting mixture was then allowed to warm to rt. After 1 h, the reaction mixture was diluted with dichloromethane (50 mL), washed with saturated an aqueous sodium bicarbonate solution (50 mL) and brine (50 mL), dried over anhydrous sodium sulfate, and concentrated under reduced pressure. The crude residue was purified by silica gel chromatography eluting with 0-100% ethyl acetate in hexanes to afford the product. $^1$H NMR (400 MHz, chloroform-$d_1$) δ 8.30-8.07 (m, 2H), 7.42-7.28 (m, 7H), 5.18-5.09 (m, 2H), 4.70 (s, 1H), 4.08-3.95 (m, 2H), 3.68 (q, J=9.4 Hz, 1H), 1.55-1.18 (m, 8H), 0.87 (t, J=7.4 Hz, 6H). $^{31}$P NMR (162 MHz, chloroform-$d_1$) δ 2.32 (s), 2.28 (s). LCMS: MS m/z=463.00 [M−1], $t_R$=1.56 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min.

Intermediate 17. 2-ethylbutyl ((S)-(4-nitrophenoxy)(phenoxy)(phosphoryl)-L-alaninate

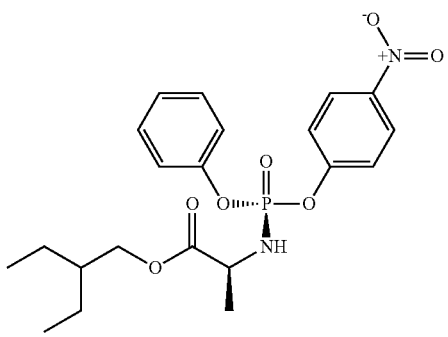

Prepared as described in WO 2016/069825.

Intermediate 18. isopropyl ((S)-(4-nitrophenoxy)(phenoxy)phosphoryl)-L-alaninate

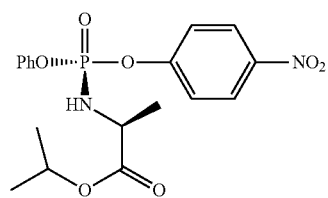 [SMILES: CC(C)OC(=O)[C@H](C)N[P@](=O)(Oc1ccccc1)Oc1ccc([N+](=O)[O-])cc1]

Prepared as described in Cho et al., J. Med. Chem. 2014, 57, 1812-1825.

Intermediate 19. ethyl ((S)-(4-nitrophenoxy)(phenoxy)phosphoryl)-L-alaninate

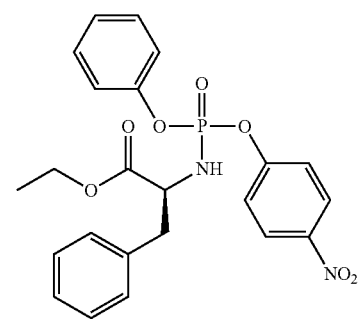 [SMILES: CCOC(=O)[C@H](Cc1ccccc1)NP(=O)(Oc1ccccc1)Oc1ccc([N+](=O)[O-])cc1]

Prepared as described in US20120009147A1.

Intermediate 20. Cyclopropylmethyl ((4-nitrophenoxy)(phenoxy)phosphoryl)-L-alaninate

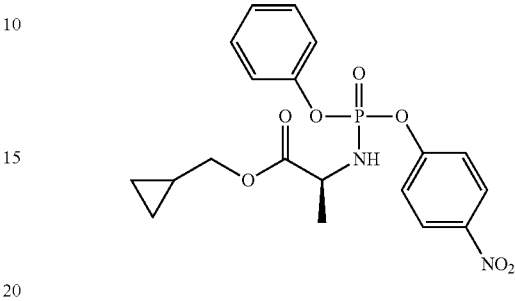

L-Alanine cyclopropylmethyl ester-HCl (1.0 g, 5.57 mmol) was suspended in methylene chloride (10 mL), cooled to −78° C., and phenyl dichlorophosphate (0.83 mL, 5.57 mmol) was added quickly. Triethylamine (1.54 mL, 11.13 mmol) in DCM (1.5 mL) was added over 30 min at −78° C. and stirred 30 min. 4-Nitrophenol (774 mg, 5.57 mmol) was added in one portion at −78° C. Then triethylamine (0.77 mL, 7.16 mmol) in DCM (2 mL) was added over 30 min. Then the mixture was stirred for 30 min at the same temperature, washed with water, saturated $Na_2CO_3$ solution, and brine, and dried with sodium sulfate, and concentrated in vacuo. The residue was purified by silica gel column chromatography (EtOAc 0 to 20% in hexanes) to give the product. $^{1}$H NMR (400 MHz, chloroform-d) δ 8.22 (m, 2H), 7.58-7.29 (m, 4H), 7.32-7.14 (m, 3H), 4.25-4.07 (m, 1H), 4.07-3.80 (m, 3H), 1.44 (d, J=2.9 Hz, 1.5H), 1.42 (d, J=2.9 Hz, 1.5H), 1.26-1.01 (m, 1H), 0.66-0.49 (m, 2H), 0.42-0.15 (m, 2H). $^{31}$P NMR (162 MHz, chloroform-d) δ −3.07, −3.11. MS m/z=420.97.

Intermediate 21. 2-(((4-nitrophenoxy)(phenoxy)phosphoryl)amino)ethyl pivalate

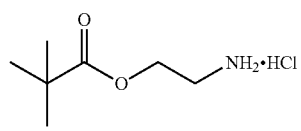

2-aminoethyl pivalate hydrochloride. Pivaloyl chloride (3.82 mL, 31.0 mmol) was added to a solution of tert-butyl (2-hydroxyethyl)carbamate (4.8 mL, 31.0 mmol) and diisopropylethylamine (5.4 mL, 31.0 mmoL) in dichloromethane (150 mL) at RT. After 4 h, the resulting mixture was washed with saturated aqueous sodium bicarbonate solution (150 mL) and brine (150 mL), was dried over anhydrous sodium sulfate, and was concentrated under reduced pressure. The crude colorless oil was taken up into a solution of hydrochloric acid in dioxane (4 M, 50 mL), and was stirred at RT and white solids slowly precipitated from the solution. After 3 h, The solids were collected by vacuum filtration to afford the product. ¹H NMR (400 MHz, CD₃OD) δ 4.32-4.25 (m, 2H), 3.26 (t, J=5.4 Hz, 2H), 1.23 (s, 9H).

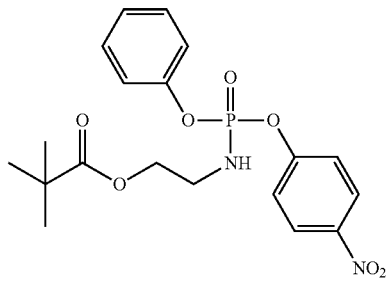 [SMILES: CC(C)(C)C(=O)OCCNP(=O)(Oc1ccccc1)Oc1ccc([N+](=O)[O-])cc1]

2-(((4-nitrophenoxy)(phenoxy)phosphoryl)amino)ethyl pivalate. To a solution of 2-aminoethyl pivalate hydrochloride (0.861 g, 4.74 mmol) and phenyl dichlorophosphate (0.705 mL, 4.74 mmol) in dichloromethane (23 mL) was added triethylamine (1.2 mL, 9.4 mmol) at 0° C. under and argon atmosphere. The resulting mixture was allowed to warm to RT and was stirred for 1.5 h. 4-Nitrophenol (660 mg, 4.74 mmol) and triethylamine (0.66 mL, 4.7 mmol) were then added. After 1 h, the reaction mixture was diluted with dichloromethane (50 mL) and the resulting mixture was washed with saturated aqueous sodium bicarbonate solution (50 mL) and brine (50 mL), was dried over anhydrous sodium sulfate, and was concentrated under reduced pressure. The crude residue was purified via SiO₂ column chromatography (40 g SiO₂ Combiflash HP Gold Column, 0-100% ethyl acetate/hexanes) to afford the product. ¹H NMR (400 MHz, CDCl₃) δ 8.23 (d, J=9.2 Hz, 2H), 7.47-7.31 (m, 4H), 7.29-7.16 (m, 3H), 4.18-4.06 (m, 2H), 3.45-3.31 (m, 2H), 1.17 (s, 9H). ³¹P NMR (162 MHz, DMSO-d₆) δ −1.48 (s). MS m/z=422.95 [M+1].

Intermediate 22. (2S)-tetrahydro-2H-pyran-4-yl 2-(((4-nitrophenoxy)(phenoxy)phosphoryl)amino) propanoate

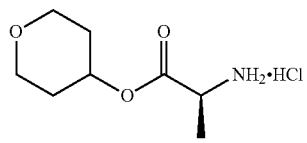

(S)-tetrahydro-2H-pyran-4-yl 2-aminopropanoate hydrochloride. To a mixture of L-alanine (500 mg, 5.61 mmol) and tetrahydro-2H-pyran-4-ol (5 g, 49.0 mmol) was added TMSCI (2 mL). The resulting mixture was stirred at 70° C. for 15 h and concentrated in vacuo and the resulting solid was tritulated with 5% EtOAc in hexanes, filtered, and washed with 5% EtOAc in hexanes several times, and dried under high vacuum for 15 h to give the product which was used in next reaction without any characterization.

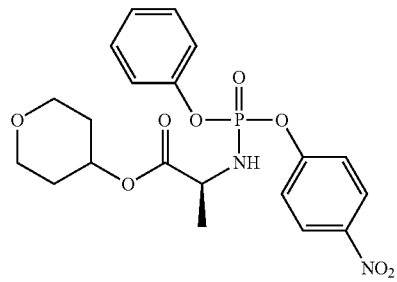 [SMILES: C[C@H](NP(=O)(Oc1ccccc1)Oc1ccc([N+](=O)[O-])cc1)C(=O)OC1CCOCC1]

(2S)-tetrahydro-2H-pyran-4-yl 2-(((4-nitrophenoxy)(phenoxy)phosphoryl)amino)propanoate. (S)-tetrahydro-2H-pyran-4-yl 2-aminopropanoate hydrochloride (1.33 g, 6.34 mmol) was dissolved in methylene chloride (15 mL), cooled to −78° C., and phenyl dichlorophosphate (1.137 mL, 7.61 mmol) added quickly. Triethylamine (2.2 mL, 15.2 mmol) was added over 30 min at −78° C. and the resulting mixture was stirred for 30 min at −78° C. Then 4-nitrophenol (882 mg, 6.34 mmol) was added in one portion and triethylamine (1.1 mL, 7.61 mmol) was added over 30 min at −78° C. The mixture was stirred for 30 min at −78° C., washed with water twice and brine, dried over sodium sulfate, and concentrated in vacuo. The residue was purified by silica gel column chromatography (EtOAc 0 to 70% in hexanes) to give the product. ¹H NMR (400 MHz, Chloroform-d) δ 8.22 (m, 2H), 7.49-7.06 (m, 7H), 4.95 (m, 1H), 4.14 (m, 1H), 4.07-3.80 (m, 3H), 3.52 (m, 2H), 1.95-1.81 (m, 2H), 1.64 m, 2H), 1.42 (m, 3H). ³¹P NMR (162 MHz, Chloroform-d) δ −3.09, −3.13. MS m/z=451 (M+H)+.

Intermediate 23. (S)-1-methylpyrrolidin-3-Yl ((4-nitrophenoxy)(phenoxy)phosphoryl)-L-alaninate

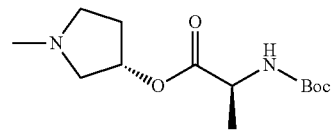 [SMILES: C[C@H](NC(=O)OC(C)(C)C)C(=O)O[C@H]1CCN(C)C1]

(S)-1-methylpyrrolidin-3-yl (tert-butoxycarbonyl)-L-alaninate. Boc-L-Alanine (2.1 g, 11 mmol) and (R)-3-hydroxy-1-methylpyrrolidine (1.1 mL, 10 mmol) were dissolved in anhydrous THF (20 mL). Triphenylphosphine (3.4 g, 13 mmol) was added in one portion. Diisopropyl azodicarboxylate (2.4 mL, 12 mmol) was added dropwise. Reaction was stirred for 2 hrs. More diisopropyl azodicarboxylate (240 uL, 1.2 mmol) was added dropwise, and the reaction was stirred for 16 hrs. Reaction was diluted with EtOAc (10 mL) and washed with saturated aqueous sodium bicarbonate solution (10 mL). Organic was then extracted with 5% aqueous citric acid solution (30 mL). Citric acid extract was washed with EtOAc (2×5 mL). Citric acid portion was basified with 1 N aqueous NaOH solution to give pH of 9 and extracted with EtOAc (2×10 mL). Organic extracts were combined, dried over anhydrous sodium sulfate and then concentrated under reduced pressure to give the product. ¹H NMR (400 MHz, chloroform-d) δ 5.24 (m, 1H), 5.01 (m, 1H), 4.27 (m, 1H), 2.88-2.69 (m, 2H), 2.64 (m, 1H), 2.37 (s, 3H), 2.29 (m, 1H), 1.96-1.80 (m, 1H), 1.44 (s, 9H), 1.37 (d, J=7.2 Hz, 3H).

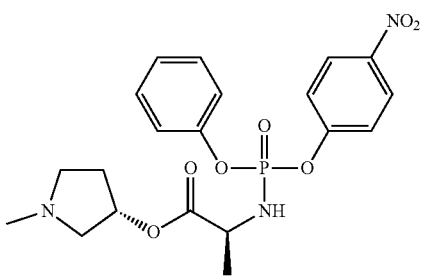 [SMILES: C[C@H](NP(=O)(Oc1ccccc1)Oc1ccc([N+](=O)[O-])cc1)C(=O)O[C@H]1CCN(C)C1]

(S)-1-methylpyrrolidin-3-yl ((4-nitrophenoxy)(phenoxy)phosphoryl)-L-alaninate. (S)-1-methylpyrrolidin-3-yl (tert-butoxycarbonyl)-L-alaninate (545 mg, 2 mmol) was mixed with 10 mL of 4 N HCl in dioxane and stirred for 1 hr. Reaction was concentrated under reduced pressure to give foam which was then mixed with 20 mL anhydrous DCM and stirred under atmospheric nitrogen in an ice bath. Phenyl dichlorophosphate (298 uL, 2 mmol) was added to reaction in one portion. Reaction was stirred for 15 mins. Triethylamine (837 uL, 6 mmol) was added to the reaction dropwise. Reaction was stirred for 1 hr. Triethylamine (279 μL, 2 mmol) was added to the reaction dropwise and then stirred for 30 mins. p-Nitrophenol (250 mg, 1.8 mmol) was added in one portion. Reaction mixture was stirred for 16 hrs. Reaction was diluted with DCM (20 mL) and washed with water (5×20 mL). Organic was dried over anhydrous sodium sulfate and concentrated under reduced pressure. The crude residue was purified via SiO$_2$ column chromatography (12 g SiO$_2$ Combiflash HP Gold Column, 0-10% methanol/DCM). Fractions were combined and concentrated under reduced pressure to give the product. $^1$H NMR (400 MHz, chloroform-d) δ 8.28-8.15 (m, 2H), 7.46-7.28 (m, 4H), 7.28-7.13 (m, 3H), 5.17 (m, 1H), 4.21-4.04 (m, 1H), 4.01-3.85 (m, 1H), 2.81 (m, 1H), 2.70-2.55 (m, 2H), 2.35 (s, 3H), 2.33-2.21 (m, 2H), 1.84-1.70 (m, 1H), 1.39 (m, 3H). $^{31}$P NMR (162 MHz, chloroform-d) δ −3.16, −3.21. LCMS: MS m/z=450.3 [M+1]; 448.1 [M−1], $t_R$=1.15 min; LC system: Thermo Dionex Ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=2.61 min; HPLC system: Agilent 1100 series; Column: Phenomenex Gemini 5μ C18 110 A, 50×4.6 mm; Solvent: A: Water with 0.1% TFA, B: Acetonitrile with 0.1% TFA; Gradient: 2-98% B in 5 min at 2 mL/min.

Intermediate 24. (R)-1-methylpyrrolidin-3-yl ((4-nitrophenoxy)(phenoxy)phosphoryl)-L-alaninate

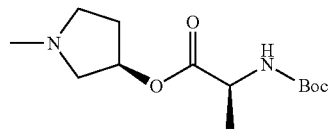 [SMILES: C[C@H](NC(=O)OC(C)(C)C)C(=O)O[C@@H]1CCN(C)C1]

(R)-1-methylpyrrolidin-3-yl (tert-butoxycarbonyl)-L-alaninate. Boc-L-Alanine (5.2 g, 27.5 mmol) and (R)-3-hydroxy-1-methylpyrrolidine (2.74 mL, 25 mmol) were dissolved in anhydrous THF (25 mL). N,N'-Diisopropylcarbodiimide (4.67 mL, 30 mmol) was added dropwise. Reaction was stirred for 2 hrs. More N,N'-diisopropylcarbodiimide (467 uL, 3 mmol) was added dropwise, and the reaction was stirred for 2 hrs. More N,N'-diisopropyl carbodiimide (467 uL, 3 mmol) was added dropwise, and the reaction was stirred for 16 hrs.

Reaction was diluted with EtOAc (25 mL) and stirred for 10 mins. Solid was filtered off and washed with small amount of EtOAc. Filtrate was washed with saturated aqueous sodium bicarbonate solution (3×10 mL). Organic was then extracted with 5% aqueous citric acid solution (50 mL). Citric acid extract was washed with EtOAc (5 mL). Citric acid portion was basified with 1 N aqueous NaOH solution to give pH of 9 and then extracted with EtOAc (3×15 mL). Organic extracts were combined, dried over anhydrous sodium sulfate and then concentrated under reduced pressure to give the product. $^1$H NMR (400 MHz, chloroform-d) δ 5.28-5.18 (m, 1H), 5.02 (m, 1H), 4.28 (m, 1H), 2.84-2.75 (m, 1H), 2.69 (d, J=4.2 Hz, 2H), 2.36 (s, 3H), 2.34-2.22 (m, 2H), 1.87-1.76 (m, 1H), 1.44 (s, 9H), 1.37 (d, J=7.2 Hz, 3H).

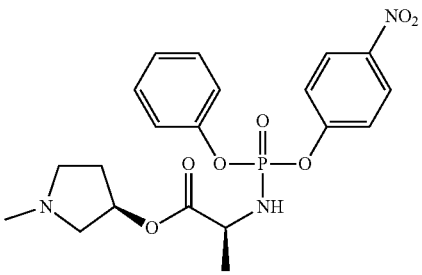 [SMILES: C[C@H](NP(=O)(Oc1ccccc1)Oc1ccc([N+](=O)[O-])cc1)C(=O)O[C@@H]1CCN(C)C1]

(R)-1-methylpyrrolidin-3-yl ((4-nitrophenoxy)(phenoxy)phosphoryl)-L-alaninate. (R)-1-methylpyrrolidin-3-yl (tert-butoxycarbonyl)-L-alaninate (3.9 g, 14.3 mmol) was mixed with 30 mL of 4 N HCl in dioxane and stirred for 3 hrs. Reaction was concentrated under reduced pressure to give foam which was then mixed with 30 mL anhydrous DCM and stirred under atmospheric nitrogen in an ice bath. Phenyl dichlorophosphate (2.34 mL, 15.75 mmol) was added to reaction in one portion. Reaction was stirred for 15 mins. Triethylamine (4.4 mL, 31.5 mmol) was mixed with anhydrous DCM (5 mL) and added to the reaction dropwise. Reaction was stirred for 1 hr. Triethylamine (2.2 mL, 15.75 mmol) was mixed with anhydrous DCM (3 mL) and added to the reaction dropwise. Reaction was stirred for 15 mins. p-Nitrophenol (1.8 g, 12.87 mmol) was added in one portion. Reaction mixture was stirred for 2 hrs.

Reaction was diluted with DCM (20 mL) and washed with aqueous sodium bicarbonate solution (3×20 mL). Organic was dried over anhydrous sodium sulfate and concentrated under reduced pressure. The crude residue was purified via SiO$_2$ column chromatography (40 g SiO$_2$ Combiflash HP Gold Column, 0-10% methanol/DCM). Fractions were combined and concentrated under reduced pressure to give the product. $^1$H NMR (400 MHz, chloroform-d) δ 8.29-8.15 (m, 2H), 7.48-7.29 (m, 4H), 7.29-7.13 (m, 3H), 5.20 (m, 1H), 4.21-4.07 (m, 1H), 3.99 (m, 1H), 2.86 (m, 1H), 2.70 (m, 1H), 2.63 (m, 1H), 2.37 (m, 3H), 2.35-2.21 (m, 2H), 1.86-1.73 (m, 1H), 1.40 (m, 3H). $^{31}$P NMR (162 MHz, chloroform-d) δ −3.12, −3.14. LCMS: MS m/z=450.3 [M+1]; 448.1 [M−1], $t_R$=1.24 min; LC system: Thermo Dionex Ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=2.63 min; HPLC system: Agilent 1100 series; Column: Phenomenex Gemini 5µ C18 110 A, 50×4.6 mm; Solvent: A: Water with 0.1% TFA, B: Acetonitrile with 0.1% TFA; Gradient: 2-98% B in 5 min at 2 mL/min.

Intermediate 25. (2S)-cyclohexyl 2-(((4-nitrophenoxy)(phenoxy)phosphoryl)amino)propanoate

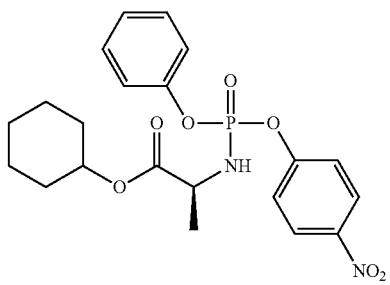 [SMILES: C[C@H](NP(=O)(Oc1ccccc1)Oc1ccc([N+](=O)[O-])cc1)C(=O)OC1CCCCC1]

Intermediate 11 (3.4 g, 16.37 mmol) was dissolved in methylene chloride (45 mL), cooled to −78° C., and phenyl dichlorophosphate (2.45 mL, 16.37 mmol) added quickly. Triethylamine (4.54 mL, 32.74 mmol) was added over 60 min at −78° C. and then 4-nitrophenol (2277 mg, 16.37 mmol) was added in one portion. Triethylamine (2.27 mL, 16.37 mmol) was added over 60 min at −78° C. The resulting mixture was stirred for 2 h at −78° C., diluted with methylene chloride (100 mL), washed with water twice and brine, dried over sodium sulfate, and concentrated in vacuo. The residue was purified by silica gel column chromatography (EtOAc 0 to 20% in hexanes) to give the product. $^1$H NMR (400 MHz, Chloroform-d) δ 8.22 (m, 2H), 7.46-7.30 (m, 4H), 7.29-7.09 (m, 3H), 4.76 (m, 1H), 4.20-4.02 (m, 1H), 3.92 (m, 1H), 1.87-1.64 (m, 4H), 1.54 (m, 2H), 1.46-1.18 (m, 7H). $^{31}$P NMR (162 MHz, Chloroform-d) δ −2.94, −3.00. MS m/z=449 (M+H)+.

Intermediate 26. tert-butyl 4-(((2S)-2-(((4-nitrophenoxy)(phenoxy)phosphoryl)amino)propanoyl)oxy)piperidine-1-carboxylate

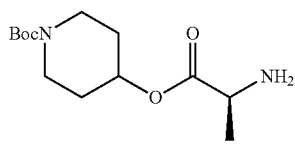 [SMILES: C[C@H](N)C(=O)OC1CCN(C(=O)OC(C)(C)C)CC1]

tert-butyl 4-((L-alanyl)oxy)piperidine-1-carboxylate. To a mixture of ((benzyloxy)carbonyl)-L-alanine (1.26 g, 5.65 mmol), tert-butyl 4-hydroxypiperidine-1-carboxylate (5.68 g, 28.22 mmol), and EDCI (1.05 g, 6.77 mmol) in acetonitrile (15 mL) was added DMAP (1.03 g, 8.47 mmol). Then the mixture was stirred at room temperature for 15 h, diluted with EtOAc, washed with brine, dried over sodium sulfate, and concentrated in vacuo. The obtained residue was purified by silica gel chromatography (EtOAc 0 to 100% in hexanes) to give a Cbz-L-alanine piperidyl ester, which was dissolved in THF (10 mL) and 20% palladium hydroxide (400 mg) on carbon was added. The resulting mixture was stirred under $H_2$ gas for 2 h, filtered, and the filtrate concentrated in vacuo. The obtained residue was dried under high vacuum to afford the product. $^1$H NMR (400 MHz, Chloroform-d) δ 4.95 (tt, J=7.9, 3.8 Hz, 1H), 3.79-3.62 (m, 2H), 3.56 (q, J=7.0 Hz, 1H), 3.25 (ddd, J=13.6, 8.5, 3.7 Hz, 2H), 1.85 (ddd, J=13.4, 6.4, 3.4 Hz, 2H), 1.73 (s, 2H), 1.62 (ddq, J=12.7, 8.7, 4.3, 3.9 Hz, 2H), 1.46 (s, 9H), 1.34 (d, J=7.0 Hz, 3H). MS m/z=273 [M+H].

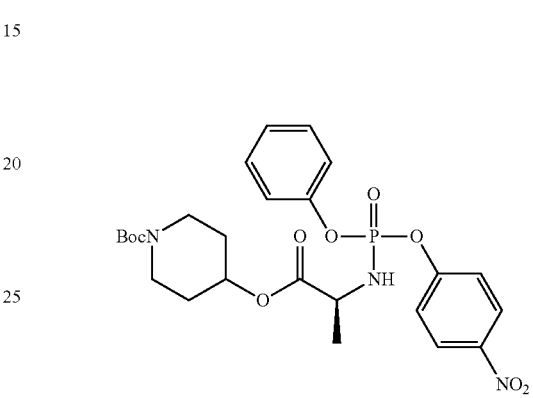

tert-butyl 4-(((2S)-2-(((4-nitrophenoxy)(phenoxy)phosphoryl)amino)propanoyl)oxy)piperidine-1-carboxylate. tert-butyl 4-((L-alanyl)oxy)piperidine-1-carboxylate (0.9 g, 3.31 mmol) was dissolved in methylene chloride (10 mL), cooled to −78° C., and phenyl dichlorophosphate (0.49 mL, 3.31 mmol) added quickly. Triethylamine (0.46 mL, 3.31 mmol) was added over 30 min at −78° C. and 4-nitrophenol (460 mg, 3.31 mmol) was added in one portion. Then triethylamine (0.49 mL, 3.31 mmol) was added over 30 min at −78° C. The resulting mixture was stirred for 2 h at −78° C., diluted with methylene chloride, washed with water twice and brine, dried over sodium sulfate, and concentrated in vacuo. The residue was purified by silica gel column chromatography (EtOAc 0 to 70% in hexanes) to afford the product. $^1$H NMR (400 MHz, Chloroform-d) δ 8.23 (m, 2H), 7.42-7.31 (m, 4H), 7.25-7.16 (m, 3H), 4.93 (m, 1H), 4.26-4.03 (m, 1H), 3.85 (m, 1H), 3.75-3.56 (m, 2H), 3.21 (m, 2H), 1.91-1.75 (m, 2H), 1.66-1.48 (m, 2H), 1.46 (s, 9H), 1.44-1.38 (m, 3H). $^{31}$P NMR (162 MHz, Chloroform-d) δ −3.07, −3.13. MS m/z=550 (M+H)+.

Intermediate 27. trans-4-(trifluoromethyl)cyclohexyl ((4-nitrophenoxy)(phenoxy)phosphoryl)-L-alaninate

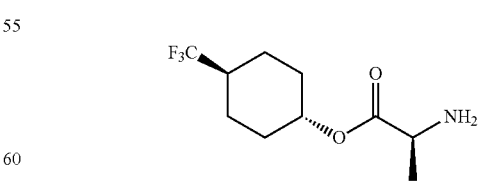

trans-4-(trifluoromethyl)cyclohexyl L-alaninate. The product was prepared from Cbz-1-alanine (900 mg, 4.03 mmol) and trans-4-(trifluoromethyl)cyclohexan-1-ol (1.02 g, 6.05 mmol) in a manner similar to that described for Intermediate 26. MS m/z=240 [M+H].

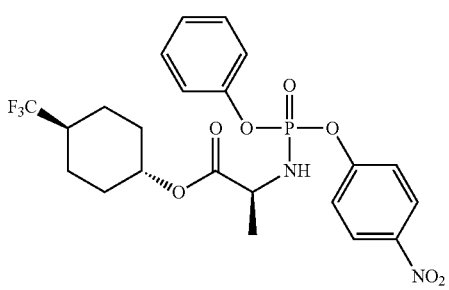 [SMILES: C[C@H](NP(=O)(Oc1ccccc1)Oc1ccc([N+](=O)[O-])cc1)C(=O)O[C@H]1CC[C@H](C(F)(F)F)CC1]

trans-4-(trifluoromethyl)cyclohexyl ((4-nitrophenoxy)(phenoxy)phosphoryl)-L-alaninate. The product (840 mg) was prepared as isomeric mixture from trans-4-(trifluoromethyl)cyclohexyl L-alaninate (974 mg, 4.07 mmol) in a manner similar to that described for Intermediate 25. $^1$H NMR (400 MHz, Chloroform-d) δ 8.27-8.19 (m, 2H), 7.43-7.31 (m, 4H), 7.26-7.16 (m, 3H), 4.68 (m, 1H), 4.11 (m, 1H), 3.84 (m, 1H), 2.02 (m, 4H), 1.50-1.27 (m, 8H). $^{19}$F NMR (377 MHz, Chloroform-d) δ -73.91 (d, J=7.7 Hz). $^{31}$P NMR (162 MHz, Chloroform-d) δ -3.08, -3.12. MS m/z=517 [M+H].

The product was separated by Chiralpak SFC (Chiralpak IF 20×250 mm column, 30% isopropanol) to afford Intermediate 28 and Intermediate 29:

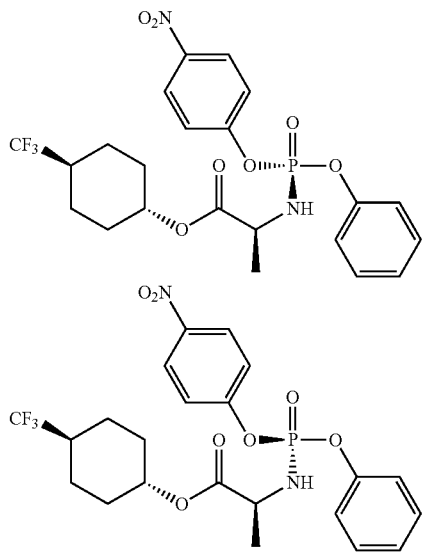

Intermediate 28. trans-4-(trifluoromethyl)cyclohexyl ((R)-(4-nitrophenoxy)(phenoxy)phosphoryl)-L-alaninate. First eluting diastereomer of Intermediate 27: $^1$H NMR (400 MHz, Chloroform-d) δ 8.22 (d, J=9.1 Hz, 2H), 7.42-7.31 (m, 4H), 7.29-7.16 (m, 3H), 4.69 (tt, J=10.7, 4.2 Hz, 1H), 4.19-4.04 (m, 1H), 3.90 (dd, J=11.9, 9.5 Hz, 1H), 2.12-1.97 (m, 5H), 1.52-1.21 (m, 7H). $^{19}$F NMR (376 MHz, Chloroform-d) δ -73.90 (d, J=7.7 Hz). $^{31}$P NMR (162 MHz, Chloroform-d) δ -3.07.

Intermediate 29. trans 4-(trifluoromethyl)cyclohexyl ((S)-(4-nitrophenoxy)(phenoxy)phosphoryl)-L-alaninate. Second eluting diastereomer of Intermediate 27: $^1$H NMR (400 MHz, Chloroform-d) δ 8.21 (d, J=9.08 Hz, 2H), 7.42-7.31 (m, 4H), 7.26-7.13 (m, 3H), 4.67 (tt, J=10.8, 4.2 Hz, 1H), 4.11 (ddt, J=15.8, 8.9, 7.1 Hz, 1H), 3.97 (dd, J=12.0, 9.4 Hz, 1H), 2.07-1.91 (m, 5H), 1.51-1.19 (m, 7H). $^{19}$F NMR (376 MHz, Chloroform-d) δ -73.90 (d, J=7.9 Hz). $^{31}$P NMR (162 MHz, Chloroform-d) δ -3.08.

Intermediate 30. 1-Methylpiperidin-4-yl((4-nitrophenoxy) (phenoxy)phosphoryl)-L-alaninate

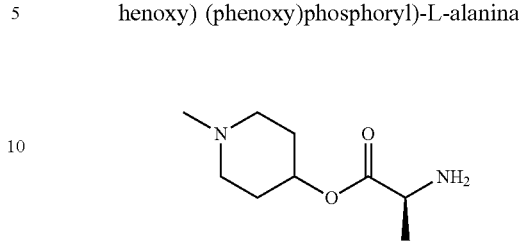

1-Methylpiperidin-4-yl L-alaninate. To a mixture of N-Cbz-L-alanine (1.047 g, 4.688 mmol), 4-hydroxy-N-methylpiperidine (450 mg, 3.907 mmol), and EDCI (788 mg, 5.079 mmol) in acetonitrile (20 mL) was added DMAP (716 mg, 5.861 mmol). Then the mixture was stirred at room temperature for 15 h, then diluted with EtOAc, washed with brine, dried over sodium sulfate, and concentrated in vacuo. The obtained residue was purified by silica gel chromatography (MeOH 0 to 10% in DCM) to give an Cbz-L-alanine 4-piperidyl ester, which was dissolved in THF (10 mL) and 20% Pd(OH)$_2$ (300 mg, 0.427 mmol) was added at room temperature. The resulting mixture was stirred under H$_2$ gas at room temperature for 2 h, filtered, concentrated in vacuo, co-evaporated with DCM several times, and dried under high vacuum overnight to afford the product. $^1$H NMR (400 MHz, Chloroform-d) δ 4.81 (td, J=8.3, 7.7, 3.8 Hz, 1H), 3.52 (q, J=7.0 Hz, 1H), 2.63 (s, 2H), 2.29 (s, 5H), 2.14-1.86 (m, 4H), 1.73 (ddt, J=12.9, 8.8, 4.5 Hz, 2H), 1.32 (d, J=7.0 Hz, 3H). LCMS: MS m/z=187.09 [M+1]; t$_R$=0.12 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min.

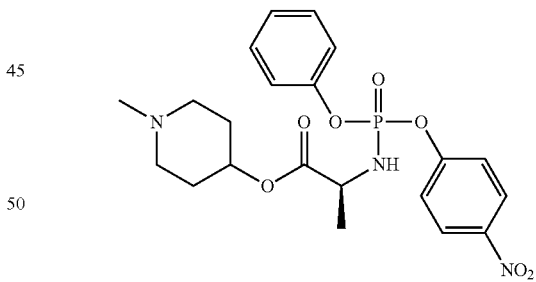

1-Methylpiperidin-4-yl((4-nitrophenoxy) (phenoxy)phosphoryl)-L-alaninate. To a solution of 1-Methylpiperidin-4-yl L-alaninate (360 mg, 1.706 mmol) in DCM (10 mL) was added phenyl phosphorodichloridate (0.255 mL, 1.706 mmol) in one portion at -78° C. and then triethylamine (0.24 mL, 1.706 mmol) in DCM (2.76 mL) was added over 30 min at -78° C. The resulting mixture was stirred for 30 min after removal of dry ice bath and then recooled to -78° C. p-Nitrophenol (0.237 g, 1.706 mmol) was added in one portion and triethylamine (0.237 mL, 1.706 mmol) added over 30 min at -78° C. The resulting mixture was stirred for 30 min after removal of dry ice bath, then diluted with EtOAc, washed with water and brine, concentrated in vacuo, and the resulting residue purified by silica gel column chromatography (MeOH 0 to 10% in DCM) to afford the product. $^1$H NMR (400 MHz, Chloroform-d) δ 8.28-8.15 (m, 2H), 7.36 (m, 4H), 7.25-7.17 (m, 3H), 4.80 (s, 1H), 4.19-4.04 (m, 1H), 3.93 (m, 1H), 2.64 (s, 2H), 2.31 (m, 5H), 1.90 (m, 2H), 1.78-1.67 (m, 2H), 1.47-1.33 (m, 3H). $^{31}$P NMR (162 MHz, Chloroform-d) δ −3.04, −3.07. LCMS: MS m/z=464.32 [M+1]; $t_R$=0.74 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

Intermediate 31. (tetrahydro-2H-pyran-4-Yl)methyl ((4-nitrophenoxy)(phenoxy)phosphoryl)-L-alaninate

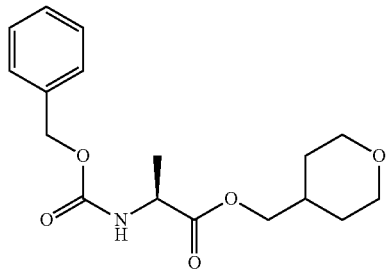 [SMILES: C[C@H](NC(=O)OCc1ccccc1)C(=O)OCC1CCOCC1]

(tetrahydro-2H-pyran-4-yl)methyl ((benzyloxy)carbonyl)-L-alaninate. Cbz-L-Ala (446 mg, 2 mmol) was dissolved in anhydrous MeCN (10 mL). EDCI (422 mg, 2.2 mmol) was added in one portion and the reaction was stirred for 15 mins. Tetrahydropyran-4-methanol (279 uL, 2.4 mmol) was added. DMAP (269 mg, 2.2 mmol) was then added in one portion. Reaction was stirred for 16 hrs.

Reaction was diluted reaction with EtOAc (30 mL) and washed with 5% aqueous citric acid solution (10 mL), followed with saturated aqueous sodium bicarbonate solution (10 mL) and finally with brine (10 mL). Organic was dried over anhydrous sodium sulfate and concentrated under reduced pressure. The crude residue was purified via SiO$_2$ column chromatography (12 g SiO$_2$ Combiflash HP Gold Column, 0-80% ethyl acetate/hexanes). Fractions were combined and concentrated under reduced pressure to afford the product. $^1$H NMR (400 MHz, Chloroform-d) δ 7.40-7.28 (m, 5H), 5.28 (d, J=7.9 Hz, 1H), 5.11 (s, 2H), 4.39 (t, J=7.4 Hz, 1H), 4.07-3.84 (m, 4H), 3.38 (t, J=11.7 Hz, 2H), 1.92 (s, 1H), 1.68-1.50 (m, 3H), 1.39 (m, 4H).

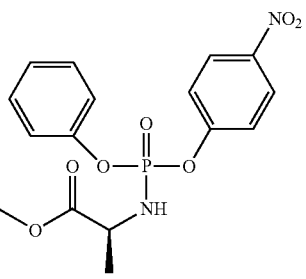

(tetrahydro-2H-pyran-4-yl)methyl ((4-nitrophenoxy)(phenoxy)phosphoryl)-L-alaninate. (tetrahydro-2H-pyran-4-yl)methyl ((benzyloxy)carbonyl)-L-alaninate (530 mg, 1.65 mmol) was dissolved in anhydrous THF (12 mL). 10% Pd/C Degussa type was added and the reaction mixture was stirred under atmospheric hydrogen for 2 hrs. Catalyst was filtered and the filtrate was used without purification.

Phenyl dichlorophosphate (294 uL, 1.98 mmol) was dissolved in anhydrous DCM (10 mL) and stirred in an ice bath under atmospheric nitrogen. Above THF solution was added to the reaction dropwise and then stirred for 10 mins. Triethylamine (300 uL, 2.15 mmol) was added dropwise and then stirred for 30 mins. p-Nitrophenol (207 mg, 1.49 mmol) and triethylamine (300 uL, 2.15 mmol) were added. Ice bath was removed and the reaction mixture was stirred for 14 hrs at RT.

Reaction was diluted with EtOAc (30 mL) and washed with 0.2 M sodium carbonate solution (2×10 mL) and followed with brine (10 mL). Organic was dried over anhydrous sodium sulfate and concentrated under reduced pressure. The crude residue was purified via SiO$_2$ column chromatography (12 g SiO$_2$ Combiflash HP Gold Column, 0-50% ethyl acetate/hexanes). Fractions were combined and concentrated under reduced pressure to afford the product. $^1$H NMR (400 MHz, Chloroform-d) δ 8.23 (d, J=9.0 Hz, 2H), 7.45-7.30 (m, 4H), 7.30-7.16 (m, 3H), 4.23-4.07 (m, 2H), 3.97 (m, 4H), 3.85 (t, J=10.5 Hz, 1H), 3.35 (t, J=11.8 Hz, 2H), 1.99-1.79 (m, 1H), 1.56 (d, J=8.4 Hz, 3H), 1.48-1.29 (m, 4H). $^{31}$P NMR (162 MHz, Chloroform-d) δ −3.13 (s), −3.16 (s). MS m/z=464.9 [M+1]; 463.1 [M−1].

Intermediate 32. trans-4-(tert-butyl)cyclohexyl ((S)-(4-nitrophenoxy)(phenoxy)phosphoryl)-L-alaninate

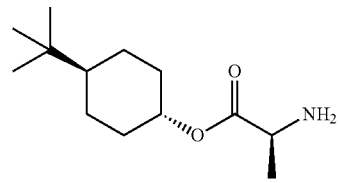 [SMILES: C[C@H](N)C(=O)O[C@H]1CC[C@H](C(C)(C)C)CC1]

trans-4-(tert-butyl)cyclohexyl L-alaninate. The product (845 mg) was prepared from Cbz-1-alanine (960 mg, 4.03 mmol) and trans-4-(tert-butyl)cyclohexanol (1.0 g, 6.45 mmol) in a manner similar to that described for Intermediate 26. $^1$H NMR (400 MHz, Chloroform-d) δ 4.65 (tt, J=11.2, 4.5 Hz, 1H), 3.51 (q, J=7.1 Hz, 1H), 2.07-1.93 (m, 2H), 1.87-1.73 (m, 4H), 1.40-1.23 (m, 4H), 1.19-0.94 (m, 4H), 0.85 (d, J=2.6 Hz, 9H). MS m/z=228 [M+H].

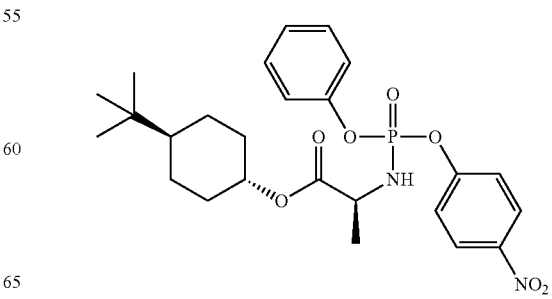

trans-4-(tert-butyl)cyclohexyl ((4-nitrophenoxy)(phenoxy) phosphoryl)-L-alaninate. The product (520 mg) was prepared as isomeric mixture from trans-4-(tert-butyl)cyclohexyl L-alaninate (420 mg, 1.85 mmol) in a manner similar to that described for Intermediate 25. $^1$H NMR (400 MHz, Chloroform-d) δ 8.27-8.19 (m, 2H), 7.37 (m, 4H), 7.28-7.16 (m, 3H), 4.62 (m, 1H), 4.17-4.00 (m, 1H), 3.88 (m, 1H), 1.95 (m, 2H), 1.80 (m, 2H), 1.39 (m, 3H), 1.35-1.22 (m, 2H), 1.15-0.92 (m, 3H), 0.85 (s, 9H). $^{31}$P NMR (162 MHz, Chloroform-d) δ −2.98, −3.04. MS m/z=505 [M+H].

Intermediate 33. ((1r, 4S)-4-(trifluoromethyl)cyclohexyl)methyl ((4-nitrophenoxy)(phenoxy)phosphoryl)-L-alaninate

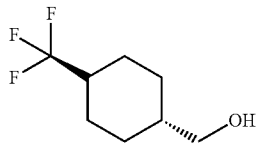

((1s, 4s)-4-(trifluoromethyl)cyclohexyl)methanol. To an ice cold solution of (1s,4s)-4-(trifluoromethyl)cyclohexane carboxylic acid (3 g, 15.29 mmol) in anhydrous tetrahydrofuran (40 mL) was added lithium aluminum hydride (0.871 g, 22.94 mmol) portion wise in 30 min. The reaction mixture was stirred at room temperature for 3 h. Cooled to 0° C. and quenched with water (0.8 mL), 5 N aqueous sodium hydroxide (0.8 mL) followed by water (2.4 mL). Solids separated were filtered and filtrate was diluted with ethyl acetate and saturated aqueous sodium bicarbonate solution. Organic layer was separated, washed with brine and dried over sodium sulfate. Ethyl acetate was filtered and concentrated under reduced pressure to afford the product. The residue obtained was dried at high vacuum for 1 h and is used as such in subsequent reactions. $^1$H NMR (400 MHz, Chloroform-d) δ 3.47 (dd, J=6.3, 1.9 Hz, 2H), 2.08-1.77 (m, 5H), 1.62-1.18 (m, 4H), 0.99 (qd, J=13.0, 3.2 Hz, 2H). $^{19}$F NMR (376 MHz, Chloroform-d) δ −74.33 (d, J=8.2 Hz).

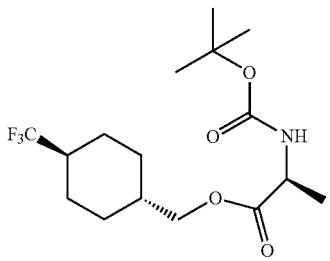 [SMILES: C[C@H](NC(=O)OC(C)(C)C)C(=O)OC[C@H]1CC[C@H](C(F)(F)F)CC1]

((1r, 4S)-4-(trifluoromethyl)cyclohexyl)methyl (tert-butoxycarbonyl)-L-alaninate. The product (1.48 g) was prepared in a manner similar to that described for Intermediate 12. $^1$H NMR (400 MHz, Chloroform-d) δ 5.00 (s, 1H), 4.30 (s, 1H), 4.04-3.89 (m, 2H), 2.08-1.79 (m, 5H), 1.74-1.57 (m, 1H), 1.44 (s, 9H), 1.38 (d, J=7.2 Hz, 3H), 1.30 (m, 2H), 1.12-0.93 (m, 2H). $^{19}$F NMR (376 MHz, Chloroform-d) δ −74.38 (d, J=7.8 Hz).

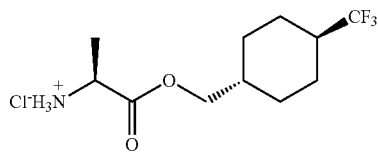

(S)-1-oxo-1-(((1r, 4S)-4-(trifluoromethyl)cyclohexyl)methoxy)propan-2-aminium chloride. The product (1.184 g) was prepared in a manner similar to that described for Intermediate 13. $^1$H NMR (400 MHz, DMSO-d6) δ 8.55 (s, 3H), 4.17-3.88 (m, 3H), 2.21 (dtd, J=12.2, 8.8, 3.3 Hz, 1H), 1.83 (ddd, J=29.5, 13.4, 3.4 Hz, 4H), 1.63 (tdd, J=11.9, 6.0, 3.3 Hz, 1H), 1.41 (d, J=7.2 Hz, 3H), 1.32-0.93 (m, 4H). $^{19}$F NMR (377 MHz, DMSO-d6) δ −72.84 (d, J=8.8 Hz).

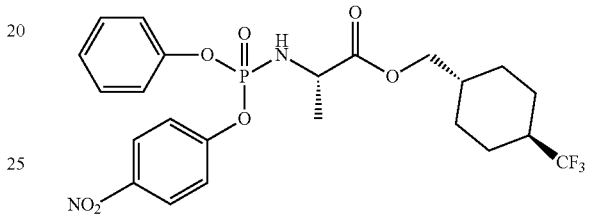

((1r, 4S)-4-(trifluoromethyl)cyclohexyl)methyl ((4-nitrophenoxy)(phenoxy)phosphoryl)-L-alaninate. The product (1.4 g) was prepared in a manner similar to that described for Intermediate 35. $^1$H NMR (400 MHz, DMSO-d6) δ 8.37-8.22 (m, 2H), 7.56-7.31 (m, 4H), 7.30-7.14 (m, 2H), 6.72 (ddd, J=13.7, 10.1, 8.6 Hz, 1H), 4.10-3.91 (m, 1H), 3.88-3.75 (m, 2H), 2.20-1.99 (m, 1H), 1.86-1.63 (m, 4H), 1.54-1.41 (m, 1H), 1.29-1.06 (m, 5H), 0.98 (td, J=12.7, 3.2 Hz, 2H). MS m/z=531.02 [M+1].

Intermediate 34. Ethyl ((S)-(perfluorophenoxy)(phenoxy)phosphoryl)-L-alaninate

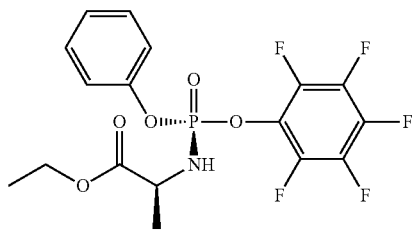 [SMILES: CCOC(=O)[C@H](C)N[P@](=O)(Oc1ccccc1)Oc1c(F)c(F)c(F)c(F)c1F]

To a solution of L-alanine ethyl ester-HCl (631 mg, 2.465 mmol) in DCM (15 mL) was added phenyl phosphorodichloridate (0.368 mL, 2.465 mmol) in one portion at −78° C. and triethylamine (0.68 mL, 4.93 mmol) was added dropwise over 5 min at −78° C. The resulting mixture was stirred for 30 min after removal of dry ice bath and then cooled to −78° C. Pentafluorophenol (454 mg, 2.465 mmol) was added in one portion and triethylamine (0.34 mL, 2.465 mmol) added over 5 min at −78° C. The resulting mixture was stirred for 1 h after removal of dry ice bath, then diluted with DCM, washed with brine, concentrated in vacuo, and the resulting residue purified by silica gel column chromatography (EtOAc 0 to 60% in hexanes) to give a diastereomeric mixture, to which diisopropyl ether (4 mL) was added.

The suspension was sonicated and filtered. $^1$H NMR of the filter cake showed it is 3:1 ratio of mixture. Diisopropyl ether (5 mL) was added to the filter cake and the suspension was heated at 70° C. to a clear solution. Upon removal of heating bath, needle like crystals started to form and after 10 min, the mixture was filtered and the filter cake was dried under high vacuum for 30 min to afford the Sp isomer.

Diastereomeric mixture: $^1$H NMR (400 MHz, Chloroform-d) δ 7.43-7.30 (m, 2H), 7.32-7.17 (m, 3H), 4.29-4.11 (m, 3H), 3.94 (m, 1H), 1.52-1.42 (m, 3H), 1.28 (q, J=7.0 Hz, 3H).

Sp isomer: $^1$H NMR (400 MHz, Acetonitrile-d3) δ 7.50-7.36 (m, 2H), 7.32-7.21 (m, 3H), 4.75 (t, J=11.5 Hz, 1H), 4.17-3.98 (m, 3H), 1.37 (dd, J=7.1, 1.1 Hz, 3H), 1.22 (t, J=7.1 Hz, 3H). $^{31}$P NMR (162 MHz, Acetonitrile-d3) δ −0.51. $^{19}$F NMR (376 MHz, Acetonitrile-d3) δ −155.48-−155.76 (m), −162.73 (td, J=21.3, 3.7 Hz), −165.02-−165.84 (m). LCMS m/z=440.5 (M-ethyl+H), $t_R$=1.57 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

Intermediate 35. (2S)-2-ethylbutyl 2-cyclohexyl-2-(((4-nitrophenoxy) (phenoxy)phosphoryl)amino) acetate

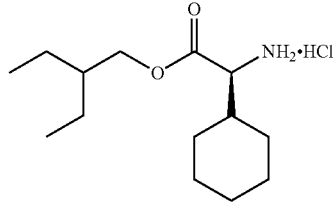

(S)-2-ethylbutyl 2-amino-2-cyclohexylacetate hydrochloride. Took up L-cyclohexylglycine (0.90 g, 5.75 mmol) in 2-ethyl-1-butanol (20 mL) and added chlorotimethylsilane (1.31 mL, 10.30 mmol) in one portion. Placed in a preheated 60° C. oil bath for 16 h. Concentrated and co-evaporated with toluene 5 times in a 60° C. rotary evaporator bath. Placed under high vacuum overnight to afford the product. The material was used as is for the next step. $^1$H NMR (400 MHz, DMSO-$d_6$) δ 8.38 (s, 3H), 4.17-3.96 (m, 2H), 3.84 (d, J=4.5 Hz, 1H), 1.90-1.40 (m, 5H), 1.41-0.88 (m, 11H), 0.83 (t, J=7.3 Hz, 6H).

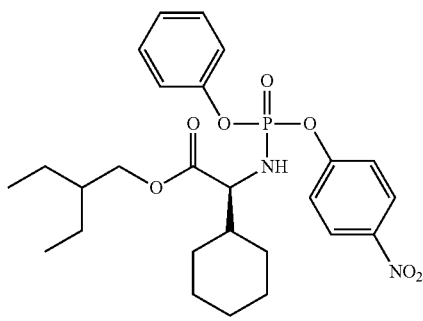 [SMILES: CCC(CC)COC(=O)[C@@H](NP(=O)(Oc1ccccc1)Oc1ccc([N+](=O)[O-])cc1)C1CCCCC1]

(2S)-2-ethylbutyl 2-cyclohexyl-2-(((4-nitrophenoxy)(phenoxy)phosphoryl)amino)acetate. To a solution of (S)-2-ethylbutyl 2-amino-2-cyclohexylacetate hydrochloride (1.50 g, 5.39 mmol) and phenyl dichlorophosphate (0.803 mL, 5.39 mmol) in dichloromethane (50 mL) was added triethylamine (1.56 mL, 11.16 mmol) at 0° C. under an argon atmosphere. The resulting mixture was allowed to warm to RT and was stirred for 1 h. 4-Nitrophenol (713 mg, 5.13 mmol) and triethylamine (0.81 mL, 5.63 mmol) were then added. After 2 h, the reaction mixture was diluted with Et$_2$O (100 mL) and the solids were filtered off. The crude was concentrated under reduced pressure and was purified by silica gel chromatography (120 g SiO$_2$ Combiflash HP Gold Column, 0-50% ethyl acetate/hexanes), followed by purification by reverse phase HPLC without modifier 20-100% ACN in Water to afford the product. $^1$H NMR (400 MHz, DMSO-$d_6$) δ 8.28 (br d, J=9.3 Hz, 2H), 7.55-7.28 (m, 4H), 7.28-7.01 (m, 3H), 6.61-6.52 (m, 1H), 3.85 (d, J=4.0 Hz, 2H) 3.75-3.53 (m, 1H), 1.67-1.31 (m, 7H), 1.25 (m, 6H), 1.16-0.67 (m, 9H). LC/MS: $t_R$=1.48 min, MS m/z=519.03 [M+1]; LC system: Thermo Accela 1250 UHPLC. MS system: Thermo LCQ Fleet; Column: Kinetex 2.6μ XB-C18 100 A, 50×3.00 mm. Solvents: Acetonitrile with 0.1% formic acid, Water with 0.1% formic acid. Gradient: 0 min-2.4 min 2-100% ACN, 2.4 min-2.80 min 100% ACN, 2.8 min-2.85 min 100%-2% ACN, 2.85 min-3.0 min 2% ACN at 1.8 m/min.

Intermediate 36. (1-(2,2,2-trifluoroethyl)piperidin-4-yl)methyl ((4-nitrophenoxy)(phenoxy)phosphoryl) alaninate

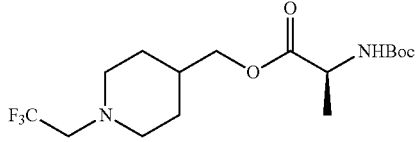 [SMILES: C[C@H](NC(=O)OC(C)(C)C)C(=O)OCC1CCN(CC(F)(F)F)CC1]

(1-(2,2,2-trifluoroethyl)piperidin-4-yl)methyl (tert-butoxycarbonyl)alaninate. The product (3.8 g) was prepared in a manner similar to that described for Intermediate 12. $^1$H NMR (400 MHz, DMSO-$d_6$) δ 7.25 (d, J=7.4 Hz, 1H), 4.08-3.72 (m, 3H), 3.10 (q, J=10.3 Hz, 2H), 2.88 (d, J=11.0 Hz, 2H), 2.37-2.18 (m, 2H), 1.66-1.47 (m, 3H), 1.36 (s, 9H), 1.21 (d, J=7.5 Hz, 5H). $^{19}$F NMR (376 MHz, DMSO-$d_6$) δ −68.52 (t, J=10.3 Hz).

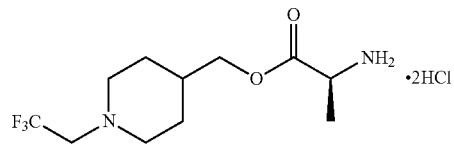 [SMILES: C[C@H](N)C(=O)OCC1CCN(CC(F)(F)F)CC1]

(1-(2,2,2-trifluoroethyl)piperidin-4-yl)methyl alaninate dihydrochloride. The product (3.52 g) was prepared in a manner similar to that described for Intermediate 13. $^1$H NMR (400 MHz, DMSO-$d_6$) δ 8.67 (s, 3H), 4.44-3.75 (m, 5H), 3.49-2.81 (m, 4H), 2.00-1.61 (m, 5H), 1.43 (d, J=7.2 Hz, 3H). $^{19}$F NMR (376 MHz, DMSO-$d_6$) δ −63.30 (d, J=443.2 Hz).

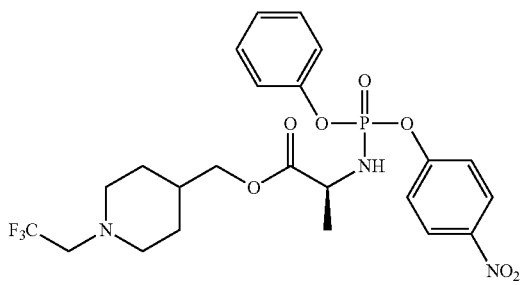 [SMILES: C[C@H](NP(=O)(Oc1ccccc1)Oc1ccc([N+](=O)[O-])cc1)C(=O)OCC1CCN(CC(F)(F)F)CC1]

(1-(2,2-trifluoroethyl)piperidin-4-yl)methyl ((4-nitrophenoxy)(phenoxy)phosphoryl)alaninate. The product (4.25 g) was prepared in a manner similar to that described for Intermediate 35. $^1$H NMR (400 MHz, DMSO-d$_6$) δ 8.32-8.24 (m, 2H), 7.53-7.40 (m, 2H), 7.39 (ddd, J=8.1, 6.8, 3.1 Hz, 2H), 7.24 (ddd, J=17.4, 6.5, 1.6 Hz, 3H), 6.69 (ddd, J=13.7, 10.0, 8.4 Hz, 1H), 4.07-3.92 (m, 1H), 3.88-3.77 (m, 2H), 3.08 (qd, J=10.3, 1.6 Hz, 2H), 2.87-2.79 (m, 2H), 2.25-2.14 (m, 2H), 1.56-1.39 (m, 3H), 1.26-1.08 (m, 5H). $^{31}$P NMR (162 MHz, DMSO-d$_6$) δ −1.26, −1.49. $^{19}$F NMR (376 MHz, DMSO-d$_6$) δ −68.45 (td, J=10.2, 2.4 Hz). LCMS: MS m/z=546.27 [M+1];]; t$_R$=1.12 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

Intermediate 37. (1-Ethyl-3,3-difluoropiperidin-4-yl ((4-nitrophenoxy)(phenoxy)phosphoryl)-L-alaninate

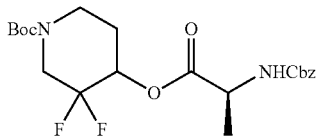 [SMILES: C[C@H](NC(=O)OCc1ccccc1)C(=O)OC1CCN(C(=O)OC(C)(C)C)CC1(F)F]

tert-Butyl 4-((((benzyloxy)carbonyl)-L-alanyl)oxy)-3,3-difluoropiperidine-1-carboxylate. To a mixture of N-Cbz-L-alanine (2.0 g, 8.96 mmol), tert-butyl 3,3-difluoro-4-hydroxypiperidine-1-carboxylate (2.12 g, 8.96 mmol), and EDCI (1.67 g, 10.75 mmol) in acetonitrile (20 mL) was added DMAP (1.64 g, 13.44 mmol). Then the mixture was stirred at room temperature for 15 h, then diluted with EtOAc, washed with brine, dried over sodium sulfate, and concentrated in vacuo. The obtained residue was purified by silica gel chromatography (EtOAc 50 to 100% in hexanes) to afford the product. $^{19}$F NMR (377 MHz, Chloroform-d) δ −114.32 (m), −117.73-−121.11 (m). LCMS: MS m/z=343.14 [M+1-Boc], 386.82 (M+1-t-Bu); t$_R$=1.23 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

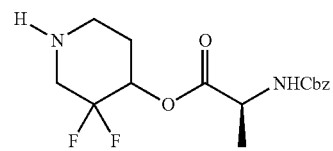 [SMILES: C[C@H](NC(=O)OCc1ccccc1)C(=O)OC1CCNCC1(F)F]

3,3-difluoropiperidin-4-yl ((benzyloxy)carbonyl)-L-alaninate. To a mixture of tert-Butyl 4-((((benzyloxy)carbonyl)-L-alanyl)oxy)-3,3-difluoropiperidine-1-carboxylate (330 mg, 0.746 mmol) in DCM (5 mL) was added 4 M HCL in dioxane (0.9 mL) slowly at room temperature. The resulting mixture was stirred at room temperature for 2 h, concentrated in vacuo, co-evaporation with DCM several times, and dried under high vacuum for 15 h to afford the product. $^1$H NMR (400 MHz, Chloroform-d) δ 7.33 (m, 5H), 5.59 (m, 1H), 5.27-5.01 (m, 3H), 4.53-4.25 (m, 1H), 3.12 (m, 1H), 3.03-2.76 (m, 2H), 2.73 (s, 1H), 1.94 (s, 1H), 1.80 (s, 1H), 1.41 (d, J=7.2 Hz, 3H). $^{19}$F NMR (376 MHz, Chloroform-d) δ −114.66 (dd, J=245.9, 61.8 Hz), −119.63.

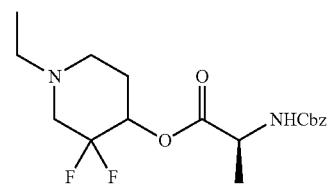 [SMILES: CCN1CCC(OC(=O)[C@H](C)NC(=O)OCc2ccccc2)C(F)(F)C1]

1-ethyl-3,3-difluoropiperidin-4-yl ((benzyloxy)carbonyl)-L-alaninate. A mixture of 3,3-difluoropiperidin-4-yl ((benzyloxy)carbonyl)-L-alaninate (450 mg, 1.190 mmol), acetaldehyde (0.194 mL, 2.629 mmol), and acetic acid (0.15 mL, 2.629 mmol) in DCM (9 mL) was stirred for 20 min at room temperature and sodium cyanoborohydride (330 mg, 5.258 mmol) was added. The resulting mixture was stirred for 1 h and purified by preparative HPLC (Phenominex Gemini 10 u C18 110 Å 250×21.2 mm column, 20-80% acetonitrile (0.1% TFA)/water (0.1% TFA) gradient) to afford the product. $^1$H NMR (400 MHz, Acetonitrile-d$_3$) δ 10.18 (bs, 2H), 7.38 (m, 5H), 6.19 (m, 1H), 5.47-5.26 (m, 1H), 4.33 (m, 1H), 3.82-2.98 (m, 6H), 2.30 (s, 1H), 2.16 (s, 1H), 1.42 (m, 3H), 1.31 (td, J=7.3, 1.5 Hz, 3H). LCMS: MS m/z=371.27 [M+1]; t$_R$=0.66 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

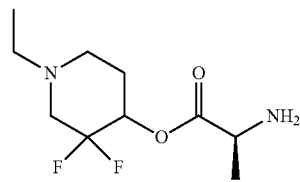 [SMILES: CCN1CCC(OC(=O)[C@H](C)N)C(F)(F)C1]

1-ethyl-3,3-difluoropiperidin-4-yl L-alaninate. A mixture of 1-ethyl-3,3-difluoropiperidin-4-yl ((benzyloxy)carbonyl)-L-alaninate (450 mg, 0.929 mmol) and 20% Pd(OH)₂/C in THF (10 mL) was stirred at room temperature under H₂ gas for 1 h, filtered, concentrated in vacuo, co-evaporated with DCM several time, and dried under high vacuum for 1 h to afford the product. LCMS: MS m/z=237.09 [M+1]; $t_R$=0.15 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

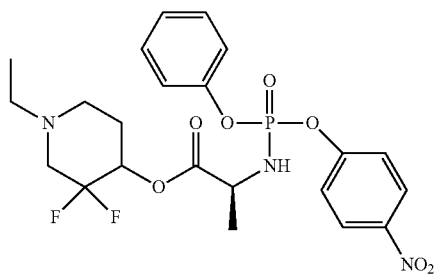 [SMILES: CCN1CCC(OC(=O)[C@H](C)NP(=O)(Oc2ccccc2)Oc2ccc([N+](=O)[O-])cc2)C(F)(F)C1]

(1-Ethyl-3,3-difluoropiperidin-4-yl ((4-nitrophenoxy)(phenoxy)phosphoryl)-L-alaninate. Methylene chloride (10 mL) was added to the syrup of 1-ethyl-3,3-difluoropiperidin-4-yl L-alaninate (480 mg, 1.37 mmol) and TEA (0.190 mL, 0.370 mmol) was added to achieve a solution, which was cooled to −78° C. and phenyl dichlorophosphate (0.205 mL, 1.370 mmol) was added quickly. Triethylamine (0.190 mL, 1.37 mmol) was added over 30 min at −78° C. The resulting mixture was stirred for 30 min at the same temperature and 4-nitrophenol (191 mg, 1.370 mmol) added in one portion. Then triethylamine (0.190 mL, 1.370 mmol) was added over 30 min at −78° C. Then the mixture was stirred for 2 h at room temperature, washed with water and brine, dried over sodium sulfate, and concentrated in vacuo. The residue was then purified by silica gel column chromatography (EtOAc 0 to 100% in hexanes) to give the product. ¹H NMR (400 MHz, Chloroform-d) δ 8.29-8.15 (m, 2H), 7.44-7.28 (m, 4H), 7.27-7.11 (m, 3H), 5.03 (m, 1H), 4.34-4.14 (m, 1H), 3.94-3.75 (m, 1H), 2.88 (s, 1H), 2.63-2.49 (m, 4H), 2.39 (m, 1H), 2.03-1.93 (m, 1H), 1.93-1.77 (m, 1H), 1.44 (m, 3H), 1.09 (td, J=7.2, 1.0 Hz, 3H). ³¹P NMR (162 MHz, Chloroform-d) δ −3.21, −3.26, −3.32, −3.46. ¹⁹F NMR (377 MHz, Chloroform-d) δ −110.50 (d, J=244.0 Hz), −116.76 (m). LCMS: MS m/z=514.29 [M+1]; $t_R$=0.80 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

Intermediate 38. 4-nitrophenyl-N,N'-ethyl L-alaninatephosphorodiamidate

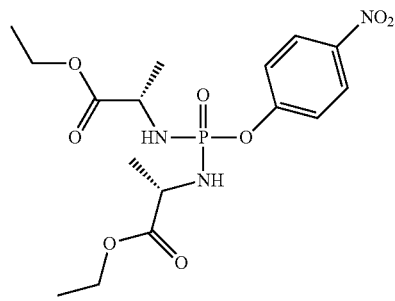 [SMILES: CCOC(=O)[C@H](C)NP(=O)(N[C@@H](C)C(=O)OCC)Oc1ccc([N+](=O)[O-])cc1]

To a solution of ethyl L-alaninate HCl salt (1.8 g, 11.72 mmol) in DCM (20 mL) was added 4-nitrophenyl phosphorodichloridate (1.5 g, 5.86 mmol) in one portion. The resulting mixture was cooled to 0° C. and triethylamine (2.37 g, 23.44 mmol) was added dropwise. The resulting mixture was stirred for 30 min after removal of ice bath and was stirred for overnight. The reaction mixture was then diluted with EtOAc, washed with water and brine, the organic solvent was concentrated in vacuum, and the resulting residue was purified by silica gel column chromatography eluting with 0-100% ethyl acetate in hexanes to afford the product. LCMS: MS m/z=417.93 [M+1], $t_R$=1.23 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.02 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Intermediate 39. benzyl ((4-nitrophenoxy)(phenoxy)phosphoryl)-L-alaninate

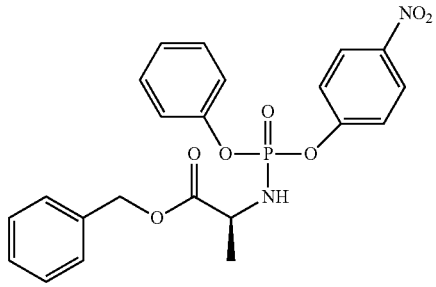 [SMILES: C[C@H](NP(=O)(Oc1ccccc1)Oc1ccc([N+](=O)[O-])cc1)C(=O)OCc1ccccc1]

Phenyl dichlorophosphate (1.49 mL, 10 mmol) was dissolved in 20 mL anhydrous dichloromethane and stirred under atmospheric nitrogen in an ice bath. L-Alanine benzyl ester HCl (2.2 g, 10 mmol) was added to the reaction solution in one portion and stirred for 10 min. Triethylamine (3 mL, 22 mmol) was dissolved in 5 mL of anhydrous dichloromethane and added to the reaction dropwise. The reaction mixture was stirred for 2 h. p-Nitrophenol (1.25 g, 9 mmol) was added in one portion. Triethylamine (1.5 mL, 11 mmol) was dissolved in 3 mL of anhydrous dichloromethane and added to the reaction dropwise. The reaction mixture was stirred for 1 h, and was diluted with dichloromethane (10 mL) and washed with water (3×10 mL). Organic extract was dried over anhydrous sodium sulfate and concentrated under reduced pressure. The crude residue was purified via SiO$_2$ column chromatography (4 g SiO$_2$ Combiflash HP Gold Column, 0-30% ethyl acetate/hexanes). Fractions containing the desired product were combined and concentrated under reduced pressure to afford the product. $^1$H NMR (400 MHz, chloroform-d) δ 8.24-8.10 (m, 2H), 7.40-7.10 (m, 12H), 5.14 (m, 2H), 4.19 (m, 1H), 3.87 (m, 1H), 1.47-1.36 (m, 3H). $^{31}$P NMR (162 MHz, chloroform-d) δ −3.15, −3.29. LCMS: MS m/z=457.1 [M+1]; 455.1 [M−1], $t_R$=1.45 min; LC system: Thermo Dionex ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 m/min. HPLC: $t_R$=4.03 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min.

Intermediate 40. 4-nitrophenyl-N,N'-methyl L-alaninatephosphorodiamidate

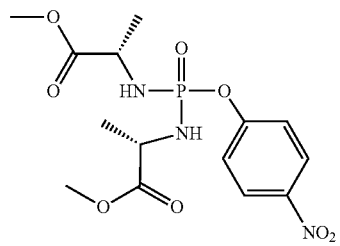 [SMILES: COC(=O)[C@H](C)NP(=O)(N[C@@H](C)C(=O)OC)Oc1ccc([N+](=O)[O-])cc1]

Triethylamine (3.68 mL, 26.4 mmol) was added to a solution of methyl L-alaninate hydrochloride (1.63 g, 12.0 mmol) and 4-nitrophenyl phosphorodichloridate (1.5 g, 5.9 mmol) in dichloromethane (23 mL) at 0° C. under an argon atmosphere. After 3 h, the reaction mixture was diluted with dichloromethane (50 mL), washed with saturated aqueous sodium bicarbonate solution (50 mL) and brine (50 mL), dried over anhydrous sodium sulfate, and concentrated under reduced pressure. The crude residue was purified by silica gel chromatography eluting with 0-100% ethyl acetate in hexanes to afford the product. $^1$H NMR (400 MHz, chloroform-d$_1$) 8.25-8.16 (m, 2H), 7.38 (dd, J=9.3, 1.0 Hz, 2H), 4.17-3.95 (m, 2H), 3.73 (br s, 6H), 3.61 (br t, J=10.0 Hz, 2H), 1.42 (s, 3H), 1.40 (s, 1H). $^{31}$P NMR (162 MHz, chloroform-d$_1$) δ 7.82 (s). LCMS: MS m/z=389.98 [M+1], $t_R$=1.11 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=2.81 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Intermediate 41. methyl ((4-nitrophenoxy)(phenoxy)phosphoryl)-L-alaninate

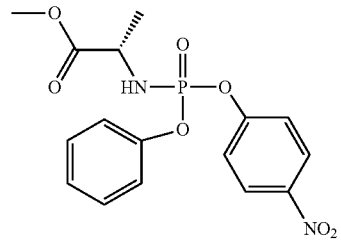 [SMILES: COC(=O)[C@H](C)NP(=O)(Oc1ccccc1)Oc1ccc([N+](=O)[O-])cc1]

Phenyl dichlorophosphate (2.81 mL, 18.9 mmol) and triethylamine (5.38 mL, 37.9 mmol) were sequentially added to a suspension of methyl L-alaninate hydrochloride (2.64 g, 18.9 mmol) in dichloromethane (100 mL) at 0° C. After 1 h, 4-nitrophenol (2.64 g, 18.9 mmol) and triethylamine (2.64 mL, 18.9 mmol) were then sequentially added at 0° C., and the resulting mixture was then allowed to warm to RT. After 2.5 h, the reaction mixture was diluted with dichloromethane (100 mL), washed with saturated a aqueous sodium bicarbonate solution (100 mL) and brine (100 mL), dried over anhydrous sodium sulfate, and concentrated under reduced pressure. The crude residue was purified by silica gel chromatography eluting with 0-100% ethyl acetate in hexanes to afford the product. $^1$H NMR (400 MHz, chloroform-d$_1$) δ 8.25-8.18 (m, 2H), 7.43-7.29 (m, 4H), 7.29-7.15 (m, 3H), 4.24-4.07 (m, 1H), 3.97 (br q, J=9.8 Hz, 1H), 3.70 (s, 3H), 1.45-1.35 (m, 3H). $^{31}$P NMR (162 MHz, chloroform-d$_1$) δ −3.12 (s), −3.17 (s). LCMS: MS m/z=380.98 [M+1], $t_R$=1.59 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.49 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Intermediate 42. methyl ((4-nitrophenoxy)(phenoxy)phosphoryl)-L-alaninate

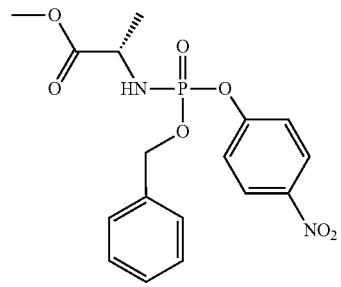 [SMILES: COC(=O)[C@H](C)NP(=O)(OCc1ccccc1)Oc1ccc([N+](=O)[O-])cc1]

4-Nitrophenyl phosphorodichloridate (2.00 g, 7.81 mmol) and triethylamine (2.18 mL, 15.6 mmol) were sequentially added to a suspension of methyl L-alaninate hydrochloride (1.091 g, 18.9 mmol) in dichloromethane (23 mL) at 0° C. under an argon atmosphere. After 1 h, benzyl alcohol (0.810 mL, 7.81 mmol) and triethylamine (1.09 mL, 7.81 mmol) were then sequentially added at 0° C., and the resulting mixture was then allowed to warm to RT. After 1 h, the reaction mixture was diluted with dichloromethane (50 mL), washed with saturated an aqueous sodium bicarbonate solution (50 mL) and brine (50 mL), dried over anhydrous sodium sulfate, and concentrated under reduced pressure. The crude residue was purified by silica gel chromatography eluting with 0-100% ethyl acetate in hexanes to afford the product. $^1$H NMR (400 MHz, chloroform-$d_1$) δ 8.32-8.09 (m, 2H), 8.32-8.09 (m, 7H), 5.15 (app t, J=8.4 Hz, 2H), 4.70 (s, 1H), 4.07-3.93 (m, 1H), 3.73-3.65 (m, 3H), 1.42-1.31 (m, 3H). $^{31}$P NMR (162 MHz, chloroform-$d_1$) δ 2.23 (s), 2.15 (s). LCMS: MS m/z=394.9[M+1], $t_R$=1.34 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min.

Intermediate 43. Isopropyl ((4-(dimethylcarbamoyl)phenoxy)(4-nitrophenoxy)phosphoryl)-L-alaninate

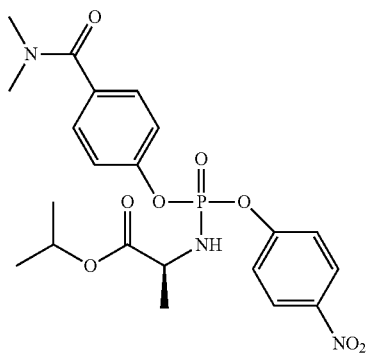 [SMILES: CC(C)OC(=O)[C@H](C)NP(=O)(Oc1ccc(C(=O)N(C)C)cc1)Oc1ccc([N+](=O)[O-])cc1]

To a solution of 4-nitrophenyl phosphorodichloridate (620 mg, 2.422 mmol) and isopropyl L-alanine-HCl (406 mg, 2.422 mmol) in DCM-THF (10:3 mL) was added TEA (0.68 mL, 4.844 mmol) in DCM (3.32 mL) over 30 min at −78° C. The resulting mixture was stirred for 30 min after removal of dry ice bath and cooled to −78° C. and N,N-dimethyl-4-hydroxybenzamide (400 mg, 2.422 mmol) was added in one portion and TEA (0.34 mL, 2.422 mmol) in DCM (3.66 mL) added over 30 min at −78° C. The resulting mixture was stirred for 1 h after removal of dry ice bath, then diluted with EtOAc, washed with brine, concentrated in vacuo, and the resulting residue purified by silica gel column chromatography (EtOAc 0 to 100% in hexanes) to afford the product. $^1$H NMR (400 MHz, Chloroform-d) δ 8.26-8.18 (m, 2H), 7.45-7.35 (m, 3H), 7.27 (m, 2H), 6.76 (m, 1H), 5.01 (m, 1H), 4.17-3.94 (m, 2H), 3.19-2.84 (m, 6H), 1.39 (m, 3H), 1.27-1.16 (m, 6H). $^{31}$P NMR (162 MHz, Chloroform-d) δ −3.13, −3.21. MS m/z=480 (M+H). LCMS: MS m/z=480.26 [M+1]; $t_R$=1.00 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

Intermediate 44. oxetan-3-yl ((4-nitrophenoxy)(phenoxy)phosphoryl)-L-alaninate

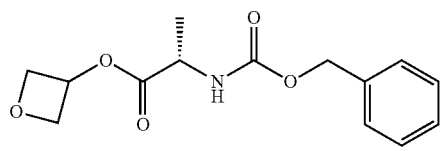 [SMILES: C[C@H](NC(=O)OCc1ccccc1)C(=O)OC1COC1]

oxetan-3-yl ((benzyloxy)carbonyl)-L-alaninate. To a mixture of ((benzyloxy)carbonyl)-L-alanine (1.8 g, 8.1 mmol), 3-hydroxyoxetane (0.5 g, 6.75 mmol) and 1-Ethyl-3-(3-dimethylaminopropyl)carbodiimide HCl salt (EDCI) (1.68 g, 8.77 mmol) in acetonitrile (100 mL) was added 4-(Dimethylamino)pyridine (DMAP, 1.24 g, 10.12 mmol). Then the mixture was stirred at room temperature for 2 h, then the reaction mixture was diluted with EtOAc, washed with brine, dried organic solvent over sodium sulfate, and then concentrated in vacuum. The obtained residue was purified by silica gel chromatography eluting with 0-100% ethyl acetate in hexanes to afford the product. $^1$H NMR (400 MHz, Chloroform-d) δ 7.40-7.28 (m, 5H), 5.47 (p, J=5.9 Hz, 1H), 5.30 (d, J=8.0 Hz, 1H), 5.10 (s, 2H), 4.88 (t, J=7.1 Hz, 2H), 4.62 (ddd, J=17.5, 7.7, 5.3 Hz, 2H), 4.41 (p, J=7.3 Hz, 1H), 1.44 (d, J=7.3 Hz, 3H). LCMS: MS m/z=280.04 [M+1], $t_R$=1.11 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=2.82 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

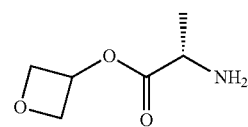

oxetan-3-yl L-alaninate. Dissolved oxetan-3-yl ((benzyloxy)carbonyl)-L-alaninate (0.1 g, 0.36 mmol) in DCM (5 mL), to the solution was added 15 mg of Pd—C (10%, wet), the reaction flask was degassed and then charged with $H_2$ balloon, stirred at RT for 2 h, the reaction mixture was then filtered, solvent was evaporated under vacuum, the residue was dried on high vacuum for 5 min to afford the product. $^1$H NMR (400 MHz, Chloroform-d) δ 5.42 (p, J=5.7 Hz, 1H), 4.87 (t, J=6.9 Hz, 2H), 4.65-4.54 (m, 2H), 3.58 (qd, J=7.0, 2.1 Hz, 1H), 1.49 (d, J=7.1 Hz, 2H), 1.34 (dd, J=7.2, 2.1 Hz, 3H).

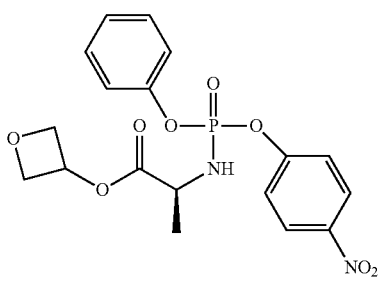 [SMILES: C[C@H](NP(=O)(Oc1ccccc1)Oc1ccc([N+](=O)[O-])cc1)C(=O)OC1COC1]

oxetan-3-yl ((4-nitrophenoxy)(phenoxy)phosphoryl)-L-alaninate. To a solution of oxetan-3-yl L-alaninate (120 mg, 0.83 mmol) in DCM (10 mL) was added phenyl phosphorodichloridate (175 mg, 0.83 mmol) in one portion. The resulting mixture was cooled to 0° C. and triethylamine (252 mg, 2.49 mmol) was added dropwise. The resulting mixture was stirred for 30 min after removal of ice bath and cooled to 0° C. and para-nitrophenol (115 mg, 0.83 mmol) was added in one portion and triethylamine (252 mg, 2.49 mmol) was added dropwise. The resulting mixture was stirred for 30 min after removal of ice bath, diluted with EtOAc, washed with water and brine, the organic solvent was concentrated in vacuum, and the resulting residue was purified by silica gel column chromatography eluting with 0-100% ethyl acetate in hexanes to afford the product. LCMS: MS m/z=423.06 [M+1], $t_R$=1.25 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.15 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Intermediate 45. propyl ((4-nitrophenoxy)(phenoxy)phosphoryl)-L-alaninate

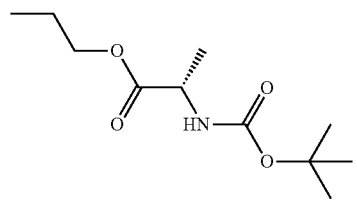 [SMILES: CCCOC(=O)[C@H](C)NC(=O)OC(C)(C)C]

propyl (tert-butoxycarbonyl)-L-alaninate. N-(3-Dimethylaminopropyl)-N'-ethylcarbodiimide hydrochloride (6.08 g, 31.71 mmol) was added to a solution of Boc-Ala-OH (5 g, 26.43 mmol) and n-propyl alcohol (6.02 mL, 80.6 mmol) in acetonitrile (125 mL) at RT. After 15 min, 4-(dimethylamino)pyridine (3.23 g, 26.43 mmol) was added. After 16 h, the reaction mixture was concentrated to half the volume, and the mixture was diluted with ethyl acetate (250 mL) and the resulting mixture was washed with saturated aqueous sodium carbonate solution (2×200 mL) and brine (200 mL). The organic layer was dried over anhydrous sodium sulfate and concentrated under reduced pressure. The crude residue was subjected to silica gel chromatography eluting with 0-20% EtOAc in hexane to afford the product. $^1$H NMR (400 MHz, Acetonitrile-$d_3$) δ 5.57 (s, 1H), 4.19-3.92 (m, 3H), 1.63 (h, J=7.1 Hz, 2H), 1.40 (s, 9H), 1.30 (d, J=7.3 Hz, 3H), 0.93 (t, J=7.4 Hz, 3H). LCMS: MS m/z=231.60 [M+1], $t_R$=1.10 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min.

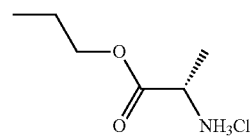

propyl L-alaninate hydrochloride. 4 M Hydrochloric acid solution in dioxane (16.91 mL) was added to propyl (tert-butoxycarbonyl)-L-alaninate (3.91 g, 16.91 mmol) in dichloromethane (10 mL) at RT. After 16 h, reaction mixture was concentrated under reduced pressure to afford the product. $^1$H NMR (400 MHz, Acetonitrile-$d_3$) δ 8.45 (s, 3H), 4.22-4.11 (m, 2H), 4.11-3.99 (m, 1H), 1.68 (dtd, J=14.0, 7.4, 6.6 Hz, 2H), 1.60 (d, J=7.2 Hz, 3H), 0.95 (t, J=7.4 Hz, 3H). LCMS: MS m/z=131.94 [M+1], $t_R$=0.32 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

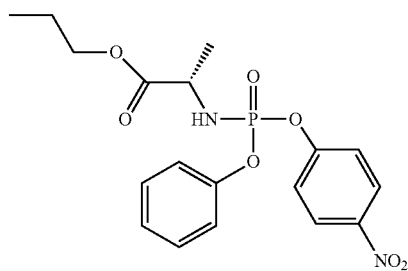 [SMILES: CCCOC(=O)[C@H](C)NP(=O)(Oc1ccccc1)Oc1ccc([N+](=O)[O-])cc1]

propyl ((4-nitrophenoxy)(phenoxy)phosphoryl)-L-alaninate. Phenyl dichlorophosphate (0.89 mL, 5.97 mmol) in dichloromethane (12 mL) was added dropwise over 15 minutes to a solution of propyl L-alaninate hydrochloride (1.0 g, 5.97 mmol) in dichloromethane (12 mL) at 0° C. After the addition was complete, triethylamine (2.0 mL, 14.32 mmol) in dichloromethane (2.5 mL) was added over 5 minutes. After 3.5 h, 4-nitrophenol (0.83 g, 5.97 mmol) and triethylamine (1.0 mL, 7.16 mmol) were then sequentially added at 0° C., and the resulting mixture was then allowed to warm to RT. After 2 h, the reaction mixture was diluted with dichloromethane (50 mL), washed with water (2×100 mL) and brine (50 mL), dried over anhydrous sodium sulfate, and concentrated under reduced pressure. The crude residue was purified by silica gel chromatography eluting with 0-100% ethyl acetate in hexanes to afford the product. $^1$H NMR (400 MHz, Acetonitrile-$d_3$) δ 8.28-8.20 (m, 2H), 7.49-7.35 (m, 4H), 7.31-7.19 (m, 3H), 4.72-4.56 (m, 1H), 4.14-4.02 (m, 1H), 3.99 (td, J=6.6, 2.5 Hz, 2H), 1.58 (dtdd, J=13.9, 7.4, 6.5, 0.9 Hz, 2H), 1.31 (ddd, J=7.1, 4.2, 1.1 Hz, 3H), 0.88 (t, J=7.4 Hz, 3H). $^{31}$P NMR (162 MHz, Acetonitrile-d$_3$) δ −2.12, −2.22. LCMS: MS m/z=409.12 [M+1], t$_R$=1.15 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: t$_R$=5.73 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Intermediate 46. oxetan-3-ylmethyl ((4-nitrophenoxy)(phenoxy)phosphoryl)-L-alaninate

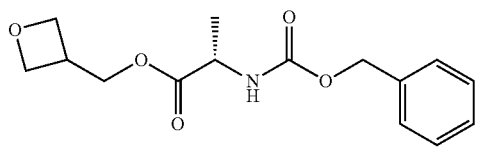 [SMILES: C[C@H](NC(=O)OCc1ccccc1)C(=O)OCC1COC1]

oxetan-3-ylmethyl ((benzyloxy)carbonyl)-L-alaninate. To a mixture of ((benzyloxy)carbonyl)-L-alanine (6.08 g, 27.24 mmol), oxetan-3-ylmethanol (2 g, 22.7 mmol) and 1-Ethyl-3-(3-dimethylaminopropyl)carbodiimide HCl salt (EDCI) (5.66 g, 29.51 mmol) in acetonitrile (100 mL) was added 4-(Dimethylamino)pyridine (DMAP, 4.16 g, 34.05 mmol). Then the mixture was stirred at room temperature for 2 h, the reaction mixture was then diluted with EtOAc, washed with brine, dried organic solvent over sodium sulfate, and then concentrated in vacuum. The obtained residue was purified by silica gel chromatography eluting with 0-100% ethyl acetate in hexanes to afford the product. LCMS: MS m/z=280.04 [M+1], t$_R$=1.11 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: t$_R$=2.88 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

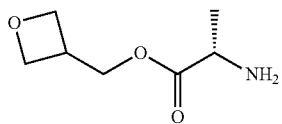

oxetan-3-ylmethyl L-alaninate. Dissolved oxetan-3-ylmethyl ((benzyloxy)carbonyl)-L-alaninate (2.2 g, 8 mmol) in DCM (25 mL), to the solution was added 500 mg of Pd—C (10%, wet), the reaction flask was degassed and then charged with H$_2$ balloon, stirred at RT for 2 h, the reaction mixture was then filtered, solvent was evaporated under vacuum, the residue was dried on high vacuum for 5 min to afford the product. $^1$H NMR (400 MHz, Chloroform-d) δ 4.77 (dd, J=7.9, 6.3 Hz, 2H), 4.44 (td, J=6.1, 2.5 Hz, 2H), 4.38-4.23 (m, 2H), 3.55 (q, J=7.0 Hz, 1H), 3.34-3.19 (m, 1H), 1.31 (d, J=7.0 Hz, 3H).

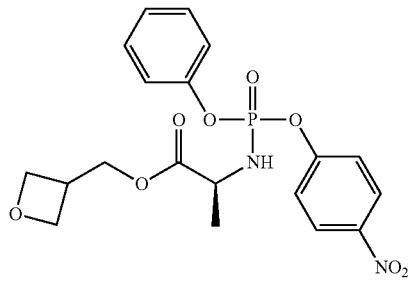 [SMILES: C[C@H](NP(=O)(Oc1ccccc1)Oc1ccc([N+](=O)[O-])cc1)C(=O)OCC1COC1]

oxetan-3-ylmethyl ((4-nitrophenoxy)(phenoxy)phosphoryl)-L-alaninate. To a solution of oxetan-3-ylmethyl L-alaninate (1.19 g, 7.11 mmol) in DCM (20 mL) was added phenyl phosphorodichloridate (1.5 g, 7.11 mmol) in one portion. The resulting mixture was cooled to 0° C. and triethylamine (1.44 g, 14.22 mmol) was added drop wise. The resulting mixture was stirred for 30 min after removal of ice bath and cooled to 0° C. and para-nitrophenol (0.99 g, 7.1 mmol) was added in one portion and triethylamine (1.44 g, 14.22 mmol) was added dropwise. The resulting mixture was stirred for 30 min after removal of ice bath, diluted with EtOAc, washed with water and brine, the organic solvent was concentrated in vacuum, and the resulting residue was purified by silica gel column chromatography eluting with 0-100% ethyl acetate in hexanes to afford the product. LCMS: MS m/z=437.14 [M+1], t$_R$=1.25 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: t$_R$=3.36 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Intermediate 47. cyclobutyl ((4-nitrophenoxy)(phenoxy)phosphoryl)-L-alaninate

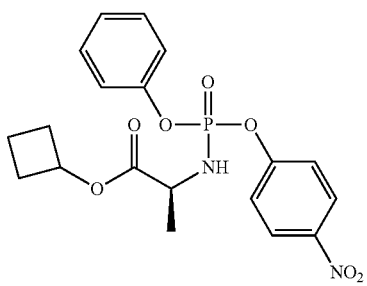 [SMILES: C[C@H](NP(=O)(Oc1ccccc1)Oc1ccc([N+](=O)[O-])cc1)C(=O)OC1CCC1]

To a solution of L-Alanine, cyclobutyl ester (1.8 g, 10 mmol) in DCM (10 mL) under a nitrogen atmosphere in an ice bath was added phenyl phosphorodichloridate (2.1 g, 10 mmol) in one portion. Then triethylamine (1.11 g, 11 mmol) was added dropwise. The resulting mixture was stirred for 2 h after removal of ice bath and cooled to 0° C. and para-nitrophenol (2.5 g, 18 mmol) was added in one portion and triethylamine (1.11 g, 11 mmol) was added dropwise. The resulting mixture was stirred for 2 h after removal of ice bath, diluted with EtOAc, washed with 5% aqueous citric acid solution twice, followed by washing with brine, the organic solvent was concentrated in vacuum, and the resulting residue was purified by silica gel column chromatography eluting with 0-100% ethyl acetate in hexanes to afford the product. MS m/z=422.0 (M+H)+.

Resolution of the Sp and Rp diastereomers. The product was purified via chiral preparatory HPLC (Chiralpak IA, 150×4.6 mm, Heptane 70%, IPA 30%) to form Intermediate 48 and Intermediate 49:

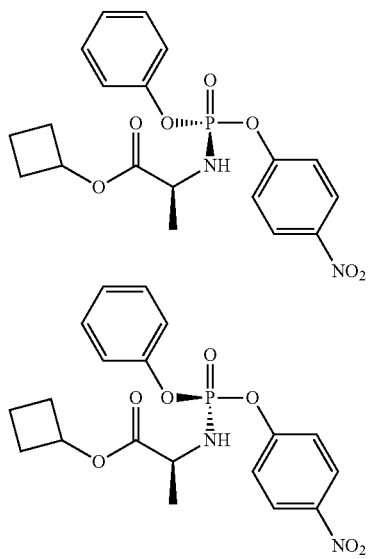

Intermediate 48. First Eluting Diastereomer of Intermediate 47: $^1$H NMR (400 MHz, Methanol-d4) δ 8.33-8.23 (m, 2H), 7.52-7.33 (m, 4H), 7.33-7.17 (m, 3H), 4.96-4.85 (m, 1H), 4.07-3.96 (m, 1H), 2.27 (m, 2H), 2.07-1.91 (m, 2H), 1.83-1.70 (m, 1H), 1.70-1.55 (m, 1H), 1.32 (ddd, J=7.2, 5.3, 1.2 Hz, 3H). $^{31}$P NMR (162 MHz, Methanol-d4) δ 1.36. LCMS: MS m/z=421.05 [M+1], $t_R$=1.42 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=8.07 min; HPLC system: Chiralpak IC, 150×4.6 mm, 5 micron, CN=IC00CD-QC005, 1 CV=2.49 mL, CV #1, Col Valve: Position 3, 15 mL/15 min @ 1 mL/min. Pmax=300 bar; Solvent Valves: D: Heptane 70%, #6: IPA.

Intermediate 49. Second Eluting Diastereomer of Intermediate 47: $^1$H NMR (400 MHz, Methanol-d4) δ 8.33-8.23 (m, 2H), 7.52-7.33 (m, 4H), 7.33-7.17 (m, 3H), 4.96-4.85 (m, 1H), 4.07-3.96 (m, 1H), 2.27 (m, 2H), 2.07-1.91 (m, 2H), 1.83-1.70 (m, 1H), 1.70-1.55 (m, 1H), 1.32 (ddd, J=7.2, 5.3, 1.2 Hz, 3H). $^{31}$P NMR (162 MHz, Methanol-d4) δ 1.59. LCMS: MS m/z=420.90 [M+1], $t_R$=1.42 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=11.50 min; HPLC system: Chiralpak IC, 150×4.6 mm, 5 micron, CN=IC00CD-QC005, 1 CV=2.49 mL, CV #1, Col Valve: Position 3, 15 mL/15 min @ 1 mL/min. Pmax=300 bar; Solvent Valves: D: Heptane 70%, #6: IPA 30%.

Intermediate 50. methyl ((S)-(perfluorophenoxy)(phenoxy)phosphoryl)-L-alaninate

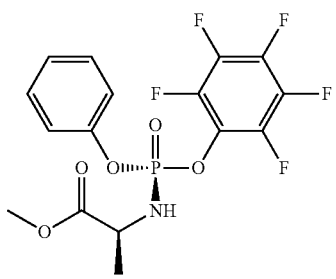 [SMILES: COC(=O)[C@H](C)N[P@](=O)(Oc1ccccc1)Oc1c(F)c(F)c(F)c(F)c1F]

L-Alanine methyl ester hydrochloride (14 g, 100 mmol) was mixed with 50 mL of anhydrous DCM and stirred under atmospheric nitrogen in an ice bath. Phenyl dichlorophosphate (16.4 mL, 110 mmol) was added to the reaction dropwise, and the reaction mixture was stirred for 30 mins. Triethylamine (29.4 mL, 210 mmol) was mixed with 20 mL anhydrous DCM and added to the reaction dropwise. Reaction was stirred for 1 hr. Pentafluorophenol (18.4 g, 100 mmol) was added in one portion. Triethylamine (14.7 mL, 105 mmol) was mixed with 30 mL of anhydrous DCM and added to reaction dropwise. The reaction mixture was stirred for 16 hrs at RT.

Reaction was diluted with DCM (50 mL) and washed with water (5×10 mL). Organic was dried over anhydrous sodium sulfate and then concentrated under reduced pressure to give solid. Isopropyl ether (130 mL) was added to solid. Big pieces of solid were broke down and then sonicated for 20 mins, after which the mixture was then stirred for 24 hrs.

Solid was collected and washed with small amount of isopropyl ether (30 mL). Solid was dried under high vacuum to give the product. $^1$H NMR (400 MHz, chloroform-d) δ 7.40-7.32 (m, 2H), 7.28-7.19 (m, 3H), 4.20 (m, 1H), 3.96-3.85 (m, 1H), 3.74 (s, 3H), 1.47 (d, J=7.1 Hz, 3H). $^{31}$P NMR (162 MHz, chloroform-d) δ −1.62. $^{19}$F NMR (376 MHz, chloroform-d) δ −153.82 (dd, J=18.5, 2.7 Hz), −159.99 (td, J=21.8, 3.8 Hz), −162.65 (dd, J=22.2, 17.6 Hz). LCMS: MS m/z=425.9 [M+1], 423.9 [M−1], $t_R$=1.68 min; LC system: Thermo Dionex Ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=3.76 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min.

Intermediate 51. isopropyl ((4-(2-methoxyethoxy) phenoxy)(4-nitrophenoxy)phosphoryl)-L-alaninate

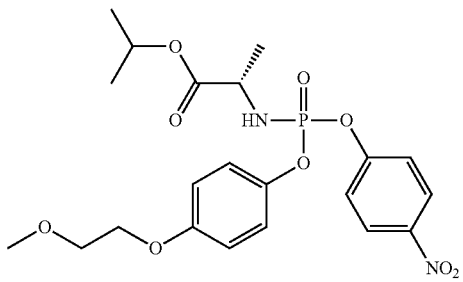 [SMILES: COCCOc1ccc(OP(=O)(N[C@@H](C)C(=O)OC(C)C)Oc2ccc([N+](=O)[O-])cc2)cc1]

4-Nitrophenyl phosphorodichloridate (503 mg, 1.97 mmol) in dichloromethane (20 mL) was added dropwise over 10 minutes to a solution of L-alanine isopropyl ester hydrochloride (329 mg, 1.97 mmol) in dichloromethane (20 mL) at 0° C. After addition was complete, triethylamine (0.55 mL, 3.93 mmol) was added dropwise. After 90 minutes, 4-(2-methoxy-ethoxy)phenol (331 mg, 1.97 mmol) and triethylamine (0.28 mL, 1.97 mmol) were sequentially added at 0° C., and the resulting mixture was then allowed to warm to RT. After 30 minutes, the reaction mixture was washed with water (2×50 mL) and brine (50 mL), dried over anhydrous sodium sulfate, and concentrated under reduced pressure. The crude residue was purified by silica gel chromatography eluting with 20-100% ethyl acetate in hexanes to afford the product. $^1$H NMR (400 MHz, Methanol-$d_4$) δ 8.32-8.24 (m, 2H), 7.51-7.39 (m, 2H), 7.24-7.12 (m, 2H), 6.97-6.90 (m, 2H), 4.94 (heptd, J=6.2, 3.2 Hz, 1H), 4.12-4.07 (m, 2H), 4.05-3.93 (m, 1H), 3.76-3.68 (m, 2H), 3.41 (d, J=0.5 Hz, 3H), 1.32 (td, J=7.1, 1.2 Hz, 3H), 1.19 (dt, J=6.3, 2.0 Hz, 6H). $^{31}$P NMR (162 MHz, Methanol-$d_4$) δ −0.86, −1.06. LCMS: MS m/z=483.06 [M+1], $t_R$=1.39 min; LC system: Thermo Accela 1250 UHPLC; MS system: Thermo LCQ Fleet; Column: Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=5.58 min; HPLC system: Agilent 1100 series; Column: Gemini 5µ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Intermediate 52. butyl ((4-nitrophenoxy)(phenoxy)phosphoryl)-L-alaninate

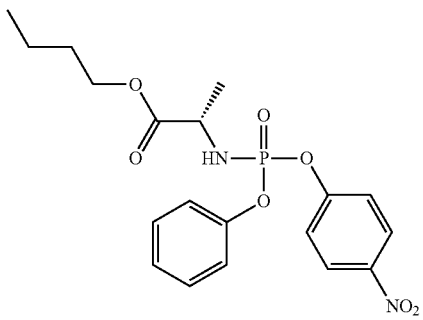 [SMILES: CCCCOC(=O)[C@H](C)NP(=O)(Oc1ccccc1)Oc1ccc([N+](=O)[O-])cc1]

Phenyl dichlorophosphate (0.89 mL, 5.97 mmol) in dichloromethane (12 mL) was added dropwise over 15 minutes to a solution of butyl L-alaninate hydrochloride (CAS #81305-85-3, 1.0 g, 5.97 mmol) in dichloromethane (12 mL) at 0° C. After the addition was complete, triethylamine (2.0 mL, 14.32 mmol) in dichloromethane (2.5 mL) was added over 5 minutes. After 3.5 h, 4-nitrophenol (0.83 g, 5.97 mmol) and triethylamine (1.0 mL, 7.16 mmol) were then sequentially added at 0° C., and the resulting mixture was then allowed to warm to RT. After 2 h, the reaction mixture was diluted with dichloromethane (50 mL), washed with water (2×100 mL) and brine (50 mL), dried over anhydrous sodium sulfate, and concentrated under reduced pressure. The crude residue was purified by silica gel chromatography eluting with 0-100% ethyl acetate in hexanes to afford the product. $^1$H NMR (400 MHz, methanol-$d_4$) δ 8.31-8.23 (m, 1H), 7.52-7.34 (m, 2H), 7.32-7.18 (m, 2H), 4.04 (td, J=6.6, 2.7 Hz, 2H), 1.60-1.48 (m, 1H), 1.40-1.26 (m, 3H), 0.89 (t, J=7.4 Hz, 2H). $^{31}$P NMR (162 MHz, methanol-$d_4$) δ −1.36, −1.59. LCMS: MS m/z=423.13 [M+1], $t_R$=1.22 min; LC system: Thermo Accela 1250 UHPLC; MS system: Thermo LCQ Fleet; Column: Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min.

Intermediate 53. 3-Methoxypropyl ((4-nitrophenoxy)(phenoxy)phosphoryl)-L-alaninate

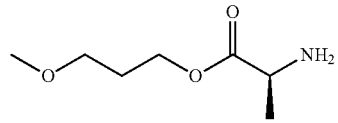

3-Methoxypropyl L-alaninate. To a mixture of Cbz-L-alanine (2.80 g, 12.54 mmol), 3-methoxypropanol (1.00 mL, 10.45 mmol), and EDCI (2.11 g, 13.59 mmol) in acetonitrile (40 mL) was added DMAP (1.92 g, 15.68 mmol). Then the mixture was stirred at room temperature for 15 h, then diluted with EtOAc, washed with brine, dried over sodium sulfate, and concentrated in vacuo. The obtained residue was purified by silica gel chromatography (EtOAc 0 to 50% in hexanes, 35 min run) to give a Cbz-L-alanine ester (2.78 g), which was dissolved in THF (20 mL) and 20% Pd(OH)$_2$ (800 mg, 1.14 mmol) added at room temperature. The resulting mixture was stirred at room temperature for 4 h under a hydrogen gas atmosphere, filtered, concentrated in vacuo, and dried under high vacuum to afford the product. $^1$H NMR (400 MHz, Chloroform-d) δ 4.28-4.14 (m, 2H), 3.55 (q, J=7.0 Hz, 1H), 3.43 (t, J=6.2 Hz, 2H), 3.32 (s, 3H), 1.98-1.85 (m, 4H), 1.33 (d, J=7.0 Hz, 3H). LCMS m/z=161.98 (M+H), $t_R$=0.12 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min.

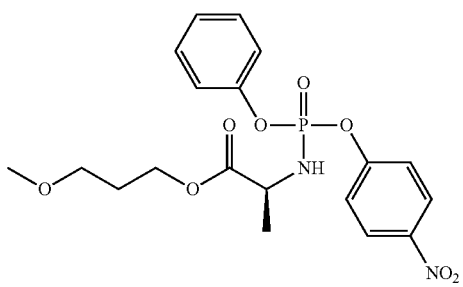 [SMILES: COCCCOC(=O)[C@H](C)NP(=O)(Oc1ccccc1)Oc1ccc([N+](=O)[O-])cc1]

3-Methoxypropyl ((4-nitrophenoxy)(phenoxy)phosphoryl)-L-alaninate. To a solution of 3-Methoxypropyl L-alaninate (1.32 g, 8.20 mmol) in DCM (20 mL) was added phenyl phosphorodichloridate (1.23 mL, 8.20 mmol) in one portion quickly at −78° C. Then triethylamine (1.14 mL, 8.20 mmol) was added over 5 min at −78° C. The resulting mixture was stirred for 30 min after removal of dry ice bath and cooled to −78° C. p-Nitrophenol (1.14 g, 8.20 mmol) was added in one portion and triethylamine (1.14 mL, 8.20 mmol) added over 5 min at −78° C. The resulting mixture was stirred for 2 h after removal of dry ice bath. After dilution with DCM, the mixture was washed with brine, concentrated in vacuo, and the resulting residue purified by silica gel column chromatography (EtOAc 0 to 100% in hexanes) to afford the product. $^1$H NMR (400 MHz, Chloroform-d) δ 8.26-8.19 (m, 2H), 7.36 (m, 4H), 7.27-7.15 (m, 3H), 4.20 (m, 2H), 4.17-4.06 (m, 1H), 3.91 (m, 1H), 3.40 (m, 2H), 3.30 (m, 3H), 1.87 (m, 2H), 1.40 (m, 3H). $^{31}$P NMR (162 MHz, Chloroform-d) δ −3.07, −3.10. LCMS: m/z=439.11 (M+H). $t_R$=1.36 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min Intermediate 54. methyl (2S)-2-(((benzyloxy)carbonyl)amino)-3-(4-(((((S)-1-methoxy-1-oxopropan-2-yl)amino)(4-nitrophenoxy)phosphoryl)oxy)phenyl)propanoate

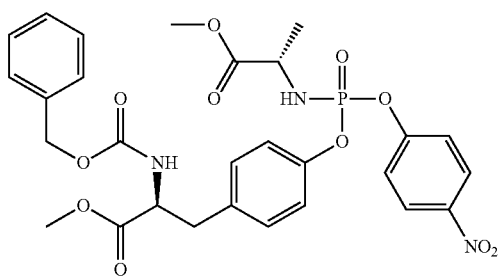 [SMILES: COC(=O)[C@H](C)NP(=O)(Oc1ccc(C[C@H](NC(=O)OCc2ccccc2)C(=O)OC)cc1)Oc1ccc([N+](=O)[O-])cc1]

L-Alanine methyl ester hydrochloride (275 mg, 1.97 mmol) in dichloromethane (20 mL) was added dropwise over 10 minutes to a solution of 4-nitrophenyl phosphorodichloridate (504 mg, 1.97 mmol) in dichloromethane (20 mL) at 0° C. After addition was complete, triethylamine (0.55 mL, 3.93 mmol) was added dropwise. After 60 minutes, N-carbobenzyloxy-L-tyrosine methyl ester (649 mg, 1.97 mmol) and triethylamine (0.28 mL, 1.97 mmol) were sequentially added at 0° C., and the resulting mixture was then allowed to warm to RT. After 3 hr, the reaction mixture was washed with water (2×50 mL) and brine (50 mL), dried over anhydrous sodium sulfate, and concentrated under reduced pressure. The crude residue was purified by silica gel chromatography eluting with 0-100% ethyl acetate in hexanes to afford the product. $^1$H NMR (400 MHz, Methanol-$d_4$) δ 8.34-8.17 (m, 2H), 7.53-7.37 (m, 2H), 7.37-7.09 (m, 9H), 5.02 (s, 2H), 4.43 (dd, J=9.4, 5.2 Hz, 1H), 4.19-3.97 (m, 1H), 3.70 (s, 3H), 3.62 (d, J=4.4 Hz, 3H), 3.16 (dd, J=14.0, 5.4 Hz, 1H), 2.93 (dd, J=14.1, 9.8 Hz, 1H), 1.32 (td, J=7.3, 1.2 Hz, 3H). $^{31}$P NMR (162 MHz, Methanol-$d_4$) δ −1.30, −1.51. LCMS: MS m/z=616.03 [M+1], $t_R$=1.63 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=5.81 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Intermediate 55. (S)-Tetrahydrofuran-3-yl ((4-nitrophenoxy)(phenoxy)

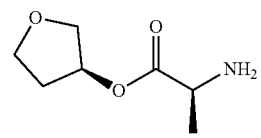

(S)-Tetrahydrofuran-3-yl-L-alaninate. To a mixture of N-Cbz-L-alanine (3.31, 14.83 mmol), (S)-THF-3-ol (1.0 mL, 12.34 mmol), and EDCI (2.49 g, 16.04 mmol) in acetonitrile (20 mL) was added DMAP (2.26 g, 18.51 mmol). Then the mixture was stirred at room temperature for 15 h, then diluted with EtOAc, washed with brine, dried over sodium sulfate, and concentrated in vacuo. The obtained residue was purified by silica gel chromatography (EtOAc 0 to 80% in hexanes) to give a Cbz-L-alanine 4-THF ester, which was dissolved in THF (20 mL) and 20% palladium hydroxide (433 mg, 0.617 mmol) was added at room temperature. The resulting mixture was stirred at room temperature for 2 h under $H_2$ gas, filtered, and concentrated in vacuo, co-evaporated with DCM multiple times, and dried 15 h under high vacuum to afford the product. $^1$H NMR (400 MHz, Chloroform-d) δ 5.37-5.29 (m, 1H), 3.97-3.77 (m, 4H), 3.61-3.52 (m, 1H), 2.27-2.12 (m, 1H), 2.02 (dt, J=12.8, 5.6 Hz, 1H), 1.76 (s, 2H), 1.34 (dd, J=7.1, 1.5 Hz, 3H). LCMS m/z=159.94 (M+H), $t_R$=0.12 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

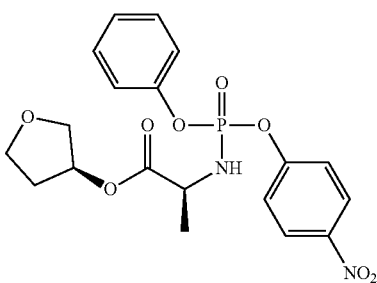 [SMILES: C[C@H](NP(=O)(Oc1ccccc1)Oc1ccc([N+](=O)[O-])cc1)C(=O)O[C@H]1CCOC1]

(S)-Tetrahydrofuran-3-yl ((4-nitrophenoxy)(phenoxy) phosphoryl)-L-alaninate. To a solution of (S)-Tetrahydrofuran-3-yl-L-alaninate (1.45 g, 9.10 mmol) in DCM (20 mL) was added phenyl phosphorodichloridate (1.37 mL, 9.10 mmol) in one portion quickly at −78° C. Then triethylamine (1.27 mL, 9.10 mmol) was added over 5 min at −78° C. The resulting mixture was stirred for 30 min after removal of dry ice bath and cooled to −78° C. p-Nitrophenol (1.27 g, 9.10 mmol) was added in one portion and triethylamine (1.27 mL, 9.10 mmol) added over 5 min at −78° C. The resulting mixture was stirred for 2 h after removal of dry ice bath. After dilution with DCM, the mixture was washed with brine, concentrated in vacuo, and the resulting residue purified by silica gel column chromatography (EtOAc 0 to 100% in hexanes) to afford the product. $^1$H NMR (400 MHz, Chloroform-d) δ 8.22 (m, 2H), 7.49-7.31 (m, 4H), 7.30-7.12 (m, 3H), 5.29 (m, 1H), 4.14 (m, 1H), 4.00-3.79 (m, 4H), 3.82-3.60 (m, 1H), 2.17 (m, 1H), 1.95 (m, 1H), 1.40 (m, 3H). $^{31}$P NMR (162 MHz, Chloroform-d) δ −3.18, −3.20. LCMS: m/z=437.05 (M+H), $t_R$=1.41 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

Intermediate 56. 3-morpholinopropyl ((4-nitrophenoxy)(phenoxy)phosphoryl)-L-alaninate

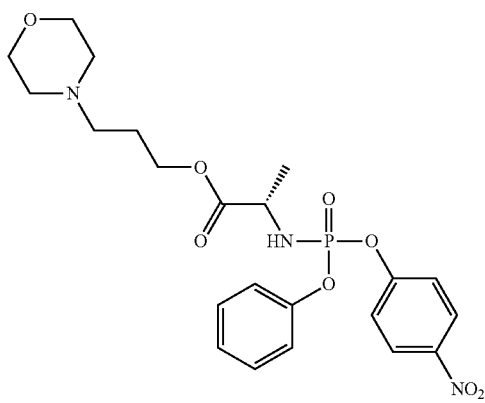 [SMILES: C[C@H](NP(=O)(Oc1ccccc1)Oc1ccc([N+](=O)[O-])cc1)C(=O)OCCCN1CCOCC1]

4-Nitrophenyl phosphorodichloridate (503 mg, 1.97 mmol) in dichloromethane (20 mL) was added dropwise over 10 minutes to a solution of 3-morpholinopropyl L-alaninate hydrochloride (496 mg, 1.97 mmol) in dichloromethane (20 mL) at 0° C. After addition was complete, triethylamine (0.55 mL, 3.93 mmol) was added dropwise. After 90 minutes, phenol (185 mg, 1.97 mmol) and triethylamine (0.28 mL, 1.97 mmol) were sequentially added at 0° C., and the resulting mixture was then allowed to warm to RT. After 30 minutes, the reaction mixture was washed with water (2×50 mL) and brine (50 mL), dried over anhydrous sodium sulfate, and concentrated under reduced pressure. The crude residue was purified by silica gel chromatography eluting with 20-100% ethyl acetate in hexanes to afford the product. $^1$H NMR (400 MHz, Methanol-$d_4$) δ 8.32-8.24 (m, 2H), 7.51-7.39 (m, 2H), 7.24-7.12 (m, 2H), 6.97-6.90 (m, 2H), 4.94 (m, 1H), 4.12-4.07 (m, 2H), 4.05-3.93 (m, 1H), 3.76-3.68 (m, 2H), 3.41 (d, J=0.5 Hz, 3H), 1.32 (td, J=7.1, 1.2 Hz, 3H), 1.19 (dt, J=6.3, 2.0 Hz, 6H). $^{31}$P NMR (162 MHz, Acetonitrile-$d_3$) δ −2.12, −2.22. LCMS: MS m/z=494.35 [M+1], $t_R$=1.03 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

Intermediate 57. (R)-Tetrahydrofuran-3-yl ((4-nitrophenoxy)(phenoxy)

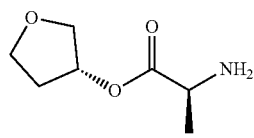

(R)-Tetrahydrofuran-3-yl-L-alaninate. To a mixture of N-Cbz-L-alanine (3.31 g, 14.83 mmol), (R)-THF-3-ol (1.0 mL, 12.34 mmol), and EDCI (2.49 g, 16.04 mmol) in acetonitrile (20 mL) was added DMAP (2.26 g, 18.51 mmol). Then the mixture was stirred at room temperature for 15 h, then diluted with EtOAc, washed with brine, dried over sodium sulfate, and concentrated in vacuo. The obtained residue was purified by silica gel chromatography (EtOAc 0 to 50% in hexanes, 35 min run) to give a Cbz-L-alanine ester (2.78 g), which was dissolved in THF (20 mL) and 20% Pd(OH)$_2$ (433 mg, 0.617 mmol) added at room temperature. The resulting mixture was stirred at room temperature for 4.5 h under a hydrogen atmosphere, filtered, concentrated in vacuo, and dried under high vacuum to afford the product. $^1$H NMR (400 MHz, Chloroform-d) δ 5.32 (ddt, J=6.5, 4.3, 1.9 Hz, 1H), 3.98-3.78 (m, 4H), 3.56 (q, J=7.0 Hz, 1H), 2.19 (dtd, J=13.7, 8.4, 6.4 Hz, 1H), 2.05-1.92 (m, 1H), 1.79 (s, 2H), 1.34 (d, J=7.0 Hz, 3H). LCMS: m/z=159.92 (M+H), $t_R$=0.21 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

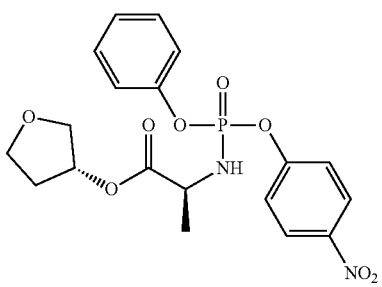 [SMILES: C[C@H](NP(=O)(Oc1ccccc1)Oc1ccc([N+](=O)[O-])cc1)C(=O)O[C@@H]1CCOC1]

(R)-Tetrahydrofuran-3-yl ((4-nitrophenoxy)(phenoxy) phosphoryl)-L-alaninate. To a solution of (R)-Tetrahydrofuran-3-yl-L-alaninate (1.66 g, 10.44 mmol) in DCM (40 mL) was added phenyl phosphorodichloridate (1.56 mL, 10.44 mmol) added in one portion quickly at −78° C. Then triethylamine (1.45 mL, 10.44 mmol) was added over 5 min at −78° C. The resulting mixture was stirred for 30 min after removal of dry ice bath and cooled to −78° C. p-Nitrophenol (1.45 g, 10.44 mmol) was added in one portion and triethylamine (1.45 mL, 10.44 mmol) added over 5 min at −78° C. The resulting mixture was stirred for 2 h after removal of dry ice bath. After dilution with DCM, the mixture was washed with brine, concentrated in vacuo, and the resulting residue purified by silica gel column chromatography (EtOAc 0 to 100% in hexanes) to afford the product. $^{1}$H NMR (400 MHz, Chloroform-d) δ 8.22 (m, 2H), 7.43-7.31 (m, 4H), 7.25-7.14 (m, 3H), 5.29 (m, 1H), 4.21-4.10 (m, 1H), 3.93-3.79 (m, 4H), 3.79-3.71 (m, 1H), 2.17 (m, 1H), 1.97-1.85 (m, 1H), 1.44-1.37 (m, 3H). $^{31}$P NMR (162 MHz, Chloroform-d) δ −3.24, −3.26. LCMS: m/z=437.02 (M+H), $t_R$=1.42 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min.

Intermediate 58. methyl (chloro(phenoxy)phosphorothioyl)-L-alaninate

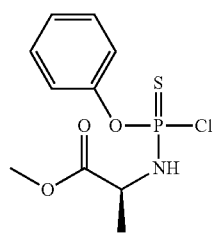 [SMILES: COC(=O)[C@H](C)NP(=S)(Cl)Oc1ccccc1]

Thiophosphoryl chloride (5.08 mL, 50.0 mmol) and triethylamine (6.97 mL, 50.0 mmol) were sequentially added to a solution of phenol (4.70 mg, 50.0 mmol) in TBME (72 mL) at −78° C. under an argon atmosphere. The reaction mixture was then allowed to warm to RT. After 1 h, the resulting mixture was filtered and the filtrate was concentrated under reduced pressure. The residue was dissolved in dichloromethane (72 mL) and L-alanine methyl ester hydrochloride (6.97 mg, 50.0 mmol) was added. The resulting suspension was cooled to −78° C. and triethylamine (13.9 mL, 100 mmol) was added dropwise. The reaction mixture was then allowed to warm to RT. After 16 h, the reaction mixture was concentrated under reduced pressure and TBME (100 mL) was added to the residue. The resulting white solids were removed by vacuum filtration and the filtrate was concentrated under reduced pressure to afford the product used directly in the next step. $^{1}$H NMR (400 MHz, chloroform-d$_1$) δ 7.45-7.12 (m, 5H), 4.67-4.44 (m, 1H), 4.44-4.24 (m, 1H), 3.81 (s, 1.5H), 3.78 (s, 1.5H), 1.53 (app t, J=6.8 Hz, 3H). $^{31}$P NMR (162 MHz, chloroform-d$_1$) δ 64.78 (s), 64.63 (s).

Intermediate 59. Cyclohexyl ((((S)-1-(2-ethylbutoxy)-1-oxopropan-2-yl)amino)(4-nitrophenoxy) phosphoryl)-L-alaninate and cyclohexyl ((((S)-1-cyclohexyloxy-1-oxopropan-2-yl)amino)(4-nitrophenoxy)phosphoryl)-L-alaninate

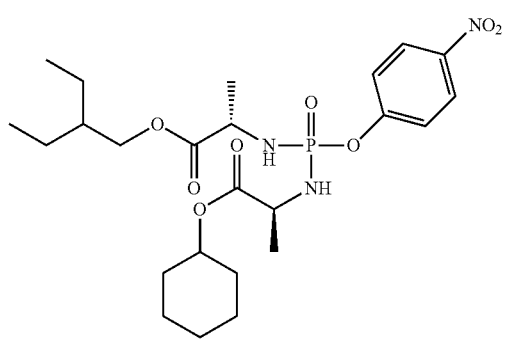 [SMILES: CCC(CC)COC(=O)[C@H](C)NP(=O)(N[C@@H](C)C(=O)OC1CCCCC1)Oc1ccc([N+](=O)[O-])cc1]

To a solution of (S)-1-(cyclohexyloxy)-1-oxopropan-2-aminium chloride Intermediate 11 (680 mg, 3.27 mmol) in THF (10 mL) was added 4-nitrophenyl phosphorodichloridate (838 mg, 3.27 mmol) in one portion. The resulting mixture was cooled in ice bath and triethylamine (1.0 mL, 6.54 mmol) in THF (2 mL) was added over 30 min. The resulting mixture was stirred under ice bath for 1.5 h and (S)-1-(2-ethylbutoxy)-1-oxopropan-2-aminium chloride (687 mg, 3.27 mmol) was added in one portion and triethylamine (1.0 mL, 6.54 mmol) in THF (2 mL) added over 30 min under ice bath. The resulting mixture was stirred under ice bath for 1.5 h, diluted with EtOAc, washed with water and brine, concentrated in vacuo, and the resulting residue purified by preparative HPLC (Phenomenex Gemini-NX 10µ C18 110° A 250×30 mm column, 0%-100% acetonitrile/water gradient in 25 min run) to afford the product. $^{1}$H NMR (400 MHz, Chloroform-d) δ 8.20 (m, 2H), 7.38 (m, 2H), 4.77 (m, 1H), 4.15-3.91 (m, 4H), 3.60 (m, 2H), 1.91-1.77 (m, 2H), 1.75-1.67 (m, 2H), 1.51 (m, 2H), 1.45-1.23 (m, 15H), 0.88 (m, 6H). $^{31}$P NMR (162 MHz, Chloroform-d) δ 8.04. LCMS: MS m/z=528.10 [M+1].

Intermediate 60. 4-nitrophenyl-N,N'-cyclohexyl L-alaninatephosphorodiamidate

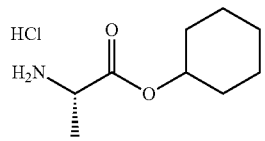

(S)-cyclohexyl 2-aminopropanoate hydrochloride. L-Alanine (891 mg, 10 mmol) was mixed with cyclohexanol (10 mL). Trimethylsilyl chloride (12.7 mL, 100 mmol) was added dropwise and stirred for 20 mins. Reaction mixture was heated to 60° C. and stirred for 16 hrs. Reaction was concentrated under reduced pressure and azeotroped with toluene (5×) to give an oil. Hexanes (100 mL) was added and stirred for 15 hrs to give a solid which was collected, washed with hexanes (100 mL) and dried under high vacuum to give the product. $^1$H NMR (400 MHz, DMSO-$d_6$) δ 8.45 (s, 3H), 4.77 (tt, J=8.4, 3.7 Hz, 1H), 4.02 (q, J=7.2 Hz, 1H), 1.71 (m, 4H), 1.53-1.17 (m, 9H).

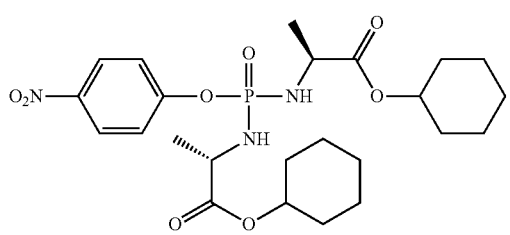 [SMILES: C[C@H](NP(=O)(N[C@@H](C)C(=O)OC1CCCCC1)Oc1ccc([N+](=O)[O-])cc1)C(=O)OC1CCCCC1]

4-nitrophenyl-N,N'-cyclohexyl L-alaninatephosphorodiamidate. 4-Nitrophenyl dichlorophosphate (256 mg, 1 mmol) was dissolved in anhydrous dichloromethane (10 mL) and stirred under atmosphere nitrogen in an ice bath. (S)-cyclohexyl 2-aminopropanoate hydrochloride (415 mg, 2 mmol) was added in one portion. Triethylamine (698 μL, 5 mmol) was added dropwise and stirred for 2 hrs. Reaction was diluted with dichloromethane (15 mL) and washed with 2% aqueous citric acid solution (20 mL). Organic was dried over anhydrous sodium sulfate and concentrated under reduced pressure. The crude was purified via SiO$_2$ column chromatography (12 g SiO$_2$ Combiflash HP Gold Column 0-50% ethyl acetate/hexanes) to afford the product. $^1$H NMR (400 MHz, DMSO-$d_6$) δ 8.30-8.13 (m, 2H), 7.49-7.27 (m, 2H), 5.50 (m, 2H), 4.62 (m, 2H), 3.85 (m, 2H), 1.67 (m, 8H), 1.51-1.18 (m, 18H). $^{31}$P NMR (162 MHz, DMSO-$d_6$) δ 9.50. MS m/z=526.0 [M+1], 524.1 [M-1].

Intermediate 61. 4-nitrophenyl-N,N'-isopropyl L-alaninatephosphorodiamidate

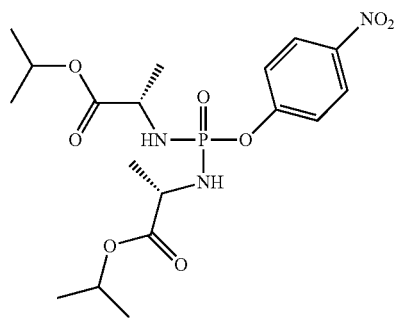 [SMILES: CC(C)OC(=O)[C@H](C)NP(=O)(N[C@@H](C)C(=O)OC(C)C)Oc1ccc([N+](=O)[O-])cc1]

To a solution of isopropyl L-alaninate HCl salt (1.97 g, 11.72 mmol) in DCM (20 mL) was added 4-nitrophenyl phosphorodichloridate (1.5 g, 5.86 mmol) in one portion. The resulting mixture was cooled to about 0° C. and triethylamine (2.37 g, 23.44 mmol) was added dropwise. The resulting mixture was stirred for about 30 min after removal of ice bath and was stirred overnight. The reaction mixture was then diluted with EtOAc, washed with water and brine, the organic solvent was concentrated in vacuum, and the resulting residue was purified by silica gel column chromatography eluting with 0-100% ethyl acetate in hexanes to afford the product. LCMS: MS m/z=445.96 [M+1].

Intermediate 62.
4-nitrophenyl-N,N'-cyclobutylmethyl L-alaninatephosphorodiamidate

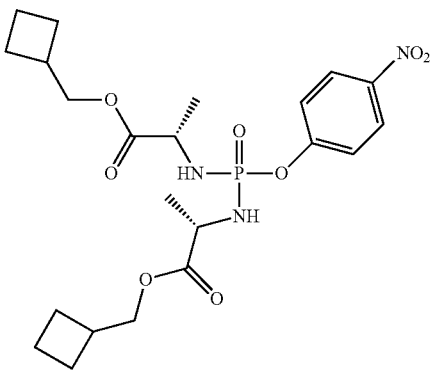 [SMILES: C[C@H](NP(=O)(N[C@@H](C)C(=O)OCC1CCC1)Oc1ccc([N+](=O)[O-])cc1)C(=O)OCC1CCC1]

To a solution of cyclobutylmethyl L-alaninate HCl salt (1.51 g, 7.8 mmol) in DCM (20 mL) was added 4-nitrophenyl phosphorodichloridate (1 g, 3.9 mmol) in one portion. The resulting mixture was cooled to 0° C. and triethylamine (1.58 g, 15.6 mmol) was added dropwise. The resulting mixture was stirred for 30 min after removal of ice bath and was stirred for overnight. The reaction mixture was then diluted with EtOAc, washed with water and brine, the organic solvent was concentrated in vacuum, and the resulting residue was purified by silica gel column chromatography eluting with 0-100% ethyl acetate in hexanes to afford the product. LCMS: MS m/z=497.98 [M+1].

Intermediate 63. (1r,4S)-4-((tert-butoxycarbonyl) amino)cyclohexyl ((4-nitrophenoxy)(phenoxy)phosphoryl)-L-alaninate

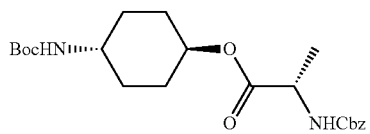 [SMILES: C[C@H](NC(=O)OCc1ccccc1)C(=O)O[C@H]1CC[C@H](NC(=O)OC(C)(C)C)CC1]

(1r,4S)-4-((tert-butoxycarbonyl)amino)cyclohexyl ((benzyloxy)carbonyl)-L-alaninate. 4-Dimethylaminopyridine (2.84 g, 23 mmol) was added to a solution of tert-butyl ((1r,4r)-4-hydroxycyclohexyl)carbamate (4.00 g, 19.0 mmol) and ((benzyloxy)carbonyl)-L-alanine (4.98 g, 22.0 mmol), and EDCI (3.13 g, 20.0 mmol) in acetonitrile (100 mL) at RT. After 4 h, the reaction mixture was diluted with dichloromethane (200 mL), washed with brine (50 mL), dried over anhydrous sodium sulfate, and concentrated under reduced pressure. The crude residue was purified by silica gel chromatography eluting with 0-50% ethyl acetate in hexanes to afford the product. $^1$H NMR (400 MHz, CDCl$_3$) δ 7.40-7.28 (m, 5H), 5.29 (br d, J=7.7 Hz, 1H), 5.10

(s, 2H), 4.78-4.60 (m, 1H), 4.47-4.19 (m, 2H), 3.45 (s, 1H), 2.08-1.89 (m, 4H), 1.54-1.34 (m, 14H), 1.28-1.16 (m, 2H). LCMS: MS m/z=420.99 [M+1].

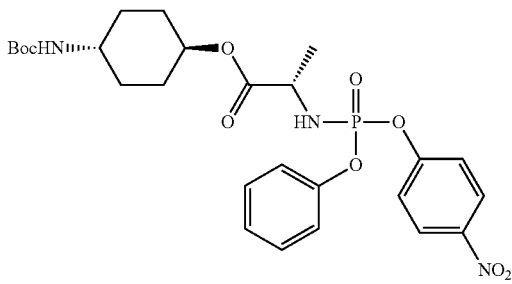 [SMILES: C[C@H](NP(=O)(Oc1ccccc1)Oc1ccc([N+](=O)[O-])cc1)C(=O)O[C@H]1CC[C@H](NC(=O)OC(C)(C)C)CC1]

(1r,4S)-4-((tert-butoxycarbonyl)amino)cyclohexyl ((4-nitrophenoxy)(phenoxy)phosphoryl)-L-alaninate. A hydrogen balloon was appended to a flask containing a solution of (1r,4S)-4-((tert-butoxycarbonyl)amino)cyclohexyl ((benzyloxy)carbonyl)-L-alaninate (1.96 g, 4.66 mmol) and palladium on carbon (10% wt, 2.0 g) in tetrahydrofuran (50 mL) at RT under an argon atmosphere. The vessel was evacuated and refilled with hydrogen atmosphere (3×) and the reaction mixture was stirred vigorously. After 1.5 h, the reaction mixture was filtered through a pad of celite and the filtrate was concentrated under reduced pressure to afford the crude Cbz-deprotected material. The crude residue was taken up into dichloromethane (23 mL) and the resulting mixture was cooled to 0° C. Phenyl dichlorophosphate (0.70 mL, 4.7 mmol) and triethylamine (0.66 mL, 4.7 mmol) were sequentially added. After 1 h, 4-nitrophenol (660 mg, 4.74 mmol) and triethylamine (0.66 mL, 4.7 mmol) were then added. After 1.5 h, the reaction mixture was diluted with dichloromethane (50 mL), washed with saturated aqueous sodium bicarbonate solution (50 mL) and brine (50 mL), dried over anhydrous sodium sulfate, and concentrated under reduced pressure. The crude residue was purified by silica gel chromatography eluting with 0-100% ethyl acetate in hexanes to afford the product. $^1$H NMR (400 MHz, chloroform-$d_1$) δ 8.26-8.18 (m, 2H), 7.43-7.30 (m, 4H), 7.25-7.17 (m, 3H), 4.77-4.58 (m, 1H), 4.40 (br s, 1H), 4.18-3.99 (m, 1H), 3.93-3.80 (m, 1H), 3.44 (br s, 1H), 2.07-1.87 (m, 4H), 1.52-1.36 (m, 14H), 1.30-1.16 (m, 2H). $^{31}$P NMR (162 MHz, chloroform-$d_1$) δ −3.15 (s). LCMS: MS m/z=563.88 [M+1].

Intermediate 64. ((1r,4S)-4-((tert-butoxycarbonyl)amino)cyclohexyl)methyl ((4-nitrophenoxy)(phenoxy)phosphoryl)-L-alaninate Method 1.

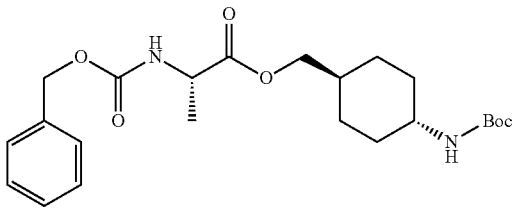 [SMILES: C[C@H](NC(=O)OCc1ccccc1)C(=O)OC[C@H]1CC[C@H](NC(=O)OC(C)(C)C)CC1]

((1r,4S)-4-((tert-butoxycarbonyl)amino)cyclohexyl) methyl ((benzyloxy) carbonyl)-L-alaninate. Cbz-L-Alanine (223 mg, 1.00 mmol) was dissolved in anhydrous MeCN (10 mL). trans-1-(Boc-amino)-4-(hydroxymethyl)cyclohexane (229 mg, 1.00 mmol) and EDCI (230 mg, 1.2 mmol) were added to the reaction, which was then stirred for 25 min. DMAP (122 mg, 1 mmol) was added in one portion, and the reaction was stirred for 4 h. The reaction mixture was diluted with ethyl acetate (15 mL) and washed with 5% aqueous citric acid solution (2×5 mL), followed with brine (10 mL). Organic extract was dried over anhydrous sodium sulfate and concentrated under reduced pressure. The crude residue was purified via SiO$_2$ column chromatography (12 g SiO$_2$ Combiflash HP Gold Column, 0-40% ethyl acetate/ hexanes). Fractions containing the desired product were combined and concentrated under reduced pressure to give the product. $^1$H NMR (400 MHz, chloroform-d) δ 7.41-7.27 (m, 5H), 5.29 (d, J=7.6 Hz, 1H), 5.11 (s, 2H), 4.47-4.24 (m, 2H), 3.96 (d, J=6.6 Hz, 2H), 3.37 (bs, 1H), 2.03 (m, 2H), 1.78 (m, 2H), 1.58 (m, 2H), 1.44 (m, 12H), 1.10 (m, 4H).

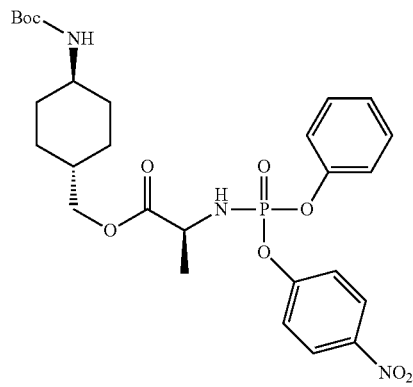 [SMILES: C[C@H](NP(=O)(Oc1ccccc1)Oc1ccc([N+](=O)[O-])cc1)C(=O)OC[C@H]1CC[C@H](NC(=O)OC(C)(C)C)CC1]

((1r,4S)-4-((tert-butoxycarbonyl)amino)cyclohexyl) methyl ((4-nitrophenoxy)(phenoxy)phosphoryl)-L-alaninate. ((1r,4S)-4-((tert-butoxycarbonyl)amino)cyclohexyl) methyl ((benzyloxy) carbonyl)-L-alaninate (348 mg, 0.800 mmol) was dissolved in 12 mL of anhydrous tetrahydrofuran. Degussa type 10% Palladium on carbon (25 mg) was added to the reaction and then stirred under atmospheric hydrogen for 3 h. Palladium on carbon was filtered off, and the filtrate was used in the next reaction without further purification. Phenyl dichlorophosphate (119 μL, 0.800 mmol) was dissolved in 15 mL anhydrous dichloromethane and stirred under atmospheric nitrogen in an ice bath. The filtrate from above was then added to the reaction solution dropwise and then stirred for 30 min. Triethylamine (120 μL, 0.88 mmol) was added dropwise and stirred for 1 h. p-Nitrophenol (100 mg, 0.72 mmol) was added in one portion. Triethylamine (123 μL, 0.88 mol) was added dropwise, and the reaction mixture was stirred for 2 h at RT. The reaction mixture was then diluted with dichloromethane (10 mL) and washed with water (3×10 mL). The organic extract was dried over anhydrous sodium sulfate and concentrated under reduced pressure. The crude residue was purified via SiO$_2$ column chromatography (12 g SiO$_2$ Combiflash HP Gold Column, 0-40% ethyl acetate/hexanes). Fractions containing the desired product were combined and concentrated under reduced pressure to give the product. $^1$H NMR (400 MHz, chloroform-d) δ 8.27-8.18 (m, 2H), 7.44-7.30 (m, 4H), 7.27-7.17 (m, 3H), 4.35 (s, 1H), 4.22-4.06 (m, 1H), 3.99-3.88 (m, 2H), 3.85 (t, J=10.6 Hz, 1H), 3.36 (s, 1H), 2.03 (m, 2H), 1.75 (m, 2H), 1.57 (m, 2H), 1.48-1.36 (m, 12H), 1.15-0.98 (m, 4H). $^{31}$P NMR (162 MHz, chloroform-d) δ 3.12, 3.13. LCMS: MS m/z=478.2 [M+1].

Method 2.

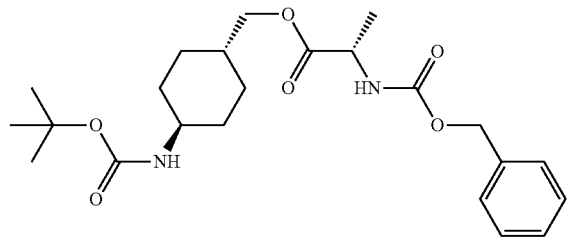 [SMILES: C[C@H](NC(=O)OCc1ccccc1)C(=O)OC[C@H]1CC[C@H](NC(=O)OC(C)(C)C)CC1]

((1r,4S)-4-((tert-butoxycarbonyl)amino)cyclohexyl) methyl ((benzyloxy)carbonyl)-L-alaninate. trans-1-((tert-Butoxycarbonyl)amino)-4-(hydroxymethyl)cyclohexane (510 mg, 2.18 mmol) followed by N-(3-dimethylaminopropyl)-N'-ethylcarbodiimide hydrochloride (509 g, 2.62 mmol) were added to a solution of Z-Ala-OH (489 g, 2.18 mmol) in acetonitrile (22 mL) at RT. After 30 min, 4-(dimethylamino)pyridine (267 mg, 2.18 mmol) was added. After 18 h, the reaction was diluted with ethyl acetate (100 mL) and the resulting mixture was washed with 10% aqueous citric acid (2×100 mL) and brine (100 mL). The organic layer was dried over anhydrous sodium sulfate and concentrated under reduced pressure. The crude residue was subjected to silica gel chromatography eluting with 0-50% methanol in ethyl acetate to afford the product. $^1$H NMR (400 MHz, Chloroform-d) δ 7.41-7.29 (m, 5H), 5.28 (s, 1H), 5.11 (s, 2H), 4.46-4.27 (m, 2H), 3.96 (d, J=6.6 Hz, 2H), 3.37 (s, 1H), 2.03 (s, 2H), 1.78 (s, 2H), 1.56 (s, 2H), 1.44 (s, 9H), 1.42 (d, J=7.2 Hz, 3H), 1.08 (t, J=9.7 Hz, 4H). LCMS: MS m/z=434.87 [M+1], $t_R$=1.21 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=5.96 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

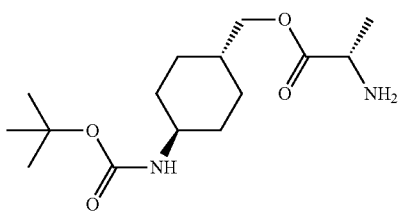 [SMILES: C[C@H](N)C(=O)OC[C@H]1CC[C@H](NC(=O)OC(C)(C)C)CC1]

((1r,4S)-4-((tert-butoxycarbonyl)amino)cyclohexyl) methyl L-alaninate. Palladium on carbon (198 mg, 10 wt %) was added to a solution of ((1r,4S)-4-((tert-butoxycarbonyl)amino)cyclohexyl)methyl ((benzyloxy)carbonyl)-L-alaninate (719 g, 1.65 mmol) in tetrahydrofuran (24 mL) that was purged with argon. The mixture was then purged with hydrogen and stirred at RT. After 1 h, the mixture was filtered through celite, the filter was rinsed with tetrahydrofuran, and the volatiles were removed under reduce pressure to obtain the product. $^1$H NMR (400 MHz, Chloroform-d) δ 4.38 (s, 1H), 4.02-3.85 (m, 2H), 3.55 (q, J=7.0 Hz, 1H), 3.38 (s, 1H), 2.04 (d, J=7.1 Hz, 2H), 1.83-1.73 (m, 2H), 1.63 (s, 2H), 1.44 (s, 10H), 1.34 (d, J=7.0 Hz, 3H), 1.09 (t, J=10.0 Hz, 4H). LCMS: MS m/z=300.93 [M+1], $t_R$=0.65 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

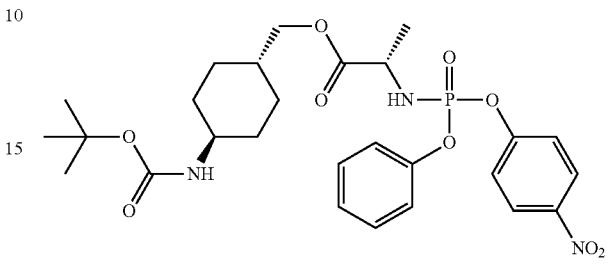

((1r,4S)-4-((tert-butoxycarbonyl)amino)cyclohexyl) methyl ((4-nitrophenoxy)(phenoxy)phosphoryl)-L-alaninate. To ((1r,4S)-4-((tert-butoxycarbonyl)amino)cyclohexyl)methyl L-alaninate (553 mg, 1.65 mmol) in tetrahydrofuran (24 mL) at 0° C. was added a solution of phenyl dichlorophosphate (247 μL, 1.65 mmol) in dichloromethane (30 mL) slowly over 15 min. After the addition was complete, triethylamine (0.26 mL, 1.82 mmol) was added dropwise. After 1 h, 4-nitrophenol (240 mg, 1.65 mmol) and triethylamine (0.26 mL, 1.82 mmol) were then sequentially added at 0° C., and the resulting mixture was then allowed to warm to RT. After 1 h, the reaction mixture was diluted with dichloromethane (50 mL) and washed with water (3×75 mL). The organic layer was dried over anhydrous sodium sulfate and concentrated under reduced pressure. The crude residue was purified by silica gel chromatography eluting with 0-100% ethyl acetate in hexanes to afford the product. $^1$H NMR (400 MHz, Chloroform-d) δ 8.23 (ddd, J=9.3, 1.3, 0.6 Hz, 2H), 7.44-7.31 (m, 4H), 7.25-7.16 (m, 3H), 4.36 (s, 1H), 4.22-4.06 (m, 1H), 3.96-3.90 (m, 2H), 3.84 (t, J=10.6 Hz, 1H), 3.36 (s, 1H), 2.02 (s, 2H), 1.83-1.68 (m, 2H), 1.57 (s, 2H), 1.44 (s, 9H), 1.41 (dd, J=7.1, 3.2 Hz, 3H), 1.06 (t, J=9.6 Hz, 3H). $^{31}$P NMR (162 MHz, Chloroform-d) δ −3.13 (d, J=2.9 Hz). LCMS: MS m/z=577.8 [M+1], $t_R$=1.28 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=6.35 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Intermediate 65. 4-nitrophenyl-N,N'-butryl L-alaninatephosphorodiamidate

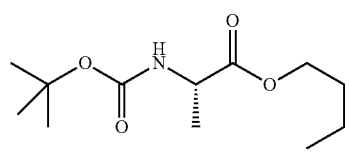 [SMILES: CCCCOC(=O)[C@H](C)NC(=O)OC(C)(C)C]

butyl (tert-butoxycarbonyl)-L-alaninate. Boc-L-alanine (380 mg, 2.0 mmol) was dissolved in anhydrous MeCN (10 mL). 1-Butanol (920 µL, 10.0 mmol) and EDCI (460 mg, 2.4 mmol) were added to the reaction which was then stirred for 15 min. DMAP (240 mg, 2.0 mmol) was added in one portion, and the reaction was stirred for 14 h. The reaction mixture was diluted reaction with ethyl acetate (15 mL) and washed with saturated aqueous sodium bicarbonate solution (2×10 mL), followed with brine (5 mL). The organic extracts were dried over anhydrous sodium sulfate and concentrated under reduced pressure. The crude residue was purified via SiO$_2$ column chromatography (12 g SiO$_2$ Combiflash HP Gold Column, 0-20% ethyl acetate/hexanes). Fractions containing the desired product were combined and concentrated under reduced pressure to give the product. $^1$H NMR (400 MHz, chloroform-d) δ 5.04 (m, 1H), 4.29 (m, 1H), 4.18-4.07 (m, 2H), 1.67-1.59 (m, 2H), 1.44 (s, 9H), 1.38 (m, 5H), 0.93 (t, J=7.4 Hz, 3H).

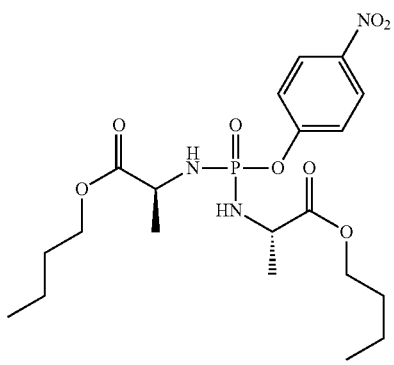 [SMILES: CCCCOC(=O)[C@H](C)NP(=O)(N[C@@H](C)C(=O)OCCCC)Oc1ccc([N+](=O)[O-])cc1]

4-nitrophenyl-N,N'-butryl L-alaninatephosphorodiamidate. Butyl (tert-butoxycarbonyl)-L-alaninate (291 mg, 1.18 mmol) was dissolved in 7 mL of 4 M HCl in dioxane and stirred for 1 h. The reaction mixture was concentrated under reduced pressure to give an oil which was then dissolved in anhydrous dichloromethane (10 mL) and stirred under atmospheric nitrogen in an ice bath. 4-Nitrophenyl phosphorodichloridate (152 mg, 0.59 mmol) was added in one portion, and the reaction was stirred for 10 min. Triethylamine (270 µL, 1.95 mmol) was dissolved in 1 mL of anhydrous dichloromethane and added to the reaction solution dropwise. The reaction mixture was stirred for 1 h. Triethylamine (270 µL, 1.95 mmol) was dissolved with 700 µL of anhydrous dichloromethane and added to reaction dropwise. The reaction mixture was stirred for 16 h at RT. The reaction mixture was diluted with dichloromethane (15 mL) and washed with water (3×20 mL). The organic extract was dried over anhydrous sodium sulfate and concentrated under reduced pressure. The crude residue was purified via SiO$_2$ column chromatography (12 g SiO$_2$ Combiflash HP Gold Column, 0-50% ethyl acetate/hexanes). Fractions containing the desired product were combined and concentrated under reduced pressure to give the product. $^1$H NMR (400 MHz, chloroform-d) δ 8.27-8.15 (m, 2H), 7.43-7.34 (m, 2H), 4.19-3.98 (m, 5H), 3.80-3.61 (m, 1H), 3.58 (m, 2H), 1.67-1.59 (m, 4H), 1.45-1.30 (m, 10H), 0.93 (m, 6H). $^{31}$P NMR (162 MHz, chloroform-d) δ 7.93. LCMS: MS m/z=474.0 [M+1].

Intermediate 66. methyl (2S)-2-(((benzyloxy)carbonyl)amino)-3-(4-(((((S)-1-isopropoxy-1-oxopropan-2-yl)amino)(4-nitrophenoxy)phosphoryl)oxy)phenyl) propanoate

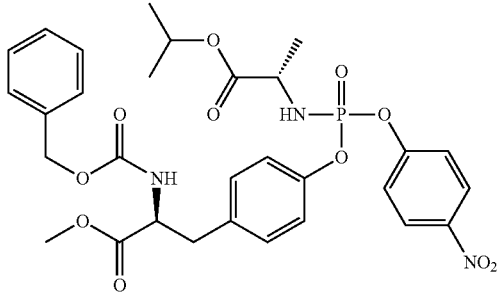 [SMILES: COC(=O)[C@H](Cc1ccc(OP(=O)(N[C@@H](C)C(=O)OC(C)C)Oc2ccc([N+](=O)[O-])cc2)cc1)NC(=O)OCc1ccccc1]

4-Nitrophenyl phosphorodichloridate (504 mg, 1.97 mmol) in dichloromethane (20 mL) was added dropwise over 10 minutes to a solution of L-alanine isopropyl ester hydrochloride (330 mg, 1.97 mmol) in dichloromethane (20 mL) at 0° C. After addition was complete, triethylamine (0.55 mL, 3.93 mmol) was added dropwise. After 60 minutes, N-carbobenzyloxy-L-tyrosine methyl ester (649 mg, 1.97 mmol) and triethylamine (0.28 mL, 1.97 mmol) were sequentially added at 0° C., and the resulting mixture was then allowed to warm to RT. After 30 minutes, the reaction mixture was washed with water (2×50 mL) and brine (50 mL), dried over anhydrous sodium sulfate, and concentrated under reduced pressure. The crude residue was purified by silica gel chromatography eluting with 20-100% ethyl acetate in hexanes to afford the product. $^1$H NMR (400 MHz, Methanol-d$_4$) δ 8.32-8.22 (m, 2H), 7.49-7.37 (m, 2H), 7.35-7.13 (m, 9H), 5.02 (s, 2H), 4.93 (pd, J=6.3, 1.1 Hz, 1H), 4.43 (dd, J=9.4, 5.2 Hz, 1H), 4.00 (dtd, J=10.1, 7.7, 6.5 Hz, 1H), 3.70 (s, 3H), 3.15 (dd, J=14.0, 5.4 Hz, 1H), 2.93 (dd, J=13.9, 9.6 Hz, 1H), 1.32 (td, J=7.2, 1.2 Hz, 3H), 1.20-1.16 (m, 6H). $^{31}$P NMR (162 MHz, Methanol-d$_4$) δ −1.26, −1.49. LCMS: MS m/z=644.11 [M+1], t$_R$=1.56 min; LC system: Thermo Accela 1250 UHPLC; MS system: Thermo LCQ Fleet; Column: Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: t$_R$=6.21 min; HPLC system: Agilent 1100 series; Column: Gemini 5µ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Intermediate 67. 2-morpholinoethyl ((4-nitrophenoxy)(phenoxy)phosphoryl)-L-alaninate

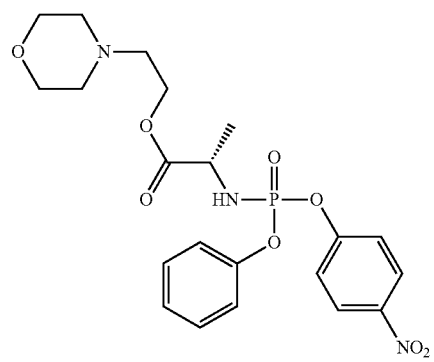 [SMILES: C[C@H](NP(=O)(Oc1ccccc1)Oc1ccc([N+](=O)[O-])cc1)C(=O)OCCN1CCOCC1]

4-Nitrophenyl phosphorodichloridate (505 mg, 1.97 mmol) in dichloromethane (20 mL) was added dropwise over 10 minutes to a solution of 2-morpholinoethyl L-alaninate hydrochloride (496 mg, 1.97 mmol) in dichloromethane (20 mL) at 0° C. After addition was complete, triethylamine (0.55 mL, 3.93 mmol) was added dropwise. After 90 minutes, phenol (185 mg, 1.97 mmol) and triethylamine (0.28 mL, 1.97 mmol) were sequentially added at 0° C., and the resulting mixture was then allowed to warm to RT. After 30 minutes, the reaction mixture was washed with water (2×50 mL) and brine (50 mL), dried over anhydrous sodium sulfate, and concentrated under reduced pressure. The crude residue was purified by silica gel chromatography eluting with 20-100% ethyl acetate in hexanes to afford the product. $^1$H NMR (400 MHz, CDCl$_3$) δ 8.28-8.14 (m, 2H), 7.41-7.29 (m, 4H), 7.24-7.16 (m, 4H), 6.87-6.81 (m, 1H), 4.14-4.04 (bs, 2H), 2.61-2.57 (bs, 4H), 2.45-3.40 (bs, 4H), 1.42 (dt, J=6.3, 2.0 Hz, 6H). $^{31}$P NMR (162 MHz, CDCl$_3$) δ −2.70. LCMS: MS m/z=480.27 [M+1], $t_R$=0.96 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=5.23 min; HPLC system: Agilent 1100 series; Column: Kinetx 2.6 u 100 A C18, 100 mm×4.6 mm; Solvents: Acetonitrile with 0.1% TFA, Water with 0.1% TFA; Gradient: 0 min-8.5 min 2-98% ACN, 8.5 min-10.0 min 98% ACN at 1.5 mL/min.

Intermediate 68. 2-(diisopropylamino)ethyl ((4-nitrophenoxy)(phenoxy)phosphoryl)-L-alaninate

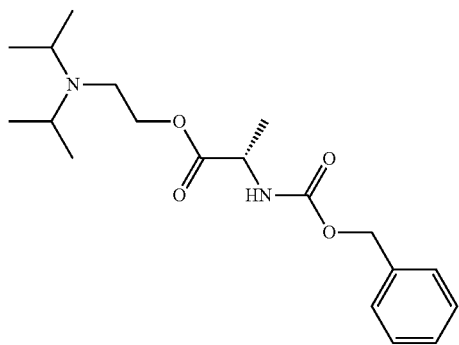 [SMILES: CC(C)N(CCOC(=O)[C@H](C)NC(=O)OCc1ccccc1)C(C)C]

2-(diisopropylamino)ethyl ((benzyloxy)carbonyl)-L-alaninate. N-(3-Dimethylaminopropyl)-N'-ethylcarbodiimide hydrochloride (2.06 g, 10.8 mmol) was added to a solution of Z-Ala-OH (2.00 g, 8.96 mmol) and 2-(diisopropylamino)ethanol (3.2 mL, 17.9 mmol) in acetonitrile (125 mL) at RT. After 10 min, 4-(dimethylamino)pyridine (1.09 g, 8.96 mmol) was added. After 2 d, the reaction mixture was concentrated to half the volume, and the mixture was diluted with ethyl acetate (100 mL) and the resulting mixture was washed with saturated aqueous sodium carbonate solution (100 mL) and brine (100 mL). The organic layer was dried over anhydrous sodium sulfate and concentrated under reduced pressure. The crude residue was subjected to silica gel chromatography eluting with 0-20% methanol in ethyl acetate to afford the product. $^1$H NMR (400 MHz, Acetonitrile-d$_3$) δ 7.48-7.23 (m, 5H), 5.96 (s, 1H), 5.07 (s, 2H), 4.30-4.00 (m, 3H), 2.28 (t, J=7.1 Hz, 2H), 2.14 (s, 6H), 1.73 (p, J=6.9 Hz, 2H), 1.34 (d, J=7.3 Hz, 3H). LCMS: MS m/z=351.26 [M+1], $t_R$=1.05 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.10 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

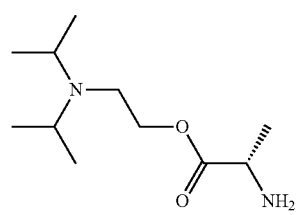

2-(diisopropylamino)ethyl L-alaninate. Palladium on carbon (587 mg, 10 wt %) was added to a solution of 2-(diisopropylamino)ethyl ((benzyloxy)carbonyl)-L-alaninate (1.93 g, 5.52 mmol) in ethanol (50 mL) that was purged with argon. The mixture was then purged with hydrogen and stirred at RT. After 18 hr, the mixture was filtered through celite, the filter was rinsed with ethyl acetate, and the volatiles were removed under reduce pressure to afford the product. $^1$H NMR (400 MHz, Acetonitrile-d3) δ 4.06-3.90 (m, 2H), 3.43 (q, J=7.0 Hz, 1H), 3.01 (hept, J=6.5 Hz, 2H), 2.65 (t, J=6.9 Hz, 2H), 1.22 (d, J=7.0 Hz, 3H), 0.99 (d, J=6.6 Hz, 12H). LCMS: MS m/z=217.01 [M+1], $t_R$=0.17 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min.

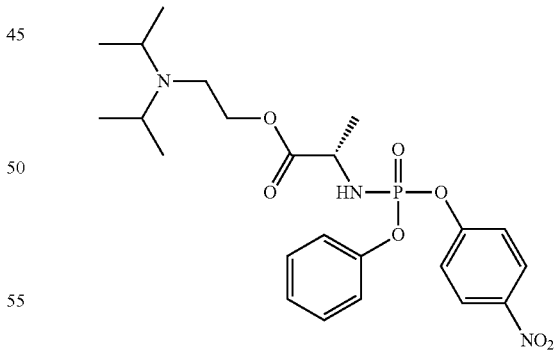

2-(diisopropylamino)ethyl ((4-nitrophenoxy)(phenoxy) phosphoryl)-L-alaninate. 2-(diisopropylamino)ethyl L-alaninate (511 mg, 2.43 mmol) in tetrahydrofuran (7 mL) was added dropwise over 15 minutes to a solution of phenyl dichlorophosphate (0.36 mL, 2.43 mmol) in tetrahydrofuran (25 mL) at 0° C. After the addition was complete, triethylamine (0.36 mL, 2.43 mmol) was added dropwise. After 90 min, 4-nitrophenol (337 mg, 2.43 mmol) and triethylamine (1.0 mL, 7.16 mmol) were then sequentially added at 0° C., and the resulting mixture was then allowed to warm to RT. After 17 h, the reaction mixture was diluted with ethyl acetate (100 mL) and washed with water (2×100 mL) and brine (100 mL). The organic layer was dried over anhydrous sodium sulfate and concentrated under reduced pressure to afford the product. $^1$H NMR (400 MHz, Acetonitrile-d$_3$) δ 8.29-8.18 (m, 2H), 7.49-7.35 (m, 4H), 7.30-7.21 (m, 3H), 4.71-4.52 (m, 1H), 4.12-3.99 (m, 2H), 4.00-3.83 (m, 3H), 3.06-2.86 (m, 2H), 2.56 (td, J=7.0, 3.8 Hz, 2H), 1.31 (ddd, J=7.1, 4.7, 1.1 Hz, 4H), 0.94 (d, J=6.5 Hz, 13H). $^{31}$P NMR (162 MHz, Acetonitrile-d$_3$) δ −2.15, −2.30. LCMS: MS m/z=494.25 [M+1], t$_R$=1.27 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: t$_R$=3.97 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Intermediate 69. isopropyl (2S)-2-(((benzyloxy)carbonyl)amino)-3-(4-(((((S)-1-methoxy-1-oxopropan-2-yl)amino)(4-nitrophenoxy)phosphoryl)oxy)phenyl)propanoate

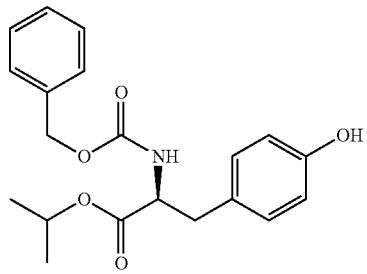 [SMILES: CC(C)OC(=O)[C@H](Cc1ccc(O)cc1)NC(=O)OCc1ccccc1]

isopropyl ((benzyloxy)carbonyl)-L-tyrosinate. Benzyl chloroformate (0.94 mL, 6.58 mmol) was added dropwise to a mixture of L-tyrosine isopropyl ester (1.0 g, 4.48 mmol) in acetone (4.5 mL) and 7 wt % aqueous sodium carbonate (4.5 mL). After 2 hr, reaction mixture was diluted with ethyl acetate (25 mL) and the resulting mixture was washed with water (10 mL) and brine (10 mL). The organic layer was dried over anhydrous sodium sulfate and concentrated under reduced pressure. The crude residue was subjected to silica gel chromatography eluting with 0-100% ethyl acetate in hexanes to afford the product. $^1$H NMR (400 MHz, Methanol-d$_4$) δ 7.39-7.20 (m, 5H), 7.06-6.97 (m, 2H), 6.74-6.62 (m, 2H), 5.05 (d, J=2.6 Hz, 2H), 4.94 (p, J=6.3 Hz, 1H), 4.31 (dd, J=8.6, 6.1 Hz, 1H), 2.99 (dd, J=13.9, 6.1 Hz, 1H), 2.84 (dd, J=13.9, 8.6 Hz, 1H), 1.22 (d, J=6.3 Hz, 3H), 1.14 (d, J=6.3 Hz, 3H). LCMS: MS m/z=357.87 [M+1], t$_R$=1.36 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: t$_R$=5.19 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

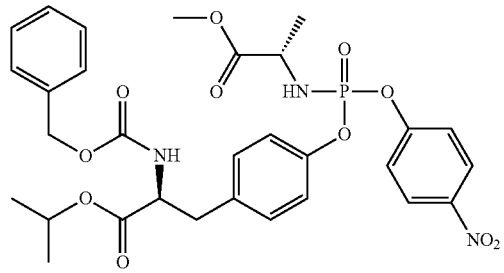 [SMILES: COC(=O)[C@H](C)NP(=O)(Oc1ccc(C[C@H](NC(=O)OCc2ccccc2)C(=O)OC(C)C)cc1)Oc1ccc([N+](=O)[O-])cc1]

isopropyl (2S)-2-(((benzyloxy)carbonyl)amino)-3-(4-(((((S)-1-methoxy-1-oxopropan-2-yl)amino)(4-nitrophenoxy)phosphoryl)oxy)phenyl)propanoate. L-Alanine isopropyl ester hydrochloride (97.2 mg, 0.70 mmol) in dichloromethane (8.0 mL) was added to a solution of 4-nitrophenyl phosphorodichloridate (179.7 mg, 0.70 mmol) in dichloromethane (7.5 mL) at 0° C. After addition was complete, triethylamine (0.22 mL, 1.57 mmol) was added dropwise. After 60 minutes, isopropyl ((benzyloxy)carbonyl)-L-tyrosinate (250.9 mg, 0.70 mmol) in dichloromethane (8.0 mL) and triethylamine (0.11 mL, 0.78 mmol) were sequentially added at 0° C., and the resulting mixture was then allowed to warm to RT. After 20 minutes, the reaction mixture was washed with water (2×20 mL) and brine (20 mL), dried over anhydrous sodium sulfate, and concentrated under reduced pressure. The crude residue was purified by silica gel chromatography eluting with 0-100% ethyl acetate in hexanes to afford the product. $^1$H NMR (400 MHz, Methanol-d$_4$) δ 8.32-8.24 (m, 2H), 7.43 (ddd, J=16.0, 9.2, 1.1 Hz, 2H), 7.36-7.09 (m, 9H), 5.03 (s, 2H), 4.97 (p, J=6.2 Hz, 1H), 4.35 (d, J=8.2 Hz, 1H), 4.14-3.95 (m, 1H), 3.62 (d, J=4.5 Hz, 3H), 3.12 (dt, J=12.6, 5.9 Hz, 1H), 2.92 (t, J=11.6 Hz, 1H), 1.35-1.30 (m, 3H), 1.22 (d, J=6.2 Hz, 3H), 1.16 (d, J=6.2 Hz, 4H). $^{31}$P NMR (162 MHz, Methanol-d$_4$) δ −1.31, −1.52. LCMS: MS m/z=644.07 [M+1], t$_R$=1.56 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=6.17 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Intermediate 70. isopropyl ((2-(methylthio)ethoxy)(4-nitrophenoxy)phosphoryl)-L-alaninate

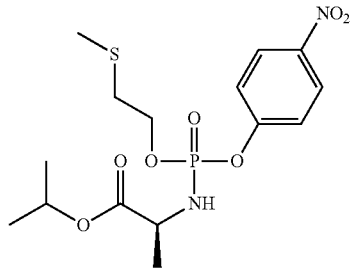 [SMILES: CSCCOP(=O)(N[C@@H](C)C(=O)OC(C)C)Oc1ccc([N+](=O)[O-])cc1]

4-Nitrophenyl phosphorodichloridate (512 mg, 2 mmol) was mixed with 10 mL of anhydrous dichloromethane and stirred under atmospheric nitrogen in an ice bath. L-Alanine isopropyl ester hydrogen chloride (335 mg, 2 mmol) was dissolved in anhydrous dichloromethane (3 mL) and added to the reaction dropwise. The reaction mixture was stirred for 30 min. Triethylamine (927 µL, 6.6 mmol) was dissolved in anhydrous dichloromethane (1 mL) and added to reaction dropwise, and the reaction was stirred for 60 min. 2-(methylthio)ethanol (74 µL, 2 mmol) was added in one portion, and the reaction mixture was stirred for 16 h. The reaction mixture was diluted with dichloromethane (15 mL) and washed with water (3×20 mL). The organic extract was dried over anhydrous sodium sulfate and concentrated under reduced pressure. The crude residue was purified via $SiO_2$ column chromatography (12 g $SiO_2$ Combiflash HP Gold Column, 0-50% ethyl acetate/hexanes). Fractions containing the desired product were combined and concentrated under reduced pressure to give the product. $^1$H NMR (400 MHz, chloroform-d) δ 8.27-8.18 (m, 2H), 7.44-7.33 (m, 2H), 5.02 (m, 1H), 4.33-4.21 (m, 2H), 4.07-3.94 (m, 1H), 3.70 (m, 1H), 2.84-2.73 (m, 2H), 2.14 (m, 3H), 1.40 (m, 3H), 1.29-1.19 (m, 6H). $^{31}$P NMR (162 MHz, chloroform-d) δ 2.08, 2.20. LCMS: MS m/z=834.5 [2M+Na]; 405.1 [M−1], $t_R$=1.33 min; LC system: Thermo Dionex ultimate 3000 UHPLC; Column: Phenomenex Kinetex 2.6µ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 m/min. HPLC: $t_R$=3.60 min; HPLC system: Agilent 1100 series; Column: Phenomenex Gemini 5µ C18 110A, 50×4.6 mm; Solvent: A: Water with 0.1% TFA, B: Acetonitrile with 0.1% TFA; Gradient: 2-98% B in 5 min at 2 mL/min.

Intermediate 71. isopropyl ((2-methoxyethoxy)(4-nitrophenoxy)phosphoryl)-L-alaninate

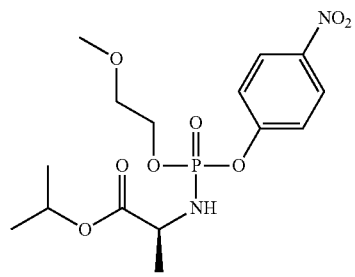 [SMILES: COCCOP(=O)(N[C@@H](C)C(=O)OC(C)C)Oc1ccc([N+](=O)[O-])cc1]

4-Nitrophenyl phosphorodichloridate (512 mg, 2 mmol) was mixed with 10 mL of anhydrous dichloromethane and stirred under atmospheric nitrogen in an ice bath. L-Alanine isopropyl ester hydrogen chloride (335 mg, 2 mmol) was dissolved in anhydrous dichloromethane (3 mL) and added to the reaction dropwise. The reaction mixture was stirred for 30 min. Triethylamine (927 µL, 6.6 mmol) was dissolved in anhydrous dichloromethane (1 mL) and added to the reaction mixture dropwise. The reaction mixture was stirred for 60 min. 2-methoxyethanol (158 µL, 2 mmol) was added in one portion, and the reaction mixture was stirred for 16 h. The reaction mixture was diluted with dichloromethane (15 mL) and washed with water (3×10 mL). The organic extract was dried over anhydrous sodium sulfate and concentrated under reduced pressure. The crude residue was purified via $SiO_2$ column chromatography (4 g $SiO_2$ Combiflash HP Gold Column, 0-50% ethyl acetate/hexanes). Fractions containing the desired product were combined and concentrated under reduced pressure to give the product. $^1$H NMR (400 MHz, chloroform-d) δ 8.25-8.15 (m, 2H), 7.43-7.32 (m, 2H), 5.00 (m, 1H), 4.36-4.17 (m, 2H), 4.06-3.82 (m, 2H), 3.65-3.55 (m, 2H), 3.37 (m, 3H), 1.41-1.34 (m, 3H), 1.27-1.18 (m, 6H). $^{31}$P NMR (162 MHz, chloroform-d) δ 2.52, 2.69. LCMS: MS m/z=391.0 [M+1]; 389.1 [M−1], $t_R$=1.24 min; LC system: Thermo Dionex ultimate 3000 UHPLC; Column: Phenomenex Kinetex 2.6µ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=3.29 min; HPLC system: Agilent 1100 series; Column: Phenomenex Gemini 5µ C18 110A, 50×4.6 mm; Solvent: A: Water with 0.1% TFA, B: Acetonitrile with 0.1% TFA; Gradient: 2-98% B in 5 min at 2 mL/min.

Intermediate 72. isopropyl ((2-(methylsulfonyl)ethoxy)(4-nitrophenoxy)phosphoryl)-L-alaninate

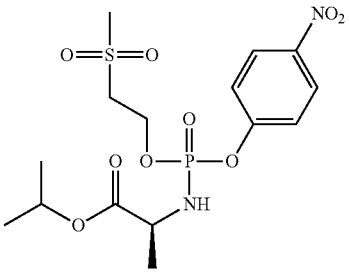 [SMILES: CC(C)OC(=O)[C@H](C)NP(=O)(OCCS(C)(=O)=O)Oc1ccc([N+](=O)[O-])cc1]

Phosphorous oxychloride (280 µL, 3 mmol) was dissolved in anhydrous tetrahydrofuran (10 mL) and stirred in an ice bath under atmospheric nitrogen. 2-(methylsulfonyl)ethanol (280 µL, 3 mmol) was dissolved in anhydrous tetrahydrofuran (2 mL) and added to reaction dropwise. Reaction was stirred for 1 h. L-Alanine isopropyl ester hydrochloride (503 mg, 3 mmol) was added in one portion and the reaction mixture was stirred for 1 h. Triethylamine (1.38 mL, 9.9 mmol) was dissolved in anhydrous tetrahydrofuran (2 mL) and added to the reaction dropwise. The reaction was stirred for 90 min. p-Nitrophenol (417 mg, 3 mmol) was added in one portion. Triethylamine (460 µL, 3.3 mmol) was added. The reaction mixture was stirred for 16 h.

The reaction mixture was then diluted with ethyl acetate (20 mL) and washed with water (5×15 mL) followed with brine (5 mL). The organic extract was dried over anhydrous sodium sulfate and concentrated under reduced pressure. The crude residue was purified via $SiO_2$ column chromatography (4 g $SiO_2$ Combiflash HP Gold Column, 0-80% ethyl acetate/hexanes). Fractions containing the desired product were combined and concentrated under reduced pressure to give the product. $^1$H NMR (400 MHz, chloroform-d) δ 8.28-8.16 (m, 2H), 7.44-7.32 (m, 2H), 5.00 (m, 1H), 4.71-4.51 (m, 2H), 4.06-3.85 (m, 2H), 3.51-3.33 (m, 2H), 2.96 (m, 3H), 1.40-1.35 (m, 3H), 1.27-1.20 (m, 6H). $^{31}$P NMR (162 MHz, chloroform-d) δ 2.06, 2.29. LCMS: MS m/z=439.0 [M+1]; $t_R$=1.18 min; LC system: Thermo Dionex ultimate 3000 UHPLC; Column: Phenomenex Kinetex 2.6µ C18 100 A, 50×3 mm; Solvents: A: Water with 0.1% acetic acid, B: Acetonitrile with 0.1% acetic acid;

Gradient: 0 min-0.3 min 5% B, 0.3 min-1.5 min 5-100% B, 1.5 min-2 min 100% B, 2 min-2.2 min 100-5% B at 2 m/min. HPLC: $t_R$=3.08 min; HPLC system: Agilent 1100 series; Column: Phenomenex Gemini 5µ C18 110A, 50×4.6 mm; Solvent: A: Water with 0.1% TFA, B: Acetonitrile with 0.1% TFA; Gradient: 2-98% B in 5 min at 2 mL/min.

Intermediate 73. 2-(2-ethoxyethoxy)ethyl ((perfluorophenoxy)(phenoxy)phosphoryl)-L-alaninate single isomer

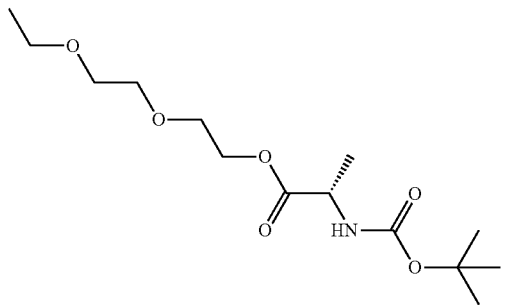 [SMILES: CCOCCOCCOC(=O)[C@H](C)NC(=O)OC(C)(C)C]

2-(2-ethoxyethoxy)ethyl tert-butoxycarbonyl)-L-alaninate. To a stirred solution of (tert-butoxycarbonyl)-L-alanine (12.41 g, 66 mmol) and 2-(2-ethoxyethoxy)ethan-1-ol (8.00 g, 60 mmol) in dry dichloromethane (100 mL) were added N-methylmorpholine (19.67 mL, 179 mmol), 4-(dimethylamino)pyridine (0.15 g, 1.2 mmol) and tri-propylphosphonic acid cyclic anhydride (42.6 mL, 72 mmol, 50% in ethyl acetate) at 0° C. under an atmosphere of argon. The reaction mixture was then stirred at room temperature for 2 hours. The reaction mixture was washed with water (50 mL), twice with 10% solution of citric acid (2×40 mL), twice with saturated aqueous sodium bicarbonate solution (2×40 mL) and once with brine (50 mL), dried over sodium sulfate, filtered through a 3 cm layer of silica gel which was washed with additional dichloromethane. The combined organics were concentrated down under reduced pressure, co-distilled with dichloromethane and dried under high vacuum overnight to afford the product. $^1$H NMR (400 MHz, DMSO-$d_6$) δ 7.27 (d, J=7.4 Hz, 1H), 4.23-4.14 (m, 1H), 4.14-4.06 (m, 1H), 4.05-3.94 (m, 1H), 3.64-3.56 (m, 2H), 3.55-3.49 (m, 2H), 3.49-3.39 (m, 4H), 1.38 (s, 9H), 1.23 (d, J=7.4 Hz, 3H), 1.09 (t, J=7.0 Hz, 3H).

2-(2-ethoxyethoxy)ethyl ((perfluorophenoxy)(phenoxy)phosphoryl)-L-alaninate single isomer. The intermediate 2-(2-ethoxyethoxy)ethyl (tert-butoxycarbonyl)-L-alaninate (18.3 g, 59.93 mmol) was dissolved in 50 mL of 4 M HCl in 1,4-dioxane and the reaction mixture was stirred at room temperature for 2 hours, concentrated under reduced pressure and co-distilled with toluene to give the solid which was dried under high vacuum for 1 hour. The solids were suspended in dichloromethane (100 mL) and phenyl dichlorophosphate (9.81 mL, 65.92 mmol) and triethylamine (18.28 mL, 131.84 mmol) were sequentially added at −78° C. and the resulting mixture was stirred at room temperature for 2 hours. The reaction mixture was cooled down to 0° C. and pentafluorophenol (11.03 g, 59.93 mmol) and triethylamine (10.80 mL, 78.05 mmol) were then sequentially added and the resulting mixture was then allowed to warm to room temperature. After 3 hours, the reaction mixture was cooled down to 0° C. and solids were filtered off, the filtrate was washed with saturated ammonium chloride water solution (100 mL), water (100 mL) and brine (50 mL). The organics were dried over sodium sulfate and filtered through a 3 cm layer of silica gel which was washed with 1:1 ethyl acetate and dichloromethane mixture (100 mL). The combined organics were concentrated down under reduced pressure to afford 21.7 g of the crude product (as a mixture of both isomers on phosphorus based on the NMR). The solids were dissolved in minimum amount of boiling diisopropyl ether and the mixture was vigorously stirred at room temperature overnight. The solid product was filtered off and washed with cold diisopropyl ether (2×20 mL) and hexane (3×40 mL) to afford the product (a single isomer at phosphorus based on the NMR). $^1$H NMR (400 MHz, DMSO-$d_6$) δ 7.47-7.36 (m, 2H), 7.30-7.20 (m, 3H), 6.92 (dd, J=14.2, 9.9 Hz, 1H), 4.21-4.08 (m, 2H), 4.07-3.92 (m, 1H), 3.62-3.56 (m, 2H), 3.53-3.47 (m, 2H), 3.45-3.36 (m, 4H), 1.29 (d, J=7.1 Hz, 3H), 1.07 (t, J=7.0 Hz, 3H). $^{19}$F NMR (376 MHz, DMSO-$d_6$) δ −154.24 (d, J=21.5 Hz, 2F), −160.86 (t, J=23.1 Hz, 1F), −163.68 (t, J=21.7 Hz, 2F). $^{31}$P NMR (162 MHz, DMSO-$d_6$) δ 0.40. LCMS: MS m/z=528.06 [M+1], $t_R$=1.64 min; LC system: Thermo Accela 1250 UHPLC; MS system: Thermo LCQ Fleet; Column: Kinetex 2.6µ XB-C18 100 A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 µL/min.

Intermediate 74. cyclohexyl ((S)-(4-nitrophenoxy)(phenoxy)phosphoryl)-L-alaninate

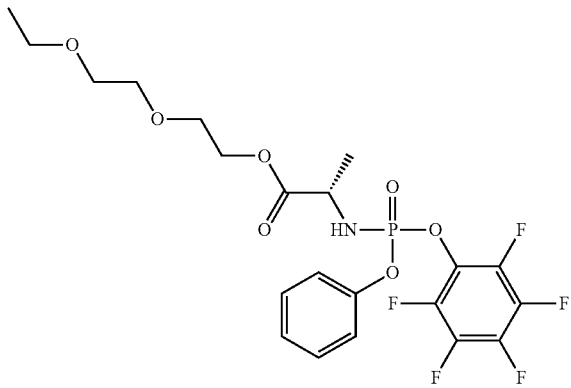 [SMILES: CCOCCOCCOC(=O)[C@H](C)NP(=O)(Oc1ccccc1)Oc1c(F)c(F)c(F)c(F)c1F]

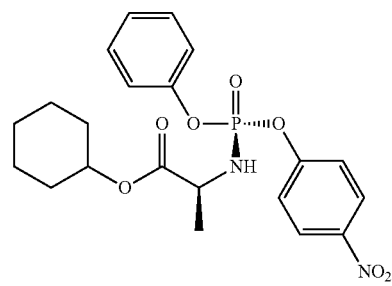 [SMILES: C[C@H](N[P@](=O)(Oc1ccccc1)Oc1ccc([N+](=O)[O-])cc1)C(=O)OC1CCCCC1]

Intermediate 25 (1.3 g, 2.90 mmol) was suspended in diisopropyl ether (3 mL) and para-nitrophenol (14 mg, 0.1 mmol) and DBU (0.05 mL, 0.335 mmol) were added at RT. The resulting mixture was stirred for 4 h and 1 N aqueous hydrochloric acid solution and ethyl acetate were added. The organic layer was split and was dried over anhydrous sodium sulfate and concentrated under reduced pressure. The resulting residue was taken up into diisopropyl ether (2 mL) and was sonicated to disperse the solids. The solids were collected by vacuum filtration to afford the product. $^1$H NMR (400 MHz, Methanol-$d_4$) δ 8.27 (d, J=9.1 Hz, 2H), 7.51-7.44 (m, 2H), 7.38 (dd, J=8.6, 7.2 Hz, 2H), 7.28-7.17 (m, 3H), 4.68 (dt, J=8.9, 4.6 Hz, 1H), 4.02 (dq, J=9.9, 7.2 Hz, 1H), 1.80-1.64 (m, 5H), 1.52 (s, 1H), 1.57-1.46 (m, 1H), 1.44-1.22 (m, 9H). $^{31}$P NMR (162 MHz, Methanol-$d_4$) δ −1.32. MS m/z=449 (M+H)+.

B. Compound Precursors

Example 1. (S)-isopropyl 2-(((S)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)amino)propanoate

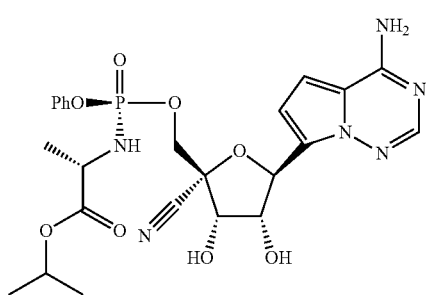 [SMILES: CC(C)OC(=O)[C@H](C)N[P@](=O)(OC[C@@]1(C#N)O[C@@H](c2ccc3c(N)ncnn23)[C@H](O)[C@@H]1O)Oc1ccccc1]

Intermediate 1 (50 mg, 0.172 mmol) and Intermediate 18 (84 mg, 0.206 mmol) were mixed in anhydrous N,N-dimethylformamide (2 mL). Magnesium chloride (36 mg, 0.378 mmol) was added in one portion. The reaction mixture was heated at 50° C. N,N-Diisopropylethylamine (75 μL, 0.43 mmol) was added, and the reaction was stirred for 4.5 hrs at 50° C. The reaction mixture was cooled, diluted with ethyl acetate (30 mL) and washed with 5% aqueous citric acid solution (10 mL) and then brine (10 mL). The organic layer was dried over anhydrous sodium sulfate and concentrated under reduced pressure. The crude product was purified via SiO$_2$ column chromatography (4 g SiO$_2$ Combiflash HP Gold Column 0-2-5% methanol/dichloromethane) to afford the product. $^1$H NMR (400 MHz, Methanol-$d_4$) δ 7.79 (s, 1H), 7.36-7.25 (m, 2H), 7.25-7.12 (m, 3H), 6.84 (d, J=4.5 Hz, 1H), 6.73 (d, J=4.5 Hz, 1H), 5.49 (d, J=5.1 Hz, 1H), 4.91-4.84 (m, 1H), 4.62 (dd, J=5.6, 5.0 Hz, 1H), 4.47 (d, J=5.6 Hz, 1H), 4.45-4.30 (m, 2H), 3.85 (dq, J=10.0, 7.1 Hz, 1H), 1.25 (d, J=7.2 Hz, 3H), 1.15 (t, J=6.4 Hz, 6H). $^{31}$P NMR (162 MHz, Methanol-$d_4$) δ 3.31. MS m/z=561.0 [M+1], 559.0 [M−1].

Example 2. (2S)-cyclobutylmethyl 2-(((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)amino)propanoate

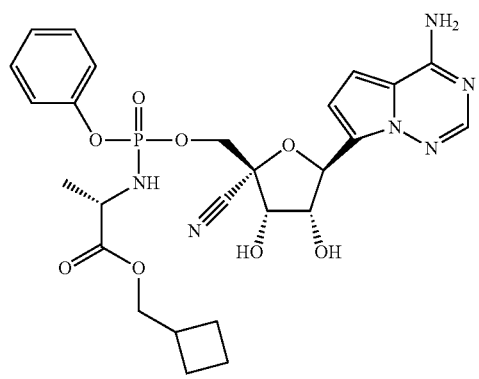 [SMILES: C[C@H](NP(=O)(OC[C@@]1(C#N)O[C@@H](c2ccc3c(N)ncnn23)[C@H](O)[C@@H]1O)Oc1ccccc1)C(=O)OCC1CCC1]

Intermediate 2 (50 mg, 0.116 mmol) and Intermediate 15 (60 mg, 0.139 mmol) were dissolved in anhydrous tetrahydrofuran (3 mL). Magnesium chloride (17 mg, 0.174 mmol) was added in one portion. Reaction was warmed to 60° C. and stirred for 20 min. N,N-Diisopropylethylamine (50 μL, 0.29 mmol) was added, and the reaction was stirred at 60° C. for 17 h. The reaction was cooled to room temperature, diluted with ethyl acetate (30 mL) and washed with 5% aqueous sodium carbonate solution (3×20 mL) and then brine (20 mL), dried over anhydrous sodium sulfate and concentrated under reduced pressure. Residue was dissolved in acetonitrile (2 mL) and stirred in an ice bath. 12 M hydrochloric acid (330 μL) was added dropwise and stirred for 20 h. The reaction was diluted with ethyl acetate (30 mL) and cooled in an ice bath. 1 N sodium hydroxide solution was added dropwise to give pH of 10. Organic layer was collected and washed with saturated aqueous sodium bicarbonate solution (10 mL) and then brine (10 mL). Organic layer was dried over anhydrous sodium sulfate and concentrated under reduced pressure. The crude product was purified via SiO$_2$ column chromatography (4 g SiO$_2$ Combiflash HP Gold Column 0-3-8% methanol/dichloromethane). Fractions having the desired product were combined and concentrated under reduced pressure. Residue was dissolved in acetonitrile and water and freeze dried to give the product. $^1$H NMR (400 MHz, Methanol-$d_4$) δ 7.79 (m, 1H), 7.37-7.10 (m, 5H), 6.84 (dd, J=4.5, 2.3 Hz, 1H), 6.73 (dd, J=4.5, 2.4 Hz, 1H), 5.53-5.45 (m, 1H), 4.62 (q, J=5.5 Hz, 1H), 4.54-4.28 (m, 3H), 4.10-3.80 (m, 3H), 2.65-2.45 (m, 1H), 2.08-1.62 (m, 6H), 1.26 (d, J=7.2 Hz, 3H). $^{31}$P NMR (162 MHz, Methanol-$d_4$) δ 3.25, 3.24. MS m/z=587.2 [M+1], 585.2 [M−1].

Example 3. (2S)-ethyl 2-(((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)amino)-3-phenylpropanoate

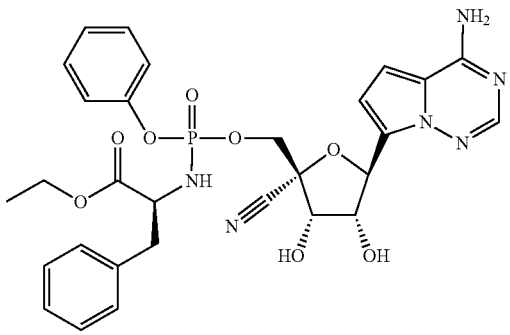 [SMILES: CCOC(=O)[C@H](Cc1ccccc1)NP(=O)(OC[C@@]1(C#N)O[C@@H](c2ccc3c(N)ncnn23)[C@H](O)[C@@H]1O)Oc1ccccc1]

To a mixture of Intermediate 4 (52.0 mg, 0.121 mmol), Intermediate 19 (68.0 mg, 0.145 mmol), and magnesium chloride (17.2 mg, 0.181 mmol) was added THF (1.0 mL) at RT. The resulting suspension was warmed to 50° C., and was allowed to stir for 10 min. N,N-Diisopropylethylamine (0.052 mL, 0.301 mmol) was then added and the resulting mixture was stirred at 50° C. for 30 min. The reaction mixture was then allowed to cool to RT, and concentrated aqueous hydrochloric acid solution (12 M, 0.200 mL, 2.4 mmol) was added. After 1 h, the reaction mixture was cooled in an ice bath and quenched with saturated aqueous sodium carbonate solution to pH=7. The crude mixture was purified by preparatory HPLC (Phenominex Gemini NX 10 u C18 250×30 mm column, 40-100% acetonitrile/water gradient) to afford the product. LC/MS: $t_R$=1.27 min, MS m/z=623.00 [M+1]; LC system: Thermo Accela 1250 UHPLC. MS system: Thermo LCQ Fleet; Column: Kinetex 2.6μ XB-C18 100 A, 50×3.00 mm. Solvents: Acetonitrile with 0.1% formic acid, Water with 0.1% formic acid. Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min. $^1$H NMR (400 MHz, DMSO-$d_6$) δ 7.88 (m, 3H), 7.37-6.84 (m, 12H), 6.71 (t, J=4.2 Hz, 2H), 6.22 (ddd, J=23.7, 12.9, 10.5 Hz, 1H), 5.36 (dd, J=9.2, 6.1 Hz, 1H), 4.39 (s, 1H), 4.16 (dd, J=16.2, 5.3 Hz, 1H), 4.09-3.83 (m, 5H), 2.93 (dt, J=14.3, 7.3 Hz, 1H), 2.78 (td, J=13.2, 12.2, 8.6 Hz, 1H), 1.01 (t, 7.1 Hz, 3H). $^{31}$P NMR (162 MHz, DMSO-$d_6$) δ 3.85 (s), 2.86 (s).

Example 4. (2S)-cyclohexyl 2-(((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)amino)propanoate

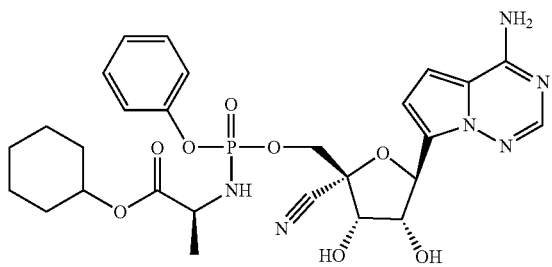 [SMILES: C[C@H](NP(=O)(OC[C@@]1(C#N)O[C@@H](c2ccc3c(N)ncnn23)[C@H](O)[C@@H]1O)Oc1ccccc1)C(=O)OC1CCCCC1]

To a mixture of Intermediate 4 (99 mg, 0.30 mmol), Intermediate 25 (201 mg, 0.45 mmol), and MgCl$_2$ (43 mg, 0.45 mmol) in DMF (4 mL) was added N,N-diisopropylethylamine (0.13 mL, 0.75 mmol) dropwise at room temperature. The resulting mixture was stirred at room temperature for 15 h and purified by preparative HPLC (Phenominex Synergi 4 u Hydro-RR 80 Å 150×30 mm column, 10-100% acetonitrile/water gradient) to give an intermediate, which was dissolved in ACN (3 mL) and c-HCl (0.1 mL) was added. The resulting mixture was stirred at 50° C. for 2 h, cooled, and purified by preparative HPLC (Phenominex Synergi 4 u Hydro-RR 80 Å 150×30 mm column, 10-80% acetonitrile/water gradient) to give the product. $^1$H NMR (400 MHz, Methanol-d4) δ 7.80 (s, 0.5H), 7.78 (s, 0.5H), 7.42-7.05 (m, 5H), 6.84 (m, 1H), 6.73 (m, 1H), 5.50 (m, 1H), 4.64 (m, 2H), 4.57-4.25 (m, 3H), 3.86 (m, 1H), 1.91-1.61 (m, 4H), 1.61-1.09 (m, 9H). $^{31}$P NMR (162 MHz, Methanol-d4) δ 3.3. MS m/z=601 (M+H)+. Separation of the Diastereomers. The product was purified via chiral preparatory HPLC (Chiralpak IA, 150×4.6 mm, Heptane 70% Ethanol 30%).

Example 5. cyclohexyl ((R)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

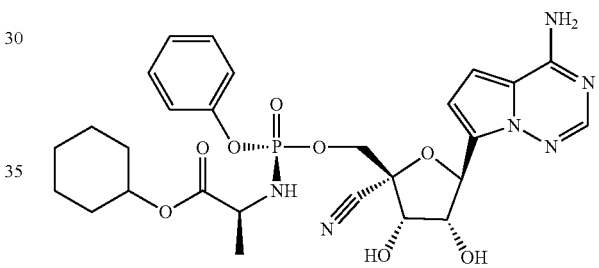

First Eluting Diastereomer of Example 4: $^1$H NMR (400 MHz, Methanol-$d_4$) δ 7.78 (s, 1H), 7.34-7.23 (m, 2H), 7.19-7.10 (m, 3H), 6.85 (d, J=4.5 Hz, 1H), 6.73 (d, J=4.5 Hz, 1H), 5.51 (d, J=5.0 Hz, 1H), 4.69 (td, J=8.8, 4.2 Hz, 1H), 4.62 (t, J=5.3 Hz, 1H), 4.53-4.44 (m, 2H), 4.36 (dd, J=10.9, 5.2 Hz, 1H), 3.86 (dq, J=9.4, 7.1 Hz, 1H), 1.85-1.62 (m, 4H), 1.58-1.20 (m, 9H). $^{31}$P NMR (162 MHz, Methanol-$d_4$) δ 3.31.

Example 6. cyclohexyl ((S)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

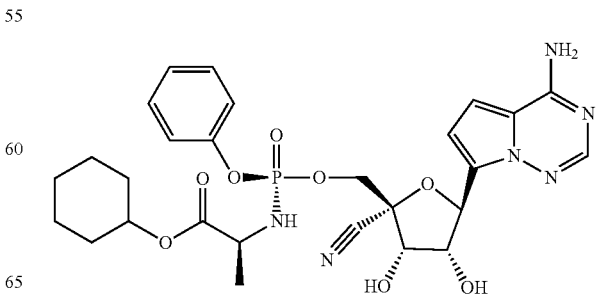

Second Eluting Diastereomer of Example 4: $^1$H NMR (400 MHz, Methanol-d$_4$) δ 7.80 (s, 1H), 7.37-7.27 (m, 2H), 7.26-7.13 (m, 3H), 6.84 (d, J=4.5 Hz, 1H), 6.73 (d, J=4.5 Hz, 1H), 5.49 (d, J=5.0 Hz, 1H), 4.71-4.56 (m, 2H), 4.46 (d, J=5.6 Hz, 1H), 4.45-4.30 (m, 2H), 3.87 (dq, J=10.0, 7.1 Hz, 1H), 1.80-1.61 (m, 4H), 1.55-1.21 (m, 9H). $^{31}$P NMR (162 MHz, Methanol-d$_4$) δ 3.31.

Example 7

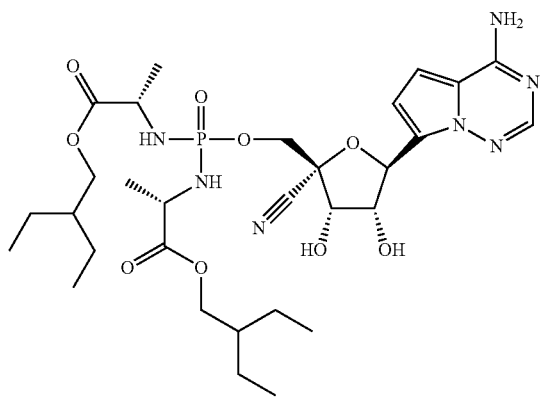 [SMILES: CCC(CC)COC(=O)[C@H](C)NP(=O)(N[C@@H](C)C(=O)OCC(CC)CC)OC[C@@]1(C#N)O[C@@H](c2ccc3c(N)ncnn23)[C@H](O)[C@@H]1O]

Intermediate 2 (60 mg, 0.139 mmol) was dissolved in anhydrous tetrahydrofuran (2 mL). Phosphorus oxychloride (25 µL, 0.278 mmol) was added in one portion and stirred for 30 mins. More phosphorus oxychloride (100 µL) was added and stirred for 30 mins. (S)-2-ethylbutyl 2-aminopropanoate hydrochloride (87 mg, 0.417 mmol) and triethylamine (116 µL, 0.834 mmol) were added and stirred for 30 mins. More (S)-2-ethylbutyl 2-aminopropanoate hydrochloride (500 mg) was added. Triethylamine was added to give pH of 9. Reaction was stirred for 16 hrs, diluted with ethyl acetate (20 mL) and washed with saturated aqueous sodium bicarbonate solution (2×20 mL), 5% aqueous citric acid solution (20 mL) followed with brine (20 mL). Organic layer was dried over anhydrous sodium sulfate and concentrated under reduced pressure. Residue was dissolved in acetonitrile (2 mL), 12 M hydrochloric acid (400 uL) was added and the mixture was stirred for 4 hrs. Reaction was diluted with ethyl acetate (30 mL) and washed with saturated aqueous sodium bicarbonate solution (2×10 mL) followed with brine (10 mL). Organic layer was dried over anhydrous sodium sulfate and concentrated under reduced pressure. The crude product was purified via SiO$_2$ column chromatography (4 g SiO$_2$ Combiflash HP Gold Column 0-3-8% methanol/dichloromethane). Fractions having the desired product were combined and concentrated under reduced pressure. Residue was dissolved in acetonitrile and water and freeze dried to give the product. $^1$H NMR (400 MHz, Methanol-d$_4$) δ 7.82 (s, 1H), 6.86 (d, J=4.5 Hz, 1H), 6.77 (d, J=4.5 Hz, 1H), 5.50 (d, J=4.8 Hz, 1H), 4.64-4.57 (m, 1H), 4.49 (d, J=5.7 Hz, 1H), 4.31 (dd, J=11.1, 7.1 Hz, 1H), 4.21 (dd, J=11.1, 5.8 Hz, 1H), 4.11-3.94 (m, 4H), 3.94-3.84 (m, 2H), 1.58-1.29 (m, 10H), 0.98-0.82 (m, 18H). $^{31}$P NMR (162 MHz, Methanol-d$_4$) δ 13.61. MS m/z=682.1 [M+1], 680.1 [M−1].

Example 8. (2S)-cyclopropylmethyl 2-(((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)amino)propanoate

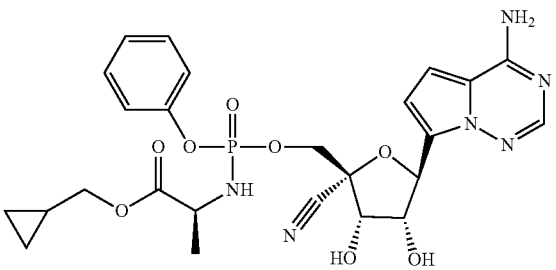 [SMILES: C[C@H](NP(=O)(OC[C@@]1(C#N)O[C@@H](c2ccc3c(N)ncnn23)[C@H](O)[C@@H]1O)Oc1ccccc1)C(=O)OCC1CC1]

To a mixture of Intermediate 4 (70 mg, 0.211 mmol), Intermediate 20 (133 mg, 0.32 mmol), and MgCl$_2$ (30 mg, 0.32 mmol) in THF (3 mL) was added N,N-diisopropylethylamine (0.092 mL, 0.53 mmol) dropwise at room temperature. The resulting mixture was stirred at 60° C. for 15 h, diluted with EtOAc, washed with water and brine, dried with sodium sulfate, and concentrated in vacuo. The resulting residue was dissolved in ACN (3 mL) and c-HCl (0.3 mL) was added. The mixture was stirred at room temperature for 2 h and purified by preparative HPLC (Phenominex Synergi 4 u Hydro-RR 80 Å 150×30 mm column, 10-70% acetonitrile/water gradient) to give the product. $^1$H NMR (400 MHz, Methanol-d4) δ 7.79 (m, 1H), 7.39-7.10 (m, 5H), 6.85 (m, 1H), 6.73 (m, 1H), 5.50 (m, 1H), 4.62 (m, 1H), 4.58-4.24 (m, 3H), 4.00-3.69 (m, 3H), 1.27 (m, 3H), 1.17-0.95 (m, 1H), 0.49 (m, 2H), 0.29-0.15 (m, 2H). $^{31}$P NMR (162 MHz, Methanol-d4) δ 3.29, 3.22. MS m/z 573 (M+H)+.

Separation of the (S) and (R) diastereomers. The product was separated by chiral preparatory HPLC (Chiralpak IA, 150×4.6 mm, Heptane 80% Ethanol 20%) to afford the diastereomers:

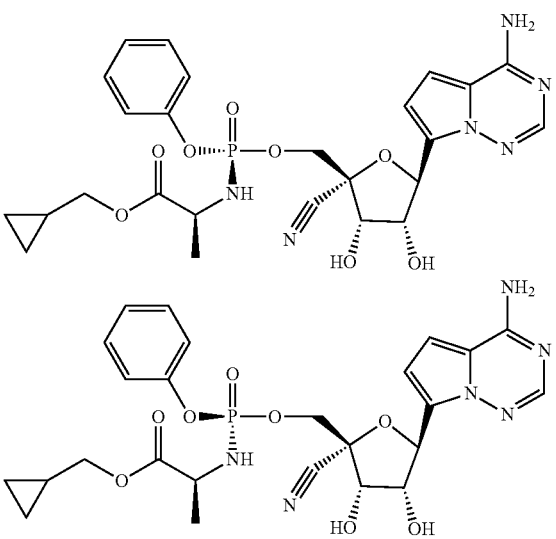

Example 9

First eluting diastereomer of Example 8: $^1$H NMR (400 MHz, Methanol-d4) δ 7.78 (s, 1H), 7.29 (dd, J=8.7, 7.1 Hz, 2H), 7.22-7.06 (m, 3H), 6.85 (d, J=4.5 Hz, 1H), 6.73 (d, J=4.5 Hz, 1H), 5.50 (d, J=5.0 Hz, 1H), 4.63 (t, J=5.3 Hz, 1H), 4.55-4.44 (m, 2H), 4.36 (dd, J=10.9, 5.1 Hz, 1H), 3.97-3.77 (m, 3H), 1.26 (dd, J=7.2, 1.2 Hz, 3H), 1.15-1.04 (m, 1H), 0.58-0.45 (m, 2H), 0.32-0.18 (m, 2H). $^{31}$P NMR (162 MHz, Methanol-d4) δ 3.30.

Example 10

Second eluting diastereomer of Example 8: $^1$H NMR (400 MHz, Methanol-d4) δ 7.80 (s, 1H), 7.38-7.26 (m, 2H), 7.29-7.11 (m, 3H), 6.84 (d, J=4.5 Hz, 1H), 6.73 (d, J=4.5 Hz, 1H), 5.49 (d, J=5.1 Hz, 1H), 4.62 (t, J=5.3 Hz, 1H), 4.47 (d, J=5.6 Hz, 1H), 4.42 (dd, J=10.9, 6.3 Hz, 1H), 4.34 (dd, J=10.9, 5.4 Hz, 1H), 3.98-3.82 (m, 2H), 3.78 (dd, J=11.4, 7.3 Hz, 1H), 1.27 (dd, J=7.2, 1.1 Hz, 3H), 1.11-0.98 (m, 1H), 0.52-0.45 (m, 2H), 0.25-0.14 (m, 2H). $^{31}$P NMR (162 MHz, Methanol-d4) δ 3.23.

Example 11. 2-(((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)amino)ethyl pivalate

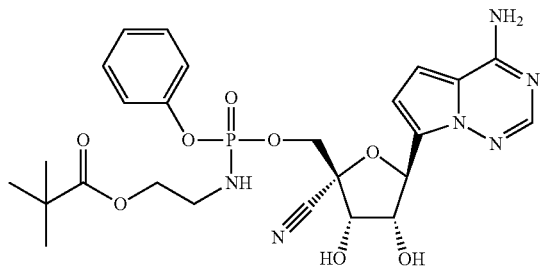 [SMILES: CC(C)(C)C(=O)OCCNP(=O)(OC[C@@]1(C#N)O[C@@H](c2ccc3c(N)ncnn23)[C@H](O)[C@@H]1O)Oc1ccccc1]

To a mixture of Intermediate 4 (22.0 mg, 0.066 mmol), Intermediate 21 (28.1 mg, 0.066 mmol), and magnesium chloride (6.3 mg, 0.166 mmol) was added acetonitrile (0.50 mL) at RT. The resulting suspension was warmed to 50° C., and was allowed to stir for 5 min. N,N-Diisopropylethylamine (0.03 mL, 0.066 mmol) was then added and the resulting mixture was stirred at 50° C. for 1 h. The reaction mixture was then allowed to cool to RT, and concentrated aqueous hydrochloric acid solution (12 M, 0.077 mL, 0.93 mmol) was added. After 1 h, the reaction mixture was diluted with saturated aqueous sodium carbonate solution (20 mL) and ethyl acetate (20 mL). The layers were split and the organic layer was washed with brine (20 mL), was dried over anhydrous sodium sulfate, and was concentrated under reduced pressure. The crude residue was purified by preparatory HPLC (Phenominex Synergi 4 u Hydro-RR 80 Å 150×30 mm column, 40-100% acetonitrile/water gradient) to afford the product. MS m/z=575.00 [M+H].

Separation of the (S) and (R) Diastereomers. The product was purified via chiral preparatory HPLC (Chiralpak IC, 150×4.6 mm, Heptane 80% Ethanol 20%) to afford the diastereomers:

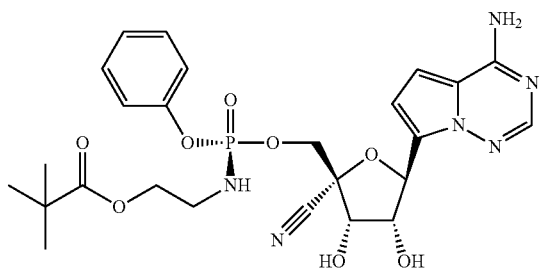

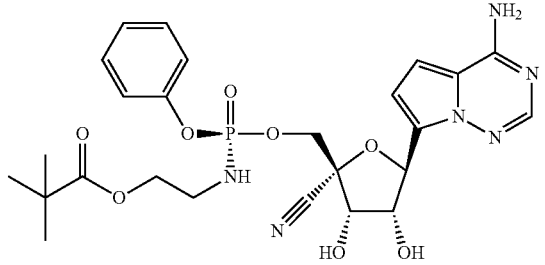

Example 12

First Eluting Diastereomer of Example 11: $^1$H NMR (400 MHz, CD$_3$OD) δ 7.80 (s, 1H), 7.33 (t, J=7.9 Hz, 2H), 7.27-7.13 (m, 3H), 6.84 (d, J=4.5 Hz, 1H), 6.74 (d, J=4.5 Hz, 1H), 5.50 (d, J=4.9 Hz, 1H), 4.63 (t, J=5.3 Hz, 1H), 4.47 (d, J=5.6 Hz, 1H), 4.45-4.29 (m, 2H), 3.96 (t, J=5.7 Hz, 2H), 3.14 (dt, J=11.8, 5.7 Hz, 2H), 1.12 (s, 9H). $^{31}$P NMR (162 MHz, CD$_3$OD) δ 5.24 (s). MS m/z=575.00 [M+H].

Example 13

Second Eluting Diastereomer of Example 11: $^1$H NMR (400 MHz, CD$_3$OD) δ 7.77 (s, 1H), 7.32-7.25 (m, 2H), 7.19-7.12 (m, 3H), 6.85 (d, J=4.5 Hz, 1H), 6.72 (d, J=4.5 Hz, 1H), 5.50 (d, J=4.9 Hz, 1H), 4.62 (t, J=5.2 Hz, 1H), 4.49 (d, J=5.5 Hz, 1H), 4.42 (dd, J=10.9, 6.1 Hz, 1H), 4.33 (dd, J=10.9, 5.5 Hz, 1H), 3.99 (d, J=5.3 Hz, 1H), 3.19-3.10 (m, 2H), 1.15 (s, 9H). $^{31}$P NMR (162 MHz, CD$_3$OD) δ 5.05 (br s). MS m/z=575.00 [M+H].

Example 14

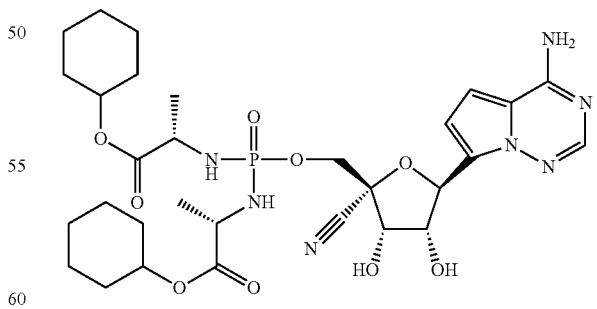

Intermediate 4 (50 mg, 0.15 mmol) and Intermediate 60 (95 mg, 0.18 mmol) were dissolved in anhydrous tetrahydrofuran (3 mL). Magnesium chloride (21 mg, 0.225 mmol) was added in one portion. Reaction was warmed to 50° C. and stirred for 30 mins. N,N-Diisopropylethylamine (65 µL, 0.375 mmol) was added, and the reaction was stirred for 16 hrs at 50° C. Reaction was cooled to room temperature, diluted with ethyl acetate (30 mL) and washed with 5% aqueous sodium carbonate solution (3×20 mL) and then brine (20 mL). Dried over anhydrous sodium sulfate and concentrated under reduced pressure. Residue was dissolved in acetonitrile (2 mL) and stirred in an ice bath. 12 M hydrochloric acid (300 μL) was added dropwise and stirred in an ice bath for 60 mins. Reaction was diluted with ethyl acetate (30 mL) and cooled in an ice bath. Saturated aqueous sodium bicarbonate solution was added dropwise to give pH of 16. Organic layer was collected, washed with brine (10 mL), dried over anhydrous sodium sulfate and concentrated under reduced pressure. The crude product was purified via SiO$_2$ column chromatography (4 g SiO$_2$ Combiflash HP Gold Column 0-3-8% methanol/dichloromethane). Fractions having the desired product were combined and concentrated under reduced pressure. Residue was dissolved in acetonitrile and water and freeze dried to give the product. $^1$H NMR (400 MHz, Methanol-d$_4$) δ 7.82 (s, 1H), 6.86 (d, J=4.5 Hz, 1H), 6.77 (d, J=4.5 Hz, 1H), 5.51 (d, J=4.8 Hz, 1H), 4.70 (m, 2H), 4.61 (dd, J=5.7, 4.9 Hz, 1H), 4.49 (d, J=5.7 Hz, 1H), 4.36-4.17 (m, 2H), 3.86 (m, 2H), 1.88-1.63 (m, 8H), 1.58-1.25 (m, 18H). $^{31}$P NMR (162 MHz, Methanol-d$_4$) δ 13.64. MS m/z=678.1 [M+1], 676.2 [M-1].

Example 15. (S)-1-methylpyrrolidin-3-yl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

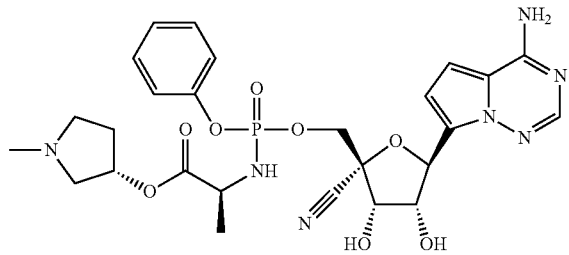 [SMILES: C[C@H](NP(=O)(OC[C@@]1(C#N)O[C@@H](c2ccc3c(N)ncnn23)[C@H](O)[C@@H]1O)Oc1ccccc1)C(=O)O[C@H]1CCN(C)C1]

Intermediate 4 (99 mg, 0.3 mmol) and Intermediate 23 (162 mg, 0.36 mmol) were mixed and dissolved in 2 mL of anhydrous THF. Magnesium chloride (86 mg, 0.9 mmol) was added in one portion. DIPEA (131 uL, 0.75 mmol) was added, and the reaction was stirred at 50° C. for 5 hrs.

Reaction was diluted with EtOAc (15 mL) and washed with water (4×15 mL) and then with brine (5 mL). Organic extract was dried over anhydrous sodium sulfate and concentrated under reduced pressure. The crude residue was purified via SiO$_2$ column chromatography (4 g SiO$_2$ Combiflash HP Gold Column, 0-5-10-20% methanol/DCM). Fractions having the desired product were combined and concentrated under reduced pressure. Residue was dissolved in MeCN (7 mL) and stirred in an ice bath. Concentrate aqueous hydrochloric acid (500 uL) was added dropwise. Reaction was stirred in an ice bath for 2 hrs. Reaction was diluted with EtOAc (30 mL) and added saturated aqueous sodium bicarbonate solution (30 mL). Mixture was stirred for 10 mins. Organic extract was collected and aqueous portion was extracted with EtOAc (2×10 mL). Organic extracts were combined, dried over anhydrous sodium sulfate and concentrated under reduced pressure. Residue was dissolved in MeCN and water and freeze-dried to give the product. $^1$H NMR (400 MHz, methanol-d$_4$) δ 7.79 (m, 1H), 7.39-7.26 (m, 2H), 7.26-7.10 (m, 3H), 6.84 (m, 1H), 6.73 (m, 1H), 5.49 (m, 1H), 5.18-4.98 (m, 1H), 4.62 (m, 1H), 4.55-4.28 (m, 3H), 3.89 (m, 1H), 2.78 (m, 1H), 2.69-2.54 (m, 2H), 2.32 (m, 4H), 2.23-2.08 (m, 1H), 1.78 (m, 1H), 1.27 (m, 3H). $^{31}$P NMR (162 MHz, methanol-d$_4$) δ 3.28, 3.14. LCMS: MS m/z=602.2 [M+1], 600.2 [M-1], t$_R$=0.99 min; LC system: Thermo Dionex Ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: t$_R$=1.84 min; HPLC system: Agilent 1100 series; Column: Phenomenex Gemini 5μ C18 110A, 50×4.6 mm; Solvent A: Water with 0.1% TFA, B: Acetonitrile with 0.1% TFA; Gradient: 2-98% B in 5 min at 2 mL/min. HPLC: t$_R$=3.868 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 16. trans-4-(trifluoromethyl)cyclohexyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

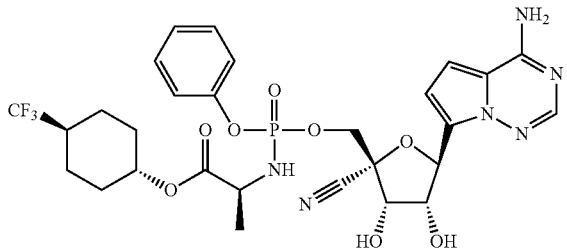

The product was obtained from Intermediate 27 (129 mg, 0.25 mmol) and Intermediate 4 (55 mg, 0.25 mmol) in a manner similar to that described for Example 3. $^1$H NMR (400 MHz, Methanol-d4) δ 7.78 (m, 1H), 7.32 (m, 2H), 7.25-7.12 (m, 3H), 6.84 (m, 1H), 6.73 (m, 1H), 5.50 (dd, J=5.1, 1.9 Hz, 1H), 4.69-4.49 (m, 2H), 4.49-4.32 (m, 3H), 3.93-3.75 (m, 1H), 2.23-1.71 (m, 5H), 1.44-1.20 (m, 7H). $^{31}$P NMR (162 MHz, Methanol-d4) δ 3.28, 3.22. $^{19}$F NMR (377 MHz, Methanol-d4) δ -75.31-75.40 (m). MS m/z=669 [M+H].

The product was separated by SFC using 30% ethanol (AD-H4.6×100 m column).

Example 17. trans-4-(trifluoromethyl)cyclohexyl ((R)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

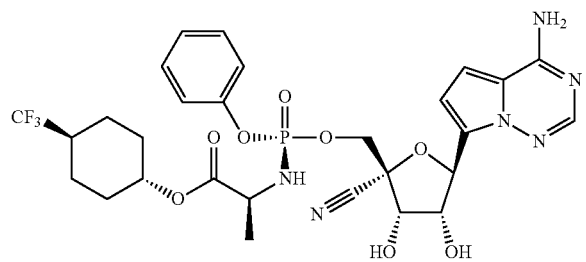

First eluting diastereomer of Example 16: $^1$H NMR (400 MHz, Methanol-d4) δ 7.78 (s, 1H), 7.29 (t, J=7.9 Hz, 2H), 7.21-7.10 (m, 3H), 6.85 (d, J=4.5 Hz, 1H), 6.73 (d, J=4.5 Hz, 1H), 5.50 (d, J=5.0 Hz, 1H), 4.62 (q, J=5.2 Hz, 2H), 4.52 (d, J=5.6 Hz, 1H), 4.47 (dd, J=10.9, 6.0 Hz, 1H), 4.35 (dd, J=10.9, 5.1 Hz, 1H), 3.83 (dq, J=9.1, 7.1 Hz, 1H), 2.10 (m, 1H), 1.96 (m, 4H), 1.38 (m, 4H), 1.23 (dd, J=7.1, 1.2 Hz, 3H). $^{31}$P NMR (162 MHz, Methanol-d4) δ 3.29. $^{19}$F NMR (377 MHz, Methanol-d4) δ -75.41 (d, J=8.6 Hz).

Example 18. trans-4-(trifluoromethyl)cyclohexyl ((S)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

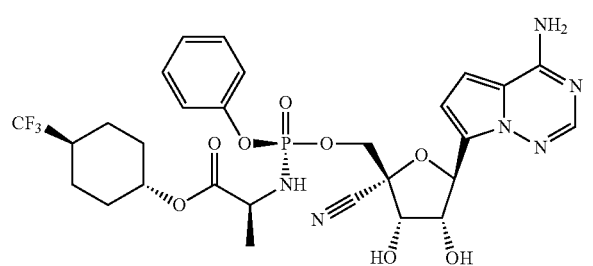

Second eluting diastereomer of Example 16: $^1$H NMR (400 MHz, Methanol-d4) δ 7.79 (s, 1H), 7.39-7.27 (m, 2H), 7.29-7.13 (m, 3H), 6.84 (d, J=4.5 Hz, 1H), 6.73 (d, J=4.5 Hz, 1H), 5.50 (d, J=5.0 Hz, 1H), 4.58 (m, 2H), 4.43 (m, 2H), 4.35 (dd, J=10.9, 5.5 Hz, 1H), 3.86 (dq, J=9.9, 7.4 Hz, 1H), 2.14-1.81 (m, 5H), 1.32 (m, 4H), 1.24 (dd, J=7.1, 1.0 Hz, 3H). $^{31}$P NMR (162 MHz, Methanol-d4) δ 3.22. $^{19}$F NMR (377 MHz, Methanol-d4) δ -75.33 (d, J=8.5 Hz).

The product was also obtained from Intermediate 29 (701 mg, 1.36 mmol) and Intermediate 4 (300 mg, 0.91 mmol) in a manner similar to that described for Example 3.

Example 19. 1-methylpiperidin-4-yl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

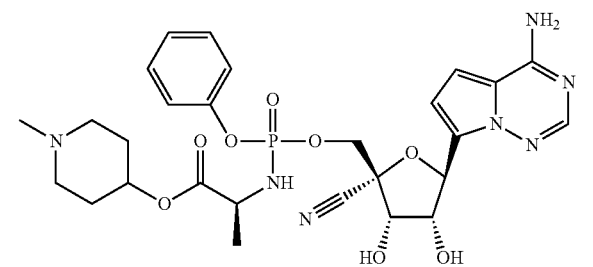 [SMILES: C[C@H](NP(=O)(OC[C@@]1(C#N)O[C@@H](c2ccc3c(N)ncnn23)[C@H](O)[C@@H]1O)Oc1ccccc1)C(=O)OC1CCN(C)CC1]

To a mixture of Intermediate 4 (70 mg, 0.211 mmol), Intermediate 30 (293 mg, 0.317 mmol), and MgCl$_2$ (30 mg, 0.317 mmol) in THF (3 mL) was added N,N-diisopropylethylamine (0.09 mL, 0.528 mmol) dropwise at room temperature. The resulting mixture was stirred at 50° C. for 2 h, purified by preparative HPLC (Phenomenex Gemini-NX 10µ C18 110° A 250×30 mm column, 0%-100% acetonitrile/water gradient in 25 min run) to give an acetonide intermediate, which was dissolved in acetonitrile (3 mL) and c-HCl (0.5 mL) was added. The resulting mixture was stirred for 2 h, concentrated in vacuo, and lyophilized to afford the product. $^1$H NMR (400 MHz, Methanol-d4) δ 7.85 (m, 1H), 7.41-7.12 (m, 5H), 6.97 (m, 1H), 6.79 (m, 1H), 5.51 (m, 1H), 5.04 (m, 1H), 4.62 (m, 1H), 4.53-4.31 (m, 3H), 3.98 (m, 1H), 3.66 (m, 5H), 2.82 (m, 2H), 2.10 (m, 4H), 1.30 (m, 3H). $^{31}$P NMR (162 MHz, Methanol-d4) δ 3.32, 3.10. LCMS: MS m/z=616.24 [M+1-HCl]; t$_R$=0.54 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min.

Example 20. (tetrahydro-2H-pyran-4-yl)methyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy) phosphoryl)-L-alaninate

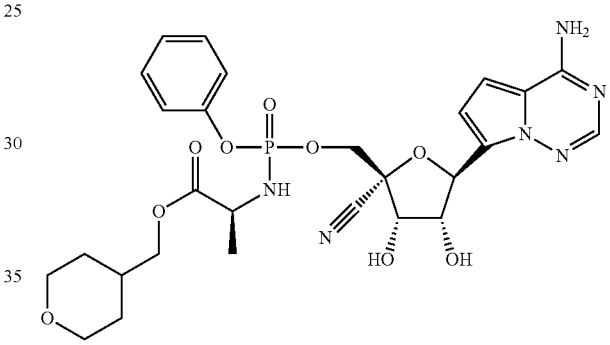

Intermediate 4 (50 mg, 0.15 mmol) and Intermediate 31 (84 mg, 0.18 mmol) were mixed and dissolved in anhydrous THF (5 mL). Magnesium chloride (86 mg, 0.906 mmol) was added in one portion and the reaction was stirred at 50° C. for 10 mins. DIPEA (158 uL, 0.906 mmol) was added and the reaction was stirred at 50° C. for 2 hrs. More magnesium chloride (50 mg) was added and stirred at 50° C. for 16 hrs. Reaction was diluted with EtOAc (20 mL) and washed with water (5×20 mL) and with brine (10 mL). Organic layer was dried over anhydrous sodium sulfate and concentrated under reduced pressure which was then dissolved in MeCN (5 mL). 12 M HCl (aq) (300 uL) was added dropwise. Reaction was stirred for 1 hr. Reaction was diluted with EtOAc (25 mL) and washed with saturated aqueous sodium bicarbonate solution (10 mL) and then with brine (10 mL). Organic layer was dried over anhydrous sodium sulfate and concentrated under reduced pressure. The crude residue was purified via SiO$_2$ column chromatography (4 g SiO$_2$ Combiflash HP Gold Column, 0-10% methanol/DCM). Fractions containing the desired product were combined and concentrated under reduced pressure to give oil which was then dissolved in MeCN and water and freeze-dried to afford the product. $^1$H NMR (400 MHz, Methanol-d4) δ 7.79 (m, 1H), 7.41-7.07 (m, 5H), 6.84 (m, 1H), 6.73 (m, 1H), 5.57-5.40 (m, 1H), 4.62 (m, 1H), 4.56-4.28 (m, 3H), 3.87 (m, 5H), 3.31 (m, 2H), 1.94-1.72 (m, 1H), 1.63-1.46 (m, 2H), 1.34-1.16

(m, 5H). $^{31}$P NMR (162 MHz, Methanol-d4) δ 3.23 (s), 3.19 (s). MS m/z=617.1 [M+1]; 615.0 [M−1].

Example 21. trans-4-(tert-butyl)cyclohexyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

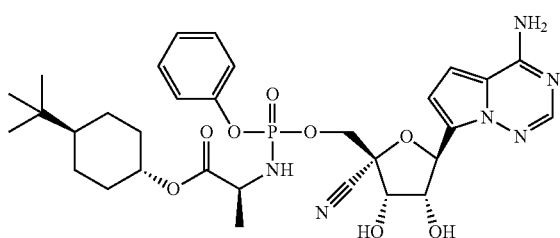 [SMILES: C[C@H](NP(=O)(OC[C@@]1(C#N)O[C@@H](c2ccc3c(N)ncnn23)[C@H](O)[C@@H]1O)Oc1ccccc1)C(=O)O[C@H]1CC[C@H](C(C)(C)C)CC1]

The product was obtained from Intermediate 32 (116 mg, 0.23 mmol) and Intermediate 4 (51 mg, 0.15 mmol) in a manner similar to that described for Example 3. $^{1}$H NMR (400 MHz, Methanol-d4) δ 7.79 (m, 1H), 7.32 (m, 2H), 7.25-7.18 (m, 2H), 7.19-7.10 (m, 1H), 6.85 (m, 1H), 6.76-6.69 (m, 1H), 5.51 (m, 1H), 4.65-4.57 (m, 1H), 4.51 (m, 1H), 4.47-4.39 (m, 2H), 4.35 (m, 1H), 3.93-3.76 (m, 1H), 1.93 (m, 2H), 1.74 (m, 2H), 1.24 (m, 5H), 1.13-0.89 (m, 3H), 0.84 (m, 9H). $^{31}$P NMR (162 MHz, Methanol-d4) δ 3.35, 3.28. MS m/z=657 [M+H].

The mixture was separated by Chiralpak SFC (Chiralpak ID 21×250 mm column, 30% methanol).

Example 22. trans-4-(tert-butyl)cyclohexyl ((S)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

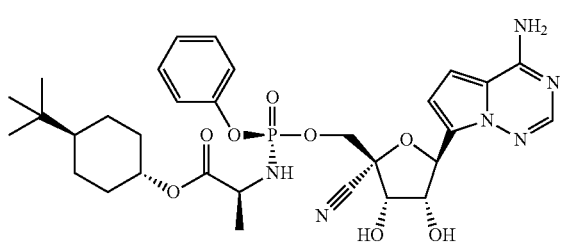 [SMILES: C[C@H](N[P@](=O)(OC[C@@]1(C#N)O[C@@H](c2ccc3c(N)ncnn23)[C@H](O)[C@@H]1O)Oc1ccccc1)C(=O)O[C@H]1CC[C@H](C(C)(C)C)CC1]

First eluting diastereomer of Example 21. $^{1}$H NMR (400 MHz, Methanol-d4) δ 7.80 (s, 1H), 7.33 (t, J=7.8 Hz, 2H), 7.26-7.12 (m, 3H), 6.85 (d, J=4.5 Hz, 1H), 6.74 (d, J=4.5 Hz, 1H), 5.51 (d, J=4.9 Hz, 1H), 4.59 (t, J=5.3 Hz, 1H), 4.51 (tt, J=11.3, 4.5 Hz, 1H), 4.46-4.39 (m, 2H), 4.35 (dd, J=10.9, 5.6 Hz, 1H), 3.89-3.81 (m, 1H), 1.99-1.86 (m, 2H), 1.75 (t, J=12.0 Hz, 2H), 1.31-1.18 (m, 5H), 1.12-0.89 (m, 3H), 0.83 (s, 9H). $^{31}$P NMR (162 MHz, Methanol-d4) δ 3.25.

Example 23. trans-4-(tert-butyl)cyclohexyl ((R)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

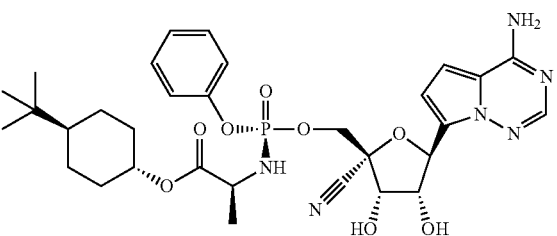 [SMILES: C[C@H](N[P@@](=O)(OC[C@@]1(C#N)O[C@@H](c2ccc3c(N)ncnn23)[C@H](O)[C@@H]1O)Oc1ccccc1)C(=O)O[C@H]1CC[C@H](C(C)(C)C)CC1]

Second eluting diastereomer of Example 21. $^{1}$H NMR (400 MHz, Methanol-d4) δ 7.78 (s, 1H), 7.29 (t, J=7.8 Hz, 2H), 7.18-7.11 (m, 3H), 6.85 (d, J=4.5 Hz, 1H), 6.73 (d, J=4.5 Hz, 1H), 5.51 (d, J=5.0 Hz, 1H), 4.62 (t, J=5.3 Hz, 1H), 4.59-4.43 (m, 3H), 4.36 (dd, J=10.9, 5.2 Hz, 1H), 3.82 (q, J=7.9 Hz, 1H), 1.94 (m, 2H), 1.79 (m, 2H), 1.36-1.20 (m, 5H), 1.13-0.94 (m, 3H), 0.85 (s, 9H). $^{31}$P NMR (162 MHz, Methanol-d4) δ 3.32.

Example 24. 2-ethylbutyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(benzyloxy)phosphoryl)-L-alaninate

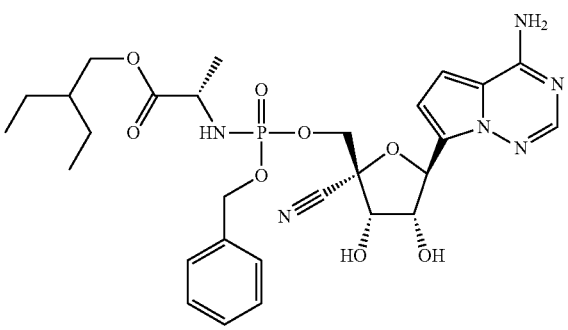 [SMILES: CCC(CC)COC(=O)[C@H](C)NP(=O)(OCc1ccccc1)OC[C@@]1(C#N)O[C@@H](c2ccc3c(N)ncnn23)[C@H](O)[C@@H]1O]

Acetonitrile (2.5 mL) was added to a mixture of Intermediate 4 (200 mg, 0.604 mmol), Intermediate 16 (280 mg, 0.604 mmol), and magnesium chloride (57 mg, 0.60 mmol) at RT. The mixture was heated to 50° C. for 5 min, and N,N-diisopropylethylamine (0.263 mL, 0.604 mmol) was added. After 22 h, the reaction mixture was allowed to cool to RT, and concentrated aqueous hydrochloric acid solution (0.5 mL) was added dropwise. After 1 h, the reaction mixture was diluted with ethyl acetate (100 mL) and the resulting mixture was washed with saturated aqueous sodium carbonate solution (50 mL) and brine (50 mL). The organic layer was dried over anhydrous sodium sulfate and concentrated under reduced pressure. The crude residue was subjected to silica gel chromatography eluting with 0-100% ethyl acetate in hexanes to afford the product. $^{1}$H NMR (400 MHz, methanol-d$_4$) δ 7.78 (s, 0.6H), 7.75 (s, 0.4H), 7.40-7.26 (m, 5H), 6.85-6.80 (m, 1H), 6.75-6.69 (m, 1H), 5.54-5.48 (m, 2H), 5.06 (d, J=7.5 Hz, 1.2H), 4.99 (d, J=7.3 Hz, 0.8H), 4.64-4.58 (m, 1H), 4.52-4.46 (m, 1H), 4.41-4.20 (m, 2H), 4.07-3.77 (m, 2H), 1.54-1.21 (m, 8H), 0.95-0.77 (m, 6H) $^{31}$P NMR (162 MHz, methanol-d$_4$) δ 7.90 (s), 7.82 (s). LCMS: MS m/z=617.14 [M+1], t$_R$=1.26 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: t$_R$=3.057 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 25. 2-ethylbutyl ((S)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)alaninate

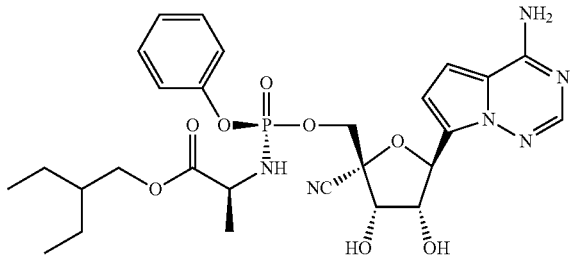 [SMILES: CCC(CC)COC(=O)[C@H](C)N[P@](=O)(OC[C@@]1(C#N)O[C@@H](c2ccc3c(N)ncnn23)[C@H](O)[C@@H]1O)Oc1ccccc1]

To a mixture of Intermediate 4 (700 mg, 2.113 mmol), Intermediate 17 (998 mg, 2.218 mmol), and magnesium chloride (302 mg, 3.169 mmol) was added tetrahydrofuran (8.5 mL) at room temperature followed by the addition of N,N-Diisopropylethylamine (0.92 mL, 5.282 mmol). The resulting mixture was stirred at 50° C. for 3 h. The reaction mixture was then concentrated under reduced pressure and the residue obtained was diluted with saturated sodium chloride solution and dichloromethane. The layers were split and the organic layer was dried over anhydrous sodium sulfate, filtered and was concentrated under reduced pressure. The crude residue was purified via SiO$_2$ column chromatography (80 g SiO$_2$ Combiflash HP Gold Column, 100% Dichloromethane-14% Methanol in dichloromethane as eluent). Pure material obtained was dissolved in an anhydrous acetonitrile (10 mL) and was cooled in an ice bath followed by the dropwise addition of concentrated hydrochloric acid (4 mL, 48 mmol). The reaction mixture was stirred at room temperature for 1 h. After 1 h the reaction mixture was cooled in an ice bath and was diluted with water. Neutralized the solution with 3 N sodium hydroxide and extracted with dichloromethane. Organic layer was separated, dried over sodium sulfate, filtered and concentrated. The residue obtained was purified by SiO$_2$ column chromatography (40 g SiO$_2$ Combiflash HP Gold Column, 100% Dichloromethane-20% Methanol in dichloromethane) to afford the product. $^1$H NMR (400 MHz, Methanol-d4) δ 7.80 (s, 1H), 7.38-7.29 (m, 2H), 7.27-7.13 (m, 3H), 6.84 (d, J=4.5 Hz, 1H), 6.74 (d, J=4.5 Hz, 1H), 5.49 (d, J=5.0 Hz, 1H), 4.61 (t, J=5.3 Hz, 1H), 4.49-4.29 (m, 3H), 4.04-3.82 (m, 3H), 1.43 (dq, J=12.5, 6.1 Hz, 1H), 1.37-1.23 (m, 7H), 0.84 (td, J=7.5, 1.1 Hz, 6H). $^{31}$P NMR (162 MHz, Acetonitrile-d3) δ 2.73. MS m/z=603 [M+1].

Example 26. ((1r, 4S)-4-(trifluoromethyl)cyclohexyl)methyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)alaninate

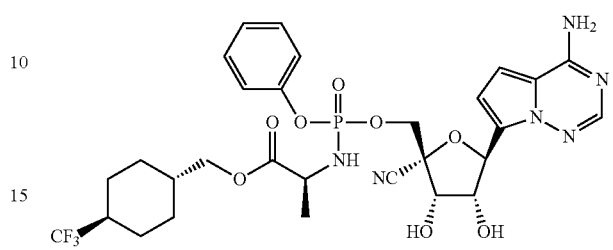

To a mixture of Intermediate 4 (0.06 g, 0.181 mmol), Intermediate 33 (0.115 g, 0.217 mmol), and magnesium chloride (0.028 g, 0.29 mmol) was added tetrahydrofuran (1.5 mL) at room temperature followed by the addition of N,N-Diisopropylethylamine (0.079 mL, 0.453 mmol). The resulting mixture was stirred at 50° C. for 3 h. The reaction mixture was then concentrated under reduced pressure and the residue obtained was diluted with saturated sodium chloride solution and dichloromethane. The layers were split and the organic layer was dried over anhydrous sodium sulfate, filtered and was concentrated under reduced pressure. The crude residue was purified via SiO$_2$ column chromatography (40 g SiO$_2$ Combiflash HP Gold Column, 100% Dichloromethane-14% Methanol in dichloromethane as eluent). Pure material obtained was dissolved in an anhydrous acetonitrile (2 mL) and was cooled in an ice bath followed by the dropwise addition of concentrated hydrochloric acid (0.1 mL, 1.2 mmol). The reaction mixture was stirred at room temperature for 1 h. After 1 h the reaction mixture was cooled in an ice bath and was diluted with saturated sodium bicarbonate solution (1 mL). The resulting mixture was purified by preparative HPLC (Phenominex Synergi 4 u Hydro-RR 80 Å 150×30 mm column, 15%-85% acetonitrile/water gradient in 30 min run) to afford the product. $^1$H NMR (400 MHz, Acetonitrile-d3) δ 7.82 (d, J=3.1 Hz, 1H), 7.40-7.10 (m, 5H), 6.81-6.67 (m, 2H), 6.54 (s, 2H), 5.50 (t, J=5.0 Hz, 1H), 4.72-4.26 (m, 6H), 4.05-3.69 (m, 3H), 2.17-1.93 (m, 1H), 1.88 (dt, J=13.3, 3.6 Hz, 2H), 1.82-1.69 (m, 2H), 1.55 (dtq, J=12.0, 5.8, 3.0 Hz, 1H), 1.33-1.14 (m, 5H), 1.10-0.86 (m, 2H). $^{31}$P NMR (162 MHz, Acetonitrile-d3) δ 2.77, −2.68. $^{19}$F NMR (376 MHz, Acetonitrile-d3) δ −74.72 (d, J=8.7 Hz). MS m/z=683.20 [M+1].

Separation of the (S) and (R) Diastereomers. The product was purified via chiral preparatory HPLC (AD-H 5 um 21×250 mm, Heptane 70%, Ethanol 30%) to afford the diastereomers:

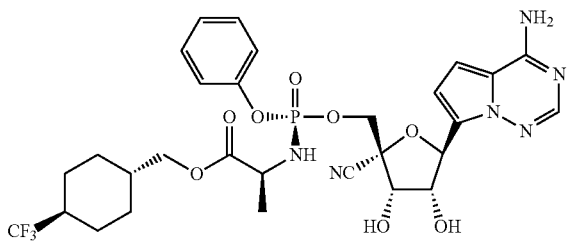 [SMILES: C[C@H](NP(=O)(OC[C@@]1(C#N)O[C@@H](c2ccc3c(N)ncnn23)[C@H](O)[C@@H]1O)Oc1ccccc1)C(=O)OC[C@H]1CC[C@H](C(F)(F)F)CC1]

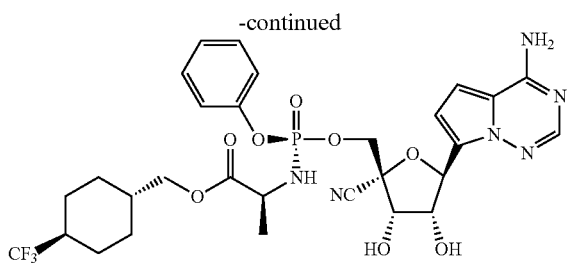

Example 27

First Eluting Diastereomer of Example 26: ¹H NMR (400 MHz, Acetonitrile-d3) δ 7.88 (s, 1H), 7.35 (t, J=7.8 Hz, 2H), 7.25-7.15 (m, 3H), 6.79-6.71 (m, 2H), 6.23 (s, 2H), 5.48 (d, J=4.9 Hz, 1H), 4.66-4.55 (m, 1H), 4.50 (t, J=6.0 Hz, 1H), 4.43 (dd, J=11.1, 6.5 Hz, 1H), 4.37-4.17 (m, 3H), 4.07-3.83 (m, 4H), 1.93 (d, J=13.5 Hz, 2H), 1.81 (d, J=13.5 Hz, 2H), 1.62 (d, J=6.2 Hz, 1H), 1.40-1.20 (m, 6H), 1.03 (q, J=12.9 Hz, 2H). ¹⁹F NMR (376 MHz, Acetonitrile-d3) δ −74.83 (d, J=8.8 Hz). ³¹P NMR (162 MHz, Acetonitrile-d3) δ 2.59. MS m/z=683.20 [M+1].

Example 28

Second Eluting Diastereomer of Example 26: ¹H NMR (400 MHz, Acetonitrile-d3) δ 7.89 (s, 1H), 7.37 (t, J=7.8 Hz, 2H), 7.31-7.14 (m, 3H), 6.75 (s, 2H), 6.24 (s, 2H), 5.47 (d, J=4.9 Hz, 1H), 4.58 (q, J=5.1 Hz, 1H), 4.48 (t, J=6.0 Hz, 1H), 4.43-4.20 (m, 4H), 4.05-3.73 (m, 4H), 1.91 (d, J=13.2 Hz, 2H), 1.78 (d, J=13.0 Hz, 2H), 1.65-1.47 (m, 1H), 1.39-1.19 (m, 6H), 1.01 (t, J=13.0 Hz, 2H). ¹⁹F NMR (376 MHz, Acetonitrile-d3) δ −74.83 (d, J=8.8 Hz). ³¹P NMR (162 MHz, Acetonitrile-d3) a 2.67. MS m/z=683.20 [M+1].

Example 29. Ethyl ((S)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

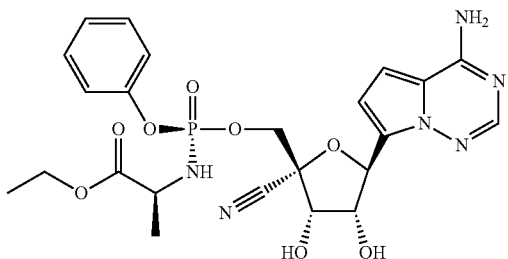 [SMILES: CCOC(=O)[C@H](C)N[P@](=O)(OC[C@@]1(C#N)O[C@@H](c2ccc3c(N)ncnn23)[C@H](O)[C@@H]1O)Oc1ccccc1]

To a mixture of Intermediate 4 (150 mg, 0.45 mmol), Intermediate 34 (298 mg, 0.68 mmol), and MgCl₂ (65 mg, 0.68 mmol) in THF (6 mL) was added N,N-diisopropylethylamine (0.20 mL, 1.13 mmol) dropwise. The resulting mixture was stirred at 50° C. for 2 h, cooled, diluted with EtOAc (150 mL), washed with brine (50 mL×2), dried, concentrated in vacuo, redissolved in acetonitrile (6 mL), and c-HCL (0.3 mL) added in ice bath. The resulting mixture was stirred for 1 h in ice bath and 1 h at room temperature, treated with saturated NaHCO₃ (2 mL), purified by HPLC (Phenomenex Gemini-NX 10μ C18 110°A 250×30 mm column, 5-70% acetonitrile/water gradient in 25 min run) to afford the product. ¹H NMR (400 MHz, Methanol-d4) δ 7.80 (s, 1H), 7.31 (d, J=7.7 Hz, 2H), 7.25-7.14 (m, 3H), 6.84 (d, J=4.5 Hz, 1H), 6.73 (d, J=4.6 Hz, 1H), 5.49 (d, J=5.1 Hz, 1H), 4.62 (t, J=5.3 Hz, 1H), 4.46 (d, J=5.6 Hz, 1H), 4.40 (dd, J=10.9, 6.2 Hz, 1H), 4.33 (dd, J=10.9, 5.4 Hz, 1H), 4.11-3.98 (m, 2H), 3.87 (dd, J=9.9, 7.1 Hz, 1H), 1.25 (dd, J=7.1, 1.0 Hz, 3H), 1.16 (t, J=7.1 Hz, 3H). ³¹P NMR (162 MHz, Methanol-d4) δ 3.26. LCMS: MS m/z=547.12 [M+1]; t_R=0.76 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t_R=4.03 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 30. cyclohexyl ((((2R,3S,4R,5S)-5-(4-aminopyrrolo[2,1-f][1,2,4] triazin-7-yl)-2-cyano-3,4-dihydroxytetrahydrofuran-2-yl)methoxy)(((S)-1-(2-ethylbutoxy)-1-oxopropan-2-yl)amino)phosphoryl)-L-alaninate

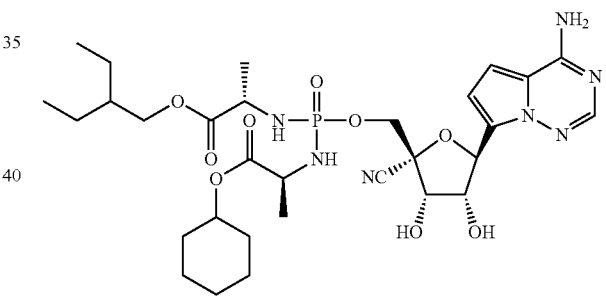

To a mixture of Intermediate 4 (65 mg, 0.196 mmol), Intermediate 59 (124 mg, 0.235 mmol), and MgCl₂ (40 mg, 0.42 mmol) in THF (2 mL) was added N,N-diisopropylethylamine (0.085 mL, 0.490 mmol) dropwise. The resulting mixture was stirred at about 50° C. for about 2 h, cooled, purified by preparative HPLC (Phenomenex Gemini-NX 10μ C18 110° A 250×30 mm column, 0%-100% acetonitrile/water gradient in 25 min run) to give an acetonide intermediate, which was dissolved in acetonitrile (2 mL) and c-HCl (0.1 mL) was added under icebath. The resulting mixture was then stirred under ice-bath for about 2 h and saturated NaHCO₃ (2 mL) added slowly. The resulting mixture was then purified by preparative HPLC (Phenomenex Gemini-NX 10μ C18 110° A 250×30 mm column, 0%-80% acetonitrile/water gradient in 25 min run) to afford the product. ¹H NMR (400 MHz, Acetonitrile-d3) δ 7.86 (s, 1H), 6.81-6.67 (m, 2H), 6.48 (s, 2H), 5.53-5.44 (m, 2H), 4.71 (m, 1H), 4.58 (m, 1H), 4.50 (m, 1H), 4.29 (m, 1H), 4.18 (m, 1H), 4.13-3.69 (m, 7H), 1.72 (m, 4H), 1.58-1.19 (m, 17H), 0.88 (m, 6H). ³¹P NMR (162 MHz, Acetonitrile-d3) δ 12.68, 12.66. LCMS: MS m/z=680.31 [M+1].

Example 31. (1-(2,2,2-trifluoroethyl)piperidin-4-yl) methyl ((((2R,3S,4R,5S)-5-(4-aminopyrrolo[2,1-f][1,2,4]triazin-7-yl)-2-cyano3,4-dihydroxytetrahydrofuran-2-yl)methoxy)(phenoxy)phosphoryl)alaninate

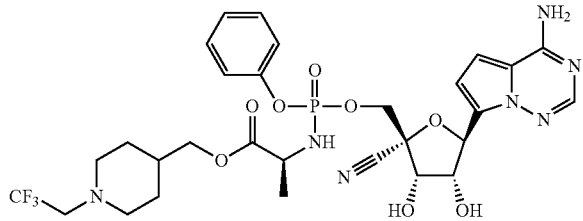 [SMILES: C[C@H](NP(=O)(OC[C@@]1(C#N)O[C@@H](c2ccc3c(N)ncnn23)[C@H](O)[C@@H]1O)Oc1ccccc1)C(=O)OCC1CCN(CC(F)(F)F)CC1]

To a mixture of Intermediate 4 (0.5 g, 1.509 mmol), Intermediate 36 (0.905 g, 1.66 mmol), and magnesium chloride (0.206 g, 2.264 mmol) was added tetrahydrofuran (7 mL) followed by the addition of N,N-Diisopropylethylamine (0.657 mL, 3.773 mmol) and the resulting mixture was stirred at 50° C. for 3 h. The reaction mixture was then concentrated under reduced pressure and the residue obtained was diluted with acetonitrile (11 mL) and cooled to 0° C. Concentrated hydrochloric acid (1 mL, 12 mmol) was added and the reaction mixture was stirred at room temperature for 2 h. After 2 h, the reaction mixture was cooled in an ice bath and was neutralized with 5 N aqueous sodium hydroxide solution. The resulting mixture was extracted with ethyl acetate. Organic layer was separated, dried over sodium sulfate, filtered and concentrated. The crude residue was purified via $SiO_2$ column chromatography (80 g $SiO_2$ Combiflash HP Gold Column, 100% Dichloromethane-20% Methanol in dichloromethane) to afford the product. $^1$H NMR (400 MHz, methanol-$d_4$) δ 7.79 (d, J=8.8 Hz, 1H), 7.38-7.12 (m, 5H), 6.85 (dd, J=4.5, 1.8 Hz, 1H), 6.74 (dd, J=4.5, 3.2 Hz, 1H), 5.49 (t, J=5.2 Hz, 1H), 4.63 (q, J=5.5 Hz, 1H), 4.55-4.30 (m, 3H), 3.98-3.86 (m, 3H), 3.91-3.76 (m, 2H), 3.07-2.86 (m, 4H), 2.32-2.17 (m, 2H), 1.61 (t, J=12.5 Hz, 4H), 1.26 (ddd, J=7.1, 3.5, 1.1 Hz, 4H). $^{19}$F NMR (377 MHz, methanol-$d_4$) δ -71.22 (td, J=9.8, 4.6 Hz). $^{31}$P NMR (162 MHz, methanol-$d_4$) δ 3.23, 3.18. LCMS: MS m/z=349.86 [M+1]; $t_R$=0.70 min (minor isomer)-0.72 min (major isomer); LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=3.525 min (minor isomer), 3.56 min (major isomer); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 32. 1-ethyl-3,3-difluoropiperidin-4-yl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

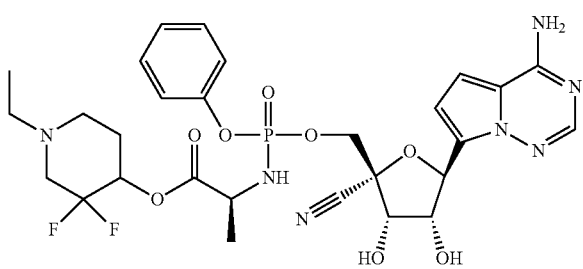 [SMILES: CCN1CCC(OC(=O)[C@H](C)NP(=O)(OC[C@@]2(C#N)O[C@@H](c3ccc4c(N)ncnn34)[C@H](O)[C@@H]2O)Oc2ccccc2)C(F)(F)C1]

To a mixture of Intermediate 4 (50 mg, 0.151 mmol), Intermediate 37 (116 mg, 0.226 mmol), and $MgCl_2$ (22 mg, 0.226 mmol) in THF (2 mL) was added N,N-diisopropylethylamine (0.1 mL, 0.574 mmol) was added dropwise. The resulting mixture was stirred at 50° C. for 2 h, cooled, purified by prep HPLC (Phenomenex Gemini-NX 10μ C18 110° A 250×30 mm column, 0%-100% acetonitrile/water gradient in 25 min run) to give an acetonide intermediate, which was dissolved in ACN (2 mL) and added c-HCl (0.1 mL). The resulting mixture was stirred at room temperature for 1 h, neutralized with 5 N NaOH, and purified by preparative HPLC (Phenominex Gemini 10 u C18 110 Å 250×21.2 mm column, 20-65% acetonitrile (0.1% TFA)/water (0.1% TFA) gradient). Upon concentration, the residue was dissolved in EtOAc and washed with sat $NaHCO_3$ solution, concentrated in vacuo, redissolved in DCM and a drop of c-HCl added, which resulted in white precipitation. After concentration, the residue was dissolved in water-acetonitrile, and lyophilized to afford the product. $^1$H NMR (400 MHz, Methanol-d4) δ 7.91 (m, 1H), 7.40-7.10 (m, 6H), 6.86 (m, 1H), 5.55-5.47 (m, 1H), 5.30 (m, 1H), 4.57 (m, 1H), 4.49-4.30 (m, 3H), 4.06 (m, 1H), 3.68 (m, 2H), 3.32-3.09 (m, 2H), 2.19 (s, 2H), 1.40-1.23 (m, 8H). $^{31}$P NMR (162 MHz, Methanol-d4) δ 3.19, 3.01, 2.97, 2.96. $^{19}$F NMR (376 MHz, Methanol-$d_4$) δ -77.5. LCMS: MS m/z=666.23 [M+1] as neutral form; $t_R$=0.68 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.35, 3.37, 3.38, 3.41 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 33. (1r,4S)-4-aminocyclohexyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

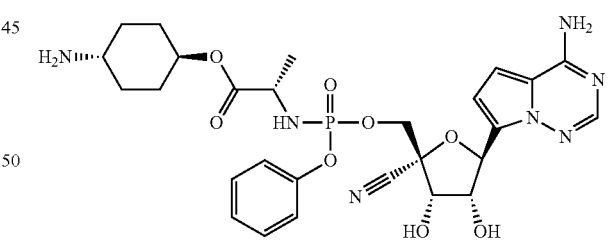

(1r,4S)-4-((tert-butoxycarbonyl)amino)cyclohexyl ((((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methoxy)(phenoxy)phosphoryl)-L-alaninate.
Acetonitrile (4.5 mL) was added to a mixture of Intermediate 4 (300 mg, 0.91 mmol), Intermediate 63 (510 mg, 0.91 mmol), and magnesium chloride (86 mg, 0.91 mmol) at RT. The mixture was heated to 50° C. for 20 min, and N,N-diisopropylethylamine (0.39 mL, 2.26 mmol) was added. After 3.5 h, the reaction mixture was allowed to cool to RT, and the reaction mixture was diluted with ethyl acetate (200 mL) and the resulting mixture was washed with saturated aqueous sodium carbonate solution (200 mL) and brine (200 mL). The organic layer was dried over anhydrous sodium sulfate and concentrated under reduced pressure. The crude residue was subjected to silica gel chromatography eluting with 0-10% methanol in dichloromethane to afford the product. $^1$H NMR (400 MHz, chloroform-d$_1$) δ 7.92 (s, 0.25H), 7.91 (s, 0.75H), 7.35-7.08 (m, 5H), 6.71-6.68 (m, 1H), 6.66-6.62 (m, 1H), 5.92 (br s, 2H), 5.65-5.60 (m, 1H), 5.27-5.22 (m, 1H), 5.10 (d, J=6.7 Hz, 0.25H), 5.00 (d, J=6.6 Hz, 0.75H), 4.69-4.57 (m, 1H), 4.51-4.27 (m, 3H), 4.06-3.92 (m, 1H), 3.86-3.74 (m, 1H), 3.41 (br s, 1H), 2.03-1.84 (m, 4H), 1.76 (br s, 3H), 1.44 (br s, 9H), 1.41-1.29 (m, 8H), 1.24-1.12 (m, 2H). $^{31}$P NMR (162 MHz, chloroform-d$_1$) δ −3.15 (s). LCMS: MS m/z=756.11 [M+1].

(1r,4S)-4-aminocyclohexyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate. Concentrated hydrochloric acid solution (12 M, 0.47 mL) was added to a solution of (1r,4S)-4-((tert-butoxycarbonyl)amino)cyclohexyl ((((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methoxy)(phenoxy)phosphoryl)-L-alaninate (470 mg, 0.62 mmol) in acetonitrile (4.7 mL) at RT. After 1 h, the reaction mixture was diluted with ethyl acetate (20 mL) and neutralized to pH=7 with saturated aqueous sodium carbonate solution. The resulting mixture was concentrated under reduced pressure, and methanol (4 mL) was added to the residue. Ethyl acetate (2 mL) was then added and the resulting solids were removed by filtration. The filtrate was concentrated under reduced pressure and the crude residue was purified by preparatory HPLC (Gemini 5 u C18 100 Å 100×30 mm column, 10-100% acetonitrile/water gradient 0.1% TFA) to afford the product. $^1$H NMR (400 MHz, methanol-d4) δ 8.03 (s, 0.75H), 7.99 (s, 0.25H), 7.42-7.12 (m, 6H), 6.96-6.92 (m, 1H), 5.57-5.51 (m, 1H), 4.74-4.60 (m, 1H), 4.56-4.49 (m, 1H), 4.49-4.34 (m, 3H), 3.96-3.84 (m, 1H), 3.18-3.04 (m, 1H), 2.12-1.99 (m, 4H), 1.57-1.42 (m, 4H), 1.33-1.28 (m, 3H). $^{31}$P NMR (162 MHz, methanol-d$_4$) δ 3.36 (s), 3.24 (s). LCMS: MS m/z=616.07 [M+1].

Example 34

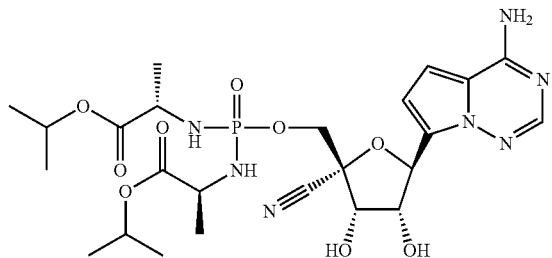 [SMILES: CC(C)OC(=O)[C@H](C)NP(=O)(N[C@@H](C)C(=O)OC(C)C)OC[C@@]1(C#N)O[C@@H](c2ccc3c(N)ncnn23)[C@H](O)[C@@H]1O]

To a mixture of Intermediate 61 (161 mg, 0.36 mmol), Intermediate 4 (100 mg, 0.3 mmol), and MgCl$_2$ (43 mg, 0.45 mmol) in THF (2 mL) was added N,N-diisopropylethylamine (98 mg, 0.76 mmol) dropwise. The resulting mixture was stirred at about 50° C. for about 2 h, reaction mixture was cooled, diluted with EtOAc, washed with water and brine, the organic solvent was evaporated under vacuum, the residue was then dissolved in acetonitrile (2 mL), cooled in ice bath, and con. HCl was added dropwise. The resulting mixture was stirred at about room temperature for about 2 h, cooled in ice bath, neutralized by dropwise addition of 2 N NaOH and NaHCO$_3$ solution, diluted with EtOAc (150 mL), washed with water (50 mL) and brine (50 mL). The aqueous phase was extracted with EtOAc (50 mL×2) and the combined organic layers were dried under sodium sulfate, concentrated in vacuum, and residue was purified by Prep HPLC to afford the product. $^1$H NMR (400 MHz, Methanol-d4) δ 7.83 (s, 1H), 6.87 (d, J=4.5 Hz, 1H), 6.78 (d, J=4.5 Hz, 1H), 5.50 (d, J=4.9 Hz, 1H), 5.00-4.92 (m, 1H), 4.91-4.85 (m, 1H), 4.62 (t, J=5.3 Hz, 1H), 4.50 (d, J=5.7 Hz, 1H), 4.35-4.12 (m, 2H), 3.91-3.72 (m, 2H), 1.34-1.13 (m, 18H). $^{31}$P NMR (162 MHz, Methanol-d4) δ 13.61. LCMS: MS m/z=598.05 [M+1].

Example 35. ((2R,3S,4R,5S)-5-(4-aminopyrrolo[2,1-f][1,2,4]triazin-7-yl)-2-cyano-3,4-dihydroxytetrahydrofuran-2-yl)methyl bis-ethyl L-alaninate phosphate

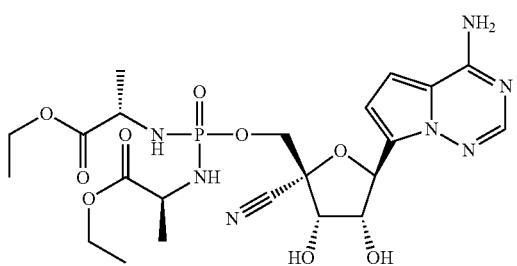 [SMILES: CCOC(=O)[C@H](C)NP(=O)(N[C@@H](C)C(=O)OCC)OC[C@@]1(C#N)O[C@@H](c2ccc3c(N)ncnn23)[C@H](O)[C@@H]1O]

To a mixture of Intermediate 38 (100 mg, 0.3 mmol), Intermediate 4 (151 mg, 0.36 mmol), and MgCl$_2$ (43 mg, 0.45 mmol) in THF (2 mL) was added N,N-diisopropylethylamine (98 mg, 0.76 mmol) dropwise. The resulting mixture was stirred at 50° C. for 2 h, reaction mixture was cooled, diluted with EtOAc, washed with water and brine, the organic solvent was evaporated under vacuum, the residue was then dissolved in acetonitrile (2 mL), cooled in ice bath, and con. HCl was added dropwise. The resulting mixture was stirred at room temperature for 2 h, cooled in ice bath, neutralized by dropwise addition of 2 N NaOH and NaHCO$_3$ solution, diluted with EtOAc (150 mL), washed with water (50 mL) and brine (50 mL). The aqueous phase was extracted with EtOAc (50 mL×2) and the combined organic layer was dried under sodium sulfate, concentrated in vacuum, and residue purified by Prep HPLC to afford the product. $^1$H NMR (400 MHz, Methanol-d4) δ 7.82 (s, 1H), 6.85 (d, J=4.5 Hz, 1H), 6.77 (d, J=4.5 Hz, 1H), 5.50 (d, J=4.9 Hz, 1H), 4.63 (t, J=5.3 Hz, 1H), 4.50 (d, J=5.7 Hz, 1H), 4.30 (dd, J=11.1, 7.0 Hz, 1H), 4.23-3.99 (m, 5H), 3.86 (ddq, J=19.6, 9.4, 7.1 Hz, 2H), 1.35-1.13 (m, 12H). $^{31}$P NMR (162 MHz, Methanol-d4) δ 13.61. LCMS: MS m/z=570.10 [M+1], t$_R$=0.99 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 L/min. HPLC: t$_R$=2.19 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 36. (2R,3S,4R,5S)-5-(4-aminopyrrolo[2,1-f][1,2,4]triazin-7-yl)-2-cyano-3,4-dihydroxytetrahydrofuran-2-yl)methyl bis-cyclobutylmethyl L-alaninate phosphate

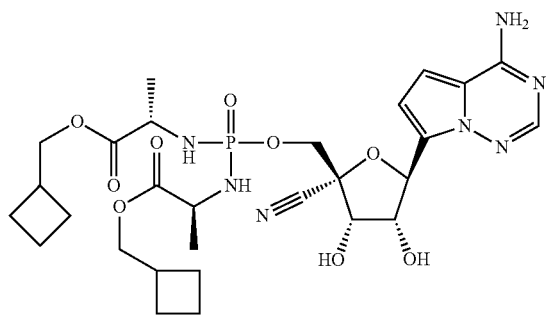 [SMILES: C[C@H](NP(=O)(N[C@@H](C)C(=O)OCC1CCC1)OC[C@@]1(C#N)O[C@@H](c2ccc3c(N)ncnn23)[C@H](O)[C@@H]1O)C(=O)OCC1CCC1]

To a mixture of Intermediate 62 (132 mg, 0.27 mmol), Intermediate 4 (80 mg, 0.24 mmol), and MgCl$_2$ (34 mg, 0.36 mmol) in THF (2 mL) was added N,N-diisopropylethylamine (78 mg, 0.6 mmol) dropwise. The resulting mixture was stirred at 50° C. for 2 h, reaction mixture was cooled, diluted with EtOAc, washed with water and brine, the organic solvent was evaporated under vacuum, the residue was then dissolved in acetonitrile (2 mL), cooled in ice bath, and con. HCl was added dropwise. The resulting mixture was stirred at room temperature for 2 h, cooled in ice bath, neutralized by dropwise addition of 2 N NaOH and NaHCO$_3$ solution, diluted with EtOAc (150 mL), washed with water (50 mL) and brine (50 mL). The aqueous phase was extracted with EtOAc (50 mL×2) and the combined organic layer was dried under sodium sulfate, concentrated in vacuum, and residue was purified by Prep HPLC to afford the product. $^1$H NMR (400 MHz, Methanol-d4) δ 7.82 (s, 1H), 6.85 (d, J=4.5 Hz, 1H), 6.77 (d, J=4.5 Hz, 1H), 5.50 (d, J=4.9 Hz, 1H), 4.61 (t, J=5.3 Hz, 1H), 4.49 (d, J=5.7 Hz, 1H), 4.30 (dd, J=11.1, 7.1 Hz, 1H), 4.20 (dd, J=11.1, 5.7 Hz, 1H), 4.14-3.98 (m, 3H), 3.98-3.80 (m, 3H), 2.60 (dp, J=22.0, 7.4 Hz, 2H), 2.10-1.95 (m, 4H), 1.94-1.64 (m, 8H), 1.39-1.17 (m, 6H). $^{31}$P NMR (162 MHz, Methanol-d4) δ 13.54. LCMS: MS m/z=650.12 [M+1].

Example 37. benzyl ((((2R,3S,4R,5S)-5-(4-aminopyrrolo[2,1-f][1,2,4]triazin-7-yl)-2-cyano-3,4-dihydroxytetrahydrofuran-2-yl)methoxy) (phenoxy)phosphoryl)-L-alaninate

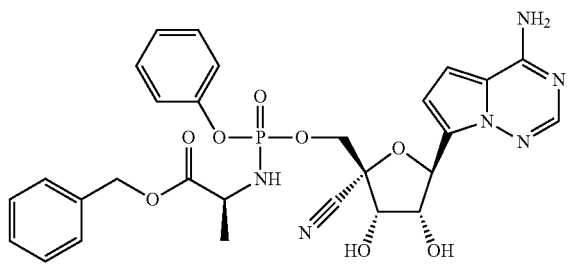 [SMILES: C[C@H](NP(=O)(OC[C@@]1(C#N)O[C@@H](c2ccc3c(N)ncnn23)[C@H](O)[C@@H]1O)Oc1ccccc1)C(=O)OCc1ccccc1]

Intermediate 4 (83 mg, 0.25 mmol) was mixed with Intermediate 39 (126 mg, 0.275 mmol) and dissolved in 2 mL of anhydrous tetrahydrofuran. Magnesium chloride (71 mg, 0.75 mmol) was added in one portion. DIPEA (87 μL, 0.5 mmol) was then added, and the reaction was stirred at 60° C. for 16 h.

More Intermediate 39 (30 mg) and DIPEA (52 μL) were added. The reaction mixture was stirred at 60° C. for 6 h. The reaction mixture was then cooled to RT, diluted with ethyl acetate (10 mL) and washed with water (5×10 mL) followed with brine (5 mL). The organic extract was dried over anhydrous sodium sulfate and concentrated under reduced pressure. The resulted material was dissolved in 5 mL of MeCN and stirred in an ice bath. Concentrated HCl (aq) (300 μL) was added dropwise, and reaction was stirred in an ice bath for 2 h. The reaction mixture was diluted with ethyl acetate (10 mL) and washed with saturated aqueous sodium bicarbonate solution and followed with brine. Organic extract was dried over anhydrous sodium sulfate and concentrated under reduced pressure. The crude residue was purified via SiO$_2$ column chromatography (4 g SiO$_2$ Combiflash HP Gold Column, 0-10% methanol in dichloromethane). Fractions containing the desired product were combined and concentrated under reduced pressure as oil which was then dissolved in MeCN and water and freeze-dried to afford the product. $^1$H NMR (400 MHz, methanol-d$_4$) δ 7.77 (m, 1H), 7.35-7.08 (m, 10H), 6.83 (m, 1H), 6.71 (m, 1H), 5.52-5.48 (m, 1H), 5.14-4.93 (m, 2H), 4.61 (m, 1H), 4.53-4.27 (m, 3H), 4.01-3.87 (m, 1H), 1.26 (m, 3H). $^{31}$P NMR (162 MHz, methanol-d4) δ 3.22, 3.19. LCMS: MS m/z=609.1 [M+1]; 607.4 [M−1], t$_R$=1.19 min; LC system: Thermo Dionex ultimate 3000 UHPLC; Column: Phenomenex Kinetex 2.6μ C18 100A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: t$_R$=2.78 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min. HPLC: t$_R$=4.626 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 38

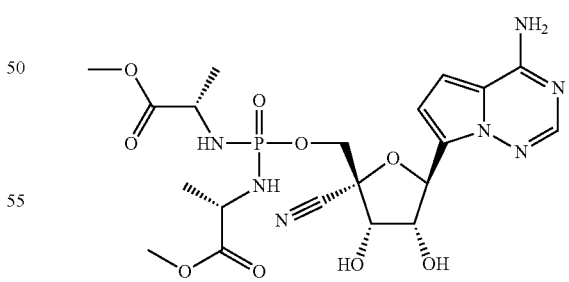

Acetonitrile (1 mL) was added to a mixture of Intermediate 4 (150 mg, 0.453 mmol), Intermediate 40 (176 mg, 0.453 mmol), and magnesium chloride (43 mg, 0.453 mmol) at RT. The mixture was heated to 50° C. for 10 min, and N,N-diisopropylethylamine (0.197 mL, 1.13 mmol) was added. After 2 h, the reaction mixture was allowed to cool to RT, and concentrated aqueous hydrochloric acid solution (0.25 mL) was added dropwise. After 1 h, the reaction mixture was diluted with ethyl acetate (20 mL) and the resulting mixture was washed with saturated aqueous sodium carbonate solution (20 mL) and brine (20 mL). The organic layer was dried over anhydrous sodium sulfate and concentrated under reduced pressure. The crude residue was subjected to silica gel chromatography eluting with 0-100% ethyl acetate in hexanes to afford the product. $^1$H NMR (400 MHz, methanol-d$_4$) δ 7.82 (s, 1H), 6.86 (d, J=4.5 Hz, 1H), 6.77 (d, J=4.5 Hz, 1H), 5.50 (d, J=4.9 Hz, 1H), 4.64 (dd, J=5.6, 5.0 Hz, 1H), 4.51 (d, J=5.7 Hz, 1H), 4.30 (dd, J=11.1, 6.9 Hz, 1H), 4.19 (dd, J=11.1, 5.6 Hz, 1H), 3.86 (ddd, J=14.7, 9.4, 7.2 Hz, 2H), 3.69 (s, 3H), 3.64 (s, 3H), 1.30 (dd, J=7.2, 1.0 Hz, 3H), 1.25 (dd, J=7.2, 0.8 Hz, 3H). $^{31}$P NMR (162 MHz, methanol-d$_4$) δ 13.58 (s). LCMS: MS m/z=542.08 [M+1], $t_R$=0.88 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=1.87 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=3.052 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 39. methyl (((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

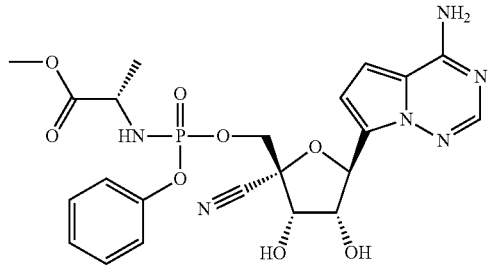 [SMILES: COC(=O)[C@H](C)NP(=O)(OC[C@@]1(C#N)O[C@@H](c2ccc3c(N)ncnn23)[C@H](O)[C@@H]1O)Oc1ccccc1]

Acetonitrile (5 mL) was added to a mixture of Intermediate 4 (348 mg, 1.05 mmol), Intermediate 41 (399 mg, 1.05 mmol), and magnesium chloride (100 mg, 1.05 mmol) at RT. The mixture was heated to 50° C. for 10 min, and N,N-diisopropylethylamine (0.475 mL, 2.63 mmol) was added. After 2.5 h, the reaction mixture was allowed to cool to RT, and concentrated aqueous hydrochloric acid solution (0.5 mL) was added dropwise. After 1 h, the reaction mixture was diluted with ethyl acetate (100 mL) and the resulting mixture was washed with saturated aqueous sodium carbonate solution (100 mL) and brine (100 mL). The organic layer was dried over anhydrous sodium sulfate and concentrated under reduced pressure. The crude residue was subjected to silica gel chromatography eluting with 0-100% ethyl acetate in hexanes to afford the product. $^1$H NMR (400 MHz, methanol-d$_4$) δ 7.80 (s, 0.65H), 7.78 (s, 0.35H), 7.37-7.25 (m, 2H), 7.25-7.12 (m, 3H), 6.87-6.82 (m, 1H), 6.75-6.71 (m, 1H), 5.52-5.47 (m, 1H), 4.66-4.60 (m, 1H), 4.55-4.29 (m, 3H), 3.95-3.80 (m, 1H), 3.64 (s, 1H), 3.60 (s, 2H), 1.27-1.22 (m, 3H). $^{31}$P NMR (162 MHz, methanol-d$_4$) δ 3.24 (s). LCMS: MS m/z=533.13 [M+1], $t_R$=1.02 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=2.28 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=3.712 min (minor isomer), 3.775 min (major isomer); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 40. isopropyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(2-(methylthio)ethoxy)phosphoryl)-L-alaninate

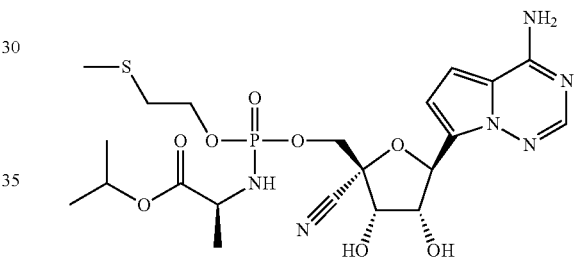

Intermediate 4 (50 mg, 0.15 mmol) and Intermediate 70 (67 mg, 0.165 mmol) were mixed and dissolved in 1.5 mL of anhydrous tetrahydrofuran. Magnesium chloride (43 mg, 0.45 mmol) was in one portion. DIPEA (65 μL, 0.75 mmol) was added, and the reaction was stirred at RT for 36 h. The reaction was diluted with ethyl acetate (15 mL) and washed with water (5×10 mL) and then with brine (5 mL). The organic extract was dried over anhydrous sodium sulfate and concentrated under reduced pressure. The crude residue was purified via SiO$_2$ column chromatography (4 g SiO$_2$ Combiflash HP Gold Column, 0-3% methanol/dichloromethane). Fractions containing the desired product were combined and concentrated under reduced pressure. The residue was dissolved in MeCN (5 mL) and stirred in an ice bath. Concentrate aqueous hydrochloric acid (300 μL) was added dropwise. The reaction mixture was stirred in an ice bath for 2 h. The reaction mixture was diluted with ethyl acetate (15 mL) and added saturated aqueous sodium bicarbonate solution (10 mL). The mixture was stirred for 10 min. The organic extract was collected and washed with saturated aqueous sodium bicarbonate solution (10 mL) and then with brine (5 mL). The organic extract was dried over anhydrous sodium sulfate and concentrated under reduced pressure. The crude residue was purified via SiO$_2$ column chromatography (4 g SiO$_2$ Combiflash HP Gold Column, 0-5% methanol/dichloromethane). Fractions containing the desired product were combined and concentrated under reduced pressure. The residue was dissolved in MeCN and water and freeze-dried to give the product. $^1$H NMR (400 MHz, methanol-d$_4$) δ 7.81 (m, 1H), 6.85 (m, 1H), 6.76 (m, 1H), 5.50 (m, 1H), 4.92 (m, 1H), 4.64 (m, 1H), 4.50 (m, 1H), 4.40-4.21 (m, 2H), 4.17 (m, 1H), 4.09 (m, 1H), 3.85-3.72 (m, 1H), 2.72 (m, 2H), 2.09 (m, 3H), 1.29 (m, 3H), 1.25-1.21 (m, 3H), 1.17 (m, 3H). $^{31}$P NMR (162 MHz, methanol-d$_4$) δ 7.74, 7.82. LCMS: MS m/z=559.0 [M+1]; 557.2 [M−1], $t_R$=1.04 min; LC system: Thermo Dionex ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 m/min. HPLC: $t_R$=2.36 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min. HPLC: $t_R$=3.976, 4.022 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 41. isopropyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(2-methoxyethoxy)phosphoryl)-L-alaninate

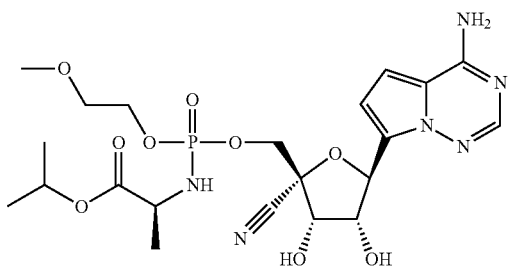 [SMILES: COCCOP(=O)(N[C@@H](C)C(=O)OC(C)C)OC[C@@]1(C#N)O[C@@H](c2ccc3c(N)ncnn23)[C@H](O)[C@@H]1O]

Intermediate 4 (50 mg, 0.15 mmol) and Intermediate 71 (64 mg, 0.165 mmol) were mixed and dissolved in 1.5 mL of anhydrous tetrahydrofuran. Magnesium chloride (43 mg, 0.45 mmol) was added in one portion. DIPEA (65 μL, 0.375 mmol) was added, and the reaction was stirred at RT for 20 h.

The reaction mixture was diluted with ethyl acetate (15 mL) and washed with water (5×10 mL) and then with brine (5 mL). The organic extract was dried over anhydrous sodium sulfate and concentrated under reduced pressure. The crude residue was purified via SiO$_2$ column chromatography (4 g SiO$_2$ Combiflash HP Gold Column, 0-3% methanol/dichloromethane). Fractions containing the desired product were combined and concentrated under reduced pressure. The resulting material was dissolved in MeCN (5 mL) and stirred in an ice bath. Concentrate aqueous hydrochloric acid (300 μL) was added dropwise. The reaction mixture was stirred in an ice bath for 2 h. The reaction was diluted with ethyl acetate (15 mL) and saturated aqueous sodium bicarbonate solution was added. The mixture was stirred for 10 min. The organic extract was washed with saturated aqueous sodium bicarbonate solution (10 mL) and then with brine (5 mL). The organic extract was dried over anhydrous sodium sulfate and concentrated under reduced pressure. The crude residue was purified via SiO$_2$ column chromatography (4 g SiO$_2$ Combiflash HP Gold Column, 0-5% methanol/dichloromethane). Fractions containing the desired product were combined and concentrated under reduced pressure. The residue was dissolved in MeCN and water and freeze-dried to give the product. $^1$H NMR (400 MHz, methanol-d4) δ 7.82 (s, 1H), 6.89-6.83 (m, 1H), 6.76 (m, 1H), 5.50 (m, 1H), 5.01-4.84 (m, 1H), 4.63 (m, 1H), 4.50 (m, 1H), 4.35 (m, 1H), 4.30-4.19 (m, 1H), 4.19-4.13 (m, 2H), 3.77 (m, 1H), 3.63-3.51 (m, 2H), 3.35 (m, 3H), 1.28 (m, 3H), 1.17 (m, 6H). $^{31}$P NMR (162 MHz, methanol-d4) δ 7.98, 8.04. LCMS: MS m/z=543.1 [M+1]; 541.2 [M−1], $t_R$=0.96 min; LC system: Thermo Dionex ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 m/min. HPLC: $t_R$=2.18 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min. HPLC: $t_R$=3.599, 3.619 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 42. isopropyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(2-(methylsulfonyl)ethoxy)phosphoryl)-L-alaninate

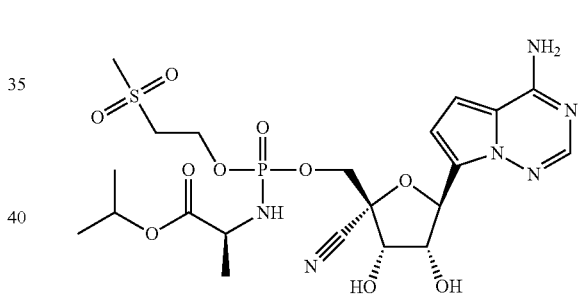

Intermediate 4 (66 mg, 0.2 mmol) and Intermediate 72 (100 mg, 0.22 mmol) were mixed and dissolved in 2 mL of anhydrous tetrahydrofuran. Magnesium chloride (57 mg, 0.6 mmol) was added in one portion. DIPEA (87 μL, 0.5 mmol) was added and the reaction was stirred at 35° C. for 16 h. The reaction was diluted with ethyl acetate (15 mL) and washed with water (5×10 mL) and then with brine (5 mL). The organic extract was dried over anhydrous sodium sulfate and concentrated under reduced pressure. The crude residue was purified via SiO$_2$ column chromatography (4 g SiO$_2$ Combiflash HP Gold Column, 0-100% B/hexanes (B=3% MeOH in ethyl acetate)). Fractions containing the desired product were combined and concentrated under reduced pressure.

The resulting material was dissolved in MeCN (5 mL) and stirred in an ice bath. Concentrate aqueous hydrochloric acid (250 μL) was added dropwise. The reaction was stirred in an ice bath for 2 h. The reaction was diluted with ethyl acetate (15 mL) and added saturated aqueous sodium bicarbonate solution (10 mL). The mixture was stirred for 10 min. The organic extract was washed with saturated aqueous sodium bicarbonate solution (10 mL) and then with brine (5 mL). The organic extract was dried over anhydrous sodium sulfate and concentrated under reduced pressure. The crude residue was purified via SiO$_2$ column chromatography (4 g SiO$_2$ Combiflash HP Gold Column, 0-10% methanol/dichloromethane). Fractions containing the desired product were combined and concentrated under reduced pressure. The residue was dissolved in MeCN and water and freeze-dried to give the product. $^1$H NMR (400 MHz, methanol-d$_4$) δ 7.82 (m, 1H), 6.86 (m, 1H), 6.77 (m, 1H), 5.50 (m, 1H), 5.03-4.85 (m, 1H), 4.64 (m, 1H), 4.54-4.44 (m, 2H), 4.43-4.21 (m, 2H), 3.80 (m, 1H), 3.57-3.36 (m, 2H), 2.97 (m, 3H), 1.30 (m, 3H), 1.26-1.14 (m, 6H). $^{31}$P NMR (162 MHz, methanol-d$_4$) δ 7.79, 7.92. LCMS: MS m/z=591.1 [M+1], t$_R$=0.92 min; LC system: Thermo Dionex ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: t$_R$=2.07 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min. HPLC: t$_R$=3.435 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 43. Isopropyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(4-(dimethylcarbamoyl)phenoxy)phosphoryl)-L-alaninate

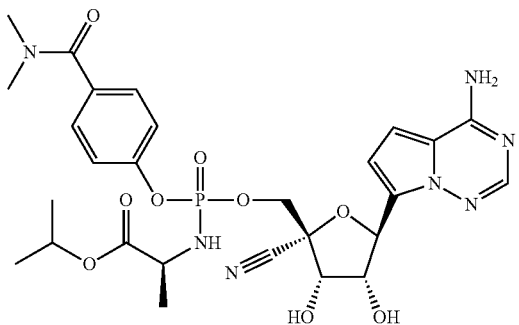 [SMILES: CC(C)OC(=O)[C@H](C)NP(=O)(OC[C@@]1(C#N)O[C@@H](c2ccc3c(N)ncnn23)[C@H](O)[C@@H]1O)Oc1ccc(C(=O)N(C)C)cc1]

To a mixture of Intermediate 4 (70 mg, 0.211 mmol), Intermediate 43 (160 mg, 0.317 mmol), and MgCl$_2$ (30 mg, 0.317 mmol) in THF (3 mL) was added N,N-diisopropylethylamine (0.1 mL, 0.528 mmol) dropwise at room temperature. The resulting mixture was stirred at 50° C. for 2 h, and purified by preparative HPLC (Phenomenex Gemini-NX 10μ C18 110° A 250×30 mm column, 0%-100% acetonitrile/water gradient in 25 min run) to give an acetonide intermediate, which was dissolved in acetonitrile (2 mL) and c-HCl (0.2 mL) was added. The mixture was stirred for 2 h, aq. NaHCO$_3$ (2 mL) added under ice bath, and purified by preparative HPLC (Phenomenex Gemini-NX 10μ C18 110°A 250×30 mm column, 0%-100% acetonitrile/water gradient in 25 min run) to afford the product. $^1$H NMR (400 MHz, Methanol-d4) δ 7.80 (m, 1H), 7.40 (m, 1H), 7.37-7.28 (m, 2H), 7.23 (m, 1H), 6.86 (m, 1H), 6.74 (m, 1H), 5.50 (m, 1H), 5.00-4.81 (m, 1H), 4.61 (m, 1H), 4.54-4.38 (m, 2H), 4.35 (m, 1H), 3.92-3.79 (m, 1H), 3.07 (d, J=3.4 Hz, 3H), 2.95 (m, 3H), 1.28 (m, 3H), 1.22-1.12 (m, 6H). $^{31}$P NMR (162 MHz, Methanol-d4) δ 3.18. LCMS: MS m/z=632.32 [M+1]; t$_R$=0.67 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=3.84 min (18%), 3.85 (81%); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 44. oxetan-3-yl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

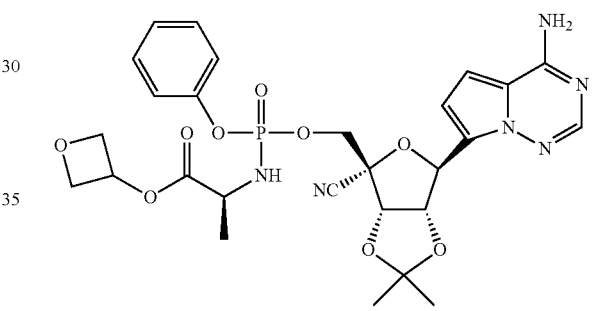

oxetan-3-yl ((((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methoxy)(phenoxy)phosphoryl)-L-alaninate. To a mixture of Intermediate 44 (133 mg, 0.31 mmol), Intermediate 4 (130 mg, 0.39 mmol), and MgCl$_2$ (45 mg, 0.47 mmol) in THF (5 mL) was added N,N-diisopropylethylamine (127 mg, 0.98 mmol) dropwise. The resulting mixture was stirred at 50° C. for 2 h, reaction mixture was cooled, diluted with EtOAc, washed with water and brine, the organic solvent was evaporated under vacuum, the residue was purified with silica gel column chromatography eluting with 0-100% MeOH in DCM to afford the product. LCMS: MS m/z=615.18 [M+1], t$_R$=1.18 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: t$_R$=3.40 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

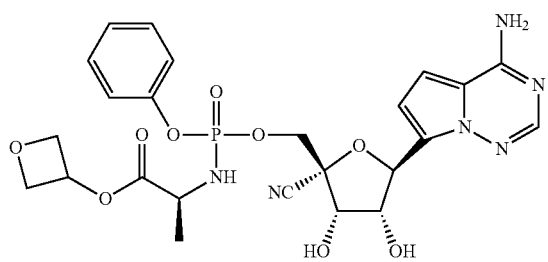 [SMILES: C[C@H](NP(=O)(OC[C@@]1(C#N)O[C@@H](c2ccc3c(N)ncnn23)[C@H](O)[C@@H]1O)Oc1ccccc1)C(=O)OC1COC1]

oxetan-3-yl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate. Dissolved oxetan-3-yl ((((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methoxy)(phenoxy)phosphoryl)-L-alaninate (500 mg, 0.81 mmol) in 10 mL ACN, mixed 20 mL of TFA with 10 mL water, then added the TFA solution to above reaction mixture, stirred at RT for 30 mins, quenched with aq. NaHCO₃ solution, extracted with EtOAc, evaporated organic solvent, purified with Prep HPLC to afford the product. $^1$H NMR (400 MHz, Methanol-d4) δ 7.79 (d, J=9.7 Hz, 1H), 7.38-7.11 (m, 5H), 6.85 (d, J=4.5 Hz, 1H), 6.73 (dd, J=5.6, 4.5 Hz, 1H), 5.50 (t, J=4.5 Hz, 1H), 5.32 (dtt, J=23.9, 6.3, 5.1 Hz, 1H), 4.82-4.73 (m, 2H), 4.63 (td, J=5.3, 4.1 Hz, 1H), 4.60-4.44 (m, 4H), 4.44-4.26 (m, 2H), 4.01-3.85 (m, 1H), 1.29 (dt, J=7.2, 1.3 Hz, 3H). $^{31}$P NMR (162 MHz, Methanol-d4) δ 3.3, 3.29. LCMS: MS m/z=575.11 [M+1], $t_R$=0.98 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.63 and 3.70 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 45. propyl ((S)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

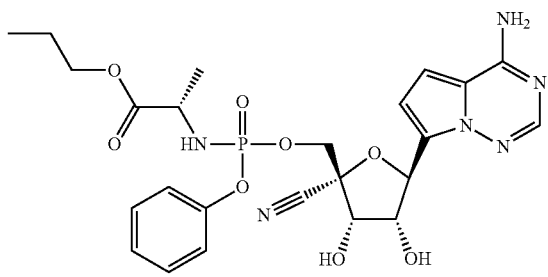 [SMILES: CCCOC(=O)[C@H](C)NP(=O)(OC[C@@]1(C#N)O[C@@H](c2ccc3c(N)ncnn23)[C@H](O)[C@@H]1O)Oc1ccccc1]

N,N-Diisopropylethylamine (0.33 mL, 1.89 mmol) and magnesium chloride (107.8 mg, 1.13 mmol) were added to a mixture of Intermediate 4 (250.0 mg, 0.76 mmol) and Intermediate 45 (462.16 mg, 1.13 mmol) in tetrahydrofuran (7.5 mL) at RT. The mixture was heated to 55° C. After 2 h, the reaction mixture was allowed to cool to RT, diluted with ethyl acetate (30 mL) and the resulting mixture was washed with water (5×20 mL) and brine (20 mL). The organic layer was dried over anhydrous sodium sulfate and concentrated under reduced pressure. Concentrated aqueous hydrochloric acid solution (0.53 mL) was added dropwise to the crude residue in acetonitrile (7.5 mL) at 0° C. The mixture was warmed to RT. After 2 h, the reaction mixture was diluted with ethyl acetate (100 mL) and the resulting mixture was washed with saturated aqueous sodium carbonate solution (75 mL) and brine (75 mL). The organic layer was dried over anhydrous sodium sulfate and concentrated under reduced pressure. The crude residue was subjected to silica gel chromatography eluting with 0-20% methanol in dichloromethane to afford the product. $^1$H NMR (400 MHz, Methanol-d₄) δ 7.80 (d, J=7.2 Hz, 1H), 7.37-7.27 (m, 2H), 7.26-7.13 (m, 3H), 6.85 (dd, J=4.5, 2.9 Hz, 1H), 6.74 (dd, J=4.6, 2.1 Hz, 1H), 5.50 (t, J=5.3 Hz, 1H), 4.63 (q, J=5.3 Hz, 1H), 4.54-4.31 (m, 3H), 4.07-3.82 (m, 3H), 1.68-1.49 (m, 2H), 1.31-1.26 (m, 3H), 0.90 (dt, J=9.9, 7.4 Hz, 3H). $^{31}$P NMR (162 MHz, Methanol-d4) δ 3.27. LCMS: MS m/z=561.20 [M+1], $t_R$=0.78 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.70 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Resolution of the Sp and Rp diastereomers. The product was purified via chiral SFC (Chiralpak AD-H, Sum, 21×250 mm, Isopropyl alcohol 30%) to afford the diastereomers:

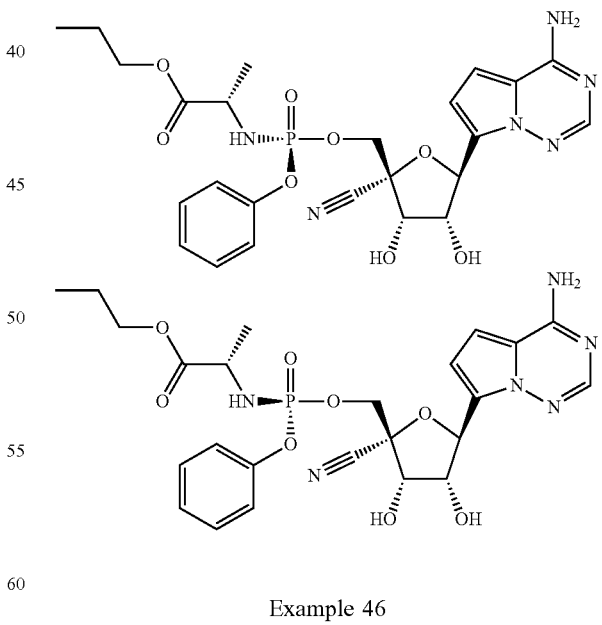

Example 46

First Eluting Diastereomer of Example 45: $^1$H NMR (400 MHz, Methanol-d₄) a 7.79 (s, 1H), 7.33-7.26 (m, 2H), 7.20-7.12 (m, 3H), 6.85 (d, J=4.5 Hz, 1H), 6.73 (d, J=4.5 Hz, 1H), 5.51 (d, J=5.0 Hz, 1H), 4.68-4.60 (m, 1H), 4.53 (d, J=5.6 Hz, 1H), 4.48 (dd, J=10.9, 6.0 Hz, 1H), 4.36 (dd, J=10.9, 5.1 Hz, 1H), 4.06-3.95 (m, 2H), 3.88 (dq, J=9.4, 7.1 Hz, 1H), 1.62 (h, J=7.3 Hz, 2H), 1.26 (dd, J=7.1, 1.3 Hz, 3H), 0.91 (t, J=7.5 Hz, 3H). $^{31}$P NMR (162 MHz, Methanol-d4) δ 3.26. LCMS: MS m/z=561.21 [M+1], $t_R$=0.76 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.63 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Example 47

Second Eluting Diastereomer of Example 45: $^1$H NMR (400 MHz, Methanol-d$_4$) δ 7.80 (s, 1H), 7.37-7.29 (m, 2H), 7.26-7.14 (m, 3H), 6.84 (d, J=4.5 Hz, 1H), 6.74 (d, J=4.5 Hz, 1H), 5.50 (d, J=5.0 Hz, 1H), 4.62 (dd, J=5.6, 5.1 Hz, 1H), 4.47 (d, J=5.6 Hz, 1H), 4.42 (dd, J=10.9, 6.3 Hz, 1H), 4.34 (dd, J=10.9, 5.5 Hz, 1H), 4.02-3.85 (m, 3H), 1.58 (dtd, J=14.0, 7.4, 6.6 Hz, 2H), 1.27 (dd, J=7.2, 1.1 Hz, 3H), 0.88 (t, J=7.5 Hz, 3H). $^{31}$P NMR (162 MHz, Methanol-d$_4$) δ 3.27. LCMS: MS m/z=561.26 [M+1], $t_R$=0.77 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.74 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Example 48. oxetan-3-ylmethyl ((((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methoxy)(phenoxy)phosphoryl)-L-alaninate

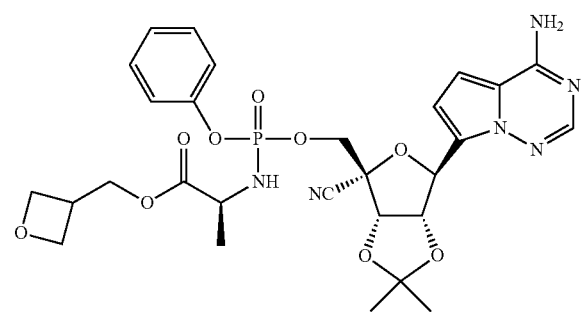 [SMILES: C[C@H](NP(=O)(OC[C@@]1(C#N)O[C@@H](c2ccc3c(N)ncnn23)[C@@H]2OC(C)(C)O[C@@H]21)Oc1ccccc1)C(=O)OCC1COC1]

To a mixture of Intermediate 46 (350 mg, 1.06 mmol), Intermediate 4 (507 mg, 1.16 mmol), and MgCl2 (130 mg, 1.37 mmol) in THF (10 mL) was added N,N-diisopropylethylamine (341 mg, 2.64 mmol) dropwise. The resulting mixture was stirred at 50° C. for 2 h, reaction mixture was cooled, diluted with EtOAc, washed with water and brine, the organic solvent was evaporated under vacuum, the residue was purified with silica gel column chromatography eluting with 0-100% MeOH in DCM to afford the product. LCMS: MS m/z=629.10 [M+1], $t_R$=1.21 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.51 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 49. oxetan-3-ylmethyl (((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

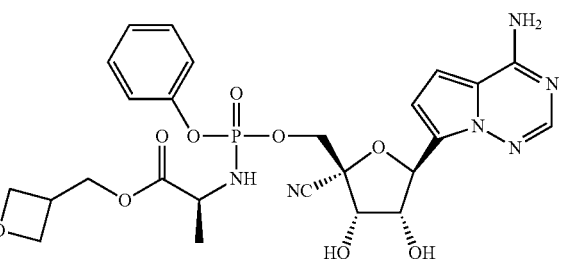

Dissolved Example 48 (385 mg, 0.61 mmol) in 12 mL ACN, mixed 17 mL of TFA with 12 mL water, then added the TFA solution to above reaction mixture, stirred at RT for 30 mins, quenched with aq. NaHCO$_3$ solution, extracted with EtOAc, evaporated organic solvent, purified with Prep HPLC to afford the product. $^1$H NMR (400 MHz, Methanol-d4) δ 7.80 (d, J=8.5 Hz, 1H), 7.31 (dt, J=16.0, 7.8 Hz, 2H), 7.25-7.10 (m, 3H), 6.86 (dd, J=4.6, 2.8 Hz, 1H), 6.74 (t, J=4.3 Hz, 1H), 5.49 (t, J=4.9 Hz, 1H), 4.72 (dddd, J=11.0, 7.9, 6.3, 3.6 Hz, 2H), 4.67-4.57 (m, 1H), 4.55-4.29 (m, 5H), 4.29-4.23 (m, 1H), 4.24-4.09 (m, 1H), 3.91 (td, J=9.4, 8.9, 6.9 Hz, 1H), 3.28-3.10 (m, 1H), 1.27 (ddd, J=7.2, 2.7, 1.2 Hz, 3H). $^{31}$P NMR (162 MHz, Methanol-d4) δ 3.22, 3.15. LCMS: MS m/z=589.15 [M+1], $t_R$=1.01 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.66 and 3.72 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 50. cyclobutyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate single diastereomer

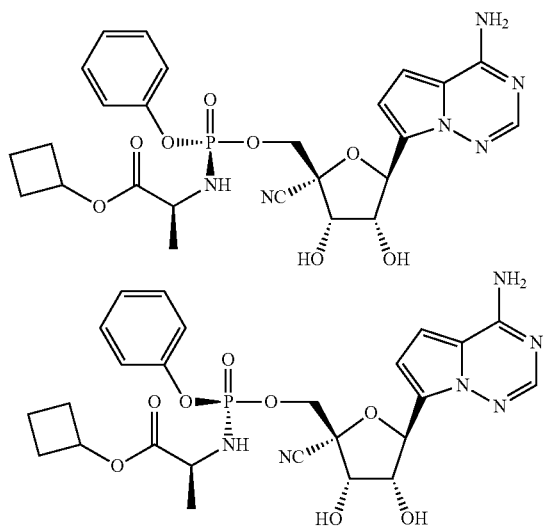

To a mixture of Intermediate 48 (330 mg, 0.79 mmol), Intermediate 4 (260 mg, 0.79 mmol), and MgCl2 (97 mg, 1.02 mmol) in THF (10 mL) was added N,N-diisopropylethylamine (254 mg, 1.96 mmol) dropwise. The resulting mixture was stirred at 50° C. for 2 h, reaction mixture was cooled, diluted with EtOAc, washed with water and brine, the organic solvent was evaporated under vacuum, the residue was purified with silica gel column chromatography eluting with 0-100% MeOH in DCM to afford acetonide intermediate, which is then dissolved in acetonitrile (10 mL), cooled in ice bath, and con. HCl was added dropwise. The resulting mixture was stirred at room temperature for 2 h, cooled in ice bath, neutralized by dropwise addition of 2 N NaOH and NaHCO$_3$ solution, diluted with EtOAc (150 mL), washed with water (50 mL) and brine (50 mL). The aqueous phase was extracted with EtOAc (50 mL×2) and the combined organic layer was dried under sodium sulfate, concentrated in vacuum, and residue was dissolved in DCM and purified by silica gel column chromatography eluting with 0-100% MeOH in DCM to afford the product. $^1$H NMR (400 MHz, Methanol-d4) δ 7.78 (s, 1H), 7.31 (dd, J=8.7, 7.1 Hz, 2H), 7.22 (dt, J=8.6, 1.3 Hz, 2H), 7.20-7.08 (m, 1H), 6.84 (d, J=4.5 Hz, 1H), 6.72 (d, J=4.5 Hz, 1H), 5.51 (dt, J=5.0, 1.4 Hz, 1H), 4.82-4.80 (m, 1H), 4.63 (t, J=5.3 Hz, 1H), 4.53-4.38 (m, 2H), 4.35 (ddd, J=10.3, 5.0, 1.4 Hz, 1H), 3.86 (dq, J=9.7, 7.1 Hz, 1H), 2.32-2.09 (m, 2H), 2.04-1.89 (m, 2H), 1.79-1.64 (m, 1H), 1.64-1.46 (m, 1H), 1.29-1.18 (m, 3H). $^{31}$P NMR (162 MHz, Methanol-d4) δ 3.25. LCMS: MS m/z=573.11 [M+1], $t_R$=1.12 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 L/min. HPLC: $t_R$=4.395 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 51. cyclobutyl (((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate single diastereomer

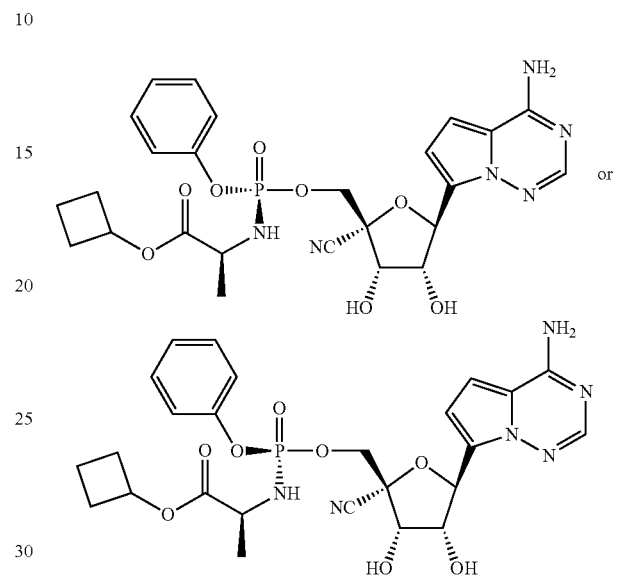

To a mixture of Intermediate 49 (355 mg, 0.85 mmol), Intermediate 4 (280 mg, 0.85 mmol), and MgCl2 (105 mg, 1.1 mmol) in THF (10 mL) was added N,N-diisopropylethylamine (273 mg, 2.1 mmol) dropwise. The resulting mixture was stirred at 50° C. for 2 h, reaction mixture was cooled, diluted with EtOAc, washed with water and brine, the organic solvent was evaporated under vacuum, the residue was purified with silica gel column chromatography eluting with 0-100% MeOH in DCM to afford acetonide intermediate, which is then dissolved in acetonitrile (10 mL), cooled in ice bath, and con. HCl was added dropwise. The resulting mixture was stirred at room temperature for 2 h, cooled in ice bath, neutralized by dropwise addition of 2 N NaOH and NaHCO$_3$ solution, diluted with EtOAc (150 mL), washed with water (50 mL) and brine (50 mL). The aqueous phase was extracted with EtOAc (50 mL×2) and the combined organic layer was dried under sodium sulfate, concentrated in vacuum, and residue was dissolved in DCM and purified by silica gel column chromatography eluting with 0-100% MeOH in DCM to afford the product. $^1$H NMR (400 MHz, Methanol-d4) δ 7.78 (s, 1H), 7.28 (dd, J=8.8, 7.0 Hz, 2H), 7.20-7.08 (m, 3H), 6.85 (d, J=4.5 Hz, 1H), 6.73 (d, J=4.6 Hz, 1H), 5.51 (d, J=5.0 Hz, 1H), 4.97-4.86 (m, 1H), 4.63 (t, J=5.3 Hz, 1H), 4.52 (d, J=5.6 Hz, 1H), 4.47 (dd, J=10.9, 5.9 Hz, 1H), 4.35 (dd, J=10.9, 5.1 Hz, 1H), 3.84 (dq, J=9.2, 7.1 Hz, 1H), 2.34-2.19 (m, 2H), 2.13-1.91 (m, 2H), 1.84-1.69 (m, 1H), 1.69-1.52 (m, 1H), 1.25 (dd, J=7.2, 1.2 Hz, 3H). $^{31}$P NMR (162 MHz, Methanol-d4) δ 3.21. LCMS: MS m/z=573.10 [M+1], $t_R$=1.15 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 L/min.

HPLC: $t_R$=4.364 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 52. methyl ((S)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

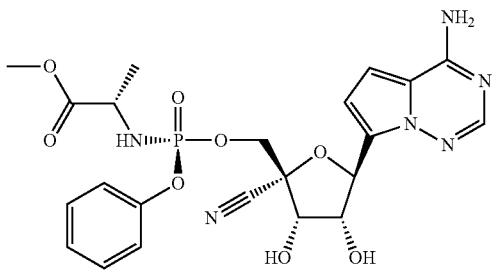 [SMILES: COC(=O)[C@H](C)N[P@](=O)(OC[C@@]1(C#N)O[C@@H](c2ccc3c(N)ncnn23)[C@H](O)[C@@H]1O)Oc1ccccc1]

Method 1. N,N-Diisopropylethylamine (0.12 mL, 0.68 mmol) and magnesium chloride (38.8 mg, 0.41 mmol) were added to a mixture of Intermediate 4 (100.0 mg, 0.30 mmol) and Intermediate 50 (141.2 mg, 0.33 mmol) in tetrahydrofuran (3 mL) at RT. The mixture was heated to 50° C. After 1 h, the reaction mixture was allowed to cool to RT, diluted with ethyl acetate (25 mL) and the resulting mixture was washed with water (5×10 mL) and brine (10 mL). The organic layer was dried over anhydrous sodium sulfate and concentrated under reduced pressure. Concentrated aqueous hydrochloric acid solution (0.2 mL) was added dropwise to the crude residue in acetonitrile (3 mL) at 0° C. The mixture was warmed to RT. After 3 h, the reaction mixture was diluted with ethyl acetate (25 mL) and the resulting mixture was washed with saturated aqueous sodium carbonate solution (20 mL) and brine (20 mL). The organic layer was dried over anhydrous sodium sulfate and concentrated under reduced pressure. The crude residue was subjected to silica gel chromatography eluting with 0-20% methanol in dichloromethane to afford the product. $^{1}$H NMR (400 MHz, Acetonitrile-d$_3$) δ 7.87 (s, 1H), 7.40-7.30 (m, 2H), 7.27-7.14 (m, 3H), 6.73 (s, 2H), 6.20 (s, 2H), 5.46 (d, J=5.0 Hz, 1H), 4.63-4.51 (m, 1H), 4.51-4.40 (m, 1H), 4.35 (dd, J=11.1, 6.6 Hz, 2H), 4.28 (dd, J=11.1, 6.4 Hz, 2H), 4.00-3.83 (m, 2H), 3.59 (s, 3H), 1.26 (dd, J=7.1, 1.0 Hz, 3H). $^{31}$P NMR (162 MHz, Acetonitrile-d$_3$) δ 2.64. LCMS: MS m/z=533.15 [M+1], $t_R$=0.65 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.03 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Method 2. Intermediate 4 (150 mg, 0.5 mmol) and Intermediate 50 (234 mg, 0.55 mmol) were mixed and dissolved in 4 mL of anhydrous THF. Magnesium chloride (143 mg, 1.5 mmol) was added in one portion. DIPEA (218 uL, 1.25 mmol) was added, and the reaction was stirred at 50° C. for 4 hrs.

Reaction was diluted with EtOAc (20 mL) and washed with water (5×15 mL) and then with brine (5 mL). Organic extract was dried over anhydrous sodium sulfate and concentrated under reduced pressure. Residue was dissolved in MeCN (10 mL) and stirred in an ice bath. Concentrate aqueous hydrochloric acid (500 uL) was added dropwise. Reaction was stirred in an ice bath for 4 hrs. Reaction was diluted with EtOAc (30 mL) and added saturated aqueous sodium bicarbonate solution (30 mL). Mixture was stirred for 10 mins. Organic extract was collected and washed with brine (10 mL). Organic extract was dried over anhydrous sodium sulfate and concentrated under reduced pressure. The crude residue was purified via SiO$_2$ column chromatography (12 g SiO$_2$ Combiflash HP Gold Column, 0-10% methanol/DCM). Fractions having the desired product were combined and concentrated under reduced pressure. Residue was dissolved in MeCN and water and freeze-dried to give the product. $^{1}$H NMR (400 MHz, methanol-d$_4$) δ 7.79 (s, 1H), 7.37-7.27 (m, 2H), 7.22 (m, 2H), 7.16 (m, 1H), 6.83 (d, J=4.5 Hz, 1H), 6.73 (d, J=4.5 Hz, 1H), 5.51 (d, J=5.1 Hz, 1H), 4.63 (t, J=5.3 Hz, 1H), 4.48 (d, J=5.6 Hz, 1H), 4.45-4.30 (m, 2H), 3.90 (m, 1H), 3.59 (s, 3H), 1.25 (d, J=7.1 Hz, 3H). $^{31}$P NMR (162 MHz, methanol-d$_4$) δ 3.24. LCMS: MS m/z=533.0 [M+1], 531.0 [M−1], $t_R$=1.31 min; LC system: Thermo Dionex Ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=2.29 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min. HPLC: $t_R$=3.791 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 53. isopropyl (((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

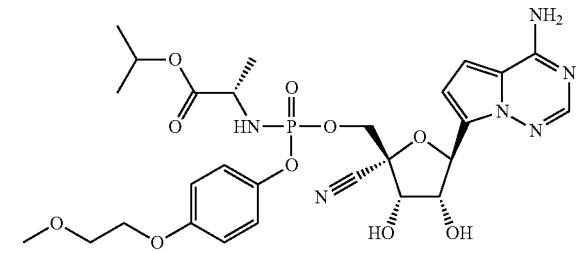 [SMILES: COCCOc1ccc(OP(=O)(N[C@@H](C)C(=O)OC(C)C)OC[C@@]2(C#N)O[C@@H](c3ccc4c(N)ncnn34)[C@H](O)[C@@H]2O)cc1]

N,N-Diisopropylethylamine (0.06 mL, 0.33 mmol) and magnesium chloride (12.0 mg, 0.13 mmol) were added to a mixture of Intermediate 4 (41.8 mg, 0.13 mmol) and Intermediate 51 (60.9 mg, 0.13 mmol) in tetrahydrofuran (1.5 mL) at RT. The mixture was heated to 55° C. After 5 h, the reaction mixture was allowed to cool to RT, diluted with ethyl acetate (20 mL) and the resulting mixture was washed with water (5×15 mL) and brine (20 mL). The organic layer was dried over anhydrous sodium sulfate and concentrated under reduced pressure. Concentrated aqueous hydrochloric acid solution (0.06 mL) was added dropwise to the crude residue in acetonitrile (1.5 mL) at 0° C. The mixture was warmed to RT. After 2 h, the reaction mixture was diluted with ethyl acetate (20 mL) and the resulting mixture was washed with saturated aqueous sodium carbonate solution (20 mL) and brine (20 mL). The organic layer was dried over anhydrous sodium sulfate and concentrated under reduced pressure. The crude residue was subjected to silica gel chromatography eluting with 0-20% methanol in dichloromethane to afford the product. $^1$H NMR (400 MHz, Methanol-d$_4$) δ 7.80 (d, J=3.7 Hz, 1H), 7.14 (dd, J=9.0, 1.4 Hz, 1H), 7.09-7.03 (m, 1H), 6.90-6.80 (m, 3H), 6.73 (dd, J=4.8, 1.0 Hz, 1H), 5.50 (dd, J=7.8, 5.0 Hz, 1H), 4.99-4.86 (m, 1H), 4.62 (q, J=5.1 Hz, 1H), 4.53-4.29 (m, 3H), 4.10-4.01 (m, 2H), 3.90-3.77 (m, 1H), 3.77-3.68 (m, 2H), 3.41 (d, J=2.1 Hz, 3H), 1.26 (ddd, J=7.1, 3.7, 1.1 Hz, 3H), 1.23-1.13 (m, 6H). $^{31}$P NMR (162 MHz, Methanol-d$_4$) δ 3.71. LCMS: MS m/z=635.19 [M+1], t$_R$=0.95 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: t$_R$=3.68 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Example 54. butyl ((S)-(((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

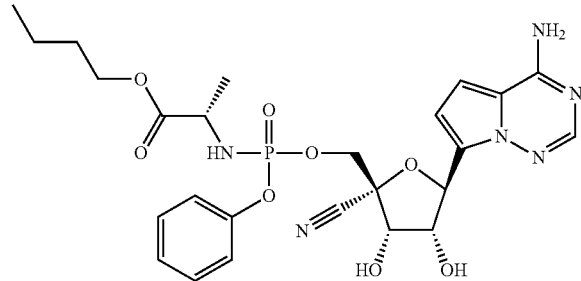 [SMILES: CCCCOC(=O)[C@H](C)NP(=O)(OC[C@@]1(C#N)O[C@@H](c2ccc3c(N)ncnn23)[C@H](O)[C@@H]1O)Oc1ccccc1]

N,N-diisopropylethylamine (0.13 mL, 0.76 mmol) and magnesium chloride (43 mg, 0.45 mmol) were added to a mixture of Intermediate 4 (100.0 mg, 0.30 mmol) and Intermediate 52 (191 mg, 0.45 mmol) in tetrahydrofuran (7.5 mL) at RT. The mixture was heated to 55° C. After 2 h, the reaction mixture was allowed to cool to RT, diluted with ethyl acetate (30 mL) and the resulting mixture was washed with water (5×20 mL) and brine (20 mL). The organic layer was dried over anhydrous sodium sulfate and concentrated under reduced pressure. Concentrated aqueous hydrochloric acid solution (0.53 mL) was added dropwise to the crude residue in acetonitrile (7.5 mL) at 0° C. The mixture was warmed to RT. After 2 h, the reaction mixture was diluted with ethyl acetate (100 mL) and the resulting mixture was washed with saturated aqueous sodium carbonate solution (75 mL) and brine (75 mL). The organic layer was dried over anhydrous sodium sulfate and concentrated under reduced pressure. The crude residue was subjected to silica gel chromatography eluting with 0-20% methanol in dichloromethane to afford the product. $^1$H NMR (400 MHz, Methanol-d4) δ 7.79 (d, J=7.2 Hz, 1H), 7.37-7.10 (m, 4H), 6.84 (dd, J=4.5, 2.8 Hz, 1H), 6.73 (dd, J=4.5, 2.0 Hz, 1H), 5.49 (t, J=5.2 Hz, 1H), 4.62 (q, J=5.3 Hz, 1H), 4.55-4.28 (m, 3H), 4.15-3.80 (m, 3H), 1.68-1.46 (m, 2H), 1.46-1.22 (m, 5H), 0.99-0.83 (m, 3H). $^{31}$P NMR (162 MHz, Methanol-d$_4$) δ 3.25. LCMS: MS m/z=575.14 [M+1], t$_R$=0.83 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: t$_R$=6.50 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-19.0 min 2-95% ACN, 19.0 min-20.0 min 95% ACN at 2 mL/min.

Example 55. tetrahydro-2H-pyran-4-yl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

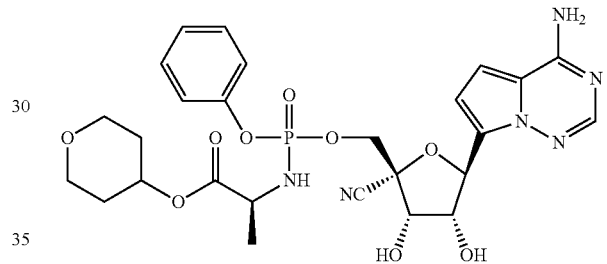

To a mixture of Intermediate 22 (1.7 g, 3.77 mmol), Intermediate 4 (1 g, 3 mmol), and MgCl$_2$ (359 mg, 3.77 mmol) in acetonitrile (40 mL) was added N,N-diisopropylethylamine (0.98 g, 8 mmol) dropwise. The resulting mixture was stirred at 50° C. for 2 h, reaction mixture was cooled, diluted with EtOAc, washed with water and brine, the organic solvent was evaporated under vacuum, the residue was then dissolved in acetonitrile, cooled in ice bath, and con. HCl was added dropwise. The resulting mixture was stirred at room temperature for 2 h, cooled in ice bath, neutralized by dropwise addition of 2 N NaOH and NaHCO$_3$ solution, diluted with EtOAc (150 mL), washed with water (50 mL) and brine (50 mL). The aqueous phase was extracted with EtOAc (50 mL×2) and the combined organic layer was dried under sodium sulfate, concentrated in vacuum, and residue was purified by silica gel column chromatography eluting with 0-100% MeOH in DCM to afford the product. $^1$H NMR (400 MHz, Methanol-d4) δ 7.80 (s, 1H), 7.78 (s, 1H), 7.33-7.24 (m, 2H), 7.24-7.10 (m, 3H), 6.84 (d, J=4.5 Hz, 1H), 6.73 (d, J=4.5 Hz, 1H), 5.50 (d, J=5.0 Hz, 1H), 4.62 (t, J=5.3 Hz, 1H), 4.54-4.42 (m, 2H), 4.35 (dd, J=10.9, 5.2 Hz, 1H), 3.97-3.80 (m, 3H), 3.56-3.44 (m, 2H), 1.89-1.81 (m, 2H), 1.60 (dtd, J=12.9, 8.6, 3.9 Hz, 2H), 1.27 (dd, J=7.2, 1.3 Hz, 4H), 1.14 (d, J=6.1 Hz, 5H). $^{31}$P NMR (162 MHz, Methanol-d4) δ 3.23. LCMS: MS m/z=603.14 [M+1], t$_R$=1.20 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: $t_R$=2.87 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 56. Single Diastereomer of tetrahydro-2H-pyran-4-yl (((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

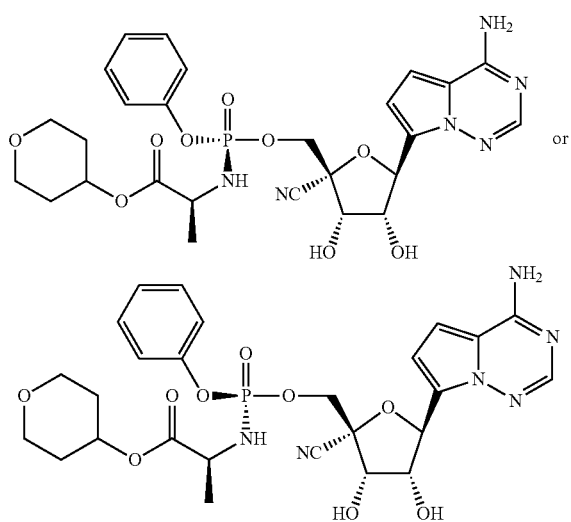

First Eluting Diastereomer of Example 55: $^1$H NMR (400 MHz, Methanol-d4) δ 7.78 (s, 1H), 7.29 (dd, J=8.7, 7.0 Hz, 2H), 7.16 (ddd, J=7.1, 2.1, 1.1 Hz, 3H), 6.85 (d, J=4.5 Hz, 1H), 6.73 (d, J=4.5 Hz, 1H), 5.50 (d, J=5.0 Hz, 1H), 4.88 (dq, J=9.4, 5.1, 4.7 Hz, 1H), 4.63 (t, J=5.3 Hz, 1H), 4.55-4.44 (m, 2H), 4.36 (dd, J=10.9, 5.2 Hz, 1H), 3.86 (m, 3H), 3.50 (dtd, J=11.3, 5.4, 2.7 Hz, 2H), 1.94-1.76 (m, 2H), 1.60 (dtd, J=12.9, 8.4, 3.9 Hz, 2H), 1.27 (dd, J=7.1, 1.3 Hz, 3H). $^{31}$P NMR (162 MHz, Methanol-d4) δ 3.23. MS m/z=603 (M+H)+.

Example 57. Single Diastereomer of tetrahydro-2H-pyran-4-yl (((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

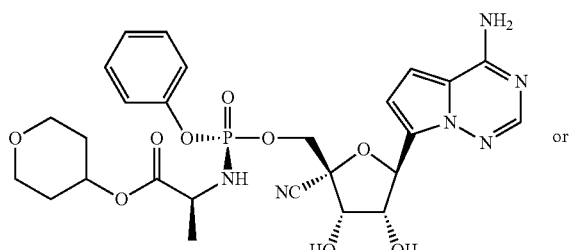

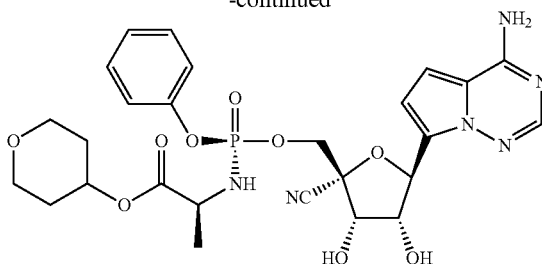

Second eluting diastereomer of Example 55: $^1$H NMR (400 MHz, Methanol-d4) δ 7.80 (s, 1H), 7.33 (dd, J=8.6, 7.2 Hz, 2H), 7.27-7.11 (m, 3H), 6.84 (d, J=4.5 Hz, 1H), 6.74 (d, J=4.5 Hz, 1H), 5.49 (d, J=5.0 Hz, 1H), 4.80 (m, 1H), 4.61 (t, J=5.3 Hz, 1H), 4.50-4.38 (m, 2H), 4.35 (dd, J=10.9, 5.5 Hz, 1H), 3.90 (dq, J=9.9, 7.1 Hz, 1H), 3.85-3.75 (m, 2H), 3.46 (dddd, J=11.8, 8.9, 6.0, 3.2 Hz, 2H), 1.81 (tdd, J=9.6, 4.6, 2.5 Hz, 2H), 1.57 (dtd, J=12.7, 8.4, 3.9 Hz, 2H), 1.27 (dd, J=7.1, 1.1 Hz, 3H). $^{31}$P NMR (162 MHz, Methanol-d4) δ 3.23. MS m/z=603 (M+H)+.

Example 58. 3-3-Methoxypropyl (((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

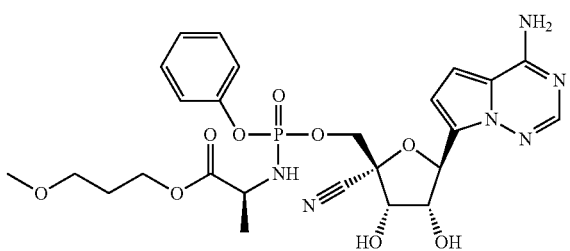 [SMILES: COCCCOC(=O)[C@H](C)NP(=O)(OC[C@@]1(C#N)O[C@@H](c2ccc3c(N)ncnn23)[C@H](O)[C@@H]1O)Oc1ccccc1]

To a mixture of Intermediate 4 (127 mg, 0.38 mmol), Intermediate 53 (252 mg, 0.58 mmol), and MgCl$_2$ (55 mg, 0.58 mmol) in THF (5 mL) was added N,N-diisopropylethylamine (0.17 mL, 0.97 mmol) dropwise at room temperature. The resulting mixture was stirred at 50° C. for 2 h and purified by preparative HPLC (Phenominex Gemini-NX 10 u C18 110 Å 250×30 mm column, ACN 10 to 100% in water). The obtained residue was dissolved in ACN (8 mL) and c-HCl (0.2 mL) added. The resulting mixture was stirred at room temperature for 1 h, cooled under ice bath, and aq. NaHCO$_3$ (4 mL) added slowly. The mixture was concentrated to half volume and purified by preparative HPLC (Phenominex Gemini-NX 10 u C18 110 Å 250×30 mm column, ACN 10 to 100% in water) to afford the product. $^1$H NMR (400 MHz, Methanol-d4) δ 7.80 (s, 0.64H), 7.78 (s, 0.36H), 7.31 (m, 2H), 7.25-7.12 (m, 3H), 6.84 (m, 1H), 6.73 (m, 1H), 5.50 (m, 1H), 4.62 (m, 1H), 4.53-4.38 (m, 2H), 4.34 (m, 1H), 4.17-4.00 (m, 2H), 3.93-3.83 (m, 1H), 3.39 (m, 2H), 3.27 (m, 3H), 1.81 (m, 2H), 1.26 (m, 3H). $^{31}$P NMR (162 MHz, Methanol-d4) δ 3.24. LCMS: m/z=591.18 (M+H), $t_R$=0.96 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.96 min (35%) and 4.02 min (64%); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Resolution of the Sp and Rp diastereomers. The product was separated by IA SFC 5 um, 21×250 mm (30% 2-propanol) to afford the diastereomers:

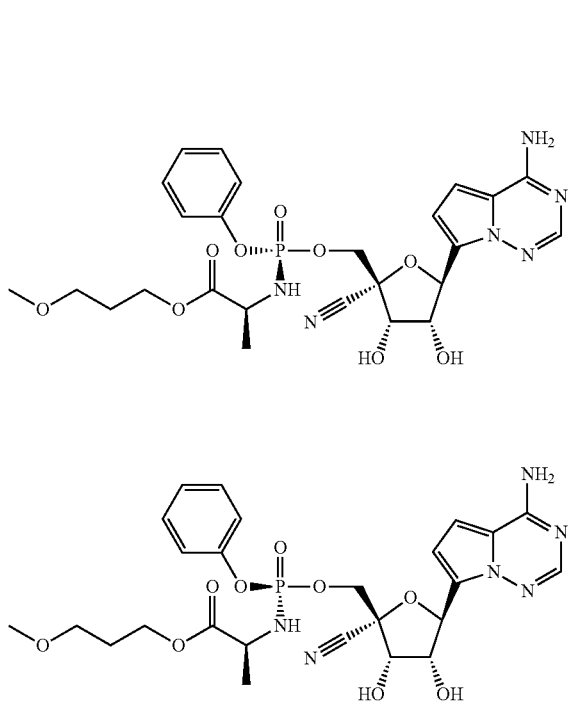 [SMILES: COCCCOC(=O)[C@H](C)N[P@@](=O)(OC[C@@]1(C#N)O[C@@H](c2ccc3c(N)ncnn23)[C@H](O)[C@@H]1O)Oc1ccccc1 ; COCCCOC(=O)[C@H](C)N[P@](=O)(OC[C@@]1(C#N)O[C@@H](c2ccc3c(N)ncnn23)[C@H](O)[C@@H]1O)Oc1ccccc1]

Example 59. First eluting diastereomer of Example 58: $^1$H NMR (400 MHz, Methanol-d4) δ 7.78 (s, 1H), 7.33-7.25 (m, 2H), 7.19-7.12 (m, 3H), 6.84 (d, J=4.5 Hz, 1H), 6.72 (d, J=4.5 Hz, 1H), 5.51 (d, J=5.0 Hz, 1H), 4.63 (t, J=5.3 Hz, 1H), 4.52 (d, J=5.6 Hz, 1H), 4.47 (dd, J=10.9, 6.0 Hz, 1H), 4.35 (dd, J=10.9, 5.1 Hz, 1H), 4.12 (td, J=6.5, 2.1 Hz, 2H), 3.89 (ddd, J=14.4, 10.8, 6.6 Hz, 1H), 3.39 (t, J=6.2 Hz, 2H), 3.26 (s, 3H), 1.83 (m, 2H), 1.25 (dd, J=7.1, 1.2 Hz, 3H). $^{31}$P NMR (162 MHz, Methanol-d4) δ 3.24. HPLC: $t_R$=3.96 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 60

Second eluting diastereomer of Example 58: $^1$H NMR (400 MHz, Methanol-d4) δ 7.79 (s, 1H), 7.32 (dd, J=8.6, 7.2 Hz, 2H), 7.22 (dt, J=8.6, 1.3 Hz, 2H), 7.20-7.13 (m, 1H), 6.83 (d, J=4.5 Hz, 1H), 6.73 (d, J=4.5 Hz, 1H), 5.50 (d, J=5.0 Hz, 1H), 4.62 (t, J=5.3 Hz, 1H), 4.47 (d, J=5.6 Hz, 1H), 4.41 (dd, J=10.9, 6.3 Hz, 1H), 4.34 (dd, J=10.9, 5.5 Hz, 1H), 4.07 (qt, J=10.9, 6.4 Hz, 2H), 3.90 (dq, J=10.0, 7.1 Hz, 1H), 3.37 (t, J=6.2 Hz, 2H), 3.25 (s, 3H), 1.79 (m, 2H), 1.26 (dd, J=7.2, 1.0 Hz, 3H). $^{31}$P NMR (162 MHz, Methanol-d4) δ 3.24. HPLC: $t_R$=4.02 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 61. (R)-1-methylpyrrolidin-3-yl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

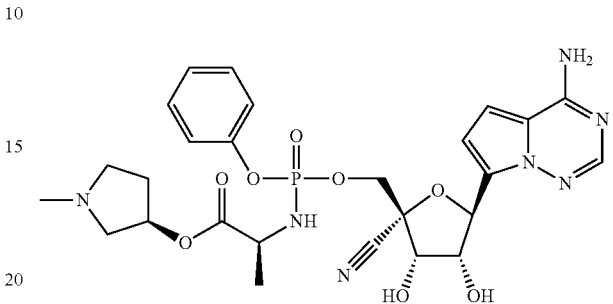

Intermediate 4 (50 mg, 0.15 mmol) and Intermediate 24 (81 mg, 0.18 mmol) were mixed and dissolved in 1.5 mL of anhydrous THF. Magnesium chloride (43 mg, 0.45 mmol) was added in one portion. DIPEA (65 uL, 0.375 mmol) was added, and the reaction was stirred at 50° C. for 16 hrs.

Reaction was diluted with EtOAc (15 mL) and washed with water (6×10 mL) and then with brine (5 mL). Organic extract was dried over anhydrous sodium sulfate and concentrated under reduced pressure. The crude residue was purified via SiO$_2$ column chromatography (4 g SiO$_2$ Combiflash HP Gold Column, 0-5-10-20% methanol/DCM). Fractions were combined and concentrated under reduced pressure. Residue was dissolved in MeCN (5 mL) and stirred in an ice bath. Concentrate aqueous hydrochloric acid (300 uL) was added dropwise. Reaction was stirred in an ice bath for 2 hrs. Reaction was diluted with EtOAc (20 mL) and added saturated aqueous sodium bicarbonate solution (30 mL). Mixture was stirred for 10 mins. Organic extract was collected and aqueous portion was extracted with EtOAc (2×10 mL). Organic extracts were combined, dried over anhydrous sodium sulfate and concentrated under reduced pressure. Residue was dissolved in MeCN and water and freeze-dried to give the product. $^1$H NMR (400 MHz, methanol-d$_4$) δ 7.80 (m, 1H), 7.41-7.09 (m, 5H), 6.85 (m, 1H), 6.74 (m, 1H), 5.49 (m, 1H), 5.33-5.15 (m, 1H), 4.70-4.58 (m, 1H), 4.56-4.28 (m, 3H), 4.00-3.86 (m, 1H), 3.28-3.07 (m, 3H), 3.03-2.83 (m, 1H), 2.69 (m, 3H), 2.35 (m, 1H), 2.00 (m, 1H), 1.28 (m, 3H). $^{31}$P NMR (162 MHz, methanol-d4) δ 3.39, 3.05. LCMS: MS m/z=602.2 [M+1], 599.9 [M−1], $t_R$=1.00 min; LC system: Thermo Dionex Ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=1.85 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min. HPLC: $t_R$=3.142, 3.190 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 62. methyl (2S)-3-(4-(((((2R,3S,4R,5S)-5-(4-aminopyrrolo[2,1-f][1,2,4]triazin-7-yl)-2-cyano-3,4-dihydroxytetrahydrofuran-2-yl)methoxy)(((S)-1-methoxy-1-oxopropan-2-yl)amino)phosphoryl)oxy)phenyl)-2-(((benzyloxy)carbonyl)amino)propanoate

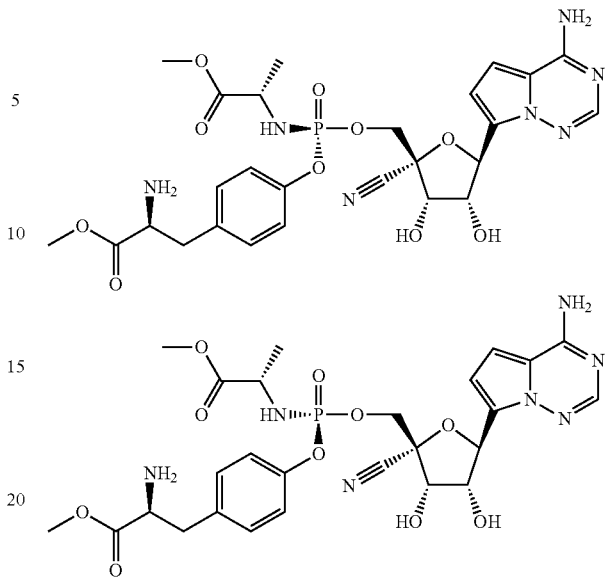

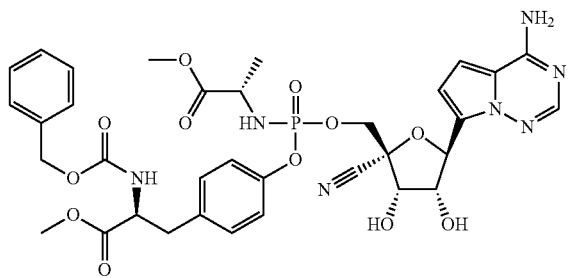 [SMILES: COC(=O)[C@H](C)NP(=O)(OC[C@@]1(C#N)O[C@@H](c2ccc3c(N)ncnn23)[C@H](O)[C@@H]1O)Oc1ccc(C[C@H](NC(=O)OCc2ccccc2)C(=O)OC)cc1]

methyl (2S)-3-(4-(((((2R,3S,4R,5S)-5-(4-aminopyrrolo[2,1-f][1,2,4]triazin-7-yl)-2-cyano-3,4-dihydroxytetrahydrofuran-2-yl)methoxy)(((S)-1-methoxy-1-oxopropan-2-yl)amino)phosphoryl)oxy)phenyl)-2-(((benzyloxy)carbonyl)amino)propanoate. N,N-Diisopropylethylamine (0.11 mL, 0.604 mmol) and magnesium chloride (23 mg, 0.24 mmol) were added to a mixture of Intermediate 4 (80 mg, 0.24 mmol) and Intermediate 54 (178 mg, 0.29 mmol) in tetrahydrofuran (3.8 mL) at RT. The mixture was heated to 55° C. After 2 h, the reaction mixture was allowed to cool to RT, diluted with ethyl acetate (50 mL) and the resulting mixture was washed with water (5×50 mL) and brine (50 mL). The organic layer was dried over anhydrous sodium sulfate and concentrated under reduced pressure. Concentrated aqueous hydrochloric acid solution (0.11 mL) was added dropwise to the crude residue in acetonitrile (3.8 mL) at 0° C. The mixture was warmed to RT. After 3.5 h, the reaction mixture was diluted with ethyl acetate (50 mL) and the resulting mixture was washed with saturated aqueous sodium carbonate solution (2×50 mL) and brine (50 mL). The organic layer was dried over anhydrous sodium sulfate and concentrated under reduced pressure. The crude residue was subjected to silica gel chromatography eluting with 0-25% methanol in dichloromethane to afford the product. $^{1}$H NMR (400 MHz, Methanol-$d_4$) δ 7.78 (d, J=9.1 Hz, 1H), 7.38-7.25 (m, 5H), 7.19-7.09 (m, 3H), 7.06 (dd, J=8.7, 1.2 Hz, 1H), 6.84 (dd, J=4.5, 1.3 Hz, 1H), 6.72 (dd, J=7.2, 4.5 Hz, 1H), 5.56-5.46 (m, 1H), 5.03 (d, J=2.9 Hz, 2H), 4.63 (td, J=5.3, 4.4 Hz, 1H), 4.54-4.29 (m, 4H), 3.87 (ddq, J=16.7, 9.4, 7.1 Hz, 1H), 3.69 (d, J=3.0 Hz, 3H), 3.61 (d, J=15.9 Hz, 4H), 3.20-3.06 (m, 1H), 2.91 (dt, J=14.0, 8.4 Hz, 1H), 1.24 (td, J=7.1, 1.1 Hz, 3H). $^{31}$P NMR (162 MHz, Methanol-$d_4$) δ 3.27 (d, J=2.1 Hz). LCMS: MS m/z=768.49 [M+1], $t_R$=1.12 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.95 min, 4.02 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

methyl (2S)-3-(4-(((((2R,3S,4R,5S)-5-(4-aminopyrrolo[2,1-f][1,2,4]triazin-7-yl)-2-cyano-3,4-dihydroxytetrahydrofuran-2-yl)methoxy)(((S)-1-methoxy-1-oxopropan-2-yl)amino)phosphoryl)oxy)phenyl)-2-(((benzyloxy)carbonyl)amino)propanoate. Palladium on carbon (10.3 mg, 10 wt %) was added to a solution of methyl (2S)-3-(4-(((((2R,3S,4R,5S)-5-(4-aminopyrrolo[2,1-f][1,2,4]triazin-7-yl)-2-cyano-3,4-dihydroxytetrahydrofuran-2-yl)methoxy)(((S)-1-methoxy-1-oxopropan-2-yl)amino)phosphoryl)oxy)phenyl)-2-(((benzyloxy)carbonyl)amino)propanoate (30.6 mg, 0.04 mmol) in ethanol (5 mL) that was purged with argon. The mixture was then purged with hydrogen and stirred at RT. After 18 hr, the mixture was filtered through celite, the filter was rinsed with ethanol, and the volatiles were removed under reduce pressure. The crude residue was subjected to preparatory HPLC (Phenomenex Synergi 4 um Polar-RP 80 Å 150×21.2 mm column, 10-60% acetonitrile/water gradient with 0.1% TFA) to afford the product as TFA salts.

Example 62

First Eluting Diastereomer: $^{1}$H NMR (400 MHz, Methanol-$d_4$) δ 7.95 (s, 1H), 7.29-7.16 (m, 5H), 6.93 (s, 1H), 5.53 (d, J=5.3 Hz, 1H), 4.59 (t, J=5.4 Hz, 1H), 4.52-4.43 (m, 2H), 4.37 (dd, J=10.9, 5.2 Hz, 1H), 4.30 (dd, J=7.6, 6.1 Hz, 1H), 4.03-3.87 (m, 1H), 3.81 (s, 3H), 3.69 (s, 3H), 3.25 (dd, J=14.5, 6.1 Hz, 1H), 3.13 (dd, J=14.6, 7.4 Hz, 1H), 1.34 (dd, J=7.4, 1.2 Hz, 3H). $^{19}$F NMR (376 MHz, Methanol-$d_4$) δ −77.68. $^{31}$P NMR (162 MHz, Methanol-$d_4$) δ 3.54. LCMS: MS m/z=634.18 [M+1], $t_R$=0.77 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=2.30 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Example 63

Second Eluting Diastereomer: $^1$H NMR (400 MHz, Methanol-d$_4$) δ 7.94 (s, 1H), 7.32-7.22 (m, 4H), 7.14 (s, 1H), 6.89 (s, 1H), 5.52 (d, J=4.9 Hz, 1H), 4.58 (t, J=5.3 Hz, 1H), 4.40 (dd, J=12.5, 5.8 Hz, 2H), 4.37-4.28 (m, 2H), 3.92 (dd, J=10.0, 7.3 Hz, 1H), 3.83 (s, 3H), 3.61 (s, 3H), 3.27-3.08 (m, 2H), 1.31 (d, J=7.1 Hz, 3H). $^{19}$F NMR (376 MHz, Methanol-d$_4$) δ −77.65. $^{31}$P NMR (162 MHz, Methanol-d$_4$) δ 3.48. LCMS: MS m/z=634.24 [M+1], t$_R$=0.80 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: t$_R$=2.43 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Example 64. (S)-Tetrahydrofuran-3-yl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

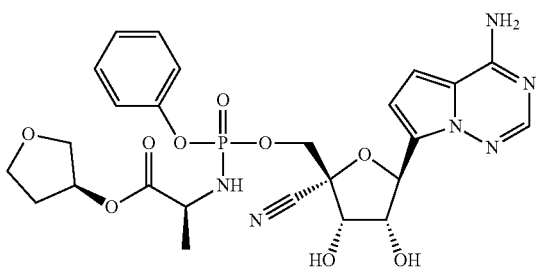 [SMILES: C[C@H](NP(=O)(OC[C@@]1(C#N)O[C@@H](c2ccc3c(N)ncnn23)[C@H](O)[C@@H]1O)Oc1ccccc1)C(=O)O[C@H]1CCOC1]

To a mixture of Intermediate 4 (132 mg, 0.40 mmol), Intermediate 55 (234 mg, 0.54 mmol), and MgCl$_2$ (46 mg, 0.48 mmol) in THF (5 mL) was added N,N-diisopropylethylamine (0.10 mL, 0.60 mmol) dropwise at room temperature. The resulting mixture was stirred at 50° C. for 2 h and purified by preparative HPLC (Phenominex Gemini-NX 10 u C18 110 Å 250×30 mm column, ACN 10 to 100% in water). The obtained residue was dissolved in ACN (4 mL) and c-HCl (0.2 mL) added. The resulting mixture was stirred at room temperature for 1 h, cooled under ice bath, neutralized with 5 N NaOH, and purified by preparative HPLC (Phenominex Gemini-NX 10 u C18 110 Å 250×30 mm column, ACN 10 to 100% in water) to afford the product. $^1$H NMR (400 MHz, Methanol-d4) δ 7.80 (s, 0.67H), 7.78 (s, 0.33H), 7.37-7.13 (m, 5H), 6.84 (m, 1H), 6.73 (m, 1H), 5.49 (m, 1H), 5.25-5.20 (m, 0.33H), 5.18-5.10 (m, 0.67H), 4.62 (m, 1H), 4.53-4.30 (m, 3H), 3.93-3.63 (m, 5H), 2.20-1.99 (m, 1H), 1.98-1.87 (m, 1H), 1.25 (m, 3H). LCMS: m/z=589.02 (M+H), t$_R$=1.06 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=3.75 min (29%), 3.81 min (68%); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Resolution of the Sp and Rp diastereomers. The mixture was separated by Chiralpak AD-H, 150×4.6 mm, 5 um (100% EtOH).

Example 65. Single Diastereomer of (S)-Tetrahydrofuran-3-yl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

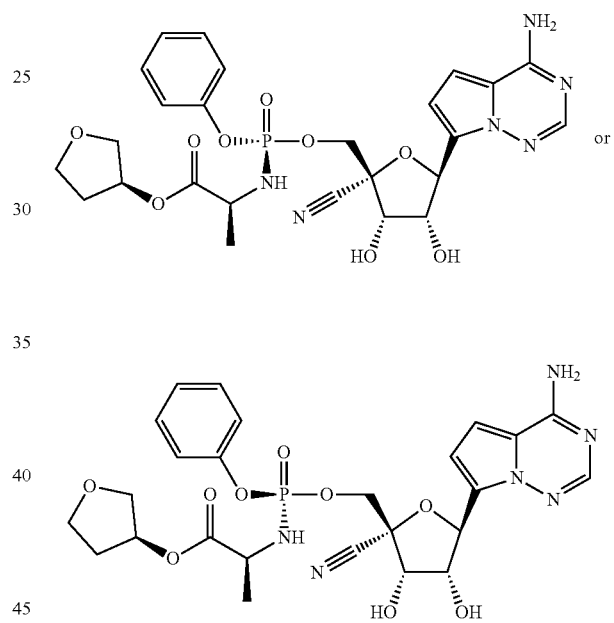

First eluting diastereomer of Example 64: $^1$H NMR (400 MHz, Methanol-d4) δ 7.78 (s, 1H), 7.28 (m, 2H), 7.16 (dt, J=8.1, 1.3 Hz, 3H), 6.84 (d, J=4.5 Hz, 1H), 6.73 (d, J=4.6 Hz, 1H), 5.50 (d, J=5.0 Hz, 1H), 5.23 (t, J=5.5 Hz, 1H), 4.63 (t, J=5.3 Hz, 1H), 4.51 (d, J=5.5 Hz, 1H), 4.47 (dd, J=10.9, 5.9 Hz, 1H), 4.35 (dd, J=10.9, 5.2 Hz, 1H), 3.92-3.68 (m, 5H), 2.23-2.06 (m, 1H), 2.01-1.91 (m, 1H), 1.25 (dd, J=7.1, 1.3 Hz, 3H). $^{31}$P NMR (162 MHz, Methanol-d4) δ 3.22. LCMS: m/z=589.02 (M+H), t$_R$=1.06 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=3.75 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 66. Single Diastereomer of (S)-Tetrahydrofuran-3-yl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

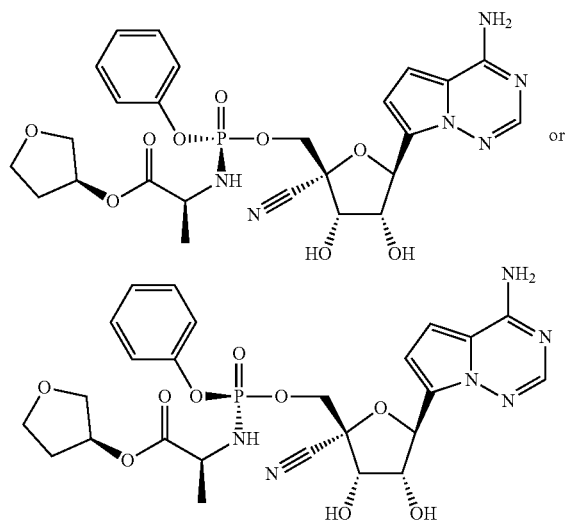

Second eluting diastereomer of Example 64: $^1$H NMR (400 MHz, Methanol-d4) δ 7.80 (s, 1H), 7.33 (dd, J=8.6, 7.2 Hz, 2H), 7.25-7.21 (m, 2H), 7.20-7.15 (m, 1H), 6.84 (d, J=4.5 Hz, 1H), 6.74 (d, J=4.5 Hz, 1H), 5.48 (d, J=5.0 Hz, 1H), 5.14 (dd, J=6.0, 4.1 Hz, 1H), 4.62 (t, J=5.3 Hz, 1H), 4.46 (d, J=5.7 Hz, 1H), 4.41 (dd, J=10.9, 6.4 Hz, 1H), 4.33 (dd, J=10.9, 5.4 Hz, 1H), 3.95-3.65 (m, 5H), 2.11-1.98 (m, 1H), 1.96-1.82 (m, 1H), 1.25 (dd, J=7.1, 1.1 Hz, 3H). $^{31}$P NMR (162 MHz, Methanol-d4) δ 3.19. LCMS: m/z=589.02 (M+H), $t_R$=1.07 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.82 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 67. 3-morpholinopropyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

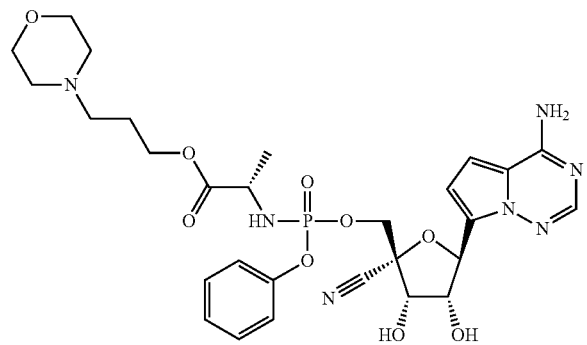 [SMILES: C[C@H](NP(=O)(OC[C@@]1(C#N)O[C@@H](c2ccc3c(N)ncnn23)[C@H](O)[C@@H]1O)Oc1ccccc1)C(=O)OCCCN1CCOCC1]

N,N-Diisopropylethylamine (0.11 mL, 0.62 mmol) and magnesium chloride (23.8 mg, 0.25 mmol) were added to a mixture of Intermediate 4 (82.7 mg, 0.25 mmol) and Intermediate 56 (133 mg, 0.27 mmol) in tetrahydrofuran (2.5 mL) at RT. The mixture was heated to 55° C. After 4.5 h, the reaction mixture was allowed to cool to RT, diluted with ethyl acetate (25 mL) and the resulting mixture was washed with water (2×15 mL) and brine (20 mL). The organic layer was dried over anhydrous sodium sulfate and concentrated under reduced pressure. Concentrated aqueous hydrochloric acid solution (0.12 mL) was added dropwise to the crude residue in acetonitrile (5 mL). After 4.5 h, the reaction mixture was concentrated under reduced pressure. 20 mg of the resulting crude residue was subjected preparatory HPLC (Phenomenex Gemini 10 u C18 110 Å AXIA 250×21.2 mm column, 30-70% acetonitrile/water gradient with 0.1% TFA) followed by silica gel chromatography eluting with 0-25% methanol in dichloromethane to afford the product. $^1$H NMR (400 MHz, Acetonitrile-d3) δ 7.94 (s, 1H), 7.43-7.19 (m, 6H), 5.51 (d, J=4.4 Hz, 1H), 4.55-4.43 (m, 3H), 4.43-4.33 (m, 2H), 4.09 (dt, J=9.4, 4.9 Hz, 2H), 3.95 (d, J=13.1 Hz, 3H), 3.77 (m, 2H), 3.38 (s, 2H), 3.13 (q, J=8.7, 7.9 Hz, 2H), 2.08-1.99 (m, 2H), 1.30 (t, J=8.6 Hz, 3H). $^{31}$P NMR (162 MHz, Methanol-d4) δ 2.70, 2.40. LCMS: MS m/z=646.35 [M+1], $t_R$=1.05 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.23 min; HPLC system: Agilent 1100 series; Column: Kinetx 2.6 u 100 A C18, 100 mm×4.6 mm; Solvents: Acetonitrile with 0.1% TFA, Water with 0.1% TFA; Gradient: 0 min-8.5 min 2-98% ACN, 8.5 min-10.0 min 98% ACN at 1.5 mL/min.

Example 68. (R)-Tetrahydrofuran-3-yl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

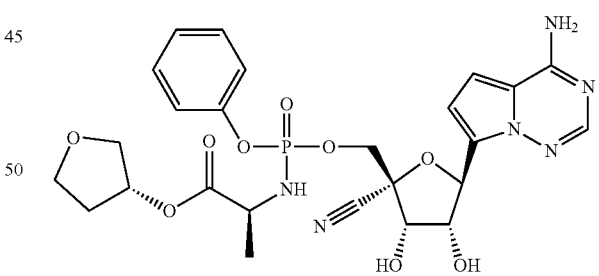

To a mixture of Intermediate 4 (130 mg, 0.40 mmol), Intermediate 57 (256 mg, 0.59 mmol), and MgCl2 (46 mg, 0.48 mmol) in THF (5 mL) was added N,N-diisopropylethylamine (0.10 mL, 0.60 mmol) dropwise at room temperature. The resulting mixture was stirred at 50° C. for 2 h and purified by preparative HPLC (Phenominex Gemini-NX 10 u C18 110 Å 250×30 mm column, ACN 10 to 100% in water). The obtained residue was dissolved in ACN (4 mL) and c-HCl (0.2 mL) added. The resulting mixture was stirred at room temperature for 1 h, cooled under ice bath, neutralized with 5 N NaOH, and purified by preparative HPLC (Phenominex Gemini-NX 10 u C18 110 Å 250×30 mm column, ACN 10 to 100% in water) to afford the product. $^1$H NMR (400 MHz, Methanol-d4) δ 7.80 (s, 0.71H), 7.78 (s, 0.29H), 7.31 (m, 2H), 7.25-7.13 (m, 3H), 6.84 (m, 1H), 6.73 (m, 1H), 5.49 (m, 1H), 5.23 (s, 0.29H), 5.20-5.14 (m, 0.71H), 4.66-4.59 (m, 1H), 4.53-4.30 (m, 3H), 3.95-3.69 (m, 5H), 2.22-2.05 (m, 1H), 1.99-1.85 (m, 1H), 1.25 (m, 3H). $^{31}$P NMR (162 MHz, Methanol-d4) δ 3.22, 3.17. LCMS: m/z=589.03 (M+H), $t_R$=1.07 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.77 min (25%), 3.82 min (75%); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The mixture was separated by Chiralpak IA (150×4.6 mm, 5 micron. 100% EtOH) to afford the diastereomers:

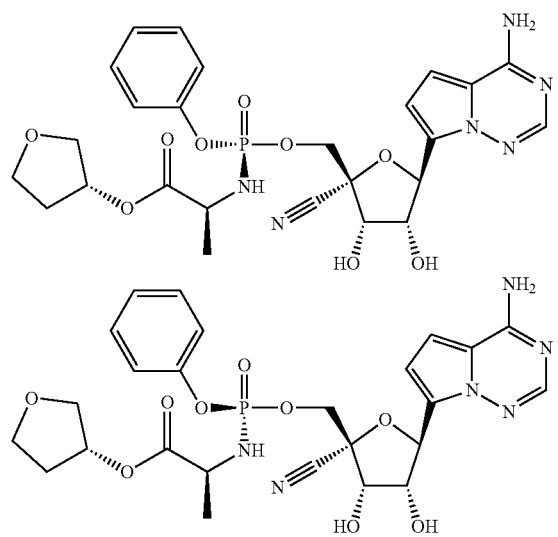

Example 69

First eluting diastereomer of Example 68: $^1$H NMR (400 MHz, Methanol-d4) δ 7.78 (s, 1H), 7.32-7.26 (m, 2H), 7.19-7.13 (m, 3H), 6.84 (d, J=4.5 Hz, 1H), 6.73 (d, J=4.6 Hz, 1H), 5.50 (d, J=5.0 Hz, 1H), 5.26-5.20 (m, 1H), 4.62 (t, J=5.3 Hz, 1H), 4.50 (d, J=5.6 Hz, 1H), 4.47 (dd, J=11.0, 6.0 Hz, 1H), 4.35 (dd, J=10.9, 5.2 Hz, 1H), 3.94-3.69 (m, 5H), 2.15 (td, J=14.5, 8.3 Hz, 1H), 1.99-1.86 (m, 1H), 1.25 (dd, J=7.2, 1.2 Hz, 3H). $^{31}$P NMR (162 MHz, Methanol-d4) δ 3.22. LCMS: m/z=589.09 (M+H), $t_R$=0.95 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.76 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 70

Second eluting diastereomer of Example 68: $^1$H NMR (400 MHz, Methanol-d4) δ 7.80 (s, 1H), 7.40-7.25 (m, 3H), 7.28-7.12 (m, 2H), 6.84 (d, J=4.5 Hz, 1H), 6.74 (d, J=4.5 Hz, 1H), 5.49 (d, J=5.1 Hz, 1H), 5.17 (td, J=4.1, 2.1 Hz, 1H), 4.62 (t, J=5.3 Hz, 1H), 4.46 (d, J=5.6 Hz, 1H), 4.41 (dd, J=10.9, 6.4 Hz, 1H), 4.34 (dd, J=10.9, 5.4 Hz, 1H), 3.98-3.68 (m, 5H), 2.18-2.03 (m, 1H), 1.96-1.83 (m, 1H), 1.25 (dd, J=7.2, 1.1 Hz, 3H). $^{31}$P NMR (162 MHz, Methanol-d4) δ 3.17. LCMS: m/z=589.10 (M+H), $t_R$=0.96 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.81 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 71. methyl (((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphorothioyl)-L-alaninate

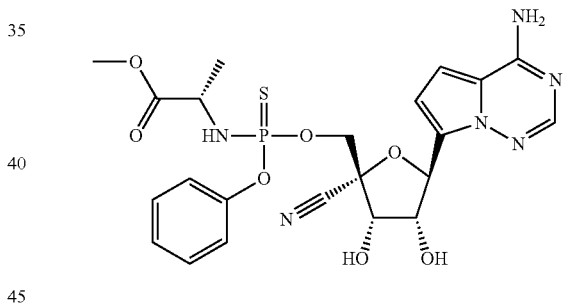

Triethylamine (170 μl, 1.2 mmol) was added to a solution of Intermediate 4 (0.40 g, 1.2 mmol) and Intermediate 58 (0.35 g, 1.2 mmol) in acetonitrile (6 mL) at RT. The reaction mixture was warmed to 65° C. After 3 h, the reaction mixture was allowed to cool to RT and concentrated aqueous hydrochloric acid solution (300 μL) was added. After 1 h, saturated aqueous sodium bicarbonate solution (5 mL) was slowly added and the resulting mixture was extracted with dichloromethane (3×5 mL). The combined organic extracts were dried over anhydrous sodium sulfate and were concentrated under reduced pressure. The crude residue was subjected to silica gel chromatography eluting with 0-100% ethyl acetate in hexanes to afford the product. $^1$H NMR (400 MHz, methanol-d$_4$) δ 7.95 (br s, 1H), 7.40-7.02 (m, 5H), 6.90-6.72 (m, 2H), 5.52-5.45 (m, 1H), 4.58-4.49 (m, 1H), 4.43-4.30 (m, 2H), 3.90-3.77 (m, 2H), 3.71-3.54 (m, 3H), 1.38-1.29 (m, 3H). LCMS: MS m/z=549.27 [M+1], $t_R$=1.23 min (minor isomer), 1.25 (major isomer); LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.21 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=5.124 min (minor isomer), 5.221 min (major isomer); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 72. methyl (2S)-3-(4-(((((2R,3S,4R,5S)-5-(4-aminopyrrolo[2,1-f][1,2,4]triazin-7-yl)-2-cyano-3,4-dihydroxytetrahydrofuran-2-yl)methoxy)(((S)-1-isopropoxy-1-oxopropan-2-yl)amino)phosphoryl)oxy)phenyl)-2-(((benzyloxy)carbonyl)amino)propanoate

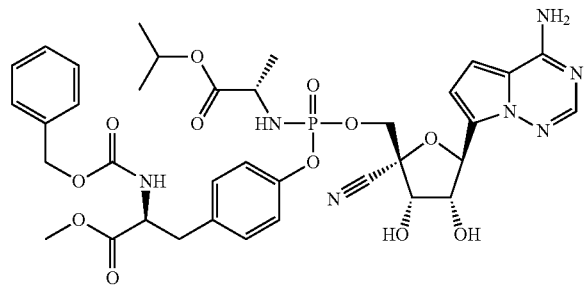 [SMILES: COC(=O)[C@H](Cc1ccc(OP(=O)(N[C@@H](C)C(=O)OC(C)C)OC[C@@]2(C#N)O[C@@H](c3ccc4c(N)ncnn34)[C@H](O)[C@@H]2O)cc1)NC(=O)OCc1ccccc1]

N,N-Diisopropylethylamine (0.06 mL, 0.33 mmol) and magnesium chloride (12.3 mg, 0.13 mmol) were added to a mixture of Intermediate 4 (42.7 mg, 0.13 mmol) and Intermediate 66 (82.9 mg, 0.13 mmol) in tetrahydrofuran (1.5 mL) at RT. The mixture was heated to 55° C. After 4 h, the reaction mixture was allowed to cool to RT, diluted with ethyl acetate (20 mL) and the resulting mixture was washed with water (5×15 mL) and brine (20 mL). The organic layer was dried over anhydrous sodium sulfate and concentrated under reduced pressure. Concentrated aqueous hydrochloric acid solution (0.06 mL) was added dropwise to the crude residue in acetonitrile (1.5 mL) at 0° C. The mixture was warmed to RT. After 2 h, the reaction mixture was diluted with ethyl acetate (20 mL) and the resulting mixture was washed with saturated aqueous sodium carbonate solution (20 mL) and brine (20 mL). The organic layer was dried over anhydrous sodium sulfate and concentrated under reduced pressure. The crude residue was subjected to silica gel chromatography eluting with 0-20% methanol in dichloromethane to afford the product. $^1$H NMR (400 MHz, Methanol-d$_4$) δ 7.79 (d, J=8.0 Hz, 1H), 7.31 (ddd, J=11.2, 6.2, 3.3 Hz, 5H), 7.20-7.10 (m, 3H), 7.06 (d, J=8.3 Hz, 1H), 6.87-6.80 (m, 1H), 6.72 (dd, J=5.5, 4.7 Hz, 1H), 5.56-5.44 (m, 1H), 5.03 (d, J=3.6 Hz, 2H), 4.91 (ddd, J=24.9, 12.6, 6.3 Hz, 1H), 4.62 (t, J=5.4 Hz, 1H), 4.48 (dd, J=11.8, 5.5 Hz, 1H), 4.45-4.28 (m, 3H), 3.90-3.77 (m, 1H), 3.69 (d, J=3.5 Hz, 3H), 3.16-3.05 (m, 1H), 2.91 (dt, J=14.0, 8.8 Hz, 1H), 1.25 (dt, J=7.2, 1.4 Hz, 3H), 1.20 (d, J=6.3 Hz, 3H), 1.16 (t, J=6.3 Hz, 3H). $^{31}$P NMR (162 MHz, Methanol-d4) δ 3.36, 3.33. LCMS: MS m/z=796.45 [M+1], $t_R$=1.17 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.44 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Example 73. isopropyl (2S)-3-(4-(((((2R,3S,4R,5S)-5-(4-aminopyrrolo[2,1-f][1,2,4]triazin-7-yl)-2-cyano-3,4-dihydroxytetrahydrofuran-2-yl)methoxy)(((S)-1-methoxy-1-oxopropan-2-yl)amino)phosphoryl)oxy)phenyl)-2-(((benzyloxy)carbonyl)amino)propanoate

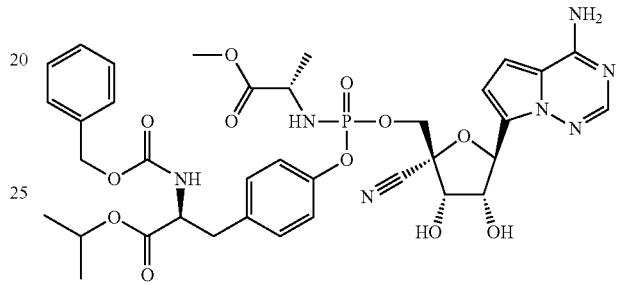

N,N-Diisopropylethylamine (0.11 mL, 0.0.62 mmol) and magnesium chloride (23.8 mg, 0.25 mmol) were added to a mixture of Intermediate 4 (82.7 mg, 0.25 mmol) and Intermediate 69 (176.6 mg, 0.27 mmol) in tetrahydrofuran (2.5 mL) at RT. The mixture was heated to 55° C. After 4.5 h, the reaction mixture was allowed to cool to RT, diluted with ethyl acetate (25 mL) and the resulting mixture was washed with water (2×15 mL) and brine (20 mL). The organic layer was dried over anhydrous sodium sulfate and concentrated under reduced pressure. Concentrated aqueous hydrochloric acid solution (0.12 mL) was added dropwise to the crude residue in acetonitrile (5 mL). After 4.5 h, the reaction mixture was diluted with ethyl acetate (25 mL) and the resulting mixture was washed with saturated aqueous sodium carbonate solution (2×20 mL) and brine (20 mL). The organic layer was dried over anhydrous sodium sulfate and concentrated under reduced pressure. The crude residue was subjected to silica gel chromatography eluting with 0-25% methanol in dichloromethane to afford the product. $^1$H NMR (400 MHz, Methanol-d$_4$) δ 7.79 (d, J=9.3 Hz, 1H), 7.36-7.21 (m, 5H), 7.20-7.10 (m, 3H), 7.09-7.03 (m, 1H), 6.84 (dd, J=4.5, 1.0 Hz, 1H), 6.73 (dd, J=7.4, 4.5 Hz, 1H), 5.51 (t, J=4.8 Hz, 1H), 5.04 (d, J=2.2 Hz, 2H), 5.01-4.89 (m, 1H), 4.66-4.60 (m, 1H), 4.55-4.28 (m, 4H), 3.87 (ddd, J=16.3, 9.6, 7.1 Hz, 1H), 3.61 (d, J=16.9 Hz, 3H), 3.09 (dt, J=14.2, 5.8 Hz, 1H), 2.91 (dt, J=15.3, 8.2 Hz, 1H), 1.24 (dtd, J=9.4, 4.9, 4.3, 1.6 Hz, 6H), 1.16 (dd, J=6.3, 3.8 Hz, 3H). $^{31}$P NMR (162 MHz, Methanol-d$_4$) δ 3.27. LCMS: MS m/z=796.51 [M+1], $t_R$=1.25 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.331 min, 4.395 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Example 74. 2-(diisopropylamino)ethyl ((((2R,3S, 4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate

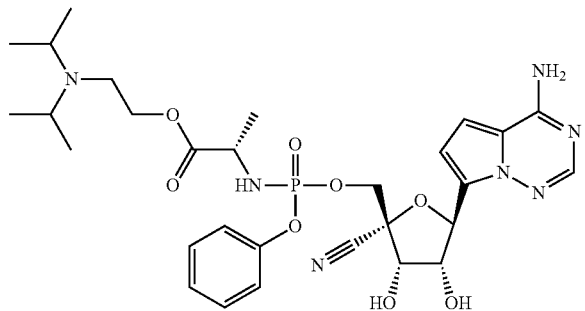 [SMILES: CC(C)N(CCOC(=O)[C@H](C)NP(=O)(OC[C@@]1(C#N)O[C@@H](c2ccc3c(N)ncnn23)[C@H](O)[C@@H]1O)Oc1ccccc1)C(C)C]

N,N-Diisopropylethylamine (0.20 mL, 1.17 mmol) and magnesium chloride (44.7 mg, 0.47 mmol) were added to a mixture of Intermediate 4 (155.6 mg, 0.47 mmol) and Intermediate 68 (231.8 mg, 0.47 mmol) in tetrahydrofuran (5.47 mL) at RT. The mixture was heated to 55° C. After 2 h, the reaction mixture was allowed to cool to RT, diluted with ethyl acetate (50 mL) and the resulting mixture was washed with water (2×50 mL) and brine (50 mL). The organic layer was dried over anhydrous sodium sulfate and concentrated under reduced pressure. Concentrated aqueous hydrochloric acid solution (0.40 mL) was added dropwise to the crude residue in acetonitrile (5 mL) at 0° C. The mixture was warmed to RT. After 20 h, the volatiles were removed under reduced pressure. The aqueous was lyophilized to afford the product that was used without further purification. LCMS: MS m/z=635.19 [M+1], $t_R$=0.95 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

Example 75. 2-(2-ethoxyethoxy)ethyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate single isomer

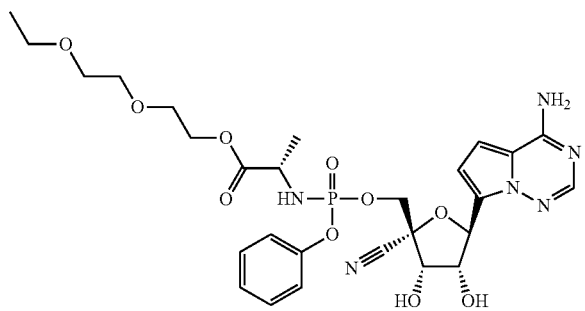 [SMILES: CCOCCOCCOC(=O)[C@H](C)NP(=O)(OC[C@@]1(C#N)O[C@@H](c2ccc3c(N)ncnn23)[C@H](O)[C@@H]1O)Oc1ccccc1]

Tetrahydrofuran (1.4 mL) was added to a mixture of Intermediate 4 (202 mg, 0.610 mmol), Intermediate 73 (418 mg, 0.793 mmol), and magnesium chloride (87 mg, 0.914 mmol) at room temperature. The mixture was heated to 40° C. for 10 min, and N,N-diisopropylethylamine (0.265 mL, 1.524 mmol) was added. After stirring for 2 hours at 40° C., the reaction mixture was allowed to cool to at room temperature, and was concentrated down under reduced pressure. The crude residue was dissolved in ethyl acetate (40 mL) and the resulting mixture was washed with water (30 mL) and brine (30 mL). The organic layer was separated, dried over anhydrous sodium sulfate and concentrated under reduced pressure. The crude residue was dissolved in acetonitrile (10 mL) and concentrated aqueous hydrochloric acid solution (0.508 mL) was added dropwise at 0° C. After 4 hours at 0° C., the reaction mixture was diluted with ethyl acetate (50 mL) and water (30 mL) at 0° C. and the resulting mixture was washed with saturated aqueous sodium bicarbonate solution (20 mL) and brine (20 mL). The organic layer was dried over anhydrous sodium sulfate and concentrated under reduced pressure. The crude residue was purified by preparatory HPLC (Phenomenex Gemini 5 μm C18 110 Å 100×30 mm column) using gradient from 10-100% acetonitrile in water to afford the product. $^1$H NMR (400 MHz, DMSO-$d_6$) δ 7.86 (s, 1H), 7.77 (bs, 2H), 7.41-7.32 (m, 2H), 7.27-7.12 (m, 3H), 6.85 (d, J=4.4 Hz, 1H), 6.74 (d, J=4.5 Hz, 1H), 6.25-6.07 (m, 2H), 5.50 (d, J=5.9 Hz, 1H), 5.38 (d, J=6.2 Hz, 1H), 4.54-4.42 (m, 1H), 4.35-4.21 (m, 2H), 4.22-4.08 (m, 2H), 4.07-3.95 (m, 1H), 3.92-3.77 (m, 1H), 3.55-3.49 (m, 2H), 3.49-3.44 (m, 2H), 3.43-3.36 (m, 4H), 1.20 (d, J=7.1 Hz, 3H), 1.07 (t, J=7.0 Hz, 3H). $^{31}$P NMR (162 MHz, DMSO-$d_6$) δ 3.24. LCMS: MS m/z=635.07 [M+1], $t_R$=1.17 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 L/min. HPLC: $t_R$=2.45 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=4.09 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 76. methyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(benzyloxy)phosphoryl)-L-alaninate

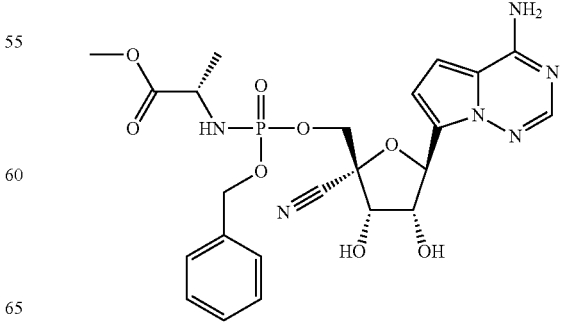

Acetonitrile (2.5 mL) was added to a mixture of Intermediate 4 (150 mg, 0.453 mmol), Intermediate 42 (179 mg, 0.453 mmol), and magnesium chloride (43 mg, 0.453 mmol) at RT. The mixture was heated to 50° C. for 5 min, and N,N-diisopropylethylamine (0.197 mL, 0.453 mmol) was added. After 22 h, the reaction mixture was allowed to cool to RT, and concentrated aqueous hydrochloric acid solution (0.5 mL) was added dropwise. After 1 h, the reaction mixture was diluted with ethyl acetate (100 mL) and the resulting mixture was washed with saturated aqueous sodium carbonate solution (50 mL) and brine (50 mL). The organic layer was dried over anhydrous sodium sulfate and concentrated under reduced pressure. The crude residue was subjected to silica gel chromatography eluting with 0-100% ethyl acetate in hexanes to afford the product. $^1$H NMR (400 MHz, methanol-$d_4$) δ 7.78 (s, 0.7H), 7.73 (s, 0.3H), 7.41-7.22 (m, 5H), 6.88-6.79 (m, 1H), 6.76-6.67 (m, 1H), 5.56-5.43 (m, 1H), 5.09-4.93 (m, 2H), 4.69-4.18 (m, 4H), 3.92-3.72 (m, 1H), 3.61 (s, 0.9H), 3.60 (s, 2.1H), 1.31-1.22 (m, 3H). $^{31}$P NMR (162 MHz, methanol-$d_4$) δ 7.88 (s), 7.81 (s). LCMS: MS m/z=547.06 [M+1], $t_R$=1.04 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=2.381 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

C. Compounds

Example 77. (2R,3S,4S,5S)-5-(4-aminopyrrolo[2,1-f][1,2,4]triazin-7-yl)-2-cyano-2-((((S)-(((S)-1-(cyclohexyloxy)-1-oxopropan-2-yl)amino)(phenoxy)phosphoryl)oxy)methyl) tetrahydrofuran-3,4-diyl bis(2-methylpropanoate)

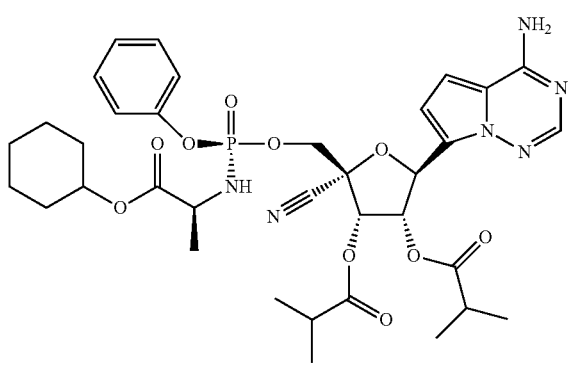 [SMILES: CC(C)C(=O)O[C@H]1[C@H](c2ccc3c(N)ncnn23)O[C@](C#N)(CO[P@@](=O)(N[C@@H](C)C(=O)OC2CCCCC2)Oc2ccccc2)[C@H]1OC(=O)C(C)C]

Example 6 (10 mg, 0.0167 mmol) was dissolved in anhydrous DMF (1 mL). Isobutyric acid (6.2 uL, 0.0667 mmol) and N, N'-diisopropylcarbodiimide (10.4 uL, 0.0667 mmol) were added to the reaction and stirred for 20 mins. DMAP (2 mg, 0.0167 mmol) was added, and the reaction was stirred for 16 hrs. More isobutyric acid (7 uL, 0.067 mmol) and N, N'-diisopropylcarbodiimide (11 uL, 0.067 mmol) were added to the reaction which was then stirred for 6 hrs. More isobutyric acid (4 uL, 0.034 mmol) and N, N'-diisopropylcarbodiimide (6 uL, 0.034 mmol) were added to the reaction which was stirred for 18 hrs. The crude residue was purified via SiO$_2$ column chromatography (4 g SiO$_2$ Combiflash HP Gold Column, 0-100% ethyl acetate/hexanes). Fractions were combined and concentrated under reduced pressure as oil which was then dissolved in MeCN and water and freeze-dried to afford the product. $^1$H NMR (400 MHz, Chloroform-d) δ 7.91 (s, 1H), 7.35-7.22 (m, 2H), 7.22-7.08 (m, 3H), 6.68 (d, J=4.5 Hz, 1H), 6.58 (d, J=4.5 Hz, 1H), 5.98-5.71 (m, 3H), 5.67 (d, J=3.7 Hz, 1H), 4.73 (dq, J=8.7, 4.2 Hz, 1H), 4.40 (d, J=6.3 Hz, 2H), 4.07-3.83 (m, 2H), 2.64 (dq, J=13.8, 6.9 Hz, 2H), 1.98-1.59 (m, 7H), 1.57-1.08 (m, 18H). $^{31}$P NMR (162 MHz, Chloroform-d) δ 2.42 (s). MS m/z=741.1 [M+1]; 739.2 [M-1].

Example 78. (2R,3S,4S,5S)-5-(4-aminopyrrolo[2,1-f][1,2,4]triazin-7-yl)-2-cyano-2-((((S)-(((S)-1-(cyclohexyloxy)-1-oxopropan-2-yl)amino)(phenoxy)phosphoryl)oxy)methyl) tetrahydrofuran-3,4-diyl bis(4-methylpentanoate)

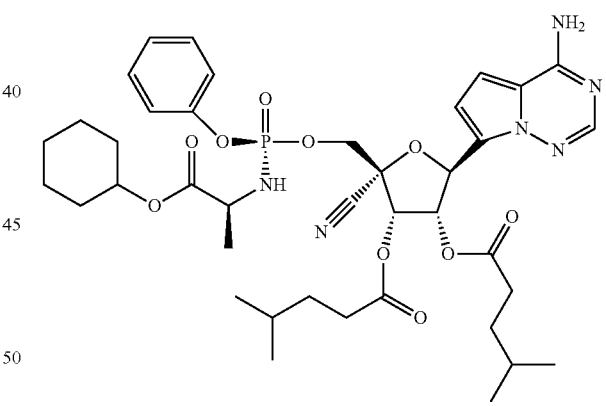

Example 6 (10 mg, 0.016 mmol) was dissolved in anhydrous DMF (1 mL). 4-Methylvaleric acid (10.4 uL, 0.083 mmol) and N, N'-diisopropylcarbodiimide (13 uL, 0.083 mmol) were added to the reaction and stirred for 20 mins. DMAP (2 mg, 0.0167 mmol) was added, and the reaction was stirred for 16 hrs.

More 4-Methylvaleric acid (10.4 uL, 0.083 mmol) and N, N'-diisopropylcarbodiimide (13 uL, 0.083 mmol) were added to the reaction which was then stirred for 5 hrs. Reaction was diluted with EtOAc (20 mL) and washed with saturated aqueous sodium bicarbonate solution (10 mL) and then with brine (10 mL). Organic fraction was dried over anhydrous sodium sulfate and concentrated under reduced pressure. The crude residue was purified via SiO$_2$ column chromatography (4 g SiO$_2$ Combiflash HP Gold Column, 0-70% ethyl acetate/hexanes). Fractions were combined and concentrated under reduced pressure as oil which was then dissolved in MeCN and water and freeze-dried to afford the product. $^1$H NMR (400 MHz, Methanol-d4) δ 7.82 (s, 1H), 7.31 (m, 2H), 7.24-7.10 (m, 3H), 6.84 (d, J=4.5 Hz, 1H), 6.73 (d, J=4.5 Hz, 1H), 5.89 (d, J=5.8 Hz, 1H), 5.79 (t, J=5.4 Hz, 1H), 5.68 (d, J=4.9 Hz, 1H), 4.68 (dt, J=8.8, 4.5 Hz, 1H), 4.51-4.36 (m, 2H), 3.95-3.79 (m, 1H), 2.54-2.26 (m, 4H), 1.83-1.45 (m, 10H), 1.45-1.26 (m, 10H), 0.97-0.82 (m, 12H). $^{31}$P NMR (162 MHz, Methanol-d4) δ 3.07 (s). MS m/z=797.1 [M+1]; 795.4 [M-1].

Example 79. (2R,3S,4S,5S)-5-(4-Aminopyrrolo[2,1-f][1,2,4]triazin-7-yl)-2-cyano-2-(((((S)-(((S)-1-oxo-1-((trans-4-(trifluoromethyl)cyclohexyl)oxy)propan-2-yl)amino) (phenoxy)phosphoryl)oxy)methyl) tetrahydrofuran-3,4-diyl bis(2-methylpropanoate)

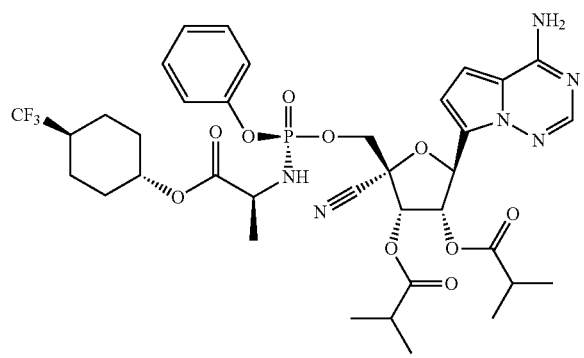 [SMILES: CC(C)C(=O)O[C@H]1[C@H](c2ccc3c(N)ncnn23)O[C@](C#N)(CO[P@@](=O)(N[C@@H](C)C(=O)O[C@H]2CC[C@H](C(F)(F)F)CC2)Oc2ccccc2)[C@H]1OC(=O)C(C)C]

A mixture of Example 18 (355 mg, 0.50 mmol), isobutyric acid (0.23 mL, 2.51 mmol), and N,N-diisopropylcarbodiimide (0.40 mL, 2.51 mmol) in DMF (5 mL), was stirred at room temperature for 20 min and DMAP (61.2 mg, 0.50 mmol) was added. The resulting mixture was stirred at room temperature for 2.5 h, diluted with EtOAc, washed with brine, and concentrated in vacuo. The resulting residue was purified by preparative HPLC (Phenomenex Gemini-NX 10μ C18 110° A 250×30 mm column, 0%-70% acetonitrile/water gradient in 25 min run) to afford the product. $^1$H NMR (400 MHz, Acetonitrile-d3) δ 7.90 (s, 1H), 7.34 (dd, J=8.6, 7.3 Hz, 2H), 7.23-7.14 (m, 3H), 6.75 (m, 2H), 6.37 (s, 2H), 5.86 (d, J=6.0 Hz, 1H), 5.80 (dd, J=5.9, 4.6 Hz, 1H), 5.68 (d, J=4.6 Hz, 1H), 4.60 (tt, J=10.6, 4.2 Hz, 1H), 4.52-4.27 (m, 3H), 3.87 (tq, J=9.6, 7.1 Hz, 1H), 2.64 (m, 2H), 2.18-2.05 (m, 1H), 2.02-1.86 (m, 4H), 1.49-1.12 (m, 19H). $^{31}$P NMR (162 MHz, Acetonitrile-d3) δ 2.46. $^{19}$F NMR (376 MHz, Acetonitrile-d3) δ -74.35 (d, J=8.7 Hz). LCMS: MS m/z=809.32 [M+1]; t$_R$=1.41 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=6.56 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 80. (2R,3S,4S,5S)-5-(4-Aminopyrrolo[2,1-f][1,2,4]triazin-7-yl)-2-((((S)-(((S)-1-(((1r,4S)-4-(tert-butyl)cyclohexyl)oxy)-1-oxopropan-2-yl)amino)(phenoxy)phosphoryl) oxy)methyl)-2-cyanotetrahydrofuran-3,4-diyl bis(2-methylpropanoate)

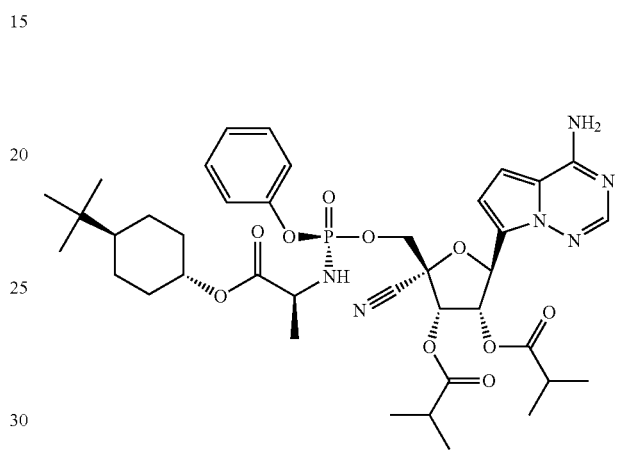

A mixture of (S)-isomer of Example 22 (40 mg, 0.061 mmol), isobutyric acid (0.023 mL, 0.244 mmol), and N,N-diisopropylcarbodiimide (0.038 mL, 0.244 mmol) in DMF (1 mL) was stirred at room temperature for 20 min and DMAP (8 mg, 0.065 mmol) was added. The resulting mixture was stirred at room temperature for 6 h and additional isobutyric acid (0.023 mL, 0.244 mmol), and DIC (0.038 mL, 0.244 mmol) were added. The resulting mixture was stirred for 1 h at room temperature and purified by preparative HPLC (Phenomenex Gemini-NX 10μ C18 110°A 250×30 mm column, 0%-70% acetonitrile/water gradient in 25 min run) to afford the product. $^1$H NMR (400 MHz, Methanol-d4) δ 7.83 (s, 1H), 7.34-7.26 (m, 2H), 7.23-7.11 (m, 3H), 6.84 (d, J=4.6 Hz, 1H), 6.73 (d, J=4.6 Hz, 1H), 5.89 (d, J=5.9 Hz, 1H), 5.77 (dd, J=5.8, 4.8 Hz, 1H), 5.68 (d, J=4.8 Hz, 1H), 4.55 (tt, J=11.2, 4.4 Hz, 1H), 4.45 (dd, J=5.8, 1.2 Hz, 2H), 3.86 (dq, J=10.0, 7.1 Hz, 1H), 2.64 (dhept, J=17.2, 7.0 Hz, 2H), 1.94 (d, J=10.6 Hz, 2H), 1.82-1.71 (m, 2H), 1.31-1.13 (m, 17H), 1.12-0.91 (m, 3H), 0.84 (s, 9H). $^{31}$P NMR (162 MHz, Methanol-d4) δ 3.03. LCMS: MS m/z=797.37 [M+1]; t$_R$=1.45 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=7.33 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 81. (2R,3S,4S,5S)-5-(4-aminopyrrolo[2,1-f][1,2,4]triazin-7-yl)-2-cyano-2-((((S)-(((S)-1-(cyclohexyloxy)-1-oxopropan-2-yl)amino)(phenoxy)phosphoryl)oxy)methyl) tetrahydrofuran-3,4-diyl diacetate

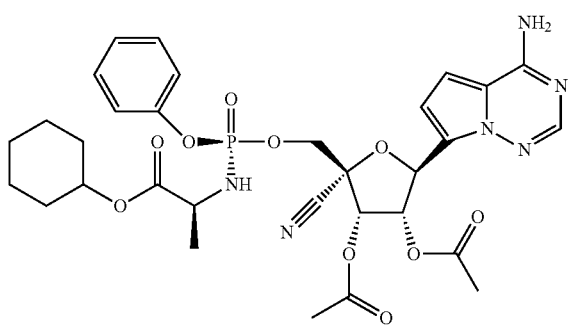 [SMILES: CC(=O)O[C@H]1[C@H](c2ccc3c(N)ncnn23)O[C@](C#N)(CO[P@@](=O)(N[C@@H](C)C(=O)OC2CCCCC2)Oc2ccccc2)[C@H]1OC(C)=O]

Example 6 (25 mg, 0.0416 mmol) was dissolved in anhydrous THF (1 mL). Acetic acid (12 uL, 0.208 mmol) and N, N'-diisopropylcarbodiimide (32 uL, 0.208 mmol) were added to the reaction and stirred for 20 mins. DMAP (5 mg, 0.0416 mmol) was added, and the reaction was stirred for 4 hrs. Reaction was concentrated under reduced pressure. The crude residue was purified via SiO$_2$ column chromatography (4 g SiO$_2$ Combiflash HP Gold Column, 0-100% ethyl acetate/hexanes). Fractions were combined and concentrated under reduced pressure as oil which was then dissolved in MeCN and water and freeze-dried to afford the product. $^1$H NMR (400 MHz, Chloroform-d) δ 7.88 (s, 1H), 7.32-7.23 (m, 2H), 7.23-7.09 (m, 3H), 6.63 (d, J=4.5 Hz, 1H), 6.52 (d, J=4.5 Hz, 1H), 5.93 (bs, 2H), 5.85 (d, J=5.7 Hz, 1H), 5.79 (dd, J=5.7, 4.1 Hz, 1H), 5.68 (d, J=4.1 Hz, 1H), 4.73 (m, 1H), 4.42 (d, J=6.4 Hz, 2H), 4.20-4.01 (m, 2H), 2.13 (s, 6H), 1.82-1.61 (m, 4H), 1.50 (m, 1H), 1.45-1.28 (m, 8H). $^{31}$P NMR (162 MHz, Chloroform-d) δ 2.49 (s). MS m/z=685.3 [M+1]; 683.3 [M−1].

Example 82. (2R,3S,4S,5S)-5-(4-aminopyrrolo[2,1-f][1,2,4]triazin-7-yl)-2-cyano-2-((((S)-(((S)-1-(cyclohexyloxy)-1-oxopropan-2-yl)amino)(phenoxy)phosphoryl)oxy)methyl) tetrahydrofuran-3,4-diyl dipropionate

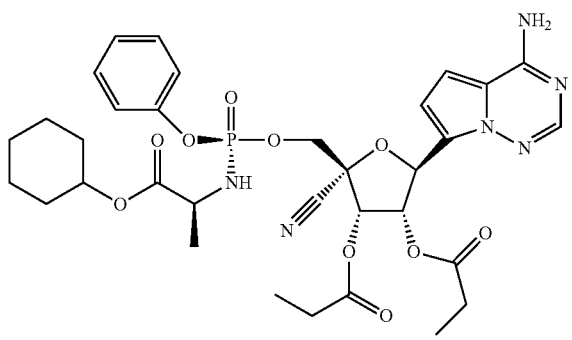 [SMILES: CCC(=O)O[C@H]1[C@H](c2ccc3c(N)ncnn23)O[C@](C#N)(CO[P@@](=O)(N[C@@H](C)C(=O)OC2CCCCC2)Oc2ccccc2)[C@H]1OC(=O)CC]

Example 6 (25 mg, 0.0416 mmol) was dissolved in anhydrous THF (1 mL). Propionic acid (16 uL, 0.208 mmol) and N, N'-diisopropylcarbodiimide (32 uL, 0.208 mmol) were added to the reaction and stirred for 20 mins. DMAP (5 mg, 0.0416 mmol) was added, and the reaction was stirred for 4 hrs. Reaction was concentrated under reduced pressure. The crude residue was purified via SiO$_2$ column chromatography (4 g SiO$_2$ Combiflash HP Gold Column, 0-100% ethyl acetate/hexanes). Fractions were combined and concentrated under reduced pressure as oil which was then dissolved in MeCN and water and freeze-dried to afford the product. $^1$H NMR (400 MHz, Chloroform-d) δ 7.89 (s, 1H), 7.35-7.22 (m, 2H), 7.22-7.09 (m, 3H), 6.65 (d, J=4.5 Hz, 1H), 6.54 (d, J=4.5 Hz, 1H), 5.95 (bs, 2H), 5.87 (d, J=5.8 Hz, 1H), 5.81 (dd, J=5.7, 3.9 Hz, 1H), 5.68 (d, J=3.9 Hz, 1H), 4.73 (m, 1H), 4.41 (d, J=6.3 Hz, 2H), 4.08-3.92 (m, 2H), 2.49-2.34 (m, 4H), 1.83-1.61 (m, 4H), 1.56-1.45 (m, 1H), 1.45-1.21 (m, 8H), 1.17 (m, 6H). $^{31}$P NMR (162 MHz, Chloroform-d) δ 2.46 (s). MS m/z=713.1 [M+1]; 711.2 [M−1].

Example 83. (2R,3S,4R,5S)-5-(4-aminopyrrolo[2,1-f][1,2,4]triazin-7-yl)-2-cyano-2-((((S)-(((S)-1-(cyclohexyloxy)-1-oxopropan-2-yl)amino)(phenoxy)phosphoryl)oxy)methyl) tetrahydrofuran-3,4-diyl dibenzoate

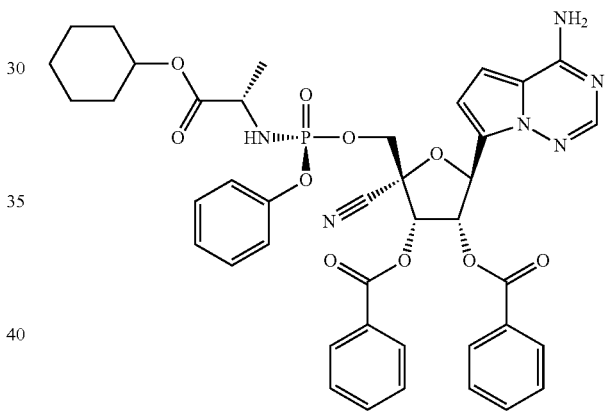

To a solution of Example 6 (50 mg, 0.083 mmol) in anhydrous N,N'-dimethylformamide (1 mL) was added benzoic acid (31 mg, 0.25 mmol) and N,N'-diisopropylcarbodiimide (0.039 mL, 0.25 mmol). The reaction mixture was stirred at room temperature for 5 min followed by the addition of 4-dimethylamino pyridine (10 mg, 0.083 mmol). Continued the stirring for 4 h followed by dilution with acetonitrile (1 mL) and purification by preparative HPLC (Phenomenex Gemini-NX 10µ C18 110° A 250×30 mm column, 25%-95% acetonitrile/water gradient in 30 min run) to afford the product. $^1$H NMR (400 MHz, acetonitrile-d$_3$) δ 8.00 (dt, J=8.4, 1.1 Hz, 4H), 7.95 (s, 1H), 7.63 (td, J=7.4, 5.7 Hz, 2H), 7.45 (t, J=7.7 Hz, 4H), 7.30 (t, J=7.8 Hz, 2H), 7.16 (d, J=7.9 Hz, 3H), 6.85 (d, J=4.6 Hz, 1H), 6.79 (d, J=4.5 Hz, 1H), 6.38-6.15 (m, 4H), 5.95 (d, J=3.9 Hz, 1H), 4.74-4.44 (m, 3H), 4.23 (t, J=11.0 Hz, 1H), 3.98-3.80 (m, 1H), 1.82-1.58 (m, 5H), 1.50 (s, 1H), 1.42-1.21 (m, 7H). $^{31}$P NMR (162 MHz, acetonitrile-d$_3$) δ 2.49. LCMS: MS m/z=809.32 [M+1]; t$_R$=1.28 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=6.539 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 84. (2R,3S,4S,5S)-5-(4-aminopyrrolo[2,1-f][1,2,4]triazin-7-yl)-2-cyano-2-((((S)-(((S)-1-isopropoxy-1-oxopropan-2-yl)amino)(phenoxy)phosphoryl)oxy)methyl) tetrahydrofuran-3,4-diyl bis(2-methylpropanoate)

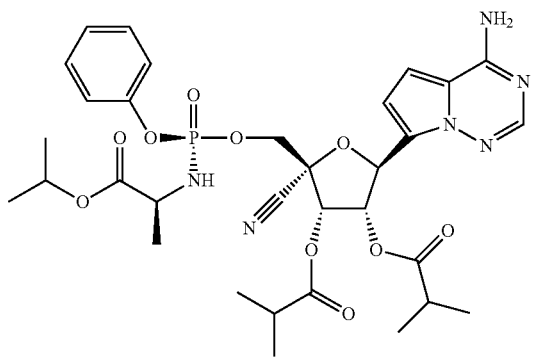 [SMILES: CC(C)OC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccccc1]

Example 1 (10 mg, 0.0178 mmol) was dissolved in anhydrous THF (1 mL). Isobutyric acid (6.6 uL, 0.0714 mmol) and N, N'-diisopropylcarbodiimide (11 uL, 0.0714 mmol) were added to the reaction and stirred for 15 mins. DMAP (2 mg, 0.0178 mmol) was added, and the reaction was stirred for 2 hrs. More isobutyric acid (7 uL, 0.0714 mmol) and N, N'-diisopropylcarbodiimide (11 uL, 0.0714 mmol) were added and the reaction was stirred for 2 hrs. Methanol (500 uL) was added and stirred for 10 mins. Reaction was diluted with EtOAc (15 mL) and washed with brine (2×10 mL). Organic was dried over anhydrous sodium sulfate and concentrated under reduced pressure. The crude residue was purified via $SiO_2$ column chromatography (4 g $SiO_2$ Combiflash HP Gold Column, 0-100% ethyl acetate/hexanes). Fractions were combined and concentrated under reduced pressure as oil which was then dissolved in MeCN and water and freeze-dried to afford the product. $^1$H NMR (400 MHz, Chloroform-d) δ 7.91 (s, 1H), 7.33-7.23 (m, 2H), 7.22-7.09 (m, 3H), 6.66 (d, J=4.5 Hz, 1H), 6.54 (d, J=4.6 Hz, 1H), 5.88 (d, J=5.8 Hz, 1H), 5.85-5.70 (m, 2H), 5.66 (d, J=3.7 Hz, 1H), 4.95 (p, J=6.3 Hz, 1H), 4.40 (d, J=6.3 Hz, 2H), 4.03-3.89 (m, 2H), 2.64 (m, 2H), 1.36-1.28 (m, 3H), 1.25-1.17 (m, 18H). $^{31}$P NMR (162 MHz, Chloroform-d) δ 2.41 (s). MS m/z=701.3 [M+1]; 699.4 [M-1].

Example 85. (2R,3S,4S,5S)-5-(4-aminopyrrolo[2,1-f][1,2,4]triazin-7-yl)-2-((((benzyloxy)(((S)-1-(2-ethylbutoxy)-1-oxopropan-2-yl)amino)phosphoryl)oxy)methyl)-2-cyanotetrahydrofuran-3,4-diyl bis(2-methylpropanoate)

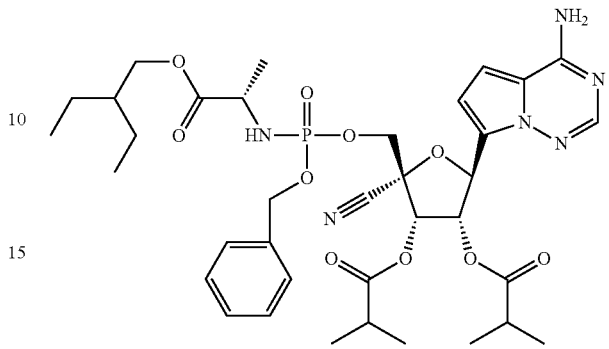

Isobutyric anhydride (0.073 mL, 0.44 mmol) and 4-dimethylaminopyridine (4 mg, 0.03 mmol) were sequentially added to a solution of Example 24 (135 mg, 0.219 mmol) in 2-methyl-tetrahydrofuran (2.0 mL) at RT. After 3.5 h, the reaction mixture was directly subjected to silica gel chromatography eluting with 0-100% ethyl acetate in hexanes to afford the product. $^1$H NMR (400 MHz, methanol-$d_4$) δ 7.82 (s, 0.6H), 7.78 (s, 0.4H), 7.38-7.26 (m, 5H), 6.84-6.82 (m, 1H), 6.78-6.74 (m, 1H), 5.95 (d, J=5.8 Hz, 0.4H), 5.91 (d, J=5.9 Hz, 0.6H), 5.86-5.79 (m, 1H), 5.71-5.66 (m, 1H), 5.06-4.98 (m, 2H), 4.45-4.28 (m, 2H), 4.05-3.75 (m, 3H), 2.74-2.55 (m, 2H), 1.49-1.13 (m, 20H), 0.87-0.81 (m, 6H). $^{31}$P NMR (162 MHz, methanol-$d_4$) δ 7.73 (s), 7.64 (s). LCMS: MS m/z=757.04 [M+1], $t_R$=1.57 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.787 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 86. (2R,3S,4R,5S)-5-(4-aminopyrrolo[2,1-f][1,2,4]triazin-7-yl)-2-cyano-2-((((S)-(((S)-1-(2-ethylbutoxy)-1-oxopropan-2-yl)amino)(phenoxy) phosphoryl)oxy)methyl) tetrahydrofuran-3,4-diyl bis(2-methylpropanoate)

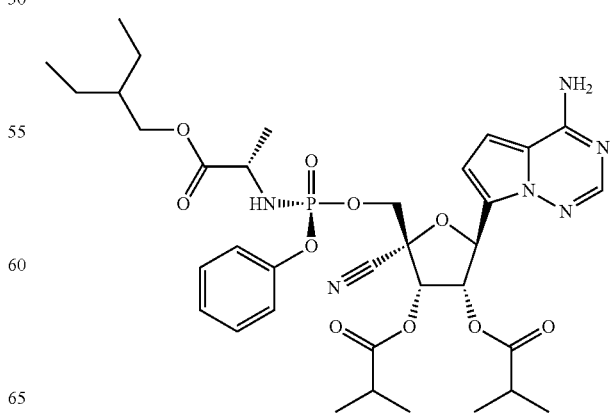

To a solution of Example 25 (15 mg, 0.025 mmol) in anhydrous N,N'-dimethylformamide (0.4 mL) was added isobutyric acid (22 mg, 0.25 mmol) and N,N'-diisopropylcarbodiimide (0.039 mL, 0.25 mmol). The reaction mixture was stirred at room temperature for 5 min followed by the addition of 4-dimethylamino pyridine (3 mg, 0.025 mmol). Continued the stirring for 4 h followed by the dilution with acetonitrile (1 mL) and purification by preparative HPLC (Phenomenex Gemini-NX 10μ C18 110° A 250×30 mm column, 25%-95% acetonitrile/water gradient in 30 min run) to afford the product. $^{1}$H NMR (400 MHz, acetonitrile-$d_3$) δ 7.91 (s, 1H), 7.34 (t, J=7.9 Hz, 2H), 7.20 (dd, J=8.3, 6.8 Hz, 3H), 6.78 (s, 2H), 6.49 (s, 2H), 5.88-5.75 (m, 2H), 5.67 (d, J=4.5 Hz, 1H), 4.49-4.33 (m, 2H), 4.31-4.16 (m, 1H), 4.04-3.84 (m, 3H), 2.64 (dp, J=28.2, 7.0 Hz, 2H), 1.46 (dt, J=12.6, 6.3 Hz, 1H), 1.38-1.21 (m, 8H), 1.24-1.11 (m, 11H), 0.86 (td, J=7.5, 1.1 Hz, 6H). $^{31}$P NMR (162 MHz, acetonitrile-$d_3$) δ 2.45. LCMS: MS m/z=743.79 [M+1]; $t_R$=1.5 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=6.547 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 87. (2R,3S,4R,5S)-5-(4-aminopyrrolo[2,1-f][1,2,4]triazin-7-yl)-2-cyano-2-(((((S)-1-(2-ethylbutoxy)-1-oxo-1-((((1r,4S)-4-(trifluoromethyl)cyclohexyl)methoxy)propan-2-yl)amino)(phenoxy)phosphoryl)oxy)methyl)tetrahydrofuran-3,4-diyl bis(2-methyl propanoate)

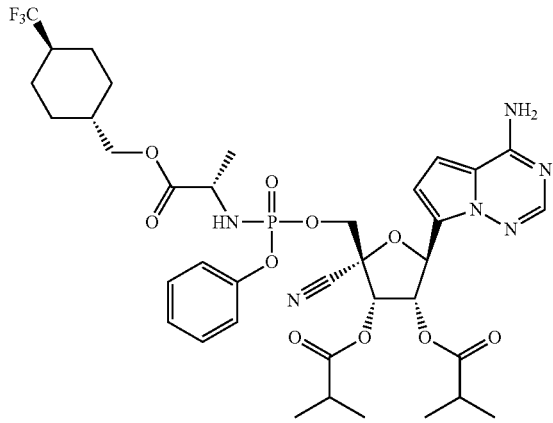 [SMILES: CC(C)C(=O)O[C@H]1[C@H](c2ccc3c(N)ncnn23)O[C@](C#N)(COP(=O)(N[C@@H](C)C(=O)OC[C@H]2CC[C@H](C(F)(F)F)CC2)Oc2ccccc2)[C@H]1OC(=O)C(C)C]

To a solution of Example 26 (72 mg, 0.105 mmol) in anhydrous N,N'-dimethylformamide (1 mL) was added isobutyric acid (93 mg, 1.055 mmol) and N,N'-diisopropylcarbodiimide (0.164 mL, 1.055 mmol). The reaction mixture was stirred at room temperature for 5 min followed by the addition of 4-dimethylamino pyridine (13 mg, 0.105 mmol). Continued the stirring for 4 h followed by the dilution with acetonitrile (1 mL) and purification by preparative HPLC (Phenomenex Gemini-NX 10μ C18 110° A 250×30 mm column, 25%-95% acetonitrile/water gradient in 30 min run) to afford the product. $^{1}$H NMR (400 MHz, acetonitrile-$d_3$) δ 7.90 (d, J=6.5 Hz, 1H), 7.35 (s, 2H), 7.18 (dd, J=12.9, 8.1 Hz, 3H), 6.81-6.73 (m, 2H), 6.33 (s, 2H), 5.93-5.75 (m, 2H), 5.68 (dd, J=6.8, 4.5 Hz, 1H), 4.53-4.33 (m, 2H), 4.26 (m, 1H), 3.95-3.73 (m, 2H), 2.74-2.55 (m, 2H), 2.14 (s, 3H), 1.91 (d, J=13.2 Hz, 3H), 1.79 (s, 2H), 1.35-1.11 (m, 15H), 1.05-0.95 (m, 2H). $^{31}$P NMR (162 MHz, acetonitrile-$d_3$) δ 2.40, 2.35. $^{19}$F NMR (376 MHz, acetonitrile-$d_3$) δ −74.83 (d, J=8.6 Hz). LCMS: MS m/z=823.59 [M+1]; $t_R$=1.27 min(minor isomer), 1.28 (major isomer); LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=6.599 min (minor isomer), 6.658 min (major isomer); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 88. (2R,3S,4S,5S)-5-(4-aminopyrrolo[2,1-f][1,2,4]triazin-7-yl)-2-cyano-2-((((S)-(((S)-1-(2-ethylbutoxy)-1-oxopropan-2-yl)amino)(phenoxy)phosphoryl)oxy) methyl) tetrahydrofuran-3,4-diyl diacetate

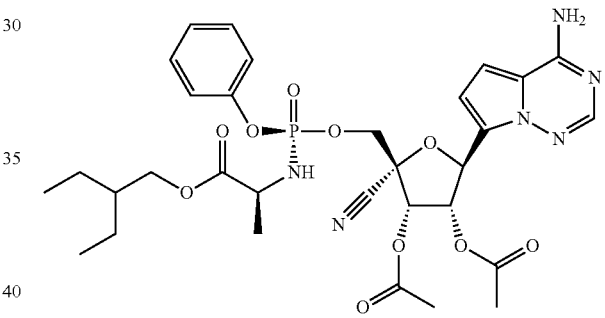

Example 25 (15 mg, 0.025 mmol) was dissolved in 1 mL of anhydrous tetrahydrofuran. Acetic acid (7 μL, 0.12 mmol) and N,N'-diisopropylcarbodiimide (19 μL, 0.12 mmol) were added to the reaction and stirred for 20 min. DMAP (3 mg, 0.025 mmol) was added and the reaction was stirred for 14 h. Methanol (1 mL) was added to the reaction and stirred for 5 min. The reaction mixture was diluted with ethyl acetate (10 mL) and washed with brine (3×5 mL). The organic extract was dried over anhydrous sodium sulfate and concentrated under reduced pressure. The crude residue was purified via SiO$_2$ column chromatography (4 g SiO$_2$ Combiflash HP Gold Column, 0-100% ethyl acetate/hexanes). Fractions containing the desired product were combined and concentrated under reduced pressure as oil which was then dissolved in MeCN and water and freeze-dried to afford the product. $^{1}$H NMR (400 MHz, chloroform-d) δ 7.90 (s, 1H), 7.33-7.24 (m, 2H), 7.22-7.10 (m, 3H), 6.65 (d, J=4.5 Hz, 1H), 6.53 (d, J=4.6 Hz, 1H), 5.85 (m, 3H), 5.79 (dd, J=5.7, 4.1 Hz, 1H), 5.69 (d, J=4.0 Hz, 1H), 4.42 (d, J=6.3 Hz, 2H), 4.11-4.00 (m, 3H), 3.95 (m, 1H), 2.14 (s, 6H), 1.53-1.43 (m, 1H), 1.38-1.26 (m, 7H), 0.85 (t, J=7.5 Hz, 6H). $^{31}$P NMR (162 MHz, chloroform-d) δ 2.41 (s). LCMS: MS m/z=701.3 [M+1]; 699.4 [M−1], $t_R$=1.32 min; LC system: Thermo Dionex ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=3.39 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min. HPLC: $t_R$=5.738 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 89. (2R,3S,4S,5S)-5-(4-Aminopyrrolo[2,1-f][1,2,4]triazin-7-yl)-2-cyano-2-((((S)-(((S)-1-isopropoxy-1-oxopropan-2-yl)amino)(phenoxy)phosphoryl)oxy)methyl) tetrahydrofuran-3,4-diyl diacetate

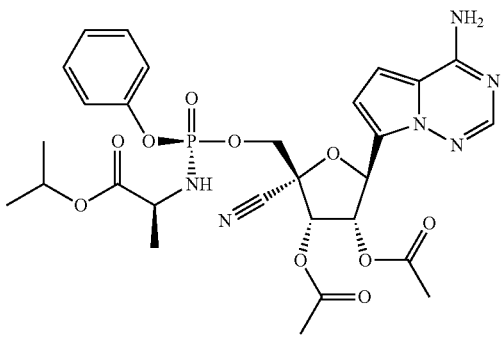 [SMILES: CC(=O)O[C@H]1[C@H](c2ccc3c(N)ncnn23)O[C@](C#N)(CO[P@@](=O)(N[C@@H](C)C(=O)OC(C)C)Oc2ccccc2)[C@H]1OC(C)=O]

A mixture of Example 1 (70 mg, 0.125 mmol), acetic acid (0.04 mL, 0.624 mmol), and N,N-diisopropylcarbodiimide (0.06 mL, 0.400 mmol) in THF (1 mL) was stirred at room temperature for 20 min and DMAP (17 mg, 0.139 mmol) was added. The resulting mixture was stirred at room temperature for 80 min and quenched by adding methanol (0.5 mL), and purified by preparative HPLC (Phenomenex Gemini-NX 10μ C18 110° A 250×30 mm column, 0%-100% acetonitrile/water gradient in 25 min run) to afford the product. $^1$H NMR (400 MHz, Acetonitrile-d3) δ 7.90 (s, 1H), 7.38-7.31 (m, 2H), 7.23-7.15 (m, 3H), 6.76 (q, J=4.6 Hz, 2H), 6.38 (s, 2H), 5.86-5.75 (m, 2H), 5.68 (d, J=4.5 Hz, 1H), 4.87 (p, J=6.3 Hz, 1H), 4.47 (dd, J=11.2, 6.7 Hz, 1H), 4.42-4.30 (m, 2H), 3.86 (tq, J=9.6, 7.1 Hz, 1H), 2.15 (s, 3H), 2.08 (s, 3H), 1.26 (dd, J=7.1, 0.9 Hz, 3H), 1.16 (d, J=6.4 Hz, 3H), 1.15 (d, J=6.4 Hz, 3H). $^{31}$P NMR (162 MHz, Acetonitrile-d3) δ 2.54. LCMS: MS m/z=645.24 [M+1]; $t_R$=1.00 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.03 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 90. (2R,3S,4S,5S)-5-(4-Aminopyrrolo[2,1-f][1,2,4]triazin-7-yl)-2-cyano-2-((((S)-(((S)-1-isopropoxy-1-oxopropan-2-yl)amino)(phenoxy)phosphoryl)oxy)methyl) tetrahydrofuran-3,4-diyl dipropionate

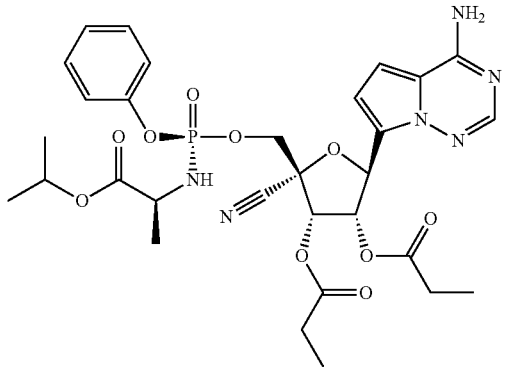 [SMILES: CCC(=O)O[C@H]1[C@H](c2ccc3c(N)ncnn23)O[C@](C#N)(CO[P@@](=O)(N[C@@H](C)C(=O)OC(C)C)Oc2ccccc2)[C@H]1OC(=O)CC]

A mixture of Example 1 (70 mg, 0.125 mmol), propionic acid (0.047 mL, 0.624 mmol), and N,N-diisopropylcarbodiimide (0.06 mL, 0.400 mmol) in THF (1 mL) was stirred at room temperature for 20 min and DMAP (17 mg, 0.139 mmol) was added. The resulting mixture was stirred at room temperature for 80 min, diluted with EtOAc, washed with brine, dried, concentrated in vacuo, and the residue purified by silica gel column chromatography (EtOAc 40-100% in hexanes) to give the product. $^1$H NMR (400 MHz, Acetonitrile-d3) δ 7.90 (s, 1H), 7.34 (m, 2H), 7.24-7.16 (m, 3H), 6.80-6.72 (m, 2H), 6.45 (s, 2H), 5.90-5.80 (m, 2H), 5.69 (d, J=4.5 Hz, 1H), 4.87 (p, J=6.3 Hz, 1H), 4.53-4.44 (m, 2H), 4.40 (dt, J=11.2, 5.6 Hz, 1H), 3.87 (tq, J=9.6, 7.1 Hz, 1H), 2.51-2.36 (m, 4H), 1.26 (dd, J=7.1, 1.0 Hz, 3H), 1.19-1.07 (m, 12H). $^{31}$P NMR (162 MHz, Acetonitrile-d3) δ 2.57. LCMS: MS m/z=673.29 [M+1]; $t_R$=1.10 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.45 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 91. (2R,3S,4R,5S)-5-(4-aminopyrrolo[2,1-f][1,2,4]triazin-7-yl)-2-cyano-2-((((((S)-1-(cyclobutylmethoxy)-1-oxopropan-2-yl)amino)(phenoxy)phosphoryl)oxy)methyl) tetrahydrofuran-3,4-diyl dipropionate

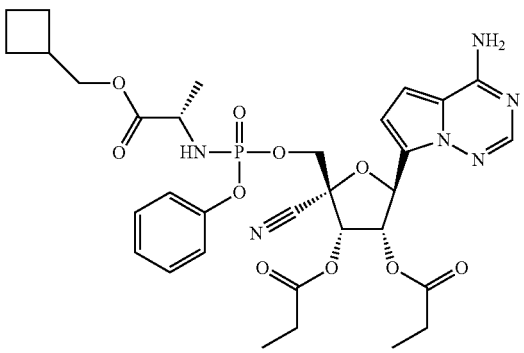 [SMILES: CCC(=O)O[C@H]1[C@H](c2ccc3c(N)ncnn23)O[C@](C#N)(COP(=O)(N[C@@H](C)C(=O)OCC2CCC2)Oc2ccccc2)[C@H]1OC(=O)CC]

To a solution of Example 2 (60 mg, 0.102 mmol) in anhydrous N,N'-dimethylformamide (1 mL) was added propionic acid (38 mg, 0.511 mmol) and N,N'-diisopropylcarbodiimide (0.08 mL, 0.511 mmol). The reaction mixture was stirred at room temperature for 5 min followed by the addition of 4-dimethylamino pyridine (12 mg, 0.102 mmol). Continued the stirring for 1 h followed by the dilution with N,N'-dimethylformamide (1 mL). Purification by preparative HPLC (Phenomenex Gemini-NX 10μ C18 110° A 250×30 mm column, 25%-95% acetonitrile/water gradient in 30 min run) afforded the product. $^1$H NMR (400 MHz, acetonitrile-d$_3$) δ 7.90 (d, J=6.4 Hz, 1H), 7.34 (td, J=8.0, 3.2 Hz, 2H), 7.25-7.13 (m, 3H), 6.83-6.73 (m, 2H), 6.30 (s, 2H), 5.91-5.77 (m, 2H), 5.69 (dd, J=6.8, 4.6 Hz, 1H), 4.54-4.32 (m, 2H), 4.24 (q, J=12.3, 11.9 Hz, 1H), 4.10-3.80 (m, 3H), 2.62-2.44 (m, 1H), 2.48-2.33 (m, 4H), 2.15 (s, 3H), 1.95-1.79 (m, 1H), 1.74 (q, J=8.3 Hz, 2H), 1.25 (ddd, J=17.0, 7.1, 1.0 Hz, 3H), 1.13 (dtd, J=17.3, 7.5, 2.6 Hz, 6H). $^{31}$P NMR (162 MHz, acetonitrile-d3) δ 2.42, 2.36 LCMS: MS m/z=699.26 [M+1]; t$_R$=1.13 min (minor), 1.28 (major); LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=5.763 min (minor isomer), 5.8 min (major isomer); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The product was purified via chiral preparatory HPLC (SFC AD-H, 5 um 21×250 mm Heptane 70% Ethanol 30%) to afford the diastereomers:

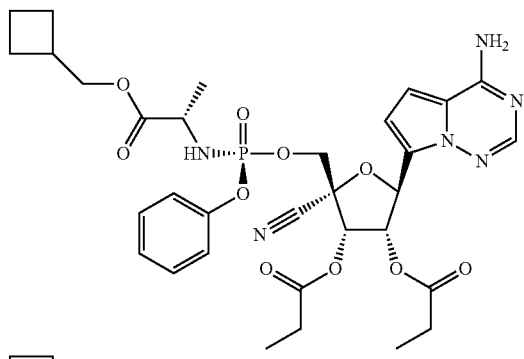

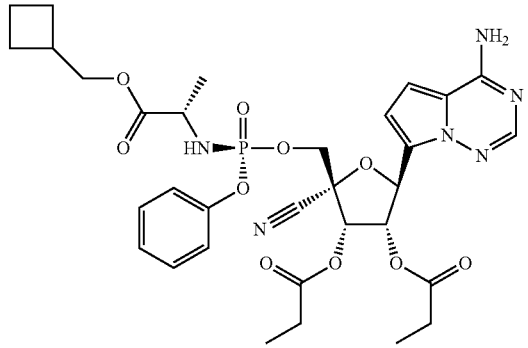

Example 92

First Eluting Diastereomer: H NMR (400 MHz, methanol-d$_4$) δ 7.80 (s, 1H), 7.30 (t, J=7.9 Hz, 2H), 7.16 (ddd, J=8.1, 2.2, 1.1 Hz, 3H), 6.85 (d, J=4.5 Hz, 1H), 6.77 (d, J=4.6 Hz, 1H), 5.96 (d, J=5.9 Hz, 1H), 5.85 (dd, J=5.9, 4.5 Hz, 1H), 5.69 (d, J=4.6 Hz, 1H), 4.51 (dd, J=11.1, 5.8 Hz, 1H), 4.42 (dd, J=11.1, 5.1 Hz, 1H), 4.10-3.94 (m, 2H), 3.91-3.78 (m, 1H), 2.58 (p, J=7.5 Hz, 1H), 2.53-2.35 (m, 4H), 2.06-1.67 (m, 6H), 1.31-1.09 (m, 9H). $^{31}$P NMR (162 MHz, methanol-d4) δ 3.05 LCMS: MS m/z=699.30 [M+1], t$_R$=1.13 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: t$_R$=5.736 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 93

Second Eluting Diastereomer: $^1$H NMR (400 MHz, methanol-d$_4$) δ 7.83 (s, 1H), 7.30 (t, J=7.8 Hz, 2H), 7.23-7.12 (m, 3H), 6.84 (d, J=4.5 Hz, 1H), 6.74 (d, J=4.5 Hz, 1H), 5.90 (d, J=6.0 Hz, 1H), 5.80 (dd, J=5.9, 4.7 Hz, 1H), 5.68 (d, J=4.7 Hz, 1H), 4.43 (dd, J=5.8, 4.3 Hz, 2H), 4.01 (dd, J=10.9, 6.8 Hz, 1H), 3.96-3.85 (m, 2H), 2.62-2.43 (m, 2H), 2.47-2.34 (m, 3H), 1.99 (ddd, J=10.6, 8.2, 4.8 Hz, 2H), 1.96-1.77 (m, 2H), 1.80-1.66 (m, 2H), 1.28 (dd, J=7.1, 1.1 Hz, 3H), 1.15 (dt, J=13.8, 7.5 Hz, 6H). $^{31}$P NMR (162 MHz, methanol-d$_4$) δ 3.01 LCMS: MS m/z=699.29 [M+1], t$_R$=1.13 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=5.793 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 94. (2R,3S,4R,5S)-5-(4-aminopyrrolo[2,1-f][1,2,4]triazin-7-yl)-2-cyano-2-((((((S)-1-(cyclobutylmethoxy)-1-oxopropan-2-yl)amino)(phenoxy)phosphoryl)oxy)methyl) tetrahydrofuran-3,4-diyl diacetate

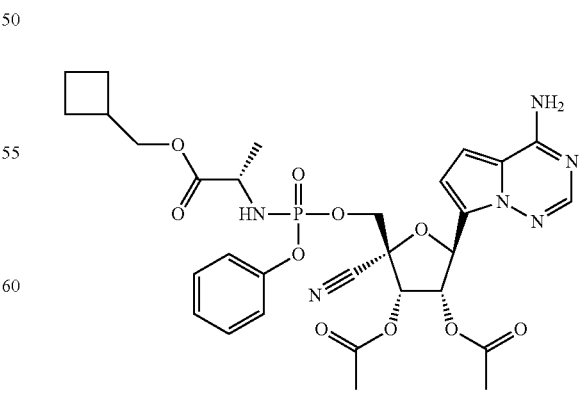

To a solution of Example 2 (60 mg, 0.102 mmol) in anhydrous N,N'-dimethylformamide (1 mL) was added acetic acid (31 mg, 0.511 mmol) and N,N'-diisopropylcarbodiimide (0.08 mL, 0.511 mmol). The reaction mixture was stirred at room temperature for 5 min followed by the addition of 4-dimethylamino pyridine (12 mg, 0.102 mmol). Continued the stirring for 1 h followed by the dilution with N,N'-dimethylformamide (1 mL). Purification by preparative HPLC (Phenomenex Gemini-NX 10μ C18 110° A 250×30 mm column, 25%-95% acetonitrile/water gradient in 30 min run) afforded the product. $^1$H NMR (400 MHz, acetonitrile-d$_3$) δ 7.90 (d, J=6.7 Hz, 1H), 7.40-7.30 (m, 2H), 7.25-7.13 (m, 3H), 6.83-6.73 (m, 2H), 6.30 (s, 2H), 5.88-5.75 (m, 2H), 5.69 (dd, J=6.5, 4.6 Hz, 1H), 4.47 (ddd, J=17.5, 11.2, 6.5 Hz, 1H), 4.38 (ddd, J=11.2, 8.8, 5.6 Hz, 1H), 4.24 (q, J=12.5, 12.0 Hz, 1H), 4.10-3.83 (m, 3H), 2.56 (tt, J=14.7, 7.3 Hz, 1H), 2.15 (d, J=3.3 Hz, 6H), 1.95-1.79 (m, 1H), 1.80-1.68 (m, 2H), 1.25 (ddd, J=17.2, 7.1, 1.0 Hz, 3H). $^{31}$P NMR (162 MHz, acetonitrile-d3) δ 2.42, 2.36 LCMS: MS m/z=671.25 [M+1]; t$_R$=1.49 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=5.346 min (minor isomer), 5.38 min (major isomer); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The product was purified via chiral preparatory HPLC (SFC AD-H, 5 um 21×250 mm Heptane 70% Ethanol 30%) to afford the diastereomers:

J=5.9 Hz, 1H), 5.83 (dd, J=5.9, 4.7 Hz, 1H), 5.69 (d, J=4.7 Hz, 1H), 4.51 (dd, J=11.1, 5.8 Hz, 1H), 4.42 (dd, J=11.1, 5.1 Hz, 1H), 4.10-3.94 (m, 2H), 3.91-3.73 (m, 1H), 2.57 (dq, J=14.6, 7.3 Hz, 1H), 2.13 (d, J=19.4 Hz, 6H), 2.06-1.67 (m, 6H), 1.23 (dd, J=7.1, 1.3 Hz, 3H). $^{31}$P NMR (162 MHz, methanol-d$_4$) δ 3.04. LCMS: MS m/z=671.43 [M+1], t$_R$=1.03 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=5.343 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 96

Second Eluting Diastereomer: $^1$H NMR (400 MHz, methanol-d$_4$) δ 7.82 (s, 1H), 7.30 (dd, J=8.6, 7.2 Hz, 2H), 7.23-7.12 (m, 3H), 6.83 (d, J=4.5 Hz, 1H), 6.74 (d, J=4.5 Hz, 1H), 5.87 (d, J=6.0 Hz, 1H), 5.79 (dd, J=5.9, 4.9 Hz, 1H), 5.68 (d, J=4.9 Hz, 1H), 4.43 (t, J=5.6 Hz, 2H), 4.01 (dd, J=10.9, 6.7 Hz, 1H), 3.90 (ddd, J=10.1, 8.7, 6.8 Hz, 2H), 2.55 (hept, J=7.4 Hz, 1H), 2.12 (d, J=19.7 Hz, 6H), 2.06-1.66 (m, 6H), 1.27 (dd, J=7.1, 1.1 Hz, 3H). $^{31}$P NMR (162 MHz, methanol-d$_4$) δ 3.02. LCMS: MS m/z=671.30 [M+1], t$_R$=1.03 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=5.376 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 97. (2R,3S,4S,5S)-5-(4-aminopyrrolo[2,1-f][1,2,4]triazin-7-yl)-2-cyano-2-(((phenoxy((2-(pivaloyloxy)ethyl)amino)phosphoryl)oxy)methyl)tetrahydrofuran-3,4-diyl bis(2-methylpropanoate)

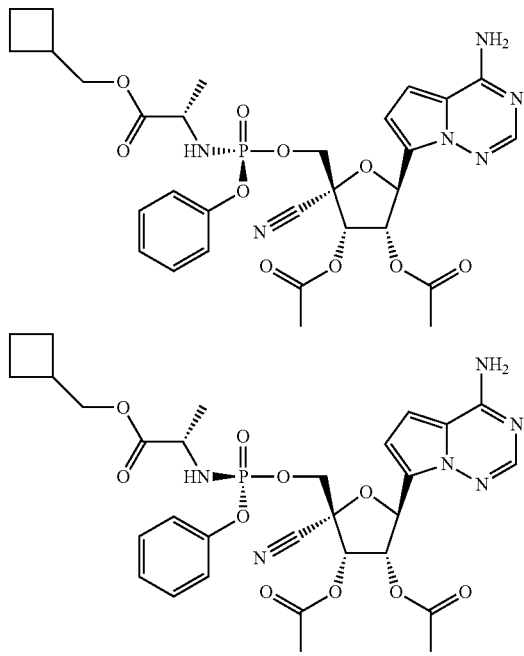

Example 95

First Eluting Diastereomer: $^1$H NMR (400 MHz, methanol-d$_4$) δ 7.80 (s, 1H), 7.30 (t, J=7.9 Hz, 2H), 7.20-7.11 (m, 3H), 6.85 (d, J=4.6 Hz, 1H), 6.77 (d, J=4.6 Hz, 1H), 5.93 (d,

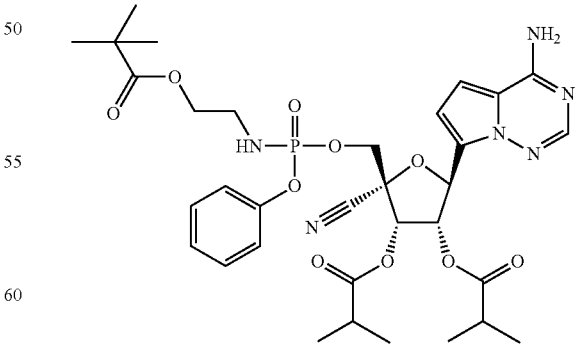

N,N'-diisopropylcarbodiimide (0.14 mL, 0.87 mmol) and 4-dimethylaminopyridine (21.0 mg, 0.174 mmol) were added to a solution of Example 11 (100 mg, 0.174 mmol) and isobutyric acid (0.081 mL, 0.87 mmol) in tetrahydrofuran (1.0 mL) at RT. After 2 h, methanol (0.2 mL) was added and the resulting mixture was concentrated under reduced pressure. The crude residue was subjected to silica gel chromatography eluting with 0-100% ethyl acetate in hexanes to afford the product. $^1$H NMR (400 MHz, methanol-d$_4$) δ 7.83 (s, 0.55H), 7.80 (s, 0.45H), 7.34-7.26 (m, 2H), 7.21-7.12 (m, 3H), 6.88-6.82 (m, 1H), 6.78-6.73 (m, 1H), 5.94 (t, J=5.8 Hz, 1H), 5.85-5.77 (m, 1H), 5.68 (d, J=4.5 Hz, 1H), 4.49-4.36 (m, 2H), 4.01-3.93 (m, 2H), 3.20-3.07 (m, 2H), 1.25-1.12 (m, 27H). $^{31}$P NMR (162 MHz, methanol-d$_4$) δ 5.02 (s), 4.86 (s). LCMS: MS m/z=715.47 [M+1], $t_R$=1.38 min; LC system: Thermo Accela 1250 UHPLC; MS system: Thermo LCQ Fleet; Column: Kinetex 2.6µ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: $t_R$=3.53 min; HPLC system: Agilent 1100 series; Column: Gemini 5µ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=5.96 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 98. (2R,3S,4R,5S)-5-(4-aminopyrrolo[2,1-f][1,2,4]triazin-7-yl)-2-cyano-2-((((((S)-1-(cyclopropylmethoxy)-1-oxopropan-2-yl)amino)(phenoxy)phosphoryl)oxy)methyl) tetrahydrofuran-3,4-diyl dipropionate

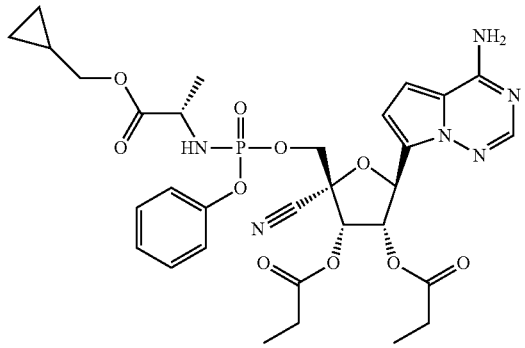 [SMILES: CCC(=O)O[C@H]1[C@H](c2ccc3c(N)ncnn23)O[C@](C#N)(COP(=O)(N[C@@H](C)C(=O)OCC2CC2)Oc2ccccc2)[C@H]1OC(=O)CC]

To a solution of Example 8 (65 mg, 0.112 mmol) in anhydrous N,N'-dimethylformamide (1 mL) was added propionic acid (38 mg, 0.511 mmol) and N,N'-diisopropylcarbodiimide (0.042 mL, 0.568 mmol). The reaction mixture was stirred at room temperature for 5 min followed by the addition of 4-dimethylamino pyridine (14 mg, 0.114 mmol). Continued the stirring for 1 h followed by the dilution with N,N'-dimethylformamide (1 mL) and purification by preparative HPLC (Phenomenex Gemini-NX 10µ C18 110° A 250×30 mm column, 25%-95% acetonitrile/water gradient in 30 min run) to afford the product. $^1$H NMR (400 MHz, acetonitrile-d$_3$) δ 7.90 (d, J=6.3 Hz, 1H), 7.34 (td, J=8.0, 3.4 Hz, 2H), 7.20 (s, 1H), 7.25-7.14 (m, 2H), 6.83-6.72 (m, 2H), 6.28 (s, 2H), 5.92-5.77 (m, 2H), 5.69 (dd, J=7.2, 4.5 Hz, 1H), 4.55-4.33 (m, 2H), 4.23 (d, J=13.3 Hz, 1H), 3.97-3.74 (m, 3H), 2.54-2.33 (m, 4H), 1.26 (ddd, J=17.5, 7.1, 1.0 Hz, 3H), 1.13 (dtd, J=17.6, 7.5, 2.6 Hz, 7H), 0.51 (ddt, J=8.4, 5.9, 4.4 Hz, 2H), 0.24 (dq, J=6.2, 4.5 Hz, 2H). $^{31}$P NMR (162 MHz, acetonitrile-d$_3$) δ 2.41, 2.37. LCMS: MS m/z=685.26 [M+1]; $t_R$=1.07 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=5.476 min (minor isomer), 5.515 min (major isomer); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Resolution of the Sp and Rp diastereomers. The product was purified via chiral preparatory HPLC (SFC AD-H, 5 um 21×250 mm Heptane 70% Ethanol 30%) to afford the diastereomers:

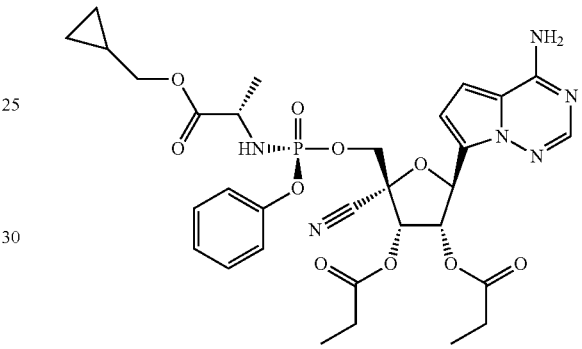

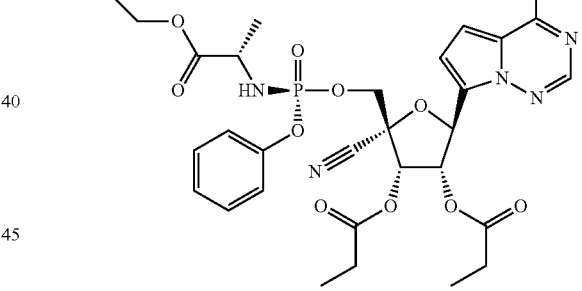

Example 99

First Eluting Diastereomer: $^1$H NMR (400 MHz, methanol-d$_4$) δ 7.71 (s, 1H), 7.25-7.17 (m, 2H), 7.08 (d, J=7.5 Hz, 3H), 6.68 (d, J=4.5 Hz, 1H), 5.88 (d, J=5.9 Hz, 1H), 5.76 (dd, J=5.8, 4.5 Hz, 1H), 5.60 (d, J=4.5 Hz, 1H), 4.43 (dd, J=11.1, 5.8 Hz, 1H), 4.34 (dd, J=11.0, 5.0 Hz, 1H), 3.86-3.68 (m, 3H), 2.46-2.26 (m, 4H), 1.14 (dd, J=7.2, 1.2 Hz, 3H), 1.06 (dt, J=13.0, 7.5 Hz, 7H), 0.45-0.36 (m, 2H), 0.19-0.12 (m, 2H). $^{31}$P NMR (162 MHz, methanol-d$_4$) δ 3.1. LCMS: MS m/z=685.26 [M+1], $t_R$=1.06 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=5.464 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 100

Second Eluting Diastereomer: $^1$H NMR (400 MHz, methanol-d4) δ 7.83 (s, 1H), 7.30 (dd, J=8.5, 7.4 Hz, 2H), 7.24-7.12 (m, 3H), 6.83 (d, J=4.6 Hz, 1H), 6.74 (d, J=4.5 Hz, 1H), 5.90 (d, J=5.9 Hz, 1H), 5.81 (dd, J=5.9, 4.8 Hz, 1H), 5.68 (d, J=4.7 Hz, 1H), 4.44 (dd, J=5.8, 2.9 Hz, 2H), 3.96-3.74 (m, 3H), 2.55-2.35 (m, 4H), 1.29 (dd, J=7.2, 1.1 Hz, 3H), 1.16-1.08 (dd, J=13.9, 7.5 Hz, 7H), 0.54-0.45 (m, 2H), 0.26-0.19 (m, 2H). $^{31}$P NMR (162 MHz, methanol-d4) δ 3.01. LCMS: MS m/z=685.22 [M+1], $t_R$=1.06 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.506 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 101. (2R,3S,4R,5S)-5-(4-aminopyrrolo[2,1-f][1,2,4]triazin-7-yl)-2-cyano-2-((((((S)-1-(cyclopropylmethoxy)-1-oxopropan-2-yl)amino)(phenoxy)phosphoryl)oxy)methyl) tetrahydrofuran-3,4-diyl diacetate

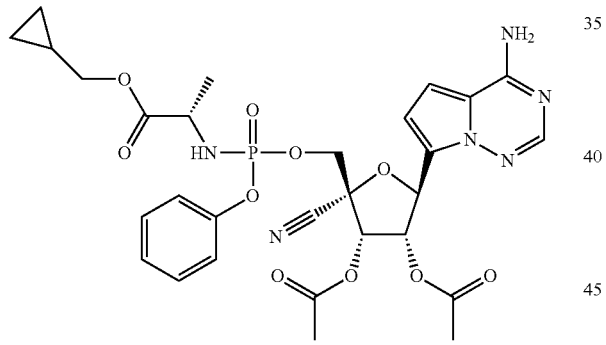

To a solution of Example 8 (65 mg, 0.114 mmol) in anhydrous N,N'-dimethylformamide (1 mL) was added acetic acid (34 mg, 0.568 mmol) and N,N'-diisopropylcarbodiimide (0.088 mL, 0.568 mmol). The reaction mixture was stirred at room temperature for 5 min followed by the addition of 4-dimethylamino pyridine (14 mg, 0.114 mmol). Continued the stirring for 1 h followed by the dilution with N,N'-dimethylformamide (1 mL) and purification by preparative HPLC (Phenomenex Gemini-NX 10μ C18 110° A 250×30 mm column, 25%-95% acetonitrile/water gradient in 30 min run) to afford the product. $^1$H NMR (400 MHz, acetonitrile-d$_3$) δ 7.90 (d, J=6.5 Hz, 1H), 7.40-7.30 (m, 2H), 7.25-7.14 (m, 3H), 6.83-6.72 (m, 2H), 6.29 (s, 2H), 5.88-5.75 (m, 2H), 5.69 (dd, J=6.9, 4.5 Hz, 1H), 4.55-4.33 (m, 2H), 4.23 (d, J=11.8 Hz, 1H), 3.99-3.74 (m, 3H), 2.12 (m, 6H), 1.26 (ddd, J=17.7, 7.1, 1.0 Hz, 3H), 1.13-0.97 (m, 1H), 0.51 (ddd, J=8.2, 4.5, 1.6 Hz, 2H), 0.25 (ddt, J=9.2, 6.0, 4.4 Hz, 2H). $^{31}$P NMR (162 MHz, acetonitrile-d$_3$) δ 2.42, 2.36. LCMS: MS m/z=657.20 [M+1]; $t_R$=0.98 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.051 min (minor isomer), 5.088 min (major isomer); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The product was purified via chiral preparatory HPLC (SFC AD-H, 5 um 21×250 mm Heptane 70% Ethanol 30%) to afford the diastereomers:

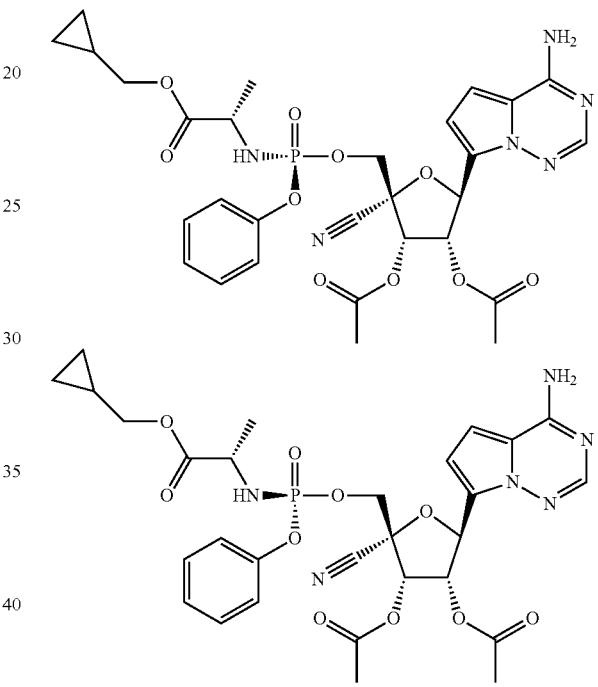

Example 102

First Eluting Diastereomer: $^1$H NMR (400 MHz, methanol-d4) δ 7.58 (s, 1H), 7.08 (dd, J=8.7, 7.1 Hz, 2H), 6.98-6.89 (m, 3H), 6.63 (d, J=4.5 Hz, 1H), 6.55 (d, J=4.5 Hz, 1H), 5.72 (d, J=5.9 Hz, 1H), 5.62 (dd, J=5.9, 4.7 Hz, 1H), 5.47 (d, J=4.7 Hz, 1H), 4.30 (dd, J=11.1, 5.8 Hz, 1H), 4.21 (dd, J=11.1, 5.0 Hz, 1H), 3.73-3.55 (m, 3H), 1.91 (d, J=19.4 Hz, 6H), 1.01 (dd, J=7.1, 1.3 Hz, 3H), 0.86 (dddd, J=15.2, 12.3, 7.8, 4.8 Hz, 1H), 0.32-0.23 (m, 2H), 0.05 (m, 2H). $^{31}$P NMR (162 MHz, methanol-d$_4$) δ 3.09. LCMS: MS m/z=657.23 [M+1], $t_R$=0.96 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.040 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2 98% B with 8.5 min gradient at 1.5 mL/min.

Example 103

Second Eluting Diastereomer: $^1$H NMR (400 MHz, methanol-d4) δ 7.61 (s, 1H), 7.13-7.04 (m, 2H), 7.02-6.90 (m, 3H), 6.62 (d, J=4.5 Hz, 1H), 6.52 (d, J=4.6 Hz, 1H), 5.66 (d, J=5.9 Hz, 1H), 5.57 (dd, J=5.9, 4.9 Hz, 1H), 5.46 (d, J=4.9 Hz, 1H), 4.29-4.14 (m, 2H), 3.74-3.58 (m, 2H), 3.57 (dd, J=11.4, 7.3 Hz, 1H), 1.90 (d, J=20.1 Hz, 6H), 1.07 (dd, J=7.2, 1.0 Hz, 3H), 0.91-0.76 (m, 1H), 0.32-0.21 (m, 2H), 0.05 (m, 2H); $^{31}$P NMR (162 MHz, methanol-d4) δ 3.04. LCMS: MS m/z=657.28 [M+1], $t_R$=0.97 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.080 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 104. (2R,3S,4S,5S)-5-(4-aminopyrrolo[2,1-f][1,2,4]triazin-7-yl)-2-cyano-2-((((S)-(((S)-1-ethoxy-1-oxopropan-2-yl)amino)(phenoxy)phosphoryl)oxy)methyl) tetrahydrofuran-3,4-diyl diacetate

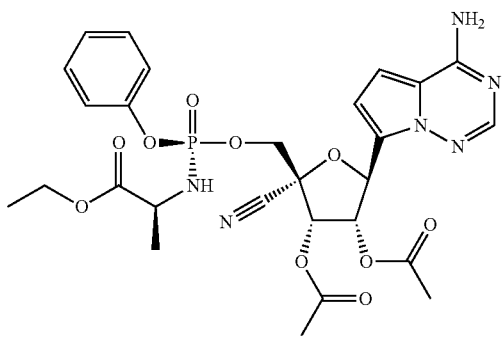 [SMILES: CCOC(=O)[C@H](C)N[P@](=O)(OC[C@@]1(C#N)O[C@@H](c2ccc3c(N)ncnn23)[C@H](OC(C)=O)[C@@H]1OC(C)=O)Oc1ccccc1]

A mixture of Example 29 (70 mg, 0.128 mmol), acetic acid (0.04 mL, 0.64 mmol), and N,N-diisopropylcarbodiimide (0.06 mL, 0.39 mmol) in THF (1 mL) was stirred at room temperature for 20 min and DMAP (16 mg, 0.128 mmol) was added. The resulting mixture was stirred at room temperature for 80 min and quenched by adding methanol (0.5 mL), and purified by preparative HPLC (Phenomenex Gemini-NX 10μ C18 110° A 250×30 mm column, 0%-100% acetonitrile/water gradient in 25 min run) to afford the product. $^1$H NMR (400 MHz, Acetonitrile-d3) δ 7.90 (s, 1H), 7.39-7.29 (m, 2H), 7.25-7.16 (m, 3H), 6.76 (d, J=3.8 Hz, 2H), 6.39 (s, 2H), 5.86-5.76 (m, 2H), 5.69 (d, J=4.3 Hz, 1H), 4.47 (dd, J=11.2, 6.6 Hz, 1H), 4.38 (dd, J=11.2, 5.7 Hz, 1H), 4.10-3.96 (m, 2H), 3.90 (tq, J=9.6, 7.1 Hz, 1H), 2.15 (s, 3H), 2.07 (s, 3H), 1.26 (dd, J=7.1, 0.9 Hz, 3H), 1.16 (t, J=7.1 Hz, 3H). $^{31}$P NMR (162 MHz, Acetonitrile-d3) δ 2.48. LCMS: MS m/z=631.18 [M+1]; $t_R$=0.94 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.80 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 105. (2R,3S,4S,5S)-5-(4-Aminopyrrolo[2,1-f][1,2,4]triazin-7-yl)-2-cyano-2-((((S)-(((S)-1-ethoxy-1-oxopropan-2-yl)amino)(phenoxy)phosphoryl)oxy)methyl) tetrahydrofuran-3,4-diyl dipropionate

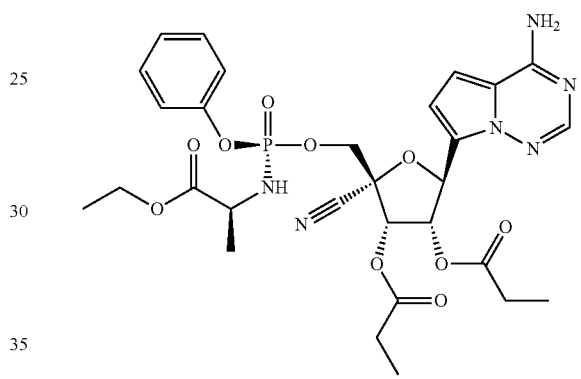

A mixture of Example 29 (70 mg, 0.128 mmol), propionic acid (0.05 mL, 0.64 mmol), and N,N-diisopropylcarbodiimide (0.06 mL, 0.39 mmol) in THF (1 mL) was stirred at room temperature for 20 min and DMAP (16 mg, 0.128 mmol) was added. The resulting mixture was stirred at room temperature for 80 min and quenched by adding methanol (0.5 mL), and purified by preparative HPLC (Phenomenex Gemini-NX 10μ C18 110° A 250×30 mm column, 0%-100% acetonitrile/water gradient in 25 min run) to afford the product. $^1$H NMR (400 MHz, Acetonitrile-d3) δ 7.90 (s, 1H), 7.34 (t, J=7.8 Hz, 2H), 7.20 (ddd, J=8.1, 2.4, 1.2 Hz, 3H), 6.81-6.69 (m, 2H), 6.40 (s, 2H), 5.87-5.76 (m, 2H), 5.68 (d, J=4.4 Hz, 1H), 4.42 (dd, J=21.1, 6.0 Hz, 2H), 4.12-3.96 (m, 2H), 3.89 (td, J=9.6, 7.0 Hz, 1H), 2.45 (qd, J=7.5, 3.4 Hz, 2H), 2.38 (q, J=7.6 Hz, 2H), 1.29-1.24 (m, 3H), 1.15 (td, J=7.4, 4.3 Hz, 6H), 1.10 (t, J=7.6 Hz, 3H). $^{31}$P NMR (162 MHz, Acetonitrile-d3) δ 2.49. LCMS: MS m/z=659.30 [M+1]; $t_R$=1.04 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.25 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 106. (2R,3S,4S,5S)-5-(4-aminopyrrolo[2,1-f][1,2,4]triazin-7-yl)-2-cyano-2-((((S)-(((S)-1-isopropoxy-1-oxopropan-2-yl)amino)(phenoxy)phosphoryl)oxy) methyl) tetrahydrofuran-3,4-diyl bis(2-methylpropanoate)

Example 107. (2R,3S,4R,5S)-5-(4-aminopyrrolo[2,1-f][1,2,4]triazin-7-yl)-2-cyano-2-((((((S)-1-oxo-1-((tetrahydro-2H-pyran-4-yl)methoxy)propan-2-yl)amino)(phenoxy)phosphoryl) oxy)methyl) tetrahydrofuran-3,4-diyl dipropionate

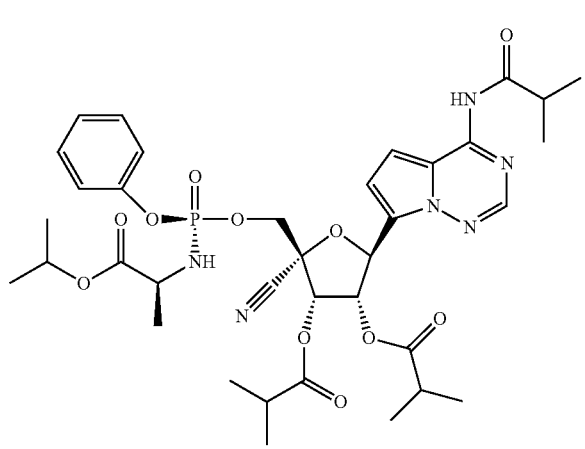 [SMILES: CC(C)OC(=O)[C@H](C)N[P@](=O)(OC[C@@]1(C#N)O[C@@H](c2ccc3c(NC(=O)C(C)C)ncnn23)[C@H](OC(=O)C(C)C)[C@@H]1OC(=O)C(C)C)Oc1ccccc1]

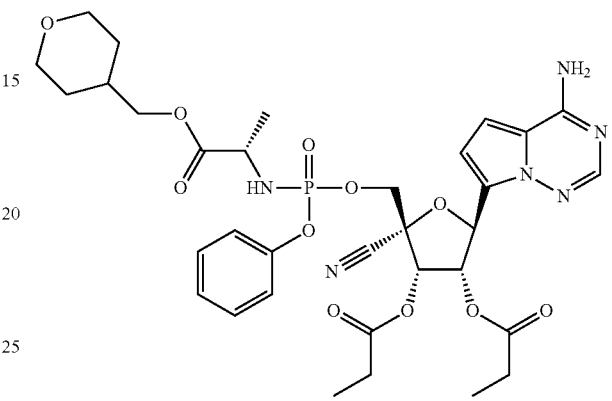

Example 1 (40 mg, 0.071 mmol) was dissolved in 3 mL anhydrous tetrahydrofuran. Isobutyric acid (26 μL, 0.27 mmol) and N,N'-diisopropylcarbodiimide (44 μL, 0.29 mmol) were added to the reaction which was stirred for 15 min. DMAP (8.7 mg, 0.71 mmol) was added and the reaction mixture was stirred for 4 h. More isobutyric acid (26 μL, 0.29 mmol) and N,N'-diisopropylcarbodiimide (44 μL, 0.286 mmol) were added and the reaction was stirred for 1 h. The reaction mixture was diluted with ethyl acetate (10 mL) and washed with brine (4×5 mL). The organic layer was dried over anhydrous sodium sulfate and concentrated under reduced pressure. The crude residue was purified via SiO₂ column chromatography (4 g SiO₂ Combiflash HP Gold Column, 0-80% ethyl acetate/hexanes). Fractions containing the desired product were combined and concentrated under reduced pressure as oil which was then dissolved in MeCN and water and freeze-dried to afford the product. $^1$H NMR (400 MHz, chloroform-d) δ 8.12 (s, 1H), 7.32-7.20 (m, 3H), 7.20-7.09 (m, 3H), 6.85 (d, J=4.8 Hz, 1H), 5.81 (d, J=5.8 Hz, 1H), 5.77 (dd, J=5.8, 3.8 Hz, 1H), 5.71 (d, J=3.7 Hz, 1H), 4.95 (m, 1H), 4.41 (d, J=6.1 Hz, 2H), 4.05-3.91 (m, 2H), 3.02 (m, 1H), 2.63 (m, 2H), 1.32 (d, J=6.4 Hz, 3H), 1.30-1.25 (m, 6H), 1.21 (m, 18H). $^{31}$P NMR (162 MHz, chloroform-d) δ 2.41. LCMS: MS m/z=771.3 [M+1]; 769.5 [M−1], $t_R$=1.46 min; LC system: Thermo Dionex ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=6.686 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

To a solution of Example 20 (75 mg, 0.122 mmol) in anhydrous N,N'-dimethylformamide (1 mL) was added propionic acid (45 mg, 0.608 mmol) and N,N'-diisopropylcarbodiimide (0.095 mL, 0.608 mmol). The reaction mixture was stirred at room temperature for 5 min followed by the addition of 4-dimethylamino pyridine (15 mg, 0.122 mmol). Continued the stirring for 1 h followed by the dilution with N,N'-dimethylformamide (1 mL) and purification by preparative HPLC (Phenomenex Gemini-NX 10μ C18 110° A 250×30 mm column, 25%-95% acetonitrile/water gradient in 30 min run) to afford the product. $^1$H NMR (400 MHz, methanol-d₄) δ 7.82 (d, J=8.8 Hz, 1H), 7.31 (s, 2H), 7.18 (dd, J=15.0, 7.9 Hz, 3H), 6.88-6.72 (m, 2H), 5.93-5.76 (m, 2H), 5.69 (t, J=4.2 Hz, 1H), 4.54-4.37 (m, 2H), 3.95-3.79 (m, 5H), 3.3 (m, 2H), 2.50-2.35 (m, 4H), 1.85 (s, 1H), 1.55 (d, J=13.0 Hz, 2H), 1.31-1.08 (m, 11H). $^{31}$P NMR (162 MHz, methanol-d4) δ 2.99, 3.04. LCMS: MS m/z=729.25 [M+1];], $t_R$=1.00 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.159 min (minor isomer), 5.216 min (major isomer); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The product was purified via chiral preparatory HPLC (SFC AD-H, 5 um 21×250 mm Heptane 70% Ethanol 30%) to afford the diastereomers:

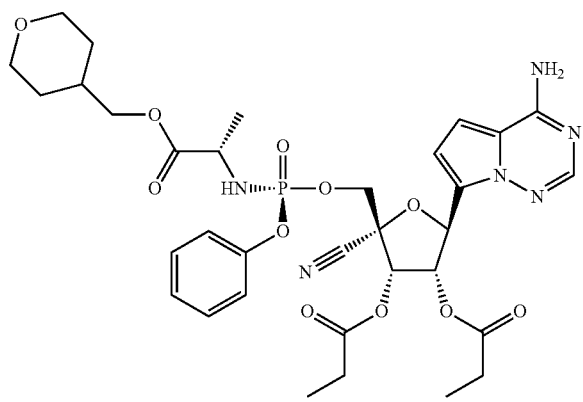 [SMILES: CCC(=O)O[C@H]1[C@H](c2ccc3c(N)ncnn23)O[C@](C#N)(COP(=O)(N[C@@H](C)C(=O)OCC2CCOCC2)Oc2ccccc2)[C@H]1OC(=O)CC]

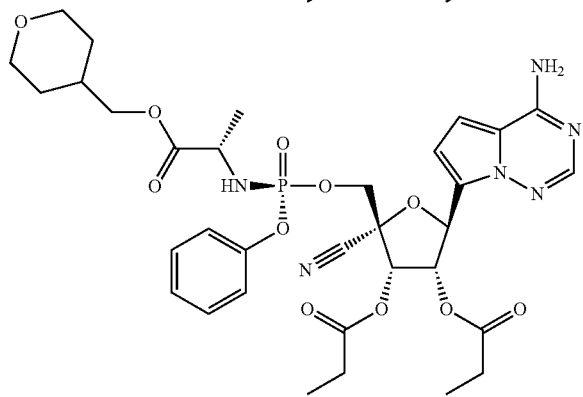

Example 108

First Eluting Diastereomer: $^1$H NMR (400 MHz, methanol-d$_4$) δ 7.81 (s, 1H), 7.35-7.26 (m, 2H), 7.20-7.12 (m, 3H), 6.85 (d, J=4.5 Hz, 1H), 6.78 (d, J=4.5 Hz, 1H), 5.97 (d, J=5.9 Hz, 1H), 5.86 (dd, J=5.9, 4.6 Hz, 1H), 5.69 (d, J=4.6 Hz, 1H), 4.46 (ddd, J=36.1, 11.1, 5.5 Hz, 2H), 3.94-3.79 (m, 5H), 3.3 (m, 2H), 2.54-2.36 (m, 4H), 1.86 (dp, J=10.6, 3.8 Hz, 1H), 1.64-1.46 (m, 2H), 1.35-1.09 (m, 11H). $^{31}$P NMR (162 MHz, methanol-d4) δ 3.03. LCMS: MS m/z=729.30 [M+1], $t_R$=1.00 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=5.151 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 109

Second Eluting Diastereomer: $^1$H NMR (400 MHz, methanol-d4) δ 7.83 (s, 1H), 7.31 (t, J=7.9 Hz, 2H), 7.24-7.13 (m, 3H), 6.84 (d, J=4.6 Hz, 1H), 6.75 (d, J=4.5 Hz, 1H), 5.89 (d, J=5.9 Hz, 1H), 5.80 (dd, J=5.9, 4.8 Hz, 1H), 5.68 (d, J=4.9 Hz, 1H), 4.50-4.37 (m, 2H), 3.97-3.78 (m, 5H), 3.34 (m, 2H), 2.53-2.35 (m, 4H), 1.95-1.68 (m, 1H), 1.55 (d, J=13.3 Hz, 2H), 1.34-1.22 (m, 5H), 1.15 (dt, J=14.3, 7.5 Hz, 6H). $^{31}$P NMR (162 MHz, methanol-d$_4$) δ 2.98. LCMS: MS m/z=729.27 [M+1], $t_R$=1.01 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.214 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 110. (2R,3S,4R,5S)-5-(4-aminopyrrolo[2,1-f][1,2,4]triazin-7-yl)-2-cyano-2-(((((S)-1-oxo-1-((tetrahydro-2H-pyran-4-yl)methoxy)propan-2-yl)amino)(phenoxy)phosphoryl) oxy)methyl) tetrahydrofuran-3,4-diyl diacetate

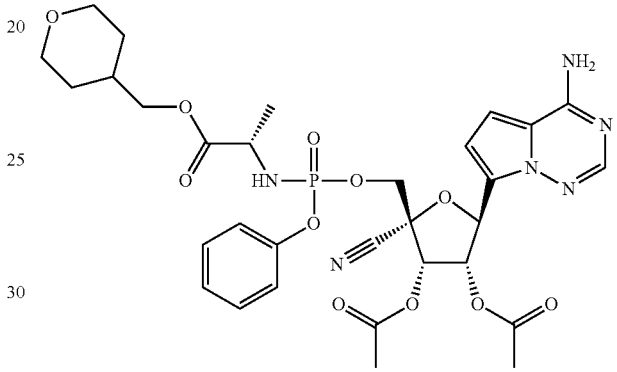

To a solution of Example 20 (75 mg, 0.122 mmol) in anhydrous N,N'-dimethylformamide (1 mL) was added acetic acid (37 mg, 0.608 mmol) and N,N'-diisopropylcarbodiimide (0.095 mL, 0.608 mmol). The reaction mixture was stirred at room temperature for 5 min followed by the addition of 4-dimethylamino pyridine (15 mg, 0.122 mmol). Continued the stirring for 1 h followed by the dilution with N,N'-dimethylformamide (1 mL) and purification by preparative HPLC (Phenomenex Gemini-NX 10μ C18 110° A 250×30 mm column, 25%-95% acetonitrile/water gradient in 30 min run) to afford the product. $^1$H NMR (400 MHz, methanol-d$_4$) δ 7.82 (d, J=9.3 Hz, 1H), 7.36-7.26 (m, 2H), 7.24-7.13 (m, 3H), 6.88-6.71 (m, 2H), 5.90-5.75 (m, 2H), 5.69 (dd, J=4.8, 3.7 Hz, 1H), 4.56-4.37 (m, 2H), 3.97-3.78 (m, 3H), 2.13 (dd, J=20.6, 4.2 Hz, 6H), 1.84 (s, 1H), 1.55 (d, J=13.1 Hz, 2H), 1.34-1.20 (m, 5H). $^{31}$P NMR (162 MHz, methanol-d4) δ 2.99, 3.03. LCMS: MS m/z=701.27 [M+1];]; $t_R$=0.90-0.91 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.726 min (minor isomer), 4.786 min (major isomer); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Resolution of the Sp and Rp diastereomers. The product was purified via chiral preparatory HPLC (SFC AD-H, 5 um 21×250 mm Heptane 70% Ethanol 30%) to afford the diastereomers:

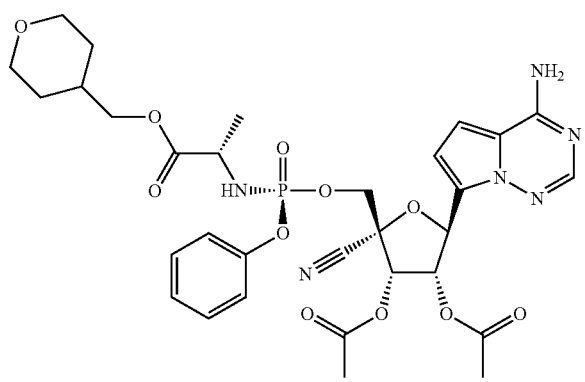 [SMILES: CC(=O)O[C@H]1[C@H](c2ccc3c(N)ncnn23)O[C@](C#N)(COP(=O)(N[C@@H](C)C(=O)OCC2CCOCC2)Oc2ccccc2)[C@H]1OC(C)=O]

Example 111

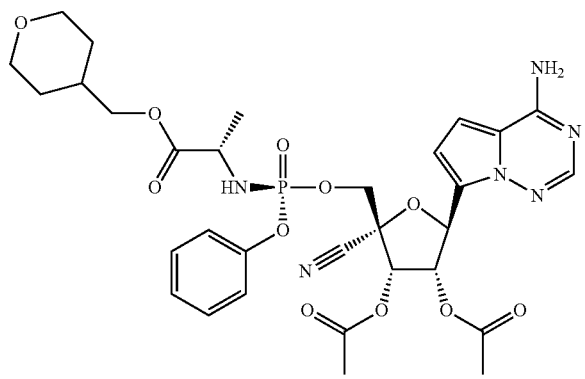

Example 112

First Eluting Diastereomer: $^1$H NMR (400 MHz, methanol-$d_4$) δ 7.80 (s, 1H), 7.30 (t, J=7.9 Hz, 2H), 7.20-7.12 (m, 3H), 6.85 (d, J=4.5 Hz, 1H), 6.77 (d, J=4.6 Hz, 1H), 5.94 (d, J=5.9 Hz, 1H), 5.84 (dd, J=5.9, 4.8 Hz, 1H), 5.69 (d, J=4.8 Hz, 1H), 4.51 (dd, J=11.1, 5.9 Hz, 1H), 4.42 (dd, J=11.1, 5.1 Hz, 1H), 3.94-3.80 (m, 5H), 3.34 (d, J=11.6 Hz, 2H), 2.13 (d, J=20.4 Hz, 6H), 1.86 (s, 1H), 1.56 (d, J=13.6 Hz, 2H), 1.35-1.20 (m, 5H). $^{31}$P NMR (162 MHz, methanol-$d_4$) δ 3.02. LCMS: MS m/z=701.28 [M+1], $t_R$=0.89 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.721 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Second Eluting Diastereomer: $^1$H NMR (400 MHz, methanol-$d_4$) δ 7.83 (s, 1H), 7.31 (dd, J=8.7, 7.2 Hz, 2H), 7.24-7.13 (m, 3H), 6.83 (d, J=4.6 Hz, 1H), 6.74 (d, J=4.6 Hz, 1H), 5.87 (d, J=5.9 Hz, 1H), 5.78 (dd, J=5.9, 4.9 Hz, 1H), 5.68 (d, J=4.9 Hz, 1H), 4.44 (t, J=5.5 Hz, 2H), 3.97-3.78 (m, 5H), 3.35 (dt, 2H), 2.15 (s, 3H), 2.09 (s, 3H), 1.83 (ddd, J=11.6, 7.8, 5.0 Hz, 1H), 1.55 (d, J=11.8 Hz, 2H), 1.34-1.18 (m, 5H). $^{31}$P NMR (162 MHz, methanol-$d_4$) δ 2.99. LCMS: MS m/z=701.28 [M+1], $t_R$=0.90 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.779 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 113. (2R,3S,4S,5S)-5-(4-Aminopyrrolo[2,1-f][1,2,4]triazin-7-yl)-2-cyano-2-((((((S)-1-(cyclohexyloxy)-1-oxopropan-2-yl)amino)(((S)-1-(2-ethylbutoxy)-1-oxopropan-2-yl)amino)phosphoryl)oxy)methyl)tetrahydrofuran-3,4-diyl diacetate A mixture of Example 30 (47 mg, 0.069 mmol), acetic acid (0.05 mL, 0.874 mmol), and N,N-diisopropylcarbodiimide (0.05 mL, 0.319 mmol) in THF (3 mL) was stirred at room temperature for 20 min and DMAP (16 mg, 0.131 mmol) was added. The resulting mixture was stirred at room temperature for 80 min and quenched by adding methanol (0.5 mL), and purified by preparative HPLC (Phenomenex Gemini-NX 10μ C18 110° A 250×30 mm column, 0%-100% acetonitrile/water gradient in 25 min run) to afford the product. $^1$H NMR (400 MHz, Acetonitrile-d3) δ 7.91 (s, 1H), 6.82 (d, J=4.6 Hz, 1H), 6.77 (d, J=4.5 Hz, 1H), 6.48 (s, 2H), 5.80 (d, J=2.4 Hz, 2H), 5.71-5.64 (m, 1H), 4.70 (qd, J=8.5, 3.8 Hz, 1H), 4.33 (dd, J=11.3, 7.1 Hz, 1H), 4.22 (ddd, J=11.3, 5.8, 2.3 Hz, 1H), 4.05 (td, J=11.0, 5.7 Hz, 1H), 3.94 (ddd, J=20.8, 10.9, 5.6 Hz, 1H), 3.88-3.72 (m, 4H), 2.16 (s, 3H), 2.07 (s, 3H), 1.78 (m, 2H), 1.73-1.65 (m, 2H), 1.51 (m, 2H), 1.35 (m, 9H), 1.26 (m, 6H), 0.88 (m, 6H). LCMS: MS m/z=764.54 [M+1]; $t_R$=1.19 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=6.05 min (37%), 6.07 min (60%); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 114. (2R,3S,4S,5S)-5-(4-Aminopyrrolo[2,1-f][1,2,4]triazin-7-yl)-2-cyano-2-((((((S)-1-(2-ethyl-butoxy)-1-oxopropan-2-yl)amino)(((2S)-1-(2-ethyl-butoxy)-1-oxopropan-2-yl)amino)phosphoryl)oxy)methyl)tetrahydrofuran-3,4-diyl diacetate

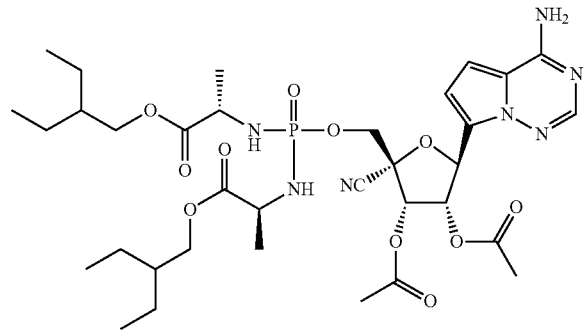 [SMILES: CCC(CC)COC(=O)[C@H](C)NP(=O)(N[C@@H](C)C(=O)OCC(CC)CC)OC[C@@]1(C#N)O[C@@H](c2ccc3c(N)ncnn23)[C@H](OC(C)=O)[C@@H]1OC(C)=O]

A mixture of Example 7 (60 mg, 0.088 mmol), acetic acid (0.05 mL, 0.874 mmol), and N,N-diisopropylcarbodiimide (0.05 mL, 0.319 mmol) in THF (3 mL) was stirred at room temperature for 20 min and DMAP (16 mg, 0.131 mmol) was added. The resulting mixture was stirred at room temperature for 80 min and quenched by adding methanol (0.5 mL), and purified by preparative HPLC (Phenomenex Gemini-NX 10µ C18 110° A 250×30 mm column, 0%-100% acetonitrile/water gradient in 25 min run) to afford the product. $^1$H NMR (400 MHz, Acetonitrile-d3) δ 7.91 (s, 1H), 6.82 (d, J=4.6 Hz, 1H), 6.77 (d, J=4.6 Hz, 1H), 6.46 (s, 2H), 5.84-5.76 (m, 2H), 5.72-5.63 (m, 1H), 6 4.33 (dd, J=11.3, 7.1 Hz, 1H), 4.22 (dd, J=11.3, 5.8 Hz, 1H), 4.10-3.89 (m, 4H), 3.88-3.73 (m, 4H), 2.16 (s, 3H), 2.07 (s, 3H), 1.57-1.43 (m, 2H), 1.34 (hd, J=7.3, 2.0 Hz, 8H), 1.29-1.23 (m, 6H), 0.88 (td, J=7.5, 4.6 Hz, 12H). $^{31}$P NMR (162 MHz, Acetonitrile-d3) δ 12.10. LCMS: MS m/z=766.51 [M+1]; $t_R$=1.22 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=6.25 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 115. (2R,3S,4R,5S)-5-(4-aminopyrrolo[2,1-f][1,2,4]triazin-7-yl)-2-cyano-2-((((((S)-1-oxo-1-((1-(2,2,2-trifluoroethyl)piperidin-4-yl)methoxy)propan-2-yl)amino)(phenoxy) phosphoryl)oxy)methyl)tetrahydrofuran-3,4-diyl dipropionate

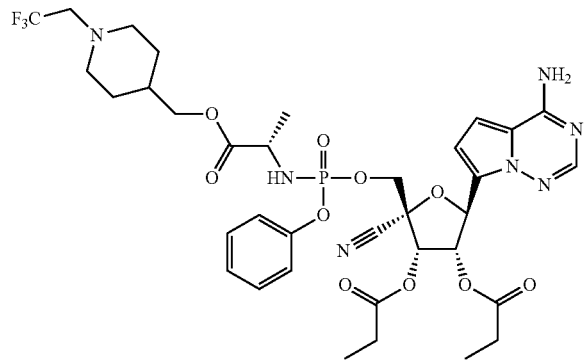 [SMILES: CCC(=O)O[C@H]1[C@H](c2ccc3c(N)ncnn23)O[C@](C#N)(COP(=O)(N[C@@H](C)C(=O)OCC2CCN(CC(F)(F)F)CC2)Oc2ccccc2)[C@H]1OC(=O)CC]

To a solution of Example 31. (100 mg, 0.143 mmol) in anhydrous N,N'-dimethylformamide (1 mL) was added propionic acid (53 mg, 0.717 mmol) and N,N'-diisopropylcarbodiimide (0.112 mL, 0.717 mmol). The reaction mixture was stirred at room temperature for 5 min followed by the addition of 4-dimethylamino pyridine (18 mg, 0.143 mmol). Continued the stirring for 1 h followed by the dilution with N,N'-dimethylformamide (1 mL) and purification by preparative HPLC (Phenomenex Gemini-NX 10µ C18 110° A 250×30 mm column, 25%-95% acetonitrile/water gradient in 30 min run) to afford the product. $^1$H NMR (400 MHz, methanol-d$_4$) δ 7.82 (d, J=8.9 Hz, 1H), 7.35-7.26 (m, 2H), 7.24-7.13 (m, 3H), 6.88-6.71 (m, 2H), 5.92-5.76 (m, 2H), 5.69 (t, J=4.5 Hz, 1H), 4.55-4.37 (m, 2H), 3.95-3.78 (m, 3H), 3.09-2.88 (m, 4H), 2.49-2.35 (m, 4H), 2.26 (t, J=11.8 Hz, 2H), 1.61 (d, J=12.3 Hz, 3H), 1.35-1.08 (m, 11H). $^{31}$P NMR (162 MHz, methanol-d4) δ 2.99, 3.05. LCMS: MS m/z=405.90 [M+1];]; $t_R$=1.01-1.02 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=4.633 min (minor isomer), 4.677 min (major isomer); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Resolution of the Sp and Rp diastereomers. The product was purified via chiral preparatory HPLC (SFC AD-H, 5 um 21×250 mm Heptane 70% Ethanol 30%) to afford the diastereomers:

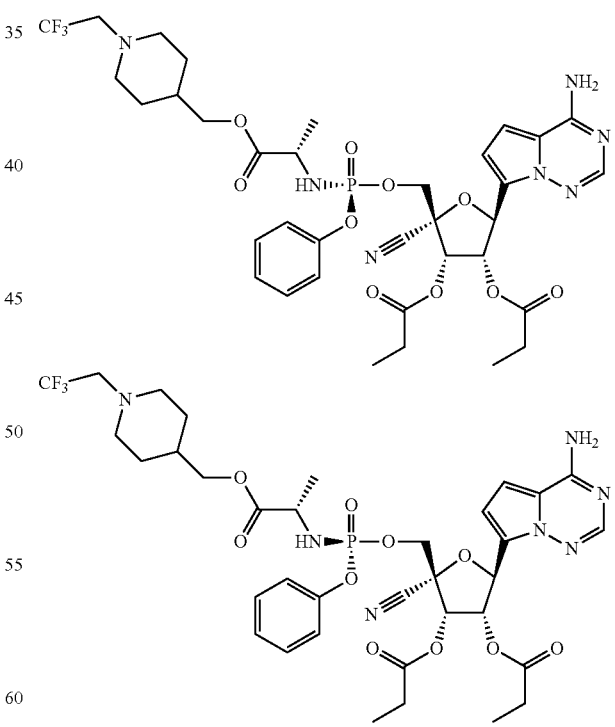

Example 116

First Eluting Diastereomer: $^1$H NMR (400 MHz, methanol-d$_4$) δ 7.81 (s, 1H), 7.35-7.26 (m, 2H), 7.20-7.12 (m, 3H), 6.85 (d, J=4.6 Hz, 1H), 6.78 (d, J=4.5 Hz, 1H), 5.96 (d, J=5.9 Hz, 1H), 5.85 (dd, J=5.9, 4.6 Hz, 1H), 5.69 (d, J=4.6 Hz, 1H), 4.56-4.37 (m, 2H), 3.94-3.78 (m, 3H), 3.04-2.87 (m, 4H), 2.53-2.35 (m, 4H), 2.26 (t, J=12.0 Hz, 2H), 1.61 (s, 3H), 1.35-1.20 (m, 5H), 1.15 (dt, J=13.2, 7.5 Hz, 6H). $^{19}$F NMR (376 MHz, methanol-d$_4$) δ -71.22 (t, J=10.0 Hz). $^{31}$P NMR (162 MHz, methanol-d$_4$) δ 3.05. LCMS: MS m/z=405.89 [M+1], t$_R$=1.03 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: t$_R$=4.628 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 117

Second Eluting Diastereomer: $^1$H NMR (400 MHz, methanol-d$_4$) δ 7.83 (s, 1H), 7.31 (dd, J=8.6, 7.1 Hz, 2H), 7.24-7.12 (m, 3H), 6.84 (d, J=4.5 Hz, 1H), 6.74 (d, J=4.6 Hz, 1H), 5.89 (d, J=5.9 Hz, 1H), 5.80 (dd, J=5.9, 4.8 Hz, 1H), 5.68 (d, J=4.8 Hz, 1H), 4.50-4.37 (m, 2H), 3.97-3.78 (m, 3H), 3.04-2.88 (m, 4H), 2.53-2.35 (m, 4H), 2.26 (t, J=11.7 Hz, 2H), 1.65-1.51 (m, 3H), 1.34-1.08 (m, 11H). $^{19}$F NMR (376 MHz, methanol-d$_4$) δ -71.22 (t, J=9.9 Hz). $^{31}$P NMR (162 MHz, methanol-d$_4$) δ 2.99. LCMS: MS m/z=405.88 [M+1], t$_R$=1.04 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: t$_R$=4.673 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 118. (2R,3S,4R,5S)-5-(4-aminopyrrolo[2,1-f][1,2,4]triazin-7-yl)-2-cyano-2-(((((S)-1-oxo-1-((1-(2,2,2-trifluoroethyl)piperidin-4-yl)methoxy)propan-2-yl)amino)(phenoxy) phosphoryl)oxy)methyl)tetrahydrofuran-3,4-diyl diacetate

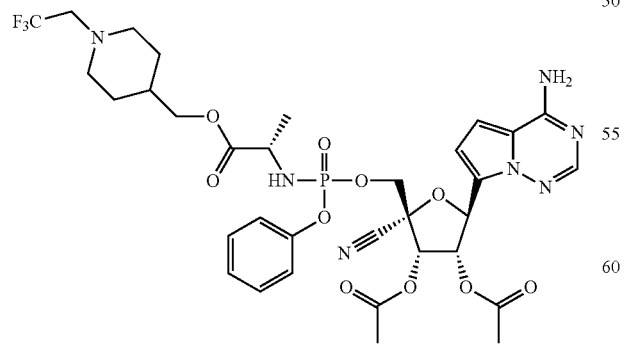

To a solution of Example 31. (100 mg, 0.143 mmol) in anhydrous N,N'-dimethylformamide (1 mL) was added acetic acid (43 mg, 0.717 mmol) and N,N'-diisopropylcarbodiimide (0.112 mL, 0.717 mmol). The reaction mixture was stirred at room temperature for 5 min followed by the addition of 4-dimethylamino pyridine (18 mg, 0.143 mmol). Continued the stirring for 1 h followed by dilution with N,N'-dimethylformamide (1 mL) and purification by preparative HPLC (Phenomenex Gemini-NX 10µ C18 110° A 250×30 mm column, 25%-95% acetonitrile/water gradient in 30 min run) to afford the product. $^1$H NMR (400 MHz, methanol-d4) δ 7.82 (d, J=10.0 Hz, 1H), 7.31 (ddd, J=10.2, 7.4, 2.9 Hz, 2H), 7.25-7.12 (m, 3H), 6.89-6.72 (m, 2H), 5.90-5.75 (m, 2H), 5.69 (t, J=4.6 Hz, 1H), 4.56-4.38 (m, 2H), 3.97-3.78 (m, 3H), 3.05-2.83 (m, 4H), 2.26 (t, J=11.8 Hz, 2H), 2.13 (dd, J=20.1, 4.5 Hz, 6H), 1.65-1.51 (m, 3H), 1.26 (ddd, J=20.1, 7.2, 1.2 Hz, 5H). $^{31}$P NMR (162 MHz, methanol-d$_4$) δ 3.02, 3.06. $^{19}$F NMR (377 MHz, methanol-d$_4$) δ -71.22 (t, J=9.9 Hz) LCMS: MS m/z=391.90 [M+1];]; t$_R$=0.89 min (minor isomer)-0.91 min (major isomer); LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: t$_R$=4.217 min (minor isomer), 4.258 min (major isomer); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Resolution of the Sp and Rp diastereomers. The product was purified via chiral preparatory HPLC (SFC AD-H, 5 um 21×250 mm Heptane 70% Ethanol 30%) to afford the diastereomers:

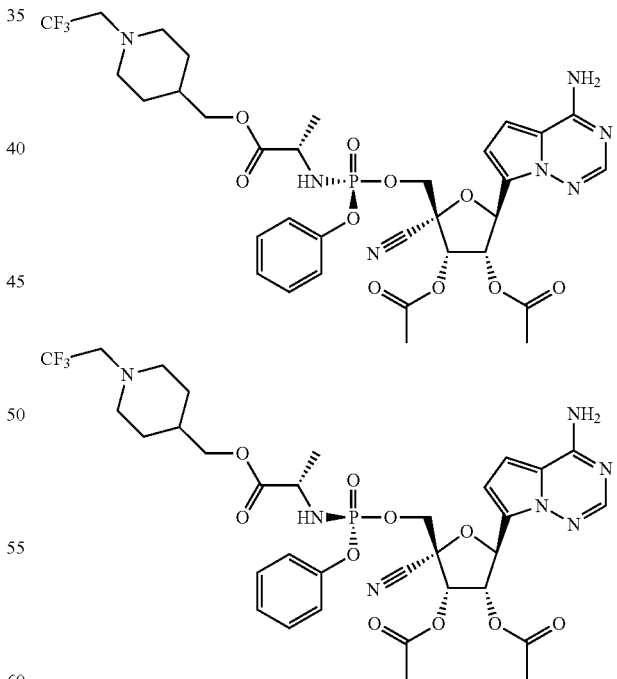

Example 119

First Eluting Diastereomer: $^1$H NMR (400 MHz, methanol-d$_4$) δ 7.80 (s, 1H), 7.35-7.26 (m, 2H), 7.20-7.11 (m, 3H), 6.85 (d, J=4.5 Hz, 1H), 6.77 (d, J=4.6 Hz, 1H), 5.94 (d, J=5.9

Hz, 1H), 5.84 (dd, J=5.9, 4.8 Hz, 1H), 5.69 (d, J=4.8 Hz, 1H), 4.51 (dd, J=11.1, 5.9 Hz, 1H), 4.42 (dd, J=11.1, 5.1 Hz, 1H), 3.94-3.78 (m, 3H), 2.95 (dd, J=28.2, 10.6 Hz, 4H), 2.26 (t, J=11.9 Hz, 2H), 2.13 (d, J=19.8 Hz, 6H), 1.60 (s, 3H), 1.34-1.20 (m, 5H). $^{19}$F NMR (376 MHz, methanol-$d_4$) δ −71.21 (t, J=10.0 Hz). $^{31}$P NMR (162 MHz, methanol-$d_4$) δ 3.04. LCMS: MS m/z=391.83 [M+1], $t_R$=0.91 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.212 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 120

Second Eluting Diastereomer: $^1$H NMR (400 MHz, methanol-$d_4$) δ 7.83 (s, 1H), 7.35-7.26 (m, 2H), 7.24-7.12 (m, 3H), 6.83 (d, J=4.5 Hz, 1H), 6.74 (d, J=4.6 Hz, 1H), 5.87 (d, J=5.9 Hz, 1H), 5.79 (dd, J=5.9, 5.0 Hz, 1H), 5.68 (d, J=5.0 Hz, 1H), 4.44 (t, J=5.5 Hz, 2H), 3.97-3.78 (m, 3H), 3.04-2.88 (m, 4H), 2.26 (t, J=11.8 Hz, 2H), 2.15 (s, 3H), 2.09 (s, 3H), 1.60 (d, J=12.8 Hz, 3H), 1.35-1.20 (m, 5H). $^{19}$F NMR (376 MHz, methanol-$d_4$) δ −71.22 (t, J=9.9 Hz). $^{31}$P NMR (162 MHz, methanol-$d_4$) δ 3.00. LCMS: MS m/z=391.87 [M+1], $t_R$=0.92 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=4.256 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 121. (2R,3S,4S,5S)-5-(4-Aminopyrrolo[2,1-f][1,2,4]triazin-7-yl)-2-cyano-2-((((((S)-1-(cyclohexyloxy)-1-oxopropan-2-yl)amino)(((S)-1-cyclohexyloxy-1-oxopropan-2-yl)amino)phosphoryl)oxy)methyl)tetrahydrofuran-3,4-diyl diacetate

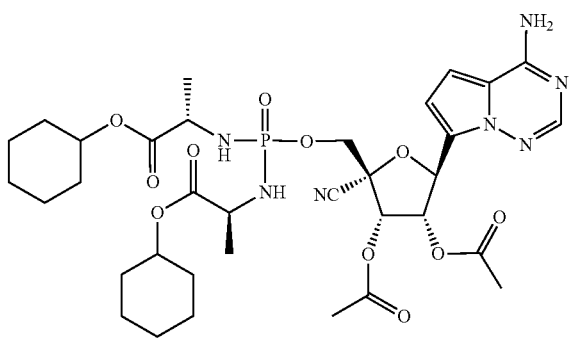 [SMILES: CC(=O)O[C@H]1[C@H](c2ccc3c(N)ncnn23)O[C@](C#N)(COP(=O)(N[C@@H](C)C(=O)OC2CCCCC2)N[C@@H](C)C(=O)OC2CCCCC2)[C@H]1OC(C)=O]

A mixture of Example 14 (52 mg, 0.077 mmol), acetic acid (0.0544 mL, 0.762 mmol), and N,N-diisopropylcarbodiimide (0.044 mL, 0.278 mmol) in THF (3 mL) was stirred at room temperature for 20 min and DMAP (15 mg, 0.124 mmol) was added. The resulting mixture was stirred at room temperature for 80 min and quenched by adding methanol (0.5 mL), and purified by preparative HPLC (Phenomenex Gemini-NX 10μ C18 110° A 250×30 mm column, 0%-100% acetonitrile/water gradient in 25 min run) to afford the product. $^1$H NMR (400 MHz, Acetonitrile-d3) δ 7.92 (s, 1H), 6.82 (d, J=4.6 Hz, 1H), 6.77 (d, J=4.6 Hz, 1H), 6.45 (s, 2H), 5.80 (m, 2H), 5.68 (t, J=2.3 Hz, 1H), 4.69 (qd, J=8.7, 3.8 Hz, 2H), 4.33 (dd, J=11.3, 7.2 Hz, 1H), 4.22 (dd, J=11.3, 5.8 Hz, 1H), 3.88-3.67 (m, 4H), 2.16 (s, 3H), 2.07 (s, 3H), 1.86-1.59 (m, 8H), 1.51 (m, 2H), 1.38 (m, 10H), 1.25 (m, 6H). $^{31}$P NMR (162 MHz, Acetonitrile-d3) δ 12.16. LCMS: MS m/z=762.53 [M+1]; $t_R$=1.14 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.86 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 122. (2R,3S,4S,5S)-5-(4-aminopyrrolo[2,1-f][1,2,4]triazin-7-yl)-2-cyano-2-((((S)-(((S)-1-(cyclohexyloxy)-1-oxopropan-2-yl)amino)(phenoxy) phosphoryl) oxy)methyl)tetrahydrofuran-3,4-diyl (2S,2'S)-bis(2-amino-3-methylbutanoate)

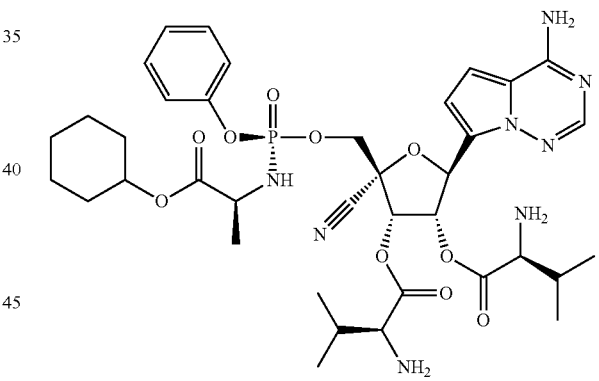

Example 6 (50 mg, 0.083 mmol was dissolved in 1 mL of anhydrous tetrahydrofuran. Boc-L-valine (72 mg, 0.33 mmol) and N,N'-diisopropylcarbodiimide (52 μL, 0.33 mmol) were added to the reaction and the resulting mixture was stirred for 20 min. DMAP (10 mg, 0.083 mmol) was added and the mixture was stirred for 16 h. Methanol (0.5 mL) was added to the reaction and stirred for 25 min. The reaction mixture was diluted with ethyl acetate (10 mL) and washed with 2% aqueous citric acid solution (10 mL) and then with brine (5 mL). The organic extract was dried over anhydrous sodium sulfate and concentrated under reduced pressure. The crude residue was purified via SiO$_2$ column chromatography (4 g SiO$_2$ Combiflash HP Gold Column, 0-100% ethyl acetate/hexanes). The fractions containing desired product were combined and concentrated under reduced pressure. The residue was dissolved in MeCN (5 mL) and stirred under atmospheric nitrogen in an ice bath. Concentrated HCl(aq) (300 μL) was added dropwise and the reaction mixture was stirred for 4 h. The crude reaction mixture was loaded directly onto a prep HPLC column and eluted with a linear gradient from 5-100% MeCN without acid modifier. Fractions containing the desired product were combined and freeze-dried. The resulting material was repurified with prep HPLC with TFA as modifier (5-100% MeCN/water). The fractions containing the desired product were combined and freeze-dried to afford the product. $^1$H NMR (400 MHz, methanol-$d_4$) δ 8.03 (s, 1H), 7.37-7.29 (m, 2H), 7.27 (d, J=4.7 Hz, 1H), 7.24-7.15 (m, 3H), 6.99 (d, J=4.7 Hz, 1H), 6.32 (d, J=5.8 Hz, 1H), 6.04 (dd, J=5.8, 3.2 Hz, 1H), 5.87 (d, J=3.2 Hz, 1H), 4.59 (m, 1H), 4.50 (qd, J=11.5, 6.4 Hz, 2H), 4.14 (dd, J=9.7, 4.1 Hz, 2H), 3.79 (dq, J=10.1, 7.1 Hz, 1H), 2.51 (m, 2H), 1.79-1.60 (m, 4H), 1.57-1.44 (m, 1H), 1.44-1.20 (m, 8H), 1.20-1.06 (m, 12H). $^{31}$P NMR (162 MHz, methanol-$d_4$) δ 3.15 (s). LCMS: MS m/z=799.3 [M+1]; 797.6 [M−1], $t_R$=1.00 min; LC system: Thermo Dionex ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 m/min. HPLC: $t_R$=2.65 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min. HPLC: $t_R$=4.472 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 123. ((2R,3S,4R,5S)-5-(4-aminopyrrolo[2,1-f][1,2,4]triazin-7-yl)-2-cyano-3,4-dipropionatetetrahydrofuran-2-yl)methyl bis-isopropyl L-alaninate phosphate

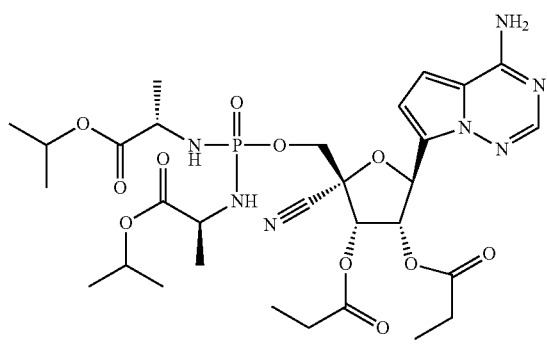 [SMILES: CCC(=O)O[C@H]1[C@H](c2ccc3c(N)ncnn23)O[C@](C#N)(COP(=O)(N[C@@H](C)C(=O)OC(C)C)N[C@@H](C)C(=O)OC(C)C)[C@H]1OC(=O)CC]

Dissolved Example 34 (20 mg, 0.033 mmol) in 3 mL THF, to the solution were added propionic acid (20 mg, 0.27 mmol) and DIC (17 mg, 0.13 mmol). The reaction mixture was stirred for 10 mins at RT, then DMAP (8.2 mg, 0.07 mmol) was added. The resulting mixture was stirred at RT for 30 mins and then solvent was evaporated. The residue was purified with Prep HPLC to afford the product. $^1$H NMR (400 MHz, Methanol-d4) δ 7.91 (s, 1H), 6.86 (d, J=4.6 Hz, 1H), 6.82 (d, J=4.5 Hz, 1H), 5.91 (d, J=6.0 Hz, 1H), 5.84 (dd, J=5.9, 4.6 Hz, 1H), 5.00-4.90 (m, 1H), 4.90-4.83 (m, 1H), 4.35 (dd, J=11.2, 6.8 Hz, 1H), 4.27 (dd, J=11.2, 5.2 Hz, 1H), 3.82 (dp, J=9.2, 7.1 Hz, 2H), 2.56-2.34 (m, 4H), 1.35-1.07 (m, 24H). $^{31}$P NMR (162 MHz, Methanol-d4) δ 13.51. LCMS: MS m/z=710.29 [M+1], $t_R$=1.34 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.14 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 124. ((2R,3S,4R,5S)-5-(4-aminopyrrolo[2,1-f][1,2,4]triazin-7-yl)-2-cyano-3,4-dipropionatetetrahydrofuran-2-yl)methyl bis-ethyl L-alaninate phosphate

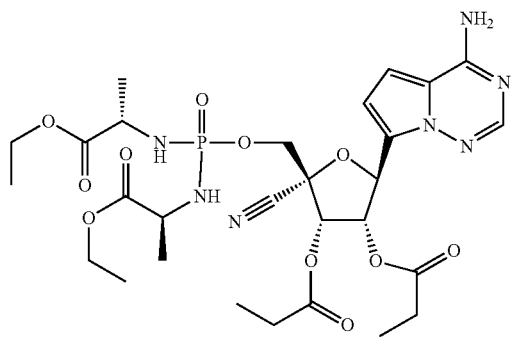 [SMILES: CCOC(=O)[C@H](C)NP(=O)(N[C@@H](C)C(=O)OCC)OC[C@@]1(C#N)O[C@@H](c2ccc3c(N)ncnn23)[C@H](OC(=O)CC)[C@@H]1OC(=O)CC]

Dissolved Example 35 (21 mg, 0.037 mmol) in 3 mL THF, to the solution were added propionic acid (22 mg, 0.30 mmol) and DIC (19 mg, 0.15 mmol). The reaction mixture was stirred for 10 mins at RT, then DMAP (9 mg, 0.07 mmol) was added. The resulting mixture was stirred at RT for 30 mins and then solvent was evaporated. The residue was purified with Prep HPLC to afford the product. $^1$H NMR (400 MHz, Methanol-d4) δ 7.93 (s, 1H), 7.00 (d, J=4.6 Hz, 1H), 6.89 (d, J=4.6 Hz, 1H), 5.88 (d, J=6.0 Hz, 1H), 5.84 (dd, J=5.9, 4.6 Hz, 1H), 5.69 (d, J=4.6 Hz, 1H), 4.36 (dd, J=11.2, 6.7 Hz, 1H), 4.27 (dd, J=11.2, 5.1 Hz, 1H), 4.11 (dp, J=18.8, 7.1 Hz, 4H), 3.89-3.75 (m, 2H), 2.58-2.32 (m, 4H), 1.37-1.04 (m, 18H). $^{31}$P NMR (162 MHz, Methanol-d4) δ 13.49. LCMS: MS m/z=682.14 [M+1], $t_R$=1.25 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=2.92 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 125. ((2R,3S,4R,5S)-5-(4-aminopyrrolo[2,1-f][1,2,4]triazin-7-yl)-2-cyano-3,4-dipropionatetetrahydrofuran-2-yl)methyl bis-cyclobutylmethyl L-alaninate phosphate

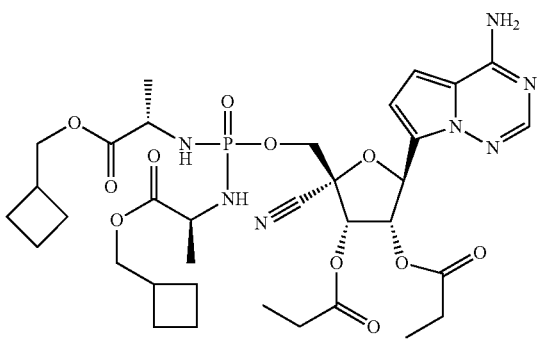 [SMILES: CCC(=O)O[C@H]1[C@H](c2ccc3c(N)ncnn23)O[C@](C#N)(COP(=O)(N[C@@H](C)C(=O)OCC2CCC2)N[C@@H](C)C(=O)OCC2CCC2)[C@H]1OC(=O)CC]

Dissolved Example 36 (17 mg, 0.026 mmol) in 3 mL THF, to the solution were added propionic acid (15.5 mg, 0.21 mmol) and DIC (13 mg, 0.11 mmol). The reaction mixture was stirred for 10 mins at RT, then DMAP (6 mg, 0.05 mmol) was added. The resulting mixture was stirred at RT for 30 mins and then solvent was evaporated. The residue was purified with Prep HPLC to afford the product. $^1$H NMR (400 MHz, Methanol-d4) δ 7.86 (s, 1H), 6.87 (d, J=4.5 Hz, 1H), 6.82 (d, J=4.6 Hz, 1H), 5.90 (d, J=6.0 Hz, 1H), 5.83 (t, J=5.3 Hz, 1H), 5.68 (d, J=4.7 Hz, 1H), 4.35 (dd, J=11.2, 6.7 Hz, 1H), 4.26 (dd, J=11.2, 5.1 Hz, 1H), 4.15-3.81 (m, 6H), 2.65-2.34 (m, 6H), 2.02 (dq, J=13.7, 7.0 Hz, 4H), 1.96-1.65 (m, 8H), 1.29 (d, J=7.1 Hz, 6H), 1.16 (dt, J=21.0, 7.5 Hz, 6H). $^{31}$P NMR (162 MHz, Methanol-d4) δ 13.44. LCMS: MS m/z=762.36 [M+1], $t_R$=1.47 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.51 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 126. (2R,3S,4S,5S)-5-(4-aminopyrrolo[2,1-f][1,2,4]triazin-7-yl)-2-((((((S)-1-(benzyloxy)-1-oxopropan-2-yl)amino)(phenoxy)phosphoryl)oxy)methyl)-2-cyanotetrahydrofuran-3,4-diyl diacetate

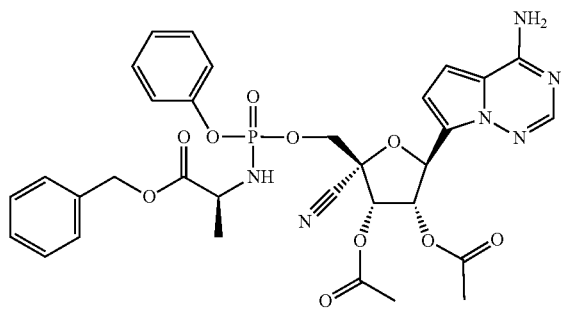 [SMILES: CC(=O)O[C@H]1[C@H](c2ccc3c(N)ncnn23)O[C@](C#N)(COP(=O)(N[C@@H](C)C(=O)OCc2ccccc2)Oc2ccccc2)[C@H]1OC(C)=O]

Example 37 (25 mg, 0.041 mmol) was dissolved in 1.5 mL of anhydrous tetrahydrofuran. Acetic acid (12 μL, 0.205 mmol) and N,N'-diisopropylcarbodiimide (32 μL, 0.205 mmol) were added to the reaction which was stirred for 30 min. DMAP (5 mg, 0.041 mmol) was added and the reaction was stirred for 14 h. More acetic acid (5 μL) and N,N'-diisopropylcarbodiimide (12 μL) were added and the reaction was stirred for 45 min. The reaction was diluted with ethyl acetate (10 mL) and washed with saturated aqueous sodium bicarbonate solution (2×10 mL) and then with brine (2×5 mL). The organic extract was dried over anhydrous sodium sulfate and concentrated under reduced pressure. The crude residue was purified via SiO$_2$ column chromatography (4 g SiO$_2$ Combiflash HP Gold Column, 0-100% ethyl acetate/hexanes). Fractions containing the desired product were combined and concentrated under reduced pressure as oil which was then dissolved in MeCN and water and freeze-dried to afford the product. $^1$H NMR (400 MHz, chloroform-d) δ 7.86 (m, 1H), 7.36-7.21 (m, 7H), 7.21-7.07 (m, 3H), 6.63 (m, 1H), 6.50 (m, 1H), 6.02 (bs, 2H), 5.95-5.75 (m, 2H), 5.68 (m, 1H), 5.16-4.98 (m, 2H), 4.58-4.19 (m, 3H), 4.11-3.97 (m, 1H), 2.14 (m, 6H), 1.31 (m, 3H). $^{31}$P NMR (162 MHz, chloroform-d) δ 2.32, 2.33. LCMS: MS m/z=693.2 [M+1]; 691.4 [M−1], $t_R$=1.32 min; LC system: Thermo Dionex ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=3.16 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min. HPLC: $t_R$=5.287, 5.309 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 127

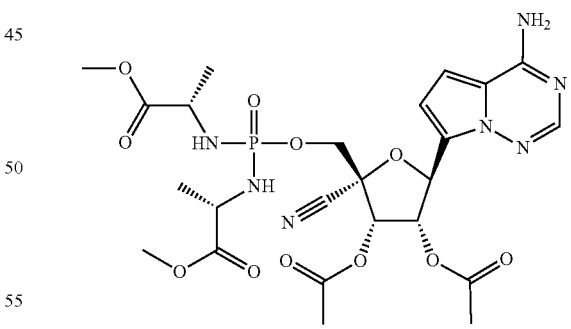

N,N'-diisopropylcarbodiimide (0.086 mL, 0.55 mmol) and 4-dimethylaminopyridine (14.0 mg, 0.11 mmol) were added to a solution of Example 38. (60 mg, 0.110 mmol) and acetic acid (0.032 mL, 0.55 mmol) in tetrahydrofuran (1.0 mL) at RT. After 1.5 h, methanol (0.2 mL) was added and the resulting mixture was concentrated under reduced pressure. The crude residue was subjected to silica gel chromatography eluting with 0-100% ethyl acetate in hexanes to afford a mixture of the product and the triacetate compound Example 128. $^1$H NMR (400 MHz, methanol-d$_4$) δ 7.87 (s, 1H), 6.86 (d, J=4.6 Hz, 1H), 6.86 (d, J=4.6 Hz, 1H), 5.93-5.80 (m, 2H), 5.69 (d, J=4.8 Hz, 1H), 4.35 (dd, J=11.2, 6.7 Hz, 1H), 4.26 (dd, J=11.2, 5.1 Hz, 1H), 3.91-3.76 (m, 2H), 3.67 (s, 3H), 3.65 (s, 3H), 2.18 (s, 3H), 2.10 (s, 3H), 1.31-1.22 (m, 6H). $^{31}$P NMR (162 MHz, methanol-d$_4$) δ 13.49 (s). LCMS: MS m/z=626.32 [M+1], t$_R$=1.07 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: t$_R$=2.38 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: t$_R$=3.93 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 128

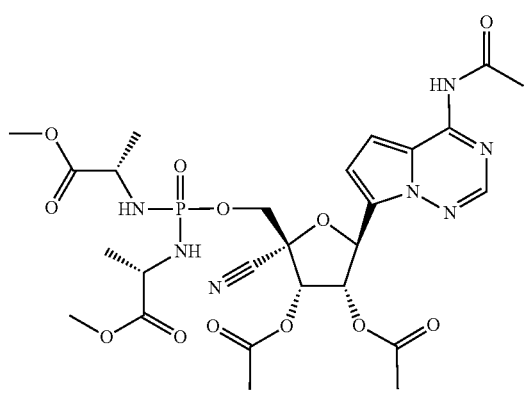 [SMILES: COC(=O)[C@H](C)NP(=O)(N[C@@H](C)C(=O)OC)OC[C@@]1(C#N)O[C@@H](c2ccc3c(NC(C)=O)ncnn23)[C@H](OC(C)=O)[C@@H]1OC(C)=O]

Triacetate prepared by the method of Example 127. $^1$H NMR (400 MHz, methanol-d$_4$) δ 8.25 (s, 1H), 7.21 (d, J=4.8 Hz, 1H), 7.05 (d, J=4.7 Hz, 1H), 5.89-5.82 (m, 2H), 5.78 (d, J=3.9 Hz, 1H), 4.36 (dd, J=11.2, 6.6 Hz, 1H), 4.28 (dd, J=11.2, 5.1 Hz, 1H), 3.92-3.77 (m, 2H), 3.67 (s, 3H), 3.65 (s, 3H), 2.39 (s, 3H), 2.19 (s, 3H), 2.10 (s, 3H), 1.32-1.23 (m, 6H). $^{31}$P NMR (162 MHz, methanol-d$_4$) δ 13.48 (s). LCMS: MS m/z=668.08 [M+1], t$_R$=1.11 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: t$_R$=2.66 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: t$_R$=4.28 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 129. (2R,3S,4S,5S)-5-(4-aminopyrrolo[2,1-f][1,2,4]triazin-7-yl)-2-cyano-2-((((((S)-1-methoxy-1-oxopropan-2-yl)amino)(phenoxy)phosphoryl)oxy)methyl)tetrahydrofuran-3,4-diyl diacetate

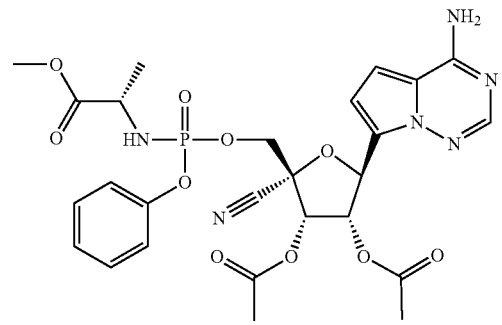 [SMILES: COC(=O)[C@H](C)NP(=O)(OC[C@@]1(C#N)O[C@@H](c2ccc3c(N)ncnn23)[C@H](OC(C)=O)[C@@H]1OC(C)=O)Oc1ccccc1]

N,N'-diisopropylcarbodiimide (0.307 mL, 1.97 mmol) and 4-dimethylaminopyridine (48.0 mg, 0.394 mmol) were added to a solution of Example 39 (210 mg, 0.394 mmol) and acetic acid (0.113 mL, 1.97 mmol) in tetrahydrofuran (2.0 mL) at RT. After 1.5 h, methanol (0.2 mL) was added and the resulting mixture was concentrated under reduced pressure. The crude residue was subjected to silica gel chromatography eluting with 0-100% ethyl acetate in hexanes to afford the product. $^1$H NMR (400 MHz, methanol-d$_4$) δ 7.82 (s, 0.66H), 7.80 (s, 0.33H), 7.36-7.25 (m, 2H), 7.22-7.12 (m, 3H), 6.86-6.81 (m, 1H), 6.78-6.71 (m, 1H), 5.96 (d, J=5.9 Hz, 0.33H), 5.89 (d, J=5.9 Hz, 0.66H), 5.87-5.78 (m, 1H), 5.71-5.68 (m, 1H), 4.54-4.35 (m, 2H), 3.95-3.75 (m, 1H), 3.62 (s, 1H), 3.60 (s, 2H), 2.16 (s, 1H), 2.15 (s, 2H), 2.11 (s, 1H), 2.10 (s, 2H), 1.27 (dd, J=7.2, 1.1 Hz, 2H), 1.21 (dd, J=7.2, 1.3 Hz, 1H). $^{31}$P NMR (162 MHz, methanol-d4) δ 3.02 (s), 3.00 (s). LCMS: MS m/z=617.16 [M+1], t$_R$=1.18 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: t$_R$=2.74 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: t$_R$=4.513 min (minor isomer), 4.570 min (major isomer); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The product was purified via chiral preparatory SFC (Chiralpak ADH, 30% Ethanol).

Example 130. (2R,3S,4S,5S)-5-(4-aminopyrrolo[2,1-f][1,2,4]triazin-7-yl)-2-cyano-2-((((R)-(((S)-1-methoxy-1-oxopropan-2-yl)amino)(phenoxy)phosphoryl)oxy)methyl) tetrahydrofuran-3,4-diyl diacetate

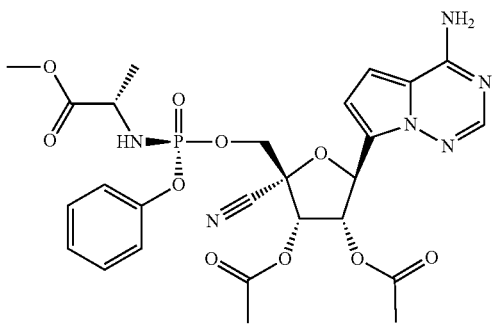 [SMILES: COC(=O)[C@H](C)N[P@@](=O)(OC[C@@]1(C#N)O[C@@H](c2ccc3c(N)ncnn23)[C@H](OC(C)=O)[C@@H]1OC(C)=O)Oc1ccccc1]

First Eluting Diastereomer of Example 129: $^1$H NMR (400 MHz, methanol-d$_4$) δ 7.80 (s, 1H), 7.34-7.24 (m, 2H), 7.19-7.12 (m, 3H), 6.85 (d, J=4.5 Hz, 1H), 6.77 (d, J=4.5 Hz, 1H), 5.95 (d, J=5.9 Hz, 1H), 5.85 (dd, J=5.9, 4.6 Hz, 1H), 5.70 (d, J=4.6 Hz, 1H), 4.52 (dd, J=11.1, 5.9 Hz, 1H), 4.42 (dd, J=11.1, 4.9 Hz, 1H), 3.80 (dq, J=9.4, 7.1 Hz, 1H), 3.63 (s, 3H), 2.16 (s, 3H), 2.11 (s, 3H), 1.21 (dd, J=7.2, 1.3 Hz, 3H). $^{31}$P NMR (162 MHz, methanol-d$_4$) δ 3.00 (s). LCMS: MS m/z=617.16 [M+1], t$_R$=1.18 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLCt$_R$=4.51 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 131. (2R,3S,4S,5S)-5-(4-aminopyrrolo[2,1-f][1,2,4]triazin-7-yl)-2-cyano-2-((((S)-(((S)-1-methoxy-1-oxopropan-2-yl)amino)(phenoxy)phosphoryl)oxy)methyl) tetrahydrofuran-3,4-diyl diacetate

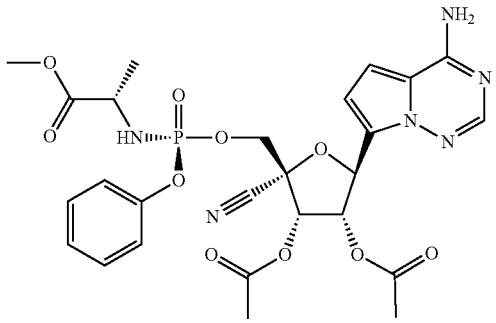 [SMILES: COC(=O)[C@H](C)N[P@](=O)(OC[C@@]1(C#N)O[C@@H](c2ccc3c(N)ncnn23)[C@H](OC(C)=O)[C@@H]1OC(C)=O)Oc1ccccc1]

Second Eluting Diastereomer of Example 129: $^1$H NMR (400 MHz, methanol-d$_4$) δ 7.82 (s, 1H), 7.34-7.26 (m, 2H), 7.23-7.11 (m, 3H), 6.82 (d, J=4.5 Hz, 1H), 6.74 (d, J=4.6 Hz, 1H), 5.89 (d, J=5.9 Hz, 1H), 5.81 (dd, J=5.9, 4.9 Hz, 1H), 5.69 (d, J=4.9 Hz, 1H), 4.49-4.37 (m, 2H), 3.96-3.83 (m, 1H), 3.60 (s, 3H), 2.15 (s, 3H), 2.10 (s, 3H), 1.27 (dd, J=7.1, 1.1 Hz, 3H). $^{31}$P NMR (162 MHz, methanol-d$_4$) δ 3.02 (s). LCMS: MS m/z=617.16 [M+1], t$_R$=1.18 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 L/min. HPLCt$_R$=4.57 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 132. (2R,3S,4S,5S)-5-(4-acetamidopyrrolo[2,1-f][1,2,4]triazin-7-yl)-2-cyano-2-((((((S)-1-methoxy-1-oxopropan-2-yl)amino)(phenoxy)phosphoryl)oxy)methyl) tetrahydrofuran-3,4-diyl diacetate

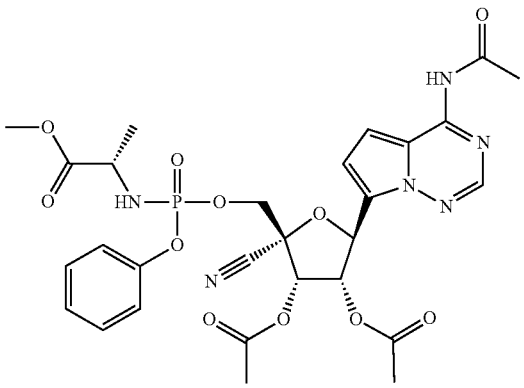 [SMILES: COC(=O)[C@H](C)NP(=O)(OC[C@@]1(C#N)O[C@@H](c2ccc3c(NC(C)=O)ncnn23)[C@H](OC(C)=O)[C@@H]1OC(C)=O)Oc1ccccc1]

N,N'-diisopropylcarbodiimide (0.307 mL, 1.97 mmol) and 4-dimethylaminopyridine (48.0 mg, 0.394 mmol) were added to a solution of Example 39 (210 mg, 0.394 mmol) and acetic acid (0.113 mL, 1.97 mmol) in tetrahydrofuran (2.0 mL) at RT. After 1.5 h, methanol (0.2 mL) was added and the resulting mixture was concentrated under reduced pressure. The crude residue was subjected to silica gel chromatography eluting with 0-100% ethyl acetate in hexanes to afford the product. $^1$H NMR (400 MHz, methanol-d$_4$) δ 8.20 (s, 0.6H), 8.18 (s, 0.4H), 7.37-7.25 (m, 2H), 7.23-7.12 (m, 3H), 6.99 (d, J=4.8 Hz, 0.4H), 6.95 (d, J=4.7 Hz, 0.6H), 5.93-5.76 (m, 2H), 4.57-4.37 (m, 2H), 3.95-3.75 (m, 1H), 3.63 (s, 1.2H), 3.61 (s, 1.8H), 2.38 (d, J=1.7 Hz, 3H), 2.17 (s, 1.2H), 2.16 (s, 1.8H), 2.11 (s, 1.2H), 2.10 (s, 1.8H), 1.28 (dd, J=7.2, 1.1 Hz, 1.8H), 1.23 (dd, J=7.2, 1.3 Hz, 1.2H). $^{31}$P NMR (162 MHz, methanol-d$_4$) δ 3.04 (s), 3.02 (s). LCMS: MS m/z=659.24 [M+1], t$_R$=1.22 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2

µL/min. HPLC: $t_R$=2.38 min; HPLC system: Agilent 1100 series; Column: Gemini 5µ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=4.92 min (minor isomer), 4.95 min (major isomer); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 133. ((2R,3S,4R,5S)-5-(4-aminopyrrolo[2,1-f][1,2,4]triazin-7-yl)-2-cyano-3,4-diacetatetetrahydrofuran-2-yl)methyl bis-isopropyl L-alaninate phosphate

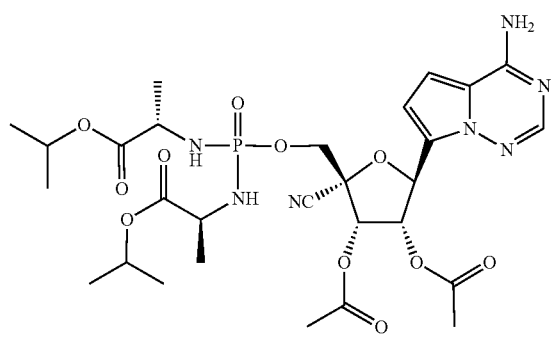 [SMILES: CC(=O)O[C@H]1[C@H](c2ccc3c(N)ncnn23)O[C@](C#N)(COP(=O)(N[C@@H](C)C(=O)OC(C)C)N[C@@H](C)C(=O)OC(C)C)[C@H]1OC(C)=O]

Dissolved ((2R,3S,4R,5S)-5-(4-aminopyrrolo[2,1-f][1,2,4]triazin-7-yl)-2-cyano-3,4-dihydroxytetrahydrofuran-2-yl)methyl bis-isopropyl L-alaninate phosphate Example 34 (40 mg, 0.067 mmol) in 3 mL THF, to the solution were added acetic acid (32 mg, 0.54 mmol) and DIC (34 mg, 0.27 mmol). The reaction mixture was stirred for 10 mins at RT, then DMAP (16 mg, 0.13 mmol) was added. The resulting mixture was stirred at RT for 30 mins and then solvent was evaporated. The residue was purified with Prep HPLC to afford the product. $^1$H NMR (400 MHz, Methanol-d4) δ 7.86 (s, 1H), 6.86 (d, J=4.5 Hz, 1H), 6.81 (d, J=4.6 Hz, 1H), 5.88 (d, J=6.0 Hz, 1H), 5.82 (dd, J=6.0, 4.8 Hz, 1H), 5.68 (d, J=4.8 Hz, 1H), 4.92 (dp, J=27.0, 6.3 Hz, 2H), 4.36 (dd, J=11.2, 6.8 Hz, 1H), 4.27 (dd, J=11.2, 5.2 Hz, 1H), 3.82 (dt, J=9.1, 7.2 Hz, 2H), 2.17 (s, 3H), 2.10 (s, 3H), 1.34-1.09 (m, 18H). $^{31}$P NMR (162 MHz, Methanol-d4) δ 13.52. LCMS: MS m/z=682.40 [M+1], $t_R$=1.25 min; LC system: Thermo Accela 1250 UHPLC; MS system: Thermo LCQ Fleet; Column: Kinetex 2.6µ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: $t_R$=3.02 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 134. ((2R,3S,4R,5S)-5-(4-aminopyrrolo[2,1-f][1,2,4]triazin-7-yl)-2-cyano-3,4-diacetatetetrahydrofuran-2-yl)methyl bis-ethyl L-alaninate phosphate

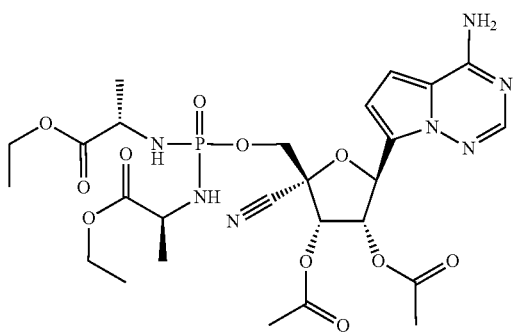 [SMILES: CCOC(=O)[C@H](C)NP(=O)(N[C@@H](C)C(=O)OCC)OC[C@@]1(C#N)O[C@@H](c2ccc3c(N)ncnn23)[C@H](OC(C)=O)[C@@H]1OC(C)=O]

Dissolved Example 35 (30 mg, 0.053 mmol) in 3 mL THF, to the solution were added acetic acid (25 mg, 0.42 mmol) and DIC (27 mg, 0.21 mmol). The reaction mixture was stirred for 10 mins at RT, then DMAP (13 mg, 0.11 mmol) was added. The resulting mixture was stirred at RT for 30 mins and then solvent was evaporated. The residue was purified with Prep HPLC to afford the product. $^1$H NMR (400 MHz, Methanol-d4) δ 7.86 (s, 1H), 6.86 (d, J=4.5 Hz, 1H), 6.82 (d, J=4.6 Hz, 1H), 5.88 (d, J=6.0 Hz, 1H), 5.83 (dd, J=6.0, 4.8 Hz, 1H), 5.68 (d, J=4.8 Hz, 1H), 4.35 (dd, J=11.2, 6.7 Hz, 1H), 4.26 (dd, J=11.2, 5.1 Hz, 1H), 4.19-3.99 (m, 4H), 3.84 (dq, J=9.2, 7.1 Hz, 2H), 2.17 (s, 3H), 2.10 (s, 3H), 1.27 (dt, J=7.1, 1.1 Hz, 6H), 1.22 (dt, J=14.1, 7.1 Hz, 6H). $^{31}$P NMR (162 MHz, Methanol-d4) δ 13.50. LCMS: MS m/z=654.35 [M+1], $t_R$=1.17 min; LC system: Thermo Accela 1250 UHPLC; MS system: Thermo LCQ Fleet; Column: Kinetex 2.6µ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: $t_R$=3.58 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 135. (2R,3S,4S,5S)-5-(4-Aminopyrrolo[2,1-f][1,2,4]triazin-7-yl)-2-cyano-2-(((((2S)-1-((1-ethyl-3,3-difluoropiperidin-4-yl)oxy)-1-oxopropan-2-yl)amino)(phenoxy) phosphoryl)oxy)methyl) tetrahydrofuran-3,4-diyl dipropionate

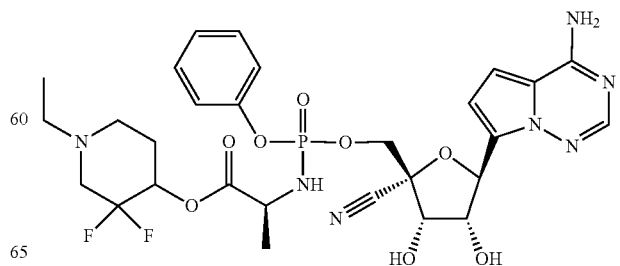

1-ethyl-3,3-difluoropiperidin-4-yl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy) phosphoryl)-L-alaninate. To a mixture of Intermediate 4 (70 mg, 0.211 mmol), Intermediate 37 (130 mg, 0.254 mmol), and MgCl₂ (30 mg, 0.317 mmol) in THF (2 mL) was added N,N-diisopropylethylamine (0.14 mL, 0.574 mmol) dropwise. The resulting mixture was stirred at 50° C. for 2 h, cooled, and purified by preparative HPLC (Phenomenex Gemini-NX 10μ C18 110° A 250×30 mm column, 5%-100% acetonitrile/water gradient in 25 min run) to afford an acetonide intermediate, which was dissolved in ACN (3 mL) and added c-HCl (0.1 mL). The resulting mixture was stirred at room temperature for 1 h, diluted with EtOAc, washed with saturated NaHCO₃ solution, concentrated in vacuo, co-evaporated with methylene chloride several times, and used in next reaction.

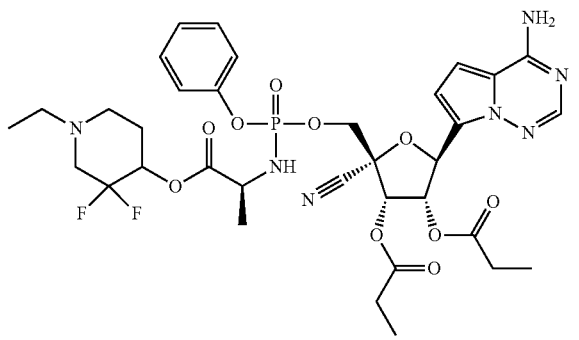 [SMILES: CCC(=O)O[C@H]1[C@H](c2ccc3c(N)ncnn23)O[C@](C#N)(COP(=O)(N[C@@H](C)C(=O)OC2CCN(CC)CC2(F)F)Oc2ccccc2)[C@H]1OC(=O)CC]

(2R,3S,4S,5S)-5-(4-Aminopyrrolo[2,1-f][1,2,4]triazin-7-yl)-2-cyano-2-((((((2S)-1-((1-ethyl-3,3-difluoropiperidin-4-yl)oxy)-1-oxopropan-2-yl)amino)(phenoxy) phosphoryl)oxy)methyl)tetrahydrofuran-3,4-diyl dipropionate. A mixture of ((((((2R,3S,4R,5S)-5-(4-Aminopyrrolo[2,1-f][1,2,4]triazin-7-yl)-2-cyano-3,4-dihydroxytetrahydrofuran-2-yl)methoxy)(phenoxy)phosphoryl)-L-alanyl)oxy)-1-ethylpiperidine (44 mg, 0.066 mmol, crude), propionic acid (0.026 mL, 0.331 mmol), and N,N-diisobutylcarbodiimide (0.03 mL, 0.193 mmol) in THF (2 mL) was stirred at room temperature for 20 min and DMAP (8.08 mg, 0.066 mmol) was added. The resulting mixture was stirred at room temperature for 80 min and quenched by adding methanol (0.5 mL), and purified by preparative HPLC (Phenomenex Gemini-NX 10μ C18 110°A 250×30 mm column, 0%-100% acetonitrile/water gradient in 25 min run) to afford the product. ¹H NMR (400 MHz, Acetonitrile-d3) δ 7.90 (m, 1H), 7.34 (m, 2H), 7.24-7.12 (m, 3H), 6.82-6.71 (m, 2H), 6.36 (s, 2H), 5.93-5.76 (m, 2H), 5.73-5.66 (m, 1H), 5.08-4.89 (m, 1H), 4.53-4.32 (m, 3H), 4.00 (m, 1H), 2.82 (m, 1H), 2.70-2.51 (m, 1H), 2.50-2.28 (m, 8H), 1.95-1.82 (m, 1H), 1.75 (m, 1H), 1.33-1.24 (m, 3H), 1.13 (m, 6H), 1.06-0.99 (m, 3H). ³¹P NMR (162 MHz, Acetonitrile-d3) δ 2.34, 2.31, 2.25. ¹⁹F NMR (376 MHz, Acetonitrile-d3) δ −110.35 (d, J=51.7 Hz), −110.99 (d, J=54.2 Hz), 166.55. LCMS: MS m/z=778.27 [M+1]; $t_R$=1.01 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.38, 4.41, 4.44 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 136. (2R,3S,4S,5S)-2-((((((S)-1-(((1r,4S)-4-aminocyclohexyl) oxy)-1-oxopropan-2-yl)amino)(phenoxy)phosphoryl)oxy)methyl)-5-(4-aminopyrrolo[2,1-f][1,2,4]triazin-7-yl)-2-cyanotetrahydrofuran-3,4-diyl bis(2-methylpropanoate)

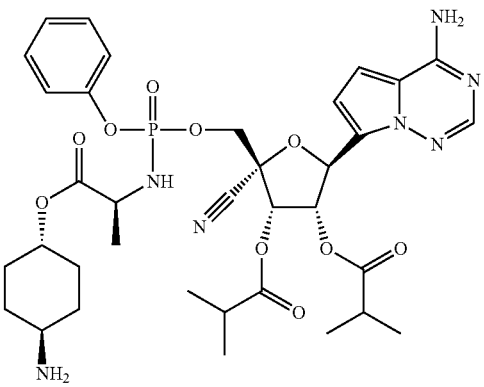 [SMILES: CC(C)C(=O)O[C@H]1[C@H](c2ccc3c(N)ncnn23)O[C@](C#N)(COP(=O)(N[C@@H](C)C(=O)O[C@H]2CC[C@H](N)CC2)Oc2ccccc2)[C@H]1OC(=O)C(C)C]

Example 33 (142 mg, 0.195 mmol) was dissolved in 5 mL of dioxane and 5 mL of water and stirred at RT. 0.1 M sodium carbonate solution was added to give pH of 9-10. Boc anhydride (47 mg, 0.214 mmol) was dissolved in 1 mL of dioxane and added to the reaction mixture. After 2 h, the reaction mixture was diluted with ethyl acetate (10 mL) and washed with brine (2×10 mL). The organic extract was dried over anhydrous sodium sulfate and concentrated under reduced pressure. The crude residue was purified via SiO₂ column chromatography (4 g SiO₂ Combiflash HP Gold Column, 0-5% methanol in dichloromethane). Fractions containing the desired product were combined and concentrated under reduced pressure to give mono Boc protected material. The mono protected Boc material (57 mg, 0.08 mmol) was dissolved in 2 mL of anhydrous tetrahydrofuran. Isobutyric acid (30 μL, 0.32 mmol) and N,N'-diisopropylcarbodiimide (50 μL, 0.32 mmol) were added to reaction and stirred for 25 min. DMAP (10 mg, 0.08 mmol) was added and stirred for 16 h. More isobutyric acid (30 μL) and N,N'-diisopropylcarbodiimide (50 μL) were added to reaction and stirred for 1 h. Methanol (0.5 mL) was then added and stirred for 30 min. The reaction mixture was diluted with ethyl acetate (10 mL) and washed with brine (4×5 mL). The organic extract was dried over anhydrous sodium sulfate and concentrated under reduced pressure. The crude residue was purified via SiO₂ column chromatography (4 g SiO₂ Combiflash HP Gold Column, 0-100% ethyl acetate/hexanes). Fractions containing the desired product were combined and concentrated under reduced pressure. The resulting material was dissolved in dichloromethane (2 mL) and stirred in an ice bath. TFA (200 μL) was added dropwise and the mixture was stirred for 1.5 h. Triethylamine was then added dropwise to give pH of 3-4. The mixture was concentrated under reduced pressure and the crude residue was dissolved in MeOH and purified with prep-HPLC under neutral conditions. Fractions containing the desired product were combined and freeze-dried to give the product. ¹H NMR (400 MHz, methanol-d₄) δ 7.84 (m, 1H), 7.35-7.25 (m, 2H), 7.23-7.12 (m, 3H), 6.91 (m, 1H), 6.77 (m, 1H), 5.92 (m, 1H), 5.82 (m, 1H), 5.68 (d, J=4.8 Hz, 1H), 4.67 (m, 1H), 4.57-4.37 (m, 2H), 3.96-3.78 (m, 1H), 3.08 (m, 1H), 2.74-2.55 (m, 2H), 2.13-1.94 (m, 4H), 1.57-1.37 (m, 4H), 1.34-1.06 (m, 15H). $^{31}$P NMR (162 MHz, methanol-d$_4$) δ 3.00, 3.07. LCMS: MS m/z=756.4[M+1]; 754.5 [M−1], t$_R$=1.19 min; LC system: Thermo Dionex ultimate 3000 UHPLC; Column: Phenomenex Kinetex 2.6µ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: t$_R$=2.80 min; HPLC system: Agilent 1100 series; Column: Phenomenex Gemini 5µ C18 110A, 50×4.6 mm; Solvent: A: Water with 0.1% TFA, B: Acetonitrile with 0.1% TFA; Gradient: 2-98% B in 5 min at 2 mL/min. HPLC: t$_R$=4.671, 4.727 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 137. ((2R,3S,4R,5S)-5-(4-aminopyrrolo[2,1-f][1,2,4]triazin-7-yl)-2-cyano-3,4-diisobutylatetetrahydrofuran-2-yl)methyl bis-ethyl L-alaninate phosphate

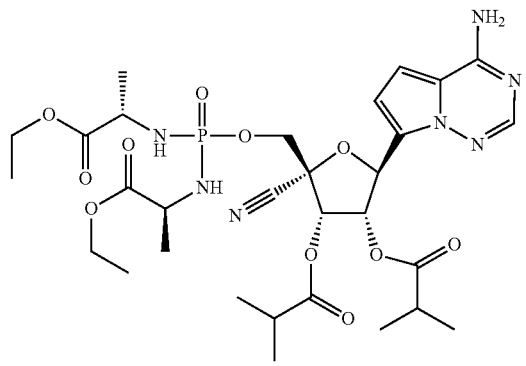 [SMILES: CCOC(=O)[C@H](C)NP(=O)(N[C@@H](C)C(=O)OCC)OC[C@@]1(C#N)O[C@@H](c2ccc3c(N)ncnn23)[C@H](OC(=O)C(C)C)[C@@H]1OC(=O)C(C)C]

Dissolved Example 35 (36 mg, 0.063 mmol) in 3 mL THF, to the solution were added isobutyric acid (45 mg, 0.51 mmol) and DIC (32 mg, 0.04 mmol). The reaction mixture was stirred for 10 mins at RT, then DMAP (15 mg, 0.13 mmol) was added. The resulting mixture was stirred at RT for 30 mins and then solvent was evaporated. The residue was purified with Prep HPLC to afford the product. $^1$H NMR (400 MHz, Methanol-d4) δ 7.34 (d, J=4.8 Hz, 1H), 7.05 (d, J=4.7 Hz, 1H), 5.88-5.75 (m, 2H), 5.71 (d, J=4.1 Hz, 1H), 4.37 (dd, J=11.3, 6.6 Hz, 1H), 4.29 (dd, J=11.3, 5.2 Hz, 1H), 4.21-4.02 (m, 4H), 3.90-3.75 (m, 2H), 2.78-2.66 (m, 1H), 2.66-2.55 (m, 1H), 1.31 (ddd, J=6.9, 5.7, 0.9 Hz, 6H), 1.27-1.09 (m, 18H). $^{31}$P NMR (162 MHz, Methanol-d4) δ 13.47. LCMS: MS m/z=710.36 [M+1], t$_R$=1.34 min; LC system: Thermo Accela 1250 UHPLC; MS system: Thermo LCQ Fleet; Column: Kinetex 2.6µ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: t$_R$=3.12 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 138. (2R,3S,4S,5S)-5-(4-aminopyrrolo[2,1-f][1,2,4]triazin-7-yl)-2-cyano-2-(((((S)-1-methoxy-1-oxopropan-2-yl)amino)(phenoxy)phosphoryl)oxy) methyl)tetrahydrofuran-3,4-diyl bis(2-methylpropanoate)

Example 39. (54 mg, 0.1 mmol) was dissolved in 2 mL of anhydrous tetrahydrofuran. Isobutyric acid (37 µL, 0.4 mmol) and N,N'-diisopropylcarbodiimide (62 µL, 0.4 mmol) were added and the reaction mixture was stirred for 30 min. DMAP (12 mg, 0.1 mmol) was added and reaction mixture was stirred for 16 h. Methanol (0.5 mL) was added and the reaction mixture was stirred for 20 min. The reaction mixture was purified with prep HPLC without acid modifier (5-100% MeCN/water). Fractions containing the desired product were combined and extracted with ethyl acetate (15 mL). The organic extract was washed with brine (2×10 mL), dried over anhydrous sodium sulfate and concentrated under reduced pressure. The resulting material was dissolved in MeCN and water and freeze-dried to give the product. $^1$H NMR (400 MHz, methanol-d$_4$) δ 7.81 (m, 1H), 7.35-7.25 (m, 2H), 7.24-7.10 (m, 3H), 6.84 (m, 1H), 6.75 (m, 1H), 5.95 (m, 1H), 5.83 (m, 1H), 5.68 (m, 1H), 4.58-4.34 (m, 2H), 3.98-3.74 (m, 1H), 3.61 (m, 3H), 2.74-2.52 (m, 2H), 1.33-1.09 (m, 15H). $^{31}$P NMR (162 MHz, methanol-d$_4$) δ 3.04. LCMS: MS m/z=673.2 [M+1]; 671.3 [M−1], t$_R$=1.37 min; LC system: Thermo Dionex ultimate 3000 UHPLC; Column: Phenomenex Kinetex 2.6µ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: t$_R$=3.24 min; HPLC system: Agilent 1100 series; Column: Phenomenex Gemini 5µ C18 110A, 50×4.6 mm; Solvent: A: Water with 0.1% TFA, B: Acetonitrile with 0.1% TFA; Gradient: 2-98% B in 5 min at 2 mL/min. HPLC: t$_R$=5.415, 5.469 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The product was purified via chiral preparatory HPLC (Chiralpak AD-H, 150×4.6 mm, SFC 35% isopropyl alcohol isocratic).

Example 139. (2R,3S,4S,5S)-5-(4-aminopyrrolo[2,1-f][1,2,4]triazin-7-yl)-2-cyano-2-((((R)-(((S)-1-methoxy-1-oxopropan-2-yl)amino)(phenoxy)phosphoryl)oxy)methyl) tetrahydrofuran-3,4-diyl bis(2-methylpropanoate)

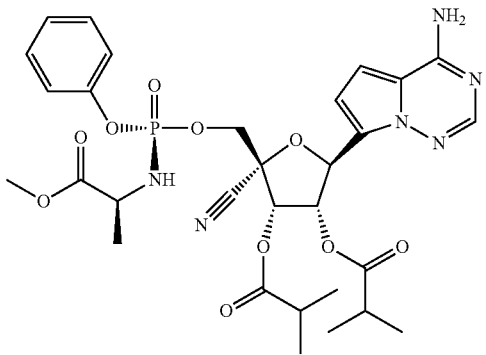 [SMILES: COC(=O)[C@H](C)N[P@@](=O)(OC[C@@]1(C#N)O[C@@H](c2ccc3c(N)ncnn23)[C@H](OC(=O)C(C)C)[C@@H]1OC(=O)C(C)C)Oc1ccccc1]

First Eluting Diastereomer of Example 138: $^1$H NMR (400 MHz, methanol-d4) δ 7.81 (s, 1H), 7.35-7.25 (m, 2H), 7.16 (m, 3H), 6.88 (d, J=4.5 Hz, 1H), 6.78 (d, J=4.5 Hz, 1H), 5.97 (d, J=5.8 Hz, 1H), 5.85 (dd, J=5.8, 4.3 Hz, 1H), 5.68 (d, J=4.3 Hz, 1H), 4.57-4.36 (m, 2H), 3.80 (m, 1H), 3.63 (s, 3H), 2.65 (m, 2H), 1.27-1.06 (m, 15H). $^{31}$P NMR (162 MHz, methanol-d4) δ 3.02 (s). MS m/z=673.2 [M+1]. HPLC: $t_R$=5.406 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 140. (2R,3S,4S,5S)-5-(4-aminopyrrolo[2,1-f][1,2,4]triazin-7-yl)-2-cyano-2-((((S)-(((S)-1-methoxy-1-oxopropan-2-yl)amino)(phenoxy)phosphoryl)oxy)methyl) tetrahydrofuran-3,4-diyl bis(2-methylpropanoate)

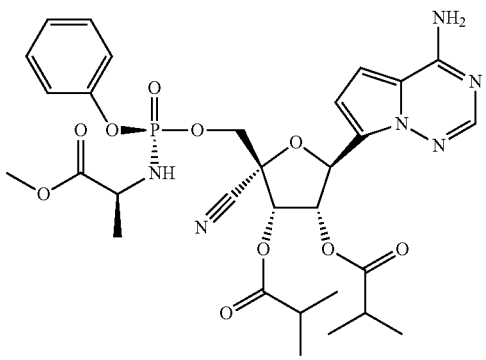 [SMILES: COC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccccc1]

Second Eluting Diastereomer of Example 138. $^1$H NMR (400 MHz, methanol-$d_4$) δ 7.84 (s, 1H), 7.36-7.23 (m, 2H), 7.23-7.11 (m, 3H), 6.85 (d, J=4.5 Hz, 1H), 6.75 (d, J=4.6 Hz, 1H), 5.91 (d, J=5.9 Hz, 1H), 5.80 (dd, J=5.9, 4.7 Hz, 1H), 5.68 (d, J=4.7 Hz, 1H), 4.52-4.37 (m, 2H), 3.98-3.83 (m, 1H), 3.61 (s, 3H), 2.73-2.55 (m, 2H), 1.35-1.07 (m, 15H). $^{31}$P NMR (162 MHz, methanol-$d_4$) δ 3.03 (s). MS m/z=673.2 [M+1] HPLC: $t_R$=5.463 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 141. (2R,3S,4S,5S)-5-(4-aminopyrrolo[2,1-f][1,2,4]triazin-7-yl)-2-cyano-2-(((((S)-1-methoxy-1-oxopropan-2-yl)amino)(phenoxy)phosphoryl)oxy) methyl)tetrahydrofuran-3,4-diyl dipropionate

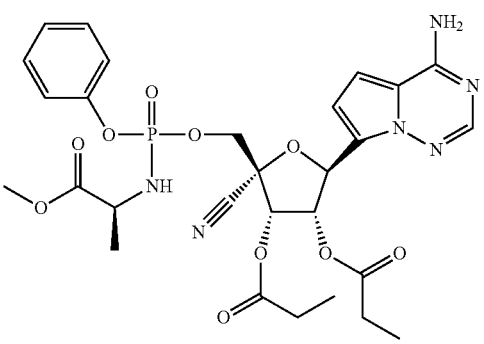 [SMILES: CCC(=O)O[C@H]1[C@H](c2ccc3c(N)ncnn23)O[C@](C#N)(COP(=O)(N[C@@H](C)C(=O)OC)Oc2ccccc2)[C@H]1OC(=O)CC]

Example 39. (54 mg, 0.1 mmol) was dissolved in 2 mL of anhydrous tetrahydrofuran. Propionic acid (30 μL, 0.4 mmol) and N,N'-diisopropylcarbodiimide (62 μL, 0.4 mmol) were added and stirred for 30 min. DMAP (12 mg, 0.1 mmol) was added and stirred for 16 h. Methanol (0.5 mL) was added and stirred for 20 min. Crude was purified with prep HPLC without acid modifier (5-100% MeCN/water). Fractions containing the desired product were combined and extracted with ethyl acetate (15 mL). Organic extract was washed with brine (2×10 mL), dried over anhydrous sodium sulfate and concentrated under reduced pressure. Result material was dissolved in MeCN and water and freeze-dried to give the product. $^1$H NMR (400 MHz, methanol-d4) δ 7.86 (m, 1H), 7.36-7.24 (m, 2H), 7.24-7.10 (m, 3H), 6.97 (m, 1H), 6.81 (m, 1H), 5.99-5.75 (m, 2H), 5.71 (m, 1H), 4.57-4.38 (m, 2H), 3.96-3.71 (m, 1H), 3.62 (m, 3H), 2.55-2.34 (m, 4H), 1.34-1.03 (m, 9H). $^{31}$P NMR (162 MHz, methanol-$d_4$) δ 3.03. LCMS: MS m/z=645.2 [M+1]; 643.3 [M−1], $t_R$=1.24 min; LC system: Thermo Dionex ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=3.00 min; HPLC system: Agilent 1100 series; Column: Phenomenex Gemini 5P C18 110A, 50×4.6 mm; Solvent: A: Water with 0.1% TFA, B: Acetonitrile with 0.1% TFA; Gradient: 2-98% B in 5 min at 2 mL/min. HPLC: $t_R$=4.986, 5.041 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The product was purified via chiral preparatory HPLC (Chiralpak IF, 150×4.6 mm, SFC 30% ethanol isocratic).

Example 142. (2R,3S,4S,5S)-5-(4-aminopyrrolo[2,1-f][1,2,4]triazin-7-yl)-2-cyano-2-((((R)-(((S)-1-methoxy-1-oxopropan-2-yl)amino)(phenoxy)phosphoryl)oxy)methyl) tetrahydrofuran-3,4-diyl dipropionate

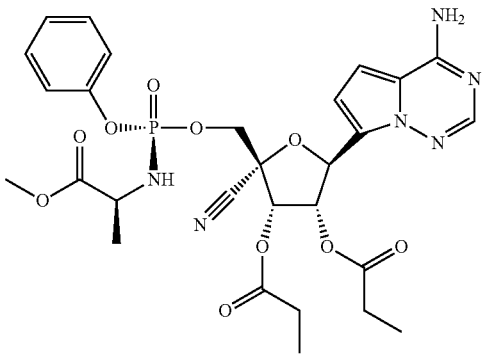 [SMILES: CCC(=O)O[C@H]1[C@H](c2ccc3c(N)ncnn23)O[C@](C#N)(CO[P@](=O)(N[C@@H](C)C(=O)OC)Oc2ccccc2)[C@H]1OC(=O)CC]

First Eluting Diastereomer of Example 141: ¹H NMR (400 MHz, methanol-d₄) δ 7.80 (s, 1H), 7.35-7.23 (m, 2H), 7.21-7.10 (m, 3H), 6.85 (d, J=4.6 Hz, 1H), 6.77 (d, J=4.5 Hz, 1H), 5.98 (d, J=5.8 Hz, 1H), 5.87 (dd, J=5.8, 4.4 Hz, 1H), 5.69 (d, J=4.4 Hz, 1H), 4.56-4.37 (m, 2H), 3.80 (m, 1H), 3.63 (s, 3H), 2.55-2.36 (m, 4H), 1.24-1.10 (m, 9H). ³¹P NMR (162 MHz, methanol-d₄) δ 3.01 (s). HPLC: $t_R$=4.982 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 143. (2R,3S,4S,5S)-5-(4-aminopyrrolo[2,1-f][1,2,4]triazin-7-yl)-2-cyano-2-((((S)-(((S)-1-methoxy-1-oxopropan-2-yl)amino)(phenoxy)phosphoryl)oxy)methyl) tetrahydrofuran-3,4-diyl dipropionate

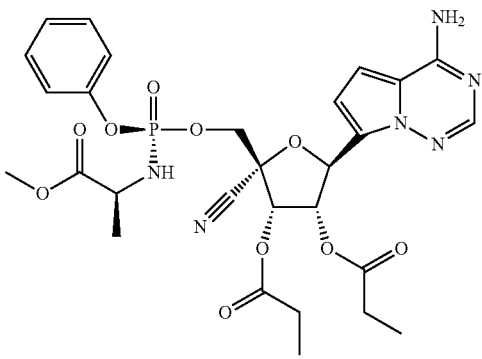 [SMILES: CCC(=O)O[C@H]1[C@H](c2ccc3c(N)ncnn23)O[C@](C#N)(CO[P@@](=O)(N[C@@H](C)C(=O)OC)Oc2ccccc2)[C@H]1OC(=O)CC]

Second Eluting Diastereomer of Example 141: ¹H NMR (400 MHz, methanol-d₄) δ 7.82 (s, 1H), 7.35-7.25 (m, 2H), 7.23-7.12 (m, 3H), 6.83 (d, J=4.6 Hz, 1H), 6.74 (d, J=4.5 Hz, 1H), 5.91 (d, J=5.9 Hz, 1H), 5.82 (dd, J=5.9, 4.8 Hz, 1H), 5.69 (d, J=4.7 Hz, 1H), 4.51-4.36 (m, 2H), 3.98-3.83 (m, 1H), 3.61 (s, 3H), 2.54-2.35 (m, 4H), 1.27 (d, J=7.1, 3H), 1.20-1.09 (m, 6H). ³¹P NMR (162 MHz, methanol-d₄) δ 3.02 (s). HPLC: $t_R$=5.043 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 144. (2R,3S,4S,5S)-5-(4-aminopyrrolo[2,1-f][1,2,4]triazin-7-yl)-2-cyano-2-(((((S)-(((S)-1-ethoxy-1-oxopropan-2-yl)amino)(phenoxy)phosphoryl)oxy)methyl) tetrahydrofuran-3,4-diyl bis(2-methylpropanoate)

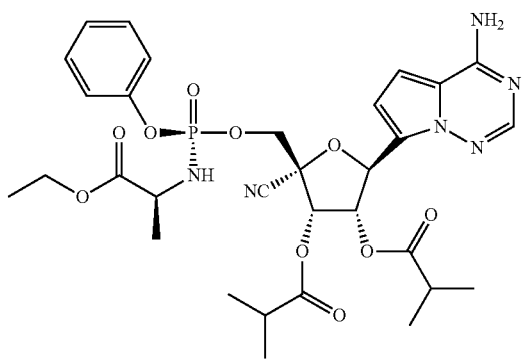 [SMILES: CCOC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccccc1]

The diol Example 29 (54 mg, 0.099 mmol) and isobutyric acid (70 mg, 0.8 mmol) was dissolved in THF (3 mL), and N,N'-Dicyclohexylcarbodiimide (82 mg, 0.4 mmol) under argon at RT. The solution was stirred for 5 min and then DMAP (24 mg, 0.19 mmol) was added. After stirring for 50 min, the reaction was quenched with MeOH (0.5 mL), volatiles removed, and the residue purified with prep HPLC to afford the product. ¹H NMR (400 MHz, Methanol-d4) δ 7.83 (s, 1H), 7.30 (dd, J=8.5, 7.3 Hz, 2H), 7.23-7.12 (m, 3H), 6.83 (d, J=4.5 Hz, 1H), 6.74 (d, J=4.5 Hz, 1H), 5.91 (d, J=5.9 Hz, 1H), 5.80 (dd, J=5.9, 4.7 Hz, 1H), 5.66 (d, J=4.7 Hz, 1H), 4.43 (dd, J=5.7, 2.6 Hz, 2H), 4.11-3.97 (m, 2H), 2.64 (dp, J=17.4, 7.0 Hz, 2H), 1.32-1.06 (m, 15H). ³¹P NMR (162 MHz, Methanol-d4) δ 3.05. LCMS: MS m/z=687.42 [M+1], $t_R$=1.41 min; LC system: Thermo Accela 1250 UHPLC; MS system: Thermo LCQ Fleet; Column: Kinetex 2.6µ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 L/min. HPLC: $t_R$=3.353 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 145. ((2R,3S,4R,5S)-5-(4-isobutyramidopyrrolo[2,1-f][1,2,4]triazin-7-yl)-2-cyano-3,4-diisobutylatetetrahydrofuran-2-yl)methyl bis-ethyl L-alaninate phosphate

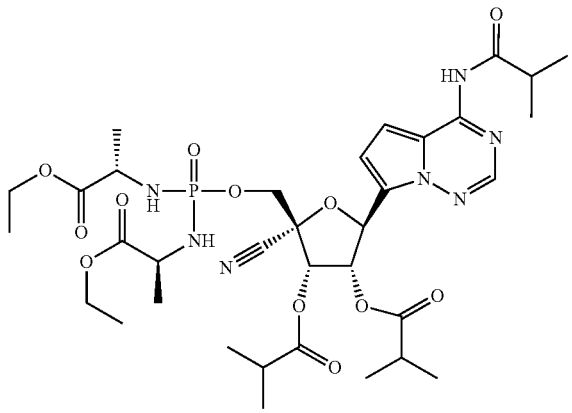 [SMILES: CCOC(=O)[C@H](C)NP(=O)(N[C@@H](C)C(=O)OCC)OC[C@@]1(C#N)O[C@@H](c2ccc3c(NC(=O)C(C)C)ncnn23)[C@H](OC(=O)C(C)C)[C@@H]1OC(=O)C(C)C]

Dissolved Example 35 (36 mg, 0.063 mmol) in 3 mL THF, to the solution were added isobutyric acid (45 mg, 0.51 mmol) and DIC (32 mg, 0.04 mmol). The reaction mixture was stirred for 10 mins at RT, then DMAP (15 mg, 0.13 mmol) was added. The resulting mixture was stirred at RT for 30 mins and then solvent was evaporated. The residue was purified with Prep HPLC to afford the product. $^1$H NMR (400 MHz, Methanol-d4) δ 7.22 (d, J=4.8 Hz, 1H), 7.06 (d, J=4.8 Hz, 1H), 5.91-5.80 (m, 2H), 5.76 (d, J=4.4 Hz, 1H), 4.43-4.30 (m, 1H), 4.32-4.20 (m, 1H), 4.18-3.98 (m, 4H), 3.84 (p, J=7.6 Hz, 2H), 2.66 (dp, J=29.7, 7.0 Hz, 2H), 1.35-1.07 (m, 30H). $^{31}$P NMR (162 MHz, Methanol-d4) δ 13.49. LCMS: MS m/z=780.15 [M+1], $t_R$=1.44 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.26 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 146. (2R,3S,4S,5S)-5-(4-Aminopyrrolo[2,1-f][1,2,4]triazin-7-yl)-2-cyano-2-(((((S)-1-oxo-1-((tetrahydro-2H-pyran-4-yl)oxy)propan-2-yl)amino)(phenoxy)phosphoryl)oxy)methyl)tetrahydrofuran-3,4-diyl bis(2-methylpropanoate)

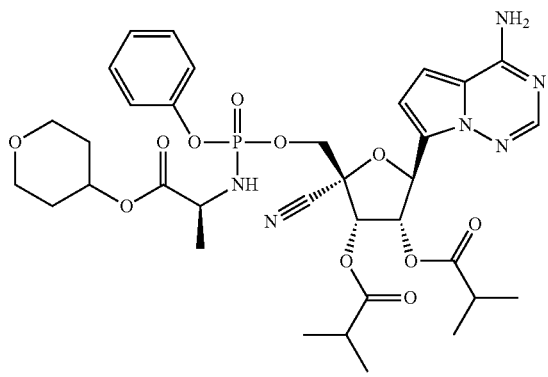 [SMILES: CC(C)C(=O)O[C@H]1[C@H](c2ccc3c(N)ncnn23)O[C@](C#N)(COP(=O)(N[C@@H](C)C(=O)OC2CCOCC2)Oc2ccccc2)[C@H]1OC(=O)C(C)C]

A mixture of Example 55. (27 mg, 0.066 mmol), isobutyric acid (0.020 mL, 0.224 mmol), and N,N-diisopropylcarbodiimide (0.022 mL, 0.143 mmol) in THF (2 mL) was stirred at room temperature for 20 min and DMAP (5.47 mg, 0.045 mmol) was added. The resulting mixture was stirred at room temperature for 80 min and quenched by adding methanol (0.5 mL), and purified by preparative HPLC (Phenomenex Gemini-NX 10μ C18 110° A 250×30 mm column, 0%-100% acetonitrile/water gradient in 25 min run) to afford the product. $^1$H NMR (400 MHz, Acetonitrile-d$_3$) δ 7.90 (m, 1H), 7.34 (m, 2H), 7.26-7.14 (m, 3H), 6.81-6.71 (m, 2H), 6.40 (s, 2H), 5.92-5.77 (m, 2H), 5.68 (m, 1H), 4.84 (m, 1H), 4.54-4.32 (m, 3H), 3.98-3.84 (m, 1H), 3.79 (m, 2H), 3.46 (m, 2H), 2.75-2.55 (m, 2H), 1.88-1.74 (m, 2H), 1.55 (m, 2H), 1.30-1.14 (m, 15H). $^{31}$P NMR (162 MHz, Acetonitrile-d3) δ 2.50, 2.41. LCMS: MS m/z=743.42 [M+1]; $t_R$=1.18 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

Resolution of Sp and Rp diastereomers. The product was separated by SFC (IF, 5 u, 21×250 mm, 20% MeOH) to afford the diastereomers:

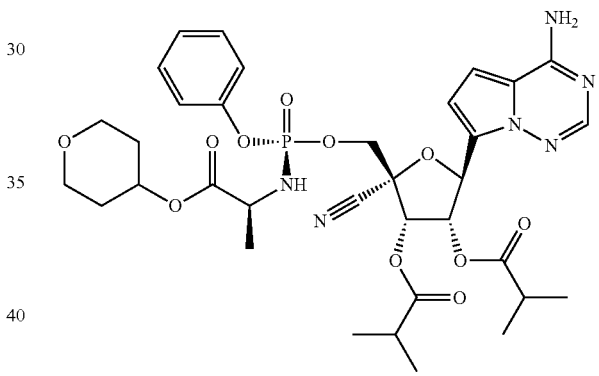

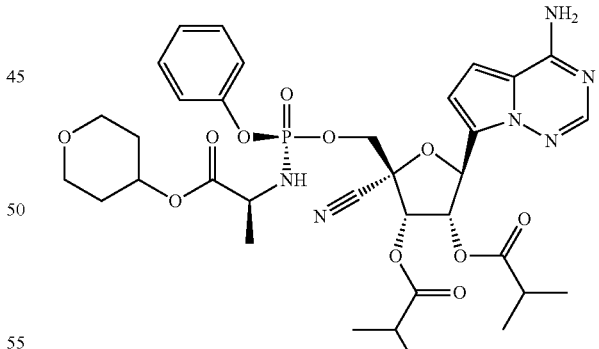

Example 147

First eluting isomer of Example 146: $^1$H NMR (400 MHz, Acetonitrile-d3) δ 7.89 (s, 1H), 7.34 (t, J=7.8 Hz, 2H), 7.23-7.13 (m, 3H), 6.81-6.75 (m, 2H), 6.34 (s, 2H), 5.89 (d, J=6.0 Hz, 1H), 5.83 (dd, J=5.9, 4.5 Hz, 1H), 5.69 (d, J=4.5 Hz, 1H), 4.87 (tt, J=8.4, 4.1 Hz, 1H), 4.49 (dd, J=11.2, 6.1 Hz, 1H), 4.40 (dd, J=11.2, 5.3 Hz, 1H), 4.29 (d, J=11.0 Hz, 1H), 3.92-3.73 (m, 3H), 3.52-3.42 (m, 2H), 2.64 (dh, J=28.0, 7.0 Hz, 2H), 1.82 (d, J=8.9 Hz, 2H), 1.56 (dtd, J=12.9, 8.6, 3.9 Hz, 2H), 1.25-1.20 (m, 9H), 1.18 (d, J=7.0 Hz, 3H), 1.15 (d, J=7.0 Hz, 3H). $^{31}$P NMR (162 MHz, Acetonitrile-d3) δ 2.39. HPLC: $t_R$=5.43 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 148

Second eluting isomer of Example 146: $^1$H NMR (400 MHz, Acetonitrile-d3) δ 7.90 (s, 1H), 7.34 (t, J=7.9 Hz, 2H), 7.24-7.16 (m, 3H), 6.76 (d, J=1.2 Hz, 2H), 6.36 (s, 2H), 5.86 (d, J=6.0 Hz, 1H), 5.80 (dd, J=6.0, 4.6 Hz, 1H), 5.67 (d, J=4.5 Hz, 1H), 4.84 (tt, J=8.3, 4.0 Hz, 1H), 4.49-4.30 (m, 3H), 3.91 (ddt, J=16.8, 9.6, 7.1 Hz, 1H), 3.78 (dt, J=10.7, 4.9 Hz, 2H), 3.45 (ddt, J=12.0, 8.0, 3.7 Hz, 2H), 2.64 (dp, J=29.4, 7.0 Hz, 2H), 1.87-1.75 (m, 2H), 1.53 (dtd, J=12.7, 8.4, 4.0 Hz, 2H), 1.28 (dd, J=7.1, 0.9 Hz, 3H), 1.21 (t, J=7.0 Hz, 6H), 1.17 (d, J=7.0 Hz, 3H), 1.14 (d, J=7.0 Hz, 3H). $^{31}$P NMR (162 MHz, Acetonitrile-d3) δ 2.48. HPLC: $t_R$=5.50 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 149. ((2R,3S,4R,5S)-5-(4-aminopyrrolo[2,1-f][1,2,4]triazin-7-yl)-2-cyano-3,4-diisobutylatetetrahydrofuran-2-yl)methyl bis-methyl L-alaninate phosphate

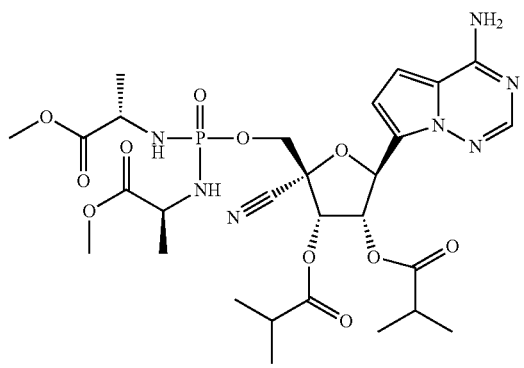 [SMILES: COC(=O)[C@H](C)NP(=O)(N[C@@H](C)C(=O)OC)OC[C@@]1(C#N)O[C@@H](c2ccc3c(N)ncnn23)[C@H](OC(=O)C(C)C)[C@@H]1OC(=O)C(C)C]

Dissolved Example 38. (58 mg, 0.11 mmol) in 3 mL THF, to the solution were added isobutyric acid (76 mg, 0.86 mmol) and DIC (54 mg, 0.43 mmol). The reaction mixture was stirred for 10 mins at RT, then DMAP (26 mg, 0.21 mmol) was added. The resulting mixture was stirred at RT for 30 mins and then solvent was evaporated. The residue was purified with Prep HPLC to afford the product. $^1$H NMR (400 MHz, Methanol-d4) δ 7.86 (s, 1H), 6.86 (d, J=4.6 Hz, 1H), 6.81 (d, J=4.6 Hz, 1H), 5.92 (d, J=5.9 Hz, 1H), 5.85 (dd, J=5.9, 4.6 Hz, 1H), 5.67 (d, J=4.6 Hz, 1H), 4.35 (dd, J=11.2, 6.6 Hz, 1H), 4.25 (dd, J=11.2, 5.0 Hz, 1H), 3.92-3.75 (m, 2H), 3.65 (d, J=10.8 Hz, 6H), 2.65 (dp, J=26.5, 7.0 Hz, 2H), 1.32-1.09 (m, 18H). $^{31}$P NMR (162 MHz, Methanol-d4) δ 13.48. LCMS: MS m/z=682.32 [M+1], $t_R$=1.27 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=2.92 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 150. ((2R,3S,4R,5S)-5-(4-isobutyramidopyrrolo[2,1-f][1,2,4]triazin-7-yl)-2-cyano-3,4-diisobutylatetetrahydrofuran-2-yl)methyl bis-methyl L-alaninate phosphate

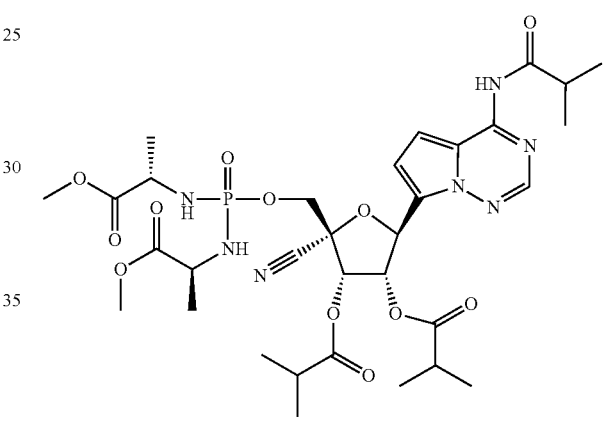

Dissolved Example 38. (58 mg, 0.11 mmol) in 3 mL THF, to the solution were added isobutyric acid (76 mg, 0.86 mmol) and DIC (54 mg, 0.43 mmol). The reaction mixture was stirred for 10 mins at RT, then DMAP (26 mg, 0.21 mmol) was added. The resulting mixture was stirred at RT for 30 mins and then solvent was evaporated. The residue was purified with Prep HPLC to afford the product. $^1$H NMR (400 MHz, Methanol-d4) δ 8.24 (s, 1H), 7.22 (d, J=4.7 Hz, 1H), 7.06 (d, J=4.7 Hz, 1H), 5.90-5.81 (m, 2H), 5.76 (d, J=4.4 Hz, 1H), 4.36 (dd, J=11.2, 6.5 Hz, 1H), 4.27 (dd, J=11.2, 5.0 Hz, 1H), 3.84 (dt, J=9.3, 7.0 Hz, 2H), 3.65 (d, J=8.9 Hz, 6H), 2.96 (h, J=6.8 Hz, 1H), 2.66 (dp, J=30.4, 7.0 Hz, 2H), 1.34-1.10 (m, 24H). $^{31}$P NMR (162 MHz, Methanol-d4) δ 13.48. LCMS: MS m/z=752.24 [M+1], $t_R$=1.37 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.51 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 151. (2R,3S,4S,5S)-5-(4-aminopyrrolo[2,1-f][1,2,4]triazin-7-yl)-2-cyano-2-((((S)-(((S)-1-isopropoxy-1-oxopropan-2-yl)amino)(phenoxy)phosphoryl)oxy)methyl) tetrahydrofuran-3,4-diyl bis(2-methoxyacetate)

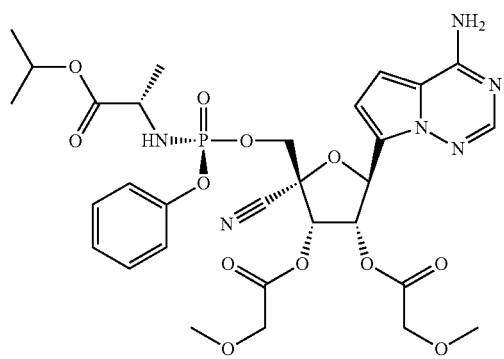 [SMILES: COCC(=O)O[C@H]1[C@H](c2ccc3c(N)ncnn23)O[C@](C#N)(CO[P@@](=O)(N[C@@H](C)C(=O)OC(C)C)Oc2ccccc2)[C@H]1OC(=O)COC]

N,N'-diisopropylcarbodiimide (0.04 mL, 0.27 mmol) was added to a solution of Example 1. (40.0 mg, 0.07 mmol) and 2-methoxyacetic acid (52 mg, 0.57 mmol) in tetrahydrofuran (6 mL) at RT. After 5 min, 4-dimethylaminopyridine (18.0 mg, 0.15 mmol) was added. After 1.5 h, methanol (0.2 mL) was added, and the reaction mixture was diluted with ethyl acetate (20 mL) and the resulting mixture was washed with water (15 mL) and brine (15 mL). The organic layer was dried over anhydrous sodium sulfate and concentrated under reduced pressure. The crude residue was subjected preparatory HPLC (Phenomenex Gemini 10 u C18 110 Å 250×30.0 mm column, 5-75% acetonitrile/water gradient) to afford the product. $^1$H NMR (400 MHz, methanol-$d_4$) δ 7.84 (s, 1H), 7.36-7.27 (m, 2H), 7.24-7.13 (m, 2H), 6.85 (d, J=4.6 Hz, 1H), 6.77 (d, J=4.6 Hz, 1H), 6.04 (d, J=5.9 Hz, 1H), 5.94 (dd, J=5.9, 4.6 Hz, 1H), 5.72 (d, J=4.6 Hz, 1H), 4.47 (t, J=5.9 Hz, 2H), 4.26-4.03 (m, 2H), 3.91-3.78 (m, 1H), 3.43 (d, J=16.4 Hz, 6H), 1.27 (dd, J=7.2, 1.1 Hz, 3H), 1.16 (dd, J=6.2, 5.4 Hz, 6H). $^{31}$P NMR (162 MHz, methanol-$d_4$) δ 3.14. LCMS: MS m/z=705.45 [M+H], $t_R$=0.94 min; LC system: Thermo Accela 1250 UHPLC; MS system: Thermo LCQ Fleet; Column: Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=4.96; HPLC system: Agilent 1100 series; Column: Phenomenex Kinetex C18, 2.6µ C18 110A, 100×4.6 mm; Solvents: Acetonitrile with 0.1% TFA, Water with 0.1% TFA; Gradient: 0 min-8.5.0 min 2-98% ACN, 8.5 min-10.0 min 98% ACN at 1.5 mL/min.

Example 152. (2R,3S,4S,5S)-5-(4-aminopyrrolo[2,1-f][1,2,4]triazin-7-yl)-2-cyano-2-((((S)-(((S)-1-isopropoxy-1-oxopropan-2-yl)amino)(phenoxy)phosphoryl)oxy)methyl) tetrahydrofuran-3,4-diyl bis(3-hydroxy-3-methylbutanoate)

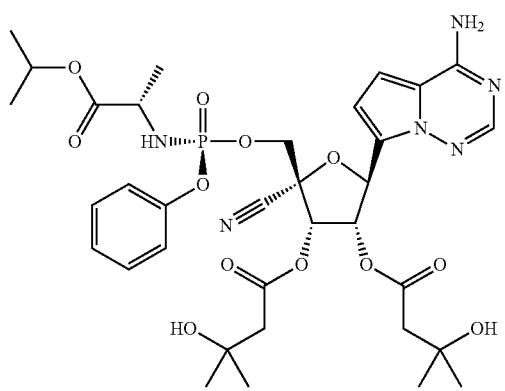 [SMILES: CC(C)OC(=O)[C@H](C)N[P@](=O)(OC[C@@]1(C#N)O[C@@H](c2ccc3c(N)ncnn23)[C@H](OC(=O)CC(C)(C)O)[C@@H]1OC(=O)CC(C)(C)O)Oc1ccccc1]

N,N'-diisopropylcarbodiimide (0.04 mL, 0.27 mmol) was added to a solution of Example 1. (40 mg, 0.07 mmol) and 3-hydroxy-3-methylbutanoic acid (67 mg, 0.57 mmol) in tetrahydrofuran (6 mL) at RT. After 5 min, 4-dimethylaminopyridine (15.0 mg, 0.11 mmol) was added. After 1.5 h, methanol (0.2 mL) was added, and the reaction mixture was diluted with ethyl acetate (20 mL) and the resulting mixture was washed with water (15 mL) and brine (15 mL). The organic layer was dried over anhydrous sodium sulfate and concentrated under reduced pressure. The crude residue was subjected preparatory HPLC (Phenomenex Gemini 10 u C18 110 Å 250×30.0 mm column, 5-75% acetonitrile/water gradient) to afford the product. $^1$H NMR (400 MHz, methanol-d4) δ 7.82 (s, 1H), 7.30 (t, J=7.8 Hz, 2H), 7.24-7.12 (m, 3H), 6.83 (d, J=4.5 Hz, 1H), 6.73 (d, J=4.6 Hz, 1H), 5.92 (d, J=6.0 Hz, 1H), 5.84 (dd, J=6.0, 5.0 Hz, 1H), 5.68 (d, J=5.0 Hz, 1H), 4.87 (q, J=6.2 Hz, 1H), 4.52-4.38 (m, 2H), 3.91-3.78 (m, 1H), 2.67-2.50 (m, 4H), 1.35 (d, J=1.7 Hz, 6H), 1.33-1.20 (m, 9H), 1.15 (t, J=5.9 Hz, 6H). $^{31}$P NMR (162 MHz, methanol-$d_4$) δ 3.14. LCMS: MS m/z=761.65 [M+H], $t_R$=0.91 min; LC system: Thermo Accela 1250 UHPLC; MS system: Thermo LCQ Fleet; Column: Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=4.54 min; HPLC system: Agilent 1100 series; Column: Gemini 5µ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Example 153. (2R,3S,4S,5S)-5-(4-aminopyrrolo[2,1-f][1,2,4]triazin-7-yl)-2-cyano-2-((((S)-(((S)-1-(cyclohexyloxy)-1-oxopropan-2-yl)amino)(phenoxy)phosphoryl)oxy)methyl)tetrahydrofuran-3,4-diyl (2R,2'R)-bis(2-amino-3-methylbutanoate)

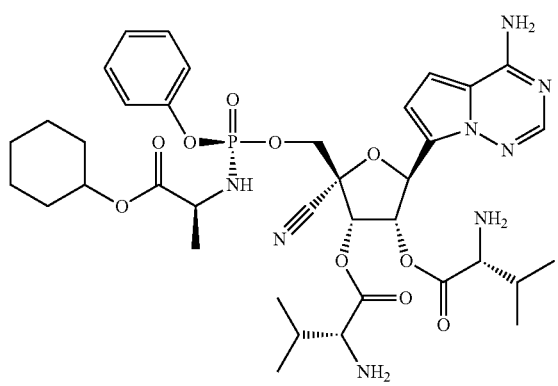 [SMILES: CC(C)[C@@H](N)C(=O)O[C@H]1[C@H](c2ccc3c(N)ncnn23)O[C@](C#N)(CO[P@@](=O)(N[C@@H](C)C(=O)OC2CCCCC2)Oc2ccccc2)[C@H]1OC(=O)[C@H](N)C(C)C]

Example 6 (10 mg, 0.0166 mmol) was dissolved in 1.5 mL of anhydrous tetrahydrofuran. Boc-D-Valine (14 mg, 0.067 mmol) and N,N'-diisopropylcarbodiimide (10 µL, 0.067 mmol) were added and stirred for 30 min. DMAP (2 mg, 0.017 mmol) was added and the reaction mixture was stirred for 16 h. More Boc-D-Valine (14 mg) and N,N'-diisopropylcarbodiimide (10 µL) were added. The reaction mixture was stirred for 2 h. Methanol (200 µL) was added and the resulting mixture was stirred for 30 min. The mixture was diluted with ethyl acetate (10 mL) and washed with saturated aqueous sodium bicarbonate solution (2×10 mL) and brine (5 mL). The organic extract was dried over anhydrous sodium sulfate and concentrated under reduced pressure. The crude residue was purified via SiO$_2$ column chromatography (4 g SiO$_2$ Combiflash HP Gold Column, 0-80% ethyl acetate/hexanes). Fractions containing the desired product were combined and concentrated under reduced pressure and dissolved in dichloromethane (2 mL) and stirred in an ice bath. TFA (200 µL) was added dropwise and the reaction mixture was stirred for 2 h. More TFA (200 µL) was added and the reaction mixture was stirred for 2 h. Triethylamine was dissolved in dichloromethane and added dropwise to give pH of 3-4. The resulting mixture was concentrated under reduced pressure and purified with prep HPLC without acid modifier (5-100% MeCN/water). Fractions containing the desired product were combined and freeze-dried to give the product. $^1$H NMR (400 MHz, methanol-d$_4$) δ 7.95 (s, 1H), 7.42-7.28 (m, 2H), 7.28-7.12 (m, 3H), 7.06 (d, J=4.6 Hz, 1H), 6.90 (d, J=4.6 Hz, 1H), 6.20-6.00 (m, 2H), 5.79-5.66 (m, 1H), 4.68-4.45 (m, 3H), 4.06 (m, 2H), 3.85 (m, 1H), 2.51-2.34 (m, 2H), 1.84-1.59 (m, 4H), 1.59-1.23 (m, 11H), 1.18 (dd, J=9.4, 6.9 Hz, 6H), 1.00 (dd, J=17.8, 7.0 Hz, 6H). $^{31}$P NMR (162 MHz, methanol-d$_4$) δ 3.45. LCMS: MS m/z=799.3 [M+1]; 797.6 [M−1], t$_R$=1.06 min; LC system: Thermo Dionex ultimate 3000 UHPLC; Column: Phenomenex Kinetex 2.6µ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 m/min. HPLC: t$_R$=2.66 min; HPLC system: Agilent 1100 series; Column: Phenomenex Gemini 5µ C18 110A, 50×4.6 mm; Solvent: A: Water with 0.1% TFA, B: Acetonitrile with 0.1% TFA; Gradient: 2-98% B in 5 min at 2 mL/min. HPLC: t$_R$=4.478 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 154. (2R,3S,4S,5S)-5-(4-aminopyrrolo[2,1-f][1,2,4]triazin-7-yl)-2-cyano-2-((((S)-(((S)-1-isopropoxy-1-oxopropan-2-yl)amino)(phenoxy)phosphoryl)oxy)methyl) tetrahydrofuran-3,4-diyl (2R,2'R)-bis(2-methoxypropanoate)

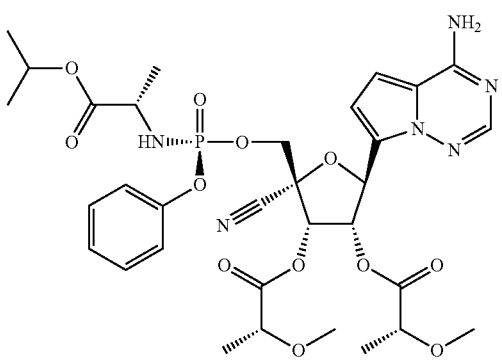 [SMILES: CO[C@H](C)C(=O)O[C@H]1[C@H](c2ccc3c(N)ncnn23)O[C@](C#N)(CO[P@@](=O)(N[C@@H](C)C(=O)OC(C)C)Oc2ccccc2)[C@H]1OC(=O)[C@@H](C)OC]

N,N'-Diisopropylcarbodiimide (0.04 mL, 0.29 mmol) was added to a solution of Example 1. (43 mg, 0.07 mmol) and (R)-(+)-2-methoxypropionic acid (68.3 mg, 0.66 mmol) in tetrahydrofuran (6 mL) at RT. After 5 min, 4-dimethylaminopyridine (18.3 mg, 0.14 mmol) was added. After 1.5 h, methanol (0.5 mL) was added, and the reaction mixture was diluted with ethyl acetate (20 mL) and the resulting mixture was washed with water (15 mL) and brine (15 mL). The organic layer was dried over anhydrous sodium sulfate and concentrated under reduced pressure. The crude residue was subjected preparatory HPLC (Phenomenex Gemini 10 u C18 110 Å 250×30.0 mm column, 5-75% acetonitrile/water gradient) to afford the product and the 2-methoxypropanamido compound of Example 155.

The product: $^1$H NMR (400 MHz, methanol-d4) δ 7.84 (s, 1H), 7.32 (t, J=7.8 Hz, 2H), 7.23 (d, J=8.1 Hz, 2H), 7.18 (t, J=7.4 Hz, 1H), 6.85 (d, J=4.5 Hz, 1H), 6.75 (d, J=4.6 Hz, 1H), 5.97-5.89 (m, 2H), 5.67 (t, J=2.6 Hz, 1H), 4.93-4.88 (m, 1H), 4.50 (qd, J=11.2, 6.1 Hz, 2H), 4.08 (q, J=6.8 Hz, 1H), 3.92 (q, J=6.8 Hz, 1H), 3.87 (dd, J=9.9, 7.2 Hz, 1H), 3.43 (s, 3H), 3.33 (s, 3H), 1.46 (d, J=6.9 Hz, 3H), 1.33 (d, J=6.9 Hz, 3H), 1.28 (dd, J=7.1, 1.1 Hz, 3H), 1.18 (d, J=4.6 Hz, 3H), 1.16 (d, J=4.6 Hz, 3H). $^{31}$P NMR (162 MHz, methanol-d$_4$) δ 3.17. LCMS: MS m/z=733.46 [M+1], t$_R$=1.00 min; LC system: Thermo Accela 1250 UHPLC; MS system: Thermo LCQ Fleet; Column: Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: t$_R$=5.65 min; HPLC system: Agilent 1100 series; Column: Gemini 5µ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Example 155. (2R,3S,4S,5S)-2-cyano-2-((((S)-(((S)-1-isopropoxy-1-oxopropan-2-yl)amino)(phenoxy)phosphoryl)oxy)methyl)-5-(4-((R)-2-methoxypropanamido)pyrrolo[2,1-f][1,2,4]triazin-7-yl)tetrahydrofuran-3,4-diyl (2R,2'R)-bis(2-methoxypropanoate)

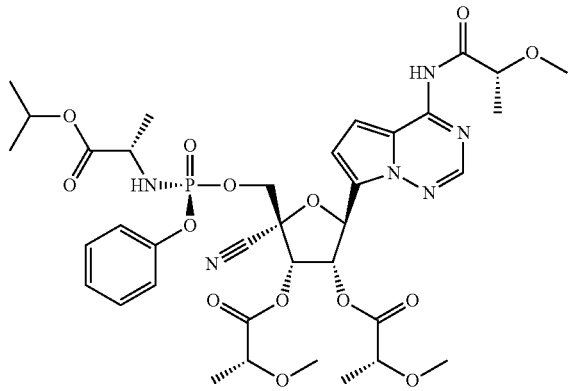 [SMILES: CO[C@H](C)C(=O)Nc1ncnn2c([C@@H]3O[C@](C#N)(CO[P@@](=O)(N[C@@H](C)C(=O)OC(C)C)Oc4ccccc4)[C@@H](OC(=O)[C@@H](C)OC)[C@H]3OC(=O)[C@@H](C)OC)ccc12]

First Eluting Example of Example 154: $^1$H NMR (400 MHz, methanol-d$_4$) δ 8.26 (s, 1H), 7.38-7.28 (m, 2H), 7.27-7.20 (m, 3H), 7.20-7.14 (m, 1H), 7.02 (d, J=4.8 Hz, 1H), 5.93 (d, J=5.4 Hz, 2H), 5.79 (d, J=4.6 Hz, 1H), 4.92-4.88 (m, 1H), 4.55-4.46 (m, 2H), 4.15 (q, J=6.5 Hz, 1H), 4.09 (q, J=6.9 Hz, 1H), 3.93 (q, J=6.8 Hz, 1H), 3.87 (dd, J=10.1, 7.3 Hz, 1H), 3.48 (s, 3H), 3.43 (s, 3H), 3.33 (s, 3H), 1.48 (d, J=2.5 Hz, 3H), 1.47 (d, J=2.7 Hz, 3H), 1.34 (d, J=6.9 Hz, 3H), 1.29 (dd, J=7.1, 1.0 Hz, 3H), 1.18 (d, J=3.7 Hz, 3H), 1.16 (d, J=3.8 Hz, 3H). $^{31}$P NMR (162 MHz, methanol-d$_4$) δ 3.20. LCMS: MS m/z=819.43 [M+1], t$_R$=1.15 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=4.84 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Example 156. (2R,3S,4S,5S)-5-(4-aminopyrrolo[2,1-f][1,2,4]triazin-7-yl)-2-cyano-2-((((S)-(((S)-1-isopropoxy-1-oxopropan-2-yl)amino)(phenoxy)phosphoryl)oxy)methyl) tetrahydrofuran-3,4-diyl bis(tetrahydro-2H-pyran-4-carboxylate)

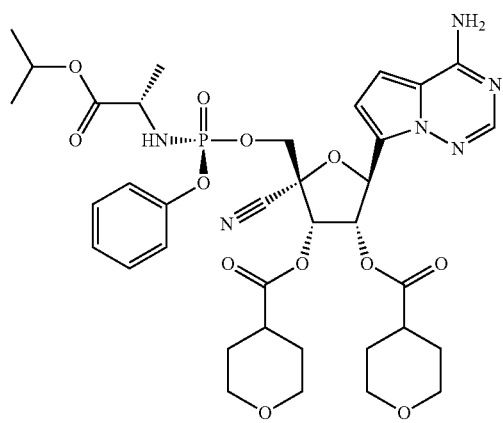 [SMILES: CC(C)OC(=O)[C@H](C)N[P@](=O)(OC[C@@]1(C#N)O[C@@H](c2ccc3c(N)ncnn23)[C@H](OC(=O)C2CCOCC2)[C@@H]1OC(=O)C1CCOCC1)Oc1ccccc1]

N,N'-diisopropylcarbodiimide (0.04 mL, 0.29 mmol) was added to a solution of Example 1. (40 mg, 0.071 mmol) and tetrahydro-2H-pyran-4-carboxylic acid (74 mg, 0.57 mmol) in tetrahydrofuran (6 mL) at RT. After 5 min, 4-dimethylaminopyridine (15.0 mg, 0.11 mmol) was added. After 1.5 h, methanol (0.2 mL) was added, and the reaction mixture was diluted with ethyl acetate (20 mL) and the resulting mixture was washed with water (15 mL) and brine (15 mL). The organic layer was dried over anhydrous sodium sulfate and concentrated under reduced pressure. The crude residue was subjected to preparatory HPLC (Phenomenex Gemini 10 u C18 110 Å 250×30.0 mm column, 5-75% acetonitrile/water gradient) to afford the product. $^1$H NMR (400 MHz, Methanol-d$_4$) δ 7.83 (s, 1H), 7.31 (t, J=7.8 Hz, 2H), 7.18 (dd, J=16.1, 7.9 Hz, 2H), 6.84 (d, J=4.6 Hz, 1H), 6.74 (d, J=4.6 Hz, 1H), 5.97 (d, J=5.8 Hz, 1H), 5.87-5.79 (m, 1H), 5.68 (d, J=4.4 Hz, 1H), 4.47-4.41 (m, 2H), 3.95-3.78 (m, 4H), 3.52-3.46 (m, 2H), 3.45 (s, 1H), 2.70 (dt, J=10.9, 4.2 Hz, 2H), 1.88 (q, J=15.7, 14.5 Hz, 4H), 1.82-1.66 (m, 4H), 1.26 (d, J=7.2 Hz, 3H), 1.16 (t, J=5.8 Hz, 5H). $^{31}$P NMR (162 MHz, Methanol-d$_4$) δ 3.12. LCMS: MS m/z=[M+1], t$_R$=0.94 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=4.68 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Example 157. (2R,3S,4S,5S)-5-(4-aminopyrrolo[2,1-f][1,2,4]triazin-7-yl)-2-cyano-2-((((S)-(((S)-1-isopropoxy-1-oxopropan-2-yl)amino)(phenoxy)phosphoryl)oxy) methyl)tetrahydrofuran-3,4-diyl (2S,2'S)-bis(2-amino-3-methylbutanoate)

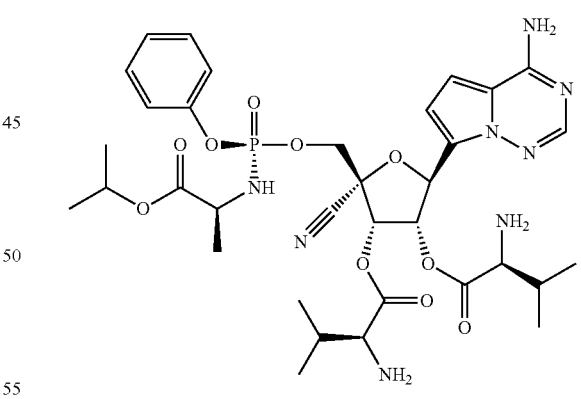

Boc-L-Valine (87 mg, 0.4 mmol) and N,N'-diisopropylcarbodiimide (62 μL, 0.4 mmol) were mixed and dissolved in 1 mL of anhydrous tetrahydrofuran. The mixture was stirred for 20 min. Example 1. (55 mg, 0.1 mmol) was dissolved in 1 mL of anhydrous tetrahydrofuran and added to above mixture. DMAP (12 mg, 0.1 mmol) was added and stirred for 2 h.

Methanol (0.5 mL) was added and stirred for 12 h. Reaction was diluted with ethyl acetate (15 mL) and washed with saturated aqueous sodium bicarbonate solution (2×10 mL) and then with brine (5 mL). Organic extract was dried over anhydrous sodium sulfate and concentrated under reduced pressure. The crude residue was purified via SiO$_2$ column chromatography (4 g SiO$_2$ Combiflash HP Gold Column, 0-50-80% ethyl acetate/hexanes). Fractions containing the desired product were combined and concentrated under reduced pressure as oil which was dissolved material in dichloromethane (4 mL) and stirred in an ice bath. TFA (300 µL) was added dropwise. Reaction was stirred for 1 h. More TFA (200 µL) was added and the reaction was stirred for 2 h. Reaction was concentrated under reduced pressure. Residue was dissolved in anhydrous dioxane and concentrated under reduced pressure several times to give foam. Material was dissolved in MeCN and water and freeze-dried to give the product. $^1$H NMR (400 MHz, methanol-d$_4$) δ 8.08 (s, 1H), 7.43-7.26 (m, 3H), 7.26-7.10 (m, 3H), 7.03 (d, J=4.7 Hz, 1H), 6.27 (d, J=5.8 Hz, 1H), 6.04 (dd, J=5.8, 3.3 Hz, 1H), 5.89 (d, J=3.3 Hz, 1H), 4.83 (m, 1H), 4.50 (m, 2H), 4.16 (m, 2H), 3.88-3.73 (m, 1H), 3.69 (m, 1H), 2.50 (m, 1H), 1.34-1.22 (m, 3H), 1.22-1.05 (m, 18H). $^{31}$P NMR (162 MHz, methanol-d$_4$) δ 3.18. LCMS: MS m/z=759.3 [M+1]; 757.5 [M−1], t$_R$=0.99 min; LC system: Thermo Dionex ultimate 3000 UHPLC; Column: Phenomenex Kinetex 2.6µ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: t$_R$=2.42 min; HPLC system: Agilent 1100 series; Column: Phenomenex Gemini 5µ C18 110A, 50×4.6 mm; Solvent: A: Water with 0.1% TFA, B: Acetonitrile with 0.1% TFA; Gradient: 2-98% B in 5 min at 2 mL/min. HPLC: t$_R$=4.068 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 158. (2R,3S,4S,5S)-5-(4-aminopyrrolo[2,1-f][1,2,4]triazin-7-yl)-2-cyano-2-((((S)-(((S)-1-isopropoxy-1-oxopropan-2-yl)amino)(phenoxy)phosphoryl)oxy)methyl) tetrahydrofuran-3,4-diyl (2S,2'S)-bis(2-methoxypropanoate)

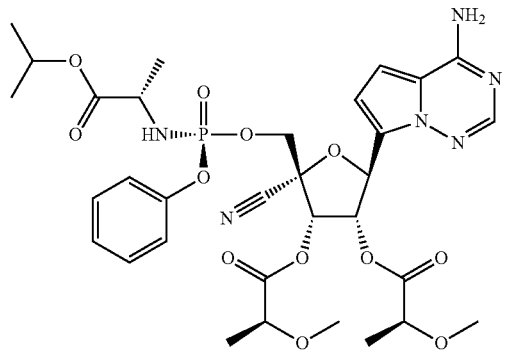 [SMILES: CO[C@@H](C)C(=O)O[C@H]1[C@H](c2ccc3c(N)ncnn23)O[C@](C#N)(CO[P@@](=O)(N[C@@H](C)C(=O)OC(C)C)Oc2ccccc2)[C@H]1OC(=O)[C@H](C)OC]

N,N'-Diisopropylcarbodiimide (0.03 mL, 0.21 mmol) was added to a solution of Example 1. (30.0 mg, 0.05 mmol) and (S)-(−)-2-methoxypropionic acid (46.6 mL, 0.43 mmol) in tetrahydrofuran (4.5 mL) at RT. After 5 min, 4-dimethylaminopyridine (14.3 mg, 0.11 mmol) was added. After 1.5 h, methanol (0.5 mL) was added, and the reaction mixture was diluted with ethyl acetate (20 mL) and the resulting mixture was washed with water (15 mL) and brine (15 mL). The organic layer was dried over anhydrous sodium sulfate and concentrated under reduced pressure. The crude residue was subjected preparatory HPLC (Phenomenex Gemini 10 u C18 110 Å AXIA 250×21.2 mm column, 40-80% acetonitrile/water gradient with 0.1% TFA) and the resulting material was dissolved in EtOAc (25 mL) and washed with saturated aqueous sodium bicarbonate solution (20 mL) and brine (20 mL) to afford the product. $^1$H NMR (400 MHz, methanol-d$_4$) δ 7.86 (s, 1H), 7.38-7.26 (m, 2H), 7.26-7.12 (m, 3H), 6.86 (d, J=4.5 Hz, 1H), 6.79 (d, J=4.5 Hz, 1H), 6.13 (d, J=5.9 Hz, 1H), 5.92 (dd, J=5.9, 4.1 Hz, 1H), 5.75 (d, J=4.1 Hz, 1H), 4.87-4.82 (m, 1H), 4.45 (d, J=5.7 Hz, 2H), 4.01 (dq, J=17.4, 6.9 Hz, 2H), 3.85 (dq, J=9.5, 6.9 Hz, 1H), 3.42 (s, 3H), 3.35 (s, 3H), 1.45 (dd, J=9.6, 6.9 Hz, 6H), 1.27 (d, J=7.1 Hz, 3H), 1.16 (dd, J=6.2, 5.1 Hz, 6H). $^{31}$P NMR (162 MHz, methanol-d$_4$) δ 3.10. LCMS: MS m/z=733.49 [M+1], t$_R$=0.99 min; LC system: Thermo Accela 1250 UHPLC; MS system: Thermo LCQ Fleet; Column: Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: t$_R$=4.51 min; HPLC system: Agilent 1100 series; Column: Gemini 5µ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Example 159. (2R,3S,4S,5S)-2-((((((S)-1-(((1r,4S)-4-aminocyclohexyl) methoxy)-1-oxopropan-2-yl)amino)(phenoxy)phosphoryl)oxy)methyl)-5-(4-amino pyrrolo[2,1-f][1,2,4]triazin-7-yl)-2-cyanotetrahydrofuran-3,4-diyl dipropionate

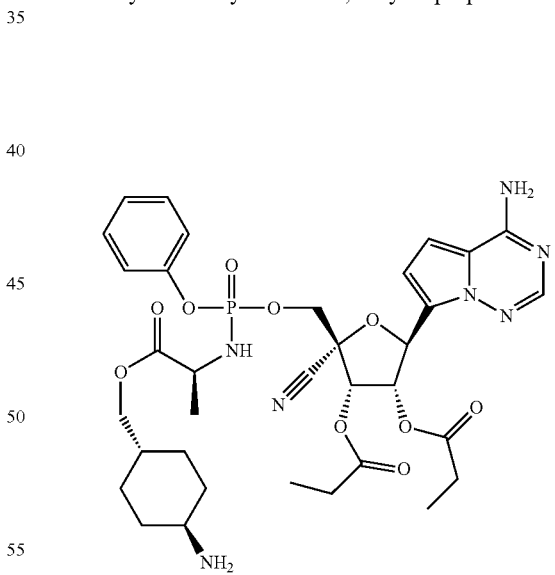

Intermediate 4 (71 mg, 0.214 mmol) and Intermediate 64 (124 mg, 0.214 mmol) were mixed dissolved in 3 mL of anhydrous tetrahydrofuran. Magnesium chloride (61 mg, 0.642 mmol) was added in one portion. DIPEA (187 µL, 1.07 mmol) was added and the reaction was stirred at 50° C. for 16 h.

The reaction mixture was diluted with ethyl acetate (15 mL) and washed with water (5×10 mL) and then with brine (10 mL). The organic extract was dried over anhydrous sodium sulfate and concentrated under reduced pressure.

The result material was dissolved in 5 mL of MeCN and stirred in an ice bath. Concentrate HCl (aq) (300 µL) was added dropwise and then stirred in an ice bath for 2 h. More concentrate HCl (aq) (200 µL) was added dropwise and then stirred in an ice bath for 2 h. 1 M aqueous sodium carbonate solution was added to reaction to give pH of 9-10. Boc anhydride (47 mg, 0.14 mmol) was added and reaction was stirred at RT for 16 h.

Reaction was diluted with ethyl acetate (15 mL) and washed with saturated aqueous sodium bicarbonate solution (10 mL) and then with brine (5 mL). The organic extract was dried over anhydrous sodium sulfate and concentrated under reduced pressure. The residue was dissolved in dioxane (5 mL) and water (3 mL) and stirred at 120° C. for 2 h. The reaction was cooled and diluted with ethyl acetate (15 mL) and washed with brine (3×5 mL). The organic extract was dried over anhydrous sodium sulfate and concentrated under reduced pressure. The crude residue was purified via SiO₂ column chromatography (4 g SiO₂ Combiflash HP Gold Column, 0-100% ethyl acetate/hexanes). The fractions containing the desired product were combined and concentrated under reduced pressure. The residue was dissolved in anhydrous tetrahydrofuran (4 mL). Propionic acid (37 µL, 0.493 mmol) was dissolved in anhydrous tetrahydrofuran (1 mL). N,N'-diisopropylcarbodiimide (77 µL, 0.493 mmol) was added in one portion to the propionic acid solution and stirred for 30 min. The resulting mixture was added to the reaction in one portion. DMAP (15 mg, 0.123 mmol) was added and the reaction was stirred for 16 h.

The reaction mixture was diluted with ethyl acetate (15 mL) and washed with brine (3×10 mL). Organic extract was dried over anhydrous sodium sulfate and concentrated under reduced pressure. The crude residue was purified via SiO₂ column chromatography (4 g SiO₂ Combiflash HP Gold Column, 0-100% ethyl acetate/hexanes). Fractions containing the desired product were combined and concentrated under reduced pressure. Result material was dissolved in anhydrous dichloromethane (5 mL) and stirred in an ice bath under atmospheric nitrogen. TFA (500 µL) was added dropwise, and the reaction was stirred for 3 h at 0° C. The reaction mixture was diluted with anhydrous MeCN and concentrated under reduced pressure. The residue was co-evaporated with anhydrous dioxane (3×). The residue was co-evaporated with anhydrous MeCN (3×). The residue was dissolved in MeCN and water and freeze-dried to give the product. $^1$H NMR (400 MHz, methanol-d₄) δ 8.04 (m, 1H), 7.43-7.25 (m, 3H), 7.25-7.11 (m, 3H), 6.97 (m, 1H), 5.88-5.69 (m, 1H), 4.59-4.40 (m, 2H), 4.01-3.84 (m, 3H), 3.73-3.49 (m, 2H), 3.01 (m, 1H), 2.54-2.37 (m, 4H), 2.02 (m, 2H), 1.92-1.79 (m, 2H), 1.64 (m, 1H), 1.44-1.27 (m, 5H), 1.22-1.05 (m, 8H). $^{31}$P NMR (162 MHz, methanol-d4) δ 3.00, 3.10. LCMS: MS m/z=742.3 [M+1]; 740.5 [M−1], $t_R$=1.06 min; LC system: Thermo Dionex ultimate 3000 UHPLC; Column: Phenomenex Kinetex 2.6µ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=2.59 min; HPLC system: Agilent 1100 series; Column: Phenomenex Gemini 5µ C18 110A, 50×4.6 mm; Solvent: A: Water with 0.1% TFA, B: Acetonitrile with 0.1% TFA; Gradient: 2-98% B in 5 min at 2 mL/min. HPLC: $t_R$=4.389, 4.429 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 160. (2R,3S,4S,5S)-5-(4-aminopyrrolo[2,1-f][1,2,4]triazin-7-yl)-2-cyano-2-((((S)-(((S)-1-iso-propoxy-1-oxopropan-2-yl)amino)(phenoxy)phosphoryl)oxy)methyl) tetrahydrofuran-3,4-diyl bis (oxetane-3-carboxylate)

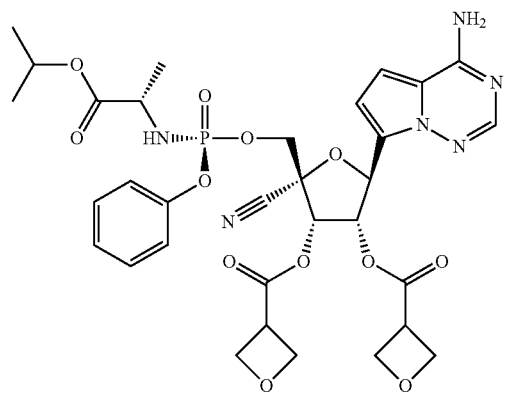 [SMILES: CC(C)OC(=O)[C@H](C)N[P@](=O)(OC[C@@]1(C#N)O[C@@H](c2ccc3c(N)ncnn23)[C@H](OC(=O)C2COC2)[C@@H]1OC(=O)C1COC1)Oc1ccccc1]

N,N'-diisopropylcarbodiimide (0.04 mL, 0.29 mmol) was added to a solution of Example 1. (40 mg, 0.071 mmol) and oxetane-3-carboxylic acid (58 mg mL, 0.57 mmol) in tetrahydrofuran (6 mL) at RT. After 5 min, 4-dimethylaminopyridine (15.0 mg, 0.11 mmol) was added. After 1.5 h, methanol (0.2 mL) was added, and the reaction mixture was diluted with ethyl acetate (20 mL) and the resulting mixture was washed with water (15 mL) and brine (15 mL). The organic layer was dried over anhydrous sodium sulfate and concentrated under reduced pressure. The crude residue was subjected to preparatory HPLC (Phenomenex Gemini 10 u C18 110 Å 250×30.0 mm column, 5-75% acetonitrile/water gradient) to afford the product. $^1$H NMR (400 MHz, Methanol-d₄) δ 7.84 (s, 1H), 7.35-7.26 (m, 2H), 7.24-7.12 (m, 3H), 6.85 (d, J=4.5 Hz, 1H), 6.77 (d, J=4.6 Hz, 1H), 6.10 (d, J=5.9 Hz, 1H), 5.94 (dd, J=5.8, 4.2 Hz, 1H), 5.72 (d, J=4.2 Hz, 1H), 4.95-4.72 (m, 7H), 4.54-4.40 (m, 2H), 4.09-3.77 (m, 2H), 3.60 (q, J=7.0 Hz, 1H), 2.02 (s, 2H), 1.26 (dd, J=7.1, 1.1 Hz, 3H), 1.27-1.07 (m, 8H). $^{31}$P NMR (162 MHz, Methanol-d₄) δ 3.31. LCMS: MS m/z=729.50 [M+H], $t_R$=0.89 min; LC system: Thermo Accela 1250 UHPLC; MS system: Thermo LCQ Fleet; Column: Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=4.11 min, HPLC system: Agilent 1100 series; Column: Gemini 5µ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Example 161. (2R,3S,4S,5S)-5-(4-aminopyrrolo[2,1-f][1,2,4]triazin-7-yl)-2-cyano-2-(((((S)-(((S)-1-isopropoxy-1-oxopropan-2-yl)amino)(phenoxy)phosphoryl)oxy)methyl) tetrahydrofuran-3,4-diyl bis(2-(2-methoxyethoxy)acetate)

Example 162. (2R,3S,4S,5S)-5-(4-aminopyrrolo[2,1-f][1,2,4]triazin-7-yl)-2-cyano-2-((((((S)-1-((1-methylpiperidin-4-yl)oxy)-1-oxopropan-2-yl)amino)(phenoxy)phosphoryl) oxy)methyl)tetrahydrofuran-3,4-diyl bis(2-methylpropanoate)

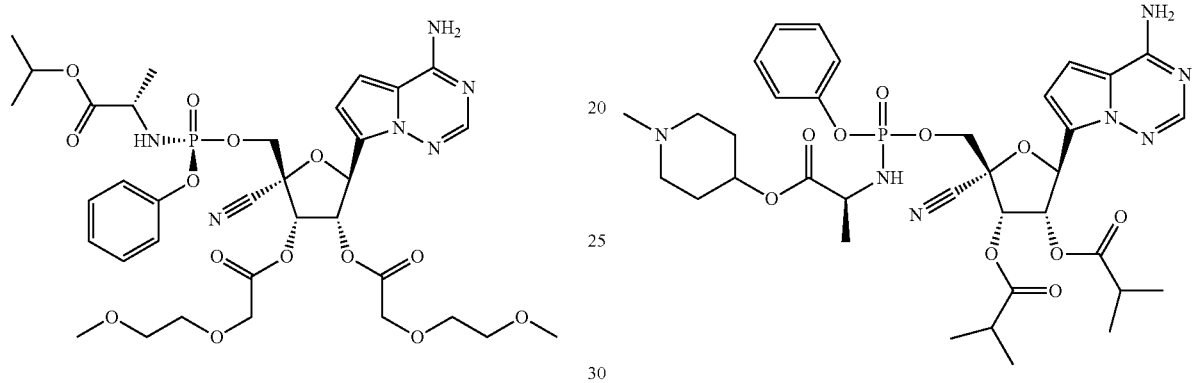

N,N'-Diisopropylcarbodiimide (0.04 mL, 0.27 mmol) was added to a solution of Example 1. (31.0 mg, 0.05 mmol) and 2-(2-methoxyethoxy)acetic acid (0.05 mL, 0.43 mmol) in tetrahydrofuran (4.5 mL) at RT. After 5 min, 4-dimethylaminopyridine (15.0 mg, 0.11 mmol) was added. After 1.5 h, methanol (0.2 mL) was added, and the reaction mixture was diluted with ethyl acetate (20 mL) and the resulting mixture was washed with water (15 mL) and brine (15 mL). The organic layer was dried over anhydrous sodium sulfate and concentrated under reduced pressure. The crude residue was subjected to preparatory HPLC (Phenomenex Gemini 10 u C18 110 Å 250×30.0 mm column, 5-75% acetonitrile/water gradient) to afford the product. $^1$H NMR (400 MHz, acetonitrile-$d_3$) δ 7.90 (s, 1H), 7.38-7.28 (m, 2H), 7.22-7.14 (m, 3H), 6.77 (d, J=4.6 Hz, 1H), 6.74 (d, J=4.6 Hz, 1H), 6.28 (s, 2H), 5.92 (d, J=6.2 Hz, 1H), 5.88 (dd, J=6.1, 4.6 Hz, 1H), 5.67 (d, J=4.6 Hz, 1H), 4.84 (p, J=6.3 Hz, 1H), 4.46 (dd, J=11.2, 6.8 Hz, 1H), 4.37 (dd, J=11.2, 5.8 Hz, 1H), 4.29-4.17 (m, 4H), 4.15 (d, J=0.8 Hz, 1H), 3.90-3.77 (m, 1H), 3.69-3.64 (m, 2H), 3.64-3.58 (m, 2H), 3.52-3.48 (m, 2H), 3.48-3.43 (m, 2H), 3.30 (s, 3H), 3.26 (s, 3H), 1.23 (dd, J=7.1, 0.9 Hz, 3H), 1.13 (dd, J=7.0, 6.2 Hz, 6H). $^{31}$P NMR (162 MHz, acetonitrile-$d_3$) δ 2.56. LCMS: MS m/z=739.63 [M+1], $t_R$=0.94 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.29 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

A mixture of Example 19 (50 mg, 0.069 mmol), isobutyric acid (0.031 mL, 0.343 mmol), and N,N-diisopropylcarbodiimide (0.053 mL, 0.343 mmol) in DMF (2 mL) was stirred at room temperature for 20 min and DMAP (25.12 mg, 0.206 mmol) was added. The resulting mixture was stirred at room temperature for 1 h and additional N,N-diisobutylcarbodiimide (0.053 mL, 0.343 mmol) was added. After 2 h stirring, the reaction was quenched by adding methanol (0.5 mL), and purified by preparative HPLC (Phenominex Gemini 10 u C18 110 Å 250×21.2 mm column, 20-65% acetonitrile (0.1% TFA)/water (0.1% TFA) gradient in 30 min run) to afford the product. $^1$H NMR (400 MHz, Methanol-d4) δ 7.95 (m, 1H), 7.32 (m, 2H), 7.25-7.11 (m, 4H), 6.88 (m, 1H), 5.90-5.73 (m, 2H), 5.70 (m, 1H), 5.04 (m, 0.7H), 4.09 (m, 0.3H), 4.50 (m, 2H), 3.97 (s, 1H), 3.54 (m, 0.7H), 3.34 (m, 1.3H), 3.14 (m, 2H), 2.91-2.76 (m, 3H), 2.74-2.55 (m, 2H), 2.20 (m, 1H), 2.03 (m, 2H), 1.83 (m, 1H), 1.41-1.27 (m, 3H), 1.26-1.08 (m, 12H). $^{31}$P NMR (162 MHz, Acetonitrile-d3) δ 2.44. LCMS: MS m/z=756.32 [M+1-TFA]; $t_R$=0.84 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.66 (29%), 4.70 min (69%); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

323

Example 163. (2R,3S,4S,5S)-5-(4-Aminopyrrolo[2,1-f][1,2,4]triazin-7-yl)-2-cyano-2-((((((S)-1-oxo-1-((tetrahydro-2H-pyran-4-yl)oxy)propan-2-yl)amino)(phenoxy)phosphoryl) oxy)methyl)tetrahydrofuran-3,4-diyl diacetate

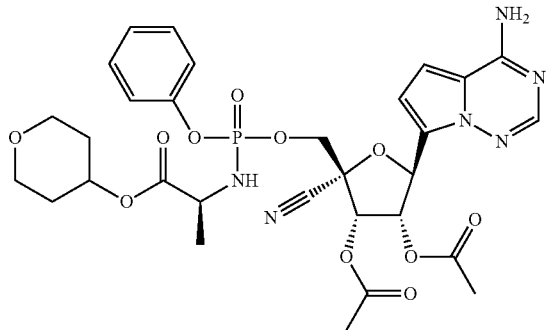 [SMILES: CC(=O)O[C@H]1[C@H](c2ccc3c(N)ncnn23)O[C@](C#N)(COP(=O)(N[C@@H](C)C(=O)OC2CCOCC2)Oc2ccccc2)[C@H]1OC(C)=O]

A mixture of Example 55. (53 mg, 0.083 mmol), acetic acid (0.023 mL, 0.415 mmol), and N,N-diisopropylcarbodiimide (0.15 mL, 0.963 mmol) in THF (2 mL) was stirred at room temperature for 20 min and DMAP (20.27 mg, 0.166 mmol) was added. The resulting mixture was stirred at room temperature for 80 min and quenched by adding methanol (0.5 mL), and purified by preparative HPLC (Phenomenex Gemini-NX 10µ C18 110° A 250×30 mm column, 0%-100% acetonitrile/water gradient in 25 min run) to afford the product. $^1$H NMR (400 MHz, Acetonitrile-d$_3$) δ 7.90 (m, 1H), 7.38-7.31 (m, 2H), 7.25-7.13 (m, 3H), 6.81-6.73 (m, 2H), 6.39 (s, 2H), 5.88-5.75 (m, 2H), 5.69 (m, 1H), 4.84 (m, 1H), 4.56-4.29 (m, 3H), 3.98-3.84 (m, 1H), 3.83-3.72 (m, 2H), 3.45 (m, 2H), 2.16 (s, 1H), 2.15 (s, 2H), 2.08 (s, 1H), 2.07 (s, 2H), 1.87-1.73 (m, 2H), 1.62-1.47 (m, 2H), 1.28 (dd, J=7.1, 1.0 Hz, 2H), 1.24 (dd, J=7.1, 1.1 Hz, 1H). $^{31}$P NMR (162 MHz, Acetonitrile-d$_3$) δ 2.51, 2.39. LCMS: MS m/z=687.39 [M+1]; t$_R$=0.84, 0.86 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min.

Resolution of the Sp and Rp diastereomers. The product was separated by SFC (IF, 5 u, 21×250 mm, 20% MeOH) to afford the diastereomers:

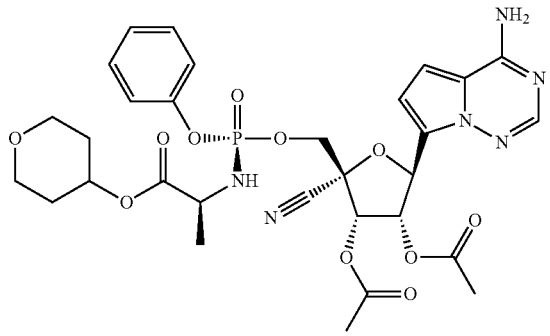

324

-continued

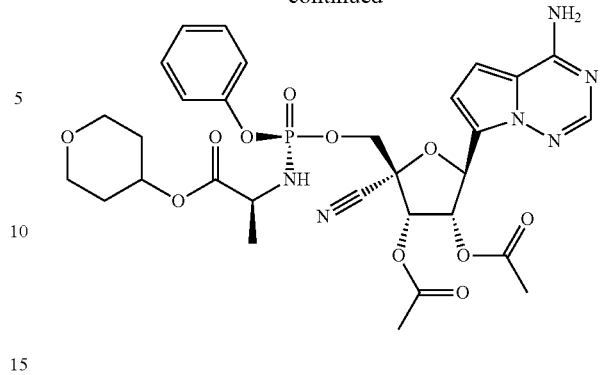

Example 164

First eluting diastereomer: H NMR (400 MHz, Acetonitrile-d3) δ 7.89 (s, 1H), 7.34 (t, J=7.8 Hz, 2H), 7.23-7.13 (m, 3H), 6.82-6.74 (m, 2H), 6.34 (s, 2H), 5.88-5.78 (m, 2H), 5.70 (d, J=4.8 Hz, 1H), 4.87 (tt, J=8.6, 4.2 Hz, 1H), 4.50 (dd, J=11.2, 6.3 Hz, 1H), 4.40 (dd, J=11.2, 5.4 Hz, 1H), 4.27 (t, J=11.1 Hz, 1H), 3.93-3.75 (m, 3H), 3.52-3.42 (m, 2H), 2.16 (s, 3H), 2.08 (s, 3H), 1.82 (q, J=6.4, 5.2 Hz, 2H), 1.56 (dtd, J=12.8, 8.7, 3.9 Hz, 2H), 1.23 (dd, J=7.1, 1.1 Hz, 3H). $^{31}$P NMR (162 MHz, Acetonitrile-d3) δ 2.37. LCMS: MS m/z=687.35 [M+1]; t$_R$=0.85 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: t$_R$=4.62 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 165

Second eluting diastereomer: $^1$H NMR (400 MHz, Acetonitrile-d3) δ 7.91 (s, 1H), 7.35 (t, J=7.8 Hz, 2H), 7.21 (ddd, J=8.3, 2.6, 1.4 Hz, 3H), 6.77 (q, J=4.6 Hz, 2H), 6.35 (s, 2H), 5.83-5.74 (m, 2H), 5.68 (d, J=4.6 Hz, 1H), 4.84 (tt, J=8.2, 4.0 Hz, 1H), 4.46 (dd, J=11.2, 6.7 Hz, 1H), 4.42-4.26 (m, 2H), 4.00-3.83 (m, 1H), 3.78 (dt, J=10.6, 4.8 Hz, 2H), 3.51-3.39 (m, 2H), 2.15 (s, 3H), 2.07 (s, 3H), 1.80 (q, J=10.4, 7.4 Hz, 2H), 1.53 (dtd, J=12.7, 8.4, 3.9 Hz, 2H), 1.28 (dd, J=7.1, 1.0 Hz, 3H). $^{31}$P NMR (162 MHz, Acetonitrile-d3) δ 2.49. LCMS: MS m/z=687.37 [M+1]; t$_R$=0.86 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: t$_R$=4.69 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 166. (2R,3S,4S,5S)-5-(4-aminopyrrolo[2,1-f][1,2,4]triazin-7-yl)-2-cyano-2-((((S)-(((S)-1-methoxy-1-oxopropan-2-Yl)amino)(phenoxy)phosphoryl)oxy)methyl) tetrahydrofuran-3,4-diyl (2R, 2'R)-bis(2-methoxypropanoate)

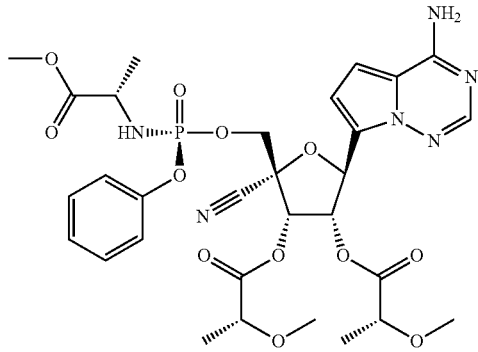 [SMILES: COC(=O)[C@H](C)N[P@](=O)(OC[C@@]1(C#N)O[C@@H](c2ccc3c(N)ncnn23)[C@H](OC(=O)[C@@H](C)OC)[C@@H]1OC(=O)[C@@H](C)OC)Oc1ccccc1]

N,N'-Diisopropylcarbodiimide (0.05 mL, 0.31 mmol) was added to a solution of Example 52 (40.0 mg, 0.08 mmol) and (R)-(+)-2-methoxypropionic acid (62.6 mg, 0.60 mmol) in tetrahydrofuran (6 mL) at RT. After 5 min, 4-dimethylaminopyridine (18.4 mg, 0.14 mmol) was added. After 2 h, methanol (0.5 mL) was added, and the reaction mixture was diluted with ethyl acetate (20 mL) and the resulting mixture was washed with water (15 mL) and brine (15 mL). The organic layer was dried over anhydrous sodium sulfate and concentrated under reduced pressure. The crude residue was subjected preparatory HPLC (Phenomenex Gemini 10 u C18 110 Å AXIA 250×21.2 mm column, 30-60% acetonitrile/water gradient with 0.1% TFA) to afford the product as a TFA salt. $^1$H NMR (400 MHz, Acetonitrile-$d_3$) δ 7.93 (s, 1H), 7.34 (t, J=7.9 Hz, 2H), 7.23-7.16 (m, 4H), 6.93 (d, J=4.8 Hz, 1H), 5.82-5.76 (m, 2H), 5.69 (d, J=4.7 Hz, 1H), 4.50 (dd, J=11.4, 6.8 Hz, 1H), 4.42 (dd, J=11.3, 6.1 Hz, 1H), 4.34-4.24 (m, 1H), 4.05 (q, J=6.9 Hz, 1H), 3.97-3.86 (m, 2H), 3.60 (s, 3H), 3.38 (s, 3H), 3.29 (s, 3H), 1.42 (d, J=6.9 Hz, 3H), 1.32 (d, J=6.8 Hz, 3H), 1.29 (dd, J=7.1, 1.0 Hz, 3H). $^{19}$F NMR (376 MHz, Acetonitrile-$d_3$) δ −77.14. $^{31}$P NMR (162 MHz, Acetonitrile-$d_3$) δ 2.47. LCMS: MS m/z=705.43 [M+1], $t_R$=0.89 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.12 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Example 167. (2R,3S,4S,5S)-5-(4-Aminopyrrolo[2,1-f][1,2,4]triazin-7-yl)-2-cyano-2-((((((S)-1-oxo-1-((tetrahydro-2H-pyran-4-yl)oxy)propan-2-yl)amino)(phenoxy)phosphoryl)oxy) methyl)tetrahydrofuran-3,4-diyl dipropionate

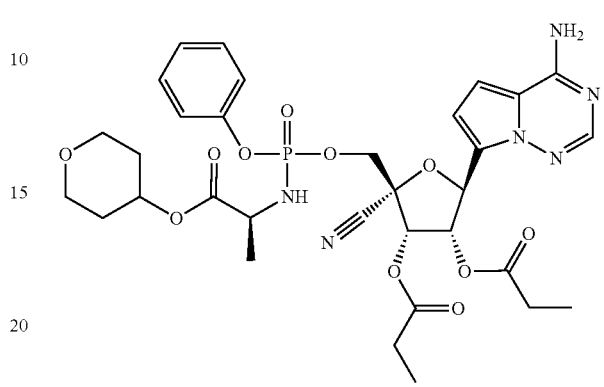

A mixture of Example 55. (54 mg, 0.085 mmol), propionic acid (0.032 mL, 0.423 mmol), and N,N-diisopropylcarbodiimide (0.132 mL, 0.423 mmol) in DMF (2 mL) was stirred at RT for 20 min and DMAP (20.65 mg, 0.169 mmol) was added. The resulting mixture was stirred at room temperature for 80 min and quenched by adding methanol (0.5 mL), and purified by preparative HPLC (Phenomenex Gemini-NX 10μ C18 110° A 250×30 mm column, 0%-100% acetonitrile/water gradient in 25 min run) to afford the product and the propionamide of Example 170. $^1$H NMR (400 MHz, Acetonitrile-$d_3$) δ 7.90 (dd, J=4.7, 1.6 Hz, 1H), 7.44-7.27 (m, 2H), 7.28-7.13 (m, 3H), 6.77 (m, 2H), 6.40 (s, 2H), 5.95-5.76 (m, 2H), 5.68 (m, 1H), 4.84 (m, 1H), 4.56-4.33 (m, 3H), 4.03-3.69 (m, 3H), 3.52-3.38 (m, 2H), 2.57-2.29 (m, 4H), 1.88-1.75 (m, 2H), 1.54 (m, 2H), 1.26 (m, 3H), 1.13 (m, 6H). $^{31}$P NMR (162 MHz, Acetonitrile-$d_3$) δ 2.50, 2.40. LCMS: MS m/z=715.33 [M+1]; $t_R$=0.95 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min.

Resolution of the Sp and Rp diastereomers. The product was separated by SFC (IF, 5 u, 21×250 mm, 30% EtOH) to afford the diastereomers:

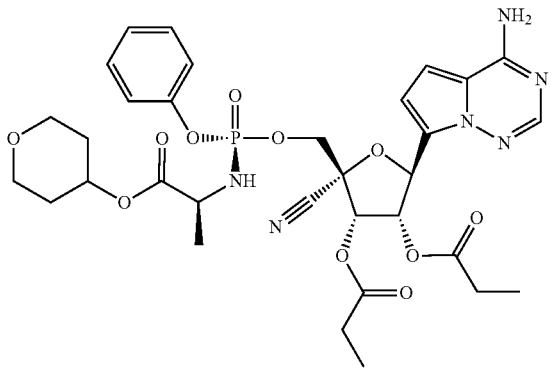 [SMILES: CCC(=O)O[C@H]1[C@H](c2ccc3c(N)ncnn23)O[C@](C#N)(COP(=O)(N[C@@H](C)C(=O)OC2CCOCC2)Oc2ccccc2)[C@H]1OC(=O)CC]

-continued

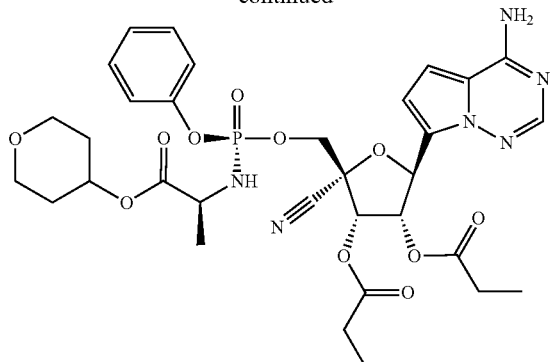

Example 168

First eluting diastereomer: $^1$H NMR (400 MHz, Acetonitrile-d3) δ 7.90 (s, 1H), 7.34 (t, J=7.8 Hz, 2H), 7.22-7.14 (m, 3H), 6.79 (q, J=4.6 Hz, 2H), 6.35 (s, 2H), 5.88 (d, J=6.0 Hz, 1H), 5.83 (dd, J=6.1, 4.7 Hz, 1H), 5.70 (d, J=4.6 Hz, 1H), 4.87 (tt, J=8.3, 4.1 Hz, 1H), 4.50 (dd, J=11.2, 6.3 Hz, 1H), 4.40 (dd, J=11.2, 5.4 Hz, 1H), 4.30-4.21 (m, 1H), 3.83 (ddt, J=21.2, 10.5, 5.9 Hz, 3H), 3.55-3.38 (m, 2H), 2.46 (qd, J=7.6, 3.3 Hz, 2H), 2.39 (q, J=7.5 Hz, 2H), 1.81 (s, 2H), 1.56 (dtd, J=12.7, 8.6, 3.9 Hz, 2H), 1.23 (dd, J=7.1, 1.1 Hz, 3H), 1.15 (t, J=7.5 Hz, 3H), 1.11 (t, J=7.6 Hz, 3H). $^{31}$P NMR (162 MHz, Acetonitrile-d3) δ 2.37. LCMS: MS m/z=715.46 [M+1]; $t_R$=0.95 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.07 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 169

Second eluting diastereomer: $^1$H NMR (400 MHz, Acetonitrile-d3) δ 7.91 (s, 1H), 7.35 (t, J=7.9 Hz, 2H), 7.25-7.15 (m, 3H), 6.81-6.72 (m, 2H), 6.38 (s, 2H), 5.87-5.77 (m, 2H), 5.68 (d, J=4.6 Hz, 1H), 4.84 (tt, J=8.4, 4.1 Hz, 1H), 4.46 (dd, J=11.2, 6.7 Hz, 1H), 4.41-4.26 (m, 2H), 3.91 (ddt, J=16.9, 9.8, 7.1 Hz, 1H), 3.78 (dt, J=10.6, 4.9 Hz, 2H), 3.46 (ddd, J=9.5, 8.1, 4.1 Hz, 2H), 2.45 (qd, J=7.5, 3.3 Hz, 2H), 2.38 (q, J=7.5 Hz, 2H), 1.86-1.75 (m, 2H), 1.53 (dtd, J=12.7, 8.4, 3.9 Hz, 2H), 1.28 (dd, J=7.1, 1.0 Hz, 3H), 1.15 (t, J=7.5 Hz, 3H), 1.10 (t, J=7.6 Hz, 3H). $^{31}$P NMR (162 MHz, Acetonitrile-d3) δ 2.48. LCMS: MS m/z=715.48 [M+1]; $t_R$=0.96 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.14 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 170. (2R,3S,4S,5S)-2-Cyano-2-((((((S)-1-oxo-1-((tetrahydro-2H-pyran-4-yl)oxy)propan-2-yl)amino)(phenoxy)phosphoryl)oxy)methyl)-5-(4-propionamidopyrrolo[2,1-f][1,2,4]triazin-7-yl)tetrahydrofuran-3,4-diyl dipropionate

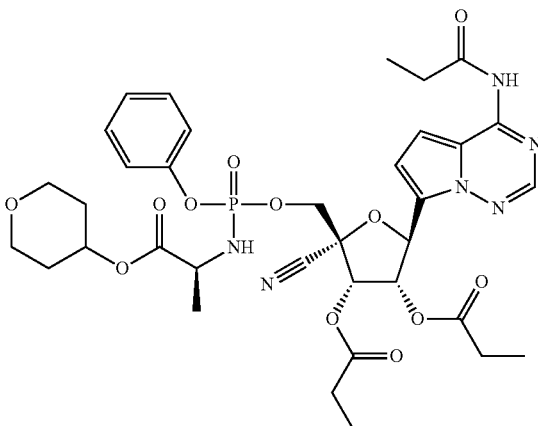

Propanamide prepared via Example 167. $^1$H NMR (400 MHz, Acetonitrile-d3) δ 8.90 (s, 1H), 8.27-8.09 (m, 1H), 7.34 (m, 2H), 7.23-7.13 (m, 4H), 6.96 (m, 1H), 5.90-5.74 (m, 3H), 4.96-4.69 (m, 1H), 4.59-4.27 (m, 3H), 4.05-3.69 (m, 3H), 3.55-3.34 (m, 2H), 2.72 (m, 2H), 2.55-2.34 (m, 4H), 1.81 (s, 2H), 1.66-1.49 (m, 2H), 1.39-0.93 (m, 12H). $^{31}$P NMR (162 MHz, Acetonitrile-d$_3$) δ 2.49, 2.35. LCMS: MS m/z=771.52 [M+1]; $t_R$=1.10 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.77 min (22%), 5.79 min (71%); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 171. (2R,3S,4S,5S)-5-(4-Aminopyrrolo[2,1-f][1,2,4]triazin-7-yl)-2-cyano-2-((((((S)-1-oxo-1-((tetrahydro-2H-pyran-4-yl)oxy)propan-2-yl)amino)(phenoxy)phosphoryl)oxy) methyl)tetrahydrofuran-3,4-diyl bis(2,2-dimethylpropanoate)

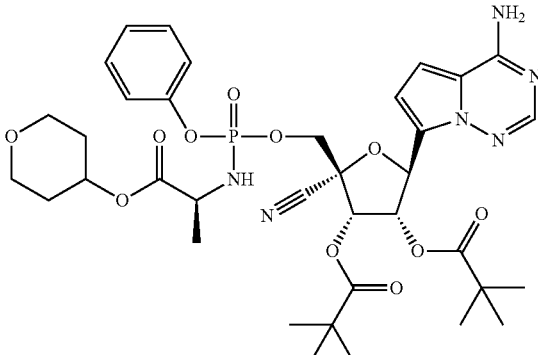

A mixture of Example 55. (54 mg, 0.066 mmol), pivalic acid (0.049 mL, 0.423 mmol), and N,N-diisopropylcarbodiimide (0.132 mL, 0.845 mmol) in DMF (2 mL) was stirred at room temperature for 20 min and DMAP (21 mg, 0.172 mmol) was added. The resulting mixture was stirred at room temperature for 80 min and quenched by adding methanol (0.5 mL), and purified by preparative HPLC (Phenomenex Gemini-NX 10µ C18 110° A 250×30 mm column, 0%-100% acetonitrile/water gradient in 25 min run) to afford the product. $^1$H NMR (400 MHz, Acetonitrile-d$_3$) δ 7.89 (m, 1H), 7.38-7.30 (m, 2H), 7.25-7.14 (m, 3H), 6.76 (m, 2H), 6.39 (s, 2H), 5.91 (m, 1H), 5.80 (m, 1H), 5.65 (m, 1H), 4.84 (m, 1H), 4.52-4.31 (m, 3H), 3.98-3.84 (m, 1H), 3.79 (m, 2H), 3.45 (m, 2H), 1.89-1.74 (m, 2H), 1.55 (m, 2H), 1.28 (m, 12H), 1.22 (m, 9H). $^{31}$P NMR (162 MHz, Acetonitrile-d$_3$) δ 2.48, 2.42. LCMS: MS m/z=771.52 [M+1]; $t_R$=1.10 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min.

Resolution of the Sp and Rp diastereomers. The product was separated by SFC (IF, 5 u, 21×250 mm, 30% 2-propanol) to afford the diastereomers:

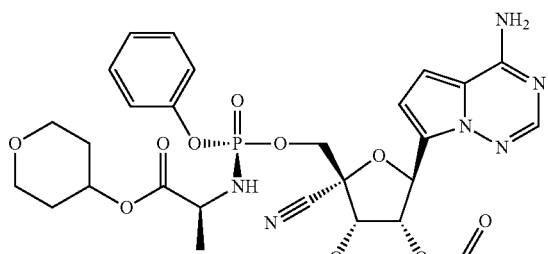

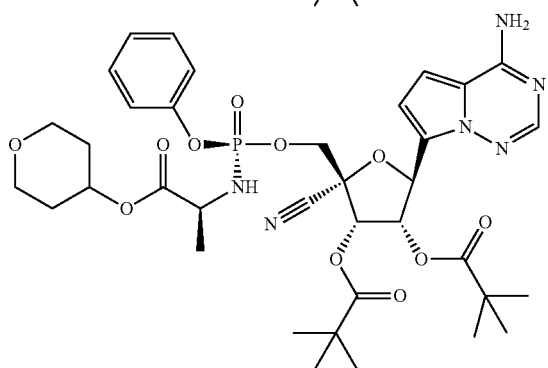

Example 172

First eluting diastereomer: $^1$H NMR (400 MHz, Acetonitrile-d3) δ 7.89 (s, 1H), 7.38-7.28 (m, 2H), 7.25-7.14 (m, 3H), 6.77 (s, 2H), 6.33 (s, 2H), 5.93 (d, J=5.8 Hz, 1H), 5.86-5.77 (m, 1H), 5.66 (d, J=4.0 Hz, 1H), 4.87 (tt, J=8.4, 4.1 Hz, 1H), 4.48 (dd, J=11.2, 6.1 Hz, 1H), 4.40 (dd, J=11.2, 5.4 Hz, 1H), 4.31-4.18 (m, 1H), 3.91-3.75 (m, 3H), 3.47 (ddt, J=11.7, 8.8, 3.0 Hz, 1H), 1.89-1.76 (m, 2H), 1.56 (dtd, J=12.8, 8.7, 4.0 Hz, 2H), 1.28 (s, 9H), 1.23 (s, 12H). $^{31}$P NMR (162 MHz, Acetonitrile-d3) δ 2.41. LCMS: MS m/z=771.47 [M+1]; $t_R$=1.14 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=5.90 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 173

Second eluting diastereomer: $^1$H NMR (400 MHz, Acetonitrile-d3) δ 7.90 (s, 1H), 7.38-7.30 (m, 2H), 7.23-7.16 (m, 3H), 6.76 (s, 2H), 6.35 (s, 2H), 5.89 (d, J=5.8 Hz, 1H), 5.79 (dd, J=5.8, 4.1 Hz, 1H), 5.64 (d, J=4.2 Hz, 1H), 4.84 (tt, J=8.3, 4.1 Hz, 1H), 4.49-4.36 (m, 2H), 4.33 (dd, J=12.0, 9.9 Hz, 1H), 3.97-3.86 (m, 1H), 3.78 (dt, J=10.6, 4.8 Hz, 2H), 3.51-3.40 (m, 2H), 1.88-1.72 (m, 2H), 1.54 (dtd, J=12.7, 8.5, 3.9 Hz, 2H), 1.28 (s, 12H), 1.22 (s, 9H). $^{31}$P NMR (162 MHz, Acetonitrile-d3) δ 2.47. LCMS: MS m/z=771.51 [M+1]; $t_R$=1.14 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=5.97 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 174. (2R,3S,4S,5S)-5-(4-aminopyrrolo[2,1-f][1,2,4]triazin-7-yl)-2-cyano-2-(((((S)-1-(oxetan-3-yloxy)-1-oxopropan-2-yl)amino)(phenoxy)phosphoryl)oxy)methyl) tetrahydrofuran-3,4-diyl dipropionate

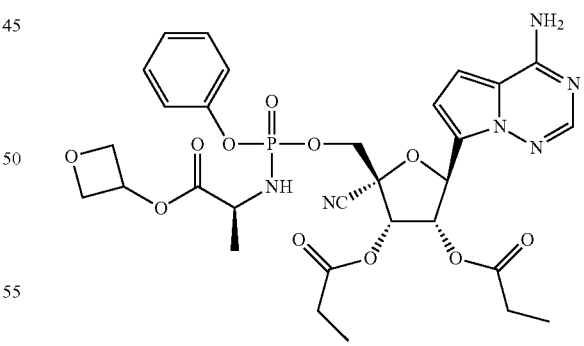

Dissolved Example 44. (20 mg, 0.035 mmol) in 3 mL THF, to the solution were added propionic acid (10 mg, 0.14 mmol) and DIC (22 mg, 0.17 mmol). The reaction mixture was stirred for 10 mins at RT, then DMAP (8.5 mg, 0.07 mmol) was added. The resulting mixture was stirred at RT for 30 mins and then solvent was evaporated. The residue was purified with Prep HPLC to afford the product. $^1$H NMR (400 MHz, Methanol-d4) δ 7.82 (d, J=12.0 Hz, 1H), 7.38-7.25 (m, 2H), 7.24-7.10 (m, 3H), 6.85 (t, J=4.5 Hz, 1H), 6.76

(dd, J=8.5, 4.6 Hz, 1H), 5.94 (dd, J=24.6, 5.9 Hz, 1H), 5.84 (ddd, J=18.2, 5.9, 4.7 Hz, 1H), 5.69 (dd, J=4.7, 2.7 Hz, 2H), 5.32 (dtt, J=16.5, 6.3, 5.1 Hz, 1H), 4.81-4.71 (m, 1H), 4.58-4.37 (m, 4H), 3.92 (ddq, J=23.9, 9.5, 7.1 Hz, 1H), 2.54-2.33 (m, 4H), 1.28 (ddd, J=16.2, 7.2, 1.2 Hz, 3H), 1.15 (dtd, J=15.1, 7.6, 2.8 Hz, 6H). $^{31}$P NMR (162 MHz, Methanol-d4) δ 2.95, 2.89. LCMS: MS m/z=687.18 [M+1], $t_R$=1.24 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=4.88 and 4.95 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The product was purified via chiral preparatory HPLC (Chiralpak IA, 150×4.6 mm, Heptane 80% Ethanol 20%) to afford the diastereomers:

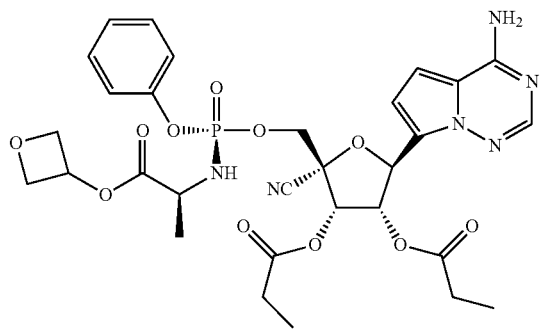

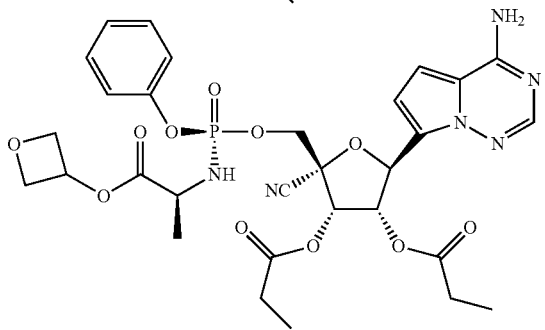

Example 175

First Eluting Diastereomer: $^1$H NMR (400 MHz, Methanol-d4) δ 7.83 (s, 1H), 7.36-7.26 (m, 2H), 7.25-7.12 (m, 3H), 6.84 (d, J=4.5 Hz, 1H), 6.75 (d, J=4.5 Hz, 1H), 5.91 (d, J=5.9 Hz, 1H), 5.82 (dd, J=5.9, 4.8 Hz, 1H), 5.69 (d, J=4.8 Hz, 1H), 5.30 (tt, J=6.3, 5.1 Hz, 1H), 4.78 (tdd, J=7.5, 6.4, 1.0 Hz, 2H), 4.57-4.47 (m, 2H), 4.43 (dt, J=11.1, 5.9 Hz, 2H), 4.02-3.84 (m, 1H), 2.50-2.33 (m, 4H), 1.30 (dd, J=7.2, 1.1 Hz, 3H), 1.20-1.07 (m, 6H). $^{31}$P NMR (162 MHz, Methanol-d4) δ 2.95. LCMS: MS m/z=687.15 [M+1], $t_R$=1.26 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=4.94 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 176

Second Eluting Diastereomer: $^1$H NMR (400 MHz, Methanol-d4) δ 7.80 (s, 1H), 7.30 (dd, J=8.8, 7.0 Hz, 2H), 7.21-7.09 (m, 3H), 6.85 (d, J=4.5 Hz, 1H), 6.77 (d, J=4.5 Hz, 1H), 5.97 (d, J=5.9 Hz, 1H), 5.86 (dd, J=5.9, 4.6 Hz, 1H), 5.69 (d, J=4.5 Hz, 1H), 5.34 (tt, J=6.3, 5.1 Hz, 1H), 4.82-4.75 (m, 2H), 4.56-4.48 (m, 3H), 4.42 (dd, J=11.1, 5.0 Hz, 1H), 3.97-3.80 (m, 1H), 2.54-2.32 (m, 4H), 1.26 (dd, J=7.2, 1.3 Hz, 3H), 1.21-1.05 (m, 6H). $^{31}$P NMR (162 MHz, Methanol-d4) δ 2.89. LCMS: MS m/z=687.14 [M+1], $t_R$=1.25 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=4.88 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 177. (2R,3S,4S,5S)-5-(4-Aminopyrrolo[2,1-f][1,2,4]triazin-7-yl)-2-cyano-2-((((4-(dimethylcarbamoyl)phenoxy)(((S)-1-isopropoxy-1-oxopropan-2-yl)amino)phosphoryl)oxy)methyl)tetrahydrofuran-3,4-diyl bis(2-methylpropanoate)

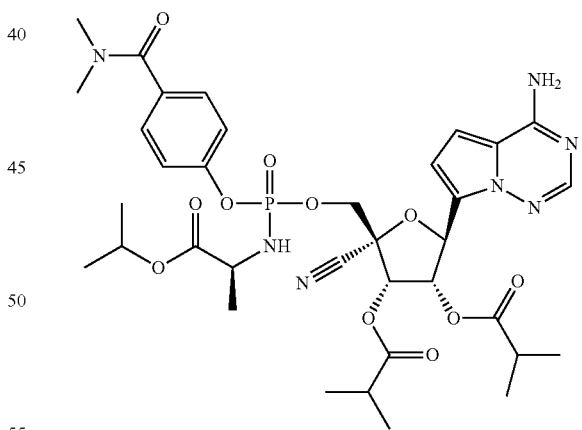

To a mixture of Example 43 (48 mg, 0.076 mmol) and isobutyric anhydride (0.028 mL, 0.167 mmol) in THF (4 mL) was added DMAP (3 mg, 0.323 mmol). The resulting mixture was stirred at room temperature for 5 min, quenched by adding methanol (1 mL), and purified by preparative HPLC (Phenomenex Gemini-NX 10μ C18 110° A 250×30 mm column, 0%-80% acetonitrile/water gradient in 25 min run) to afford the product. $^1$H NMR (400 MHz, Acetonitrile-d3) δ 7.89 (m, 1H), 7.36 (m, 2H), 7.20 (m, 2H), 6.76 (m, 2H), 6.47 (s, 2H), 5.89 (m, 1H), 5.82 (m, 1H), 5.68 (m, 1H), 4.89 (m, 1H), 4.56-4.36 (m, 3H), 3.97-3.74 (m, 1H), 2.96

(m, 6H), 2.76-2.50 (m, 2H), 1.28-1.10 (m, 21H). $^{31}$P NMR (162 MHz, Acetonitrile-d$_3$) δ 2.43, 2.34. LCMS: MS m/z=772.48 [M+1]; t$_R$=1.02 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=5.39 min (18%), 3.85 (81%); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Resolution of the Sp and Rp diastereomers. The product was separated by SFC (AD-H, 5 u, 21×250 mm, 30% 2-propanol) to afford the diastereomers:

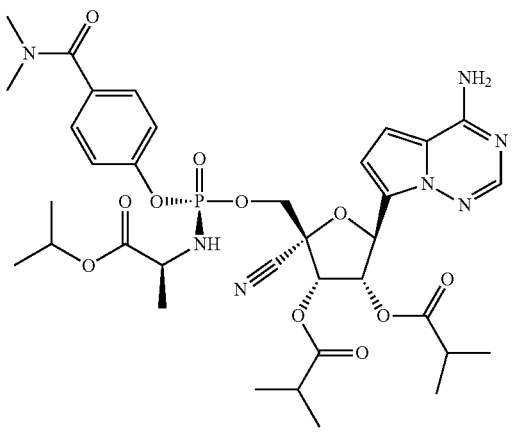 [SMILES: CC(C)OC(=O)[C@H](C)NP(=O)(OC[C@@]1(C#N)O[C@@H](c2ccc3c(N)ncnn23)[C@H](OC(=O)C(C)C)[C@@H]1OC(=O)C(C)C)Oc1ccc(C(=O)N(C)C)cc1]

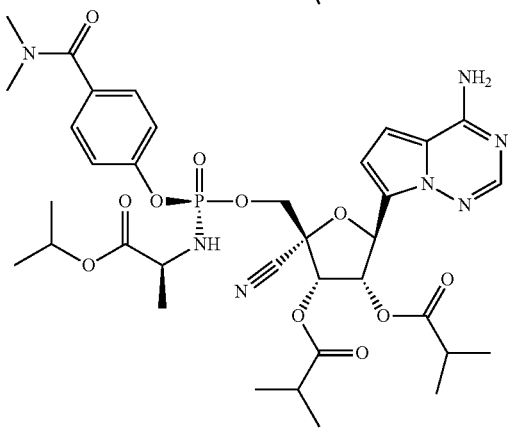

Example 178

First eluting diastereomer: $^1$H NMR (400 MHz, Acetonitrile-d3) δ 7.89 (s, 1H), 7.35 (d, J=8.5 Hz, 2H), 7.23-7.11 (m, 2H), 6.77 (t, J=3.4 Hz, 2H), 6.40 (s, 2H), 5.89 (d, J=6.0 Hz, 1H), 5.83 (dd, J=5.9, 4.4 Hz, 1H), 5.69 (d, J=4.3 Hz, 1H), 4.91 (p, J=6.3 Hz, 1H), 4.50 (dd, J=11.2, 6.1 Hz, 1H), 4.43 (dd, J=11.2, 5.6 Hz, 1H), 4.36 (dd, J=12.3, 10.0 Hz, 1H), 3.80 (ddt, J=16.5, 9.5, 7.1 Hz, 1H), 3.01 (s, 3H), 2.91 (s, 3H), 2.66 (m, 2H), 1.35-1.08 (m, 21H). $^{31}$P NMR (162 MHz, Acetonitrile-d3) δ 2.31. LCMS: MS m/z=772.48 [M+1]; t$_R$=1.03 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=5.39 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min Example 179

Second eluting diastereomer: $^1$H NMR (400 MHz, Acetonitrile-d3) δ 7.90 (s, 1H), 7.40-7.33 (m, 2H), 7.22 (dd, J=8.7, 1.2 Hz, 2H), 6.79-6.70 (m, 2H), 6.40 (s, 2H), 5.87 (d, J=6.0 Hz, 1H), 5.81 (d, J=4.5 Hz, 1H), 5.67 (d, J=4.4 Hz, 1H), 4.87 (hept, J=6.3 Hz, 1H), 4.47 (dd, J=11.2, 6.7 Hz, 1H), 4.39 (ddd, J=12.0, 8.2, 2.5 Hz, 2H), 3.87 (tq, J=9.5, 7.0 Hz, 1H), 3.02 (s, 3H), 2.91 (s, 3H), 2.65 (m, 2H), 1.30-1.06 (m, 21H). $^{31}$P NMR (162 MHz, Acetonitrile-d3) δ 2.40. LCMS: MS m/z=772.42 [M+1]; t$_R$=1.02 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=5.39 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 180. (2R,3S,4S,5S)-5-(4-aminopyrrolo[2,1-f][1,2,4]triazin-7-yl)-2-cyano-2-((((S)-(((S)-1-(2-ethylbutoxy)-1-oxopropan-2-yl)amino)(phenoxy)phosphoryl)oxy)methyl) tetrahydrofuran-3,4-diyl dipropionate

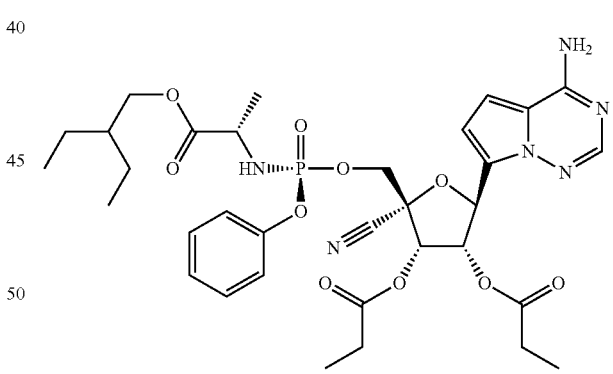

Propionic anhydride (13 μL, 0.10 mmol) was added to a solution Example 25 (30 mg, 0.050 mmol) in 2-methyltetrahydrofuran (1.0 mL) at RT. 4-dimethylaminopyridine (1 mg, 0.007 mmol) was then added. After 40 min, the reaction mixture was subjected to silica gel chromatography eluting with 0-100% ethyl acetate in hexanes to afford the product. $^1$H NMR (400 MHz, methanol-d4) δ 7.83 (s, 1H), 7.34-7.26 (m, 2H), 7.23-7.13 (m, 3H), 6.84 (d, J=4.6 Hz, 1H), 6.74 (d, J=4.6 Hz, 1H), 5.90 (d, J=5.9 Hz, 1H), 5.80 (dd, J=5.9, 4.7 Hz, 1H), 5.68 (d, J=4.7 Hz, 1H), 4.49-4.38 (m, 2H), 4.01 (dd, J=10.9, 5.7 Hz, 1H), 3.95-3.85 (m, 2H), 2.53-2.34 (m, 5H), 1.51-1.39 (m, 1H), 1.37-1.25 (m, 9H), 1.15 (dt, J=13.8, 7.5 Hz, 7H), 0.86 (td, J=7.5, 1.1 Hz, 7H). $^{31}$P NMR (162

MHz, methanol-$d_4$) δ 3.04 (s). LCMS: MS m/z=715.44 [M+1], $t_R$=1.50 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.61 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=6.22 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 181. (2R,3S,4S,5S)-5-(4-aminopyrrolo[2,1-f][1,2,4]triazin-7-yl)-2-cyano-2-((((((S)-1-oxo-1-((tetrahydro-2H-pyran-4-yl)methoxy)propan-2-yl)amino)(phenoxy) phosphoryl)oxy)methyl) tetrahydrofuran-3,4-diyl bis(2-methylpropanoate)

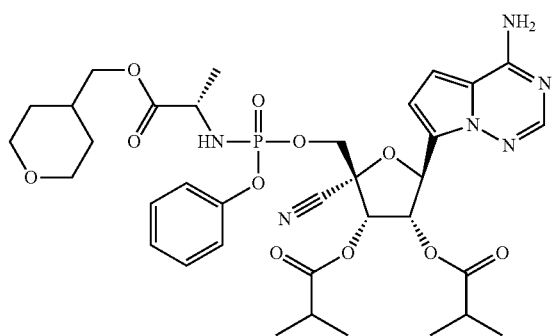 [SMILES: CC(C)C(=O)O[C@H]1[C@H](c2ccc3c(N)ncnn23)O[C@](C#N)(COP(=O)(N[C@@H](C)C(=O)OCC2CCOCC2)Oc2ccccc2)[C@H]1OC(=O)C(C)C]

Isobutyric anhydride (32 μL, 0.19 mmol) was added to a solution Example 20 (60 mg, 0.10 mmol) in 2-methyltetrahydrofuran (1.0 mL) at RT. 4-dimethylaminopyridine (2 mg, 0.02 mmol) was then added. After 40 min, the reaction mixture was subjected to silica gel chromatography eluting with 0-100% ethyl acetate in hexanes to afford the product. $^1$H NMR (400 MHz, methanol-$d_4$) δ 7.84 (s, 0.55H), 7.81 (s, 0.45H), 7.35-7.27 (m, 2H), 7.23-7.13 (m, 3H), 6.88-6.82 (m, 1H), 6.79-6.72 (m, 1H), 5.97 (d, J=5.9 Hz, 0.45H), 5.90 (d, J=5.9 Hz, 0.55H), 5.85 (dd, J=5.9, 4.5 Hz, 0.45H), 5.79 (dd, J=5.9, 4.7 Hz, 0.55H), 5.69-5.65 (m, 1H), 4.55-4.37 (m, 2H), 3.98-3.79 (m, 5H), 3.38-3.30 (m, 2H), 2.73-2.54 (m, 2H), 1.91-1.78 (m, 1H), 1.62-1.50 (m, 2H), 1.33-1.11 (m, 17H). $^{31}$P NMR (162 MHz, methanol-$d_4$) δ 3.06 (s), 2.97 (s). LCMS: MS m/z=757.45 [M+1], $t_R$=1.40 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.33 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=5.60 min (minor isomer), 5.66 min (major isomer); HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Resolution of the Sp and Rp diastereomers. The product was purified via chiral preparatory SFC (Chiralpak ADH, 20% isopropyl alcohol) to afford the diastereomers:

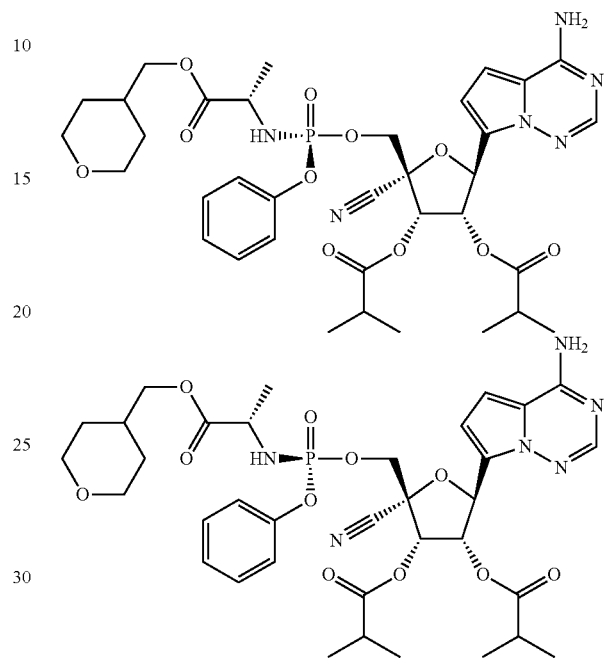

Example 182

First Eluting Diastereomer: $^1$H NMR (400 MHz, methanol-$d_4$) δ 7.82 (s, 1H), 7.35-7.26 (m, 2H), 7.20-7.13 (m, 3H), 6.86 (d, J=4.5 Hz, 1H), 6.78 (d, J=4.6 Hz, 1H), 5.97 (d, J=5.9 Hz, 1H), 5.85 (dd, J=5.9, 4.4 Hz, 1H), 5.68 (d, J=4.5 Hz, 1H), 4.51 (dd, J=11.0, 5.7 Hz, 1H), 4.42 (dd, J=11.1, 5.0 Hz, 1H), 3.95-3.79 (m, 5H), 3.38-3.29 (m, 2H), 2.75-2.55 (m, 2H), 1.94-1.78 (m, 1H), 1.62-1.50 (m, 2H), 1.35-1.11 (m, 17H). $^{31}$P NMR (162 MHz, methanol-$d_4$) δ 3.05 (s). LCMS: MS m/z=757.30 [M+1], $t_R$=1.43 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.33 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=5.59 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 183

Second Eluting Diastereomer: $^1$H NMR (400 MHz, methanol-d4) δ 7.83 (s, 1H), 7.36-7.27 (m, 2H), 7.23-7.13 (m, 3H), 6.84 (d, J=4.5 Hz, 1H), 6.74 (d, J=4.5 Hz, 1H), 5.90

(d, J=5.9 Hz, 1H), 6.74 (d, J=4.5 Hz, 1H), 5.90 (d, J=5.9 Hz, 1H), 5.79 (dd, J=5.9, 4.7 Hz, 1H), 5.67 (d, J=4.7 Hz, 1H), 4.49-4.39 (m, 2H), 3.96-3.79 (m, 5H), 3.37-3.27 (m, 2H), 2.73-2.54 (m, 2H), 1.91-1.77 (m, 1H), 1.58-1.52 (m, 2H), 1.33-1.11 (m, 17H). $^{31}$P NMR (162 MHz, methanol-d$_4$) δ 2.97 (s). LCMS: MS m/z=757.50 [M+1], $t_R$=1.45 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.34 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=5.65 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 184. (2R,3S,4S,5S)-5-(4-aminopyrrolo[2,1-f][1,2,4]triazin-7-yl)-2-cyano-2-(((((S)-1-(oxetan-3-yloxy)-1-oxopropan-2-yl)amino)(phenoxy)phosphoryl)oxy)methyl) tetrahydrofuran-3,4-diyl bis(2-methylpropanoate)

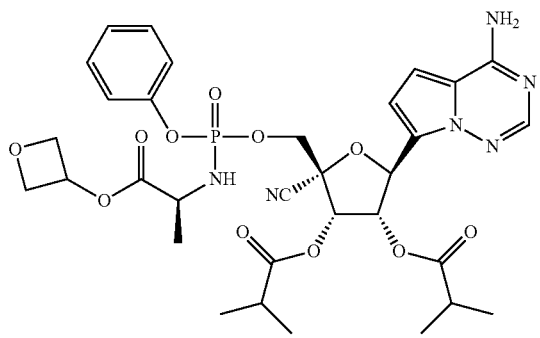 [SMILES: CC(C)C(=O)O[C@H]1[C@H](c2ccc3c(N)ncnn23)O[C@](C#N)(COP(=O)(N[C@@H](C)C(=O)OC2COC2)Oc2ccccc2)[C@H]1OC(=O)C(C)C]

Dissolved Example 44 (99 mg, 0.17 mmol) in 10 mL THF, to the solution were added isobutyric acid (38 mg, 0.43 mmol) and DIC (65 mg, 0.52 mmol). The reaction mixture was stirred for 10 mins at RT, then DMAP (42 mg, 0.34 mmol) was added. The resulting mixture was stirred at RT for 30 mins and then solvent was evaporated. The residue was purified with Prep HPLC to afford the product. $^1$H NMR (400 MHz, Methanol-d4) δ 7.82 (d, J=12.8 Hz, 1H), 7.31 (ddd, J=8.2, 6.7, 4.1 Hz, 2H), 7.25-7.10 (m, 3H), 6.85 (t, J=4.5 Hz, 1H), 6.76 (dd, J=8.2, 4.6 Hz, 1H), 5.94 (dd, J=23.8, 5.9 Hz, 1H), 5.82 (ddd, J=19.6, 5.9, 4.6 Hz, 1H), 5.67 (dd, J=4.6, 2.2 Hz, 1H), 5.32 (dtt, J=16.6, 6.4, 5.1 Hz, 1H), 4.82-4.71 (m, 2H), 4.52 (dddd, J=12.6, 7.4, 5.0, 1.2 Hz, 2H), 4.42 (ddd, J=11.2, 5.9, 4.4 Hz, 2H), 3.99-3.84 (m, 1H), 2.72-2.56 (m, 2H), 1.34-1.09 (m, 15H). $^{31}$P NMR (162 MHz, Methanol-d4) δ 2.94, 2.90. LCMS: MS m/z=715.22 [M+1], $t_R$=1.34 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=5.31 and 5.38 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The product was purified via chiral preparatory HPLC (Chiralpak IA, 150×4.6 mm, Heptane 80% Ethanol 20%) to afford the diastereomers:

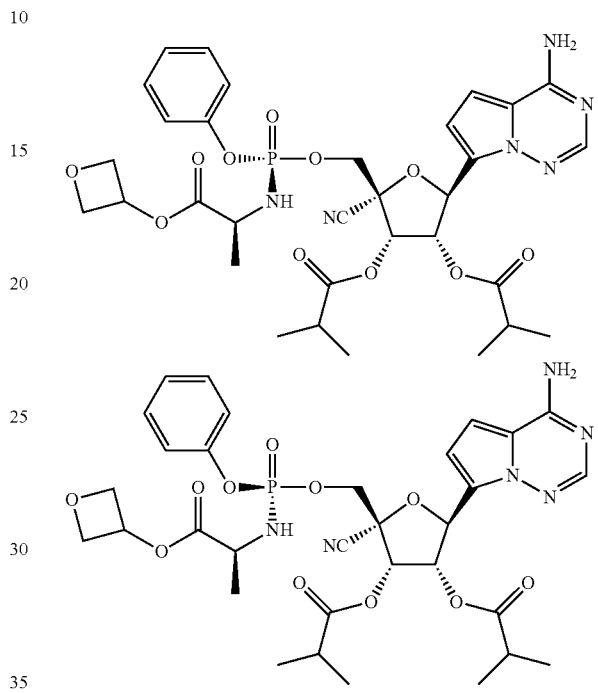

Example 185

First Eluting Diastereomer: $^1$H NMR (400 MHz, Methanol-d4) δ 7.83 (s, 1H), 7.31 (dd, J=8.7, 7.1 Hz, 2H), 7.23-7.11 (m, 3H), 6.84 (d, J=4.5 Hz, 1H), 6.75 (d, J=4.5 Hz, 1H), 5.91 (d, J=5.9 Hz, 1H), 5.80 (dd, J=5.9, 4.6 Hz, 1H), 5.67 (d, J=4.7 Hz, 1H), 5.30 (tt, J=6.4, 5.1 Hz, 1H), 4.82-4.72 (m, 2H), 4.52 (dddd, J=12.9, 7.6, 5.1, 1.0 Hz, 2H), 4.46-4.38 (m, 2H), 3.95 (dq, J=10.3, 7.2 Hz, 1H), 2.64 (dp, J=17.3, 7.0 Hz, 2H), 1.35-1.26 (m, 3H), 1.24-1.08 (m, 12H). $^{31}$P NMR (162 MHz, Methanol-d4) δ 2.94. LCMS: MS m/z=715.21 [M+1], $t_R$=1.35 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=5.38 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 186

Second Eluting Diastereomer: $^1$H NMR (400 MHz, Methanol-d4) δ 7.80 (s, 1H), 7.33-7.24 (m, 2H), 7.19-7.10 (m, 3H), 6.85 (d, J=4.6 Hz, 1H), 6.77 (d, J=4.6 Hz, 1H), 5.97 (d, J=5.8 Hz, 1H), 5.85 (dd, J=5.9, 4.4 Hz, 1H), 5.68 (d, J=4.4 Hz, 1H), 5.37-5.31 (m, 1H), 4.83-4.78 (m, 2H), 4.57-4.47 (m, 3H), 4.42 (dd, J=11.1, 5.0 Hz, 1H), 3.96-3.81 (m, 1H), 2.64 (dq, J=15.2, 7.0 Hz, 2H), 1.26 (dd, J=7.2, 1.3 Hz, 3H), 1.25-1.13 (m, 12H). $^{31}$P NMR (162 MHz, Methanol-d4) δ 2.90. LCMS: MS m/z=715.28 [M+1], $t_R$=1.34 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=5.30 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 187. (2R,3S,4S,5S)-5-(4-aminopyrrolo[2,1-f][1,2,4]triazin-7-yl)-2-cyano-2-((((((S)-1-isopropoxy-1-oxopropan-2-yl)amino)(phenoxy)phosphoryl)oxy)methyl)tetrahydrofuran-3,4-diyl dipropionate

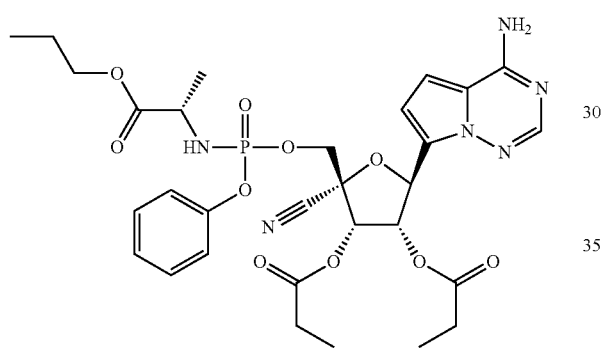

Propionic anhydride (23.5 μL, 0.18 mmol) was added to a solution of Example 45. (51.2 mg, 0.09 mmol) and 4-dimethylaminopyridine (1.8 mg, 0.1 mmol) in tetrahydrofuran (1.8 mL) at RT. After 20 min, the reaction mixture was diluted with ethyl acetate (15 mL) and the resulting mixture was washed with saturated aqueous sodium carbonate solution (10 mL) and brine (10 mL). The organic layer was dried over anhydrous sodium sulfate and concentrated under reduced pressure. The crude residue was purified by silica gel chromatography eluting with 20-100% ethyl acetate in hexanes to afford the product. $^{1}$H NMR (400 MHz, Methanol-d$_4$) δ 7.82 (d, J=9.0 Hz, 1H), 7.38-7.26 (m, 2H), 7.25-7.09 (m, 3H), 6.85 (dd, J=7.1, 4.6 Hz, 1H), 6.76 (dd, J=11.7, 4.6 Hz, 1H), 6.02-5.87 (m, 1H), 5.88-5.79 (m, 1H), 5.69 (t, J=4.7 Hz, 1H), 4.57-4.37 (m, 2H), 4.07-3.76 (m, 3H), 2.55-2.26 (m, 4H), 1.59 (dtd, J=14.0, 7.4, 6.6 Hz, 2H), 1.26 (ddd, J=18.1, 7.2, 1.2 Hz, 3H), 1.16 (dtd, J=14.0, 7.6, 2.9 Hz, 6H), 0.90 (td, J=7.4, 2.9 Hz, 3H). $^{31}$P NMR (162 MHz, Methanol-d$_4$) δ 3.05. LCMS: MS m/z=673.40 [M+1], $t_R$=1.03 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=4.83 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Resolution of the Sp and Rp diastereomers. The product was purified via chiral SFC (Chiralpak AD-H, 5 um, 21×250 mm, Isopropyl alcohol 30%) to afford the diastereomers:

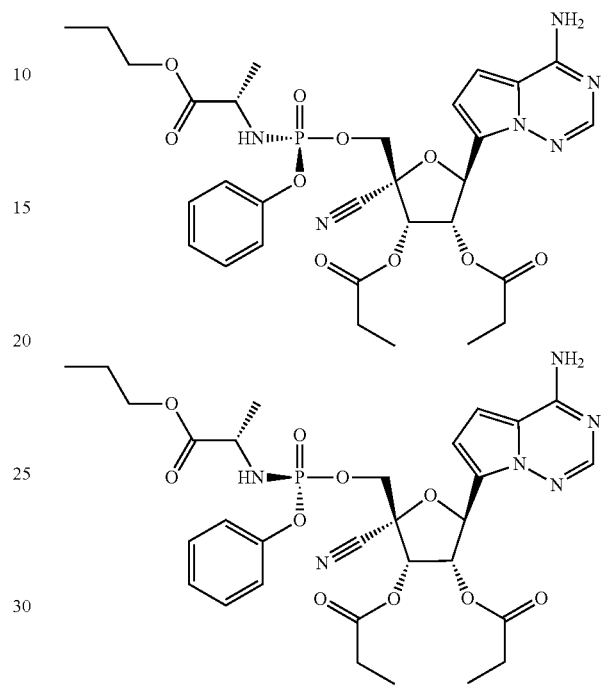

Example 188

First Eluting Diastereomer: $^{1}$H NMR (400 MHz, Methanol-d$_4$) δ 7.81 (s, 1H), 7.35-7.26 (m, 2H), 7.20-7.12 (m, 3H), 6.86 (d, J=4.5 Hz, 1H), 6.78 (d, J=4.5 Hz, 1H), 5.97 (d, J=5.9 Hz, 1H), 5.86 (dd, J=5.9, 4.5 Hz, 1H), 5.70 (d, J=4.5 Hz, 1H), 4.52 (dd, J=11.1, 5.8 Hz, 1H), 4.43 (dd, J=11.1, 5.0 Hz, 1H), 4.08-3.94 (m, 2H), 3.84 (dq, J=9.4, 7.2 Hz, 1H), 2.55-2.35 (m, 4H), 1.61 (dtd, J=14.1, 7.4, 6.6 Hz, 2H), 1.24 (dd, J=7.1, 1.3 Hz, 3H), 1.16 (dt, J=13.4, 7.5 Hz, 6H), 0.90 (t, J=7.4 Hz, 3H). $^{31}$P NMR (162 MHz, Methanol-d$_4$) δ 3.05. LCMS: MS m/z=673.41 [M+1], $t_R$=1.03 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=4.82 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Example 189

Second Eluting Diastereomer: $^{1}$H NMR (400 MHz, Methanol-d$_4$) δ 7.83 (s, 1H), 7.36-7.26 (m, 2H), 7.24-7.12 (m, 3H), 6.84 (d, J=4.5 Hz, 1H), 6.75 (d, J=4.6 Hz, 1H), 5.91 (d, J=5.9 Hz, 1H), 5.82 (dd, J=5.9, 4.7 Hz, 1H), 5.69 (d, J=4.7 Hz, 1H), 4.51-4.37 (m, 2H), 4.06-3.83 (m, 3H), 2.54-2.35 (m, 4H), 1.59 (dtd, J=14.0, 7.4, 6.6 Hz, 2H), 1.29 (dd, J=7.1, 1.1 Hz, 3H), 1.15 (dt, J=14.0, 7.6 Hz, 6H), 0.89

(t, J=7.4 Hz, 3H). ³¹P NMR (162 MHz, Methanol-d₄) δ 3.05. LCMS: MS m/z=673.34 [M+1], t_R=1.04 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t_R=4.87 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Example 190. (2R,3S,4S,5S)-5-(4-aminopyrrolo[2,1-f][1,2,4]triazin-7-yl)-2-cyano-2-(((((S)-1-isopropoxy-1-oxopropan-2-yl)amino)(phenoxy)phosphoryl)oxy)methyl)tetrahydrofuran-3,4-diyl bis(2-methylpropanoate)

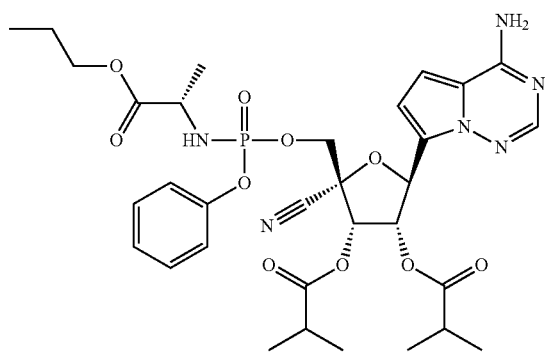 [SMILES: CCCOC(=O)[C@H](C)NP(=O)(OC[C@@]1(C#N)O[C@@H](c2ccc3c(N)ncnn23)[C@H](OC(=O)C(C)C)[C@@H]1OC(=O)C(C)C)Oc1ccccc1]

Isobutyric anhydride (30.3 μL, 0.18 mmol) was added to a solution of Example 45. (51.2 mg, 0.09 mmol) and 4-dimethylaminopyridine (1.8 mg, 0.1 mmol) in tetrahydrofuran (1.8 mL) at RT. After 30 min, the reaction mixture was diluted with ethyl acetate (15 mL) and the resulting mixture was washed with saturated aqueous sodium carbonate solution (10 mL) and brine (10 mL). The organic layer was dried over anhydrous sodium sulfate and concentrated under reduced pressure. The crude residue was purified by silica gel chromatography eluting with 20-100% ethyl acetate in hexanes to afford the product. ¹H NMR (400 MHz, Methanol-d4) δ 7.82 (d, J=9.5 Hz, 1H), 7.30 (tt, J=6.9, 1.9 Hz, 2H), 7.25-7.06 (m, 3H), 6.85 (dd, J=7.3, 4.5 Hz, 1H), 6.76 (dd, J=11.6, 4.6 Hz, 1H), 5.94 (dd, J=23.8, 5.9 Hz, 1H), 5.83 (ddd, J=20.0, 5.9, 4.5 Hz, 1H), 5.68 (t, J=4.4 Hz, 1H), 4.60-4.35 (m, 2H), 4.08-3.75 (m, 3H), 2.75-2.52 (m, 2H), 1.59 (dtd, J=14.0, 7.5, 6.6 Hz, 2H), 1.33-1.14 (m, 15H), 0.89 (td, J=7.4, 2.7 Hz, 3H). ³¹P NMR (162 MHz, Methanol-d4) δ 3.06, 3.04. LCMS: MS m/z=701.47 [M+1], t_R=1.13 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t_R=5.23 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Resolution of the Sp and Rp diastereomers. The product was purified via chiral SFC (Chiralpak AD-H, 5 um, 21×250 mm, Isopropyl alcohol 30%) to afford the diastereomers:

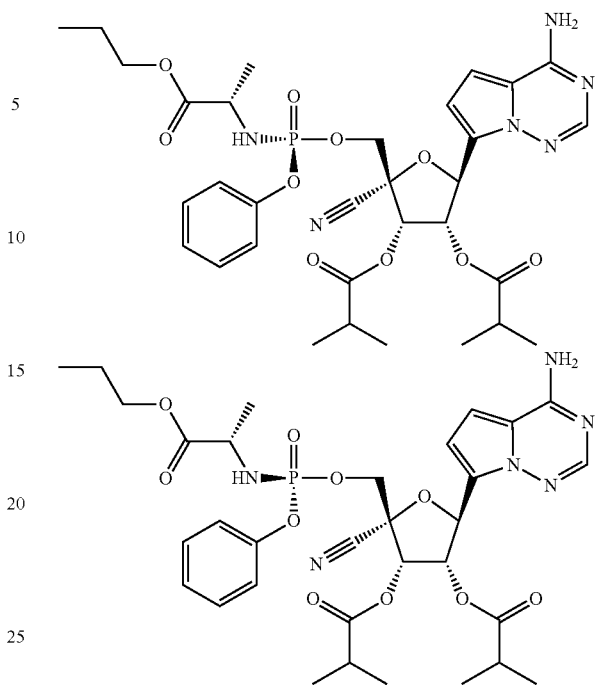

Example 191

First Eluting Diastereomer: ¹H NMR (400 MHz, Methanol-d₄) δ 7.81 (s, 1H), 7.34-7.26 (m, 2H), 7.20-7.11 (m, 3H), 6.86 (d, J=4.6 Hz, 1H), 6.77 (d, J=4.6 Hz, 1H), 5.97 (d, J=5.9 Hz, 1H), 5.85 (dd, J=5.9, 4.4 Hz, 1H), 5.68 (d, J=4.4 Hz, 1H), 4.52 (dd, J=11.1, 5.7 Hz, 1H), 4.42 (dd, J=11.0, 4.9 Hz, 1H), 4.08-3.95 (m, 2H), 3.84 (dq, J=9.4, 7.2 Hz, 1H), 2.65 (dhept, J=14.0, 7.0 Hz, 2H), 1.61 (dtd, J=14.0, 7.4, 6.6 Hz, 2H), 1.26-1.16 (m, 15H), 0.90 (t, J=7.4 Hz, 3H). ³¹P NMR (162 MHz, Methanol-d4) δ 3.07. LCMS: MS m/z=701.48 [M+1], t_R=1.14 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: t_R=5.21 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Example 192

Second Eluting Diastereomer: ¹H NMR (400 MHz, Methanol-d₄) δ 7.84 (s, 1H), 7.35-7.26 (m, 2H), 7.23-7.14 (m, 3H), 6.84 (d, J=4.6 Hz, 1H), 6.74 (d, J=4.5 Hz, 1H), 5.91 (d, J=5.9 Hz, 1H), 5.80 (dd, J=5.9, 4.7 Hz, 1H), 5.67 (d, J=4.7 Hz, 1H), 4.49-4.38 (m, 2H), 4.05-3.84 (m, 3H), 2.64 (dhept, J=17.1, 7.0 Hz, 2H), 1.59 (dtd, J=13.9, 7.4, 6.6 Hz, 2H), 1.29 (dd, J=7.1, 1.1 Hz, 3H), 1.26-1.14 (m, 12H), 0.89 (t, J=7.4 Hz, 3H). ³¹P NMR (162 MHz, Methanol-d₄) δ 3.04. LCMS: MS m/z=701.47 [M+1], t_R=1.13 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=5.24 min; HPLC system: Agilent 1100 series; Column: Gemini 5µ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Example 193

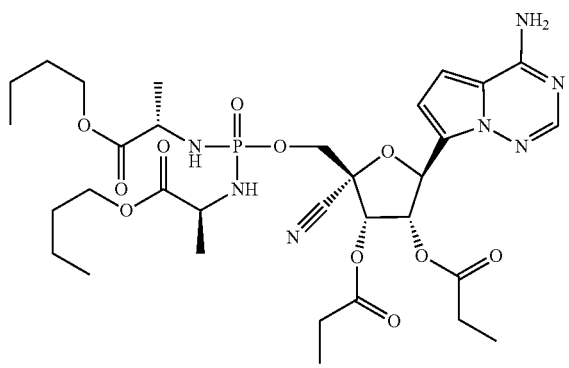 [SMILES: CCCCOC(=O)[C@H](C)NP(=O)(N[C@@H](C)C(=O)OCCCC)OC[C@@]1(C#N)O[C@@H](c2ccc3c(N)ncnn23)[C@H](OC(=O)CC)[C@@H]1OC(=O)CC]

Intermediate 4 (50 mg, 0.15 mmol) and Intermediate 65 (85 mg, 0.18 mmol) were mixed and dissolved in 1.5 mL of anhydrous tetrahydrofuran. Magnesium chloride (43 mg, 0.45 mmol) was added in one portion. DIPEA (65 µL, 0.375 mmol) and the reaction was stirred at 35° C. for 48 h.

Reaction was diluted with ethyl acetate (10 mL) and washed with water (5×10 mL) and then with brine (5 mL). The organic layer was dried over anhydrous sodium sulfate and concentrated under reduced pressure. Residue was dissolved in 5 mL of MeCN and stirred in an ice bath. Concentrate HCl (aq) (250 µL) was added dropwise and then stirred in an ice bath for 2 h. Reaction was diluted with ethyl acetate and washed with saturated aqueous sodium bicarbonate solution (10 mL) and then with brine (5 mL). Organic extract was dried over anhydrous sodium sulfate and concentrated under reduced pressure. The crude residue was purified via SiO$_2$ column chromatography (4 g SiO$_2$ Combiflash HP Gold Column, 0-10% methanol/dichloromethane). Fractions containing the desired product were combined and concentrated under reduced pressure.

Residue was dissolved in anhydrous tetrahydrofuran (5 mL). Propionic anhydride (26 µL, 0.2 mmol) was added. DMAP (1.8 mg, 0.014 mmol) was added and stirred for 30 min. Reaction was diluted with ethyl acetate (15 mL) and washed with saturated aqueous sodium bicarbonate solution (2×10 mL) and followed with brine (5 mL). Organic extract was dried over anhydrous sodium sulfate and concentrated under reduced pressure. The crude residue was purified via SiO$_2$ column chromatography (4 g SiO$_2$ Combiflash HP Gold Column, 0-100% B/hexanes (B=3% MeOH in ethyl acetate)). Fractions containing the desired product were combined and concentrated under reduced pressure. Residue was dissolved in MeCN and water and freeze-dried to give the product. $^1$H NMR (400 MHz, methanol-d$_4$) δ 7.86 (s, 1H), 6.86 (d, J=4.5 Hz, 1H), 6.82 (d, J=4.6 Hz, 1H), 5.90 (d, J=6.0 Hz, 1H), 5.84 (dd, J=6.0, 4.7 Hz, 1H), 5.69 (d, J=4.7 Hz, 1H), 4.41-4.23 (m, 2H), 4.08-3.95 (m, 3H), 3.92-3.80 (m, 2H), 2.58-2.34 (m, 4H), 1.66-1.51 (m, 4H), 1.36 (m, 4H), 1.29 (m, 6H), 1.16 (m, 6H), 0.91 (m, 6H). $^{31}$P NMR (162 MHz, methanol-d4) δ 13.47. LCMS: MS m/z=738.5 [M+1], 736.5 [M−1], $t_R$=1.43 min; LC system: Thermo Dionex ultimate 3000 UHPLC; Column: Phenomenex Kinetex 2.6µ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=3.41 min; HPLC system: Agilent 1100 series; Column: Phenomenex Gemini 5µ C18 110A, 50×4.6 mm; Solvent: A: Water with 0.1% TFA, B: Acetonitrile with 0.1% TFA; Gradient: 2-98% B in 5 min at 2 mL/min. HPLC: $t_R$=5.862 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 194. (2R,3S,4S,5S)-5-(4-Aminopyrrolo[2,1-f][1,2,4]triazin-7-yl)-2-(((bis(((S)-1-ethoxy-1-oxopropan-2-yl)amino)phosphoryl)oxy)methyl)-2-cyanotetrahydrofuran-3,4-diyl dipentanoate

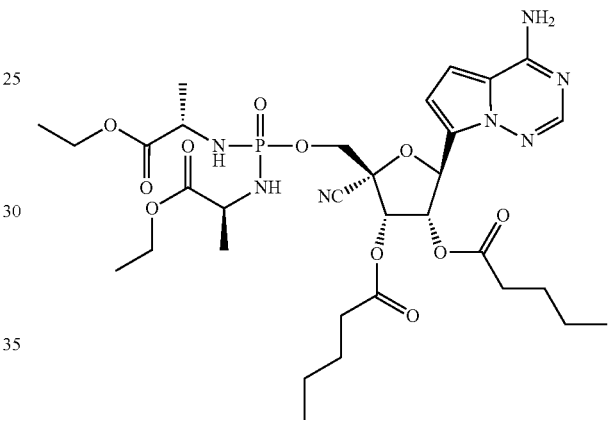

To a mixture of Example 35 (64 mg, 0.112 mmol), valeric acid (0.05 mL, 0.455 mmol), and N,N-diisopropylcarbodiimide (0.040 mL, 0.255 mmol) in THF (4 mL) was added DMAP (14 mg, 0.115 mmol). The resulting mixture was stirred at room temperature for 1 h and additional N,N-diisopropylcarbodiimide (0.04 mL, 0.255 mmol) was added. After 2 h stirring, additional valeric acid (0.05 mL, 0.455 mmol) was added. Then the mixture was stirred for 30 min, quenched by adding methanol (1 mL), and purified by preparative HPLC (Phenomenex Gemini-NX 10µ C18 110° A 250×30 mm column, 0%-100% acetonitrile/water gradient in 25 min run) to afford the product. $^1$H NMR (400 MHz, Acetonitrile-d3) δ 7.91 (s, 1H), 6.81 (d, J=4.5 Hz, 1H), 6.78 (d, J=4.6 Hz, 1H), 6.55 (s, 2H), 5.86-5.80 (m, 2H), 5.67 (dd, J=2.8, 1.8 Hz, 1H), 4.33 (dd, J=11.3, 7.0 Hz, 1H), 4.22 (dd, J=11.3, 5.5 Hz, 1H), 4.18-3.98 (m, 4H), 3.95-3.73 (m, 4H), 2.46 (td, J=7.4, 4.7 Hz, 2H), 2.36 (t, J=7.4 Hz, 2H), 1.70-1.50 (m, 4H), 1.36 (m, 4H), 1.27-1.17 (m, 12H), 0.94 (t, J=7.4 Hz, 3H), 0.89 (t, J=7.4 Hz, 3H). $^{31}$P NMR (162 MHz, Acetonitrile-d3) δ 12.18. LCMS: MS m/z=738.49 [M+1]; $t_R$=1.13 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=5.86 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 195. (2R,3S,4S,5S)-5-(4-aminopyrrolo[2,1-f][1,2,4]triazin-7-yl)-2-cyano-2-((((((S)-1-cyclobutoxy-1-oxopropan-2-yl)amino)(phenoxy)phosphoryl)oxy)methyl) tetrahydrofuran-3,4-diyl dipropionate

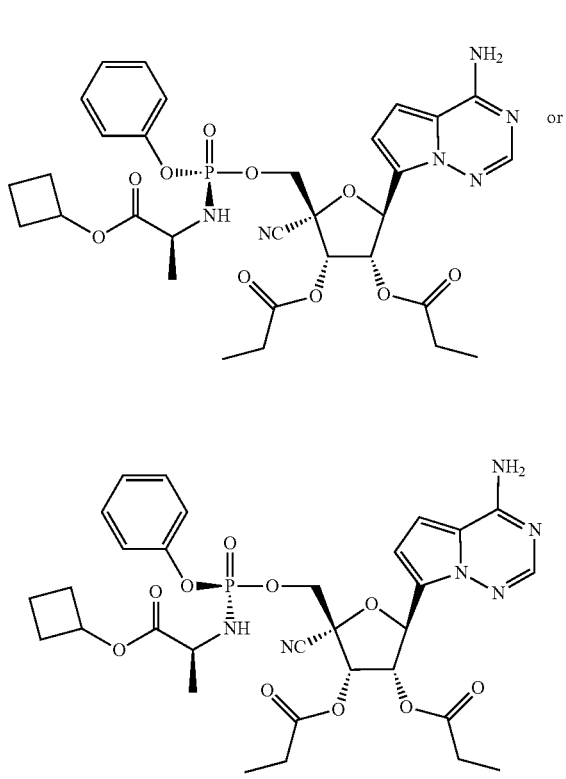

Dissolved Example 50. (50 mg, 0.087 mmol) in 3 mL THF, to the solution were added propionic acid (16 mg, 0.218 mmol) and DIC (33 mg, 0.262 mmol). The reaction mixture was stirred for 10 mins at RT, then DMAP (21 mg, 0.175 mmol) was added. The resulting mixture was stirred at RT for 1 h and then solvent was evaporated. The residue was purified with Prep HPLC to afford the product. $^1$H NMR (400 MHz, Methanol-d4) δ 7.83 (s, 1H), 7.35-7.25 (m, 2H), 7.24-7.10 (m, 3H), 6.84 (d, J=4.6 Hz, 1H), 6.74 (d, J=4.5 Hz, 1H), 5.91 (d, J=5.9 Hz, 1H), 5.81 (dd, J=5.9, 4.7 Hz, 1H), 5.68 (d, J=4.7 Hz, 1H), 4.81 (ddd, J=7.9, 7.1, 1.0 Hz, 1H), 4.50-4.35 (m, 2H), 3.85 (dq, J=10.0, 7.1 Hz, 1H), 2.54-2.35 (m, 4H), 2.31-2.13 (m, 2H), 2.09-1.90 (m, 2H), 1.74 (tddt, J=11.6, 9.0, 2.8, 1.4 Hz, 1H), 1.67-1.49 (m, 1H), 1.26 (dd, J=7.2, 1.1 Hz, 3H), 1.14 (dt, J=13.5, 7.5 Hz, 6H). $^{31}$P NMR (162 MHz, Methanol-d4) δ 3.07. LCMS: MS m/z=685.27 [M+1], $t_R$=1.40 min; LC system: Thermo Accela 1250 UHPLC; MS system: Thermo LCQ Fleet; Column: Kinetex 2.6μ XB-C18 100 A, 50×4.6 msm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=5.59 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 196. (2R,3S,4S,5S)-5-(4-aminopyrrolo[2,1-f][1,2,4]triazin-7-yl)-2-cyano-2-((((R)-(((S)-1-cyclobutoxy-1-oxopropan-2-yl)amino)(phenoxy)phosphoryl)oxy)methyl) tetrahydrofuran-3,4-diyl dipropionate

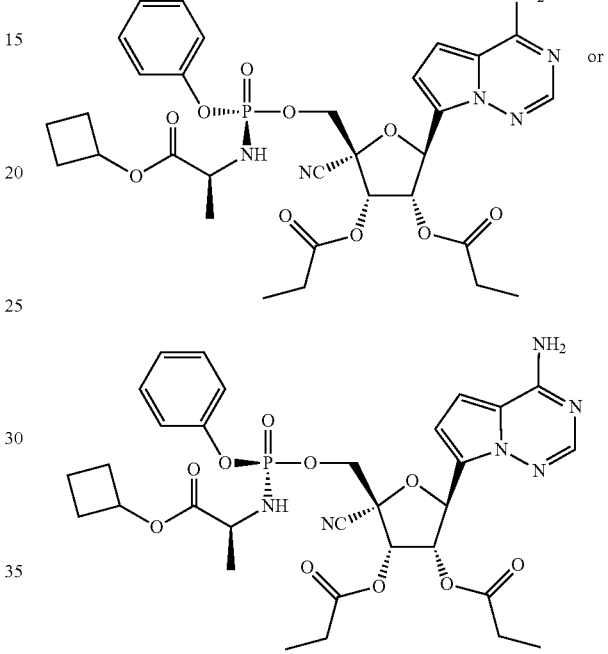

Dissolved Example 51 (40 mg, 0.07 mmol) in 3 mL THF, to the solution were added propionic acid (13 mg, 0.18 mmol) and DIC (26 mg, 0.21 mmol). The reaction mixture was stirred for 10 mins at RT, then DMAP (17 mg, 0.14 mmol) was added. The resulting mixture was stirred at RT for 1 h and then solvent was evaporated. The residue was purified with Prep HPLC to afford the product. $^1$H NMR (400 MHz, Methanol-d4) δ 7.80 (s, 1H), 7.29 (dd, J=8.7, 7.0 Hz, 2H), 7.20-7.12 (m, 3H), 6.85 (d, J=4.6 Hz, 1H), 6.77 (d, J=4.5 Hz, 1H), 5.96 (d, J=5.9 Hz, 1H), 5.85 (dd, J=5.9, 4.5 Hz, 1H), 5.69 (d, J=4.5 Hz, 1H), 4.95-4.86 (m, 1H), 4.52 (dd, J=11.0, 5.8 Hz, 1H), 4.42 (dd, J=11.1, 5.1 Hz, 1H), 3.80 (dq, J=9.2, 7.1 Hz, 1H), 2.48-2.36 (m, 4H), 2.27 (ddt, J=10.8, 7.0, 2.1 Hz, 2H), 2.09-1.92 (m, 2H), 1.76 (dtdt, J=11.6, 8.9, 2.7, 1.4 Hz, 1H), 1.67-1.54 (m, 1H), 1.23 (dd, J=7.2, 1.3 Hz, 3H), 1.15 (dt, J=13.7, 7.6 Hz, 6H). $^{31}$P NMR (162 MHz, Methanol-d4) δ 3.04. LCMS: MS m/z=685.33 [M+1], $t_R$=1.40 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=5.55 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 197. (2R,3S,4S,5S)-5-(4-aminopyrrolo[2,1-f][1,2,4]triazin-7-yl)-2-cyano-2-(((((S)-1-cyclobutoxy-1-oxopropan-2-yl)amino)(phenoxy)phosphoryl)oxy)methyl) tetrahydrofuran-3,4-diyl bis(2-methylpropanoate)

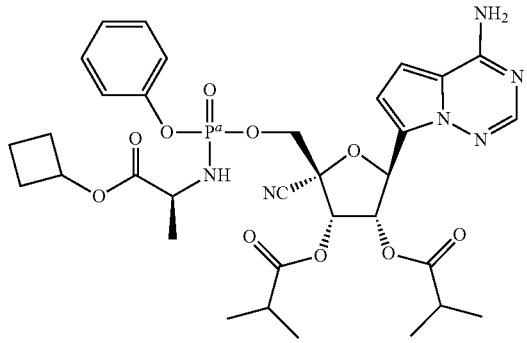

Dissolved Example 50. (50 mg, 0.087 mmol) in 3 mL THF, to the solution were added isobutyric acid (31 mg, 0.35 mmol) and DIC (55 mg, 0.44 mmol). The reaction mixture was stirred for 10 mins at RT, then DMAP (21 mg, 0.18 mmol) was added. The resulting mixture was stirred at RT for 1 h and then solvent was evaporated. The residue was purified with Prep HPLC to afford the product. $^1$H NMR (400 MHz, Methanol-d4) δ 7.83 (s, 1H), 7.35-7.25 (m, 2H), 7.22-7.10 (m, 3H), 6.84 (d, J=4.5 Hz, 1H), 6.74 (d, J=4.5 Hz, 1H), 5.91 (d, J=5.9 Hz, 1H), 5.79 (dd, J=5.9, 4.6 Hz, 1H), 5.66 (d, J=4.6 Hz, 1H), 4.83-4.79 (m, 1H), 4.43 (dd, J=5.8, 4.3 Hz, 2H), 3.85 (dq, J=9.9, 7.1 Hz, 1H), 2.64 (dp, J=16.1, 7.0 Hz, 2H), 2.31-2.14 (m, 2H), 1.99 (dtdd, J=11.1, 9.9, 8.9, 7.8 Hz, 2H), 1.82-1.65 (m, 1H), 1.67-1.49 (m, 1H), 1.30-1.11 (m, 15H). $^{31}$P NMR (162 MHz, Methanol-d4) δ 3.05. LCMS: MS m/z=713.37 [M+1], $t_R$=1.48 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 L/min. HPLC: $t_R$=6.02 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 198. (2R,3S,4S,5S)-5-(4-aminopyrrolo[2,1-f][1,2,4]triazin-7-yl)-2-cyano-2-(((((S)-1-cyclobutoxy-1-oxopropan-2-yl)amino)(phenoxy)phosphoryl)oxy)methyl) tetrahydrofuran-3,4-diyl diacetate

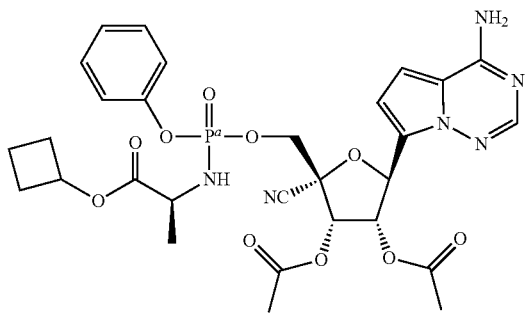

Dissolved Example 50. (50 mg, 0.087 mmol) in 3 mL THF, to the solution were added acetic acid (21 mg, 0.35 mmol) and DIC (55 mg, 0.44 mmol). The reaction mixture was stirred for 10 mins at RT, then DMAP (21 mg, 0.18 mmol) was added. The resulting mixture was stirred at RT for 1 h and then solvent was evaporated. The residue was purified with Prep HPLC to afford the product. $^1$H NMR (400 MHz, Methanol-d4) δ 7.82 (s, 1H), 7.36-7.25 (m, 2H), 7.23-7.11 (m, 3H), 6.84 (d, J=4.6 Hz, 1H), 6.74 (d, J=4.5 Hz, 1H), 5.88 (d, J=5.9 Hz, 1H), 5.83-5.75 (m, 1H), 5.68 (d, J=4.8 Hz, 1H), 4.81 (dd, J=7.5, 6.6 Hz, 1H), 4.51-4.35 (m, 2H), 3.85 (dq, J=10.0, 7.1 Hz, 1H), 2.30-2.17 (m, 2H), 2.15 (d, J=3.8 Hz, 4H), 2.10 (d, J=1.2 Hz, 4H), 2.06-1.91 (m, 2H), 1.80-1.67 (m, 1H), 1.59 (dddd, J=18.2, 11.0, 10.2, 8.1 Hz, 1H), 1.30-1.19 (m, 3H). $^{31}$P NMR (162 MHz, Methanol-d4) δ 3.07. LCMS: MS m/z=657.23 [M+1], $t_R$=1.31 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=5.15 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 199

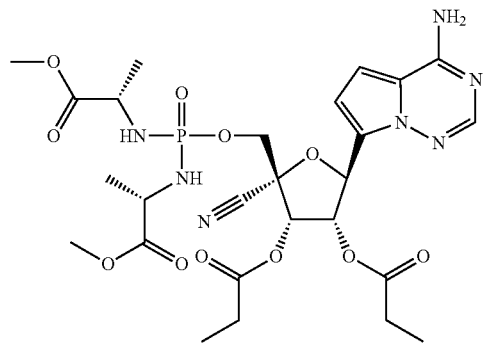 [SMILES: CCC(=O)O[C@H]1[C@H](c2ccc3c(N)ncnn23)O[C@](C#N)(COP(=O)(N[C@@H](C)C(=O)OC)N[C@@H](C)C(=O)OC)[C@H]1OC(=O)CC]

Propionic anhydride (19 μL, 0.19 mmol) was added to a solution Example 38. (40 mg, 0.07 mmol) in 2-methyltetrahydrofuran (1.0 mL) at RT. 4-dimethylaminopyridine (1 mg, 0.07 mmol) was then added. After 30 min, the reaction mixture was subjected to silica gel chromatography eluting with 0-20% methanol in dichloromethane to afford the product. $^1$H NMR (400 MHz, methanol-d4) δ 7.87 (s, 1H), 6.87 (d, J=4.6 Hz, 1H), 6.83 (d, J=4.6 Hz, 1H), 5.92 (d, J=6.0 Hz, 1H), 5.86 (dd, J=6.0, 4.7 Hz, 1H), 5.69 (d, J=4.7 Hz, 1H), 4.35 (dd, J=11.2, 6.7 Hz, 1H), 4.26 (dd, J=11.2, 5.0 Hz, 1H), 3.92-3.76 (m, 2H), 3.67 (s, 3H), 3.65 (s, 3H), 2.58-2.34 (m, 4H), 1.31-1.23 (m, 6H), 1.19 (t, J=7.5 Hz, 3H), 1.13 (t, J=7.6 Hz, 3H). $^{31}$P NMR (162 MHz, methanol-$d_4$) δ 13.49 (s). LCMS: MS m/z=654.28 [M+1], $t_R$=1.22 min; LC system: Thermo Accela 1250 UHPLC; MS system: Thermo LCQ Fleet; Column: Kinetex 2.6µ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: $t_R$=2.70 min; HPLC system: Agilent 1100 series; Column: Gemini 5µ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: $t_R$=4.46 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 200. (2R,3S,4S,5S)-5-(4-aminopyrrolo[2,1-f][1,2,4]triazin-7-yl)-2-cyano-2-((((((S)-1-(oxetan-3-ylmethoxy)-1-oxopropan-2-yl)amino)(phenoxy) phosphoryl)oxy)methyl) tetrahydrofuran-3,4-diyl bis(2-methylpropanoate)

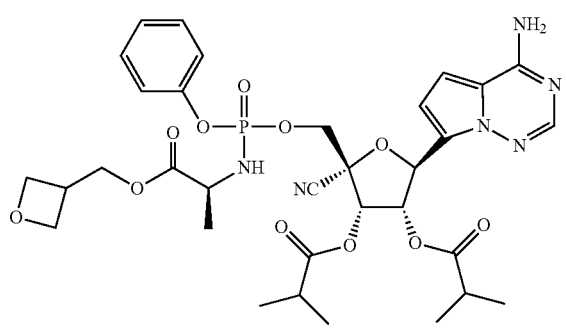 [SMILES: CC(C)C(=O)O[C@H]1[C@H](c2ccc3c(N)ncnn23)O[C@](C#N)(COP(=O)(N[C@@H](C)C(=O)OCC2COC2)Oc2ccccc2)[C@H]1OC(=O)C(C)C]

Dissolved Example 49 (60 mg, 0.1 mmol) in 5 mL THF, to the solution were added isobutyric acid (50 mg, 0.6 mmol) and DIC (80 mg, 0.6 mmol). The reaction mixture was stirred for 10 mins at RT, then DMAP (50 mg, 0.6 mmol) was added. The resulting mixture was stirred at RT for 30 mins and then solvent was evaporated. The residue was purified with Prep HPLC to afford the product. $^1$H NMR (400 MHz, Methanol-d4) δ 7.82 (d, J=10.1 Hz, 1H), 7.36-7.24 (m, 2H), 7.17 (dddd, J=13.7, 7.3, 3.5, 2.3 Hz, 3H), 6.84 (dd, J=7.2, 4.5 Hz, 1H), 6.75 (dd, J=11.2, 4.5 Hz, 1H), 5.93 (dd, J=24.5, 5.8 Hz, 1H), 5.82 (ddd, J=23.2, 5.9, 4.6 Hz, 1H), 5.67 (dd, J=4.5, 3.6 Hz, 1H), 4.72 (ddd, J=8.0, 6.2, 4.2 Hz, 2H), 4.42 (dh, J=7.2, 3.4, 2.4 Hz, 4H), 4.31-4.11 (m, 2H), 3.89 (ddq, J=26.9, 9.2, 7.1 Hz, 1H), 3.23 (dtt, J=12.5, 8.0, 6.2 Hz, 1H), 2.72-2.54 (m, 2H), 1.31-1.10 (m, 15H). $^{31}$P NMR (162 MHz, Methanol-d4) δ 3.01, 2.94. LCMS: MS m/z=729.27 [M+1], $t_R$=1.37 min; LC system: Thermo Accela 1250 UHPLC; MS system: Thermo LCQ Fleet; Column: Kinetex 2.6µ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: $t_R$=5.30 and 5.36 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The product was purified via chiral preparatory HPLC (Chiralpak IA, 150×4.6 mm, Heptane 80% Ethanol 20%) to afford the diastereomers:

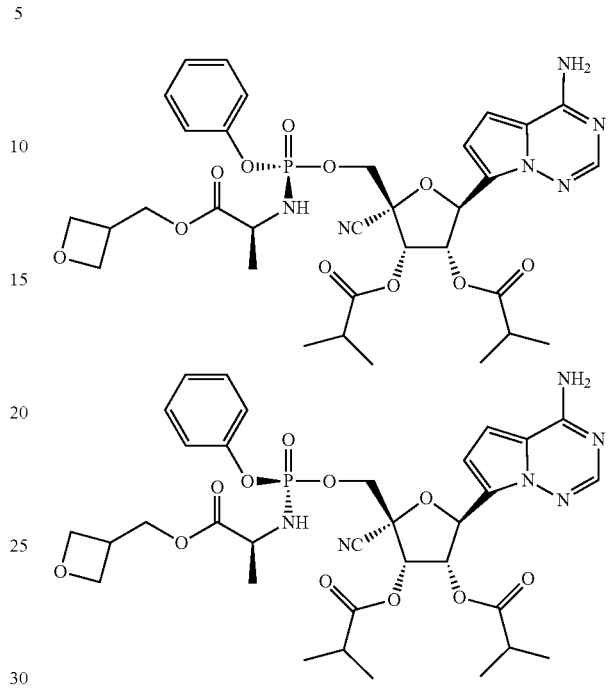

Example 201

First Eluting Diastereomer: $^1$H NMR (400 MHz, Methanol-d4) δ 7.83 (s, 1H), 7.31 (t, J=7.7 Hz, 2H), 7.18 (dd, J=15.0, 7.7 Hz, 3H), 6.83 (d, J=4.5 Hz, 1H), 6.74 (d, J=4.5 Hz, 1H), 5.90 (d, J=5.9 Hz, 1H), 5.79 (t, J=5.3 Hz, 1H), 5.67 (d, J=4.7 Hz, 1H), 4.71 (ddd, J=8.0, 6.2, 1.9 Hz, 2H), 4.51-4.35 (m, 4H), 4.20 (qd, J=11.3, 6.3 Hz, 2H), 3.93 (dq, J=9.6, 7.2 Hz, 1H), 3.22 (tt, J=7.6, 5.9 Hz, 1H), 2.63 (dp, J=17.6, 7.0 Hz, 2H), 1.29 (d, J=7.1 Hz, 3H), 1.26-1.06 (m, 12H). $^{31}$P NMR (162 MHz, Methanol-d4) δ 2.94. LCMS: MS m/z=729.22 [M+1], $t_R$=1.35 min; LC system: Thermo Accela 1250 UHPLC; MS system: Thermo LCQ Fleet; Column: Kinetex 2.6µ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: $t_R$=5.36 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 202

Second Eluting Diastereomer: $^1$H NMR (400 MHz, Methanol-d4) δ 7.81 (s, 1H), 7.30 (dd, J=8.7, 7.0 Hz, 2H), 7.16 (ddd, J=8.1, 2.4, 1.2 Hz, 3H), 6.85 (d, J=4.5 Hz, 1H), 6.77 (d, J=4.5 Hz, 1H), 5.96 (d, J=5.8 Hz, 1H), 5.85 (dd, J=5.9, 4.5 Hz, 1H), 5.68 (d, J=4.4 Hz, 1H), 4.72 (ddd, J=7.9, 6.3, 4.2 Hz, 2H), 4.51 (dd, J=11.0, 5.7 Hz, 1H), 4.46-4.36 (m, 3H), 4.33-4.19 (m, 2H), 3.86 (dq, J=9.2, 7.1 Hz, 1H), 3.27-3.19 (m, 1H), 2.64 (dp, J=15.4, 7.0 Hz, 2H), 1.26-1.10 (m, 15H). $^{31}$P NMR (162 MHz, Methanol-d4) δ 3.01.

LCMS: MS m/z=729.21 [M+1], $t_R$=1.34 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=5.30 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 203. (2R,3S,4S,5S)-5-(4-aminopyrrolo[2,1-f][1,2,4]triazin-7-yl)-2-cyano-2-((((((S)-1-(oxetan-3-ylmethoxy)-1-oxopropan-2-yl)amino)(phenoxy)phosphoryl)oxy)methyl) tetrahydrofuran-3,4-diyl dipropionate

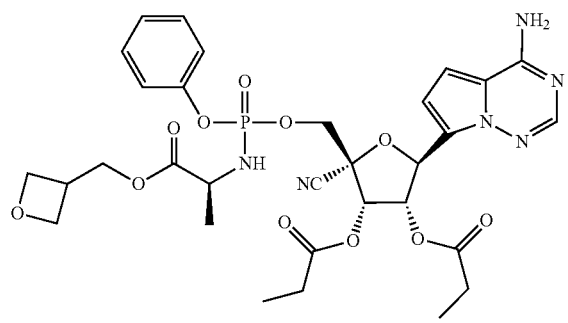 [SMILES: CCC(=O)O[C@H]1[C@H](c2ccc3c(N)ncnn23)O[C@](C#N)(COP(=O)(N[C@@H](C)C(=O)OCC2COC2)Oc2ccccc2)[C@H]1OC(=O)CC]

Dissolved Example 49 (92 mg, 0.16 mmol) in 5 mL THF, to the solution were added propionic acid (46 mg, 0.63 mmol) and DIC (99 mg, 0.78 mmol). The reaction mixture was stirred for 10 mins at RT, then DMAP (95 mg, 0.78 mmol) was added. The resulting mixture was stirred at RT for 1 h and then solvent was evaporated. The residue was purified with Prep HPLC to afford the product. $^1$H NMR (400 MHz, Methanol-d4) δ 7.82 (d, J=9.3 Hz, 1H), 7.37-7.23 (m, 2H), 7.24-7.08 (m, 3H), 6.83 (dd, J=7.2, 4.5 Hz, 1H), 6.75 (dd, J=11.1, 4.5 Hz, 1H), 5.94 (dd, J=25.1, 5.9 Hz, 1H), 5.84 (ddd, J=21.2, 5.9, 4.6 Hz, 1H), 5.69 (t, J=4.3 Hz, 1H), 4.71 (ddd, J=7.9, 6.1, 4.0 Hz, 2H), 4.55-4.35 (m, 4H), 4.31-4.10 (m, 2H), 3.99-3.79 (m, 1H), 3.22 (dddd, J=12.8, 7.9, 6.3, 1.8 Hz, 1H), 2.52-2.32 (m, 4H), 1.34-1.21 (m, 3H), 1.14 (dtd, J=13.8, 7.5, 3.1 Hz, 6H). $^{31}$P NMR (162 MHz, Methanol-d4) δ 2.99, 2.95. LCMS: MS m/z=701.28 [M+1], $t_R$=1.27 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=4.87 and 4.94 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The product was purified via chiral preparatory HPLC (Chiralpak IA, 150×4.6 mm, Heptane 80% Ethanol 20%) to afford the diastereomers:

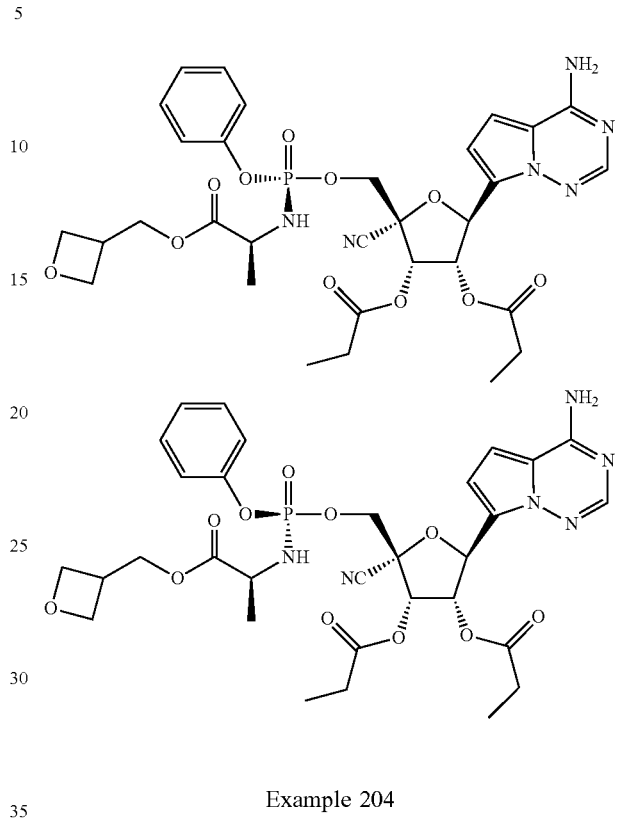

Example 204

First Eluting Diastereomer: $^1$H NMR (400 MHz, Methanol-d4) δ 7.83 (s, 1H), 7.37-7.27 (m, 2H), 7.23-7.11 (m, 3H), 6.84 (d, J=4.5 Hz, 1H), 6.75 (d, J=4.6 Hz, 1H), 5.90 (d, J=5.9 Hz, 1H), 5.81 (dd, J=5.9, 4.8 Hz, 1H), 5.68 (d, J=4.8 Hz, 1H), 4.72 (ddd, J=8.1, 6.3, 1.9 Hz, 2H), 4.48-4.35 (m, 4H), 4.20 (qd, J=11.3, 6.3 Hz, 2H), 3.99-3.86 (m, 1H), 3.22 (tt, J=8.0, 6.1 Hz, 1H), 2.53-2.33 (m, 4H), 1.29 (dd, J=7.1, 1.2 Hz, 3H), 1.15 (dt, J=14.9, 7.5 Hz, 6H). $^{31}$P NMR (162 MHz, Methanol-d4) δ 2.95. LCMS: MS m/z=701.12 [M+1], $t_R$=1.31 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=4.94 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 205

Second Eluting Diastereomer: $^1$H NMR (400 MHz, Methanol-d4) δ 7.81 (s, 1H), 7.34-7.22 (m, 2H), 7.20-7.10 (m, 3H), 6.85 (d, J=4.6 Hz, 1H), 6.78 (d, J=4.5 Hz, 1H), 5.96 (d, J=5.9 Hz, 1H), 5.86 (dd, J=5.9, 4.6 Hz, 1H), 5.69 (d, J=4.6 Hz, 1H), 4.72 (ddd, J=7.9, 6.2, 4.1 Hz, 2H), 4.51 (dd, J=11.0, 5.8 Hz, 1H), 4.42 (tdd, J=6.0, 4.7, 2.0 Hz, 3H), 4.33-4.19 (m, 2H), 3.93-3.79 (m, 1H), 3.29-3.20 (m, 1H), 2.56-2.33 (m, 4H), 1.24 (dd, J=7.1, 1.3 Hz, 3H), 1.15 (dt, J=14.2, 7.6 Hz, 6H). $^{31}$P NMR (162 MHz, Methanol-d4) δ 2.99. LCMS: MS m/z=701.20 [M+1], $t_R$=1.30 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 L/min. HPLC: $t_R$=4.87 min; Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 206. (2R,3S,4S,5S)-5-(4-aminopyrrolo[2,1-f][1,2,4]triazin-7-yl)-2-cyano-2-(((((S)-1-(oxetan-3-yloxy)-1-oxopropan-2-yl)amino)(phenoxy)phosphoryl)oxy)methyl) tetrahydrofuran-3,4-diyl bis(2,2-dimethylpropanoate)

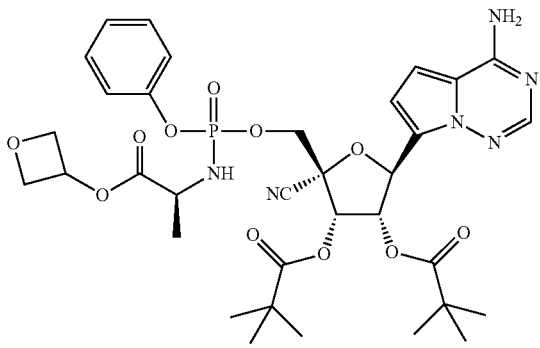 [SMILES: C[C@H](NP(=O)(OC[C@@]1(C#N)O[C@@H](c2ccc3c(N)ncnn23)[C@H](OC(=O)C(C)(C)C)[C@@H]1OC(=O)C(C)(C)C)Oc1ccccc1)C(=O)OC1COC1]

Dissolved Example 44 (67 mg, 0.12 mmol) in 5 mL THF, to the solution were added pivalic acid (96 mg, 0.94 mmol) and DIC (148 mg, 1.16 mmol). The reaction mixture was stirred for 10 mins at RT, then DMAP (142 mg, 1.16 mmol) was added. The resulting mixture was stirred at 75° C. overnight and then solvent was evaporated. The residue was purified with Prep HPLC to afford the product. $^1$H NMR (400 MHz, Methanol-d4) δ 7.82 (d, J=13.5 Hz, 1H), 7.35-7.25 (m, 2H), 7.25-7.11 (m, 3H), 6.85 (t, J=4.4 Hz, 1H), 6.75 (dd, J=6.5, 4.5 Hz, 1H), 5.95 (dd, J=21.5, 5.8 Hz, 1H), 5.79 (ddd, J=19.6, 5.7, 4.2 Hz, 1H), 5.68-5.59 (m, 1H), 5.32 (dtt, J=16.6, 6.3, 5.1 Hz, 1H), 4.82-4.74 (m, 2H), 4.52 (dddd, J=13.9, 7.8, 3.7, 1.0 Hz, 3H), 4.45-4.34 (m, 1H), 3.91 (ddq, J=32.6, 9.2, 7.1 Hz, 1H), 1.28 (d, J=0.8 Hz, 12H), 1.22 (d, J=4.0 Hz, 9H). $^{31}$P NMR (162 MHz, Methanol-d4) δ 2.93, 2.91. LCMS: MS m/z=743.22 [M+1], $t_R$=1.43 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=5.71 and 5.78 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 207. (2R,3S,4S,5S)-2-((((((S)-1-(((1r,4S)-4-aminocyclohexyl)methoxy)-1-oxopropan-2-yl)amino)(phenoxy)phosphoryl)oxy)methyl)-5-(4-aminopyrrolo[2,1-f][1,2,4]triazin-7-yl)-2-cyanotetrahydrofuran-3,4-diyl bis(2-methylpropanoate)

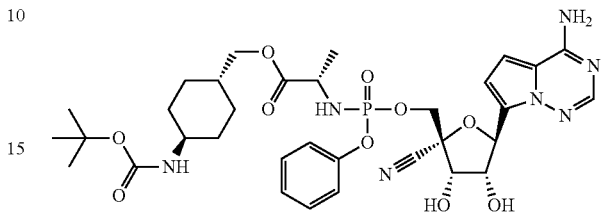

((1r,4S)-4-((tert-butoxycarbonyl)amino)cyclohexyl)methyl (((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate. N,N-Diisopropylethylamine (0.19 mL, 1.06 mmol) and magnesium chloride (61.5 mg, 0.63 mmol) were added to a mixture of Intermediate 4 (68.8 mg, 0.21 mmol) and Intermediate 64 (130.9 mg, 0.21 mmol) in tetrahydrofuran (3.0 mL) at RT. The mixture was heated to 55° C. After 90 min, the reaction mixture was allowed to cool to RT, diluted with ethyl acetate (25 mL) and the resulting mixture was washed with water (2×20 mL). The organic layer was dried over anhydrous sodium sulfate and concentrated under reduced pressure. Concentrated aqueous hydrochloric acid solution (0.20 mL) was added dropwise to the crude residue in acetonitrile (5 mL) at 0° C. The mixture was warmed to RT. After 1 h, the mixture was set in a freezer. After 16 h, the reaction was basified with saturated sodium bicarbonate solution (6 mL) and warmed to RT. To the mixture was added di-tert-butyl dicarbonate (49.8 mg, 0.21 mmol). After 6 h, more di-tert-butyl dicarbonate (31.4 mg, 0.14 mmol) was added. After 16 h, the mixture was diluted with ethyl acetate (25 mL) and the phases were separated. The organic layer was washed with saturated sodium bicarbonate solution (20 mL) and brine (20 mL). The organic layer was dried over anhydrous sodium sulfate and concentrated under reduced pressure. The crude residue was purified by silica gel chromatography eluting with 20-100% ethyl acetate in hexanes followed by 0-10% methanol in ethyl acetate to afford the product. $^1$H NMR (400 MHz, Methanol-$d_4$) δ 7.80 (d, J=8.8 Hz, 1H), 7.37-7.26 (m, 2H), 7.26-7.12 (m, 3H), 6.86 (dd, J=4.5, 1.4 Hz, 1H), 6.74 (dd, J=4.6, 2.8 Hz, 1H), 5.53-5.45 (m, 1H), 4.66-4.58 (m, 1H), 4.55-4.38 (m, 2H), 4.38-4.30 (m, 1H), 3.96-3.70 (m, 3H), 3.23 (s, 1H), 1.93-1.84 (m, 2H), 1.78-1.67 (m, 2H), 1.43 (d, J=1.3 Hz, 9H), 1.28-1.25 (m, 3H), 1.18-0.95 (m, 4H). $^{31}$P NMR (162 MHz, Methanol-$d_4$) δ 3.22. LCMS: MS m/z=730.18 [M+1], $t_R$=0.92 min, 0.93 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=4.47 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

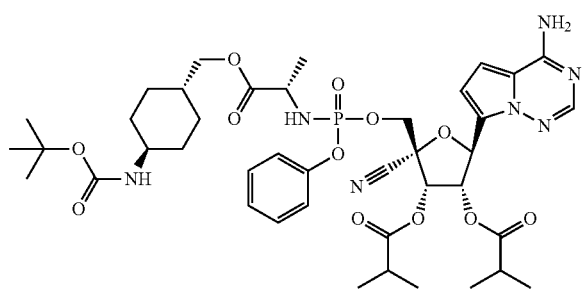 [SMILES: CC(C)C(=O)O[C@H]1[C@H](c2ccc3c(N)ncnn23)O[C@](C#N)(COP(=O)(N[C@@H](C)C(=O)OC[C@H]2CC[C@H](NC(=O)OC(C)(C)C)CC2)Oc2ccccc2)[C@H]1OC(=O)C(C)C]

(2R,3S,4S,5S)-5-(4-aminopyrrolo[2,1-f][1,2,4]triazin-7-yl)-2-((((((S)-1-(((1r,4S)-4-((tert-butoxycarbonyl)amino)cyclohexyl)methoxy)-1-oxopropan-2-yl)amino)(phenoxy)phosphoryl)oxy)methyl)-2-cyanotetrahydrofuran-3,4-diyl bis(2-methylpropanoate). Isobutyric anhydride (46.2 μL, 0.28 mmol) was added to a solution of ((1r,4S)-4-((tert-butoxycarbonyl)amino)cyclohexyl)methyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate (101.7 mg, 0.14 mmol) and 4-dimethylaminopyridine (3.3 mg, 0.03 mmol) in 2-methyltetrahydrofuran (3.0 mL) at RT. After 10 min, the reaction mixture was diluted with ethyl acetate (15 mL) and the resulting mixture was washed with saturated aqueous sodium carbonate solution (10 mL) and brine (10 mL). The organic layer was dried over anhydrous sodium sulfate and concentrated under reduced pressure. The crude residue was purified by silica gel chromatography eluting with 20-100% ethyl acetate in hexanes to afford the product. $^1$H NMR (400 MHz, Methanol-d4) δ 7.83 (d, J=10.3 Hz, 1H), 7.36-7.26 (m, 2H), 7.23-7.13 (m, 3H), 6.86 (dd, J=5.9, 4.5 Hz, 1H), 6.77 (dd, J=12.0, 4.6 Hz, 1H), 5.94 (dd, J=27.9, 5.9 Hz, 1H), 5.82 (ddd, J=24.4, 5.9, 4.6 Hz, 1H), 5.68 (t, J=4.6 Hz, 1H), 4.55-4.37 (m, 2H), 3.98-3.72 (m, 3H), 3.23 (s, 1H), 2.74-2.51 (m, 2H), 1.89 (d, J=13.7 Hz, 1H), 1.73 (d, J=12.5 Hz, 3H), 1.62-1.48 (m, 2H), 1.43 (d, J=1.1 Hz, 9H), 1.30-1.15 (m, 15H), 1.13-0.94 (m, 5H). $^{31}$P NMR (162 MHz, Methanol-d$_4$) δ 3.00. LCMS: MS m/z=870.36 [M+1], t$_R$=1.24 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: t$_R$=5.66 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

(2R,3S,4S,5S)-2-((((((S)-1-(((1r,4S)-4-aminocyclohexyl)methoxy)-1-oxopropan-2-yl)amino)(phenoxy)phosphoryl)oxy)methyl)-5-(4-aminopyrrolo[2,1-f][1,2,4]triazin-7-yl)-2-cyanotetrahydrofuran-3,4-diyl bis(2-methylpropanoate). Trifluoroacetic acid (0.5 mL) was added to a solution of (2R,3S,4S,5S)-5-(4-aminopyrrolo[2,1-f][1,2,4]triazin-7-yl)-2-((((((S)-1-(((1r,4S)-4-((tert-butoxycarbonyl)amino)cyclohexyl)methoxy)-1-oxopropan-2-yl)amino)(phenoxy)phosphoryl)oxy)methyl)-2-cyanotetrahydrofuran-3,4-diyl bis(2-methylpropanoate) (92.4 mg, 0.11 mmol) in dichloromethane (5.0 mL) at 0° C. After 4.5 hrs, the reaction mixture was diluted with acetonitrile (15 mL) and concentrated under reduced pressure. The material was co-evaporated with 2,4-dioxane (2×10 mL) and acetonitrile (10 mL) to afford the product as a TFA salt. $^1$H NMR (400 MHz, Methanol-d$_4$) δ 7.92 (d, J=9.4 Hz, 1H), 7.38-7.27 (m, 2H), 7.26-7.14 (m, 3H), 7.08 (s, 1H), 6.92-6.81 (m, 1H), 5.93-5.73 (m, 2H), 5.70 (d, J=4.9 Hz, 1H), 4.58-4.38 (m, 2H), 4.01-3.83 (m, 3H), 3.07-2.94 (m, 1H), 2.77-2.57 (m, 2H), 2.03 (d, J=12.4 Hz, 2H), 1.86 (d, J=13.1 Hz, 2H), 1.63 (s, 1H), 1.46-1.27 (m, 5H), 1.27-1.15 (m, 12H), 1.12 (d, J=13.3 Hz, 2H). $^{19}$F NMR (376 MHz, Methanol-d$_4$) δ −77.65. $^{31}$P NMR (162 MHz, Methanol-d$_4$) δ 3.08. LCMS: MS m/z=770.27 [M+1], t$_R$=0.91 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: t$_R$=4.11 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Resolution of the Sp and Rp diastereomers. The product was purified via chiral SFC (Chiralpak IA, 5 um, 4.6×150 mm, Methanol 30%) to afford the diastereomers:

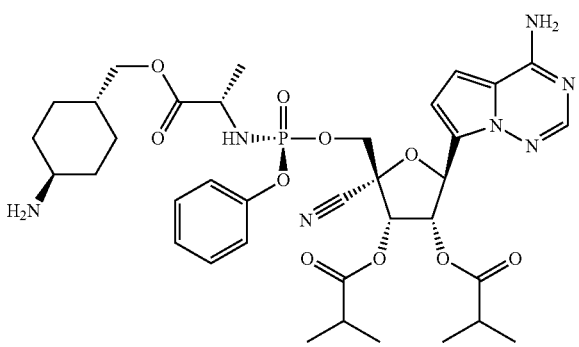

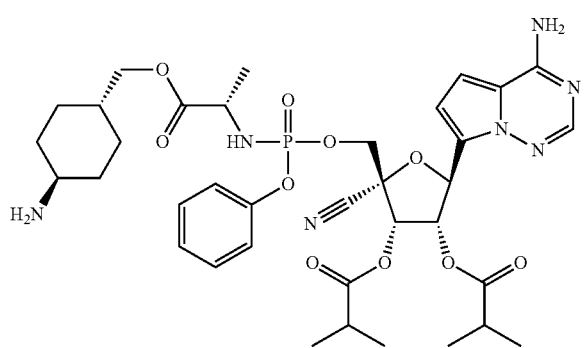 [SMILES: CC(C)C(=O)O[C@H]1[C@H](c2ccc3c(N)ncnn23)O[C@](C#N)(COP(=O)(N[C@@H](C)C(=O)OC[C@H]2CC[C@H](N)CC2)Oc2ccccc2)[C@H]1OC(=O)C(C)C]

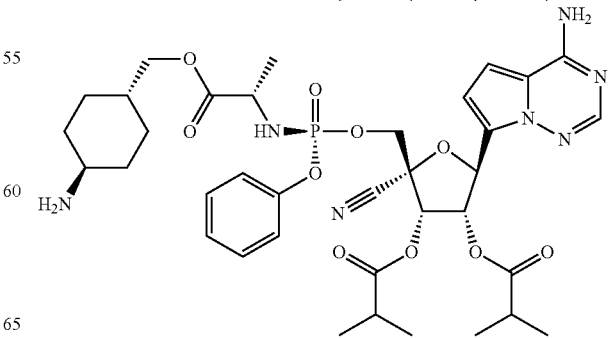

Example 208

First Eluting Diastereomer: $^1$H NMR (400 MHz, Methanol-$d_4$) δ 7.88 (s, 1H), 7.35-7.26 (m, 2H), 7.20-7.14 (m, 3H), 7.00 (d, J=4.6 Hz, 1H), 6.84 (d, J=4.6 Hz, 1H), 5.93 (d, J=5.9 Hz, 1H), 5.84 (dd, J=6.0, 4.5 Hz, 1H), 5.69 (d, J=4.5 Hz, 1H), 4.53 (dd, J=11.1, 5.5 Hz, 1H), 4.44 (dd, J=11.0, 5.1 Hz, 1H), 3.99-3.84 (m, 3H), 3.07-2.93 (m, 1H), 2.73-2.58 (m, 2H), 2.01 (d, J=12.7 Hz, 2H), 1.85 (d, J=13.4 Hz, 2H), 1.63 (s, 1H), 1.34 (d, J=12.3 Hz, 2H), 1.28 (dd, J=7.2, 1.2 Hz, 3H), 1.26-1.16 (m, 12H), 1.12 (d, J=11.8 Hz, 2H). $^{19}$F NMR (376 MHz, Methanol-d4) δ −77.59. $^{31}$P NMR (162 MHz, Methanol-d4) δ 3.05. LCMS: MS m/z=770.29 [M+1], $t_R$=1.13 min; LC system: Thermo Dionex UltiMate 3000 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.02 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Example 209

Second Eluting Diastereomer: $^1$H NMR (400 MHz, Methanol-$d_4$) δ 7.97 (s, 1H), 7.36-7.29 (m, 2H), 7.24-7.18 (m, 3H), 7.14 (s, 1H), 6.87 (d, J=4.7 Hz, 1H), 5.85 (d, J=5.7 Hz, 1H), 5.79-5.74 (m, 1H), 5.71 (d, J=4.9 Hz, 1H), 4.51-4.40 (m, 2H), 4.00-3.85 (m, 3H), 3.06-2.94 (m, 1H), 2.65 (dp, J=19.3, 7.0 Hz, 2H), 2.03 (d, J=12.4 Hz, 2H), 1.86 (d, J=13.3 Hz, 2H), 1.64 (s, 1H), 1.41-1.30 (m, 5H), 1.26-1.15 (m, 12H), 1.13 (d, J=13.7 Hz, 2H). $^{19}$F NMR (376 MHz, Methanol-$d_4$) δ −77.67. $^{31}$P NMR (162 MHz, Methanol-$d_4$) δ 3.09. LCMS: MS m/z=770.35 [M+1], $t_R$=1.14 min; LC system: Thermo Dionex UltiMate 3000 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.08 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Example 210. (2R,3S,4S,5S)-5-(4-aminopyrrolo[2,1-f][1,2,4]triazin-7-yl)-2-cyano-2-((((((S)-1-isopropoxy-1-oxopropan-2-yl)amino)(2-(methylsulfonyl)ethoxy) phosphoryl)oxy) methyl) tetrahydrofuran-3,4-diyl bis(2-methylpropanoate)

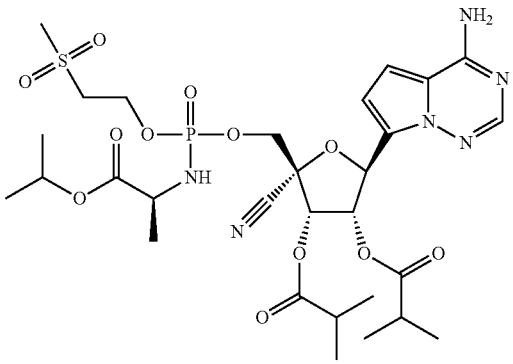 [SMILES: CC(C)OC(=O)[C@H](C)NP(=O)(OCCS(C)(=O)=O)OC[C@@]1(C#N)O[C@@H](c2ccc3c(N)ncnn23)[C@H](OC(=O)C(C)C)[C@@H]1OC(=O)C(C)C]

Isobutyric acid (4 μL, 0.0446 mmol) and N,N'-diisopropylcarbodiimide (6.6 μL, 0.0426 mmol) were mixed and dissolved in 1 mL of anhydrous tetrahydrofuran and stirred for 30 min. Example 42 (5 mg, 0.0085 mmol) was added. DMAP (1 mg, 0.0085 mmol) was added and stirred for 4 h.

Methanol (0.2 mL) was added and stirred for 20 min. Crude residue was purified with prep HPLC under neutral condition (5-100% MeCN/water). Fractions containing the desired product were combined and concentrated under reduced pressure. Residue was dissolved in MeCN and water and freeze-dried to give the product. $^1$H NMR (400 MHz, methanol-$d_4$) δ 7.87 (m, 1H), 6.87 (m, 1H), 6.82 (m, 1H), 5.92 (m, 1H), 5.84 (m, 1H), 5.68 (m, 1H), 5.01-4.85 (m, 1H), 4.50-4.30 (m, 4H), 3.85-3.71 (m, 1H), 3.52-3.38 (m, 2H), 2.97 (m, 3H), 2.78-2.53 (m, 2H), 1.35-1.12 (m, 21H). $^{31}$P NMR (162 MHz, methanol-$d_4$) δ 7.64, 7.78. LCMS: MS m/z=731.3 [M+1], $t_R$=1.60 min; LC system: Thermo Dionex ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=3.05 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min. HPLC: $t_R$=5.139, 5.199 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 211. (2R,3S,4S,5S)-5-(4-Aminopyrrolo[2,1-f][1,2,4]triazin-7-yl)-2-(((bis(((S)-1-ethoxy-1-oxopropan-2-yl)amino)phosphoryl)oxy)methyl)-2-cyanotetrahydrofuran-3,4-diyl dipentanoate

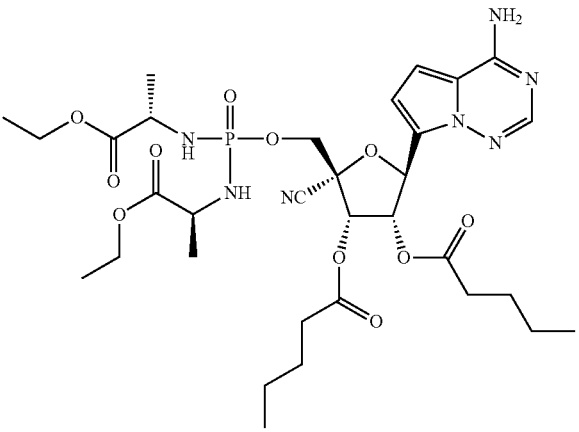 [SMILES: CCCCC(=O)O[C@H]1[C@H](c2ccc3c(N)ncnn23)O[C@](C#N)(COP(=O)(N[C@@H](C)C(=O)OCC)N[C@@H](C)C(=O)OCC)[C@H]1OC(=O)CCCC]

To a mixture of Example 35 (64 mg, 0.112 mmol), valeric acid (0.05 mL, 0.455 mmol), and N,N-diisopropylcarbodiimide (0.040 mL, 0.255 mmol) in THF (4 mL) was added DMAP (14 mg, 0.115 mmol). The resulting mixture was stirred at room temperature for 1 h and additional N,N-diisopropylcarbodiimide (0.04 mL, 0.255 mmol) added. After 2 h stirring, additional valeric acid (0.05 mL, 0.455 mmol) was added. Then the mixture was stirred for 30 min, quenched by adding methanol (1 mL), and purified by preparative HPLC (Phenomenex Gemini-NX 10μ C18 110° A 250×30 mm column, 0%-100% acetonitrile/water gradient in 25 min run) to afford the product. ¹H NMR (400 MHz, Acetonitrile-d3) δ 7.91 (s, 1H), 6.81 (d, J=4.5 Hz, 1H), 6.78 (d, J=4.6 Hz, 1H), 6.55 (s, 2H), 5.86-5.80 (m, 2H), 5.67 (dd, J=2.8, 1.8 Hz, 1H), 4.33 (dd, J=11.3, 7.0 Hz, 1H), 4.22 (dd, J=11.3, 5.5 Hz, 1H), 4.18-3.98 (m, 4H), 3.95-3.73 (m, 4H), 2.46 (td, J=7.4, 4.7 Hz, 2H), 2.36 (t, J=7.4 Hz, 2H), 1.70-1.50 (m, 4H), 1.36 (m, 4H), 1.27-1.17 (m, 12H), 0.94 (t, J=7.4 Hz, 3H), 0.89 (t, J=7.4 Hz, 3H). ³¹P NMR (162 MHz, Acetonitrile-d3) δ 12.18. LCMS: MS m/z=738.49 [M+1]; $t_R$=1.13 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.86 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 212. (2R,3S,4S,5S)-5-(4-Aminopyrrolo[2,1-f][1,2,4]triazin-7-yl)-2-(((bis(((S)-1-methoxy-1-oxopropan-2-yl)amino)phosphoryl)oxy)methyl)-2-cyanotetrahydrofuran-3,4-diyl dibutyrate

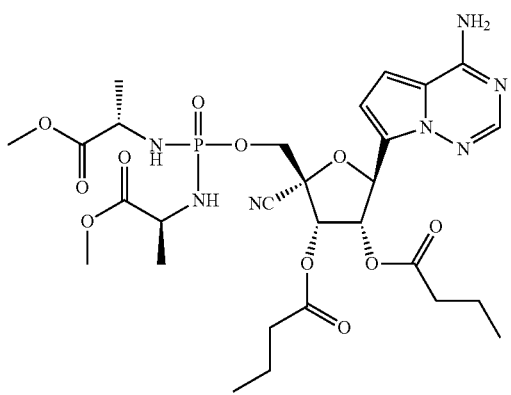 [SMILES: CCCC(=O)O[C@H]1[C@H](c2ccc3c(N)ncnn23)O[C@](C#N)(COP(=O)(N[C@@H](C)C(=O)OC)N[C@@H](C)C(=O)OC)[C@H]1OC(=O)CCC]

To a mixture of Example 38 (46 mg, 0.085 mmol), butyric acid (0.109 mL, 1.189 mmol), and N,N-diisopropylcarbodiimide (0.033 mL, 0.212 mmol) in THF (3 mL) was added DMAP (11 mg, 0.090 mmol). The resulting mixture was stirred at room temperature for 2 h and quenched by adding methanol (1 mL), and purified by preparative HPLC (Phenomenex Gemini-NX 10μ C18 110° A 250×30 mm column, 0%-100% acetonitrile/water gradient in 25 min run) to afford the product. ¹H NMR (400 MHz, Acetonitrile-d3) δ 7.91 (s, 1H), 6.81 (d, J=4.6 Hz, 1H), 6.77 (d, J=4.5 Hz, 1H), 6.50 (s, 2H), 5.87-5.83 (m, 2H), 5.67 (dd, J=3.2, 1.3 Hz, 1H), 4.33 (dd, J=11.3, 7.0 Hz, 1H), 4.22 (dd, J=11.3, 5.6 Hz, 1H), 3.83 (m, 4H), 3.65 (s, 3H), 3.63 (s, 3H), 2.51-2.37 (m, 2H), 2.34 (t, J=7.3 Hz, 2H), 1.65 (dq, J=25.7, 7.4 Hz, 4H), 1.30-1.19 (m, 6H), 0.98 (t, J=7.4 Hz, 3H), 0.92 (t, J=7.4 Hz, 3H). ³¹P NMR (162 MHz, Acetonitrile-d3) δ 12.04. LCMS: MS m/z=682.40 [M+1]; $t_R$=0.94 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.97 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 213. (2R,3S,4S,5S)-5-(4-aminopyrrolo[2,1-f][1,2,4]triazin-7-yl)-2-cyano-2-((((((S)-1-isopropoxy-1-oxopropan-2-yl)amino)(2-(methylthio)ethoxy) phosphoryl)oxy)methyl) tetrahydrofuran-3,4-diyl bis(2-methylpropanoate)

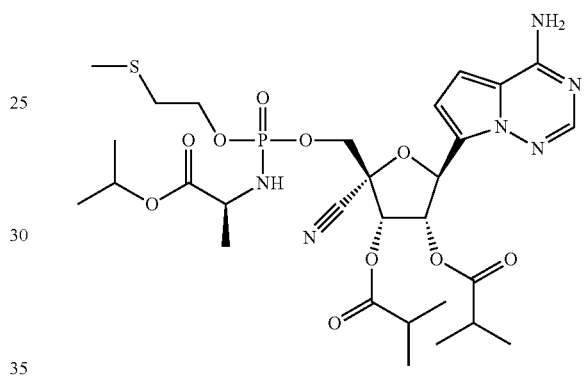

Isobutyric acid (5 μL, 0.0525 mmol) and N,N'-diisopropylcarbodiimide (8 μL, 0.05 mmol) were dissolved in 1 mL of anhydrous tetrahydrofuran and stirred for 30 min. Example 40 (5.6 mg, 0.01 mmol) and DMAP (1.2 mg, 0.01 mmol) were added and stirred for 4 h.

Methanol (0.2 mL) was added and stirred for 20 min. Crude residue was purified with prep HPLC under neutral condition (5-100% MeCN/water). Fractions containing the desired product were combined and concentrated under reduced pressure. Residue was dissolved in MeCN and water and freeze-dried to give the product. ¹H NMR (400 MHz, methanol-d₄) δ 7.86 (m, 1H), 6.87 (m, 1H), 6.81 (m, 1H), 5.93 (m, 1H), 5.84 (m, 1H), 5.67 (m, 1H), 5.02-4.84 (m, 1H), 4.45-4.27 (m, 2H), 4.20-4.04 (m, 2H), 3.84-3.68 (m, 1H), 2.79-2.55 (m, 4H), 2.09 (m, 3H), 1.33-1.12 (m, 21H). ³¹P NMR (162 MHz, methanol-d₄) δ 7.57, 7.67. LCMS: MS m/z=699.3 [M+1], 697.4 [M-1], $t_R$=1.70 min; LC system: Thermo Dionex ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 m/min. HPLC: $t_R$=3.33 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min. HPLC: $t_R$=5.662, 5.687 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 214. (2R,3S,4S,5S)-5-(4-aminopyrrolo[2,1-f][1,2,4]triazin-7-yl)-2-cyano-2-(((((S)-1-isopropoxy-1-oxopropan-2-yl)amino)(2-methoxyethoxy)phosphoryl) oxy)methyl) tetrahydrofuran-3,4-diyl bis(2-methylpropanoate)

Example 215. (2R,3S,4S,5S)-5-(4-aminopyrrolo[2,1-f][1,2,4]triazin-7-yl)-2-cyano-2-(((((S)-1-isopropoxy-1-oxopropan-2-yl)amino)(4-(2-methoxyethoxy)phenoxy)phosphoryl) oxy)methyl) tetrahydrofuran-3,4-diyl dipropionate

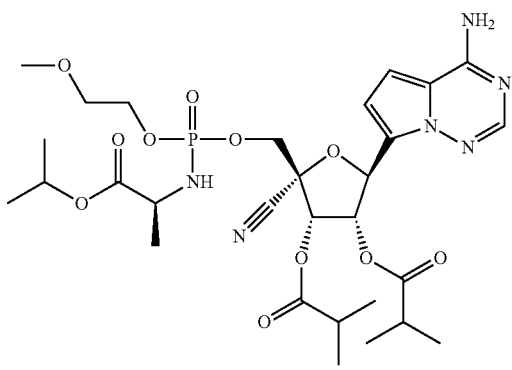 [SMILES: CSCCOP(=O)(N[C@@H](C)C(=O)OC(C)C)OC[C@@]1(C#N)O[C@@H](c2ccc3c(N)ncnn23)[C@H](OC(=O)C(C)C)[C@@H]1OC(=O)C(C)C]

Isobutyric acid (4 µL, 0.045 mmol) and N,N'-diisopropylcarbodiimide (7 µL, 0.045 mmol) were dissolved in 1 mL of anhydrous tetrahydrofuran and stirred for 30 min. Example 41 (5.1 mg, 0.009 mmol) and DMAP (1 mg, 0.009 mmol) were added and stirred for 4 h.

Methanol (0.2 mL) was added and stirred for 20 min. Crude residue was purified with prep HPLC under neutral condition (5-100% MeCN in water). Fractions containing the desired product were combined and concentrated under reduced pressure. Residue was dissolved in MeCN and water and freeze-dried to give the product. $^1$H NMR (400 MHz, methanol-d$_4$) δ 7.86 (m, 1H), 6.90-6.84 (m, 1H), 6.81 (m, 1H), 5.92 (m, 1H), 5.83 (m, 1H), 5.68 (m, 1H), 4.91 (m, 1H), 4.44-4.27 (m, 2H), 4.19-4.06 (m, 2H), 3.77 (m, 1H), 3.56 (m, 2H), 3.35 (m, 3H), 2.65 (m, 2H), 1.32-1.12 (m, 21H). $^{31}$P NMR (162 MHz, methanol-d$_4$) δ 7.79, 7.88. LCMS: MS m/z=683.2 [M+1], 681.3 [M−1], t$_R$=1.65 min; LC system: Thermo Dionex ultimate 3000 UHPLC; Column: Phenomenex Kinetex 2.6µ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 m/min. HPLC: t$_R$=3.18 min; HPLC system: Agilent 1100 series; Column: Phenomenex Gemini 5µ C18 110A, 50×4.6 mm; Solvent: A: Water with 0.1% TFA, B: Acetonitrile with 0.1% TFA; Gradient: 2-98% B in 5 min at 2 mL/min. HPLC: t$_R$=5.362 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Propionic anhydride (16.2 µL, 0.13 mmol) was added to a solution of Example 53 (45.0 mg, 0.07 mmol) and 4-dimethylaminopyridine (1.3 mg, 0.01 mmol) in tetrahydrofuran (1.5 mL) at RT. After 10 min, the reaction mixture was diluted with ethyl acetate (20 mL) and the resulting mixture was washed with saturated aqueous sodium carbonate solution (20 mL) and brine (20 mL). The organic layer was dried over anhydrous sodium sulfate and concentrated under reduced pressure. The crude residue was purified by silica gel chromatography eluting with 20-100% ethyl acetate in hexanes followed by 0-25% methanol in ethyl acetate to afford the product. $^1$H NMR (400 MHz, Methanol-d$_4$) δ 7.83 (d, J=3.6 Hz, 1H), 7.09 (ddd, J=13.9, 9.2, 1.4 Hz, 2H), 6.89-6.81 (m, 3H), 6.75 (dd, J=18.1, 4.5 Hz, 1H), 5.92 (dd, J=13.2, 5.9 Hz, 1H), 5.82 (ddd, J=21.0, 5.8, 4.7 Hz, 1H), 5.69 (dd, J=7.0, 4.7 Hz, 1H), 4.98-4.85 (m, 1H), 4.55-4.37 (m, 2H), 4.07 (ddd, J=6.2, 3.0, 1.5 Hz, 2H), 3.90-3.75 (m, 1H), 3.72 (ddt, J=4.5, 3.1, 1.4 Hz, 2H), 3.41 (d, J=1.0 Hz, 3H), 2.54-2.34 (m, 4H), 1.26 (ddd, J=20.2, 7.2, 1.1 Hz, 3H), 1.22-1.11 (m, 12H). $^{31}$P NMR (162 MHz, Methanol-d4) δ 3.49. LCMS: MS m/z=747.45 [M+1], t$_R$=1.31 min; LC system: Thermo Accela 1250 UHPLC; MS system: Thermo LCQ Fleet; Column: Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: t$_R$=4.66 min; HPLC system: Agilent 1100 series; Column: Gemini 5µ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Example 216. (2R,3S,4S,5S)-5-(4-aminopyrrolo[2,1-f][1,2,4]triazin-7-yl)-2-cyano-2-((((S)-(((S)-1-isopropoxy-1-oxopropan-2-yl)amino)(phenoxy)phosphoryl)oxy)methyl) tetrahydrofuran-3,4-diyl bis(2-morpholinoacetate)

Example 217. (2R,3S,4S,5S)-2-((((4-((S)-2-amino-3-methoxy-3-oxopropyl)phenoxy)(((S)-1-isopropoxy-1-oxopropan-2-yl)amino)phosphoryl)oxy)methyl)-5-(4-aminopyrrolo[2,1-f][1,2,4]triazin-7-yl)-2-cyanotetrahydrofuran-3,4-diyl dipropionate

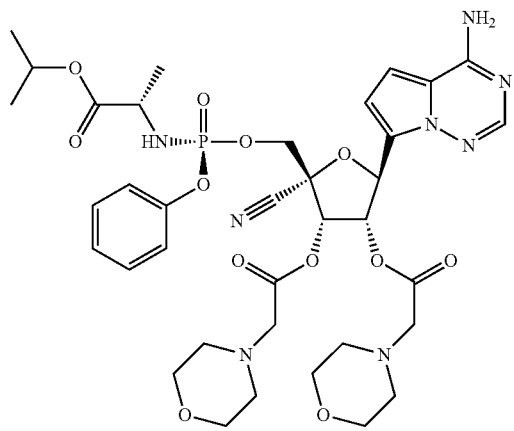 [SMILES: CC(C)OC(=O)[C@H](C)N[P@](=O)(OC[C@@]1(C#N)O[C@@H](c2ccc3c(N)ncnn23)[C@H](OC(=O)CN2CCOCC2)[C@@H]1OC(=O)CN1CCOCC1)Oc1ccccc1]

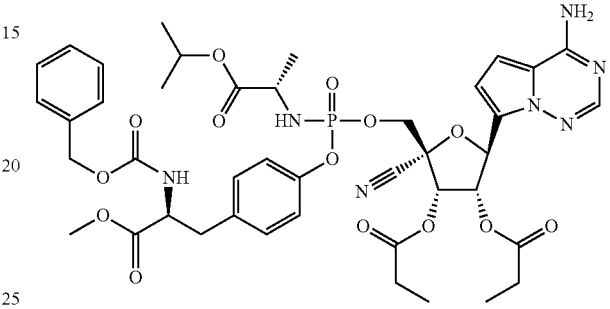

N,N'-Diisopropylcarbodiimide (0.04 mL, 0.29 mmol) was added to a solution of Example 1. (40 mg, 0.071 mmol) and 2-morpholinoacetic acid hydrochloride (107 mg, 0.57 mmol) in tetrahydrofuran (6 mL) at RT. After 5 min, 4-dimethylaminopyridine (15.0 mg, 0.11 mmol) was added. After 1.5 h, methanol (0.2 mL) was added, and the reaction mixture was diluted with ethyl acetate (20 mL) and the resulting mixture was washed with water (15 mL) and brine (15 mL). The organic layer was dried over anhydrous sodium sulfate and concentrated under reduced pressure. The crude residue was subjected to preparatory HPLC (Phenomenex Gemini 10 u C18 110 Å 250×30.0 mm column, 5-75% acetonitrile/water gradient) to afford the product. $^1$H NMR (400 MHz, Methanol-$d_4$) δ 7.83 (s, 1H), 7.31 (dd, J=8.7, 7.2 Hz, 2H), 7.26-7.12 (m, 3H), 6.84 (d, J=4.5 Hz, 1H), 6.75 (d, J=4.6 Hz, 1H), 6.00 (d, J=5.9 Hz, 1H), 5.90 (dd, J=5.9, 4.9 Hz, 1H), 5.72 (d, J=4.9 Hz, 1H), 4.88 (q, J=6.3 Hz, 4H), 4.54-4.40 (m, 2H), 3.91-3.82 (m, 1H), 3.82-3.63 (m, 6H), 3.45-3.32 (m, 4H), 2.69-2.53 (m, 7H), 1.98 (d, J=17.7 Hz, 1H), 1.30-1.17 (m, 5H), 1.17-1.09 (m, 3H). $^{31}$P NMR (162 MHz, Methanol-$d_4$) δ 3.17. LCMS: MS m/z=815.35 [M+H], $t_R$=1.00 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.11 min, HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

(2R,3S,4S,5S)-5-(4-aminopyrrolo[2,1-f][1,2,4]triazin-7-yl)-2-((((4-((S)-2-(((benzyloxy)carbonyl)amino)-3-methoxy-3-oxopropyl)phenoxy)(((S)-1-isopropoxy-1-oxopropan-2-yl)amino)phosphoryl)oxy)methyl)-2-cyanotetrahydrofuran-3,4-diyl dipropionate. Propionic anhydride (20.5 μL, 0.16 mmol) was added to a solution of Example 72 (63.4 mg, 0.08 mmol) and 4-dimethylaminopyridine (1.5 mg, 0.01 mmol) in tetrahydrofuran (1.5 mL) at RT. After 15 min, the reaction mixture was diluted with ethyl acetate (20 mL) and the resulting mixture was washed with saturated aqueous sodium carbonate solution (20 mL) and brine (20 mL). The organic layer was dried over anhydrous sodium sulfate and concentrated under reduced pressure. The crude residue was purified by silica gel chromatography eluting with 20-100% ethyl acetate in hexanes followed by 0-25% methanol in ethyl acetate to afford the product. $^1$H NMR (400 MHz, Methanol-$d_4$) δ 7.81 (d, J=12.8 Hz, 1H), 7.36-7.20 (m, 5H), 7.17-7.04 (m, 4H), 6.83 (t, J=4.6 Hz, 1H), 6.74 (dd, J=4.5, 1.0 Hz, 1H), 5.93 (dd, J=11.1, 5.9 Hz, 1H), 5.83 (ddd, J=10.5, 5.9, 4.6 Hz, 1H), 5.69 (t, J=4.9 Hz, 1H), 5.02 (d, J=5.3 Hz, 2H), 4.97-4.85 (m, 1H), 4.57-4.36 (m, 3H), 3.81 (ddq, J=21.0, 9.1, 7.0 Hz, 1H), 3.69 (d, J=1.2 Hz, 3H), 3.12 (dd, J=13.9, 5.3 Hz, 1H), 2.92 (ddd, J=14.0, 9.1, 2.2 Hz, 1H), 2.54-2.35 (m, 4H), 1.28-1.09 (m, 15H). $^{31}$P NMR (162 MHz, Methanol-$d_4$) δ 3.13 (d, J=4.0 Hz). LCMS: MS m/z=908.59 [M+1], $t_R$=1.44 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=5.21 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Example 218. Single Diastereomer of (2R,3S,4S, 5S)-2-cyano-5-(4-(((E)-(dimethylamino)methylene) amino)pyrrolo[2,1-f][1,2,4]triazin-7-yl)-2-((((((S)-1-oxo-1-((tetrahydro-2H-pyran-4-yl)oxy)propan-2-yl) amino)(phenoxy)phosphoryl)oxy)methyl) tetrahydrofuran-3,4-diyl bis(2-methylpropanoate)

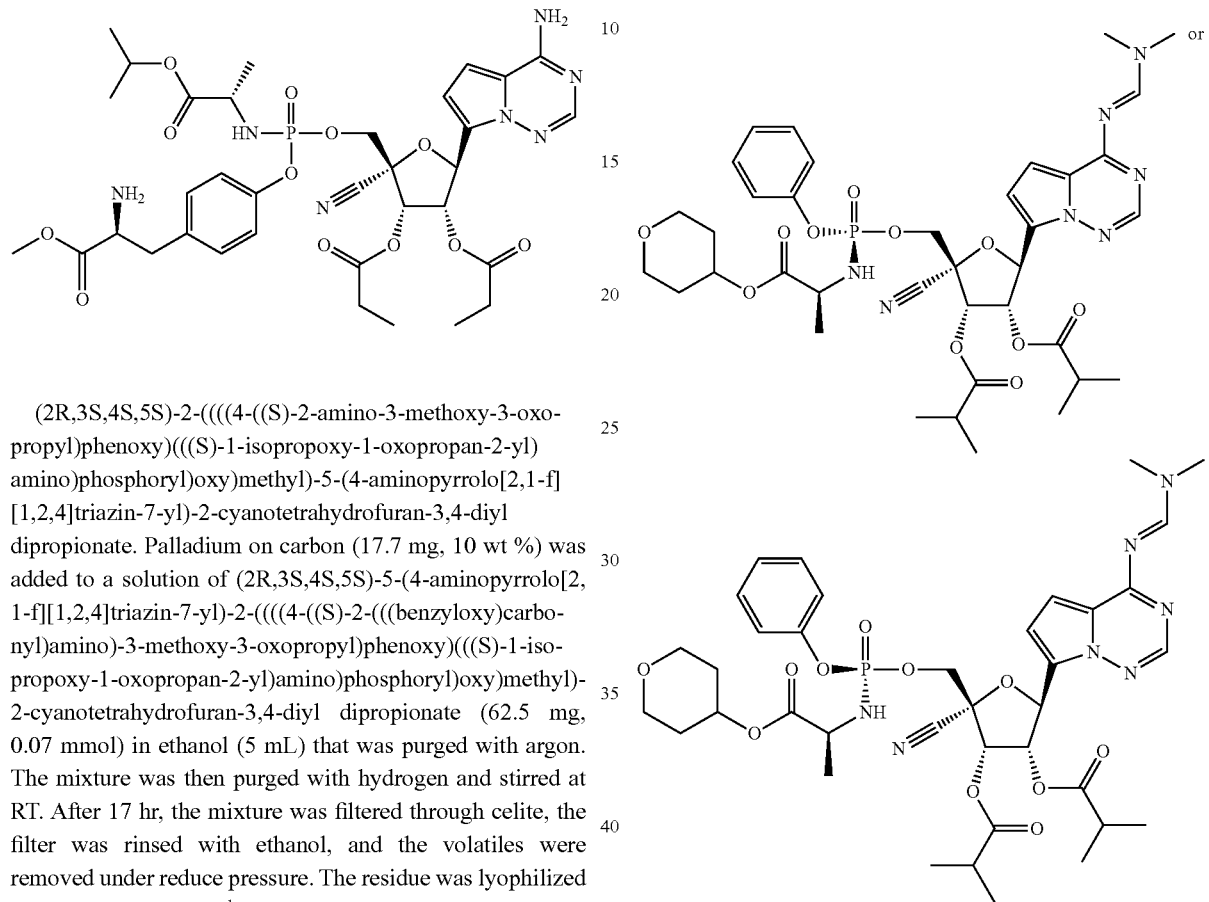

(2R,3S,4S,5S)-2-(((((4-((S)-2-amino-3-methoxy-3-oxo-propyl)phenoxy)(((S)-1-isopropoxy-1-oxopropan-2-yl) amino)phosphoryl)oxy)methyl)-5-(4-aminopyrrolo[2,1-f] [1,2,4]triazin-7-yl)-2-cyanotetrahydrofuran-3,4-diyl dipropionate. Palladium on carbon (17.7 mg, 10 wt %) was added to a solution of (2R,3S,4S,5S)-5-(4-aminopyrrolo[2, 1-f][1,2,4]triazin-7-yl)-2-((((4-((S)-2-(((benzyloxy)carbo-nyl)amino)-3-methoxy-3-oxopropyl)phenoxy)(((S)-1-iso-propoxy-1-oxopropan-2-yl)amino)phosphoryl)oxy)methyl)-2-cyanotetrahydrofuran-3,4-diyl dipropionate (62.5 mg, 0.07 mmol) in ethanol (5 mL) that was purged with argon. The mixture was then purged with hydrogen and stirred at RT. After 17 hr, the mixture was filtered through celite, the filter was rinsed with ethanol, and the volatiles were removed under reduce pressure. The residue was lyophilized to afford the product. $^1$H NMR (400 MHz, Methanol-$d_4$) δ 7.82 (d, J=8.5 Hz, 1H), 7.17-7.07 (m, 4H), 6.85 (dd, J=6.9, 4.6 Hz, 1H), 6.76 (t, J=4.7 Hz, 1H), 5.92 (dd, J=9.5, 5.9 Hz, 1H), 5.88-5.78 (m, 1H), 5.69 (dd, J=8.6, 4.6 Hz, 1H), 4.98-4.85 (m, 1H), 4.55-4.37 (m, 2H), 3.82 (ddd, J=17.7, 9.4, 7.0 Hz, 1H), 3.70 (d, J=6.0 Hz, 1H), 3.67 (d, J=3.2 Hz, 3H), 2.99 (ddd, J=13.5, 6.1, 4.1 Hz, 1H), 2.89 (dd, J=13.6, 7.0 Hz, 1H), 2.54-2.36 (m, 4H), 1.26 (ddd, J=15.1, 7.1, 1.2 Hz, 3H), 1.22-1.11 (m, 12H). $^{31}$P NMR (162 MHz, Methanol-$d_4$) δ 3.14. LCMS: MS m/z=774.20 [M+1], $t_R$=1.08 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=3.70 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

To a solution of Example 148 (50 mg, 0.067 mmol) was added N,N-Dimethylformamide dimethyl acetal (16 mg, 0.14 mmol) dropwise. The resulting mixture was stirred at overnight, the reaction mixture was then purified by Prep HPLC to afford the product. $^1$H NMR (400 MHz, Acetonitrile-d3) δ 8.90 (s, 1H), 8.06 (s, 1H), 7.34 (dd, J=8.4, 7.4 Hz, 2H), 7.20 (dddd, J=8.2, 4.4, 1.8, 0.9 Hz, 3H), 6.87-6.78 (m, 2H), 5.91-5.79 (m, 2H), 5.70 (d, J=4.6 Hz, 1H), 4.83 (tt, J=8.3, 4.1 Hz, 1H), 4.43 (qd, J=11.2, 6.3 Hz, 2H), 4.26 (dd, J=12.0, 9.9 Hz, 1H), 3.98-3.83 (m, 1H), 3.78 (dt, J=11.3, 5.5 Hz, 1H), 3.45 (ddt, J=11.6, 8.5, 3.0 Hz, 2H), 3.25-3.19 (m, 6H), 2.64 (ddq, J=31.2, 13.9, 7.0 Hz, 2H), 2.16 (s, 4H), 1.79 (ddp, J=8.0, 5.9, 4.0 Hz, 1H), 1.60-1.46 (m, 1H), 1.53 (s, 1H), 1.32-1.10 (m, 15H). $^{31}$P NMR (162 MHz, Methanol-d4) δ 3.54. LCMS: MS m/z=798.61 [M+1], $t_R$=1.72 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.77 min; HPLC system: Agilent 1290 II; Column: Phenomenex Kinetex C18, 2.6 u 110A, 100×4.6

Example 219. Single Diastereomer of (2R,3S,4S,5S)-2-cyano-5-(4-(((E)-1-(dimethylamino)ethylidene)amino)pyrrolo[2,1-f][1,2,4]triazin-7-yl)-2-((((((S)-1-oxo-1-((tetrahydro-2H-pyran-4-yl)oxy)propan-2-yl)amino)(phenoxy)phosphoryl)oxy)methyl) tetrahydrofuran-3,4-diyl bis(2-methylpropanoate)

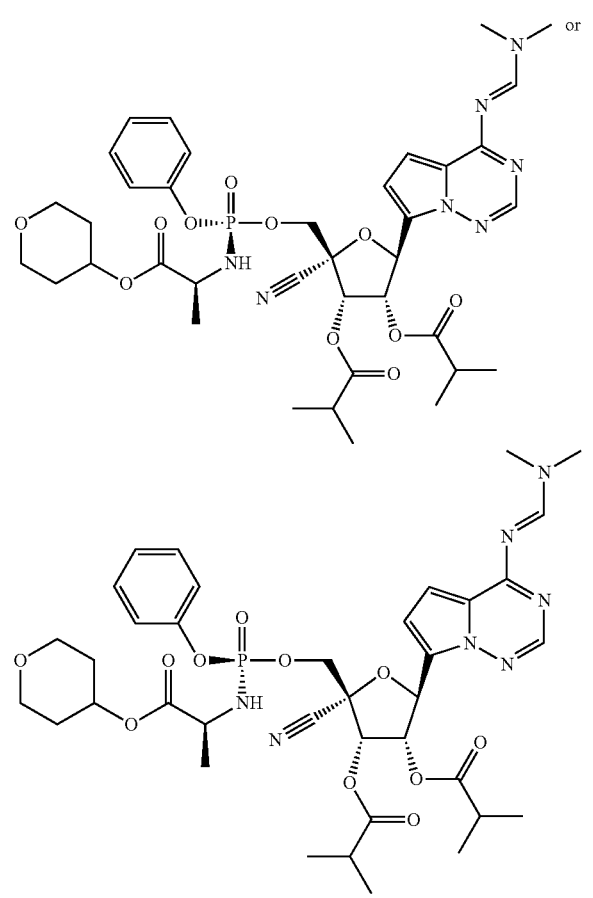

To a solution of Example 147 (65 mg, 0.088 mmol) in DMF was added N,N-Dimethylacetamide dimethyl acetal (26 mg, 0.19 mmol) dropwise. The resulting mixture was stirred overnight, the reaction mixture was then purified by Prep HPLC to afford the product. $^1$H NMR (400 MHz, Acetonitrile-d3) δ 8.06 (s, 1H), 7.34 (dd, J=8.7, 7.1 Hz, 2H), 7.24-7.16 (m, 3H), 6.77 (d, J=4.4 Hz, 1H), 6.67 (d, J=4.4 Hz, 1H), 5.92-5.79 (m, 2H), 5.69 (d, J=4.6 Hz, 1H), 4.84 (tt, J=8.3, 4.1 Hz, 1H), 4.50-4.35 (m, 2H), 4.30-4.20 (m, 1H), 3.78 (dt, J=10.6, 4.9 Hz, 2H), 3.45 (ddt, J=11.8, 8.4, 3.3 Hz, 2H), 3.20 (t, J=9.9 Hz, 6H), 2.65 (dp, J=30.7, 7.0 Hz, 2H), 2.29 (s, 3H), 1.53 (dtd, J=12.6, 8.9, 8.4, 3.7 Hz, 2H), 1.31-1.11 (m, 16H). $^{31}$P NMR (162 MHz, Methanol-d4) δ 3.52. LCMS: MS m/z=812.48 [M+1], $t_R$=1.47 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.52 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 220. (2R,3S,4S,5S)-2-cyano-2-(((((S)-(((S)-1-methoxy-1-oxopropan-2-yl)amino)(phenoxy)phosphoryl)oxy)methyl)-5-(4-(1-methylpiperidine-4-carboxamido)pyrrolo[2,1-f][1,2,4]triazin-7-yl) tetrahydrofuran-3,4-diyl bis(1-methyl piperidine-4-carboxylate)

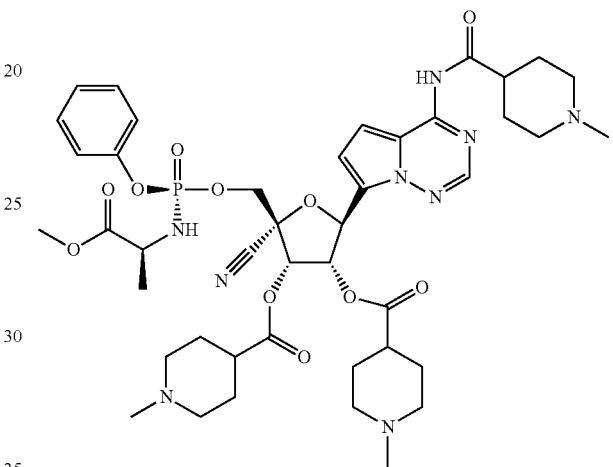

Example 52 (22 mg, 0.04 mmol) was dissolved in 2 mL of anhydrous THF. 1-methylpiperidine-4-carboxylic acid hydrochloride (29 mg, 0.16 mmol) and EDAC (31 mg, 0.16 mmol) were added to the reaction and stirred for 10 mins. Added sodium bicarbonate (200 mg) and DMAP (5 mg, 0.04 mmol) were added to the reaction and stirred for 20 hrs at RT. More 1-methylpiperidine-4-carboxylic acid hydrochloride (29 mg, 0.16 mmol) and EDAC (31 mg, 0.16 mmol) were added to the reaction. Sodium bicarbonate (200 mg) and DMAP (10 mg) were added to the reaction which was stirred then for 16 hrs at RT. Reaction was diluted with EtOAc (15 mL) and washed with saturated aqueous sodium bicarbonate solution (3×10 mL) followed with brine (5 mL). Organic extract was dried over anhydrous sodium sulfate and then concentrated under reduced pressure. Crude material was dissolved in DCM (10 mL). 1-Methylpiperidine-4-carboxylic acid hydrochloride (29 mg, 0.16 mmol), EDAC (31 mg, 0.16 mmol) and DMAP (50 mg) were added. Reaction was stirred for 3 hrs. Reaction was diluted with DCM (10 mL) and washed with sodium bicarbonate solution (2×5 mL). Organic was dried over anhydrous sodium sulfate and concentrated under reduced pressure. The crude residue was purified via $SiO_2$ column chromatography (4 g $SiO_2$ Combiflash HP Gold Column, 0-10-20% methanol/DCM with 1% triethylamine). Fractions were combined and concentrated under reduced pressure. Residue was dissolved in MeCN and water and freeze-dried to give the product. $^1$H NMR (400 MHz, methanol-d$_4$) δ 8.19 (s, 1H), 7.34-7.26 (m, 2H), 7.23-7.11 (m, 4H), 6.96 (d, J=4.7 Hz, 1H), 5.91 (d, J=5.7 Hz, 1H), 5.83 (dd, J=5.7, 4.6 Hz, 1H), 5.78 (d, J=4.6 Hz, 1H), 4.54-4.36 (m, 2H), 3.90 (dq, J=10.2, 7.1 Hz, 1H), 3.61 (s, 3H), 2.98 (m, 2H), 2.93-2.72 (m, 5H), 2.47 (m, 2H), 2.36-2.23 (m, 9H), 2.23-2.07 (m, 6H), 2.07-1.64 (m, 13H), 1.28 (d, J=7.2, 3H). $^{31}$P NMR (162 MHz, methanol-d$_4$) δ 3.08. LCMS: MS m/z=908.3 [M+1], 906.7 [M−1], t$_R$=0.94 min; LC system: Thermo Dionex Ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: t$_R$=2.08 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min. HPLC: t$_R$=3.473 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 221. Single Diastereomer of (2R,3S,4S,5S)-5-(4-aminopyrrolo[2,1-f][1,2,4]triazin-7-yl)-2-cyano-2-((((((S)-1-oxo-1-((tetrahydro-2H-pyran-4-yl)oxy)propan-2-yl)amino)(phenoxy)phosphoryl)oxy)methyl)tetrahydrofuran-3,4-diyl (2S,2'S)-bis(2-amino-3-methylbutanoate)

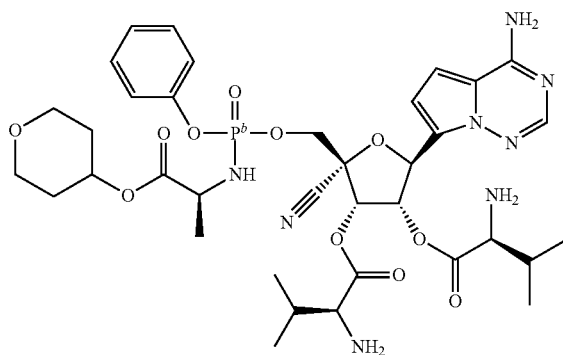

To a solution of Example 57 (30 mg, 0.05 mmol) in THF was added Boc-Val (43 mg, 0.2 mmol) and N, N'-diisopropyl carbodiimide (25 mg, 0.2 mmol), the reaction mixture was stirred at RT for 20 min before DMAP (6 mg, 0.05 mmol) was added. The reaction mixture was then stirred overnight. The reaction was then quenched with MeOH, then diluted with EtOAc, and washed with 2% aqueous citric acid solution and then with brine. The organic phase was dried over anhydrous sodium sulfate and concentrated under reduced pressure. The residue was purified with silica gel column (0-100% EtOAc in hexanes). The purified intermediate was then dissolved in MeCN (5 mL) and stirred under atmospheric nitrogen in an ice bath. Added concentrated HCl (aq) (300 uL) dropwise. Reaction was stirred for 4 hrs. Loaded crude reaction mixture onto a prep HPLC column and eluted with a linear gradient from 5-100% MeCN with TFA modifier to afford the product. $^1$H NMR (400 MHz, Methanol-d4) δ 7.87 (s, 1H), 7.33 (dd, J=8.6, 7.2 Hz, 2H), 7.25-7.10 (m, 3H), 6.90 (d, J=4.6 Hz, 1H), 6.86-6.75 (m, 1H), 6.44 (d, J=5.9 Hz, 1H), 6.04 (dd, J=5.9, 3.1 Hz, 1H), 5.80 (d, J=3.1 Hz, 1H), 4.77 (tt, J=8.2, 4.0 Hz, 1H), 4.49 (dd, J=6.1, 2.4 Hz, 2H), 4.11 (dd, J=12.2, 4.1 Hz, 2H), 3.90-3.72 (m, 3H), 3.44 (dtd, J=11.9, 8.8, 3.3 Hz, 2H), 2.49 (dtt, J=14.1, 7.0, 4.0 Hz, 2H), 1.85-1.69 (m, 2H), 1.54 (dddd, J=13.5, 8.7, 6.8, 4.1 Hz, 2H), 1.34-1.21 (m, 3H), 1.19-1.02 (m, 12H). $^{31}$P NMR (162 MHz, Methanol-d4) δ 3.65. LCMS: MS m/z=801.14 [M+1], t$_R$=1.07 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: t$_R$=2.48 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 222. (2R,3S,4S,5S)-5-(4-Aminopyrrolo[2,1-f][1,2,4]triazin-7-yl)-2-cyano-2-((((((S)-1-(3-methoxypropoxy)-1-oxopropan-2-yl)amino)(phenoxy)phosphoryl)oxy)methyl) tetrahydrofuran-3,4-diyl bis(2-methylpropanoate)

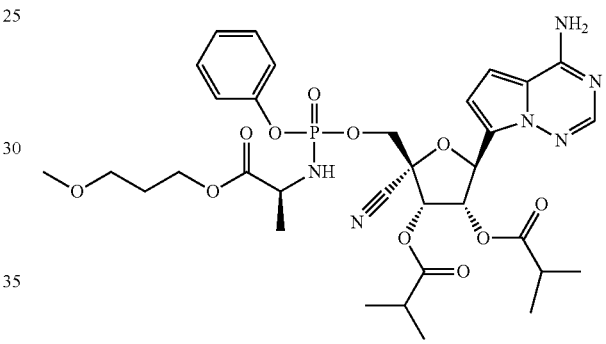

To a mixture of Example 60. (30 mg, 0.051 mmol) and isobutyric anhydride (0.019 mL, 0.164 mmol) in THF (3 mL) was added DMAP (2 mg, 0.016 mmol). The resulting mixture was stirred at room temperature for 5 min and quenched by adding methanol (0.5 mL), and purified by preparative HPLC (Phominex Synergi 4 u Hydro-RR 80 Å 150×30 mm column, 10-100% acetonitrile/water gradient) to afford the product. $^1$H NMR (400 MHz, Acetonitrile-d$_3$) δ 7.90 (s, 1H), 7.34 (dd, J=8.4, 7.4 Hz, 2H), 7.25-7.13 (m, 3H), 6.76 (d, J=0.8 Hz, 2H), 6.40 (s, 2H), 5.87 (d, J=6.0 Hz, 1H), 5.81 (dd, J=6.0, 4.5 Hz, 1H), 5.68 (d, J=4.5 Hz, 1H), 4.50-4.34 (m, 3H), 4.13-3.98 (m, 2H), 3.91 (m, 1H), 3.36 (t, J=6.2 Hz, 2H), 3.25 (s, 3H), 2.65 (m, 2H), 1.78 (m, 2H), 1.27 (dd, J=7.1, 0.9 Hz, 3H), 1.22 (t, J=6.9 Hz, 6H), 1.18 (d, J=7.0 Hz, 3H), 1.15 (d, J=7.0 Hz, 3H). $^{31}$P NMR (162 MHz, Acetonitrile-d3) δ 2.48. LCMS m/z=731.36 (M+H), t$_R$=1.37 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: t$_R$=5.66 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 223. (2R,3S,4S,5S)-5-(4-aminopyrrolo[2,1-f][1,2,4]triazin-7-yl)-2-cyano-2-(((((S)-1-(2-morpholinoethoxy)-1-oxopropan-2-yl)amino)(phenoxy)phosphoryl)oxy)methyl) tetrahydrofuran-3,4-diyl bis(2-methylpropanoate)

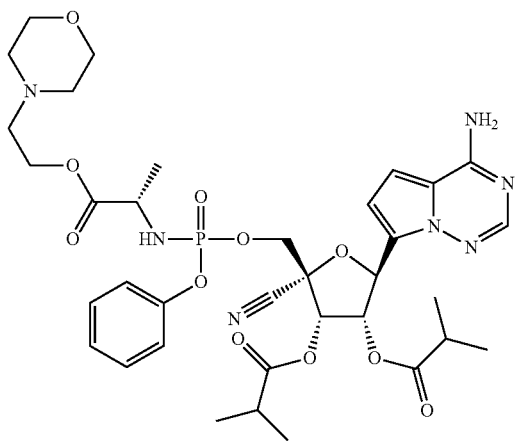 [SMILES: CC(C)C(=O)O[C@H]1[C@H](c2ccc3c(N)ncnn23)O[C@](C#N)(COP(=O)(N[C@@H](C)C(=O)OCCN2CCOCC2)Oc2ccccc2)[C@H]1OC(=O)C(C)C]

N,N-diisopropylethylamine (0.13 mL, 0.76 mmol) and magnesium chloride (43 mg, 0.45 mmol) were added to a mixture of Intermediate 4 (100.0 mg, 0.30 mmol) and Intermediate 67 (216 mg, 0.45 mmol) in tetrahydrofuran (7.5 mL) at RT. The mixture was heated to 55° C. After 2 h, the reaction mixture was allowed to cool to RT, diluted with ethyl acetate (30 mL) and the resulting mixture was washed with water (5×20 mL) and brine (20 mL). The organic layer was dried over anhydrous sodium sulfate and concentrated under reduced pressure. Concentrated aqueous hydrochloric acid solution (0.53 mL) was added dropwise to the crude residue in acetonitrile (7.5 mL) at 0° C. The mixture was warmed to RT. After 2 h, the reaction mixture was diluted with ethyl acetate (100 mL) and the resulting mixture was washed with saturated aqueous sodium carbonate solution (75 mL) and brine (75 mL). The organic layer was dried over anhydrous sodium sulfate and concentrated under reduced pressure. The resulting crude residue, 80 mg, was subjected to N,N-diisopropylethylamine (0.13 mL, 0.76 mmol), N,N'-diisopropylcarbodiimide (0.113 g, 1.0 mmol), 4-dimethylaminopyridine (33 mg, 0.27 mmol) and isobutyric acid (89 mg, 1.01 mmol) in tetrahydrofuran (6 mL) at RT. After 20 h at RT, methanol (0.5 mL) was added, and the reaction mixture was diluted with ethyl acetate (20 mL) and the resulting mixture was washed with water (15 mL) and brine (15 mL). The organic layer was dried over anhydrous sodium sulfate and concentrated under reduced pressure. The crude residue was subjected to preparatory HPLC (Phenomenex Gemini 10 u C18 110 Å AXIA 250×21.2 mm column, 30-70% acetonitrile/water gradient with 0.1% TFA) to afford the product. $^1$H NMR (400 MHz, Methanol-$d_4$) δ 7.99 (d, J=11.7 Hz, 1H), 7.34 (dt, J=15.6, 8.1 Hz, 2H), 7.28-7.13 (m, 2H), 6.99-6.83 (m, 2H), 5.87 (dd, J=8.6, 5.9 Hz, 1H), 5.83-5.75 (m, 1H), 5.73 (d, J=4.8 Hz, 1H), 4.80-4.14 (m, 6H), 3.85 (s, 6H), 3.56-3.31 (m, 7H), 2.79-2.50 (m, 3H), 1.56-0.74 (m, 13H). $^{31}$P NMR (162 MHz, Methanol-$d_4$) δ 3.36, 3.42. LCMS: MS m/z=772.47 [M+1], $t_R$=1.10 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=4.66 min, HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Example 224. (2R,3S,4S,5S)-5-(4-aminopyrrolo[2,1-f][1,2,4]triazin-7-yl)-2-cyano-2-(((((S)-1-(2-(diisopropylamino)ethoxy)-1-oxopropan-2-yl)amino)(phenoxy)phosphoryl)oxy) methyl)tetrahydrofuran-3,4-diyl bis(2-methylpropanoate)

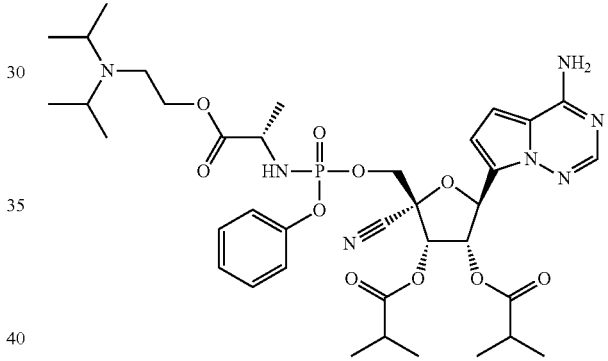

Isobutyric anhydride (36 μL, 0.39 mmol) was added to a solution of crude Example 74 (50 mg, ~0.08 mmol) in tetrahydrofuran (3 mL) and acetonitrile (1 mL) at RT. After 10 min, 4-dimethylaminopyridine (1.8 mg, 0.1 mmol) was added. After 30 min, the reaction mixture was diluted with water (3.5 mL). The crude solution was subjected preparatory HPLC (Phenomenex Synergi 4 um Polar-RP 80 Å 150×21.2 mm column, 35-55% acetonitrile/water gradient with 0.1% TFA) to afford the product as a TFA salt. $^1$H NMR (400 MHz, Acetonitrile-$d_3$) δ 8.89 (s, 1H), 7.95 (s, 1H), 7.33 (t, J=7.8 Hz, 2H), 7.26-7.10 (m, 4H), 6.89 (dd, J=8.6, 4.7 Hz, 1H), 5.76 (dq, J=9.9, 5.9 Hz, 2H), 5.69 (dd, J=5.9, 4.0 Hz, 1H), 4.65 (ddd, J=49.2, 12.4, 9.2 Hz, 1H), 4.54-4.26 (m, 4H), 3.91 (h, J=8.5, 7.9 Hz, 1H), 3.63 (s, 2H), 3.28 (s, 2H), 2.73-2.52 (m, 3H), 1.33-1.25 (m, 15H), 1.22-1.13 (m, 12H). $^{19}$F NMR (376 MHz, Acetonitrile-$d_3$) δ −76.83. $^{31}$P NMR (162 MHz, Acetonitrile-$d_3$) δ 2.31. LCMS: MS m/z=786.22 [M+1], $t_R$=1.31 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min.

HPLC: $t_R$=4.00 min, 4.06 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Example 225. (2R,3S,4S,5S)-5-(4-aminopyrrolo[2,1-f][1,2,4]triazin-7-yl)-2-(((((S)-1-butoxy-1-oxopropan-2-yl)amino)(phenoxy)phosphoryl)oxy)methyl)-2-cyanotetrahydrofuran-3,4-diyl bis(2-methylpropanoate)

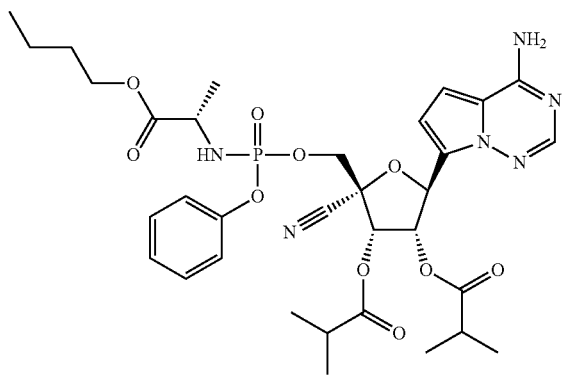 [SMILES: CCCCOC(=O)[C@H](C)NP(=O)(OC[C@@]1(C#N)O[C@@H](c2ccc3c(N)ncnn23)[C@H](OC(=O)C(C)C)[C@@H]1OC(=O)C(C)C)Oc1ccccc1]

Isobutyric anhydride (30 μL, 0.14 mmol) was added to a solution of Example 54 (40 mg, 0.07 mmol) and 4-dimethylaminopyridine (5.5 mg, 0.05 mmol) in 2-methyl tetrahydrofuran (6 mL) at RT. After 30 min, the reaction mixture was diluted with ethyl acetate (15 mL) and the resulting mixture was washed with saturated aqueous sodium carbonate solution (20 mL) and brine (20 mL). The organic layer was dried over anhydrous sodium sulfate and concentrated under reduced pressure. The crude residue was purified by silica gel chromatography eluting with 20-100% ethyl acetate in hexanes to afford the product. $^1$H NMR (400 MHz, CD$_3$CN) δ 7.82 (d, J=9.9 Hz, 1H), 7.35-7.27 (m, 2H), 7.23-7.13 (m, 3H), 6.85 (dd, J=7.5, 4.5 Hz, 1H), 6.76 (dd, J=11.1, 4.6 Hz, 1H), 5.95 (dd, J=23.4, 5.9 Hz, 1H), 5.83 (ddd, J=19.6, 5.9, 4.5 Hz, 1H), 5.68 (t, J=4.4 Hz, 1H), 4.58-4.37 (m, 2H), 4.16-3.96 (m, 2H), 3.94-3.76 (m, 1H), 2.77-2.55 (m, 2H), 1.31-1.14 (m, 20H). $^{31}$P NMR (162 MHz, CD$_3$CN) δ 2.49, 2.37. LCMS: MS m/z=715.05 [M+1], $t_R$=1.21 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.34 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Resolution of the Sp and Rp diastereomers. Example 225 was purified via chiral SFC (Chiralpak IF, 5 um, 4.6×150 mm, Methanol 30%) to afford the diastereomers:

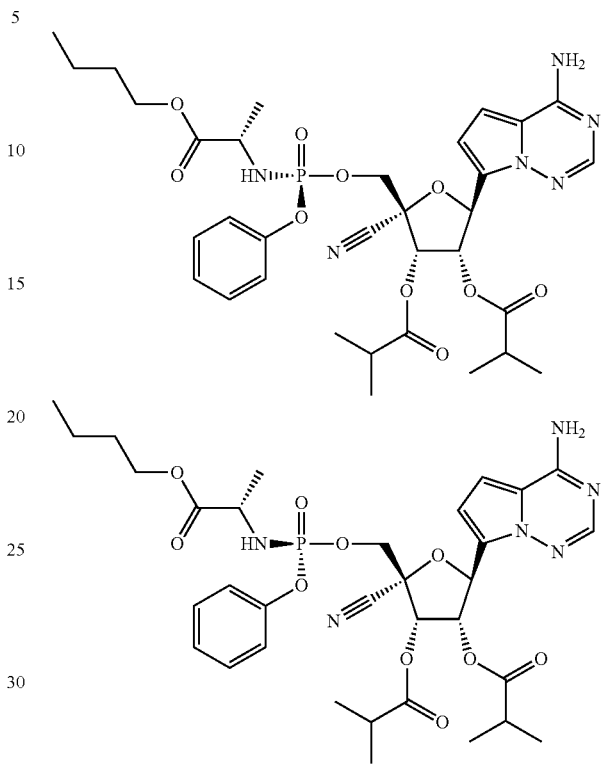

Example 226

First Eluting Diastereomer: $^1$H NMR (400 MHz, Methanol-d$_4$) δ 7.80 (s, 1H), 7.34-7.25 (m, 2H), 7.24-7.11 (m, 3H), 6.85 (d, J=4.6 Hz, 1H), 6.77 (d, J=4.5 Hz, 1H), 5.96 (d, J=5.9 Hz, 1H), 5.84 (dd, J=5.9, 4.4 Hz, 1H), 5.68 (d, J=4.5 Hz, 1H), 4.51 (dd, J=11.0, 5.7 Hz, 1H), 4.41 (dd, J=11.1, 4.9 Hz, 1H), 4.05 (td, J=6.6, 5.6 Hz, 1H), 3.94-3.74 (m, 1H), 2.64 (dp, J=14.0, 7.0 Hz, 2H), 1.64-1.50 (m, 3H), 1.43-1.13 (m, 16H), 0.89 (t, J=7.4 Hz, 4H). $^{31}$P NMR (162 MHz, Methanol-d4) δ 3.07. LCMS: MS m/z=715.14 [M+1], $t_R$=1.21 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=6.183 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Example 227

Second Eluting Diastereomer: $^1$H NMR (400 MHz, Methanol-d$_4$) δ 7.85 (s, 1H), 7.30 (t, J=7.9 Hz, 2H), 7.23-7.10 (m, 3H), 6.94-6.84 (m, 1H), 6.75 (d, J=4.5 Hz, 1H), 5.89 (d, J=5.9 Hz, 1H), 5.78 (dd, J=5.9, 4.6 Hz, 1H), 5.67 (d, J=4.7 Hz, 1H), 4.43 (dd, J=5.8, 2.4 Hz, 2H), 4.09-3.83 (m, 1H), 2.64 (dp, J=16.7, 7.0 Hz, 2H), 1.60-1.48 (m, 2H), 1.43-1.29 (m, 4H), 1.29-1.25 (m, 3H), 1.25-1.12 (m, 12H), 0.89 (t, J=7.4 Hz, 3H). $^{31}$P NMR (162 MHz, Methanol-d$_4$)

δ 3.03. LCMS: MS m/z=715.14 [M+1], $t_R$=1.21 min; LC system: Thermo Accela 1250 UHPLC; MS system: Thermo LCQ Fleet; Column: Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=6.185 min; HPLC system: Agilent 1100 series; Column: Kinetx 2.6 u C18, 100 mm×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Example 228. (2R,3S,4S,5S)-5-(4-aminopyrrolo[2,1-f][1,2,4]triazin-7-yl)-2-cyano-2-((((((S)-1-(((S)-1-methylpyrrolidin-3-yl)oxy)-1-oxopropan-2-yl)amino)(phenoxy) phosphoryl)oxy)methyl) tetrahydrofuran-3,4-diyl bis(2-methylpropanoate)

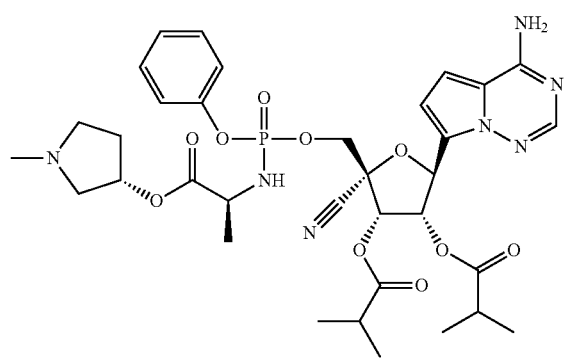 [SMILES: CC(C)C(=O)O[C@H]1[C@H](c2ccc3c(N)ncnn23)O[C@](C#N)(COP(=O)(N[C@@H](C)C(=O)O[C@H]2CCN(C)C2)Oc2ccccc2)[C@H]1OC(=O)C(C)C]

Example 15 (15 mg, 0.025 mmol) was dissolved in 2 mL anhydrous THF and stirred at RT. Isobutyric anhydride (8.3 uL, 0.05 mmol) and DMAP (0.3 mg, 0.0025 mmol) were added, and the reaction was stirred for 60 mins. More isobutyric anhydride (3 uL) was added, and the reaction was stirred for 45 mins.

Methanol (500 uL) was added and stirred for 30 mins. Reaction was then diluted with EtOAc (10 mL) and washed with saturated aqueous sodium bicarbonate solution (2×5 mL) followed with brine (5 mL). Organic extract was dried over anhydrous sodium sulfate and then concentrated under reduced pressure. The crude residue was purified via SiO$_2$ column chromatography (4 g SiO$_2$ Combiflash HP Gold Column, 0-10-20% methanol/DCM). Fractions were combined and concentrated under reduced pressure. Residue was dissolved in MeCN, diluted with water and freeze-dried to give the product. $^1$H NMR (400 MHz, methanol-d4) δ 7.83 (m, 1H), 7.36-7.24 (m, 2H), 7.23-7.10 (m, 3H), 6.85 (m, 1H), 6.76 (m, 1H), 5.92 (m, 1H), 5.82 (m, 1H), 5.67 (m, 1H), 5.16-4.99 (m, 1H), 4.57-4.37 (m, 2H), 3.88 (m, 1H), 2.76 (m, 1H), 2.72-2.53 (m, 4H), 2.32 (m, 4H), 2.25-2.06 (m, 1H), 1.86-1.70 (m, 1H), 1.37-1.06 (m, 15H). $^{31}$P NMR (162 MHz, methanol-d$_4$) δ 3.04, 2.99. LCMS: MS m/z=742.3 [M+1], 740.3 [M−1], $t_R$=1.34 min; LC system: Thermo Dionex Ultimate 3000 UHPLC; Column: Phenomenex Kinetex 2.6µ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=2.75 min; HPLC system: Agilent 1100 series; Column: Phenomenex Gemini 5µ C18 110A, 50×4.6 mm; Solvent: A: Water with 0.1% TFA, B: Acetonitrile with 0.1% TFA; Gradient: 2-98% B in 5 min at 2 mL/min. HPLC: $t_R$=4.669, 4.701 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The product was purified via chiral preparatory HPLC (Chiralpak IA, 150×4.6 mm, SFC 30% ethanol isocratic) to afford the diastereomers:

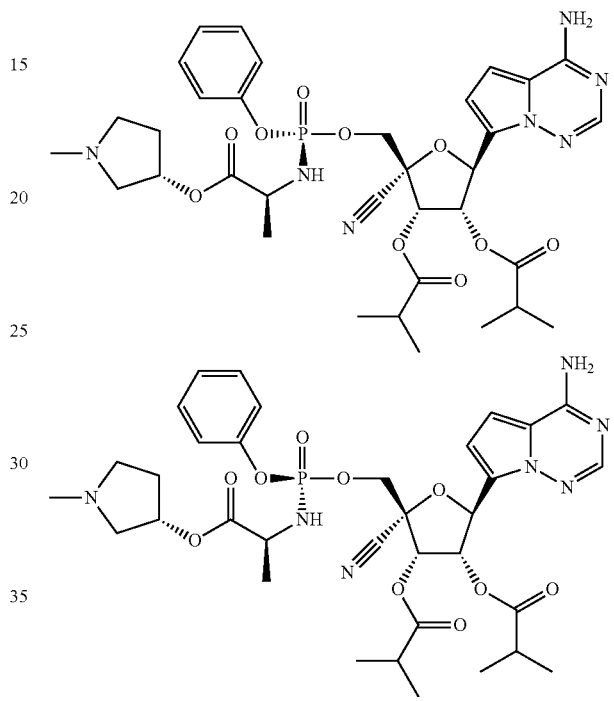

Example 229

First Eluting Diastereomer: $^1$H NMR (400 MHz, methanol-d$_4$) δ 7.81 (s, 1H), 7.35-7.25 (m, 2H), 7.21-7.11 (m, 3H), 6.86 (d, J=4.5 Hz, 1H), 6.77 (d, J=4.5 Hz, 1H), 5.94 (d, J=5.8 Hz, 1H), 5.84 (dd, J=5.8, 4.6 Hz, 1H), 5.68 (d, J=4.6 Hz, 1H), 5.13 (m, 1H), 4.59-4.36 (m, 2H), 3.86 (dq, J=9.3, 7.1 Hz, 1H), 2.83 (m, 1H), 2.78-2.55 (m, 4H), 2.42 (m, 1H), 2.36 (s, 3H), 2.23 (m, 1H), 1.82 (m, 1H), 1.35-1.10 (m, 15H). $^{31}$P NMR (162 MHz, methanol-d4) δ 3.04 (s). HPLC: $t_R$=4.655 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 230

Second Eluting Diastereomer: $^1$H NMR (400 MHz, methanol-d4) δ 7.84 (s, 1H), 7.37-7.25 (m, 2H), 7.25-7.12 (m, 3H), 6.84 (d, J=4.5 Hz, 1H), 6.75 (d, J=4.6 Hz, 1H), 5.90 (d, J=5.9 Hz, 1H), 5.83-5.75 (m, 1H), 5.67 (d, J=4.6 Hz, 1H), 5.04 (m, 1H), 4.52-4.35 (m, 2H), 3.89 (dq, J=9.8, 7.1 Hz, 1H), 2.76 (m, 1H), 2.71-2.54 (m, 4H), 2.30 (m, 4H), 2.22-2.06 (m, 1H), 1.77 (m, 1H), 1.36-1.07 (m, 15H). $^{31}$P NMR (162 MHz, methanol-d$_4$) δ 2.99 (s). HPLC: $t_R$=4.703 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 231. (2R,3S,4S,5S)-5-(4-aminopyrrolo[2,1-f][1,2,4]triazin-7-yl)-2-cyano-2-((((S)-(((S)-1-methoxy-1-oxopropan-2-yl)amino)(phenoxy)phosphoryl)oxy)methyl) tetrahydrofuran-3,4-diyl bis(3-methoxypropanoate)

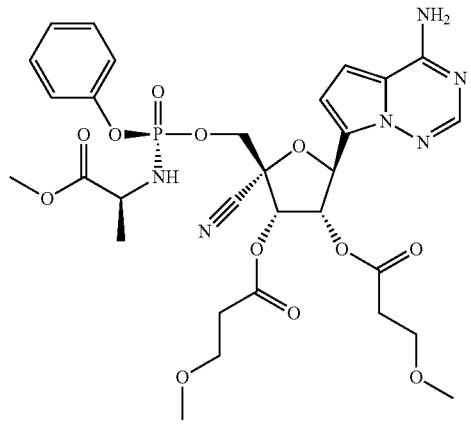 [SMILES: COCCC(=O)O[C@H]1[C@H](c2ccc3c(N)ncnn23)O[C@](C#N)(CO[P@@](=O)(N[C@@H](C)C(=O)OC)Oc2ccccc2)[C@H]1OC(=O)CCOC]

Example 52 (20 mg, 0.038 mmol) was dissolved in 1.5 mL of anhydrous THF. 3-Methoxy propionic acid (14 uL, 0.15 mmol) was added. N, N'-diisopropyl carbodiimide (23 uL, 0.15 mmol) was added, and the reaction was stirred for 30 mins. DMAP (5 mg, 0.038 mmol) was then added, and the reaction was stirred for 2 hrs.

Methanol (0.5 mL) was added and stirred for 2 hrs. Reaction was diluted with EtOAc (10 mL) and washed with saturated aqueous sodium bicarbonate solution (2×5 mL) followed with brine (5 mL). Organic extract was dried over anhydrous sodium sulfate and concentrated under reduced pressure. The crude residue was purified via SiO$_2$ column chromatography (4 g SiO$_2$ Combiflash HP Gold Column, 0-5% methanol/DCM). Fractions were combined and concentrated under reduced pressure. Residue was dissolved in MeCN and water and freeze-dried to give the product. $^1$H NMR (400 MHz, methanol-d4) δ 7.83 (s, 1H), 7.36-7.25 (m, 2H), 7.24-7.10 (m, 3H), 6.83 (d, J=4.5 Hz, 1H), 6.74 (d, J=4.5 Hz, 1H), 5.97 (d, J=5.9 Hz, 1H), 5.85 (dd, J=6.0, 4.4 Hz, 1H), 5.69 (d, J=4.5 Hz, 1H), 4.50-4.36 (m, 2H), 3.89 (dq, J=10.0, 7.1 Hz, 1H), 3.73-3.63 (m, 4H), 3.59 (s, 3H), 3.33 (s, 3H), 3.29 (s, 3H), 2.71 (t, J=6.1 Hz, 2H), 2.65 (td, J=6.0, 1.7 Hz, 2H), 1.26 (dd, J=7.2, 1.1 Hz, 3H). $^{31}$P NMR (162 MHz, methanol-d4) δ 3.01. LCMS: MS m/z=705.3 [M+1], 703.2 [M−1], t$_R$=1.43 min; LC system: Thermo Dionex Ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: t$_R$=2.83 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min. HPLC: t$_R$=4.748 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 232. (2R,3S,4S,5S)-5-(4-aminopyrrolo[2,1-f][1,2,4]triazin-7-yl)-2-cyano-2-((((((S)-1-(((R)-1-methylpyrrolidin-3-yl)oxy)-1-oxopropan-2-yl)amino)(phenoxy) phosphoryl)oxy)methyl) tetrahydrofuran-3,4-diyl bis(2-methylpropanoate)

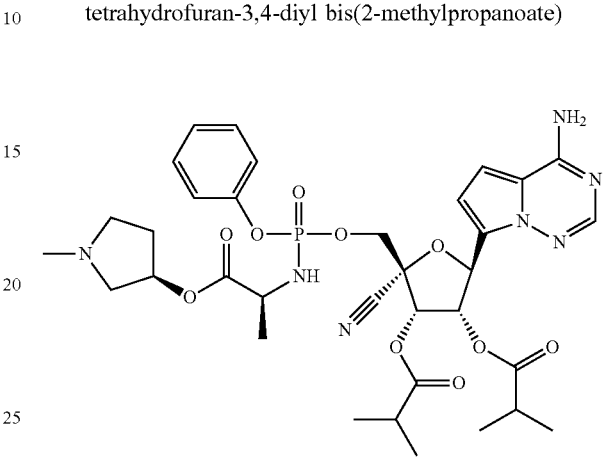

Example 61 (23 mg, 0.038 mmol) was dissolved in 4 mL anhydrous THF and stirred at RT. Isobutyric anhydride (12 uL, 0.076 mmol) and DMAP (0.5 mg, 0.0038 mmol) were added, and the reaction was stirred for 60 mins. More isobutyric anhydride (3 uL) was added, and the reaction was stirred for 45 mins.

Methanol (500 uL) was added and stirred for 30 mins. Reaction was then diluted with EtOAc (10 mL) and washed with saturated aqueous sodium bicarbonate solution (2×5 mL) followed with brine (5 mL). Organic extract was dried over anhydrous sodium sulfate and then concentrated under reduced pressure. The crude residue was purified via SiO$_2$ column chromatography (4 g SiO$_2$ Combiflash HP Gold Column, 0-10-20% methanol/DCM). Fractions were combined and concentrated under reduced pressure. Residue was dissolved in MeCN, diluted with water and freeze-dried to give the product. $^1$H NMR (400 MHz, methanol-d4) δ 7.83 (m, 1H), 7.37-7.25 (m, 2H), 7.25-7.11 (m, 3H), 6.85 (m, 1H), 6.76 (m, 1H), 5.92 (m, 1H), 5.81 (m, 1H), 5.68 (m, 1H), 5.16-5.00 (m, 1H), 4.56-4.36 (m, 2H), 3.87 (m, 1H), 2.79 (m, 1H), 2.73-2.49 (m, 4H), 2.31 (m, 4H), 2.26-2.12 (m, 1H), 1.85-1.67 (m, 1H), 1.33-1.10 (m, 15H). $^{31}$P NMR (162 MHz, methanol-d$_4$) δ 3.03, 3.01. LCMS: MS m/z=742.5 [M+1], 740.4 [M−1], t$_R$=1.29 min; LC system: Thermo Dionex Ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: t$_R$=2.74 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min. HPLC: t$_R$=4.687, 4.706 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Resolution of the Sp and Rp diastereomers. The product was purified via chiral preparatory HPLC (Chiralpak IF, 150×4.6 mm, SFC 30% ethanol isocratic) to afford the diastereomers:

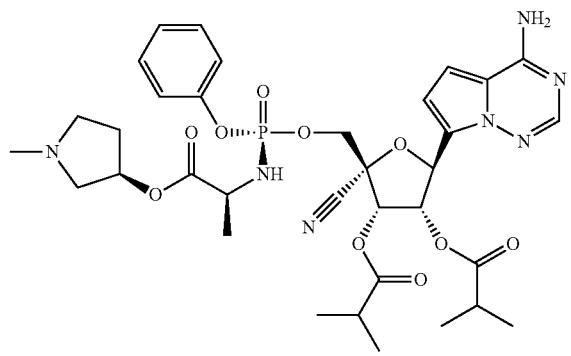

Example 233

First Eluting Diastereomer: $^1$H NMR (400 MHz, methanol-$d_4$) δ 7.81 (s, 1H), 7.36-7.22 (m, 2H), 7.22-7.10 (m, 3H), 6.85 (d, J=4.5 Hz, 1H), 6.77 (d, J=4.6 Hz, 1H), 5.95 (d, J=5.8 Hz, 1H), 5.84 (dd, J=5.8, 4.5 Hz, 1H), 5.69 (d, J=4.5 Hz, 1H), 5.11 (m, 1H), 4.57-4.37 (m, 2H), 3.85 (dq, J=9.2, 7.1 Hz, 1H), 2.77 (m, 1H), 2.71-2.56 (m, 4H), 2.39-2.32 (m, 1H), 2.30 (s, 3H), 2.22 (m, 1H), 1.76 (m, 1H), 1.30-1.13 (m, 15H). $^{31}$P NMR (162 MHz, methanol-$d_4$) δ 3.03 (s). HPLC: $t_R$=4.681 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

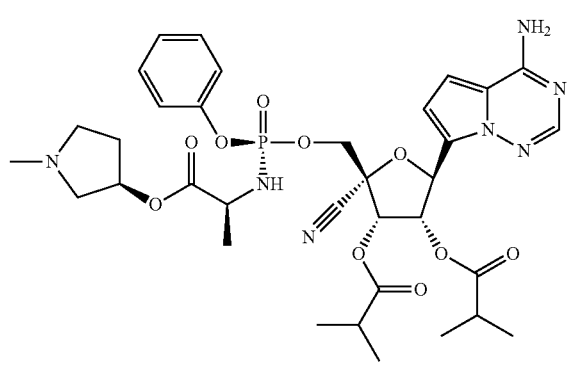

Example 234

Second Eluting Diastereomer: $^1$H NMR (400 MHz, methanol-$d_4$) δ 7.84 (s, 1H), 7.37-7.26 (m, 2H), 7.25-7.11 (m, 3H), 6.84 (d, J=4.6 Hz, 1H), 6.75 (d, J=4.6 Hz, 1H), 5.90 (d, J=5.9 Hz, 1H), 5.79 (dd, J=5.9, 4.7 Hz, 1H), 5.67 (d, J=4.7 Hz, 1H), 5.06 (ddt, J=8.1, 5.4, 2.5 Hz, 1H), 4.51-4.37 (m, 2H), 3.89 (dq, J=9.9, 7.1 Hz, 1H), 2.80 (m, 1H), 2.74-2.50 (m, 4H), 2.32 (m, 4H), 2.20 (m, 1H), 1.75 (m, 1H), 1.28 (d, J=7.1 Hz, 3H), 1.26-1.12 (m, 12H). $^{31}$P NMR (162 MHz, methanol-$d_4$) δ 3.01 (s). HPLC: $t_R$=4.706 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 235. (2R,3S,4S,5S)-2-((((4-((S)-2-amino-3-methoxy-3-oxopropyl)phenoxy)(((S)-1-methoxy-1-oxopropan-2-yl)amino)phosphoryl)oxy)methyl)-5-(4-aminopyrrolo[2,1-f][1,2,4]triazin-7-yl)-2-cyanotetrahydrofuran-3,4-diyl bis(2-methylpropanoate)

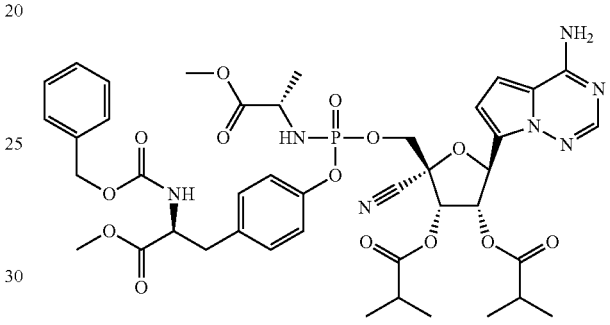

(2R,3S,4S,5S)-5-(4-aminopyrrolo[2,1-f][1,2,4]triazin-7-yl)-2-((((4-((S)-2-(((benzyloxy)carbonyl)amino)-3-methoxy-3-oxopropyl)phenoxy)(((S)-1-methoxy-1-oxopropan-2-yl)amino)phosphoryl)oxy)methyl)-2-cyanotetrahydrofuran-3,4-diyl bis(2-methylpropanoate). Isobutyric anhydride (20.0 μL, 0.12 mmol) was added to a solution of Example 62 (53.3 mg, 0.07 mmol) and 4-dimethylaminopyridine (1.3 mg, 0.01 mmol) in 2-methyl tetrahydrofuran (1.5 mL) at RT. After 5 min, the reaction mixture was diluted with ethyl acetate (25 mL) and the resulting mixture was washed with saturated aqueous sodium carbonate solution (20 mL) and brine (20 mL). The organic layer was dried over anhydrous sodium sulfate and concentrated under reduced pressure. The crude residue was purified by silica gel chromatography eluting with 0-25% methanol in ethyl acetate to afford the product. $^1$H NMR (400 MHz, Methanol-$d_4$) δ 7.80 (d, J=16.5 Hz, 1H), 7.36-7.22 (m, 5H), 7.17-7.04 (m, 4H), 6.84 (t, J=4.8 Hz, 1H), 6.74 (d, J=4.6 Hz, 1H), 5.94 (dd, J=20.9, 5.8 Hz, 1H), 5.83 (ddd, J=15.4, 5.8, 4.5 Hz, 1H), 5.68 (dd, J=4.5, 1.6 Hz, 1H), 5.02 (d, J=3.9 Hz, 2H), 4.58-4.34 (m, 3H), 3.96-3.72 (m, 1H), 3.70 (s, 3H), 3.61 (d, J=8.9 Hz, 3H), 3.12 (dd, J=14.0, 5.3 Hz, 1H), 2.91 (dd, J=14.0, 9.2 Hz, 1H), 2.75-2.54 (m, 2H), 1.29-1.14 (m, 15H). $^{31}$P NMR (162 MHz, Methanol-$d_4$) δ 3.07, 3.02. LCMS: MS m/z=908.56 [M+1], $t_R$=1.47 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetoni- (2R,3S,4S,5S)-2-(((((4-((S)-2-amino-3-methoxy-3-oxo-propyl)phenoxy)(((S)-1-methoxy-1-oxopropan-2-yl)amino)phosphoryl)oxy)methyl)-5-(4-aminopyrrolo[2,1-f][1,2,4]triazin-7-yl)-2-cyanotetrahydrofuran-3,4-diyl bis(2-methylpropanoate). Palladium on carbon (10.6 mg, 10 wt %) was added to a solution of (2R,3S,4S,5S)-5-(4-aminopyrrolo[2,1-f][1,2,4]triazin-7-yl)-2-(((((4-((S)-2-(((benzyloxy)carbonyl)amino)-3-methoxy-3-oxopropyl)phenoxy)(((S)-1-methoxy-1-oxopropan-2-yl)amino)phosphoryl)oxy)methyl)-2-cyanotetrahydrofuran-3,4-diyl bis(2-methylpropanoate) (37.3 mg, 0.04 mmol) in ethanol (5 mL) that was purged with argon. The mixture was then purged with hydrogen and stirred at RT. After 17 hr, the mixture was filtered through celite, the filter was rinsed with ethanol, and the volatiles were removed under reduce pressure. The crude residue was subjected preparatory HPLC (Phenomenex Synergi 4 um Polar-RP 80 Å 150×21.2 mm column, 20-70% acetonitrile/water gradient with 0.1% TFA) to afford the product as a TFA salt. $^1$H NMR (400 MHz, Methanol-$d_4$) δ 7.94 (dd, J=21.1, 1.3 Hz, 1H), 7.27-7.18 (m, 4H), 7.17-7.09 (m, 1H), 6.93 (d, J=4.6 Hz, 1H), 5.96-5.79 (m, 2H), 5.71 (dd, J=4.6, 2.2 Hz, 1H), 4.62-4.39 (m, 2H), 4.37-4.24 (m, 1H), 3.88 (ddd, J=19.6, 9.8, 7.1 Hz, 1H), 3.81 (d, J=3.0 Hz, 3H), 3.65 (d, J=17.3 Hz, 3H), 3.25 (ddd, J=14.4, 6.2, 4.4 Hz, 1H), 3.14 (dd, J=14.6, 7.5 Hz, 1H), 2.66 (dpd, J=21.1, 7.2, 4.7 Hz, 2H), 1.34-1.27 (m, 3H), 1.27-1.15 (m, 12H). $^{19}$F NMR (376 MHz, Methanol-$d_4$) δ −77.65. $^{31}$P NMR (162 MHz, Methanol-$d_4$) δ 3.34 (d, J=2.3 Hz). LCMS: MS m/z=774.25 [M+1], $t_R$=1.10 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=3.82 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

trile, 1.8 min-1.85 min 100%-2% acetonitrile, 1.85 min-2.00 min 2% ACN at 1800 μL/min. HPLC: $t_R$=5.424 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Example 236. (2R,3S,4S,5S)-5-(4-aminopyrrolo[2,1-f][1,2,4]triazin-7-yl)-2-((((((S)-1-(benzyloxy)-1-oxopropan-2-yl)amino)(phenoxy)phosphoryl)oxy)methyl)-2-cyanotetrahydrofuran-3,4-diyl bis(2-methylpropanoate)

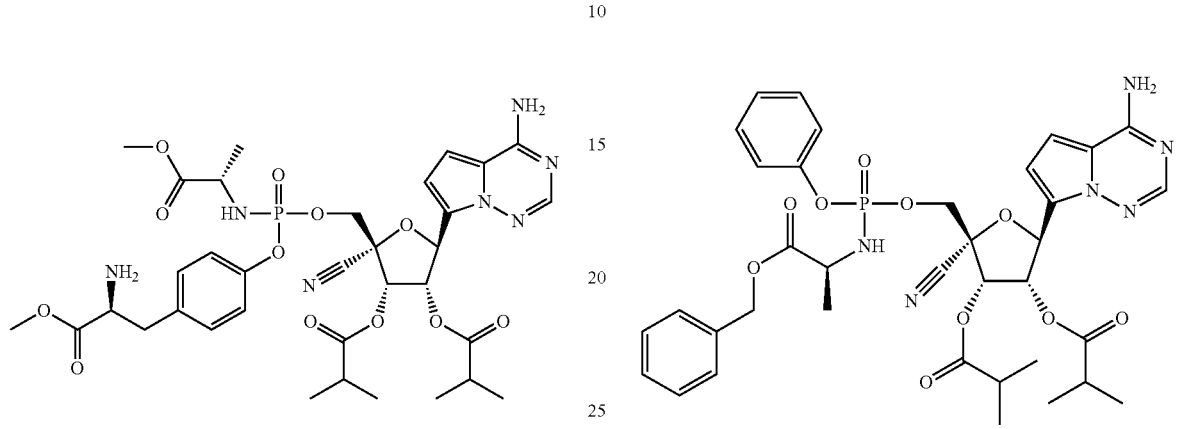

Example 37 (15 mg, 0.024 mmol) was dissolved in 1.5 mL anhydrous THF and stirred at RT. Isobutyric anhydride (8 uL, 0.048 mmol) and DMAP (0.3 mg, 0.0024 mmol) were added, and the reaction was stirred for 30 mins.

Methanol (500 uL) was added and stirred for 30 mins. Reaction was then diluted with EtOAc (10 mL) and washed with saturated aqueous sodium bicarbonate solution (2×5 mL) followed with brine (5 mL). Organic extract was dried over anhydrous sodium sulfate and then concentrated under reduced pressure. The crude residue was purified via SiO$_2$ column chromatography (4 g SiO$_2$ Combiflash HP Gold Column, 0-100% ethyl acetate/hexanes). Fractions were combined and concentrated under reduced pressure. Residue was dissolved in MeCN, diluted with water and freeze-dried to give the product. $^1$H NMR (400 MHz, methanol-$d_4$) δ 7.81 (m, 1H), 7.36-7.22 (m, 7H), 7.21-7.08 (m, 3H), 6.83 (m, 1H), 6.74 (m, 1H), 5.93 (m, 1H), 5.82 (m, 1H), 5.67 (m, 1H), 5.11-4.94 (m, 2H), 4.53-4.34 (m, 2H), 4.01-3.81 (m, 1H), 2.72-2.54 (m, 2H), 1.33-1.10 (m, 15H). $^{31}$P NMR (162 MHz, methanol-$d_4$) δ 3.03, 2.97. LCMS: MS m/z=749.5 [M+1], 747.1 [M−1], $t_R$=1.75 min; LC system: Thermo Dionex Ultimate 3000 UHPLC; Column: Phenomenex Kinetex 2.6μ C18 100 A, 50×3 mm; Solvents: A: Water with 0.1% acetic acid, B: Acetonitrile with 0.1% acetic acid; Gradient: 0 min-0.3 min 5% B, 0.3 min-1.5 min 5-100% B, 1.5 min-2 min 100% B, 2 min-2.2 min 100-5% B at 2 mL/min. HPLC: $t_R$=3.57 min; HPLC system: Agilent 1100 series; Column: Phenomenex Gemini 5μ C18 110A, 50×4.6 mm; Solvent: A: Water with 0.1% TFA, B: Acetonitrile with 0.1% TFA; Gradient: 2-98% B in 5 min at 2 mL/min. HPLC: $t_R$=6.128, 6.162 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 237. (2R,3S,4S,5S)-5-(4-aminopyrrolo[2,1-f][1,2,4]triazin-7-yl)-2-cyano-2-((((((S)-1-(3-morpholinopropoxy)-1-oxopropan-2-yl)amino)(phenoxy)phosphoryl)oxy)methyl) tetrahydrofuran-3,4-diyl bis(2-methylpropanoate)

Example 238. (2R,3S,4S,5S)-5-(4-aminopyrrolo[2,1-f][1,2,4]triazin-7-yl)-2-cyano-2-((((((S)-1-(cyclopropylmethoxy)-1-oxopropan-2-yl)amino)(phenoxy)phosphoryl)oxy)methyl) tetrahydrofuran-3,4-diyl bis(2-methylpropanoate)

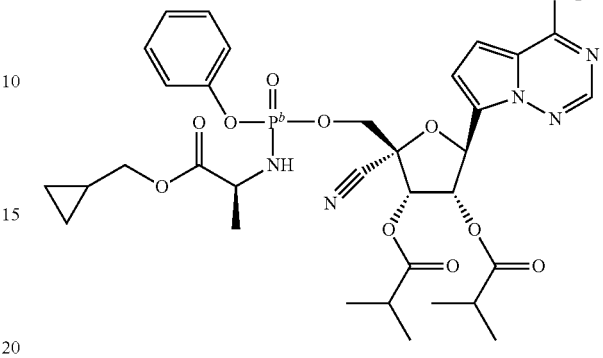

Dissolved Example 10 (84 mg, 0.15 mmol) in 3 mL THF, to the solution were added isobutyric anhydride (51 mg, 0.32 mmol) and DMAP (6 mg, 0.05 mmol). The resulting mixture was stirred at RT for 30 mins and the reaction was quenched with MeOH and then solvent was evaporated. The residue was purified with Prep HPLC to afford the product. $^1$H NMR (400 MHz, Methanol-d4) δ 7.83 (s, 1H), 7.34-7.25 (m, 2H), 7.24-7.12 (m, 3H), 6.83 (d, J=4.6 Hz, 1H), 6.73 (d, J=4.5 Hz, 1H), 5.90 (d, J=5.9 Hz, 1H), 5.79 (dd, J=5.9, 4.7 Hz, 1H), 5.66 (d, J=4.7 Hz, 1H), 4.44 (dd, J=5.7, 1.3 Hz, 2H), 3.96-3.74 (m, 3H), 2.63 (dp, J=17.0, 7.0 Hz, 2H), 1.34-1.12 (m, 15H), 1.05 (dqd, J=12.5, 7.6, 3.8 Hz, 1H), 0.54-0.44 (m, 2H), 0.26-0.19 (m, 2H). $^{31}$P NMR (162 MHz, Methanol-d4) δ 3.00. LCMS: MS m/z=713.12 [M+1], $t_R$=1.72 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 L/min. HPLC: $t_R$=3.44 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

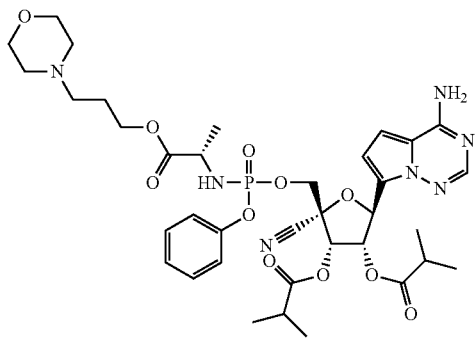 [SMILES: CC(C)C(=O)O[C@H]1[C@H](c2ccc3c(N)ncnn23)O[C@](C#N)(COP(=O)(N[C@@H](C)C(=O)OCCCN2CCOCC2)Oc2ccccc2)[C@H]1OC(=O)C(C)C]

Isobutyric anhydride (29.0 μL, 0.17 mmol) was added to a solution of Example 67 (78.4 mg, 0.10 mmol) and 4-dimethylaminopyridine (1.8 mg, 0.02 mmol) in 2-methyl tetrahydrofuran (2.0 mL) at RT. After 10 min, the reaction mixture was diluted with ethyl acetate (20 mL) and the resulting mixture was washed with saturated aqueous sodium carbonate solution (2×15 mL) and brine (20 mL). The organic layer was dried over anhydrous sodium sulfate and concentrated under reduced pressure. 100 mg of the resulting crude residue was subjected preparatory HPLC (Phenomenex Gemini 10 u C18 110 Å AXIA 250×21.2 mm column, 30-70% acetonitrile/water gradient with 0.1% TFA) to silica gel chromatography eluting with 0-25% methanol in dichloromethane to afford the product as the trifluoroacetate salt. $^1$H NMR (400 MHz, Acetonitrile-d3) δ 7.96 (d, J=2.6 Hz, 1H), 7.41-7.27 (m, 3H), 7.27-7.15 (m, 3H), 6.95 (dd, J=6.1, 4.7 Hz, 2H), 5.75 (m, 4H), 4.57-4.38 (m, 4H), 4.16-3.98 (m, 3H), 3.94 (d, J=12.9 Hz, 2H), 3.79 (s, 1H), 3.38 (d, J=12.1 Hz, 2H), 3.10 (q, J=7.2 Hz, 2H), 2.94 (s, 1H), 2.75-2.57 (m, 2H), 2.00 (d, J=13.8 Hz, 3H), 1.38-1.13 (m, 12H). $^{31}$P NMR (162 MHz, CD$_3$CN) δ −1.45, −1.59. LCMS: MS m/z=786.41 [M+1], $t_R$=1.24 min; LC system: Thermo Accela 1250 UHPLC; MS system: Thermo LCQ Fleet; Column: Kinetex 2.6μ 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.72 min; HPLC system: Agilent 1100 series; Column: Kinetx 2.6 u 100 A C18, 100 mm×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Example 239. ((2R,3S,4S,5S)-5-(4-aminopyrrolo[2,1-f][1,2,4]triazin-7-yl)-2-cyano-3,4-bis(isobutyryloxy)tetrahydrofuran-2-yl)methyl ((S)-1-(2-ethylbutoxy)-1-oxopropan-2-yl)phosphoramidate

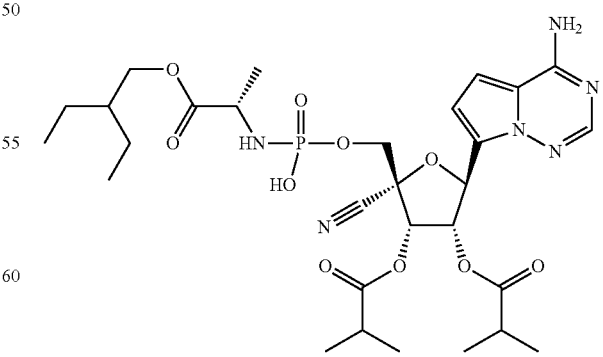

Sodium bicarbonate (50 mg) and Pd/C (10% wt, 40 mg) were added to a solution of Example 85 (38 mg, 0.050 mmol) in methanol (2.0 mL) at RT. The reaction vessel was evacuated and refilled with hydrogen gas (3×). After 10 min the resulting mixture was filtered through celite and concentrated under reduced pressure. The crude residue was subjected to preparatory HPLC (Gemini 5 u C18 100 Å 100×30 mm column) eluting with 10-100% acetonitrile in water to afford the product. $^1$H NMR (400 MHz, methanol-$d_4$) δ 7.83 (s, 1H), 6.87 (app q, J=4.6 Hz, 2H), 5.81 (d, J=5.7 Hz, 1H), 5.76 (t, J=5.4 Hz, 1H), 5.68 (d, J=5.2 Hz, 1H), 4.19-4.10 (m, 2H), 4.02 (dd, J=10.9, 5.7 Hz, 1H), 3.91-3.81 (m, 2H), 2.68 (h, J=7.0 Hz, 1H), 2.58 (h, J=7.0 Hz, 1H), 1.51-1.20 (m, 14H), 1.16 (d, J=7.0 Hz, 3H), 1.13 (d, J=7.0 Hz, 3H), 0.86 (td, J=7.5, 1.1 Hz, 6H). $^{31}$P NMR (162 MHz, methanol-$d_4$) δ 5.04 (s). LCMS: MS m/z=667.05 [M+1], $t_R$=1.55 min; LC system: Thermo Accela 1250 UHPLC; MS system: Thermo LCQ Fleet; Column: Kinetex 2.6µ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: $t_R$=5.955 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 240. Single Diastereomer of (2R,3S,4S, 5S)-5-(4-Aminopyrrolo[2,1-f][1,2,4]triazin-7-yl)-2-cyano-2-((((((S)-1-oxo-1-(((S)-tetrahydrofuran-3-yl)oxy)propan-2-yl)amino) (phenoxy)phosphoryl)oxy)methyl)tetrahydrofuran-3,4-diyl bis(2-methylpropanoate)

quenched by adding methanol (0.5 mL), and purified by preparative HPLC (Phenominex Synergi 4 u Hydro-RR 80 Å 150×30 mm column, 10-100% acetonitrile/water gradient) to afford the product. $^1$H NMR (400 MHz, Acetonitrile-d3) δ 7.90 (s, 1H), 7.40-7.30 (m, 2H), 7.24-7.15 (m, 3H), 6.82-6.69 (m, 2H), 6.40 (s, 2H), 5.86 (d, J=6.0 Hz, 1H), 5.81 (dd, J=6.0, 4.5 Hz, 1H), 5.67 (d, J=4.5 Hz, 1H), 5.14 (ddt, J=6.3, 4.5, 1.8 Hz, 1H), 4.50-4.35 (m, 2H), 3.90 (m, 1H), 3.81-3.62 (m, 5H), 2.64 (m, 2H), 2.05 (m, 1H), 1.91-1.81 (m, 1H), 1.25 (dd, J=7.1, 1.0 Hz, 3H), 1.21 (m, 6H), 1.18 (d, J=7.0 Hz, 3H), 1.15 (d, J=7.0 Hz, 3H). $^{31}$P NMR (162 MHz, Acetonitrile-d3) δ 2.47. LCMS: m/z=729.17 (M+H), $t_R$=1.37 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=5.47 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 241. Single Diastereomer of (2R,3S,4S, 5S)-5-(4-Aminopyrrolo[2,1-f][1,2,4]triazin-7-yl)-2-cyano-2-((((((S)-1-oxo-1-(((S)-tetrahydrofuran-3-yl)oxy)propan-2-yl)amino) (phenoxy)phosphoryl)oxy)methyl)tetrahydrofuran-3,4-diyl bis(2-methylpropanoate)

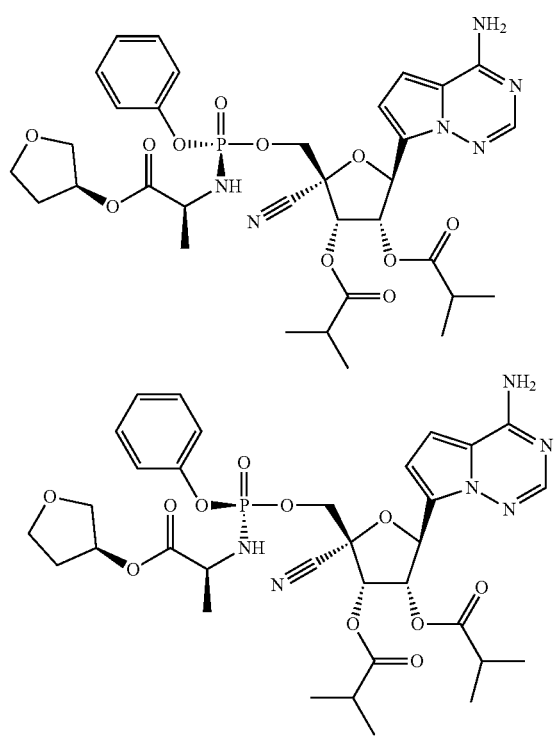

or

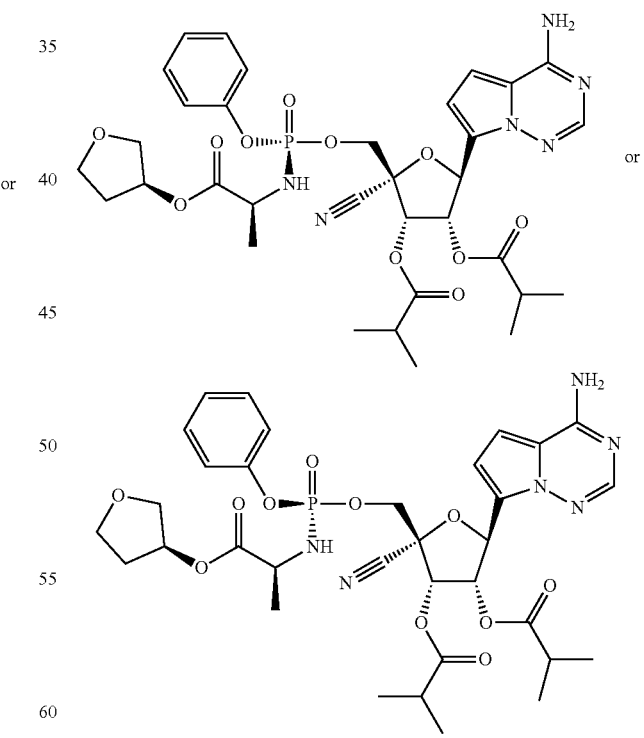

or

To a mixture of Example 66 (28 mg, 0.048 mmol) and isobutyric anhydride (0.034 mL, 0.38 mmol) in THF (2 mL) was added DMAP (5.8 mg, 0.048 mmol). The resulting mixture was stirred at room temperature for 5 min and To a mixture of Example 65 (37 mg, 0.063 mmol) and isobutyric anhydride (0.031 mL, 0.190 mmol) in THF (2 mL) was added DMAP (4 mg, 0.033 mmol). The resulting mixture was stirred at room temperature for 5 min and quenched by adding methanol (0.5 mL), and purified by preparative HPLC (Phenominex Synergi 4 u Hydro-RR 80 Å 150×30 mm column, 10-100% acetonitrile/water gradient) to afford the product. $^1$H NMR (400 MHz, Acetonitrile-d3) δ 7.89 (s, 1H), 7.37-7.30 (m, 2H), 7.22-7.15 (m, 3H), 6.77 (q, J=4.6 Hz, 2H), 6.40 (s, 2H), 5.90 (d, J=6.0 Hz, 1H), 5.84 (dd, J=6.0, 4.4 Hz, 1H), 5.69 (d, J=4.4 Hz, 1H), 5.20 (m, 1H), 4.49 (dd, J=11.2, 6.1 Hz, 1H), 4.44-4.34 (m, 2H), 3.92-3.62 (m, 5H), 2.65 (m, 2H), 2.12 (m, 1H), 1.92-1.83 (m, 1H), 1.22 (m, 9H), 1.18 (d, J=7.0 Hz, 3H), 1.15 (d, J=7.0 Hz, 3H). $^{31}$P NMR (162 MHz, Acetonitrile-d3) δ 2.37. LCMS: m/z=729.16 (M+H), $t_R$=1.36 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.41 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 242. ((2R,3S,4S,5S)-5-(4-aminopyrrolo[2,1-f][1,2,4]triazin-7-yl)-2-cyano-3,4-bis(isobutyryloxy)tetrahydrofuran-2-yl)methyl ((S)-1-methoxy-1-oxopropan-2-yl)phosphoramidate

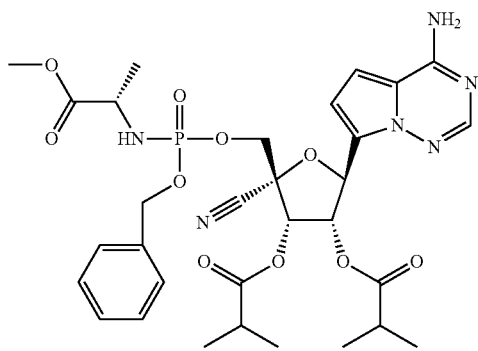 [SMILES: COC(=O)[C@H](C)NP(=O)(OCc1ccccc1)OC[C@@]1(C#N)O[C@@H](c2ccc3c(N)ncnn23)[C@H](OC(=O)C(C)C)[C@@H]1OC(=O)C(C)C]

(2R,3S,4S,5S)-5-(4-aminopyrrolo[2,1-f][1,2,4]triazin-7-yl)-2-((((benzyloxy)(((S)-1-methoxy-1-oxopropan-2-yl)amino)phosphoryl)oxy)methyl)-2-cyanotetrahydrofuran-3,4-diyl bis(2-methylpropanoate). Isobutyric anhydride (0.055 mL, 0.33 mmol) and 4-dimethylaminopyridine (3 mg, 0.03 mmol) were sequentially added to a solution of Example 76 (91 mg, 0.167 mmol) in 2-methyl-tetrahydrofuran (2.0 mL) at RT. After 3.5 h, the reaction mixture was directly subjected to silica gel chromatography eluting with 0-100% ethyl acetate in hexanes to afford the product. $^1$H NMR (400 MHz, methanol-d$_4$) δ 7.82 (s, 0.7H), 7.75 (s, 0.3H), 7.38-7.23 (m, 5H), 6.85-6.81 (m, 1H), 6.78-6.74 (m, 1H), 5.98 (d, J=5.8 Hz, 0.3H), 5.91 (d, J=5.9 Hz, 0.7H), 5.88-5.81 (m, 1H), 5.70-5.66 (m, 1H), 5.06-4.97 (m, 2H), 4.44-4.27 (m, 2H), 3.86-3.64 (m, 1H), 3.61 (s, 2.1H), 3.60 (s, 0.9H), 2.71-2.53 (m, 2H), 1.31-1.11 (m, 15H). $^{31}$P NMR (162 MHz, methanol-d$_4$) δ 7.72 (s), 7.60 (s). LCMS: MS m/z=687.22 [M+1], $t_R$=1.38 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.27 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

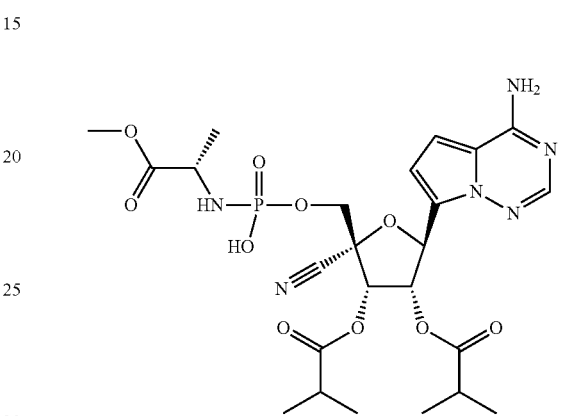

((2R,3S,4S,5S)-5-(4-aminopyrrolo[2,1-f][1,2,4]triazin-7-yl)-2-cyano-3,4-bis(isobutyryloxy)tetrahydrofuran-2-yl)methyl ((S)-1-methoxy-1-oxopropan-2-yl)phosphoramidate. Sodium Bicarbonate (50 mg) and Pd/C (10% wt, 50 mg) were added to a solution of (2R,3S,4S,5S)-5-(4-aminopyrrolo[2,1-f][1,2,4]triazin-7-yl)-2-((((benzyloxy)(((S)-1-methoxy-1-oxopropan-2-yl)amino)phosphoryl)oxy)methyl)-2-cyanotetrahydrofuran-3,4-diyl bis(2-methylpropanoate) (70 mg, 0.102 mmol) in methanol (2.0 mL) at RT. The reaction vessel was evacuated and refilled with hydrogen gas (3×). After 10 min the resulting mixture was filtered through celite and concentrated under reduced pressure. The crude residue was subjected to preparatory HPLC (Gemini 5 u C18 100 Å 100×30 mm column) eluting with 10-100% acetonitrile in water to afford the product. $^1$H NMR (400 MHz, methanol-d$_4$) δ 7.83 (s, 1H), 6.88 (d, J=4.6 Hz, 1H), 6.86 (d, J=4.6 Hz, 1H), 5.82 (d, J=5.7 Hz, 1H), 5.77 (t, J=5.4 Hz, 1H), 5.68 (d, J=5.2 Hz, 1H), 4.14 (qd, J=10.8, 4.4 Hz, 2H), 3.87-3.75 (m, 1H), 3.61 (s, 3H), 2.68 (h, J=7.0 Hz, 1H), 2.58 (p, J=7.0 Hz, 1H), 1.27-1.21 (m, 9H), 1.16 (d, J=7.0 Hz, 3H), 1.13 (d, J=7.0 Hz, 3H). $^{31}$P NMR (162 MHz, methanol-d$_4$) δ 5.02 (s). LCMS: MS m/z=597.17 [M+1], $t_R$=1.19 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=5.013 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 243. Single Diastereomer of (2R,3S,4S, 5S)-5-(4-Aminopyrrolo[2,1-f][1,2,4]triazin-7-yl)-2-cyano-2-((((((S)-1-oxo-1-(((R)-tetrahydrofuran-3-yl)oxy)propan-2-yl)amino)(phenoxy)phosphoryl)oxy)methyl)tetrahydrofuran-3,4-diyl bis(2-methylpropanoate)

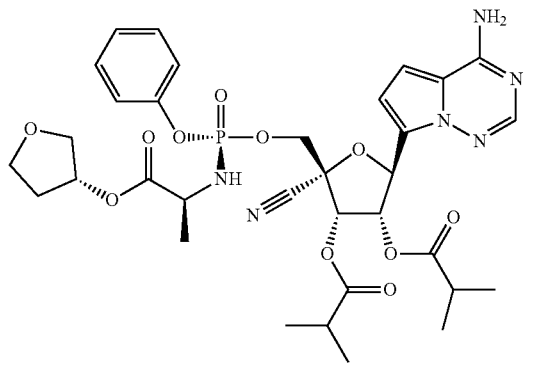

or

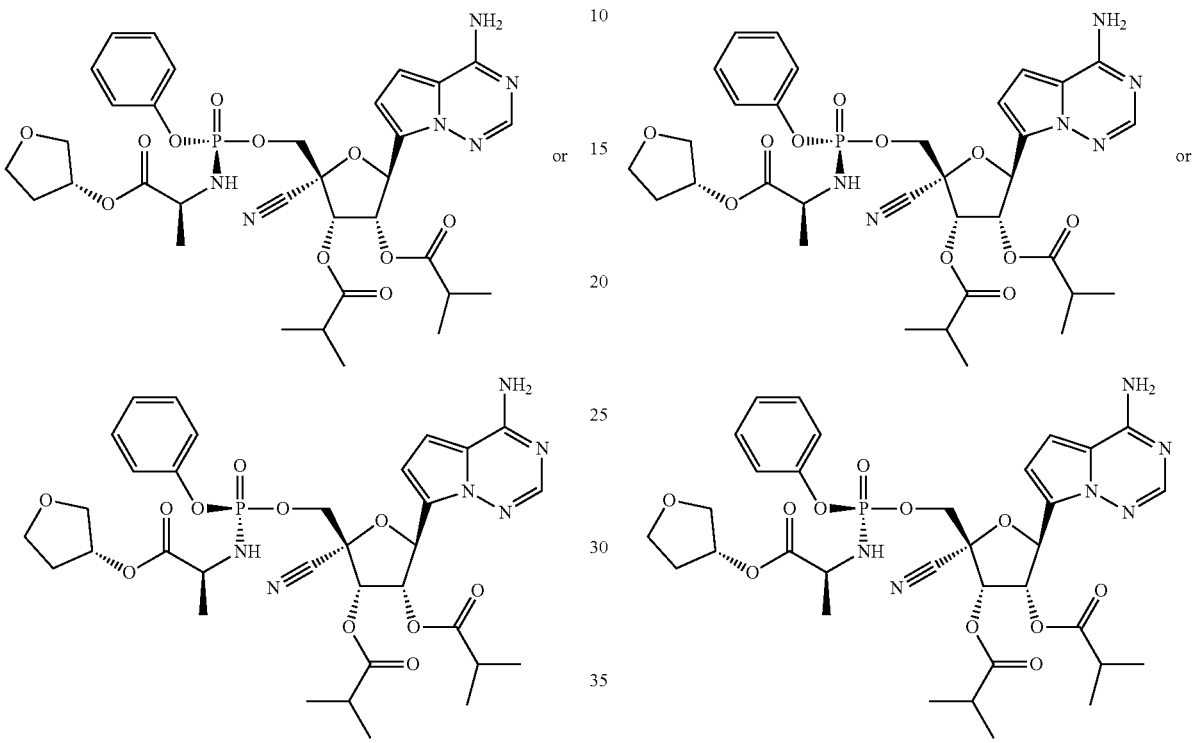

To a mixture of Example 70 (32 mg, 0.054 mmol) and isobutyric anhydride (0.027 mL, 0.163 mmol) in THF (2 mL) was added DMAP (6.6 mg, 0.048 mmol). The resulting mixture was stirred at room temperature for 5 min and quenched by adding methanol (0.5 mL), and purified by preparative HPLC (Phenominex Synergi 4 u Hydro-RR 80 Å 150×30 mm column, 10-100% acetonitrile/water gradient) to afford the product. $^1$H NMR (400 MHz, Acetonitrile-d3) δ 7.91 (s, 1H), 7.40-7.29 (m, 2H), 7.26-7.15 (m, 3H), 6.78-6.74 (m, 2H), 6.39 (s, 2H), 5.86 (d, J=5.9 Hz, 1H), 5.81 (dd, J=6.0, 4.5 Hz, 1H), 5.68 (d, J=4.5 Hz, 1H), 5.16 (ddt, J=6.2, 4.1, 1.8 Hz, 1H), 4.51-4.34 (m, 3H), 3.91 (ddt, J=16.8, 9.8, 7.1 Hz, 1H), 3.83-3.63 (m, 4H), 2.65 (m, 2H), 2.10 (dtd, J=14.5, 8.3, 6.4 Hz, 1H), 1.90-1.77 (m, 1H), 1.26 (dd, J=7.1, 1.0 Hz, 3H), 1.22 (t, J=6.9 Hz, 6H), 1.18 (d, J=7.0 Hz, 3H), 1.15 (d, J=7.0 Hz, 3H). $^{31}$P NMR (162 MHz, Acetonitrile-d3) δ 2.44. LCMS: m/z=729.16 (M+H), $t_R$=1.37 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=5.47 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 244. Single Diastereomer of (2R,3S,4S, 5S)-5-(4-Aminopyrrolo[2,1-f][1,2,4]triazin-7-yl)-2-cyano-2-((((((S)-1-oxo-1-(((R)-tetrahydrofuran-3-yl)oxy)propan-2-yl)amino)(phenoxy)phosphoryl)oxy)methyl)tetrahydrofuran-3,4-diyl bis(2-methylpropanoate)

To a mixture of Example 69 (19 mg, 0.032 mmol) and isobutyric anhydride (0.016 mL, 0.097 mmol) in THF (2 mL) was added DMAP (4 mg, 0.033 mmol). The resulting mixture was stirred at room temperature for 5 min and quenched by adding methanol (0.5 mL), and purified by preparative HPLC (Phenominex Synergi 4 u Hydro-RR 80 Å 150×30 mm column, 10-100% acetonitrile/water gradient) to afford the product. $^1$H NMR (400 MHz, Acetonitrile-d3) δ 7.89 (s, 1H), 7.41-7.27 (m, 2H), 7.26-7.16 (m, 3H), 6.86-6.71 (m, 2H), 6.37 (s, 2H), 5.89 (d, J=6.0 Hz, 1H), 5.84 (dd, J=6.0, 4.4 Hz, 1H), 5.69 (d, J=4.4 Hz, 1H), 5.21 (ddt, J=6.3, 4.6, 1.7 Hz, 1H), 4.49 (dd, J=11.2, 6.1 Hz, 1H), 4.43-4.27 (m, 2H), 3.92-3.64 (m, 5H), 2.65 (m, 2H), 2.19-2.07 (m, 1H), 1.93-1.82 (m, 1H), 1.22 (m, 9H), 1.19 (d, J=7.0 Hz, 3H), 1.15 (d, J=7.0 Hz, 3H). $^{31}$P NMR (162 MHz, Acetonitrile-d3) δ 2.38. LCMS: m/z=729.20 (M+H), $t_R$=1.36 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=5.41 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 245. Resolution of the Sp and Rp Diastereomers of Example 162

The mixture of Example 162 was separated by SFC IA (12×250 mm, 5 μm, 15% MeOH) to afford the diastereomers:

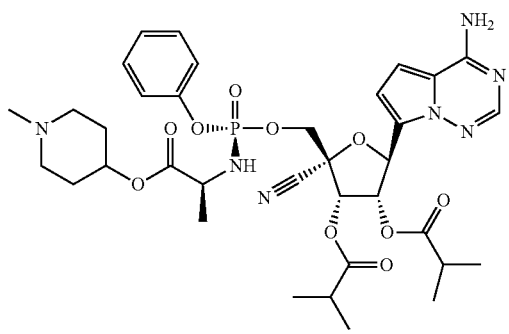

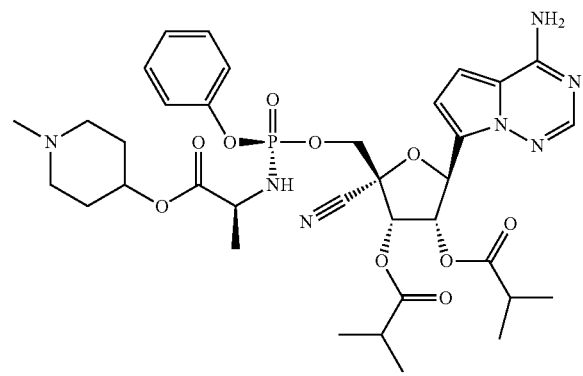

Example 246

First eluting diastereomer: H NMR (400 MHz, Acetonitrile-d3) δ 7.90 (s, 1H), 7.40-7.31 (m, 2H), 7.26-7.12 (m, 3H), 6.83-6.65 (m, 2H), 6.34 (s, 2H), 5.90 (d, J=6.0 Hz, 1H), 5.83 (dd, J=6.0, 4.5 Hz, 1H). 5.69 (d, J=4.5 Hz, 1H), 4.67 (dq, J=8.5, 4.2 Hz, 1H), 4.49 (dd, J=11.2, 6.1 Hz, 1H), 4.40 (dd, J=11.2, 5.4 Hz, 1H), 4.31-4.23 (m, 1H), 3.84 (ddd, J=10.0, 9.0, 7.1 Hz, 1H), 2.65 (dp, J=26.9, 7.0 Hz, 2H), 2.58-2.39 (m, 2H), 2.25-2.14 (m, 5H), 1.79 (d, J=6.8 Hz, 2H), 1.61 (dtd, J=12.6, 8.6, 3.8 Hz, 2H), 1.22 (m, 9H), 1.19 (d, J=7.0 Hz, 3H), 1.15 (d, J=7.0 Hz, 3H). $^{31}$P NMR (162 MHz, Acetonitrile-d3) 2.41. LCMS: m/z=756.17, $t_R$=1.13 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.68 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 247

Second eluting diastereomer: $^1$H NMR (400 MHz, Acetonitrile-d3) δ 7.91 (s, 1H), 7.34 (dd, J=8.9, 6.9 Hz, 2H), 7.25-7.15 (m, 3H), 6.76 (s, 2H), 6.36 (s, 2H), 5.86 (d, J=6.0 Hz, 1H), 5.82-5.77 (m, 1H), 5.67 (d, J=4.5 Hz, 1H), 4.65 (dt, J=8.0, 3.9 Hz, 1H), 4.45 (dd, J=11.2, 6.7 Hz, 1H), 4.39 (dd, J=11.3, 5.8 Hz, 1H), 4.33 (dd, J=12.1, 10.0 Hz, 1H), 3.97-3.81 (m, 1H), 2.78-2.36 (m, 4H), 2.20 (s, 5H), 1.87-1.73 (m, 2H), 1.59 (dp, J=12.7, 4.3 Hz, 2H), 1.27 (dd, J=7.1, 0.9 Hz, 3H), 1.22 m, 6H), 1.18 (d, J=7.1 Hz, 3H), 1.15 (d, J=7.0 Hz, 3H). $^{31}$P NMR (162 MHz, Acetonitrile-d3) δ 2.48. LCMS: m/z=756.18, $t_R$=1.13 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.71 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 248. (2R,3S,4S,5S)-5-(4-aminopyrrolo[2,1-f][1,2,4]triazin-7-yl)-2-cyano-2-((((((S)-1-ethoxy-1-oxopropan-2-yl)amino)(phenoxy)phosphoryl)oxy)methyl)tetrahydrofuran-3,4-diyl bis(2-methylpropanoate)

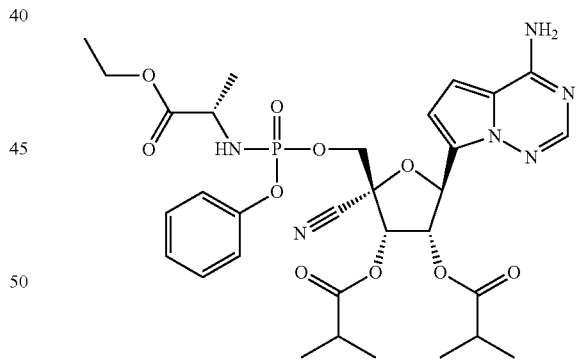

Isobutyric anhydride (85.2 μL, 0.51 mmol) was added to a solution of Example 35 of WO2015/069939 (165.2 mg, 0.30 mmol) and 4-dimethylaminopyridine (5.5 mg, 0.05 mmol) in 2-methyl tetrahydrofuran (6 mL) at RT. After 30 min, the reaction mixture was diluted with ethyl acetate (15 mL) and the resulting mixture was washed with saturated aqueous sodium carbonate solution (20 mL) and brine (20 mL). The organic layer was dried over anhydrous sodium sulfate and concentrated under reduced pressure. The crude residue was purified by silica gel chromatography eluting with 20-100% ethyl acetate in hexanes to afford the product. $^1$H NMR (400 MHz, Methanol-d$_4$) δ 7.82 (d, J=9.9 Hz, 1H), 7.35-7.27 (m, 2H), 7.23-7.13 (m, 3H), 6.85 (dd, J=7.5, 4.5

Hz, 1H), 6.76 (dd, J=11.1, 4.6 Hz, 1H), 5.95 (dd, J=23.4, 5.9 Hz, 1H), 5.83 (ddd, J=19.6, 5.9, 4.5 Hz, 1H), 5.68 (t, J=4.4 Hz, 1H), 4.58-4.37 (m, 2H), 4.16-3.96 (m, 2H), 3.94-3.76 (m, 1H), 2.77-2.55 (m, 2H), 1.31-1.14 (m, 18H). $^{31}$P NMR (162 MHz, Methanol-d4) δ 3.06. LCMS: MS m/z=687.13 [M+1], $t_R$=1.43 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.94 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Resolution of the Sp and Rp diastereomers. The product was purified via chiral SFC (Chiralpak IF, 5um, 4.6×150 mm, Methanol 30%).

Example 249. (2R,3S,4S,5S)-5-(4-aminopyrrolo[2,1-f][1,2,4]triazin-7-yl)-2-cyano-2-((((R)-(((S)-1-ethoxy-1-oxopropan-2-yl)amino)(phenoxy)phosphoryl)oxy)methyl) tetrahydrofuran-3,4-diyl bis(2-methylpropanoate)

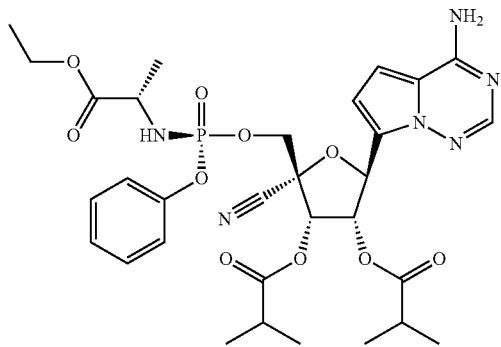 [SMILES: CCOC(=O)[C@H](C)N[P@@](=O)(OC[C@@]1(C#N)O[C@@H](c2ccc3c(N)ncnn23)[C@H](OC(=O)C(C)C)[C@@H]1OC(=O)C(C)C)Oc1ccccc1]

First Eluting Diastereomer of Example 248: $^1$H NMR (400 MHz, Methanol-d$_4$) δ 7.81 (s, 1H), 7.36-7.26 (m, 2H), 7.20-7.12 (m, 3H), 6.86 (d, J=4.5 Hz, 1H), 6.78 (d, J=4.5 Hz, 1H), 5.97 (d, J=5.9 Hz, 1H), 5.85 (dd, J=5.8, 4.4 Hz, 1H), 5.68 (d, J=4.4 Hz, 1H), 4.52 (dd, J=11.1, 5.8 Hz, 1H), 4.42 (dd, J=11.1, 4.9 Hz, 1H), 4.10 (qd, J=7.2, 2.5 Hz, 2H), 3.81 (dq, J=9.5, 7.3 Hz, 1H), 2.65 (dp, J=13.9, 7.0 Hz, 2H), 1.26-1.16 (m, 18H). $^{31}$P NMR (162 MHz, Methanol-d$_4$) δ 3.07. LCMS: MS m/z=687.14 [M+1], $t_R$=1.43 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.89 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Second Eluting Diastereomer of Example 248 is Example 144.

Example 250. (2R,3S,4S,5S)-5-(4-aminopyrrolo[2,1-f][1,2,4]triazin-7-yl)-2-cyano-2-((((((S)-1-methoxy-1-oxopropan-2-yl)amino)(phenoxy)phosphorothioyl)oxy)methyl) tetrahydrofuran-3,4-diyl bis(2-methylpropanoate)

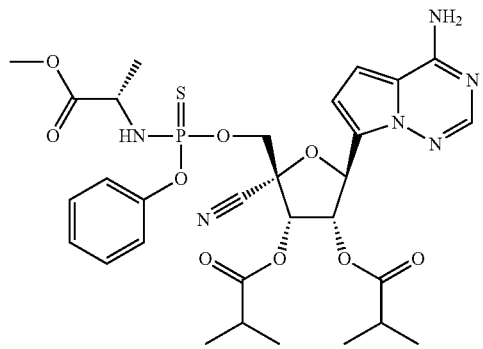 [SMILES: COC(=O)[C@H](C)NP(=S)(OC[C@@]1(C#N)O[C@@H](c2ccc3c(N)ncnn23)[C@H](OC(=O)C(C)C)[C@@H]1OC(=O)C(C)C)Oc1ccccc1]

Isobutyric anhydride (11 μL, 0.066 mmol) was added to a solution of Example 71 (18 mg, 0.33 mmol) in 2-methyltetrahydrofuran (1.0 mL) at RT. 4-dimethylaminopyridine (1 mg, 0.006 mmol) was then added. After 3 h, the reaction mixture was subjected to silica gel chromatography eluting with 0-100% ethyl acetate in hexanes to afford the product. $^1$H NMR (400 MHz, methanol-d$_4$) δ 8.21-7.78 (m, 1H), 7.38-6.98 (m, 5H), 7.00-6.65 (m, 2H), 5.99-5.42 (m, 3H), 4.66-4.20 (m, 3H), 3.75-3.41 (m, 3H), 2.75-2.53 (m, 2H), 1.47-1.02 (m, 15H). LCMS: MS m/z=688.98 [M+1], $t_R$=1.50 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 L/min. HPLC: $t_R$=4.195 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min.

Example 251. (2R,3S,4S,5S)-2-((((4-((S)-2-amino-3-isopropoxy-3-oxopropyl)phenoxy)(((S)-1-methoxy-1-oxopropan-2-yl)amino)phosphoryl)oxy)methyl)-5-(4-aminopyrrolo[2,1-f][1,2,4]triazin-7-yl)-2-cyanotetrahydrofuran-3,4-diyl bis(2-methylpropanoate)

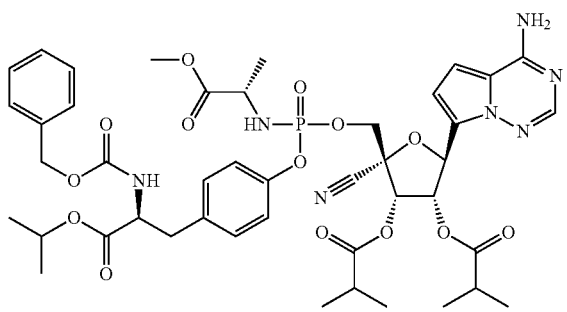 [SMILES: COC(=O)[C@H](C)NP(=O)(OC[C@@]1(C#N)O[C@@H](c2ccc3c(N)ncnn23)[C@H](OC(=O)C(C)C)[C@@H]1OC(=O)C(C)C)Oc1ccc(C[C@H](NC(=O)OCc2ccccc2)C(=O)OC(C)C)cc1]

(2R,3S,4S,5S)-5-(4-aminopyrrolo[2,1-f][1,2,4]triazin-7-yl)-2-((((4-((S)-2-(((benzyloxy)carbonyl)amino)-3-isopropoxy-3-oxopropyl)phenoxy)(((S)-1-methoxy-1-oxopropan-2-yl)amino)phosphoryl)oxy)methyl)-2-cyanotetrahydrofuran-3,4-diyl bis(2-methylpropanoate). Isobutyric anhydride (29.0 μL, 0.17 mmol) was added to a solution of Example 73 (78.4 mg, 0.10 mmol) and 4-dimethylaminopyridine (1.8 mg, 0.02 mmol) in 2-methyl tetrahydrofuran (2.0 mL) at RT. After 10 min, the reaction mixture was diluted with ethyl acetate (20 mL) and the resulting mixture was washed with saturated aqueous sodium carbonate solution (2×15 mL) and brine (20 mL). The organic layer was dried over anhydrous sodium sulfate and concentrated under reduced pressure. The crude residue was purified by silica gel chromatography eluting with 0-100% ethyl acetate in hexanes to afford the product. $^1$H NMR (400 MHz, Methanol-$d_4$) δ 7.81 (d, J=17.1 Hz, 1H), 7.36-7.23 (m, 5H), 7.19-7.13 (m, 2H), 7.13-7.04 (m, 2H), 6.84 (t, J=4.4 Hz, 1H), 6.75 (d, J=4.6 Hz, 1H), 5.94 (dd, J=21.4, 5.9 Hz, 1H), 5.83 (ddd, J=15.4, 5.7, 4.6 Hz, 1H), 5.68 (dd, J=4.5, 1.4 Hz, 1H), 5.03 (d, J=4.1 Hz, 2H), 4.97 (p, J=12.2, 6.1 Hz, 1H), 4.57-4.28 (m, 3H), 3.97-3.73 (m, 1H), 3.62 (d, J=9.7 Hz, 3H), 3.10 (dd, J=14.1, 6.0 Hz, 1H), 2.91 (dd, J=14.0, 8.9 Hz, 1H), 2.74-2.55 (m, 2H), 1.31-1.13 (m, 21H). $^{31}$P NMR (162 MHz, Methanol-$d_4$) δ 3.04 (d, J=7.6 Hz). LCMS: MS m/z=936.26 [M+1], $t_R$=1.57 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=5.55 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

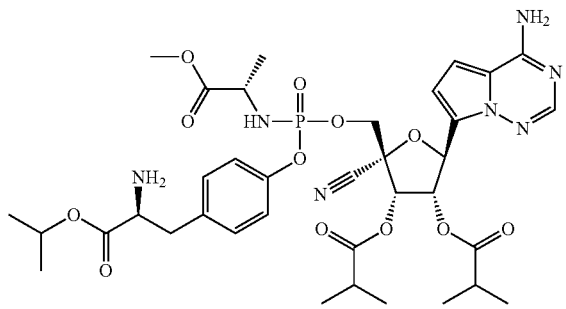 [SMILES: COC(=O)[C@H](C)NP(=O)(OC[C@@]1(C#N)O[C@@H](c2ccc3c(N)ncnn23)[C@H](OC(=O)C(C)C)[C@@H]1OC(=O)C(C)C)Oc1ccc(C[C@H](N)C(=O)OC(C)C)cc1]

(2R,3S,4S,5S)-2-((((4-((S)-2-amino-3-isopropoxy-3-oxopropyl)phenoxy)(((S)-1-methoxy-1-oxopropan-2-yl)amino)phosphoryl)oxy)methyl)-5-(4-aminopyrrolo[2,1-f][1,2,4]triazin-7-yl)-2-cyanotetrahydrofuran-3,4-diyl bis(2-methylpropanoate). Palladium on carbon (18.6 mg, 10 wt %) was added to a solution of (2R,3S,4S,5S)-5-(4-aminopyrrolo[2,1-f][1,2,4]triazin-7-yl)-2-((((4-((S)-2-(((benzyloxy)carbonyl)amino)-3-isopropoxy-3-oxopropyl)phenoxy)(((S)-1-methoxy-1-oxopropan-2-yl)amino)phosphoryl)oxy)methyl)-2-cyanotetrahydrofuran-3,4-diyl bis(2-methylpropanoate) (67.6 mg, 0.07 mmol) in tetrahydrofuran (5 mL) that was purged with argon. The mixture was then purged with hydrogen and stirred at RT. After 23 hr, the mixture was filtered through celite, the filter was rinsed with tetrahydrofuran, and the volatiles were removed under reduce pressure. The crude residue was subjected preparatory HPLC (Phenomenex Synergi 4 um Polar-RP 80 Å 150×21.2 mm column, 20-70% acetonitrile/water gradient with 0.1% TFA). The relevant product containing fractions were combined and the volatiles were removed under reduced pressure. Sodium bicarbonate (3 g) was added to the aqueous solution and the resulting mixture was extracted with ethyl acetate (2×100 mL). The combined organic layers were dried over anhydrous sodium sulfate and concentrated under reduced pressure. The residue was lyophilized to afford the product. $^1$H NMR (400 MHz, Methanol-$d_4$) δ 7.82 (d, J=11.6 Hz, 1H), 7.20-7.06 (m, 4H), 6.86 (dd, J=7.2, 4.6 Hz, 1H), 6.77 (t, J=4.7 Hz, 1H), 5.94 (dd, J=21.4, 5.9 Hz, 1H), 5.83 (ddd, J=18.0, 5.9, 4.6 Hz, 1H), 5.68 (t, J=4.6 Hz, 1H), 5.01-4.89 (m, 1H), 4.60-4.34 (m, 2H), 3.96-3.74 (m, 1H), 3.71-3.59 (m, 4H), 3.06-2.84 (m, 2H), 2.75-2.54 (m, 2H), 1.31-1.14 (m, 21H). $^{31}$P NMR (162 MHz, Methanol-d4) δ 3.07. LCMS: MS m/z=802.13 [M+1], $t_R$=1.16 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=3.97 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 mL/min.

Resolution of the Sp and Rp diastereomers. The product was purified via chiral SFC (Chiralpak IF, Sum, 4.6×150 mm, Ethanol 30%) to afford the diastereomers:

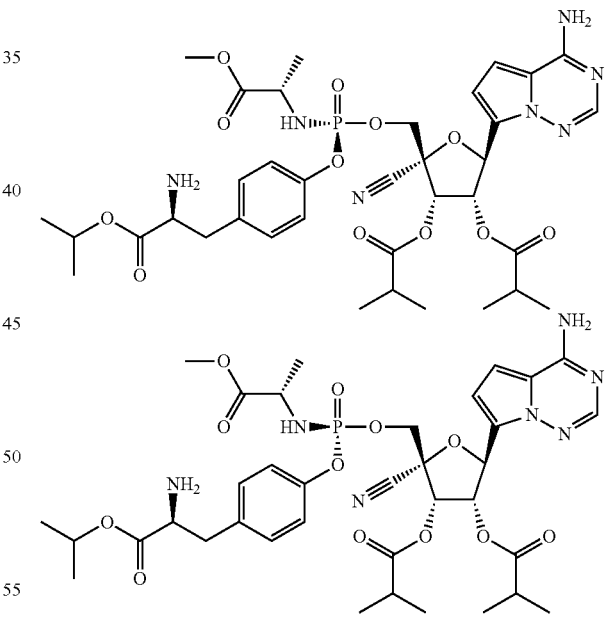

Example 252

First Eluting Diastereomer: $^1$H NMR (400 MHz, Methanol-$d_4$) δ 7.80 (s, 1H), 7.20-7.13 (m, 2H), 7.13-7.07 (m, 2H), 6.86 (d, J=4.5 Hz, 1H), 6.77 (d, J=4.6 Hz, 1H), 5.96 (d, J=5.9 Hz, 1H), 5.85 (dd, J=5.8, 4.4 Hz, 1H), 5.68 (d, J=4.4 Hz, 1H), 4.94 (p, J=6.2 Hz, 1H), 4.51 (dd, J=11.1, 5.8 Hz, 1H), 4.39 (dd, J=11.1, 4.8 Hz, 1H), 3.86-3.74 (m, 1H), 3.69-3.58 (m, 4H), 2.93 (qd, J=13.6, 6.6 Hz, 2H), 2.65 (dp, J=16.1, 7.0

Hz, 2H), 1.26-1.13 (m, 21H). $^{31}$P NMR (162 MHz, Methanol-d4) δ 3.07. LCMS: MS m/z=802.14 [M+1], $t_R$=1.19 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=4.04 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Example 253

Second Eluting Diastereomer: $^1$H NMR (400 MHz, Methanol-d4) δ 7.84 (s, 1H), 7.20-7.08 (m, 4H), 6.85 (d, J=4.5 Hz, 1H), 6.76 (d, J=4.5 Hz, 1H), 5.91 (d, J=5.9 Hz, 1H), 5.81 (dd, J=5.9, 4.7 Hz, 1H), 5.67 (d, J=4.7 Hz, 1H), 4.94 (p, J=6.2 Hz, 1H), 4.48-4.36 (m, 2H), 3.90 (dq, J=9.9, 7.4 Hz, 1H), 3.67-3.58 (m, 4H), 3.02-2.84 (m, 2H), 2.65 (dp, J=20.9, 7.0 Hz, 2H), 1.28 (dd, J=7.1, 1.0 Hz, 3H), 1.26-1.14 (m, 18H). $^{31}$P NMR (162 MHz, Methanol-d4) δ 3.06. LCMS: MS m/z=802.17 [M+1], $t_R$=1.18 min; LC system: Thermo Accela 1250 UHPLC; MS system: Thermo LCQ Fleet; Column: Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μL/min. HPLC: $t_R$=4.01 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-9.0 min 2-95% ACN, 9.0 min-10.0 min 95% ACN at 2 m/min.

Example 254. (2R,3S,4S,5S)-5-(4-aminopyrrolo[2,1-f][1,2,4]triazin-7-yl)-2-cyano-2-(((((S)-1-(cyclopentyloxy)-1-oxopropan-2-yl)amino)(phenoxy)phosphoryl)oxy)methyl) tetrahydrofuran-3,4-diyl bis(2-methylpropanoate)

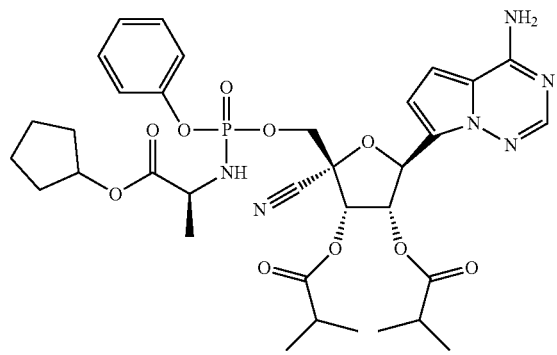 [SMILES: CC(C)C(=O)O[C@H]1[C@H](c2ccc3c(N)ncnn23)O[C@](C#N)(COP(=O)(N[C@@H](C)C(=O)OC2CCCC2)Oc2ccccc2)[C@H]1OC(=O)C(C)C]

Dissolved Intermediate 8 (75 mg, 0.27 mmol) and phenyl phosphorodichloridate (57 mg, 0.27 mmol) in 5 mL DCM, to the solution was added TEA (110 mg, 1 mmol) at 0° C. The resulting mixture was stirred for 30 mins after removal of ice bath. The reaction was again cooled to 0° C. and Intermediate 7 (45 mg, 0.1 mmol) was added followed by addition of tert-butyl magnesium bromide (0.27 mL, 1 M THF solution). The reaction was stirred for 10 min after the removal of ice bath. The reaction was quenched with NH$_4$Cl and then diluted with EtOAc, washed with NaHCO$_3$ and brine, the organic solvent was evaporated under vacuum. The residue was purified by prep HPLC to afford the product. $^1$H NMR (400 MHz, Methanol-d4) δ 7.82 (d, J=8.2 Hz, 1H), 7.41-7.24 (m, 4H), 7.24-7.05 (m, 6H), 6.75 (dd, J=11.8, 4.6 Hz, 1H), 5.93 (dd, J=18.2, 5.9 Hz, 1H), 5.81 (ddd, J=18.9, 5.9, 4.5 Hz, 1H), 5.67 (dd, J=6.1, 4.6 Hz, 1H), 5.20-4.98 (m, 3H), 4.56-4.32 (m, 2H), 3.87 (dddd, J=38.4, 16.3, 9.3, 7.1 Hz, 3H), 2.74-2.55 (m, 2H), 1.93-1.75 (m, 6H), 1.75-1.49 (m, 17H), 1.38-1.28 (m, 5H), 1.28-1.11 (m, 17H). $^{31}$P NMR (162 MHz, Methanol-d4) δ 9.85, 3.09. LCMS: MS m/z=727.27 [M+1], $t_R$=1.77 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 μL/min. HPLC: $t_R$=3.56 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 255. (2R,3S,4S,5S)-5-(4-aminopyrrolo[2,1-f][1,2,4]triazin-7-yl)-2-cyano-2-(((((S)-1-cyclopropoxy-1-oxopropan-2-yl)amino)(phenoxy)phosphoryl)oxy)methyl) tetrahydrofuran-3,4-diyl bis(2-methylpropanoate)

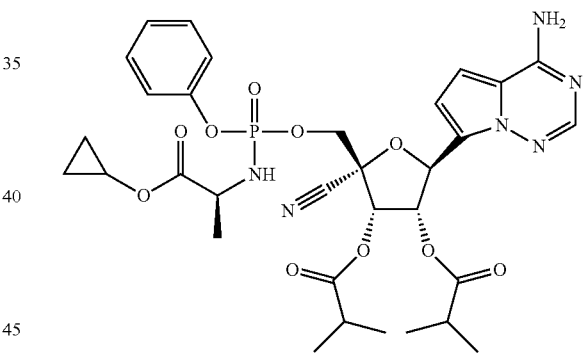

Dissolved Intermediate 9 (90 mg, 0.55 mmol) and phenyl phosphorodichloridate (115 mg, 0.55 mmol) in 5 mL DCM, to the solution was added TEA (165 mg, 2 mmol) at 0° C. The resulting mixture was stirred for 30 mins after removal of ice bath. The reaction was again cooled to 0° C. and Intermediate 7 (24 mg, 0.05 mmol) was added followed by addition of tert-butyl magnesium bromide (0.06 mL, 1 M THF solution). The reaction was stirred for 10 min after the removal of ice bath. The reaction was quenched with NH$_4$Cl and then diluted with EtOAc, washed with NaHCO$_3$ and brine, the organic solvent was evaporated under vacuum. The residue was purified by prep HPLC to afford the product. $^1$H NMR (400 MHz, Methanol-d4) δ 7.82 (d, J=8.7 Hz, 1H), 7.34-7.24 (m, 2H), 7.17 (dddd, J=15.3, 6.7, 2.5, 1.2 Hz, 3H), 6.86 (dd, J=7.9, 4.5 Hz, 1H), 6.76 (dd, J=9.7, 4.6 Hz, 1H), 5.93 (dd, J=19.6, 5.9 Hz, 1H), 5.82 (dddd, J=17.6, 5.9, 4.5 Hz, 1H), 5.67 (dd, J=4.5, 2.6 Hz, 1H), 4.54-4.34 (m, 2H), 3.88-3.70 (m, 1H), 2.75-2.53 (m, 2H), 1.28-1.09 (m, 15H), 0.70-0.51 (m, 4H). $^{31}$P NMR (162 MHz, Methanol-d4) δ 3.02, 3.00. LCMS: MS m/z=699.09 [M+1], $t_R$=1.69 min; LC system: Thermo Accela 1250 UHPLC; MS system: Thermo LCQ Fleet; Column: Kinetex 2.6µ XB-C18 100 A, 50×4.6 mm; Solvents: acetonitrile with 0.1% acetic acid, water with 0.1% acetic acid; Gradient: 0 min-2.0 min 2-100% acetonitrile, 2.0 min-3.05 min 100% acetonitrile, 3.05 min-3.2 min 100%-2% acetonitrile, 3.2 min-3.5 min 2% ACN at 2 µL/min. HPLC: $t_R$=3.36 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 256. (2R,3S,4S,5S)-5-(4-aminopyrrolo[2,1-f][1,2,4]triazin-7-yl)-2-cyano-2-((((((S)-1-(2-hydroxy-2-methylpropoxy)-1-oxopropan-2-yl)amino)(phenoxy)phosphoryl)oxy)methyl)tetrahydrofuran-3,4-diyl bis(2-methylpropanoate)

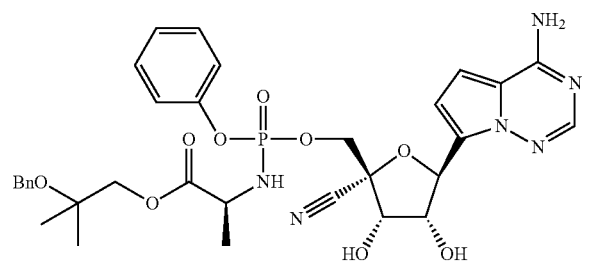 [SMILES: C[C@H](NP(=O)(OC[C@@]1(C#N)O[C@@H](c2ccc3c(N)ncnn23)[C@H](O)[C@@H]1O)Oc1ccccc1)C(=O)OCC(C)(C)OCc1ccccc1]

2-(Benzyloxy)-2-methylpropyl ((((2R,3S,4R,5S)-5-(4-aminopyrrolo[2,1-f][1,2,4]triazin-7-yl)-2-cyano-3,4-dihydroxytetrahydrofuran-2-yl)methoxy) (phenoxy)phosphoryl)-L-alaninate. To a mixture of Intermediate 1 (50 mg, 0.172 mmol), Intermediate 14 (143 mg, 0.223 mmol), and MgCl$_2$ (20 mg, 2.54 mmol) in DMF (5 mL) was added N,N-diisopropylethylamine (0.045 mL, 0.257 mmol) dropwise at room temperature. The resulting mixture was stirred at 50° C. for 15 h, purified by preparative HPLC (Phenominex Gemini-NX 10 u C18 110 Å 250×30 mm column, ACN 10 to 100% in water) to afford the product. LCMS m/z=681.07 (M+H), $t_R$=1.22 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min.

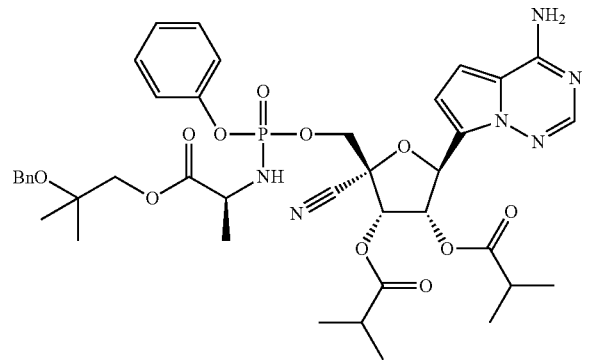 [SMILES: CC(C)C(=O)O[C@H]1[C@H](c2ccc3c(N)ncnn23)O[C@](C#N)(COP(=O)(N[C@@H](C)C(=O)OCC(C)(C)OCc2ccccc2)Oc2ccccc2)[C@H]1OC(=O)C(C)C]

(2R,3S,4S,5S)-5-(4-Aminopyrrolo[2,1-f][1,2,4]triazin-7-yl)-2-((((((S)-1-(2-(benzyloxy)-2-methylpropoxy)-1-oxopropan-2-yl)amino)(phenoxy)phosphoryl)oxy)methyl)-2-cyanotetrahydrofuran-3,4-diyl bis(2-methylpropanoate). To a solution of 2-(Benzyloxy)-2-methylpropyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate (60 mg, 0.060 mmol) in THF (3 mL) were added isobutyric anhydride (30 µL, 0.181 mmol) and then DMAP (4 mg, 0.033 mmol) at room temperature. The resulting mixture was stirred for 10 min monitoring with LCMS, quenched by adding methanol, and purified by prep HPLC (Phenominex Gemini-NX 10 u C18 110 Å 250×30 mm column, ACN 10 to 100% in water) to afford the product. LCMS m/z=821.18 (M+H), $t_R$=1.63 min: LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min.

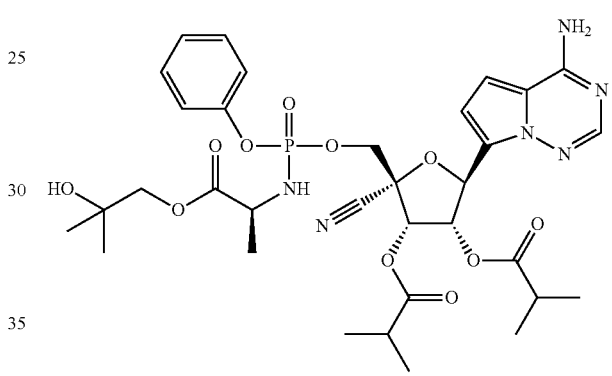

(2R,3S,4S,5S)-5-(4-aminopyrrolo[2,1-f][1,2,4]triazin-7-yl)-2-cyano-2-((((((S)-1-(2-hydroxy-2-methylpropoxy)-1-oxopropan-2-yl)amino)(phenoxy)phosphoryl)oxy)methyl)tetrahydrofuran-3,4-diyl bis(2-methylpropanoate). To a solution of (2R,3S,4S,5S)-5-(4-Aminopyrrolo[2,1-f][1,2,4]triazin-7-yl)-2-((((((S)-1-(2-(benzyloxy)-2-methylpropoxy)-1-oxopropan-2-yl)amino)(phenoxy)phosphoryl)oxy)methyl)-2-cyanotetrahydrofuran-3,4-diyl bis(2-methylpropanoate) (30 mg, 0.037 mmol) in THF (1 mL) was added 10% Pd/C (19 mg, 0.018 mmol). The resulting mixture was stirred at room temperature for 15 h under H$_2$ gas, filtered through celite, the filter cake washed with methanol several times, and the filtrate concentrated in vacuo, dissolved in ACN, and purified by prep. HPLC (Phenominex Gemini-NX 10 u C18 110 Å 250×30 mm column, ACN 10 to 100% in water) to give the product. $^1$H NMR (400 MHz, Acetonitrile-d3) δ 7.91 (s, 0.4H), 7.90 (s, 0.6H), 7.39-7.31 (m, 2H), 7.24-7.15 (m, 3H), 6.77 (m, 2H), 6.40 (m, 2H), 5.91 (m, 0.6H), 5.88-5.77 (m, 1.4H), 5.68 (m, 1H), 4.56-4.34 (m, 3H), 4.03-3.78 (m, 3H), 2.74-2.55 (m, 2H), 1.33-1.11 (m, 21H). $^{31}$P NMR (162 MHz, Acetonitrile-d3) δ 2.55, 2.48. MS m/z=731.14, $t_R$=1.35 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: $t_R$=5.30 min (53%) and 5.34 min (44%); HPLC system:

Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Resolution of the Sp and Rp diastereomers. The product (20 mg) was separated by IE SFC 5 um, 21×250 mm (30% ethanol) to afford the diastereomers:

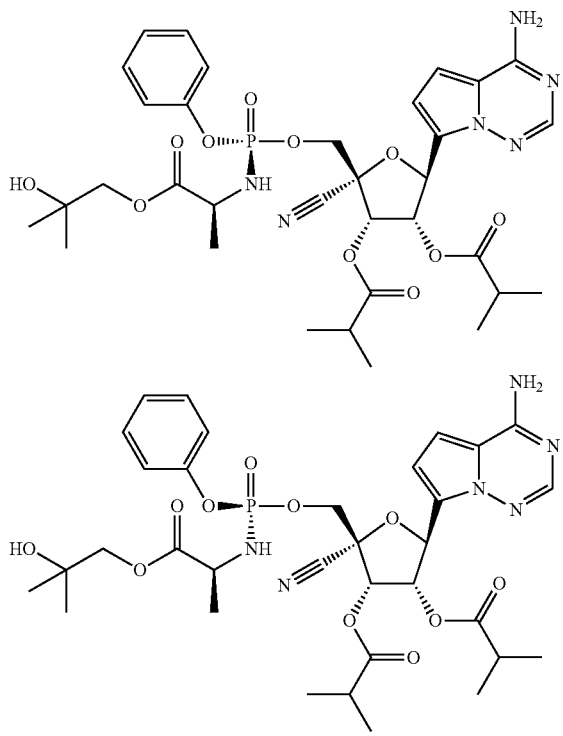 [SMILES: CC(C)C(=O)O[C@H]1[C@H](c2ccc3c(N)ncnn23)O[C@](C#N)(CO[P@](=O)(N[C@@H](C)C(=O)OCC(C)(C)O)Oc2ccccc2)[C@H]1OC(=O)C(C)C ; CC(C)C(=O)O[C@H]1[C@H](c2ccc3c(N)ncnn23)O[C@](C#N)(CO[P@@](=O)(N[C@@H](C)C(=O)OCC(C)(C)O)Oc2ccccc2)[C@H]1OC(=O)C(C)C]

Example 257

First eluting diastereomer: H NMR (400 MHz, Acetonitrile-d3) δ 7.90 (s, 1H), 7.33 (t, J=7.8 Hz, 2H), 7.25-7.12 (m, 3H), 6.82-6.71 (m, 2H), 6.35 (s, 2H), 5.90 (d, J=6.0 Hz, 1H), 5.84 (dd, J=5.9, 4.4 Hz, 1H), 5.68 (d, J=4.3 Hz, 1H), 4.50 (dd, J=11.2, 6.1 Hz, 1H), 4.40 (dd, J=11.2, 5.3 Hz, 1H), 4.35-4.23 (m, 1H), 3.90 (m, 3H), 2.64 (m, 2H), 1.30-1.08 (m, 21H). $^{31}$P NMR (162 MHz, Acetonitrile-d3) δ 2.45. LCMS m/z=731.14 (M+H), $t_R$=1.36 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=5.32 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 258

Second eluting diastereomer: $^1$H NMR (400 MHz, Acetonitrile-d$_3$) δ 7.90 (s, 1H), 7.34 (dd, J=8.6, 7.1 Hz, 2H), 7.23-7.13 (m, 3H), 6.80-6.73 (m, 2H), 6.34 (s, 2H), 5.86 (d, J=6.0 Hz, 1H), 5.81 (dd, J=5.9, 4.5 Hz, 1H), 5.67 (d, J=4.5 Hz, 1H), 4.52-4.31 (m, 3H), 4.03-3.87 (m, 2H), 3.82 (d, J=10.8 Hz, 1H), 2.64 (m, 2H), 1.30 (dd, J=7.2, 1.0 Hz, 3H), 1.26-1.09 (m, 21H). $^{31}$P NMR (162 MHz, Acetonitrile-d3) δ 2.52. LCMS m/z=731.14 (M+H), $t_R$=1.36 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min. HPLC: $t_R$=5.36 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 m/min.

Example 259. (2R,3S,4S,5S)-2-cyano-5-(4-imino-3-((phosphonooxy)methyl)-3,4-dihydropyrrolo[2,1-f][1,2,4]triazin-7-yl)-2-((((S)-(((S)-1-methoxy-1-oxopropan-2-yl)amino)(phenoxy)phosphoryl)oxy) methyl)tetrahydrofuran-3,4-diyl bis(2-methylpropanoate)

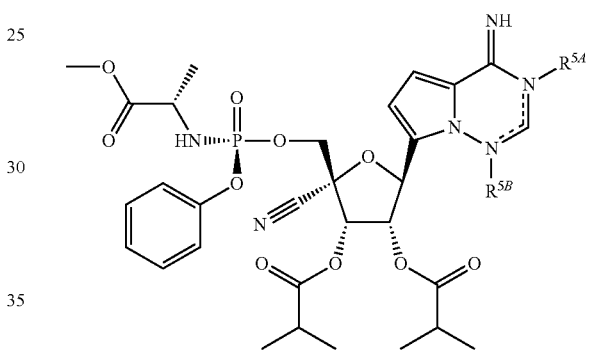

wherein $R^{5A}$ and $R^{5B}$ are each independently H or —CH$_2$OP(O)(O-benzyl)$_2$,
wherein at least one of $R^{5A}$ and $R^{5B}$ is —CH$_2$OP(O)(O-benzyl)$_2$.

(2R,3S,4S,5S)-5-(3-(((bis(benzyloxy)phosphoryl)oxy) methyl)-4-imino-3,4-dihydropyrrolo[2,1-f][1,2,4]triazin-7-yl)-2-cyano-2-((((S)-(((S)-1-methoxy-1-oxopropan-2-yl) amino)(phenoxy)phosphoryl)oxy)methyl)tetrahydrofuran-3,4-diyl bis(2-methylpropanoate). A mixture of Example 140 (115 mg, 0.171 mmol), chloromethyl dibenzylphosphate (67 mg, 0.205 mmol), and sodium iodide (77 mg, 0.514 mmol) in HMPA (3 mL) was stirred at room temperature for 24 h, diluted with DCM, washed with aqueous saturated ammonium chloride solution, and the water layer extracted back with DCM. The combined organic layer was concentrated in vacuo and purified by prep HPLC (Phenominex Gemini-NX 10 u C18 110 Å 250×30 mm column, ACN 10 to 100% in water) to afford the product. $^1$H NMR (400 MHz, Acetonitrile-d3) δ 7.96 (s, 1H), 7.56 (d, J=4.7 Hz, 1H), 7.37-7.12 (m, 11H), 6.77 (d, J=4.7 Hz, 1H), 5.76-5.67 (m, 3H), 5.67-5.63 (m, 1H), 5.60 (d, J=4.3 Hz, 1H), 4.92 (d, J=7.7 Hz, 2H), 4.80 (t, J=11.2 Hz, 1H), 4.45 (qd, J=11.4, 6.1 Hz, 2H), 4.04-3.84 (m, 1H), 2.63 (m, 2H), 3.58 (s, 3H), 1.30 (d, J=7.1 Hz, 3H), 1.23-1.13 (m, 12H). $^{31}$P NMR (162 MHz, Acetonitrile-d3) δ 2.68, −0.49. LCMS m/z=873.17 (M+H), $t_R$=1.38 min; LC system: Thermo Accela 1250 UHPLC; MS system: Thermo LCQ Fleet; Column: Phenomenex Kinetex 2.6μ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min.

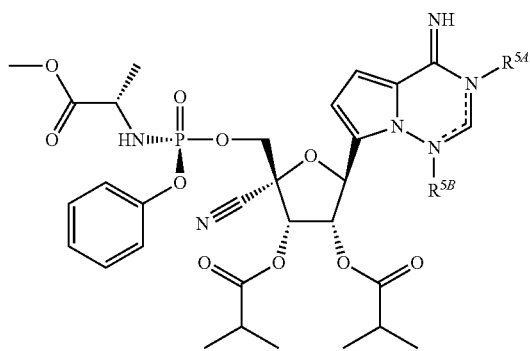

wherein $R^{5A}$ and $R^{5B}$ are each independently H or —CH$_2$OP(O)(OH)$_2$,
wherein at least one of $R^{5A}$ and $R^{5B}$ is —CH$_2$OP(O)(OH)$_2$:

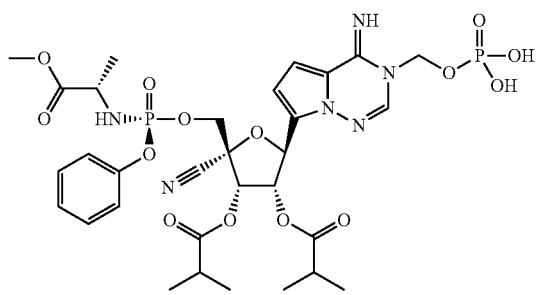

or

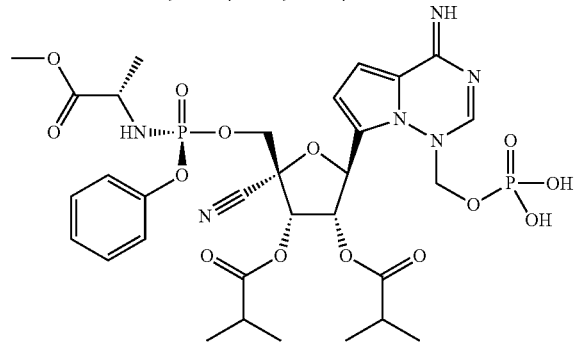

(2R,3S,4S,5S)-2-cyano-5-(4-imino-3-((phosphonooxy)methyl)-3,4-dihydropyrrolo[2,1-f][1,2,4]triazin-7-yl)-2-((((S)-(((S)-1-methoxy-1-oxopropan-2-yl)amino)(phenoxy)phosphoryl)oxy)methyl)tetrahydrofuran-3,4-diyl bis(2-methylpropanoate). (2R,3S,4S,5S)-5-(3-(((bis(benzyloxy)phosphoryl)oxy)methyl)-4-imino-3,4-dihydropyrrolo[2,1-f][1,2,4]triazin-7-yl)-2-cyano-2-((((S)-(((S)-1-methoxy-1-oxopropan-2-yl)amino)(phenoxy)phosphoryl)oxy)methyl)tetrahydrofuran-3,4-diyl bis(2-methylpropanoate) (69 mg, 0.079 mmol) was dissolved in THF (5 mL) and 10% Pd/C (40 mg, 0.038 mmol) added. The resulting mixture was stirred under H$_2$ gas at room temperature for 2 h, filtered, and the filter cake washed with MeOH several times. The combined filtrate was concentrated in vacuo and repurified by prep. HPLC (Phenominex Gemini 10 u C18 110 Å 250×21.2 mm column, 30-85% acetonitrile (0.1% TFA)/water (0.1% TFA) gradient in 30 min run) to afford the product. $^1$H NMR (400 MHz, Methanol-d4) δ 8.28 (s, 1H), 7.43 (d, J=4.8 Hz, 1H), 7.33 (t, J=7.8 Hz, 2H), 7.19 (dd, J=14.4, 7.6 Hz, 3H), 6.96 (d, J=4.8 Hz, 1H), 5.90-5.54 (m, 5H), 4.46 (dt, J=8.8, 4.7 Hz, 2H), 3.92 (dq, J=10.3, 7.1 Hz, 1H), 3.64 (s, 3H), 2.65 (m, 2H), 1.32 (d, J=7.1 Hz, 3H), 1.28-1.06 (m, 12H). $^{31}$P NMR (162 MHz, Methanol-d4) δ 3.07, 0.66 (broad). LCMS m/z=783.12 (M+H), t$_R$=1.27 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 µL/min. HPLC: t$_R$=5.81 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

Example 260. (2R,3S,4S,5S)-2-Cyano-5-(4-(((E)-(dimethylamino)methylene)amino)pyrrolo[2,1-f][1,2,4]triazin-7-yl)-2-((((S)-(((S)-1-methoxy-1-oxopropan-2-yl)amino)(phenoxy)phosphoryl)oxy)methyl)tetrahydrofuran-3,4-diyl bis(2-methylpropanoate)

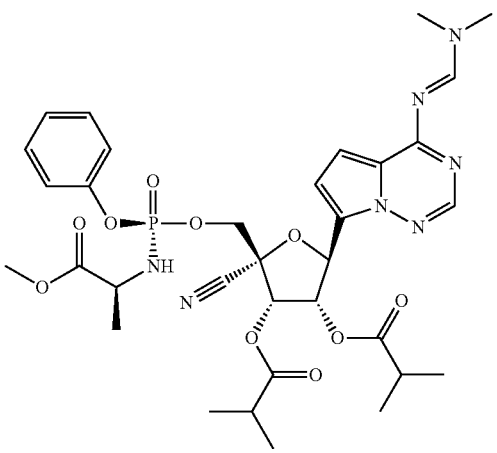

A mixture of Example 140 (80 mg, 0.119 mmol) and Intermediate 10 (62 mg, 0.357 mmol) was stirred at room temperature for 1.5 h, concentrated in vacuo, and purified by silica gel column chromatography (MeOH 0 to 15% in DCM, 50 min run) to provide the first eluting product. $^1$H NMR (400 MHz, Acetonitrile-d3) δ 8.89 (s, 1H), 8.05 (s, 1H), 7.34 (dd, J=8.8, 7.0 Hz, 2H), 7.25-7.16 (m, 3H), 6.83 (q, J=4.5 Hz, 2H), 5.88 (d, J=6.0 Hz, 1H), 5.83 (dd, J=5.9, 4.6 Hz, 1H), 5.71 (d, J=4.6 Hz, 1H), 4.50-4.33 (m, 2H), 4.30-4.21 (m, 1H), 3.99-3.82 (m, 1H), 3.58 (s, 3H), 3.22 (s, 3H), 3.22 (d, J=0.7 Hz, 3H), 2.65 (m, 2H), 1.36-1.02 (m, 15H). $^{31}$P NMR (162 MHz, Acetonitrile-d3) δ 2.39. LCMS m/z=728.25 (M+H), t$_R$=1.44 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min.

Example 261. (2R,3S,4S,5S)-2-cyano-2-((((S)-(((S)-1-methoxy-1-oxopropan-2-yl)amino)(phenoxy)phosphoryl)oxy)methyl)-5-(4-(((E)-(4-methylpiperazin-1-yl) methylene)amino)pyrrolo[2,1-f][1,2,4]triazin-7-yl)tetrahydrofuran-3,4-diyl bis(2-methylpropanoate)

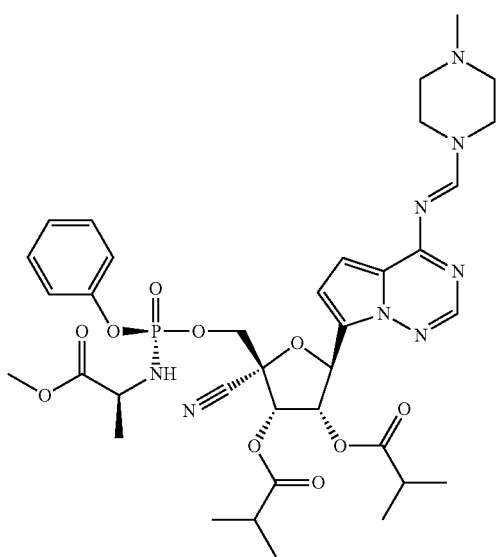 [SMILES: COC(=O)[C@H](C)N[P@](=O)(OC[C@@]1(C#N)O[C@@H](c2ccc3c(/N=C/N4CCN(C)CC4)ncnn23)[C@H](OC(=O)C(C)C)[C@@H]1OC(=O)C(C)C)Oc1ccccc1]

A mixture of Example 140 (80 mg, 0.119 mmol) and Intermediate 10 (62 mg, 0.357 mmol) was stirred at room temperature for 1.5 h, concentrated in vacuo, and purified by silica gel column chromatography (MeOH 0 to 15% in DCM, 50 min run) to provide the product. $^1$H NMR (400 MHz, Acetonitrile-d3) δ 8.92 (s, 1H), 8.06 (s, 1H), 7.34 (dd, J=8.8, 7.0 Hz, 2H), 7.27-7.17 (m, 3H), 6.82 (s, 2H), 5.88 (d, J=6.0 Hz, 1H), 5.86-5.82 (m, 1H), 5.71 (d, J=4.6 Hz, 1H), 4.49-4.35 (m, 2H), 4.32-4.23 (m, 1H), 3.99-3.78 (m, 3H), 3.62 (dd, J=5.9, 4.3 Hz, 2H), 3.58 (s, 3H), 2.65 (m, 2H), 2.47 (dt, J=12.1, 5.1 Hz, 4H), 2.29 (s, 3H), 1.34-1.10 (m, 15H). $^{31}$P NMR (162 MHz, Acetonitrile-d3) δ 2.39. LCMS m/z=783.27 (M+H), $t_R$=1.30 min; LC system: Thermo Accela 1250 UHPLC; MS system: Thermo LCQ Fleet; Column: Phenomenex Kinetex 2.6µ XB-C18 100 A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 L/min.

Example 262. (2R,3S,4S,5S)-5-(4-aminopyrrolo[2,1-f][1,2,4]triazin-7-yl)-2-cyano-2-((((((S)-1-(2-methyl-2-(phosphonooxy)propoxy)-1-oxopropan-2-yl)amino)(phenoxy) phosphoryl)oxy)methyl) tetrahydrofuran-3,4-diyl bis(2-methylpropanoate)

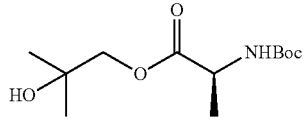

2-hydroxy-2-methylpropyl (tert-butoxycarbonyl)-L-alaninate. To a mixture of Boc-L-alanine (2.53 g, 13.38 mmol), 2-hydroxy-2-methylpropanol (1.0 mL, 11.15 mmol), and EDCI (2.25 g, 14.50 mmol) in acetonitrile (40 mL) was added DMAP (2.04 g, 16.73 mmol). The resulting mixture was stirred at room temperature for 15 h, then was concentrated, diluted with EtOAc, washed with brine, dried over sodium sulfate, and concentrated in vacuo. The residue was purified by silica gel chromatography (ethylacetate 0 to 80% in hexanes) to afford the product. $^1$H NMR (400 MHz, Chloroform-d) δ 5.00 (s, 1H), 4.45-4.24 (m, 1H), 4.15-3.91 (m, 2H), 1.44 (s, 9H), 1.41 (d, J=7.2 Hz, 3H), 1.25 (d, J=2.4 Hz, 6H). MS m/z=283.99 (M+Na).

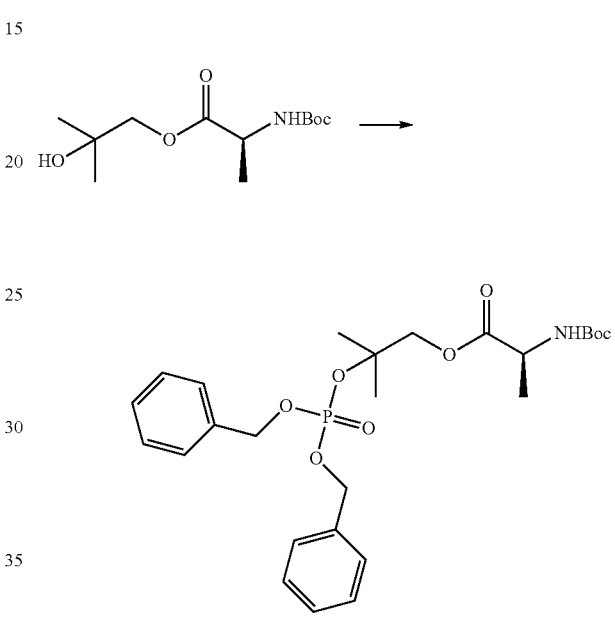

2-((bis(benzyloxy)phosphoryl)oxy)-2-methylpropyl (tert-butoxycarbonyl)-L-alaninate. A mixture of 2-hydroxy-2-methylpropyl (tert-butoxycarbonyl)-L-alaninate (1500 mg, 5.74 mmol), dibenzyl-N,N-diisopropyl phosphoramidite (3.64 mL, 11.48 mmol), and 1H-tetrazole (1.21 g, 17.22 mmol) in DCM (20 mL) was stirred at RT for 30 min. The resulting mixture was cooled under ice-water bath and t-BuOOH (2.3 mL, 11.48 mmol, 5-6 M in decane) was added. The resulting mixture was stirred for 1 h, and was diluted with DCM, washed with NH$_4$Cl solution, and brine. The organic layer was dried over sodium sulfate, concentrated in vacuo, and purified by 0.1% TFA modified prep HPLC to afford the product. MS m/z=521.80 (M+H).

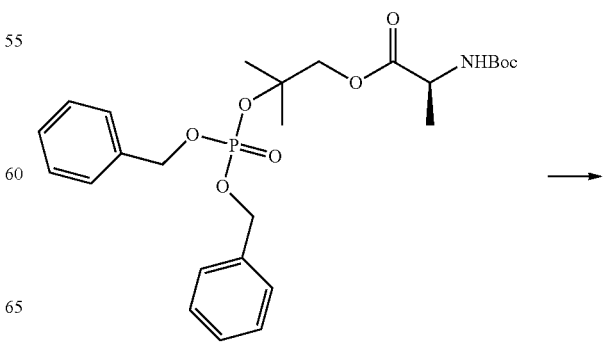

-continued

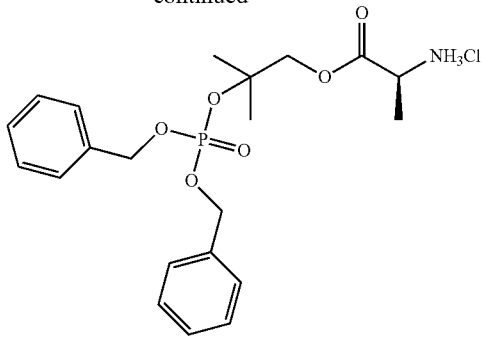

2-((bis(benzyloxy)phosphoryl)oxy)-2-methylpropyl (S)-2-(chloro-15-azaneyl)propanoate. 2-((bis(benzyloxy)phosphoryl)oxy)-2-methylpropyl (tert-butoxycarbonyl)-L-alaninate (460 mg, 60% purity, 0.529 mmol) was dissolved in dichloromethane (10 mL) and cooled under ice water bath. 4 M-HCl in dioxane (2.65 mL, 10.58 mmol) was added. The resulting mixture was stirred under ice water bath for 3 h, diluted with DCM, washed with water, dried under sodium sulfate, and concentrated to afford the product. MS m/z 422.01 (M+H).

2-((bis(benzyloxy)phosphoryl)oxy)-2-methylpropyl ((4-nitrophenoxy)(phenoxy) phosphoryl)-L-alaninate. To a solution of 2-((bis(benzyloxy)phosphoryl)oxy)-2-methylpropyl (S)-2-(chloro-15-azaneyl)propanoate (434 mg, 0.948 mmol) in dichloromethane (10 mL) was added phenyl phosphorodichloridate (0.142 mL, 0.948 mmol) and triethylamine (0.26 mL, 1.90 mmol) at −78° C. The dry ice bath was removed and the resulting mixture was stirred for 40 min. The mixture was cooled to −78° C. and p-nitrophenol (132 mg, 0.948 mmol) was added in one portion and triethylamine (0.13 mL, 0.948 mmol) added dropwise at −78° C. The resulting mixture was stirred for 60 min after removal of dry ice bath, then diluted with ethyl acetate, washed with water and brine, concentrated in vacuo, and the resulting residue purified by silica gel column chromatography (EtOAc to 90% in hexanes) to afford the product. $^1$H NMR (400 MHz, Chloroform-d) δ 8.18 (dd, J=9.2, 3.4 Hz, 2H), 7.43-7.13 (m, 19H), 4.98 (ddd, J=8.0, 6.2, 2.7 Hz, 4H), 4.61 (dd, J=12.0, 9.6 Hz, 1H), 4.25-4.03 (m, 3H), 1.47-1.40 (m, 6H), 1.37 (dd, J=7.1, 5.0 Hz, 3H). $^{31}$P NMR (162 MHz, Chloroform-d) δ −2.66, −2.74, −5.44, −5.46. MS m/z 698.87 (M+H).

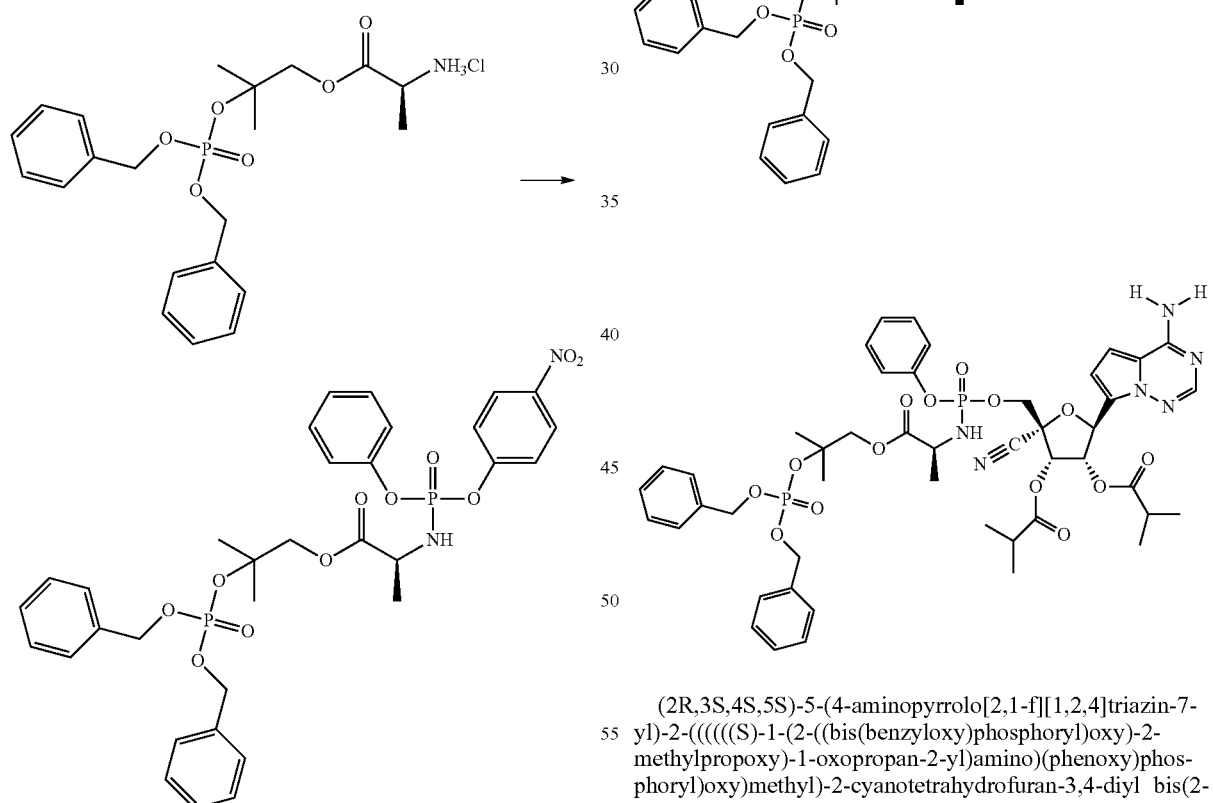

(2R,3S,4S,5S)-5-(4-aminopyrrolo[2,1-f][1,2,4]triazin-7-yl)-2-((((((S)-1-(2-((bis(benzyloxy)phosphoryl)oxy)-2-methylpropoxy)-1-oxopropan-2-yl)amino)(phenoxy)phosphoryl)oxy)methyl)-2-cyanotetrahydrofuran-3,4-diyl bis(2-methylpropanoate). To a mixture of intermediate 7 (73 mg, 0.169 mmol), 2-((bis(benzyloxy)phosphoryl)oxy)-2-methylpropyl ((4-nitrophenoxy)(phenoxy)phosphoryl)-L-alaninate (165 mg, 0.237 mmol), and MgCl$_2$ (21 mg, 0.220 mmol) in THF (5 mL) was added diisopropylethylamine (0.047 mL, 0.271 mmol) dropwise at room temperature. The resulting mixture was stirred at 50° C. for 2 h. The resulting mixture was purified by preparative HPLC (MeCN 10 to 90% in water with 0.1% TFA modifier) to afford the intermediate. MS m/z=991.04 (M+H).

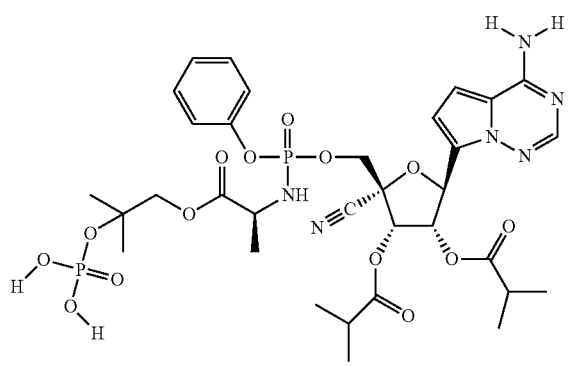 [SMILES: CC(C)C(=O)O[C@H]1[C@H](c2ccc3c(N)ncnn23)O[C@](C#N)(COP(=O)(N[C@@H](C)C(=O)OCC(C)(C)OP(=O)(O)O)Oc2ccccc2)[C@H]1OC(=O)C(C)C]

(2R,3S,4S,5S)-5-(4-aminopyrrolo[2,1-f][1,2,4]triazin-7-yl)-2-((((((S)-1-(2-((bis(benzyloxy)phosphoryl)oxy)-2-methylpropoxy)-1-oxopropan-2-yl)amino)(phenoxy)phosphoryl)oxy)methyl)-2-cyanotetrahydrofuran-3,4-diyl bis(2-methylpropanoate) was dissolved in THF (10 mL) and 10% Pd/C (140 mg, 0.131 mmol) was added. The resulting mixture was stirred at RT under a hydrogen gas atmosphere for 30 min. The resulting mixture was filtered and the filtrate was concentrated under reduced pressure. The crude residue was purified by preparatory HPLC using gradient from 10-90% acetonitrile in water with 0.1% TFA modifier to afford the product. $^1$H NMR (400 MHz, Methanol-d4) δ 8.04 (s, 0.5H), 8.03 (s, 0.5H), 7.38-7.26 (m, 3H), 7.23-7.11 (m, 3H), 6.97 (m, 1H), 5.88-5.69 (m, 3H), 4.56 (dd, J=11.2, 5.6 Hz, 0.5H), 4.51-4.41 (m, 1.5H), 4.21-4.08 (m, 1.5H), 4.03 (dd, J=11.2, 1.1 Hz, 0.5H), 3.92 (ddt, J=16.2, 9.0, 7.1 Hz, 1H), 2.81-2.48 (m, 2H), 1.51-1.42 (m, 6H), 1.35 (dd, J=7.2, 1.0 Hz, 0.5H), 1.31 (dd, J=7.2, 1.3 Hz, 0.5H), 1.27-1.09 (m, 12H). $^{31}$P NMR (162 MHz, Methanol-d$_4$) δ 3.07, −3.72. MS m/z=811.06 (M+H).

Example 263. (2R,3S,4S,5S)-5-(4-aminopyrrolo[2,1-f][1,2,4]triazin-7-yl)-2-cyano-2-((((((S)-1-(2-(2-ethoxyethoxy)ethoxy)-1-oxopropan-2-yl)amino)(phenoxy)phosphoryl)oxy)methyl)tetrahydrofuran-3,4-diyl bis(2-methylpropanoate) single isomer

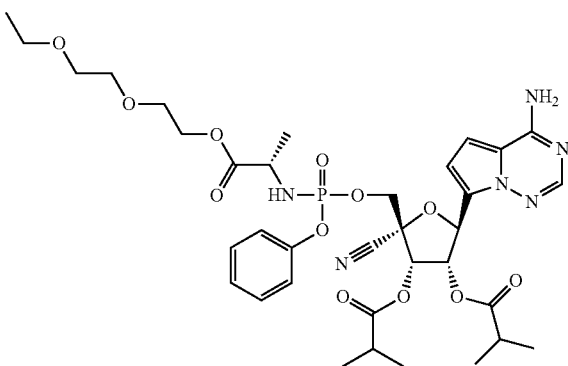 [SMILES: CCOCCOCCOC(=O)[C@H](C)NP(=O)(OC[C@@]1(C#N)O[C@@H](c2ccc3c(N)ncnn23)[C@H](OC(=O)C(C)C)[C@@H]1OC(=O)C(C)C)Oc1ccccc1]

Example 75 (232 mg, 0.366 mmol) was dissolved in anhydrous tetrahydrofuran (10.0 mL) under argon. Isobutyric anhydride (121 mg, 0.768 mmol) and 4-dimethylaminopyridine (4 mg, 0.04 mmol) were added and the reaction mixture was stirred at room temperature. After 4 hours, the reaction mixture was diluted with ethyl acetate (20 mL) and washed twice with saturated aqueous sodium bicarbonate solution (10 mL) and once with brine (10 mL). The organic layer was dried over anhydrous sodium sulfate and concentrated under reduced pressure. The crude residue was purified by preparatory HPLC (Phenomenex Gemini 5 μm C18 110 Å 100×30 mm column) using gradient from 10-100% acetonitrile in water to afford the product. $^1$H NMR (400 MHz, DMSO-d$_6$) δ 8.02-7.78 (m, 3H), 7.42-7.28 (m, 2H), 7.25-7.11 (m, 3H), 6.87 (d, J=4.5 Hz, 1H), 6.81 (d, J=4.5 Hz, 1H), 6.22 (dd, J=13.5, 10.0 Hz, 1H), 5.81-5.70 (m, 2H), 5.67-5.62 (m, 1H), 4.48-4.41 (m, 1H), 4.39-4.29 (m, 1H), 4.16-4.08 (m, 1H), 4.03-3.94 (m, 1H), 3.92-3.76 (m, 1H), 3.55-3.49 (m, 2H), 3.49-3.44 (m, 2H), 3.43-3.37 (m, 4H), 2.71-2.52 (m, 2H), 1.26-0.98 (m, 18H). $^{31}$P NMR (162 MHz, DMSO-d$_6$) δ 3.08. LCMS: MS m/z=775.09 [M+1], t$_R$=1.54 min; LC system: Thermo Accela 1250 UHPLC; MS system: Thermo LCQ Fleet; Column: Kinetex 2.6μ XB-C18 100 A, 50×4.6 mm; Solvents: acetonitrile with 0.1% acetic acid, water with 0.1% acetic acid; Gradient: 0 min-0.2 min 2% acetonitrile, 0.2 min-1.5 min 2-100% acetonitrile, 1.5 min-2.2 min 100% acetonitrile, 2.2 min-2.4 min 100%-2% acetonitrile, 2.4 min-2.5 min 2% acetonitrile at 2 μL/min. HPLC: t$_R$=3.31 min; HPLC system: Agilent 1100 series; Column: Gemini 5μ C18 110A, 50×4.6 mm; Solvents: Acetonitrile with 0.1% TFA, Water with 0.1% TFA; Gradient: 0 min-5.0 min 2-98% ACN, 5.0 min-6.0 min 98% ACN at 2 mL/min. HPLC: t$_R$=5.67 min; HPLC system: Agilent 1290 II; Column: Phenomenex Kinetex C18, 2.6 u 110A, 100×4.6 mm; Solvents: A: Water with 0.1% TFA, B: Acetonitrile with 0.1% TFA; Gradient: 2-98% B with 8.5 min gradient at 1.5 mL/min.

D. Biological Examples

Example 264. DENV Pol IC50

A 244 nucleotide secondary structureless heteropolymeric RNA (sshRNA) with sequence 5'-(UCAG)20(UCCAAG)14(UCAG)20-3' (SEQ ID NO: 1) is used as the template with 5'-CUG-3' primer in the DENV2-NS5 polymerase assay. Six two-fold dilutions of compounds starting from 200 nM and no inhibitor control are plated in 96-well plates. 100 nM DENV2 NS5 is preincubated for 5 minutes at room temperature in a reaction mixture containing 40 mM Tris-HCl (pH 7.5), 10 mM NaCl, 3 mM DTT, 0.2 unit/μL RNasin Plus RNase Inhibitor, 200 ng/μL sshRNA, 20 μM CUG and 2 mM MgCl2. Enzyme mix is added to compound dilutions and reactions initiated by the addition of a mixture containing 20 μM of three natural NTP plus 2 μM of analog:base matched competing natural NTP containing 1:100 α-33P-NTP. After 90 minutes at 30° C., 5 μL of the reaction mixtures are spotted on DE81 anion exchange paper. Filter papers are washed three times with Na$_2$HPO$_4$ (125 mM, pH 9) for 5 minutes, rinsed with water and ethanol, then air-dried and exposed to phosphorimager. Synthesized RNA is quantified using Typhoon Trio Imager and Image Quant TL Software and reaction rates are calculated by linear regression using GraphPad Prism 5.0. IC$_{50}$ values are calculated in Prism by non-linear regression analysis using the dose-response (variable slope) equation (four-parameter logistic equation): Y=Bottom+(Top-Bottom)/(1+10^((Log IC$_{50}$−X)*HillSlope)).

Example 265. RSV RNP Preparation

RSV ribonucleoprotein (RNP) complexes were prepared from a method modified from Mason et al. (1). HEp-2 cells were plated at a density of 7.1×10$^4$ cells/cm$^2$ in MEM+10% fetal bovine serum (FBS) and allowed to attach overnight at 37° C. (5% $CO_2$). Following attachment, the cells were infected with RSV A2 (MOI=5) in 35 mL MEM+2% FBS. At 20 hours post-infection, the media was replaced with MEM+2% FBS supplemented with 2 µg/mL actinomycin D and returned to 37° C. for one hour. The cells were then washed once with PBS and treated with 35 mL of PBS+250 µg/mL lyso-lecithin for one minute, after which all liquid was aspirated. The cells were harvested by scrapping them into 1.2 mL of buffer A [50 mM TRIS acetate (pH 8.0), 100 mM potassium acetate, 1 mM DTT and 2 µg/mL actinomycin D] and lysed by repeated passage through an 18 gauge needle (10 times). The cell lysate was placed in ice for 10 minutes and then centrifuged at 2400 g for 10 minutes at 4° C. The supernatant (S1) was removed and the pellet (P1) was disrupted in 600 µL of Buffer B [10 mM TRIS acetate (pH 8.0), 10 mM potassium acetate and 1.5 mM $MgCl_2$] supplemented with 1% Triton X-100 by repeated passage through an 18 gauge needle (10 times). The resuspended pellet was placed in ice for 10 minutes and then centrifuged at 2400 g for 10 minutes at 4° C. The supernatant (S2) was removed and the pellet (P2) was disrupted in 600 µL of Buffer B supplemented with 0.5% deoxycholate and 0.1% Tween 40. The resuspended pellet was placed in ice for 10 minutes and then centrifuged at 2400 g for 10 minutes at 4° C. The supernatant (S3) fraction, containing the enriched RSV RNP complexes, was collected and the protein concentration determined by UV absorbance at 280 nm. Aliquoted RSV RNP S3 fractions were stored at −80° C.

Example 266. RSV RNP Assay

Transcription reactions contained 25 µg of crude RSV RNP complexes in 30 µL of reaction buffer [50 mM TRIS-acetate (pH 8.0), 120 mM potassium acetate, 5% glycerol, 4.5 mM $MgCl_2$, 3 mM DTT, 2 mM ethyleneglycol-bis(2-aminoethylether)-tetraacetic acid (EGTA), 50 µg/mL BSA, 2.5 U RNasin (Promega), ATP, GTP, UTP, CTP and 1.5 uCi [α-32P] NTP (3000 Ci/mmol)]. The radiolabled nucleotide used in the transcription assay was selected to match the nucleotide analog being evaluated for inhibition of RSV RNP transcription. Cold, competitive NTP was added at a final concentration of one-half its Km (ATP=20 µM, GTP=12.5 µM, UTP=6 µM and CTP=2 µM). The three remaining nucleotides were added at a final concentration of 100 µM.

To determine whether nucleotide analogs inhibited RSV RNP transcription, compounds were added using a 6 step serial dilution in 5-fold increments. Following a 90 minute incubation at 30° C., the RNP reactions were stopped with 350 µL of Qiagen RLT lysis buffer and the RNA was purified using a Qiagen RNeasy 96 kit. Purified RNA was denatured in RNA sample loading buffer (Sigma) at 65° C. for 10 minutes and run on a 1.2% agarose/MOPS gel containing 2 M formaldehyde. The agarose gel was dried and exposed to a Storm phosphorimager screen and developed using a Storm phosphorimager (GE Healthcare). The concentration of compound that reduced total radiolabeled transcripts by 50% ($IC_{50}$) was calculated by non-linear regression analysis of two replicates.

Example 267. DENV moDC EC50

Human monocyte-derived dendritic cells (moDCs) were derived from CD14+ monocytes (AllCells) cultured in Human Mo-DC Differentiation medium containing GM-CSF and IL-4 (Miltenyi Biotec). On day 7, moDCs were harvested by mechanical disruption, washed and suspended in serum-free RPMI. moDCs were infected with Vero-derived Dengue 2, New Guinea strain (NGC) at a MOI=0.1 for two hours in serum-free RPMI with gentle agitation at 37° C. Cells were washed and resuspended in 10% serum-containing RPMI (Gibco, supplemented with sodium pyruvate, NEAA, Penicillin-Streptomycin). 10≡cells were plated in triplicate in 96-well plates with compounds dispensed at graded doses (Hewlett-Packard D300 Digital Dispenser). All wells were normalized to 0.25% DMSO. At 48 hours, cells were washed with 1×PBS and all supernatants removed. Total RNA was extracted using RNEasy 96 plates (Qiagen) and used to generate first-strand cDNA using XLT cDNA 5× Supermix (QuantaBio). cDNA was used as a template in a Taqman qPCR duplex reaction specific to DENV2 viral and GAPDH gene expression. $EC_{50}$ values were determined using Prism Graphpad software, with normalization to a positive control and no compound negative control wells.

Example 268. moDC CC50

Human monocyte-derived dendritic cells (moDCs) were derived from CD14+ monocytes (AllCells) cultured in Human Mo-DC Differentiation medium containing GM-CSF and IL-4 (Miltenyi Biotec). On day 7, moDCs were harvested by mechanical disruption, washed and cultured in triplicate at 1×10^5-5×10^4 cells/well in 96-well plates with compounds dispensed at graded doses (Hewlett-Packard D300 Digital Dispenser). All wells were normalized to 0.25% DMSO. After 48 hours, CellTiter Glo (Promega) was added and incubated for 10 minutes at room temp before reading on a luminometer. % viability curves were calculated against no compound and no cell control wells. $CC_{50}$ values were determined using Prism Graphpad software.

Example 269. DENV-2 Huh-7 EC50

Huh7 (Human hepatocarcinoma 7) cells were maintained in 10% FCS-containing DMEM complete media. On the day of the assay, cells were trypsinized (0.1% Trypsin-EDTA), washed and infected for 2 hours in serum-free DMEM with Dengue serotype 2 New Guinea C (NGC) strain at MOI=0.1 with gentle agitation at 37° C. After 2 hours, cells were washed with serum-free media and suspended in 10% FCS-containing DMEM (Gibco, supplemented with sodium pyruvate, NEAA, Penicillin-Streptomycin). 10^5 cells were plated in triplicate in 96-well plates with compounds dispensed at graded doses (Hewlett-Packard D300 Digital Dispenser). All wells were normalized to 0.25% DMSO. At 48 hours, cells were washed with 1×PBS and all supernatants removed. Total RNA was extracted using RNEasy 96 plates (Qiagen) and used to generate first-strand cDNA using XLT cDNA 5× Supermix (QuantaBio). cDNA was used as a template in a Taqman qPCR duplex reaction specific to DENV2 viral and GAPDH gene expression. $EC_{50}$ values were determined using Prism Graphpad software, with normalization to a positive control and no compound negative control wells.

Example 270. Huh-7 CC50

Human hepatocarcinoma 7 (Huh7) cells were maintained in 10% FCS-containing complete DMEM. On day of assay, cells were trypsinized with 0.1% Trypsin-EDTA, washed and cultured in triplicate at 1-2×10^4 cells/well in 96-well plates with compounds dispensed at graded doses (Hewlett-Packard D300 Digital Dispenser). All wells were normalized to 0.25% DMSO. After 48 hours, CellTiter Glo (Promega) was added and incubated for 10 minutes at room temp before reading on a luminometer. % viability curves were calculated against no compound and no cell control wells. $CC_{50}$ values were determined using Prism Graphpad software.

Example 271. RSV HEp-2 EC50

Antiviral activity against RSV is determined using an infectious cytopathic cell protection assay in HEp-2 cells. In this assay, compounds inhibiting viral infection and/or replication produce a cytoprotective effect against the virus-induced cell killing that can be quantified using a cell viability reagent. The techniques used here are novel adaptations of methods described in published literature (Chapman et al., Antimicrob Agents Chemother. 2007, 51(9): 3346-53.).

HEp-2 cells are obtained from ATCC (Manassas, VI) and maintained in MEM media supplemented with 10% fetal bovine serum and penicillin/streptomycin. Cells are passaged twice a week and kept at subconfluent stage. Commercial stock of RSV strain A2 (Advanced Biotechnologies, Columbia, MD) is titered before compound testing to determine the appropriate dilution of the virus stock that generates desirable cytopathic effect in HEp-2 cells.

For antiviral tests, HEp-2 cells are grown in large cell culture flasks to near confluency but not fully so. The compounds to be tested are prediluted in DMSO in 384-well compound dilution plates, either in an 8 or 40 sample per plate standardized dose response format. 3-fold serial dilution increments of each test compound are prepared in the plates and test samples are transferred via acoustic transfer apparatus (Echo, Labcyte) at 100 nL per well into cell culture assay 384-well plates. Each compound dilution is transferred in single or quadruplicate samples into dry assay plates, which are stored until assay is ready to go. The positive and negative controls are laid out in opposite on ends of the plate in vertical blocks (1 column).

Subsequently, an infectious mixture is prepared using an appropriate dilution of virus stock previously determined by titration with cells at a density of 50,000/mL and 20 L/well is added to test plates w/compounds via automation (uFlow, Biotek). Each plate includes negative and positive controls (16 replicates each) to create 0% and 100% virus inhibition standards, respectively. Following the infection with RSV, testing plates are incubated for 4 days in a 37° C. cell culture incubator. After the incubation, a cell viability reagent, Cell TiterGlo (Promega, Madison, WI) is added to the assay plates, which are incubated briefly, and a luminescent readout is measured (Envision, Perkin Elmer) in all the assay plates. The RSV-induced cytopathic effect, percentage inhibition, is determined from the levels of remaining cell viability. These numbers are calculated for each tested concentration relative to the 0% and 100% inhibition controls, and the $EC_{50}$ value for each compound is determined by non-linear regression as a concentration inhibiting the RSV-induced cytopathic effect by 50%. Various potent anti-RSV tool compounds are used as positive controls for antiviral activity.

Example 272. HEp-2 CC50

Cytotoxicity of tested compounds is determined in uninfected HEp-2 cells in parallel with the antiviral activity using the cell viability reagent in a similar fashion as described before for other cell types (Cihlar et al., Antimicrob Agents Chemother. 2008, 52(2):655-65.). The same protocol as for the determination of antiviral activity is used for the measurement of compound cytotoxicity except that the cells are not infected with RSV. Instead, an uninfected cell mixture at the same density is added at 20 uL/well to plates containing prediluted compounds, also at 100 nL/sample. Assay plates are then incubated for 4 days followed by a cell viability test using the same CellTiter Glo reagent addition and measurement of luminescent readouts. Untreated cell and cells treated at 2 µM puromycin (Sigma, St. Louis, MO) serve as 100% and 0% cell viability control, respectively. The percent of cell viability is calculated for each tested compound concentration relative to the 0% and 100% controls and the CC50 value is determined by non-linear regression as a compound concentration reducing the cell viability by 50%.

Example 273. RSV NHBE EC50

Normal human bronchial epithelial (NHBE) cells were purchased from Lonza (Walkersville, MD, Cat #CC-2540) and cultured in Bronchial Epithelial Growth Media (BEGM) (Lonza, Walkersville, MD, Cat #CC-3170). The cells were passaged 1-2 times per week to maintain <80% confluency. The NHBE cells were discarded after 6 passages in culture.

To conduct the RSV A2 antiviral assay, NHBE cells were plated in 96-well plates at a density of 7,500 cells per well in BEGM and allowed to attach overnight at 37° C. Following attachment, 100 µL of cell culture media was removed and 3-fold serially diluted compound was added using a Hewlett-Packard D300 Digital Dispenser. The final concentration of DMSO was normalized to 0.05%. Following compound addition, the NHBE cells were infected by the addition of 100 µL of RSV A2 at a titer of $1 \times 10^{4.5}$ tissue culture infectious doses/mL in BEGM and then incubated at 37° C. for 4 days. The NHBE cells were then allowed to equilibrate to 25° C. and cell viability was determined by removing 100 µL of culture medium and adding 100 µL of Cell-Titer Glo viability reagent. The mixtures were incubated for 10 minutes at 25° C., and the luminescence signal was quantified on an Envision luminescence plate reader.

Example 274. hMPV (A1, A2, B1, B2) EC50

LLC-MK2 cells were seeded in 24-well plates at 90% confluence in MEM+10% FBS. Plates were washed with PBS and 500 µL of hMPV (strains CAN99-81 (gr. A1), CAN97-83 (gr. A2), CAN97-82 (B1) or CAN98-75 (gr. B2), containing 40 PFU/mL with the different dilutions of the 4 compounds were added on the cells for 1 h 30 min at 37° C., 5% $CO_2$. After the adsorption period, the medium was removed and cells were washed with PBS. An overlay of Opti-MEM 2x+methycellulose 1.6% (1:1) containing the same concentrations of compounds as in the adsorption period was added to the wells. A positive control consisting of ribavirin was also tested with concentrations ranging from 1 µM to 100 µM. The plates were incubated at 37° C., 5% $CO_2$ for 3-5 days. After the incubation period, the cells were fixed with 7% formalin for 1 h at room temperature. hMPV titers were determined using a Mab specific for the F protein (clone hMPV24, ABD Serotec, Inc.) diluted 1/10 000 and a second anti-mouse IgG HRP antibody (GeneScriptCorp) diluted 1/2500. Finally, KPL True Blue was used to reveal infected cells.

Example 275. HRV16 HeLa $EC_{50}$

H1-HeLa cells, cultured in complete DMEM medium containing 10% heat-inactivated FBS and 1% Penicillin/

Streptomycin, were seeded in 96 well plates at 3000 cells/well one day prior to compound dosing and infection. The antiviral activity of each compound was measured in triplicate. Compounds were added directly to the cell cultures in serial 3-fold dilutions using the HP300 digital dispenser (Hewlett Packard, Palo Alto, CA) immediately prior to infection. The plates were transferred to BSL-2 containment and the appropriate dilution of virus stock, previously determined by titration and prepared in cell culture media, was added to test plates containing cells and serially diluted compounds. Each plate included 6 wells of infected untreated cells and 6 wells of uninfected cells that served as 0% and 100% virus inhibition control, respectively. Following the infection, test plates were incubated for 96 h in a tissue culture incubator set to 33° C./5% $CO_2$. Following incubation, the H1-HeLa cells were removed from incubation and allowed to equilibrate to 25° C. Cell viability was determined by removing 100 µL of culture medium and adding 100 µL of Cell-Titer Glo viability reagent. The mixtures were incubated on a shaker for 10 minutes at 25° C., and the luminescence signal was quantified on an Envision luminescence plate reader. The percentage inhibition of virus infection was calculated for each tested concentration relative to the 0% and 100% inhibition controls and the $EC_{50}$ value for each compound was determined by 4-parametric non-linear regression as the effective concentration of compound that inhibited cytopathic effect by 50%.

Example 276. DENV-2 Huh-7 Rep $EC_{50}$

In 384 well plates (Greiner, Cat #781091), compounds were acoustically transferred at 200 nl per well in a 8 compound (4 replicates) or 40 compound dose response format (3 replicates). For all plates tested, Balapiravir, GS-5734 and NITD008 were included as positive inhibition controls alongside 0% inhibition, DMSO-only negative control wells. Following compound addition, Huh-7 cells containing the DENV2 replicon construct were harvested following standard cell culture procedures and were adjusted to a concentration of 1.25E5 cells/mL in cell culture media composed of cDMEM without genticin. 40 µL of the cell stock was then added to each well for a final cell density of 5,000 cells/well. Cell and compound mixtures were incubated at 37° C./5% $CO_2$ for 48 hours. Prior to harvesting cells, EnduRen Live Cell Substrate (Promega, Cat #E6481) was prepared by suspending 3.4 mg into 100 uL of DMSO to generate a 60 mM stock solution. The stock solution was then diluted 1:200 in pre-warmed cDMEM and 10 uL of this diluted solution was added to each well of the 384 well plates. Plates were then centrifuged at 500 rpm briefly and were placed on a plate shaker for 2 min. Following mixing, plates were incubated at 7° C./5% $CO_2$ for 1.5 hours prior to measuring luminescence on an Envision luminometer. The percentage inhibition of replicon signal was calculated for each tested concentration relative to the 0% and 100% inhibition controls and the $EC_{50}$ value for each compound was determined by 4-parametric non-linear regression as the effective concentration of compound that inhibited replicon signal by 50%.

Example 277. HCV Rep 1B and 2A $EC_{50}$

Compounds were serially diluted in ten steps of 1:3 dilutions in 384-well plates. All serial dilutions were performed in four replicates per compound within the same 384-well plate. An HCV protease inhibitor ITMN-191 at 100 µM was added as a control of 100% inhibition of HCV replication while puromycin at 10 mM was included as a control of 100% cytotoxicity. To each well of a black polystyrene 384-well plate (Greiner Bio-one, Monroe, NC), 90 µL of cell culture medium (without Geneticin) containing 2000 suspended HCV replicon cells was added with a Biotek µFlow workstation. For compound transfer into cell culture plates, 0.4 µL of compound solution from the compound serial dilution plate was transferred to the cell culture plate on a Biomek FX workstation. The DMSO concentration in the final assay wells was 0.44%. The plates were incubated for 3 days at 37° C. with 5% $CO_2$ and 85% humidity. The HCV replicon assay was a multiplex assay, able to assess both cytotoxicity and antireplicon activity from the same well. The $CC_{50}$ assay was performed first. The media in the 384-well cell culture plate was aspirated, and the wells were washed four times with 100 µL of PBS each, using a Biotek ELX405 plate washer. A volume of 50 µL of a solution containing 400 nM calcein AM (Anaspec, Fremont, CA) in 1×PBS was added to each well of the plate with a Biotek µFlow workstation. The plate was incubated for 30 min at room temperature before the fluorescence signal (excitation 490 nm, emission 520 nm) was measured with a Perkin-Elmer Envision plate reader. The $EC_{50}$ assay was performed in the same wells as the $CC_{50}$ assay. The calcein-PBS solution in the 384-well cell culture plate was aspirated with a Biotek ELX405 plate washer. A volume of 20 µL of Dual-Glo luciferase buffer (Promega, Madison, WI) was added to each well of the plate with a Biotek µFlow Workstation. The plate was incubated for 10 min at room temperature. A volume of 20 µL of a solution containing a 1:100 mixture of Dual-Glo Stop & Glo substrate (Promega, Madison, WI) and Dual-Glo Stop & Glo buffer (Promega, Madison, WI) was added to each well of the plate with a Biotek µFlow Workstation. The plate was then incubated at room temperature for 10 min before the luminescence signal was measured with a Perkin-Elmer Envision Plate Reader.

Example 278. Inhibition of Human Mitochondrial RNA Polymerase (POLRMT)

All reaction mixtures contained 50 mM Tris-HCl buffer (pH 8.0), 0.2 mg/ml BSA, 2 mM DTT, 0.05 mg/ml activated fish sperm DNA, 10 mM MgCl2, 1.3 µCi [α-$^{33}$P]dTTP (3,000 Ci/mmol), and 2 µMeach of dATP, dGTP, and TTP. The optimal enzyme concentrations were chosen to be in the linear range of enzyme concentration ([E]) versus activity, and the reaction time was selected to ensure that 10% of the substrate was consumed. All reactions were run at 37° C. The inhibition of mitochondrial RNA polymerase (POLRMT) was evaluated using 20 nM POLRMT preincubated with 20 nM template plasmid (pUC18-LSP) containing POLRMT light-strand promoter region and mitochondrial transcription factor A (mtTFA) (100 nM) and mt-TFB2 (20 nM) in buffer containing 10 mM HEPES (pH 7.5), 20 mMNaCl, 10 mM DTT, 0.1 mg/ml BSA, and 10 mM $MgCl_2$. The reactions were heated to 32° C. and initiated by adding 2.5 µM each of the four natural NTPs and 1.5 µCi of [$^{33}$P]GTP. After incubation for 30 min at 32° C., the reactions were spotted on DE81 paper before being processed for quantification.

Example 279. Single Nucleotide Incorporation by Human Mitochondrial RNA Polymerase (POLRMT)

A mixture of MTCN buffer (50 mM MES, 25 mM Tris-HCl, 25 mM CAPS, and 50 mM NaCl, pH 7.5), 200 nM 5'³² P-R12/D18, 10 mM MgCl₂, 1 mM DTT, and 376 nM POLRMT was preincubated at 30° C. for 1 min. The reaction was started by addition of 500 μM (final) natural NTP or NTP analogs. At selected time points, the reaction mixture was removed and quenched with gel loading buffer containing 100 mM EDTA, 80% formamide, and bromophenol blue, and heated at 65° C. for 5 min. The samples were run on a 20% polyacrylamide gel (8 M urea), and the product formation was quantified using Typhoon Trio Imager and Image Quant TL Software (GE Healthcare, Piscataway, NJ). The rate of single nucleotide incorporation by mt RNA pol was calculated by fitting the product formation using the single exponential equation: $[1R13]=A(1-e^{-kt})$, where [1R13] represents the amount (in nM) of the elongated product formed, t represents the reaction time, k represents the observed rate, and A represents the amplitude of the exponential.

TABLE 3

| | Activity | | | | | |
|---|---|---|---|---|---|---|
| Example No. | RSV HEp-2 $EC_{50}$ | RSV NHBE $EC_{50}$ | HRV16 HeLa $EC_{50}$ | DENV-2 REP Huh7 $EC_{50}$ | DENV moDC $EC_{50}$ | DENV-2 Huh7 $EC_{50}$ |
| 77 | 57 | 24 | 152 | 5394 | 185 | 1486 |
| 78 | 1354 | 710 | 6523 | 31757 | | |
| 79 | 105 | 19 | 217 | 12413 | | |
| 80 | 1175 | 158 | 1573 | 5302 | | |
| 81 | 194 | 22 | | | | |
| 82 | 58 | 32 | 201 | 7627 | 786 | 3980 |
| 83 | >100000 | >5000 | 17417 | 5155 | | |
| 84 | 58 | 16 | 121 | 12962 | | |
| 86 | 100 | 24 | 192 | 8949 | 239 | 1407 |
| 87 | 119 | 23 | 220 | 12285 | | |
| 88 | 108 | 42 | | 8818 | | |
| 89 | 195 | 126 | 785 | 49679 | | |
| 90 | 109 | 45 | 259 | 24271 | 677 | 2157 |
| 91 | 67 | 23 | | 10178 | | |
| 92 | 41 | 33 | 104 | 13590 | | |
| 93 | 48 | 25 | 171 | 12801 | | |
| 94 | 189 | 41 | | 13702 | | |
| 95 | 90 | 20 | 429 | 19774 | | |
| 96 | 63 | 20 | 417 | 16825 | | |
| 97 | 366 | >5000 | 1119 | 9053 | | |
| 98 | 48 | 17 | | | | |
| 99 | 58 | 14 | 116 | 6313 | | |
| 100 | 58 | 13 | 147 | 18799 | | 1131 |
| 101 | 94 | 19 | | 25788 | | |
| 102 | 178 | 18 | 526 | 39094 | | |
| 103 | 94 | 32 | | 10509 | | |
| 104 | 147 | 32 | 703 | 29115 | | |
| 105 | 57 | 13 | 182 | 12929 | | |
| 106 | 173 | 15 | 805 | 14575 | | |
| 107 | 98 | 31 | 388 | 22356 | | |
| 108 | 217 | 6 | 385 | 39252 | | |
| 109 | 103 | 32 | 379 | 26293 | | |
| 110 | 327 | 40 | 2509 | 56337 | | |
| 111 | 873 | 44 | | >100000 | | |
| 112 | 284 | 40 | 2896 | 36452 | | |
| 113 | 1942 | 0 | 4677 | 31949 | | |
| 114 | 1659 | 201 | 3853 | 26332 | | |
| 115 | 112 | 22 | | 20422 | | |
| 116 | 273 | 15 | 303 | 19706 | | |
| 117 | 113 | 20 | 462 | 19079 | | |
| 118 | 224 | 26 | 736 | 54417 | | |
| 119 | 541 | 27 | 1050 | 71445 | | |
| 120 | 163 | 0 | 1140 | 35235 | | |
| 121 | 5450 | 498 | 6656 | 44401 | | |
| 122 | 79 | 90 | 301 | 5537 | | |
| 123 | 2276 | 175 | 7566 | >50000 | | |
| 124 | 2104 | 150 | 8387 | >50000 | | |
| 125 | 700 | 79 | 2028 | 48728 | 20700 | |
| 126 | 121 | 45 | 514 | 15971 | | |
| 127 | 8056 | 3363 | >50000 | >50000 | | |
| 128 | 18792 | >4138 | >50000 | >50000 | | |
| 129 | 154 | 77 | 1110 | 15453 | | |
| 130 | 198 | 59 | 1777 | 20998 | | |
| 131 | 103 | 47 | 782 | 19235 | | |
| 132 | 434 | 145 | 3480 | 29443 | | |
| 133 | 18092 | >4071 | >48866 | >50000 | | |
| 134 | 7345 | 1589 | >50000 | >50000 | | |
| 135 | 738 | 33 | 1080 | 30578 | | |
| 136 | 2954 | 244 | 15000 | 38238 | | |
| 137 | 467 | 65 | 1038 | 38426 | | |
| 138 | 63 | 17 | 101 | 5199 | | |
| 139 | 39 | 8 | 97 | 5237 | | |

TABLE 3-continued

| | Activity | | | | | |
|---|---|---|---|---|---|---|
| Example No. | RSV HEp-2 $EC_{50}$ | RSV NHBE $EC_{50}$ | HRV16 HeLa $EC_{50}$ | DENV-2 REP Huh7 $EC_{50}$ | DENV moDC $EC_{50}$ | DENV-2 Huh7 $EC_{50}$ |
| 140 | 42 | 14 | 83 | 5273 | 90 | 1215 |
| 141 | 80 | 23 | 253 | 7493 | | |
| 142 | 93 | 16 | 352 | 11148 | | |
| 143 | 92 | 18 | 221 | 5571 | 164 | 3129 |
| 144 | 34 | 22 | 93 | 6168 | 31 | 1185 |
| 145 | | | | | | |
| 147 | 44 | 20 | | 17564 | | |
| 148 | 44 | 12 | 92 | 6814 | 26 | 1239 |
| 149 | 1154 | 84 | 3193 | >35760 | | |
| 150 | 1399 | 70 | 3485 | >50000 | | |
| 151 | 226 | 751 | 946 | 19481 | | |
| 152 | 2934 | >5000 | >50000 | >50000 | | |
| 153 | 110 | 283 | 470 | 6677 | | |
| 154 | 185 | 114 | 874 | 20524 | | |
| 155 | 437 | 294 | 2685 | 29240 | | |
| 156 | 456 | >5000 | 21681 | >50000 | | |
| 157 | 227 | 1588 | 1794 | 25763 | | |
| 158 | 139 | 52 | 731 | 15707 | | |
| 159 | 7990 | 1546 | 33106 | >50000 | | |
| 160 | 204 | 860 | | 37440 | | |
| 161 | 151 | 1160 | 1228 | 22475 | | |
| 162 | 179 | 28 | 1619 | | | |
| 164 | 1692 | 148 | | >100000 | | |
| 165 | 405 | 165 | 1909 | >99677 | | |
| 166 | 157 | 112 | 1657 | 21685 | | |
| 168 | 261 | 64 | | 34932 | | |
| 169 | 43 | 23 | 175 | 7625 | | |
| 170 | 267 | 80 | 863 | 15930 | | |
| 172 | 1101 | 145 | | 16818 | | |
| 173 | 256 | 75 | 519 | 16062 | | |
| 174 | 100 | 20 | 97 | 8312 | | |
| 175 | 87 | 17 | 85 | 9512 | | |
| 176 | 182 | 16 | 142 | 9444 | | |
| 177 | 120 | 49 | | 27224 | | |
| 178 | 633 | 163 | 1066 | 53226 | | |
| 179 | 161 | 100 | 731 | 29385 | | |
| 180 | 62 | 31 | 178 | 8310 | | |
| 181 | 84 | 30 | | 6629 | | |
| 182 | 88 | 17 | 177 | 3499 | | |
| 183 | 69 | 50 | 88 | 3654 | 142 | 1113 |
| 184 | 79 | 13 | 57 | 5955 | | |
| 185 | 26 | | | | 19168 | |
| 186 | 41 | 4 | 44 | 4220 | | 1733 |
| 187 | 24 | 17 | 88 | 5930 | | |
| 188 | 31 | 28 | 102 | 6922 | | |
| 189 | 36 | 51 | 114 | 8838 | | |
| 190 | 40 | 29 | 110 | 4910 | | |
| 191 | 23 | 8 | 64 | 2696 | | |
| 192 | 29 | 45 | 101 | 8666 | | |
| 193 | 610 | 125 | 1624 | 29965 | | |
| 194 | 391 | 529 | 2091 | 30890 | | |
| 195 | 23 | 59 | 126 | 6445 | | |
| 196 | 42 | 27 | 96 | 1958 | | |
| 197 | 28 | 33 | 94 | 4458 | | |
| 198 | 48 | 37 | 319 | 6625 | | |
| 199 | 4113 | 235 | 19488 | >50000 | | |
| 200 | 58 | 12 | 120 | 2175 | | |
| 201 | 92 | 14 | 177 | 7692 | 57 | 317 |
| 202 | 90 | 14 | 120 | 10051 | | |
| 203 | 95 | 38 | 359 | 9500 | | |
| 204 | 100 | 17 | 348 | 16905 | | |
| 205 | 164 | 21 | 286 | 18953 | | |
| 206 | 338 | 36 | 308 | 7589 | | |
| 207 | 1076 | 149 | | >37509 | | |
| 208 | 2116 | 215 | 15202 | >50000 | | |
| 209 | 1566 | 168 | 8519 | 31388 | | |
| 210 | 36283 | 3415 | | >35359 | | |
| 211 | 653 | 946 | 1968 | 28929 | | |
| 212 | 1179 | 451 | 6124 | >71350 | | |

TABLE 3-continued

| Example No. | RSV HEp-2 EC$_{50}$ | RSV NHBE EC$_{50}$ | HRV16 HeLa EC$_{50}$ | DENV-2 REP Huh7 EC$_{50}$ | DENV moDC EC$_{50}$ | DENV-2 Huh7 EC$_{50}$ |
|---|---|---|---|---|---|---|
| 213 | 11779 | 2251 | 13065 | 22967 | | |
| 214 | >41731 | >3888 | 31313 | >50000 | | |
| 215 | 378 | 142 | 1021 | 27232 | | |
| 216 | 262 | 3867 | 3499 | 31180 | | |
| 217 | 9842 | 2063 | 11919 | >50000 | | |
| 218 | 30 | 17 | 112 | 5509 | | |
| 219 | 67 | 82 | 356 | 16427 | | |
| 220 | 167 | 4857 | 13474 | | | |
| 221 | 660 | 1171 | 8990 | | | |
| 222 | 27 | 25 | 146 | | | |
| 223 | 1721 | 223 | | | | |
| 224 | 378 | 986 | 1704 | | | |
| 225 | | 14 | | | | |
| 226 | 9 | 9 | | | | |
| 227 | 17 | 12 | | | | |
| 228 | 84 | 59 | 956 | | | |
| 229 | 16 | 23 | 676 | | | |
| 230 | 102 | 47 | 864 | | | |
| 231 | 124 | 75 | 1728 | | | |
| 232 | 95 | 53 | 880 | | | |
| 233 | 127 | 29 | | | | |
| 234 | 57 | 30 | | | | |
| 235 | 742 | 113 | 2265 | | | |
| 236 | 49 | 24 | 136 | | | |
| 237 | 106 | 43 | 478 | | | |
| 238 | 27 | 28 | 99 | | | |
| 239 | >9830 | 2260 | >50000 | | | |
| 240 | 20 | 24 | 125 | | | |
| 241 | 25 | 13 | 131 | | | |
| 242 | 7190 | >5000 | | | | |
| 243 | 15 | 11 | | | | |
| 244 | 63 | 21 | | | | |
| 246 | 132 | 25 | | | | |
| 247 | 113 | 25 | | | | |
| 248 | 23 | | | | | |
| 249 | 47 | 24 | | | | |
| 250 | 3932 | 2421 | | | | |
| 251 | 186 | 37 | | | | |
| 252 | 87 | 26 | | | | |
| 253 | 470 | 27 | | | | |
| 254 | 36 | 24 | | 29428 | | |
| 255 | 38 | 18 | | 2911 | | |
| 256 | | 20 | | | | |
| 257 | 72 | 24 | | 7469 | | |
| 258 | 91 | 34 | | 18314 | | |
| 259 | 36 | 11 | | 5362 | 1861 | |
| 260 | 41 | 12 | | 2795 | | |
| 261 | 42 | 13 | | 2341 | | |
| 262 | 163 | | | | | |
| 263 | 23 | | | | | |

TABLE 4

| Example No. | HCV Rep 1B EC$_{50}$ | HCV Rep 2A EC$_{50}$ |
|---|---|---|
| 77 | 608 | 936 |
| 82 | 359 | 813 |
| 86 | 929 | 1481 |
| 90 | 579 | 1143 |
| 99 | 313 | 599 |
| 100 | | |
| 144 | 442 | 1271 |
| 139 | | |
| 140 | 369 | 542 |
| 143 | | |
| 148 | | |
| 162 | | |
| 185 | 217 | 730 |
| 186 | 306 | 836 |
| 201 | | |
| 232 | | |
| 239 | | |
| 242 | | |
| 234 | 905 | 1825 |
| 259 | 1119 | 2081 |
| 261 | 524 | 1223 |

TABLE 5

Comparative Activity

| 2',3'-Substitution | Example No. | RSV HEp-2 $EC_{50}$ | RSV NHBE $EC_{50}$ | HRV16 HeLa $EC_{50}$ | DENV Rep $EC_{50}$ | DENV Huh7 $EC_{50}$ | HCV Rep1B $EC_{50}$ | HCV Rep2A $EC_{50}$ |
|---|---|---|---|---|---|---|---|---|
| —OH | 52 | | 252 | 1253 | | 5483 | 3956 | 7457 |
| —OC(O)iPr | 140 | | 14 | 83 | | 1214 | 368 | 542 |
| —OH | 29 | | 932 | 678 | 36056 | 1884 | | |
| —OC(O)iPr | 144 | | 22 | 92 | 6168 | 1284 | | |
| —OH | 44 | 997 | 1799 | 4260 | | | | |
| —OC(O)iPr | 184 | 79 | 13 | 57 | | | | |
| —OH | 19 | 4185 | >5000 | 50000 | | | | |
| —OC(O)iPr | 162 | 179 | 28 | 1619 | | | | |
| —OH | 15 | 4328 | 3255 | 11442 | | | | |
| —OC(O)iPr | 228 | 84 | 59 | 956 | | | | |
| —OH | 35 | 4066 | 1308 | 29560 | | | | |
| —OC(O)iPr | 137 | 467 | 65 | 1038 | | | | |
| —OH | 20 | 877 | 2233 | | >50000 | | | |
| —OC(O)iPr | 181 | 84 | 30 | | 6629 | | | |

TABLE 6 hMPV Activity

| Example No. | hMPVA1 LLC-MK2 $EC_{50}$ | hMPVB2 LLC-MK2 $EC_{50}$ | hMPVA2 LLC-MK2 $EC_{50}$ | hMPVB1 LLC-MK2 $EC_{50}$ |
|---|---|---|---|---|
| 140 | 0.16 | 0.23 | 0.19 | 0.21 |

TABLE 7

Comparative Nucleotide Triphosphate Activity

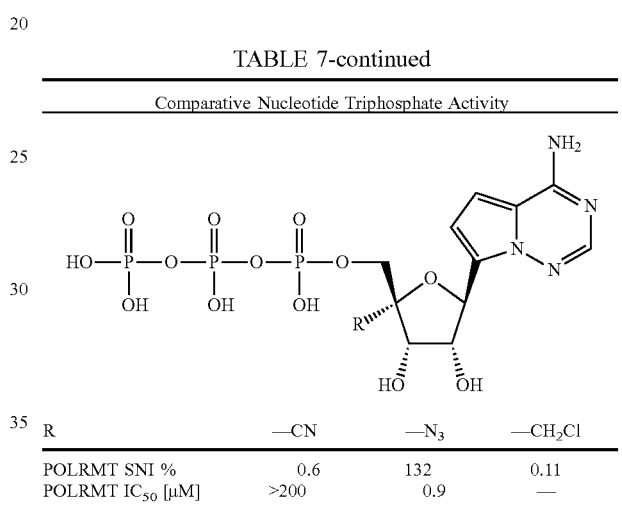

| R | —CN | —$N_3$ | —$CH_2Cl$ |
|---|---|---|---|
| RSV $IC_{50}$ [µM] | 0.044 | 0.12 | 1.1 |
| DENV $IC_{50}$ [µM] | 0.83 | 0.14 | 7.1 |

TABLE 7-continued

Comparative Nucleotide Triphosphate Activity

| R | —CN | —$N_3$ | —$CH_2Cl$ |
|---|---|---|---|
| POLRMT SNI % | 0.6 | 132 | 0.11 |
| POLRMT $IC_{50}$ [µM] | >200 | 0.9 | — |

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating a Pneumoviridae virus infection in a human in need thereof, the method comprising administering to the human a therapeutically effective amount of a compound of Formula (II):

Formula (II)

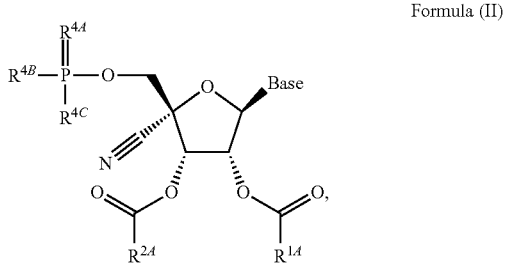

or a pharmaceutically acceptable salt thereof, wherein
Base is

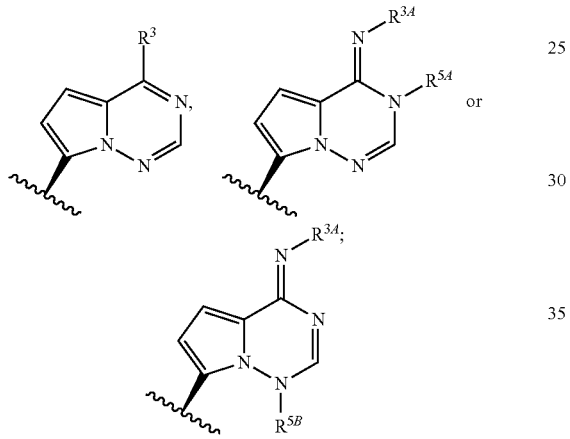

$R^{1A}$ and $R^{2A}$ are each independently:
(A) $C_{1-12}$ alkyl optionally substituted with 1 to 3 $R^{1B}$,
(B) 3 to 6 membered heterocyclyl having 1 to 3 heteroatoms independently selected from N, O and S, wherein the 3 to 6 membered heterocyclyl is optionally substituted with 1 to 3 $R^{1C}$, or
(C) phenyl, wherein
each $R^{1B}$ is independently —OH, —NH$_2$, $C_{1-6}$ alkoxy, methoxyethoxy, or 3 to 6 membered heterocyclyl having 1 to 3 heteroatoms independently selected from N, O and S, and
each $R^{1C}$ is independently $C_{1-3}$ alkyl;
$R^3$ is —N(H)$R^{3A}$ or —N=C($R^{3B}$)($R^{3C}$);
$R^{3A}$ is H, —CH$_2$OP(O)(OH)$_2$, or —C(O)$R^{3D}$, wherein
$R^{3D}$ is $C_{1-6}$ alkyl optionally substituted with 1 methoxy, or 3 to 6 membered heterocyclyl having 1 to 3 heteroatoms independently selected from N, O and S, optionally substituted with $C_{1-3}$ alkyl;
$R^{3B}$ is H or $C_{1-3}$ alkyl;
$R^{3C}$ is —N($R^{3C1}$)($R^{3C2}$);
$R^{3C1}$ and $R^{3C2}$ are each independently H or $C_{1-6}$ alkyl; or
$R^{3C1}$ and $R^{3C2}$ together with the atom to which they are attached form a 3 to 6 membered heterocyclyl having 1 to 3 heteroatoms independently selected from N, O and S, optionally substituted with $C_{1-6}$ alkyl;

$R^{4A}$ is O or S; and
$R^{4B}$ and $R^{4C}$ are each independently
(A) —OH;
(B) —OR$^{4B1}$, wherein
$R^{4B1}$ is $C_{1-6}$ alkyl optionally substituted with 1 to 3 $R^{4B2}$ groups, or $C_{6-12}$ aryl,
wherein
each $R^{4B2}$ group is independently $C_{1-6}$ alkoxy, —S—$R^{4B3}$, or —S(O)$_2$-$R^{4B3}$, and
each $R^{4B3}$ group is independently $C_{1-6}$ alkyl;

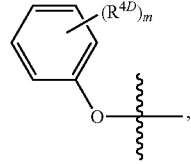

(C) wherein
m is 0, 1, 2, 3, 4, or 5; and
each $R^{4D}$ is independently $C_{1-3}$ alkyl optionally substituted with 1 to 3 $R^{4D1}$ groups, $C_{1-3}$ alkoxy optionally substituted with 1 to 3 $R^{4D2}$ groups, or —C(O)N($R^{4D3}$)$_2$, wherein
each $R^{4D1}$ group is independently —NH$_2$ or —C(O)OR$^{4D3}$,
each $R^{4D2}$ is independently $C_{1-3}$ alkoxy, and
each $R^{4D3}$ is independently $C_{1-3}$ alkyl;

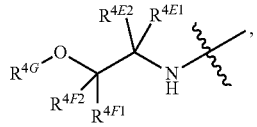

(D) wherein
$R^{4E1}$ and $R^{4E2}$ are each independently H or $C_{1-6}$ alkyl,
$R^{4F1}$ and $R^{4F2}$ are each independently H or $C_{1-6}$ alkyl, or $R^{4F1}$ and $R^{4F2}$ together are oxo,
$R^{4G}$ is $C_{1-12}$ alkyl optionally substituted with 1 to 3 $R^{4G1}$, $C_{3-7}$ cycloalkyl optionally substituted with 1 to 3 $R^{4G2}$, 3 to 8 membered heterocyclyl having 1 to 3 heteroatoms selected from N, O and S, optionally substituted with 1 to 3 $R^{4G3}$, or —C(O)$R^{4G4}$,
each $R^{4G1}$ is independently —OH, $C_{1-6}$ alkyl, $C_{1-3}$ alkoxy, —(CH$_2$OCH$_2$)$_{1-5}$-CH$_3$, —N($R^{4G8}$)$_2$, —OP(O)(OH), $C_{3-7}$ cycloalkyl optionally substituted with 1 to 3 R409, 3 to 6 membered heterocyclyl having 1 to 3 heteroatoms independently selected from N, O and S, optionally substituted with 1 to 3 $R^{4G10}$, or phenyl,
each $R^{4G2}$ is independently $C_{1-6}$ alkyl, $C_{1-3}$ haloalkyl, or —NH$_2$,
each $R^{4G3}$ is independently halogen or $C_{1-3}$ alkyl;
each $R^{4G4}$ is independently $C_{1-12}$ alkyl,
each $R^{4G8}$ is independently $C_{1-6}$ alkyl,
each $R^{4G9}$ is independently $C_{1-3}$ haloalkyl, or —NH$_2$, and
each $R^{4G10}$ is independently $C_{1-3}$ haloalkyl; or
(E) —(OP(O)(OH))$_{1-2}$—OH; and
$R^{5A}$ and $R^{5B}$ are each $C_{1-6}$ alkyl substituted with —OP(O)(OH)$_2$.

2. The method of claim 1, wherein the Pneumoviridae virus infection is a respiratory syncytial virus infection.

3. The method of claim 1, wherein the Pneumoviridae virus infection is human metapneumovirus infection.

4. A method of treating a Picornaviridae virus infection in a human in need thereof, the method comprising administering to the human a therapeutically effective amount of a compound of Formula (II):

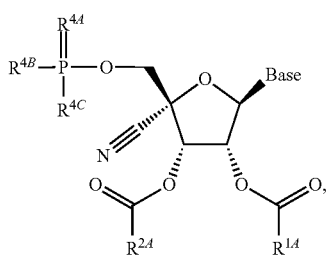

Formula (II)

or a pharmaceutically acceptable salt thereof, wherein
Base is

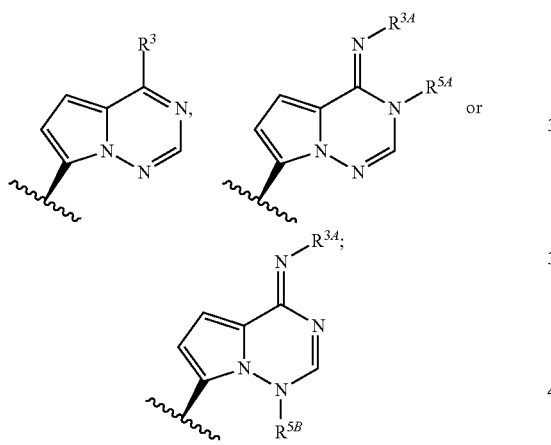

$R^{1A}$ and $R^{2A}$ are each independently:
(A) $C_{1-12}$ alkyl optionally substituted with 1 to 3 $R^{1B}$,
(B) 3 to 6 membered heterocyclyl having 1 to 3 heteroatoms independently selected from N, O and S, wherein the 3 to 6 membered heterocyclyl is optionally substituted with 1 to 3 $R^{1C}$, or
(C) phenyl, wherein
each $R^{1B}$ is independently —OH, —NH$_2$, $C_{1-6}$ alkoxy, methoxyethoxy, or 3 to 6 membered betercyclyl having 1 to 3 heteroatoms independently selected from N, O and S, and
each $R^{1C}$ is independently $C_{1-3}$ alkyl:
$R^3$ is —N(H)R$^{3A}$ or —N=C(R$^{3B}$)(R$^{3C}$);
$R^{3A}$ is H, —CH$_2$OP(O)(OH)$_2$, or —C(O)R$^{3D}$, wherein
$R^{3D}$ is $C_{1-6}$ alkyl optionally substituted with 1 methoxy, or 3 to 6 membered heterocyclyl having 1 to 3 heteroatoms independently selected from N and S, optionally substituted with $C_{1-3}$ alkyl;
$R^{3B}$ is H or $C_{1-3}$ alkyl;
$R^{3C}$ is —N(R$^{3C1}$)(R$^{3C2}$);
$R^{3C1}$ and $R^{3C2}$ are each independently H or $C_{1-6}$ alkyl; or
$R^{3C1}$ and $R^{3C2}$ together with the atom to which they are attached form a 3 to 6 membered heterocyclyl having 1 to 3 heteroatoms independently selected from N, O and S, optionally substituted with $C_{1-6}$ alkyl;
$R^{4A}$ is O or S; and
$R^{4B}$ and $R^{4C}$ are each independently
(A) —OH;
(B) —OR$^{4B1}$, wherein
$R^{4B1}$ is $C_{1-6}$ alkyl optionally substituted with 1 to 3 $R^{4B2}$ groups, or $C_{6-12}$ aryl, wherein
each $R^{4B2}$ group is independently $C_{1-6}$ alkoxy, —S—R$^{4B3}$, or —S(O)$_2$—R$^{4B3}$, and
each $R^{4B3}$ group is independently $C_{1-6}$ alkyl;

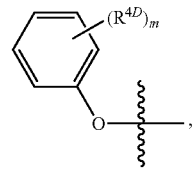

(C) wherein
m is 0, 1, 2, 3, 4, or 5; and
each $R^{4D}$ is independently $C_{1-3}$ alkyl optionally substituted with 1 to 3 $R^{4D1}$ groups, $C_{1-3}$ alkoxy optionally substituted with 1 to 3 $R^{4D2}$ groups, or —C(O)N(R$^{4D3}$)$_2$, wherein
each $R^{4D1}$ group is independently —NH$_2$ or —C(O)OR$^{4D3}$,
each $R^{4D2}$ is independently $C_{1-3}$ alkoxy, and
each $R^{4D3}$ is independently $C_{1-3}$ alkyl;

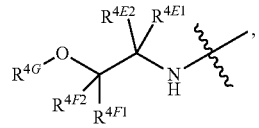

(D) wherein
$R^{4E1}$ and $R^{4E2}$ are each independently H or $C_{1-6}$ alkyl,
$R^{4F1}$ and $R^{4F2}$ are each independently H or $C_{1-6}$ alkyl, or $R^{4F1}$ and $R^{4F2}$ together are oxo,
$R^{4G}$ is $C_{1-12}$ alkyl optionally substituted with 1 to 3 $R^{4G1}$, $C_{3-7}$ cycloalkyl optionally substituted with 1 to 3 R462, 3 to 8 membered heterocyclyl having 1 to 3 heteroatoms selected from N, O and S, optionally substituted with 1 to 3 $R^{4G3}$, or —C(O) $R^{4G4}$,
each $R^{4G1}$ is independently —OH, $C_{1-6}$ alkyl, $C_{1-3}$ alkoxy, —(CH$_2$OCH$_2$)$_{1-5}$-CH$_3$, —N(R$^{4G8}$)$_2$, —OP(O)(OH), $C_{3-7}$ cycloalkyl optionally substituted with 1 to 3 $R^{4G9}$, 3 to 6 membered heterocyclyl having 1 to 3 heteroatoms independently selected from N, O and S, optionally substituted with 1 to 3 $R^{4G10}$, or phenyl,
each $R^{4G2}$ is independently $C_{1-6}$ alkyl, $C_{1-3}$ haloalkyl, or —NH$_2$,
each $R^{4G3}$ is independently halogen or $C_{1-3}$ alkyl;
each $R^{4G4}$ is independently $C_{1-12}$ alkyl,
each $R^{4G8}$ is independently $C_{1-6}$ alkyl,
each $R^{4G9}$ is independently $C_{1-3}$ haloalkyl, or —NH$_2$, and
each $R^{4G10}$ is independently $C_{1-3}$ haloalkyl; or (E) —OP(O)(OH)$_{1-2}$-OH; and $R^{5A}$ and $R^{5B}$ are each $C_{1-6}$ alkyl substituted with —OP(O)(OH)$_2$.

5. The method of claim 4, wherein the Picornaviridae virus infection is human rhinovirus infection.

6. A method for the treatment or prophylaxis of an exacerbation of a respiratory condition by a viral infection in a human in need thereof, the method comprising administering to the human a therapeutically effective amount of a compound of Formula (II):

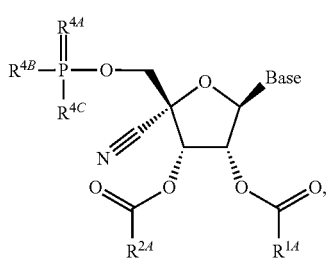

Formula (II)

or a pharmaceutically acceptable salt thereof, wherein
Base is

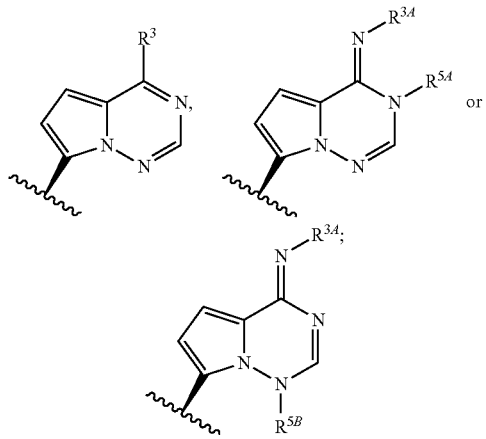

$R^{1A}$ and $R^{2A}$ are each independently:
(A) $C_{1-12}$ alkyl optionally substituted with 1 to 3 $R^{1B}$,
(B) 3 to 6 membered heterocyclyl having 1 to 3 heteroatoms independently selected from N, O and S, wherein the 3 to 6 membered heterocyclyl is optionally substituted with 1 to 3 $R^{1C}$, or
(C) phenyl, wherein
each $R^{1B}$ is independently —OH, —NH$_2$, $C_{1-6}$ alkoxy, methoxyethoxy, or 3 to 6 membered heterocyclyl having 1 to 3 heteroatoms independently selected from N, O and S, and
each $R^{1C}$ is independently $C_{1-3}$ alkyl;
$R^3$ is —N(H)$R^{3A}$ or —N=C($R^{3B}$)($R^{3C}$);
$R^{3A}$ is H, —CH$_2$OP(O)(OH)$_2$, or —C(O)$R^{3D}$, wherein
$R^{3D}$ is $C_{1-6}$ alkyl optionally substituted with 1 methoxy, or 3 to 6 membered heterocyclyl having 1 to 3 heteroatoms independently selected from N and S, optionally substituted with $C_{1-3}$ alkyl;
$R^{3B}$ is H or $C_{1-3}$ alkyl;
$R^{3C}$ is —N($R^{3C1}$)($R^{3C2}$);
$R^{3C1}$ and $R^{3C2}$ are each independently H or $C_{1-6}$ alkyl; or $R^{3C1}$ and $R^{3C2}$ together with the atom to which they are attached form a 3 to 6 membered heterocyclyl having 1 to 3 heteroatoms independently selected from N, O and S, optionally substituted with $C_{1-6}$ alkyl;

$R^{4A}$ is O or S; and $R^{4B}$ and $R^{4C}$ are each independently
(A) —OH;
(B) —OR$^{4B1}$, wherein
$R^{4B1}$ is $C_{1-6}$ alkyl optionally substituted with 1 to 3 $R^{4B2}$ groups, or $C_{6-12}$ aryl,
wherein
each $R^{4B2}$ group is independently $C_{1-6}$ alkoxy, —S—$R^{4B3}$, or —S(O)$_2$—$R^{4B3}$, and
each $R^{4B3}$ group is independently $C_{1-6}$ alkyl;
(C)

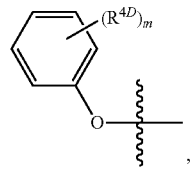

wherein
m is 0, 1, 2, 3, 4, or 5; and
each $R^{4D}$ is independently $C_{1-3}$ alkyl optionally substituted with 1 to 3 $R^{4D1}$ groups, $C_{1-3}$ alkoxy optionally substituted with 1 to 3 $R^{4D4}$ groups, or —C(O)N($R^{4D3}$)$_2$, wherein
each $R^{4D1}$ group is independently —NH$_2$ or —C(O)OR$^{4D3}$,
each $R^{4D2}$ is independently $C_{1-3}$ alkoxy, and
each $R^{4D3}$ is independently $C_{1-3}$ alkyl;
(D)

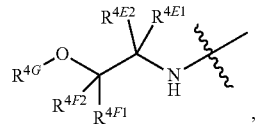

wherein
$R^{4E1}$ and $R^{4E2}$ are each independently H or $C_{1-6}$ alkyl,
$R^{4F1}$ and $R^{4F2}$ are each independently H or $C_{1-6}$ alkyl, or $R^{4F1}$ and $R^{4F2}$ together are oxo,
$R^{4G}$ is $C_{1-12}$ alkyl optionally substituted with 1 to 3 $R^{4G1}$, $C_{3-7}$ cycloalkyl optionally substituted with 1 to 3 $R^{4G2}$, 3 to 8 membered heterocyclyl having 1 to 3 heteroatoms selected from N, O and S, optionally substituted with 1 to 3 $R^{4G3}$, or —C(O)$R^{4G4}$,
each $R^{4G1}$ is independently —OH, $C_{1-6}$ alkyl, $C_{1-3}$ alkoxy, —(CH$_2$OCH$_2$)$_{1-5}$-CH$_3$, —N($R^{4G8}$)$_2$, —OP(O)(OH)$_2$, $C_{3-7}$ cycloalkyl optionally substituted with 1 to 3 R409, 3 to 6 membered heterocyclyl having 1 to 3 heteroatoms independently selected from N, O and S, optionally substituted with 1 to 3 $R^{4G10}$, or phenyl,
each $R^{4G2}$ is independently $C_{1-6}$ alkyl, $C_{1-3}$ haloalkyl or —NH$_2$,
each $R^{4G3}$ is independently halogen or $C_{1-3}$ alkyl;
each $R^{4G4}$ is independently $C_{1-12}$ alkyl,
each $R^{4G8}$ is independently $C_{1-6}$ alkyl, each $R^{4G9}$ is independently $C_{1-3}$ haloalkyl, or —$NH_2$, and
each $R^{4G10}$ is independently $C_{1-3}$ haloalkyl; or
(E) —(OP(O)(OH))$_{1-2}$—OH; and
$R^{5A}$ and $R^{5B}$ are each $C_{1-6}$ alkyl substituted with —OP(O)(OH)$_2$
wherein the respiratory condition is chronic obstructive pulmonary disease.

7. The method of claim 6, wherein the viral infection is caused by respiratory syncytial virus, rhinovirus or metapneumovirus.

8. The method of claim 2, wherein the compound is:

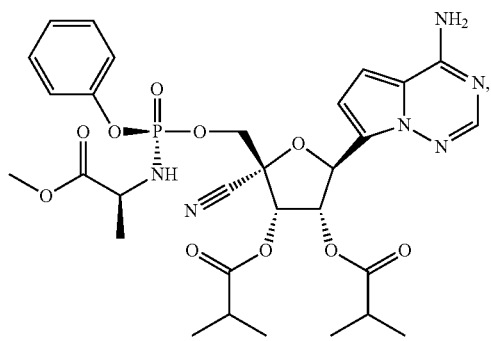 [SMILES: COC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccccc1]

or a pharmaceutically acceptable salt thereof.

9. The method of claim 2, wherein the compound is:

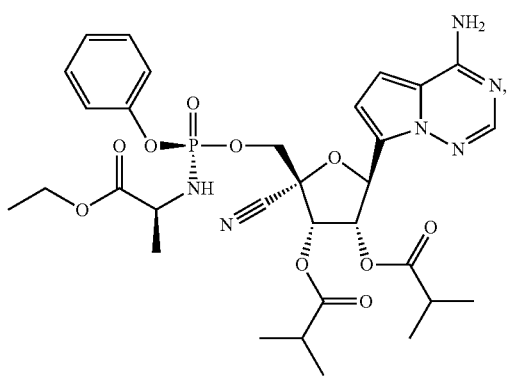 [SMILES: CCOC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccccc1]

or a pharmaceutically acceptable salt thereof.

10. The method of claim 2, wherein the compound is:

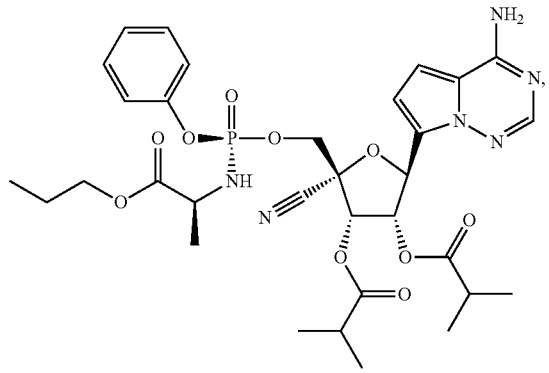 [SMILES: CCCOC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccccc1]

or a pharmaceutically acceptable salt thereof.

11. The method of claim 2, wherein the compound is:

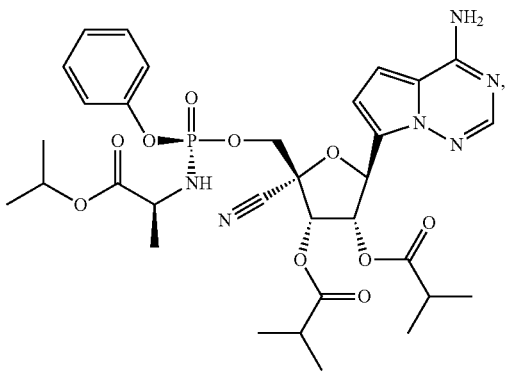 [SMILES: CC(C)OC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccccc1]

or a pharmaceutically acceptable salt thereof.

12. The method of claim 2, wherein the compound is:

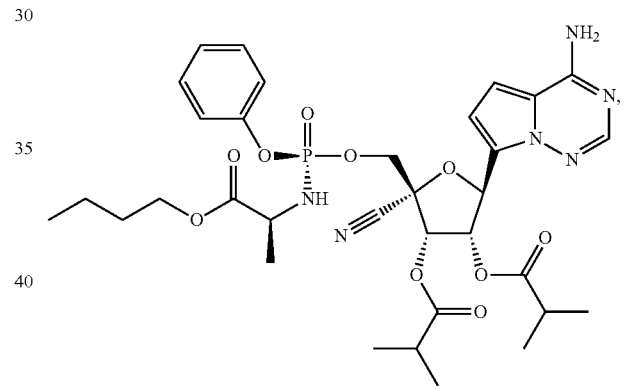

or a pharmaceutically acceptable salt thereof.

13. The method of claim 2, wherein the compound is:

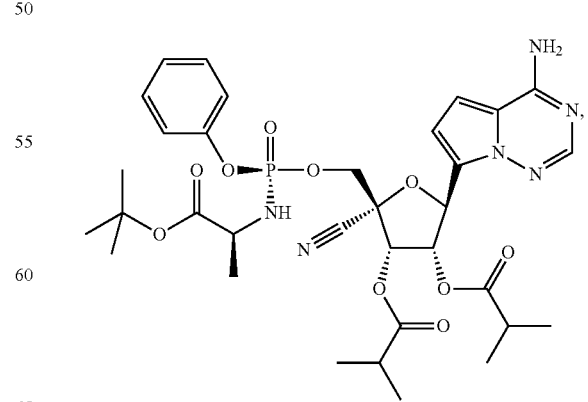

or a pharmaceutically acceptable salt thereof.

14. The method of claim 2, wherein the compound is:

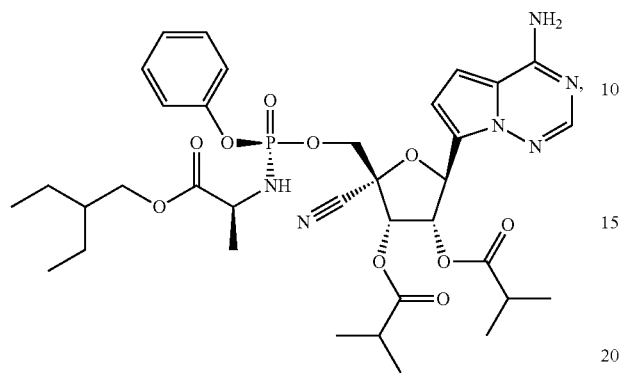

or a pharmaceutically acceptable salt thereof.

15. The method of claim 6, wherein the compound is:

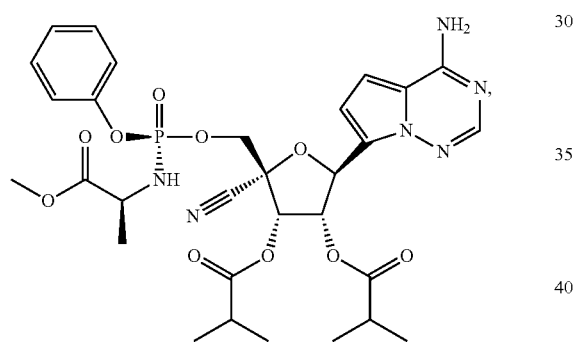

or a pharmaceutically acceptable salt thereof.

16. The method of claim 6, wherein the compound is:

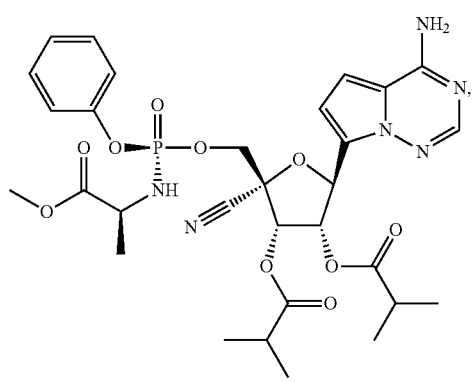 [SMILES: COC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccccc1]

or a pharmaceutically acceptable salt thereof.

17. The method of claim 6, wherein the compound is:

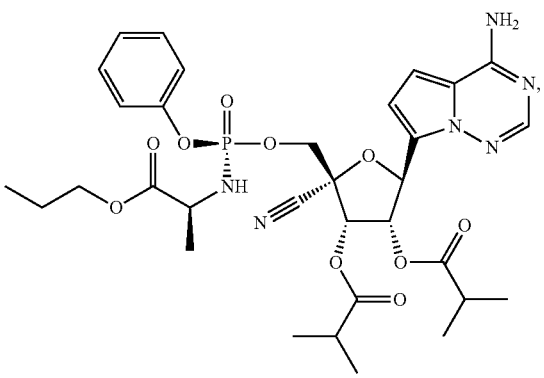 [SMILES: CCCOC(=O)[C@H](C)N[P@](=O)(OC[C@@]1(C#N)O[C@@H](c2ccc3c(N)ncnn23)[C@H](OC(=O)C(C)C)[C@@H]1OC(=O)C(C)C)Oc1ccccc1]

or a pharmaceutically acceptable salt thereof.

18. The method of claim 6, wherein the compound is:

or a pharmaceutically acceptable salt thereof.

19. The method of claim 6, wherein the compound is:

or a pharmaceutically acceptable salt thereof.

20. The method of claim 6, wherein the compound is:
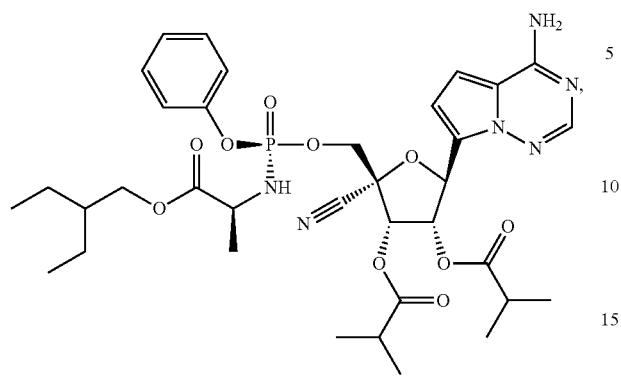
or a pharmaceutically acceptable salt thereof.